US009951086B2

(12) United States Patent
Bothe et al.

(10) Patent No.: US 9,951,086 B2
(45) Date of Patent: Apr. 24, 2018

(54) INDAZOLECARBOXAMIDES, PROCESSES FOR THEIR PREPARATION, PHARMACEUTICAL PREPARATIONS COMPRISING THEM AND THEIR USE FOR PRODUCING MEDICAMENTS

(71) Applicant: Bayer Pharma Aktiengesellschaft, Berlin (DE)

(72) Inventors: Ulrich Bothe, Berlin (DE); Holger Siebeneicher, Berlin (DE); Nicole Schmidt, San Francisco, CA (US); Andrea Rotgeri, Berlin (DE); Ulf Bömer, Glienicke (DE); Sven Ring, Jena (DE); Horst Irlbacher, Berlin (DE); Judith Günther, Berlin (DE); Holger Steuber, Berlin (DE); Martin Lange, Berlin (DE); Martina Schäfer, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/106,073

(22) PCT Filed: Dec. 16, 2014

(86) PCT No.: PCT/EP2014/077877
§ 371 (c)(1),
(2) Date: Jun. 17, 2016

(87) PCT Pub. No.: WO2015/091426
PCT Pub. Date: Jun. 25, 2015

(65) Prior Publication Data
US 2016/0311833 A1    Oct. 27, 2016

(30) Foreign Application Priority Data

Dec. 19, 2013  (EP) .................... 13198463
Oct. 16, 2014  (EP) .................... 14189216

(51) Int. Cl.
*C07D 401/12* (2006.01)
*C07D 401/14* (2006.01)
*C07D 417/12* (2006.01)
*C07D 409/12* (2006.01)
*C07D 495/10* (2006.01)
*C07D 403/12* (2006.01)
*C07D 405/14* (2006.01)
*C07D 409/14* (2006.01)
*C07D 413/12* (2006.01)
*C07D 413/14* (2006.01)
*C07D 417/14* (2006.01)
*C07D 471/10* (2006.01)
*C07D 487/10* (2006.01)
*C07D 491/107* (2006.01)

(52) U.S. Cl.
CPC ......... *C07D 495/10* (2013.01); *C07D 401/12* (2013.01); *C07D 401/14* (2013.01); *C07D 403/12* (2013.01); *C07D 405/14* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C07D 471/10* (2013.01); *C07D 487/10* (2013.01); *C07D 491/107* (2013.01)

(58) Field of Classification Search
CPC combination set(s) only.
See application file for complete search history.

(56) References Cited

U.S. PATENT DOCUMENTS

| 8,293,923 | B2 | 10/2012 | Guckian et al. |
| 2003/0153596 | A1 | 8/2003 | Suh et al. |
| 2004/0224968 | A1 | 11/2004 | Seidelmann et al. |
| 2005/0137187 | A1 | 6/2005 | Souers et al. |
| 2006/0194801 | A1 | 8/2006 | Kelly et al. |
| 2007/0015809 | A1 | 1/2007 | Bressi et al. |
| 2007/0037803 | A1 | 2/2007 | Frenkel et al. |
| 2008/0058341 | A1 | 3/2008 | Zhang et al. |
| 2009/0286800 | A1 | 11/2009 | Cheruvallath et al. |
| 2012/0015962 | A1 | 1/2012 | Arora et al. |
| 2012/0028984 | A1 | 2/2012 | Wu et al. |
| 2012/0283238 | A1 | 11/2012 | Romero et al. |
| 2013/0231328 | A1 | 9/2013 | Harriman et al. |
| 2013/0274241 | A1 | 10/2013 | Jorand-Lebrun et al. |

FOREIGN PATENT DOCUMENTS

| EP | 1403255 | 3/2004 |
| EP | 2045253 | 4/2009 |
| EP | 2103620 | 9/2009 |
| EP | 2522657 | 11/2012 |
| WO | 2008/073461 | 6/2002 |
| WO | 2003/101379 | 12/2003 |
| WO | 2004/074284 | 9/2004 |
| WO | 2005/082890 | 9/2005 |
| WO | 2006/071940 | 7/2006 |
| WO | 2007/095124 | 8/2007 |

(Continued)

OTHER PUBLICATIONS

Mattii, et al., "The balance between pro- and anti-inflammatory cytokines is critical in human allergic contact detmatitis pathogenesis: the role of IL-1 family members", Experimental Dermatology, 2013, 30 pages.

(Continued)

*Primary Examiner* — Nyeemah A Grazier
(74) *Attorney, Agent, or Firm* — Nixon & Vanderhye PC

(57) ABSTRACT

The present application relates to novel 6-substituted indazoles having a carboxamide side chain, to processes for their preparation, to their use alone or in combinations for the treatment and/or prophylaxis of diseases, and to their use for producing medicaments for the treatment and/or prophylaxis of diseases, in particular for the treatment and/or prophylaxis of endometriosis, lymphomas, macular degeneration, COPD and psoriasis.

19 Claims, 1 Drawing Sheet

(56) References Cited

FOREIGN PATENT DOCUMENTS

| | | |
|---|---|---|
| WO | 2009/019167 | 2/2009 |
| WO | 2009/058924 | 5/2009 |
| WO | 2009/102498 | 8/2009 |
| WO | 2010/062171 | 6/2010 |
| WO | 2011/043371 | 4/2011 |
| WO | 2012/097744 | 7/2012 |
| WO | 2012/107475 | 8/2012 |
| WO | 2012/129258 | 9/2012 |
| WO | 2013/042137 | 3/2013 |
| WO | 2013/053051 | 4/2013 |
| WO | 2013/066729 | 5/2013 |
| WO | 2013/106612 | 7/2013 |
| WO | 2013/106614 | 7/2013 |
| WO | 2013/106641 | 7/2013 |

OTHER PUBLICATIONS

McGettrick, et al., "Toll-like receptors: key activators of leucocytes and regulator of haematopoiesis", British Journal of Haematology, 139, 2007, pp. 185-193.

Miggin, et al., "New insight into the regulation of TLR signaling", Journal of Leukocyte Biology, vol. 80, 2006, 8 pages.

Miller, "Toll-like receptors in skin", Adv Dermatol, 24, 2008, pp. 71-87.

Minkis, et al., "Interleukin 1 Receptor Antagonist Deficiency Presenting as Infantile Pustulosis Mimicking Infantile Pustular Psoriasis", Archives of Dermatology, 148(6), 2012, pp. 747-752.

Muzio, et al., "IRAK (Pelle) Family Member IRAK-2 and MyD88 as Proximal Mediators of IL-1 Signaling", Science, 278, 1997, pp. 1612-1615.

Nadigel, et al., "Cigarette smoke increases TLR4 and TLR9 expression and induces cytokine production from CD8+ T cells in chronic obstructive pulmonary disease", Respiratory Research, 12:149, 2011, 13 pages.

Narayanan, et al., "Interleukin-1 Receptor-1-deficient Mice Show Attenuated Production of Ocular Surface Inflammatory Cytokines in Experimental Dry Eye", Cornea, vol. 27, No. 7, Aug. 2008, pp. 811-817.

Ngo, et al., "Oncogenically active MYD88 mutations in human lymphoma", Nature, vol. 470, Feb. 3, 2011, pp. 115-119.

Nickerson, et al., "TLR9 Regulates TLR7- and MyD88-Dependent Autoantibody Production and Disease in a Murine Model of Lupus", The Journal of Immunology, 2010, pp. 1840-1848.

Nicotra, et al., "Toll-like receptors in chronic pain", Experimental Neurology, 234, 2012, pp. 316-329.

Niebuhr, et al., "Dysregulation of toll-like receptor-2 (TLR-2)-induced effects in monocytes from patients with atopic dermatitis: impact of TLR-2 R753Q polymorphism", Allergy, 63, 2008, pp. 728-734.

Noelker, et al., "Toll like receptor 4 mediates cell death in a mouse MPTP model of Parkinson disease", Scientific Reports, 3, 2013, 5 pages.

Ono, et al., "The p38 signal transduction pathway Activation and function", Cellular Signaling, 12, 2000, pp. 1-13.

Oyama, et al., "Reduced Myocardial Ischemia-Reperfusion Injury in Toll-Like Receptor 4-Deficient Mice", Circulation, 109, 2004, pp. 784-789.

Pettersson, "Setting up TRAPS", Annals of Medicine, 44, 2012, pp. 109-118.

Precious, et al., "An Oligomeric Signaling Platform Formed by the Toll-like Receptor Signal Transducers MyD88 and IRAK-4", J. Biol. Chem., vol. 284, No. 37, 2009, pp. 25404-25411.

Puente, et al., "Whole-genome sequencing identifies recurrent mutations in chronic lymphocytic leukaemia", Nature, vol. 475, 2011, pp. 101-105.

Qiu, et al., "Anti-interleukin-33 inhibits cigarette smoke-induced lung inflammation in mice", Immunology, 138, 2013, pp. 76-82.

Rakoff-Nahoum, et al., "Role of Toll-like Receptors in Spontaneous Commensal-Dependent Colitis", Immunity, 25, Aug. 2006, pp. 319-329.

Ramirez, et al., "Toll-like Receptors and Diabetes Complications: Recent Advances", Current Diabetes Reviews, 8, 2012, pp. 480-488.

Ramirez Cruz, et al., "Toll-like receptors: dysregulation in vivo in patients with acute respiratory distress syndrome", Rev Alerg Mex, 51(6), 2004, pp. 210-217.

Redfern, et al., "Toll-like receptors in ocular surface disease", Experimental Eye Research, 90, 2010, pp. 679-687.

Rekhter, et al., Biochemical and Biophysical Research Communication, 367, 2008, pp. 642-648.

Roger, et al., "Protection from lethal Gram-negative bacterial sepsis by targeting Toll-like receptor 4", PNAS, vol. 106, No. 7, Feb. 17, 2009, pp. 2348-2352.

Ruperto, et al., "Two Randomized Trials of Canakinumab in Systemic Juvenile Idiopathic Arthritis", New England Journal of Medicine, 367:25, 2012, pp. 2396-2406.

Santulli, et al., "Serum and peritoneal interleukin-33 levels are elevated in deeply infiltrating endometriosis", Human Reproduction, vol. 27, No. 7, 2013, pp. 2001-2009.

Scanzello, et al., "Innate immune system activation in osteoarthritis: is osteoarthritis a chronic wound?", Curr Opin Rheumatol, 20, 2008, pp. 565-572.

Sedimbi, et al., "IL-18 in inflammatory and autoimmune disease", Cellular and Molecular Life Sciences, 2013, 14 pages.

Seki, et al., "Effect of Toll-like receptor 4 inhibitor on LPS-induced lung injury", Inflammation Research, 59, 2010, pp. 837-845.

Selway, et al., "Toll-like receptor 2 activation and comedogensis: implications for the pathogenesis of acne", BMC Dermatology, 13:10, 2013, 7 pages.

Seneviratne, et al., "Toll-like receptors and macrophage activation in atherosclerosis", Clinica Chimica Acta, 413, 2012, pp. 3-14.

Shi, et al., "Monosodium urate crystals in inflammation and immunity", Immunological Reviews, 233, 2010, pp. 203-217.

Sikora, et al., "Imbalance of cytokines from Interleukin-1 Family—Role in Pathogenesis of Endometriosis", American Journal of Reproductive Immunology, 68, 2012, pp. 138-145.

Srivastava, et al., "Augmentation of Therapeutic Responses in Melanoma by Inhibition of IRAK-1,-4", Cancer Research, 72, 2012, pp. 6209-6216.

Staschke, et al., "IRAK4 Kinase Activity is Required for Th17 Differentiation and Th17-Mediated Disease", The Journal of Immunology, 183, 2009, pp. 568-577.

Sun, et al., "Inhibition of Corneal Inflammation by the TLR4 Antagonist Eritoran Tetrasocium (E5564)", Investigative Ophthalmology & Visual Science, vol. 50, No. 3, 2009, pp. 1247-1254.

Suzuki, et al., "Severe impairment of interleukin-1 and Toll-like receptor signalling in mice lacking IRAK-4", Nature, vol. 416, 2002, pp. 750-754.

Swantek, et al., "IL-1 Receptor-Associated Kinase Modulates Host Responsiveness to Endotoxin", The Journal of Immunology, 164, 2000, pp. 4301-4306.

Terhorst, et al., "The Role of Toll-Like Receptors in Host Defenses and Their Relevance to Dermatologic Diseases", Am J Clin Dermatol, 11(1), 2010, 10 pages.

McDonald, et al., "Optimization of 1,3,4-Benzotriazepine-Based CCK2 Antagonists to Obtain Potent, Orally Active Inhibitors of Gastrin-Mediated Gastric Acid Secretion", J. Med. Chem., 50, 2007, pp. 3101-3112.

Mitchell, et al., "Palladium-Catalysed Reactions of Organotin Compounds", Synthesis, 1992, pp. 803-815.

Miura, "Rational Ligand Design in Constructing Efficient Catalyst Systems for Suzuki-Miyaura Coupling", Angewandte Chemie Int. Ed., 43, 2004, pp. 2201-2203.

Miyaura, et al., "Palladium-Catalyzed Cross-Coupling Reactions of Organoboron Compounds", Chem. Rev., 95, 1995, pp. 2457-2483.

Miyaura, "Synthesis of Biaryls via the Cross-Couple Reaction of Arylboronic Acids", Advances in Metal-Organic Chemistry, vol. 6, 1998, pp. 187-243.

Miyaura (editor), "Topics in Current Chemistry, 219", 2002, 253 pages.

(56) References Cited

OTHER PUBLICATIONS

Moroz, et al., "The Ullmann Ehter Condensation", Russian Chemical Reviews, 43(8), 1974, 13 pages.
Morytko, et al., "Synthesis and in vitro activity of N'-cyano-4-(2-phenylacetyl)-N-o-tolypiperazine-1-carboximidamide P2X7 antagonists", Bioorganic & Medicinal Chemistry Letters, 18, 2008, pp. 2093-2096.
Muci, et al., "Practical Palladium Catalysts for C—N and C—O Bond Formation", Topics in Current Chemistry, 219, 2002, pp. 131-209.
Nagaki, et al., "Flow microreactor synthesis of disubstituted pyridines from dibromopyridines via Br/Li exchange without using cryogenic conditions", Green Chemistry, 13, 2011, pp. 1110-1113.
Negishi, "Palladium- or Nickel-Catalyzed Cross Coupling. A New Selective Method for Carbon-Carbon Bond Formation", Acc. Chem. Res., 15, 1982, pp. 340-348.
Negishi, et al., "Palladium- or Nickle-catalyzed Cross-coupling with Organometals Containing Zinc, Magnesium, Aluminium, and Zirconium", Metal-Catalyzed Cross-coupling Reactions, Wiley-VCH, 1; Diederich (editor), 1998, 47 pages.
Negishi, et al., "Palladium-Catalyzed Conjugate Substitution", Handbook of Organopalladium Chemistry for Organic Synthesis, vol. 1, 2002, pp. 767-789.
Nordstrom, et al., "Beneficial Effect of Interleukin 1 Inhibition with Anakinra in Adult-onset Still's Disease: an Open, Randomized, Multicenter Study", The Journal of Rheumatology, vol. 39, No. 10, 2012, pp. 2008-2011.
Pauwels, et al., "Role of IL-1α and the Nlrp3/caspase-1/1L-1β axis in cigarette smoke-induced pulmonary inflammation and COPD", European Respiratory Journal, 38, 2011, pp. 1019-1028.
Pfefferkorn, et al., "Discovery of (S)-6-(3-Cyclopentyl-2-(4-(trifluoromethyl)-1H-imidazol-1-yl)propanamido)nicotinic Acid as a Hepatoselective Glucokinase Activator Clinical Candidate for Treating Type 2 Diabetes Mellitus", Journal of Medicinal Chemistry, 55, 2012, pp. 1318-1333.
Sagara, et al., "Discovery of 2-Aminothiazole-4-carboxamides, a Novel Class of Muscarinic M3 Selective Antagonists, through Solution-Phase Parallel Synthesis", Chemical and Pharmaceutical Bulletin, 53(4), 2005, pp. 437-440.
Sawyer, "Recent Advances in Diaryl Ether Synthesis", Tetrahedron, 56, 2000, pp. 5054-5065.
Shaw, et al., "Serotonin Analogs, the Synthesis of 5-Dimethylaminoindoles", J. Am. Chem. Soc., 76, 1954, pp. 1384-1387.
Shimada, et al., "Synthesis and structure-activity relationships of a series of substituted 2-(1H-furo[2,3-g]indazol-1-yl)ethylamine derivatives as 5-HT2C receptor agonists", Bioorganic & Medicinal Chemistry, 16, 2008, pp. 1966-1982.
Stille, "Palladium-katalysierte Kupplungsreaktionen organischer Elektrophile mit Organozinn-Verbindugen", Angew. Chem., 98, 1986, pp. 504-519.
Suzuki, et al., "Organoboron compounds in new synthetic reactions", Pure & Appl. Chem., vol. 57, No. 12, 1985, pp. 1749-1758.
Takami, et al., "Design and synthesis of Rho kinase inhibitors (I)", Bioorganic & Medicinal Chemistry, 12, 2004, pp. 2115-2137.
Tamao, et al., "Introduction to Cross-Coupling Reactions", Topics in Current Chemistry, 219, 2002, pp. 1-9.
Telfer, et al., "The Versatile, Efficient, and Stereoselective Self-Assembly of Transition-Metal Helicates by Using Hydrogen-Bonds", Chemistry: A European Journal, 11, 2005, pp. 57-68.
Todres, "Stereochemical Results of Electron Transfers", Russ. Chem. Rev., 43, 1974, 4 pages.
Tricotet, et al., "Selective Vinyl C—H Lithiation of cis-Stilbenes", J. Am. Chem. Soc., 131, 2009, pp. 3142-3143.
Valeur, et al., "Amide bond formation: beyond the myth of coupling reagents", Chemical Society Reviews, 38, 2009, pp. 606-631.
Wagner, et al., "Mepyramine-JNJ7777120-hybrid compounds show high affinity to hH1R, but low affinity to hH4R", Bioorganic & Medicinal Chemistry Letters, 21, 2011, pp. 6274-6280.
Wolf, et al., "Interleukin-1 signaling is required for induction and maintenance of postoperative incisional pain: Genetic and pharmacological studies in mice", Brain, Behavior, and Immunity, 22, 2008, pp. 1072-1077.
Wuts, et al., "Greene's Protective Groups in Organic Synthesis", 4th Edition, Wiley-Interscience, Chapter 5, Dec. 8, 2006, 114 pages.
Wuts, et al., "Greene's Protective Groups in Organic Synthesis", 4th Edition, Wiley-Interscience, Chapter 7, Dec. 8, 2006, 231 pages.
Wuts (editor), et al., "Protection for Phenols and Catechols", Chapter 3, Greene's Protective Groups in Organic Synthesis, Fourth Edition; John Wiley & Sons, Inc., 2007, 64 pages.
Wuts (editor), et al., "Protection for the Hydroxyl Group, Including 1,2- and 1,3-Diols", Chapter 2, Greene's Protective Groups in Organic Synthesis, Fourth Edition; John Wiley & Sons, Inc., 2007, 351 pages.
Zhu, et al., "Bicyclic core estrogens as full antagonists: synthesis, biological evaluation and structure-activity relationships of estrogen receptor ligands based on bridged oxabicyclic core arylsulfonamides", Organic & Biomolecular Chemistry, 10, 2012, pp. 8692-8700.
Hao, et al., "Inflammation in inflammatory bowel disease pathogenesis", Curr Opin Gastroenterol, 29, 2013, pp. 363-369.
Heimesaat, et al., "Swift Towards Pro-inflammatory Intestinal Bacteria Aggravates Acute Murine Colitis via Toll-like Receptors 2 and 4", PLoS One, Issue 7, Jul. 2007, 7 pages.
Henderson, et al., "Monogenic IL-1 mediated autoinflammatory and immunodeficiency syndromes: finding the right balance in response to danger signals", Clinical Immunology, 135, 2010, pp. 210-222.
Hilberath, et al., "Resolution of Toll-like receptor 4-mediated acute lung injury is linked to eicosanoids and suppressor of cytokine signaling 3", The FASEB Journal, 2011, pp. 1827-1835.
Holtmann, et al., "The MAPK Kinase Kinase TAK1 Plays a Central Role in Coupling the Interleukin-1 Receptor to Both Transcriptional and RNA-targeted Mechanisms of Gene Regulation", Journal of Biological Chemistry, 276, 2001, pp. 3508-3516.
Imaoka, et al., "Interleukin-18 production and pulmonary function in COPD", European Respiratory Journal, 31, 2008, pp. 287-297.
Jeyaseelan, et al., "Distinct Roles of Pattern Recognition Receptors CD14 and Toll-like Receptor 4 in Acute Lung Injury", Infection and Immunity, vol. 73, No. 3, Mar. 2005, pp. 1754-1763.
Kaarniranta, et al., "Age-related macular degeneration: activation of innate immunity system via pattern recognition receptors", J. Mol. Med., 87, 2009, pp. 117-123.
Kang, et al., "IL-18 is Induced and IL-18 Receptor α Plays a Critical Role in the Pathogenesis of Cigarette Smoke-Induced Pulmonary Emphysema and Inflammation", The Journal of Immunology, 178, 2007, pp. 1948-1959.
Kawagoe, et al., "Sequential control of Toll-like receptor-dependent responses by IRAK1 and IRAK2", Nature Immunology, vol. 9, No. 6, Jun. 2008, pp. 684-691.
Kawayama, et al., "Interleukin-18 in Pulmonary Inflammatory Diseases", Journal of Interferon & Cytokine Research, vol. 32, No. 10, 2013, 8 pages.
Kezic, et al., "Endotoxin-induced uveitis is primarily dependent on radiation-resistant cells and on MyD88 but not TRIF", Journal of Leukocyte Biology, vol. 90, Aug. 2011, pp. 305-311.
Kfoury, et al., "MyD88 in DNA Repair and Cancer Cell Resistance to Genotoxic Drugs", Journal of the National Cancer Institute, vol. 105, Issue 13, 2013, pp. 937-946.
Khan, et al., "Toll-like receptor system and endometriosis", Journal of Obstetrics and Gynecology Research, vol. 39, No. 8, 2013, pp. 1281-1292.
Khoufache, et al., "Soluble Human IL-1 Receptor Type 2 Inhibits Ectopic Endometrial Tissue Implantation and Growth," The American Journal of Pathology, vol. 181, No. 4, Oct. 2012, pp. 1197-1205.
Kim, et al., "A critical role for IRAK4 kinase activity in Toll-like receptor-mediated innate immunity", JEM, vol. 204, No. 5, 2007, pp. 1025-1036.
Kim, et al., "The Critical Role of IL-1 Receptor-Associated Kinase 4-Mediated NF-kB Activation in Modified Low-Density Lipoprotein-Induced Inflammatory Gene Expression and Atherosclerosis", The Journal of Immunology, 186, 2011, pp. 2871-2880.

(56) References Cited

OTHER PUBLICATIONS

Kim, et al., "Toll-like Receptors in Peripheral Nerve Injury and Neuropathic Pain", Toll-like Receptors: Roles in Infection and Neuropathology, 2009, pp. 169-186.

Kitazawa, et al., "Blocking IL-1 Signaling Rescues Cognition, Attenuates Tau Pathology, and Restores Neuronal β-Catenin Pathway Function in an Alzheimer's Disease Model," The Journal of Immunology, 187, 2011, pp. 6539-6549.

Kobori, et al., "Interleukin-33 expression is specifically enhanced in flamed mucosa of ulcerative colitis", J Gastroenterol, 45, 2010, pp. 999-1007.

Kollewe, et al., "Sequential Autophosphorylation Steps in the Interleukin-1 Receptor-associated Kinase-1 Regulate its Availability as an Adapter in Interleukin-1 Signaling", Journal of Biological Chemistry, 279, 2004, pp. 5227-5236.

Kovach, et al., "Toll like receptors in diseases of the lung", International Immunopharmacology, 11, 2011, pp. 1399-1406.

Kreisel, et al., "Innate immunity and organ transplantation: focus on lung transportation", Transplant International, 26, 2013, pp. 2-10.

Krysko, et al., "Immunogenic cell death and DAMPs in cancer therapy", Nat Rev Cancer, vol. 12, 2012, pp. 860-875.

Ku, et al., "Selective predisposition to bacterial infections in IRAK-4- deficient children: IRAK-4-dependent TLRs are otherwise redundant in protective immunity", JEM, vol. 204, No. 10, 2007, pp. 2407-2422.

Kwok, et al., "Increased Responsiveness of Peripheral Blood Mononuclear Cells to In Vitro TLR 2, 4 and 7 Ligand Stimulation in Chronic Pain Patients", PLoS One, vol. 7, Issue 8, Aug. 2012, 8 pages.

Lawson, et al., "Abnormal interleukin 1 receptor types I and II gene expression in eutopic and ectopic endometrial tissues of women with endometriosis", Journal of Reproductive Immunology, 77, 2008, pp. 75-84.

Lee, et al., "Expression of Toll-Like Receptor 4 Contributes to Corneal Inflammation in Experimental Dry Eye Disease", Investigative Ophthalmology & Visual Science, vol. 53, No. 9, Aug. 2012, pp. 5632-5640.

Leventhal, et al., "Toll-like receptors in transplantation: sensing and reacting to injury", Kidney International, 81, 2012, pp. 826-832.

Li, et al., "IRAK-4: a novel member of the Irak family with the properties of an IRAK-kinase", PNAS, vol. 99, No. 8, 2002, pp. 5567-5572.

Li, et al., "Toll-like receptors as therapeutic targets for autoimmune connective tissue diseases", Pharmacology & Therapeutics, 138, 2013, pp. 441-451.

Liang, et al., "Myeloid Differentiation Factor 88 Promotes Growth and Metastasis of Human Hepatocelluar Carcinoma", Clinical Cancer Research, 2013, 13 pages.

Lim, et al., "MyD88 Deficiency Ameliorates β-Amyloidosis in an Animal Model of Alzheimer's Disease", The American Journal of Pathology, vol. 179, No. 3, 2011, pp. 1095-1103.

Lin, et al., "Helical assembly in the MyD88-IRAK4-IRAK2 complex in TLR/IL-1R signalling", Nature, vol. 465, 2010, pp. 885-891.

Liu, et al., "New insights into the mechanisms of itch: are pain and itch controlled by distinct mechanisms?", Pflugers Arch—Eur J. Physiol,, 2013, 15 pages.

Liu-Bryan, et al., "Innate Immunity Conferred by Toll-like Receptors 2 and 4 and Myeloid Differentiation Factor 88 Expression is Pivotal to Monosodium Urate Monohydrate Crystal-Induced Inflammation", Arthritis & Rheumatism, vol. 52, No. 9, Sep. 2005, pp. 2936-2946.

Lloyd, "IL-33 family members and asthma—bridging innate and adaptive immune responses", Current Opinion in Immunology, 22, 2010, pp. 800-806.

Maekawa, et al., "Survival and Cardiac Remodeling After Myocardial Infarction are Critically Dependent on the Host Innate Immune Interleukin-1 Receptor-Associated Kinase-4 Signaling: a Regulator of Bone Marrow-Derived Dendritic Cells", Circulation, 120, 2009, pp. 1401-1414.

Margaritopoulos, et al., "Investigation of Toll-like receptors in the pathogenesis of fibrotic and granulomatous disorders: a bronchoalveolar lavage study", Fibrogenesis & Tissue Repair, 3:20, 2010, 9 pages.

Martinez-Gonzalez, et al., "Human Mesenchymal Stem Cells Overexpressing the IL-33 Antagonist Suluble IL-1 Receptor-Like-1 Attenuate Endotoxin-Induced Acute Lung Injury", American Journal of Respiratory Cell and Molecular Biology, vol. 49, Issue 4, 2013, pp. 552-562.

Cameron, et al., "Loss of Interleukin Receptor-Associated Kinase 4 Signaling Suppresses Amyloid Pathology and Alters Microglial Phenotype in a Mouse Model of Alzheimer's Disease", The Journal of Neuroscience, 32(43), 2012, pp. 15112-15123.

Cao, et al., "IRAK: a Kinase Associated with the Interleukin-1 Receptor", Science, vol. 271, Feb. 23, 1996, 5 pages.

Cario, "Toll-like Receptors in Inflammatory Bowel Diseases: a Decade Later", Inflammatory Bowel Diseases, vol. 16, No. 9, Sep. 2010, pp. 1583-1597.

Carty, et al., "Evaluating the role of Toll-like receptors in diseases of the central nervous system", Biochemical Pharmacology, 81, 2011, pp. 825-837.

Cevikbas, et al., "IL-33: a Novel Danger Signal System in Atopic Dermatitis", Journal of Investigative Dermatology, vol. 132, 2012, pp. 1326-1329.

Chang, et al., "Recent advances in Toll-like receptors and anterior uveitis", Clinical & Experimental Ophthalmology, 40, 2012, pp. 821-828.

Chen, et al., "Involvement of TLR7 MyD88-dependent signaling pathway in the pathogenesis of adult-onset Still's disease", Arthritis Research & Therapy, 15:R39, 2013, 12 pages.

Chen, et al., "Serum Amyloid A Regulates Granulomatous Inflammation in Sarcoidosis through Toll-like Receptor-2", American Journal of Respiratory and Critical Care Medicine, vol. 181, 2010, pp. 360-373.

Choi, et al., "MYD88 expression and L265P mutation in diffuse large B-cell lymphoma", Human Pathology, 44, 2013, pp. 1375-1381.

Chopra, et al., "Treatment of Complex Regional Pain syndrome (CRPS) Using Low Dose Naltrexone (LDN)", J Neuroimmune Pharmacol, 8, 2013, pp. 470-476.

Christensen, et al., "Toll-like Receptor 7 and TLR9 Dictate Autoantibody Specificity and Have Opposing Inflammatory and Regulatory Roles in a Murine Model of Lupus", Immunity, 25, Sep. 2006, pp. 417-428.

Christia, et al., "Targeting inflammatory pathways of myocardial infarction", European Journal of Clinical Investigation, vol. 43, 2013, pp. 986-995.

Couillin, et al., "IL-1R1/MyD88 Signaling is Critical for Elastase-Induced Lung Inflammatino and Emphysema", The Journal of Immunology, 183, 2009, pp. 8195-8202.

Dasu, et al., "Toll-like receptors and diabetes: a therapeutic perspective", Clinical Science, 122, 2012, pp. 203-214.

Datta, et al., "Toll IL-1 Receptors Differ in Their Ability to Promote the Stabilization of Adenosine and Uridine-Rich Elements Containing mRNA", The Journal of Immunology, 173, 2004, pp. 2755-2761.

David, et al., "A toll-like receptor 9 antagonist reduces pain hypersensitivity and the inflammatory response in spinal cord injury", Neurobiology of Disease, 54, 2013, pp. 194-205.

Davidson, et al., "IRAK-4 Mutation (Q293X): Rapid Detection and Characterization of Defective Post-Transcritpional TLR/IL-1R Responses in Human Myeloid and Non-Myeloid Cells", The Journal of Immunology, 2006, 11 pages.

Davis, "Signal Transduction by the JNK Group of MAP Kinases", Cell, vol. 103, 2000, pp. 239-252.

Del Rey, et al., "Chronic neuropathic pain-like behavior and brain-bourne IL-1β", Annals of the New York Academy of Sciences, 1262, 2012, pp. 101-107.

Denes, et al., "Central and haematopoietic interleukin-1 both contribute to ischaemic brain injury in mice", Disease Models & Mechanisms, 6, 2013, pp. 1043-1048.

(56) References Cited

OTHER PUBLICATIONS

Denes, et al., "Interleukin-1 and Stroke: Biomarker, Harbinger of Damager, and Therapeutic Target", Cerebrovasc Dis., 32, 2011, pp. 517-527.
Deng, et al., "Toll-Like Receptor 4 Mediates Acute Lung Injury Induced by High Mobility Group Box-1", PLoS One, vol. 8, Issue 5, May 2013, 8 pages.
Dinarello, "A clinical perspective of IL-1β as the gatekeeper of inflammation", European Journal of Immunology, 41, 2011, pp. 1203-1217.
Dinarello, "Immunological and Inflammatory Functions of the Interleukin-1 Family", Annu. Rev. Immunol., 27, 2009, pp. 519-550.
Dispenza, et al., "Systemic Isotretinoin Therapy Normalizes Exaggerated TLR-2-Mediated Innate Immune Responses in Acne Patients", Journal of Investigative Dermatology, vol. 132, 2012, pp. 2198-2205.
Dubaniewicz, et al., "Microbial and human heat shock proteins as 'danger signals'", Human Immunology, 2013, 9 pages.
Entezari, et al., "Inhibition of High-Mobility Group Box 1 Protein (HMGB1) Enhances Bacterial Clearance and Protects against Pseudomonas Aeruginosa Pneumonia in Cystic Fibrosis", Molecular Medicine 18, 2012, pp. 477-485.
European Patent Office, International Search Report (with English translation) for International Patent Application No. PCT/EP2014/077877, dated Feb. 6, 2015, 5 pages.
European Patent Office, Written Opinion (with English translation) for International Patent Application No. PCT/EP2014/077877, dated Jun. 25, 2015, 5 pages.
International Bureau of WIPO, International Preliminary Report on Patentability for International Patent Application No. PCT/EP2014/077877, dated Jun. 21, 2016, 6 pages.
Falck-Hansen, et al., "Toll-Like Receptors in Atherosclerosis", International Journal of Molecular Sciences, 14, 2013, pp. 14008-14023.
Fang, et al., "Toll-like receptor and its roles in myocardial ischemic/reperfusion injury", Med Sci Monit, 17(4), 2011, 10 pages.
Flannery, et al., "The interleukin-1 receptor-associated kinase: critical regulators of innate immune signalling", Biochemical Pharmacology, 80, 2010, pp. 1981-1991.
Freeman, et al., "Lung CD8+ T cells in COPD have increased expression of bacterial TLRs", Respiratory Research, 14(13), 2013, 13 pages.
Fresno, "Toll-like receptors, inflammation, metabolism and obesity", Archives of Physiology and Biochemistry, 117(3), 2011, pp. 151-164.
Gabrilovich, et al., "Disordered Toll-like receptor 2 responses in the pathogenesis of pulmonary sarciodosis", Clinical & Experimental Immunology, 173, 2013, pp. 512-522.
Gambuzza, et al., "Targeting Toll-like receptors: Emerging therapeutics for multiple sclerosis management", Journal of Neuroimmunology, 239, 2011, pp. 1-12.
Gasparini, et al., "NF-kB as a Target for Modulating Inflammatory Responses", Current Pharmaceutical Design, 18, 2012, pp. 5735-5745.
Gilliet, et al., "Psoriasis Triggered by Toll-like Receptor 7 Agonist Imiquimod in the Presence of Dermal Plasmacytoid Dendritic Cell Precursors", Archives of Dermatology, vol. 140, 2004, pp. 1490-1495.
Goh, et al., "Intrinsic danger: activation of Toll-like receptors in rheumatoid arthritis", Rheumatology, 51:7, 2012, 17 pages.
Guerrero, et al., "Toll-like receptor 2/MyD88 signaling mediates zymosan-induced joint hypernociception in mice: Participation of TNF-α, IL-1β and CXCL1/KC", European Journal of Pharmacology, 674, 2012, pp. 51-57.
Guo, et al., "Toll-like receptor 2 siRNA suppresses corneal inflammation and attenuates Aspergillus fumigatus keratitis in rats", Immunology and Cell Biology, 90, 2012, pp. 352-357.
Han, et al., "Interleukin-33 Mediates Formalin-Induced Inflammatory Pain in Mice", Neuroscience, 241, 2013, pp. 59-66.

"Angewandte Contents", Angew. Chem. Int. Ed., 43, 2004, pp. 1036-1043.
Afonso, et al., "Synthesis of 2,4,6-Tri-substituted-1,3,5-Triazines", Molecules, 11, 2006, pp. 86-102.
Bailey, et al., "A Convenient Procedure for the Solution Phase Preparation of 2-Aminothiazole Combinatorial Libraries", Bioorganic and Medicinal Chemistry Letters, vol. 6, No. 12, 1996, pp. 1409-1414.
Banno, et al., "Some applications of the Grignard cross-coupling reaction in the industrial field", Journal of Organometallic Chemistry, 653, 2002, pp. 288-291.
Baranano, et al., "Nickel and Palladium-Catalyzed Cross-Couplings that Form Carbon-Heteroatom and Carbon-Element Bonds", Current Organic Chemistry, 1, 1997, pp. 287-305.
Bonnat, et al., "Effect of the Temperature on the Stoichiometry of Borane Dimethyl Sulfide Reduction of Secondary and Tertiary Amides", Synthetic Communications, 21(15&16), 1991, pp. 1579-1582.
Casimiro-Garcia, et al., "Synthesis and evaluation of novel α-heteroaryl-phenylpropanoic acid derivatives as PPARα/γ dual agonists", Bioorganic & Medicinal Chemistry, 17, 2009, pp. 7113-7125.
Chen, et al., "Structure-Functional Selectivity Relationship Studies of β-Arrestin-Biased Dopamine D2 Receptor Agonists", Journal of Medicinal Chemistry, 55, 2012, pp. 7141-7153.
Cottet, et al., "Trifluoromethyl-Substituted Pyridines Through Displacement of Iodine by in situ Generated (Trifluoromethyl)copper", Eur. J. Org. Chem., 2002, pp. 327-330.
Davies, "Indazole Derivatives: the Synthesis of Various Amino- and Hydroxy-indazoles and Derived Suphonic Acids", J. Chem. Soc., 1955, pp. 2412-2423.
El Kazzouli, et al., "A mild and selective method for the N-Boc deprotection by sodium carbonate", Tetrahedron Letters, 47, 2006, pp. 8575-8577.
El Ouazzani, et al., "General Method for Asymmetric Synthesis of α-Methylsulfinyl Ketones: Application to the Synthesis of Optically Pure Oxisuran and Bioisosteres", J. Org. Chem, 62, 1997, pp. 287-291.
El-Faham, et al., "Amino Acids, Peptides and Proteins in Organic Chemistry", vol. 3—Building Blocks, Catalysis and Coupling Chemistry, Chapter 12—Peptide-Coupling Reagents; Hughes (editor), 2011, pp. 407-442.
Espinet, et al., "The Mechanisms of the Stille Reaciton", Angew. Chem., Int. Ed., 43, 2004, pp. 4704-4734.
Farina, et al., "The Stille Reaction", Organic Reactions, vol. 50, 1997, 384 pages.
Frost, et al., "Indol-3-yl-tetramethylcyclopropyl Ketones: Effects of Indole Ring Substitution on CB2 Cannabinoid Receptor Activity", J. Med. Chem., 51, 2008, pp. 1904-1912.
Gavara, et al., "Synthesis and biological activities of pyrazolo[3,4-g]quinoxaline derivatives", European Journal of Medicinal Chemistry, 45, 2010, pp. 5520-5526.
Gonzalez, "Ground State Complexes between 5-(4-Carboxyphenyl)-10,15,20-Tritolyl Prophyrin and Benzoquinones", J. prakt. Chem., 335, 1993, pp. 515-520.
Grossniklaus, et al., "Animal models of choroidal and retinal neovascularization", Progress in Retinal and Eye Research, 29, 2010, pp. 500-519.
Gul, et al., "Interleukin-1 β-regulating antibody XOMA 052 (gevokizumab) in the treatment of aute exaerbations of resistant uveitis of Behçet's disease: an open-label pilot study", Ann Rheum Dis, 71, 2012, pp. 563-566.
Guram, et al., "Palladium-Catalyzed Aminations of Aryl Halides with Amines", Chemtracts—Inorganic Chemistry, 8, 1996, pp. 1-5.
Hartwig, "Carbon-Heteroatom Bond-Forming Reductive Eliminations of Amines, Ethers, and Sulfides", Acc. Chem. Res., 31, 1998, pp. 852-860.
Hartwig, "Palladium-Catalyzed Animation of Aryl Halides: Mechanism and Rational Catalyst Design", Synlett, 1997, pp. 329-340.
Hartwig, "Transitional Metal Catalyzed Synthesis of Arylamines and Aryl Ethers from Aryl Halides and Triflates: Scope and Mechanism", Angew. Chem. Int. Ed., 37, 1998, pp. 2046-2067.

(56) References Cited

OTHER PUBLICATIONS

Henrion, et al., "Biarylphosphonite Gold (I) Complexes as Superior Catalysts for Oxidative Cyclization of Propynyl Arenes into Indan-2-ones", Angewandte Chemie, 125, 2013, pp. 6397-6402.
Hunt, et al., "Selective Synthesis of 1-Functionalized-alkyl-1H-indazoles", Organic Letters, vol. 11, No. 21, 2009, pp. 5054-5057.
Huo, et al., "Palladium-Catalyzed Alkenyl-Aryl, Aryl-Alkenyl, and Alkenyl-Alkenyl Coupling Reactions", Handbook of Organopalladium Chemistry for Organic Synthesis, 1, 2002, pp. 335-408.
Janeway, et al., "Innate Immune Recognition", Annu. Rev. Immunol., 20, 2002, pp. 197-216.
Kiselyov, et al., "Novel inhibitors of VEGF receptors-1 and -2 based on azole-5-carboxamide templates", Bioorganic & Medicinal Chemistry Letters, 17, 2007, pp. 3550-3557.
Kocienski, "Amino Protecting Groups", 3rd Revised Edition, Thieme, Chapter 8, Feb. 9, 2005, 80 pages.
Kocienski, "Carboxyl Protecting Groups", 3rd Revised Version, Thieme, Chapter 6, Feb. 9, 2005, 30 pages.
Kocienski, "Hydroxyl Protecting Groups", 3rd Revised Edition, Thieme, Chapter 4, Feb. 9, 2005, 90 pages.
Kocovsky, et al., "Transition metal catalysis in organic synthesis: reflections, chirality and new vistas", Pure & Appl. Chem., vol. 71, No. 8, 1999, pp. 1425-1433.
Kosugi, et al., "A Historical Note of the Stille Reaction", Journal of Organometallic Chemistry, 653, 2002, pp. 50-53.
Kunz, et al., "Renaissance of Ullmann and Goldberg Reactions—Progress in Copper Catalyzed C—N-, C—O- and C—S-Coupling", Synlett, No. 15, 2003, pp. 2428-2439.
Kusakabe, et al., "Indazole-Based Potent and Cell-Active Mps1 Kinase Inhibitors: Rational Design from Pan-Kinase Inhibitor Anthrapyrazolone (SP600125)", Journal of Medicinal Chemistry, 56, 2013, pp. 4343-4256.
Lessene, "Advances in the Negishi Coupling", Aust. J. Chem., 57, 2004, p. 107.
Ley, et al., "Modern Synthetic Methods for Copper-Mediated C(aryl)-O, C(aryl)-N, and C(aryl)-S Bond Formation", Angew. Chem. Int. Ed., 42, 2003, pp. 5400-5449.
Luo, et al., "Regioselective Protection at N-2 and Derivatization at C-3 of Indazoles", J. Org. Chem., 71, 2006, pp. 5392-5395.
Mahindroo, et al., "Amide conjugates of ketoprofen and indole as inhibitors of Gli1-mediated transcription in the Hedgehog pathway", Bioorganic & Medicinal Chemistry, 18, 2010, pp. 4801-4811.
Abbate, et al., "Effects of Interleukin-1 Blockade with Anakira on Adverse Cardiac Remodeling and Heart Failure After Acute Myocardial Infarction", The American Journal of Cardiology, 2013, 7 pages.
Abbate, et al., "Interleukin-1 Blockade with Anakinra to Prevent Adverse Cardiac Remodeling After Acute Myocardial Infarction", The American Journal of Cardiology, 2010, pp. 1371-1377.
Akash, et al., "Interleukin-1 Receptor Antagonist: a New Therapy for Type 2 Diabetes Mellitus", Journal of Pharmaceutical Sciences, vol. 101, No. 5, 2012, pp. 1647-1658.
Akashi-Takamura, et al., "TLR accessory molecules," Current Opinion in Immunology, 20, 2008, pp. 420-425.
Akoum, et al., "Imbalance in the expression of the activating type I and the inhibitory type II interleukin 1 receptors in endometriosis", Human Reproduction, vol. 22, No. 5, 2007, pp. 1464-1473.
Allhorn, "TLR3 and TLR4 expression in healthy and diseased human endometrium", Reproductive Biology and Endocrinology, 6:40, 2008, 11 pages.
Bauer, et al., "High Mobility Group Box 1 Contributes to the Pathogenesis of Experimental Pulmonary Hypertension via Activation of Toll-like Receptor 4", Molecular Medicine, 18, 2012, pp. 1509-1518.
Béraud, et al., "Misfolded α-synuclein and toll-like receptors: therapeutic targets for Parkinson's disease", Parkinsonism & Related Disorders, 18S1, 2012, pp. S17-S20.
Bijani, "Toll-like Receptor Signaling Pathways in Cardiovascular Diseases: Challenges and Opportunities", International Reviews of Immunology, 31, 2012, pp. 379-395.
Bomfim, et al., "Toll-like receptor 4 contributes to blood pressure regulation and vascular contraction in spontaneously hypertensive rats", Clinical Science, 122, 2012, pp. 535-543.
Brough, et al., "Regulation of interleukin-1 in acute brain injury", Trends in Pharmacological Sciences, vol. 32, No. 10, 2011, pp. 617-622.
Buckley, et al., "IRAK-4 inhibitors. Part 1: a series of amides", Biooranic & Medicinal Chemistry Letters, 18, 2008, pp. 3211-3214.
Buckley, et al., "IRAK-4 inhibitors. Part II: a structure-based assessment of imidazo[1,2-a]pyridine binding", Bioorg. Med. Chem. Lett. 18, 2008, pp. 3291-3295.
Bunting, et al., "Interleukin-33 Drives Activation of Alveolar Macrophages and Airway Inflammation in a Mouse Model of Acute Exacerbation of Chronic Asthma", BioMed Research International, vol. 2013, 2013, 11 pages.
Byers, et al., "Long-term IL-33-producing epithelial progenitor cells in chronic obstructive lung disease", The Journal of Clinical Investigation, vol. 123, No. 9, Sep. 2013, pp. 3967-3982.
English Translation of an Invitation to Respond to Written Opinion dated Aug. 17, 2017, in a corresponding Singapore Patent Application No. 11201604685R (10 pages).
Thomas, et al., "Impaired Cytokine Signaling in Mice Lacking the IL-1 Receptor-Associated Kinase", The Journal of Immunology, 1999, 8 pages.
Thompson, et al., "Potential role of Toll-like receptors in programming of vascular dysfunction", Clinical Science, 125, 2013, pp. 19-25.
Timmers, et al., "Toll-Like Receptor 4 Mediates Maladaptive Left Ventricular Remodeling and Impairs Cardiac Function After Myocardial Infarction", Circulation Research, 102, 2008, pp. 257-264.
Treon, et al., "MYD88 L265P Somatic Mutation in Waldenstrom's Macroglobulinemia", New England Journal of Medicine, 367(9), 2012, pp. 826-833.
Tual-Chalot, et al., "Whole Mount Immunofluorescent Staining of the Neonatal Mouse Retina to Investigate Angiogenesis In vivo", Journal of Visualized Experiments, 77, 2013, 5 pages.
Valaperti, et al., "Innate Immune Interleukin-1 Receptor-Associated Kinase 4 Exacerbates Viral Myocarditis by Reducing CCR5+CD11b+ Monocyte Migration and Impairing Interferon Production", Circulation, 128, 2013, pp. 1542-1554.
Viguier, et al., "Comments and Responses", Annals of Internal Medicine, 2010, 9 pages.
Vijmasi, et al., "Topical administration of interleukin-1 receptor antagonist as a therapy for aqueous-deficient dry eye in autoimmune disease", Molecular Vision, 19, 2013, pp. 1957-1965.
Volin, "Interleukin-18: a Mediator of Inflammation and Angiogensis in Rheumatoid Arthritis", Journal of Interferon & Cytokine Research, vol. 31, No. 10, 2011, 9 pages.
Walsh, et al., "Pattern Recognition Receptors—Molecular Orchestrators of Inflammation in Inflammatory Bowel Disease," Cytokine & Growth Factor Reviews (24), 2013, pp. 91-104.
Wan, "The kinase TAK1 integrates antigen and cytokine receptor signaling for T cell development, survival and function", Nature Immunology, vol. 7, No. 8, Aug. 2006, pp. 851-858.
Wang, et al., "TAK1 is a ubiquitin-dependent kinase of MKK and IKK", Nature, vol. 412, 2001, pp. 346-351.
Wang, et al., "Toll-Like Receptor 4 Antagonist Attenuates Intracerebral Hemorrhage-Induced Brain Injury", Stroke, Sep. 2013, 11 pages.
Wesche, et al., "IRAK-M is a novel member of the Pelle/Interleukin-1 Receptor-associated Kinase (IRAK) Family", Journal of Biological Chemistry, 274, 1999, pp. 19403-19410.
Wollina, et al., "Acne inverse (Hidradenitis supperativa): a review with a focus on pathogenesis and treatment", Indian Dermatology Online Journal, vol. 4, Issue 1, 2013, pp. 2-11.
Xia, et al., "Direct activation of protein kinases by unanchored polyubiquitin chai", Nature, vol. 461(3), 2009, pp. 114-120.
Xiang, et al., "Association of Toll-Like Receptor Signaling and Reactive Oxygen Species: a Potential Therapeutic Target fr Post-trauma Acute Lung Injury", Mediators of Inflammation, vol. 2010, 2010, 8 pages.
Yamada, et al., "Targeting IL-1 in Sjogren's syndrome", Opinion on Therapeutic Targets, 2013, pp. 393-401.

(56) References Cited

OTHER PUBLICATIONS

Yang, et al., "Targeting TLR2 Attenuates Pulmonary Inflammation and Fibrosis by Reversion of Suppressive Immune Microenvironment", The Journal of Immunology, 182, 2009, pp. 692-702.
Yap, et al., "The role of cytokines in the pathogenesis of systemic lupus erythematosus—from bench to bedside", Nephrology, 18, 2013, pp. 243-255.
Yin, et al., "Adenovirus-mediated delivery of soluble ST2 attenuates ovalbumin-induced allergic asthma in mice", Clinical & Experimental Immunology, 170, 2012, 9 pages.
Zhao, et al., "Spinal Interleukin-33 and its Receptor ST2 Contribute to Bone Cancer-Induced Pain in Mice", Neuroscience 253, 2013, pp. 172-182.
Zhu, et al., "A novel antagonist of Toll-like receptors 7, 8 and 9 suppresses lupus disease-associated parameters in NZBW/F1 mice", Autoimmunity, 46(7), 2013, pp. 419-428.

INDAZOLECARBOXAMIDES, PROCESSES FOR THEIR PREPARATION, PHARMACEUTICAL PREPARATIONS COMPRISING THEM AND THEIR USE FOR PRODUCING MEDICAMENTS

CROSS-REFERENCE TO RELATED APPLICATIONS

This application is a U.S. national phase application of International Patent Application No. PCT/EP2014/077877, filed Dec. 16, 2014 and titled NOVEL CARBOXAMIDES, METHOD FOR THE PRODUCTION THEREOF, PHARMACEUTICAL PREPARATIONS COMPRISING THEM, AND USE THEREOF FOR PRODUCING MEDICAMENTS, which claims priority to both European Patent Application No. 13198463.5, filed Dec. 19, 2013 and titled NOVEL CARBOXAMIDES, METHOD FOR THE PRODUCTION THEREOF, PHARMACEUTICAL PREPARATIONS COMPRISING THEM, AND USE THEREOF FOR PRODUCING MEDICAMENTS, and European Patent Application No. 14189216.6, filed Oct. 16, 2014 and titled NOVEL CARBOXAMIDES, METHOD FOR THE PRODUCTION THEREOF, PHARMACEUTICAL PREPARATIONS COMPRISING THEM, AND USE THEREOF FOR PRODUCING MEDICAMENTS, the contents of all of which are incorporated herein by reference in their entirety.

The present application relates to novel indazolecarboxamides, to processes for their preparation, to their use for the treatment and/or prophylaxis of diseases and to their use for producing medicaments for the treatment and/or prophylaxis of diseases, in particular proliferative disorders, autoimmune and inflammatory disorders such as, for example, rheumatoid arthritis, chronic obstructive pulmonary disease (abbreviation: COPD), multiple sclerosis, endometriosis and inflammation-induced or chronic pain and lymphomas.

IRAK4 plays a key role in the activation of the immune system, in particular in innate immunity. Innate immunity is based on the fact that microorganisms such as bacteria and viruses have certain inherent features which are recognized by the immune system, resulting in its activation. What is recognized are certain pathogen-associated molecular patterns (PAMPs). PAMPs are recognized by the pattern recognition receptors (PRR) which include toll-like receptors (TLR) (Janeway and Medzhitov, Annu. Rev. Immunol., 2002). In humans, ten different TLRs have been described. TLR1 and TLR6 are coreceptors for TLR2. TLR2 recognize inter alia lipoproteins and lipopeptides. TLR3 recognizes double-stranded RNA. TLR4 recognizes inter alia LPS (lipopolysaccharides) of gram-negative bacteria and lipoteichoic acid of gram-positive bacteria. TLR5 recognizes flagellin CpG motives in bacterial DNA are recognized by TLR9 (Miggin, O'Neill, J. Leukoc. Biol., 2006). Additional molecules may further modify the recognition abilities of TLRs (Akashi-Takamura and Miyake, Current Opinion in Immunology, 2008). In addition to the recognition of PAMPs, TLRs are also able to recognize DAMPs (damage-associated molecular pattern). These are endogenous cell-derived molecules formed as the result of a trauma, an ischaemia or other tissue-destroying processes in the absence of any obvious infection. DAMPs can be constituents both of the cytoplasm and the nucleus. They are secreted, for example HMGB1 (high-mobility group box 1 protein), which is recognized by TLR2 and TLR4. Other DAMPs are released de novo or accumulate, for example, in the outer plasma membrane, e.g. HSP90 (heat shock protein 90), where they are recognized by TLR2 and TLR4. Others for their part are produced as final degradation products during cell death (Krysko, Garg, et al., Nat Rev Cancer, 2012).

In addition to TLRs, other components such as cytokines also play an important role in innate immunity. Here, mention may be made in particular of the interleukin (IL)-1 family including interleukins IL-1, IL-18 and IL-33. They are produced and released by various immune cells in the presence of infections or cell or tissue stress. The immune response is then triggered by binding to the respective receptor (Dinarello, Annu. Rev. Immunol., 2009).

TLRs (except for TLR3) as well as the receptors of the IL-1 family (IL-1R (receptor), IL-18R and IL-33R) have the same signal cascade which is activated by binding of the respective ligand to its receptor. The ligand receptor binding leads to the recruitment of the adaptor molecule MyD88 [myeloid differentiation primary response gene (88)] to the receptor via TIR/TIR domain interaction which is a constituent both of the receptors and of MyD88. In addition to the TIR domain, MyD88 has an N-terminal "death domain" (DD) which interacts with the DD domain of the interleukin-1 receptor associated kinase-4 (IRAK4). IRAK4 belongs to a serine/threonine kinase family which also includes the structurally similar kinases IRAK1, IRAK2 and IRAK-M (Cao et al., Science, 1996; Muzio et al., Science, 1997; Wesche, Gao, et al., Journal of Biological Chemistry, 1999; Li, Strelow, et al., PNAS, 2002). Except for IRAK-M, which is only expressed in monocytes and macrophages, the expression of IRAK4, IRAK1 and IRAK2 is ubiquitous (Flannery and Bowie, Biochemical Pharmacology, 2010). As a result of the activation process, several MyD88 and IRAK4 molecules form a multicomplex which is referred to as "myddosome" (Precious et al., J. Biol. Chem., 2009). This myddosome now interacts with IRAK1 or IRAK2 via DD-DD interactions, forming a larger complex in the process (Lin, Lo, et al., Nature, 2010). The formation of this complex then triggers autophosphorylation of IRAK4, which subsequently results in the phosphorylation of IRAK1 or IRAK2. As a consequence of the activation of IRAK1 or IRAK2, these kinases are autophosphorylated (Kollewe, Mackensen, et al., Journal of Biological Chemistry, 2004). The activated IRAK1 or IRAK2 interacts with TRAF6 (tumor-necrosis factor-receptor-associated factor 6) which, with the ubiquitin enzyme complex (E2), acts as ubiquitin protein ligase, which leads to K62-associated ubiquitination of TRAF6. In turn, this process leads to further complex formation with other proteins. This complex induces the activation of TAK1 (Xia, Sun, et al., Nature, 2009). Activated TAK1 mediates the activation of the NF (nuclear factor)-kB signal pathway and the MAPK (mitogen-activated protein kinase) signal pathway (Wang, Deng, et al., Nature, 2001). In the first signal pathway, TAK1 leads to the activation of the IKK complex whereby the inhibiting IkB protein is phosphorylated and degraded by the proteasome. NF-kB, which had been blocked by IkB beforehand, now migrates from the cytoplasm into the nucleus where it binds to a specific DNA motive, the kB motive, leading to the transcription of various genes (Gasparini and Feldmann, Curr Pharm Des, 2012).

In the MAPK signal pathway, TAK1 phosphorylates various members of the MAPK family such as MKK3, -4, -6 and -7 (Wang, Deng, et al., Nature, 2001). The activation of these kinases results in the activation of p38 and JNK (c-Jun N-terminal kinase) (Ono and Han, Cellular Signalling, 2000; Davis, Cell, 2000). The activation both of the NF-kB signal pathway and of the MAPK signal pathway leads to various processes associated with different immune processes. Thus, this is an increased expression of various inflammatory signal molecules and enzymes such as, for example, cytokines, chemokines and COX-2, and an increased mRNA stability of certain genes (Holtmann, Enninga, et al., Journal of Biological Chemistry, 2001; Datta, Novotny, et al., The Journal of Immunology, 2004). Furthermore, these processes may be associated with the proliferation and differentiation of certain cell types (Wan, Chi, et al., Nat Immunol, 2006; McGettrick and J. O'Neill, British Journal of Haematology, 2007).

The central importance of IRAK4 in immunological processes mediated by the TLR (except for TLR3) and IL-1 receptor family is shown by the deletion of IRAK4. Cells isolated from patients where absence of IRAK4 had been demonstrated show no activity after stimulation of various TLRs (except for TLR3) and the IL-1β family (Davidson, Currie, et al., The Journal of Immunology, 2006; Ku, von Bernuth, et al., JEM, 2007). Furthermore, mice with IRAK4 deletion develop no response to IL-1β stimulation and various TLR stimulations except for TLR3 (Suzuki, Suzuki, et al., Nature, 2002). Here, in particular the kinase activity of IRAK4 plays a crucial role (Kim, Staschke, et al., JEM, 2007). In contrast, deletion of IRAK1 or IRAK2 only results in a signal pathway activity loss after stimulation (Thomas, Allen, et al., The Journal of Immunology, 1999; Swantek, Tsen, et al., The Journal of Immunology, 2000; Kawagoe, Sato, et al., Nat Immunol, 2008). For their part, mice having deletion of IRAK2 and IRAK1 show a phenotype comparable to that of animlas with IRAK4 deletion (Kawagoe, Sato, et al., Nat Immunol, 2008). The central role of IRAK4 in the pathology of various inflammatory disorders associated with the signal pathway described had already been shown by direct comparison of wild-type (WT) mice with genetically modified animals having a kinase-inactivated form of IRAK4 (IRAK4 KDKI). IRAK4 KDKI animals have an improved clinical picture in the animal model of multiple sclerosis, atherosclerosis, myocardial infarction and Alzheimer's disease (Rekhter, Staschke, et al., Biochemical and Biophysical Research Communication, 2008; Maekawa, Mizue, et al., Circulation, 2009; Staschke, Dong, et al., The Journal of Immunology, 2009; Kim, Febbraio, et al., The Journal of Immunology, 2011; Cameron, Tse, et al., The Journal of Neuroscience, 2012). Furthermore, it was found that deletion of IRAK4 in the animal model protects against virus-induced myocarditis by virtue of an improved anti-viral reaction with simultaneously reduced systemic inflammation (Valaperti, Nishii, et al., Circulation, 2013).

Owing to the central role of IRAK4 in the MyD88-mediated signal cascade of TLRs (except for TLR3) and the IL-1 receptor family, the inhibition of IRAK4 can be utilized for the prophylaxis and/or treatment of disorders mediated by the receptors mentioned. TLR-dependent processes are associated with a large number of different disorders. Thus, it has been found that TLRs are involved in the pathogenesis of multiple sclerosis, rheumatoid arthritis, metabolic syndrome, diabetes, osteoarthritis, Sjögren syndrome and sepsis (Scanzello, Plaas, et al. Curr Opin Rheumatol, 2008; Roger, Froidevaux, et al, PNAS, 2009; Gambuzza, Licata, et al., Journal of Neuroimmunology, 2011; Fresno, Archives Of Physiology And Biochemistry, 2011; Goh and Midwood, Rheumatology, 2012; Dasu, Ramirez, et al., Clinical Science, 2012; Ramirez and Dasu, Curr Diabetes Rev, 2012; Li, Wang, et al., Pharmacology & Therapeutics, 2013). Skin disorders such as psoriasis, atopic dermatitis, acne inversa and acne vulgaris are associated with the IRAK4-mediated TLR signal pathway.

The disorders mentioned are characterized by an increased expression of certain TLRs, and their pathological immune reactions are mediated by certain TLR-associated inflammation processes (Gilliet, Conrad, et al., Archives of Dermatology, 2004; Niebuhr, Langnickel, et al., Allergy, 2008; Miller, Adv Dermatol, 2008; Terhorst, Kalali, et al., Am J Clin Dermatol, 2010; Dispenza, Wolpert, et al., J Invest Dermatol, 2012; Selway, Kurczab, et al., BMC Dermatology, 2013; Wollina, Koch, et al. Indian Dermatol Online, 2013).

Pulmonary disorders such as pulmonary fibrosis, obstructive pulmonary disease (COPD), acute respiratory distress syndrome (ARDS), acute lung injury (ALI), interstitial lung disease (ILD), sarcoidosis and pulmonary hypertension show an association with various TLR-mediated signal pathways. The pathogenesis of the pulmonary disorders may be either infectiously mediated or non-infectiously mediated processes (Ramirez Cruz, Maldonado Bernal, et al., Rev Alerg Mex, 2004; Jeyaseelan, Chu, et al., Infection and Immunity, 2005; Seki, Tasaka, et al., Inflammation Research, 2010; Xiang, Fan, et al., Mediators of Inflammation, 2010; Margaritopoulos, Antoniou, et al., Fibrogenesis & Tissue Repair, 2010; Hilberath, Carlo, et al., The FASEB Journal, 2011; Nadigel, Prefontaine, et al., Respiratory Research, 2011; Kovach and Standiford, International Immunopharmacology, 2011; Bauer, Shapiro, et al., Mol Med, 2012; Deng, Yang, et al., PLoS One, 2013; Freeman, Martinez, et al., Respiratory Research, 2013; Dubaniewicz, A., Human Immunology, 2013). For instance, HMGB1 (high-mobility group box 1 protein)—an endogenous ligand of TLR2 and TLR4—is elevated in patients with pulmonary fibrosis. Blocking of these TLR signal pathways leads to reduced inflammation in the animal model (Yang, Cui, et al., The Journal of Immunology, 2009; Entezari, Weiss, et al., Mol Med, 2012). The involvement of TLR2-mediated processes in the pathogenesis of sarcoidosis has recently been demonstated in in vitro and in vivo studies (Chen, Song, et al., American Journal of Respiratory and Critical Care Medicine, 2010; Gabrilovich, Walrath, et al., Clinical & Experimental Immunology, 2013).

TLRs are also involved in the pathogenesis of other inflammatory disorders such as Behcet's disease, gout and graft rejection, therefore, here the inhibition of IRAK4 is a suitable therapeutic approach (Liu-Bryan, Scott, et al., Arthritis & Rheumatism, 2005; Shi, Mucsi, et al., Immunological Reviews, 2010; Leventhal and Schroppel, Kidney Int, 2012; Kreisel and Goldstein, Transplant International, 2013; Li, Wang, et al., Pharmacology & Therapeutics, 2013). Lesions and peritoneal macrophages of endometriosis patients also have, compared to healthy volunteers, an enhanced immune response following LPS (lipopolysaccharide) stimulation (Allhorn, Boing, et al., Reproductive Biology and Endocrinology, 2008; Khan, Kitajima, et al., Journal of Obstetrics and Gynaecology Research, 2013).

Patients having lupus erythematosus and adult onset Still disease have an elevated expression of TLR7, MyD88 and IRAK4 (Chen, Lin, et al., Arthritis Res Ther, 2013). In the disease model of lupus, inhibition of TLR7, 8 and 9 and the use of animals having a deletion of TLR7 and/or TLR9 result in an improved pathogenesis (Christensen, Shupe, et al, Immunity, 2006; Nickerson, Christensen, et al., The Journal of Immunology, 2010; Zhu, Jiang, et al., Autoimmunity, 2013). Patients suffering from chronic inflammatory bowel diseases such as ulcerative colitis or Crohn's disease do not only have polymorphisms in various TLR genes. In various animals models, it was shown that certain TLRs are also involved in the pathogenesis of these bowel disorders (Rakoff-Nahoum, Hao, et al., Immunity, 2006; Heimesaat, Fischer, et al., PLoS ONE, 2007; Cario, Inflammatory Bowel Diseases, 2010; Walsh, Carthy, et al., Cytokine & Growth Factor Reviews, 2013).

In addition to the disorders already mentioned, IRAK4-mediated TLR processes have been described in the pathogenesis of eye disorders such as keratitis, allergic conjunctivitis, keratoconjunctivitis sicca, macular degeneration and uveitis (Kaarniranta and Salminen, J Mol Med (Berl), 2009; Sun and Pearlman, Investigative Ophthalmology & Visual Science, 2009; Redfern and McDermott, Experimental Eye Research, 2010; Kezic, Taylor, et al., J Leukoc Biol, 2011; Chang, McCluskey, et al., Clinical & Experimental Ophthalmology, 2012; Guo, Gao, et al., Immunol Cell Biol, 2012; Lee, Hattori, et al., Investigative Ophthalmology & Visual Science, 2012).

The role of TLRs in arteriosclerosis has been supported not only by the analysis of human samples but also with the aid of various animal models (Seneviratne, Sivagurunathan, et al., Clinica Chimica Acta, 2012; Falck-Hansen, Kassiteridi, et al., International Journal of Molecular Sciences, 2013).

By virtue of the central role of IRAK4 in TLR-mediated processes, the inhibition of IRAK4 allows the treatment and/or prevention of cardiovascular and neurological disorders such as, for example, myocardial reperfusion damage, myocardial infarction, hypertension (Oyama, Blais, et al., Circulation, 2004; Timmers, Sluijter, et al., Circulation Research, 2008; Fang and Hu, Med Sci Monit, 2011; Bijani, International Reviews of Immunology, 2012; Bomfim, Dos Santos, et al., Clin Sci (Lond), 2012; Christia and Frangogiannis, European Journal of Clinical Investigation, 2013; Thompson and Webb, Clin Sci (Lond), 2013) and also Alzheimer's disease, stroke and Parkinson's disease (Carty and Bowie, Biochemical Pharmacology, 2011; Lim, Kou, et al., The American Journal of Pathology, 2011; Braud and Maguire-Zeiss, Parkinsonism & Related Disorders, 2012; Noelker, Morel, et al., Sci. Rep., 2013; Wang, Wang, et al., Stroke, 2013).

Neurones as well as microglia and astrocytes express a large part of the known TLRs.

In the animal model, deletion of TLR7 protects against various triggers of pruritus (Nicotra, Loram, et al., Experimental Neurology, 2012; Liu and Ji, Pflugers Arch., 2013). In addition to the role of TLRs in pruritus, it was possible to demonstrate involvement in pain processes using various animal models (Kim, Lee, et al., Toll-like Receptors: Roles in Infection and Neuropathology, 2009; Guerrero, Cunha, et al., European Journal of Pharmacology, 2012; Nicotra, Loram, et al., Experimental Neurology, 2012; David, Ratnayake, et al., Neurobiology of Disease, 2013). Studies with pain patients support these findings (Kwok, Hutchinson, et al., PLoS ONE, 2012; Chopra and Cooper, J Neuroimmune Pharmacol, 2013).

Since the TLR signals are mediated via IRAK4, it has to be assumed that there is a therapeutic effect by inhibition of IRAK4 in the indications mentioned.

This also applies to some oncological disorders. Certain lymphomas have an activating MyD88 mutation which can be treated using an IRAK4 inhibitor (Ngo, Young, et al., Nature, 2011; Treon, Xu, et al., New England Journal of Medicine, 2012; Choi, Kim, et al., Human Pathology, 2013). Chronic lymphatic leukaemia, melanomas and liver cell carcinomas are likewise associated with mutations in MyD88 or changes in MyD88 activity (Puente, Pinyol, et al., Nature, 2011; Srivastava, Geng, et al., Cancer Research, 2012; Liang, Chen, et al., Clinical Cancer Research, 2013).

Furthermore, MyD88 plays an important role in ras-dependent tumours, so IRAK4 inhibitors are also suitable for treating these (Kfoury, A., K. L. Corf, et al., Journal of the National Cancer Institute, 2013).

In addition to the mediation of MyD88- and TLR- (except for TLR3)-associated processes, IRAK4 also mediates the signals of the IL-1 receptor family. Inflammatory disorders such as CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome; FMF (familial mediterranean fever), HIDS (hyper-IgD syndrome), TRAPS (tumour necrosis factor receptor 1-associated periodic syndrom), juvenile idiopathic arthritis, adult-onset Still's disease, Adamantiades-Behcet's disease, rheumatoid arthritis, osteoarthritis, keratoconjunctivitis sicca and Sjögren syndrome are treated by blocking the IL-1 signal pathway; therefore here, too, an IRAK4 inhibitor is suitable for treatment of the diseases mentioned (Narayanan, Corrales, et al., Cornea, 2008; Henderson and Goldbach-Mansky, Clinical Immunology, 2010; Dinarello, European Journal of Immunology, 2011; Gul, Tugal-Tutkun, et al., Ann Rheum Dis, 2012; Pettersson, Annals of MedicinePetterson, 2012; Ruperto, Brunner, et al., New England Journal of Medicine, 2012; Nordstrom, Knight, et al., The Journal of Rheumatology, 2012; Vijmasi, Chen, et al., Mol Vis, 2013; Yamada, Arakaki, et al., Opinion on Therapeutic Targets, 2013). IL-18 in particular is associated with the pathogenesis of rheumatoid arthritis, adult-onset Still's disease, type-1 diabetes, multiple sclerosis and lupus erythematosus, thus, by virtue of the mechanism of action, IRAK4 inhibitors can be employed for the treatment and/or prevention of the disorders mentioned (Volin and Koch, J Interferon Cytokine Res, 2011; Sedimbi, Hagglof, et al., Cell Mol Life Sci, 2013; Yap and Lai, Nephrology, 2013). Furthermore, IRAK4 inhibitors are suitable for the treatment of type-2 diabetes and the sequelae of a myocardial infarction as there are indications that the inhibition of the IL-1 signal pathway is a promising therapeutic approach (Abbate, Kontos, et al., The American Journal of Cardiology, 2010; Akash, Shen, et al., Journal of Pharmaceutical Sciences, 2012; Abbate, Van Tassell, et al., The American Journal of Cardiology, 2013). Several components of the IL-1 receptor family are associated with various pulmonary disorders such as asthma, COPD, idiopathic interstitial pneumonia and acute respiratory distress syndrome (ARDS) and the role in its pathogenesis was supported in various animal models (Kang, Homer, et al., The Journal of Immunology, 2007; Imaoka, Hoshino, et al., European Respiratory Journal, 2008; Couillin, Vasseur, et al., The Journal of Immunology, 2009; Lloyd, Current Opinion in Immunology, 2010; Pauwels, Bracke, et al., European Respiratory Journal, 2011; Yin, Li, et al., Clinical & Experimental Immunology, 2012; Alexander-Brett, et al., The Journal of Clinical Investigation, 2013; Bunting, Shadie, et al., BioMed Research International, 2013; Byers, Alexander-Brett, et al., The Journal of Clinical Investigation, 2013; Kawayama, Okamoto, et al., J Interferon Cytokine Res, 2013; Martinez-Gonzalez, Roca, et al., American Journal of Respiratory Cell and Molecular Biology, 2013; Qiu, Li, et al., Immunology, 2013).

Furthermore, various studies have shown that there is a relation between the amount of IL-1β and its receptor, IL-18 and IL-33, and the disorder endometriosis (Akoum, Lawson, et al., Human Reproduction, 2007; Lawson, Bourcier, et al., Journal of Reproductive Immunology, 2008; Sikora, Mielczarek-Palacz, et al., American Journal of Reproductive Immunology; Santulli, Borghese, et al., Human Reproduction, 2013). Moreover, in the animal model the growth of human endometrial tissue could be blocked by administration of the endogenous IL-1β inhibitor IL-1R2 (Khoufache, Bondza, et al., The American Journal of Pathology, 2012). By way of its mechanism of action, an IRAK4 inhibitor is also effective in this case. Chronic inflammatory bowel diseases such as Crohn's disease and ulcerative colitis are associated with the dysregulation of the IL-1 receptor family (Kobori, Yagi, et al., J Gastroenterol, 2010; Hao, Liu, et al., Curr Opin Gastroenterol, 2013). In addition to the indications mentioned, IRAK4 inhibitors are also suitable for the treatment and/or prevention of neurological disorders mediated by the IL-1 receptor family, such as stroke apoplexy, Alzheimer's disease, stroke, skull-brain trauma and pain such as cancer pain, postoperative pain, inflammation-induced pain and chronic pain (Wolf, Livshits, et al., Brain, Behavior, and Immunity, 2008; Brough, Tyrrell, et al., Trends in Pharmacological, 2011; SciencesDenes, Kitazawa, Cheng, et al., The Journal of Immunology, 2011; Pinteaux, et al., Cerebrovascular Diseases, 2011; del Rey, Apkarian, et al., Annals of the New York Academy of Sciences, 2012; Denes, Wilkinson, et al., Disease Models & Mechanisms, 2013; Han, Zhao, et al., Neuroscience, 2013; Zhao, Zhang, et al., Neuroscience, 2013). Owing to the propagation of processes mediated by the IL1 receptor family by IRAK4, IRAK4 inhibitors are active in dermatological disorders such as psoriasis, atopic dermatitis and allergic contact dermatitis. The IL1 receptor family is involved in the pathogenesis of the disorders mentioned (Viguier, Guigue, et al., Annals of Internal Medicine, 2010; Cevikbas, Steinhoff, J Invest Dermatol, 2012; Minkis, Aksentijevich, et al., Archives of Dermatology, 2012; Mattii, Ayala, et al., Experimental Dermatology, 2013; Sedimbi, Hagglof, et al., Cell Mol Life Sci, 2013).

Association of IRAK4 with numerous different disorders by mediation of various signals via TLRs (except for TLR3) and the IL1 receptor family shows that by inhibition of IRAK4 it is possible to influence a large number of disorders in a positive manner.

The compounds described in the present invention are capable of inhibiting IRAK4. This is also supported by the fact that the compounds according to the invention have inhibiting activity in TLR- and IL1-mediated processes.

Accordingly, it was an object of the present invention to provide novel compounds which, in the manner described above, act as inhibitors of interleukin-1 receptor associated kinase-4 (IRAK4). The novel IRAK4 inhibitors are suitable in particular for the treatment and for the prevention of proliferative and inflammatory disorders characterized by an overreacting immune system. Particular mention may be made here of inflammatory skin disorders, cardiovascular disorders, pulmonary disorders, eye disorders, autoimmune disorders and neoplastic disorders.

Numerous IRAK4 inhibitors are known from the prior art. IRAK4 inhibitors are described, for example, in G. C. Harriman et al. in US20130231328 and in L. D. Romero et al. US20120283238. IRAK4 modulators based on a pyrazole[1,5a]pyrimidine skeleton are described by N. Arora et al. in US20120015962.

Moreover, V. R. Paidi et al. in WO2013106641 report thiazolyl- or thiadiazolyl-substituted pyridine derivatives and S. D. Dodd et al. in WO2013106614 report triazolyl-substituted pyridine derivatives. Further pyridine derivatives are disclosed in WO2013106612.

Aminopyrimidones acting as IRAK4 inhibitors are described by W. M. Seganish et al. in WO2013066729; in addition, W. T. Mcelroy et al in WO 2012129258 also describe amidopyrazoles as IRAK inhibitors.

G. Buckeley et al. report, both in Bioorg. Med. Chem. Lett. 18 (2008), 3291-3295 and in Bioorg. Med. Chem. Lett. 18 (2008), 3656-3660, imidazole[1,2-a]pyridines. Furthermore, A. D. Frenkel et al. in US20070037803 report benzimidazole derivatives as IRAK4 inhibitors.

Further IRAK inhibitors having 2-aminoimidazole or 2-aminobenzimididazole structure are claimed by A. D. Frenkel et al. in US2007/0037803.

IRAK4 inhibitors which, like the compounds according to the invention, are based on an indazole structure are described by K. Guckian et al. in U.S. Pat. No. 8,293,923. These indazole derivatives are substituted by a benzimidazol-2-ylamino group at position 3 of the indazole. U.S. Pat. No. 8,293,923 does not disclose any 2-substituted indazoles.

Further IRAK4 inhibitors based on an indazole structure are reported by C. Jorand-Lebrun et al. in US20130274241. These are indazole derivatives having a triazole-containing substituent at position 3 of the indazole. US20130274241 does not describe any 2-substitution of the indazoles disclosed.

WO2011043371 describes oxazolecarboxamides linked to monocyclic aromatic heterocycles as IRAK4 inhibitors. Oxazolecarboxamides linked to an indazole structure as in the compounds according to the invention are not described in WO2011043371.

Bicyclic heterocycles having a carboxamide structure as IRAK4 inhibitors, for example substance L1, are described by B. Anima et al. in WO2013042137. However, only benzimidazole, benzoxazole and benzothiazole derivatives are described, and no indazole derivatives.

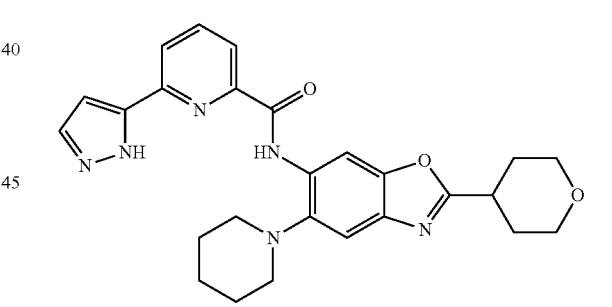

L1

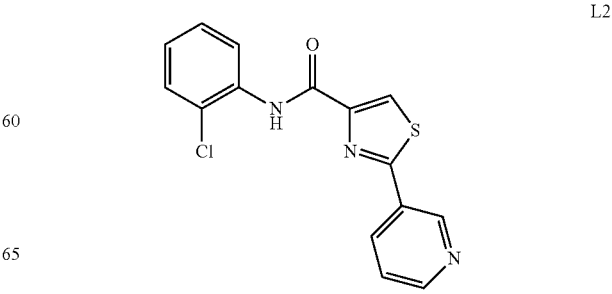

G. M. Buckley et al. report, in Bioorg. Med. Chem. Lett. 18 (2008). 3211-3214.

L2

-continued

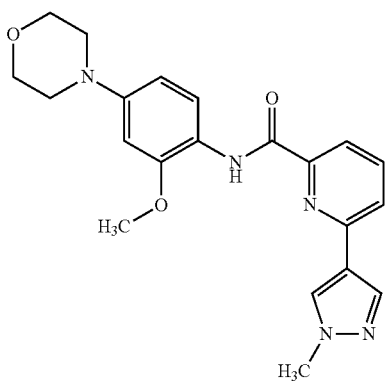

L3 carboxamide derivatives as IRAK4 inhibitors. Described are, for example, the molecules L2 and L3. Indazole derivatives are not described.

In WO2009019167, A. Bombrun et al. describe 6-aminopyrimidine-4-carboxamides having a 2-substituted indazole structure such as, for example, L4. It is reported that the substances described bind to the sphingosine-1-phosphate receptor. An inhibiting action on IRAK4 kinase is not described in WO2009019167.

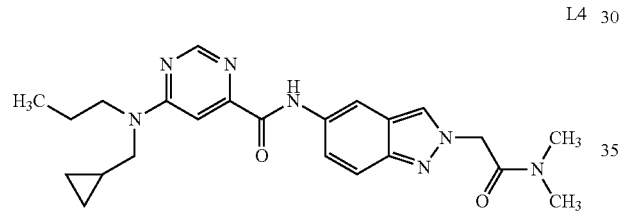

L4

US20080058341 describes azaindazoles having a carboxamide structure as CCR1 antagonists. 2-substituted indazole derivatives having an additional carboxamide structure are not disclosed. A. J. Souers et al. describe, in US20050137187, 2-substituted indazoles as antagonists of MCH (melanin-concentrating hormone). However, the 2-substituent at the indazole does not comprise a carboxamide structure.

The present invention provides compounds of the general formula (I)

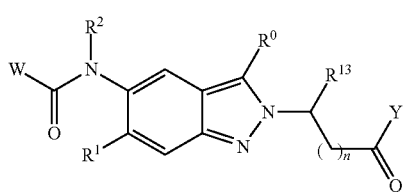

(I)

in which:
$R^0$ represents hydrogen or $C_1$-$C_4$-alkyl, where the $C_1$-$C_4$-alkyl radical may optionally be mono- or polysubstituted by identical or different radicals from the group consisting of hydroxy and halogen;
$R^1$ represents hydrogen, halogen, cyano, C(=O)OH, C(=O)$OR^a$, C(=O)$NH_2$, C(=O)N(H)$R^a$, C(=O)N($R^a$)$R^b$, C(=O)$R^d$, hydroxy or $C_1$-$C_6$-alkyl, where the $C_1$-$C_6$-alkyl radical is optionally mono- or polysubstituted by identical or different radicals from the group consisting of hydroxy, halogen, cyano, C(=O)OH, C(=O)$OR^a$, S(=O)$_2$—$C_1$-$C_6$-alkyl, $NH_2$, NH$R^a$, N($R^a$)$R^b$, $C_1$-$C_6$-alkoxy which is optionally mono- or polysubstituted by identical or different radicals from the group consisting of halogen, $C_3$-$C_8$-cycloalkoxy which is optionally mono- or polysubstituted by identical or different radicals from the group consisting of halogen, heterocycloalkyl which is optionally mono- or polysubstituted by identical or different radicals from the group consisting of $R^c$,
or represents $C_1$-$C_6$-alkoxy, where the $C_1$-$C_6$-alkoxy radical may optionally be mono- or polysubstituted by identical or different radicals from the group consisting of
hydroxy, halogen, cyano, C(=O)OH, C(=O)$OR^a$, S(=O)$_2$—$C_1$-$C_6$-alkyl, $NH_2$, NH$R^a$, N($R^a$)$R^b$, $C_3$-$C_8$-cycloalkyl which is optionally mono- or polysubstituted by identical or different radicals from the group consisting of halogen, $C_1$-$C_6$-alkoxy which is optionally mono- or polysubstituted by identical or different radicals from the group consisting of halogen, $C_3$-$C_8$-cycloalkoxy which is optionally mono- or polysubstituted by identical or different radicals from the group consisting of halogen, heterocycloalkyl which is optionally mono- or polysubstituted by identical or different radicals from the group consisting of $R^c$,
aryl which is optionally mono- or polysubstituted by identical or different radicals from the group consisting of $R^c$, or 5- or 6-membered heteroaryl which is optionally mono- or polysubstituted by identical or different radicals from the group consisting of $R^c$,
or represents $C_3$-$C_8$-cycloalkoxy or heterocycloalkoxy which may optionally be mono- or polysubstituted by identical or different radicals from the group consisting of hydroxy, halogen, cyano and $C_1$-$C_6$-alkyl,
or represents aryloxy or 5- or 6-membered heteroaryloxy in which aryloxy and
5- or 6-membered heteroaryloxy may optionally be mono- or polysubstituted by identical or different radicals from the group consisting of hydroxy, halogen, cyano, C(=O)OH, C(=O)$OR^a$, $C_1$-$C_6$-alkyl and $C_1$-$C_6$-alkoxy,
or represents $C_3$-$C_8$-cycloalkyl or heterocycloalkyl which may optionally be mono- or polysubstituted by identical or different radicals from the group consisting of hydroxy, halogen, cyano and $C_1$-$C_6$-alkyl,
or represents $C_2$-$C_6$-alkenyl or $C_2$-$C_6$-alkynyl,
or represents aryl, 5- to 10-membered heteroaryl, aryl-$C_1$-$C_4$-alkyl or 5- or 6-membered heteroaryl-$C_1$-$C_4$-alkyl, where aryl and heteroaryl may optionally be mono- or polysubstituted by identical or different radicals from the group consisting of halogen, hydroxy, cyano, C(=O)OH, C(=O)$OR^a$, $C_1$-$C_6$-alkyl, $C_3$-$C_8$-cycloalkyl and $C_1$-$C_6$-alkoxy;
$R^a$ represents $C_1$-$C_6$-alkyl, $C_3$-$C_{10}$-cycloalkyl, heterocycloalkyl, aryl or heteroaryl, where alkyl, cycloalkyl, heterocycloalkyl, aryl and heteroaryl may optionally be mono- or polysubstituted by identical or different radicals from the group consisting of halogen, hydroxy, cyano, $C_1$-$C_3$-alkyl, $C_1$-$C_3$-alkoxy, heterocycloalkyl, —C(=O) O—$C_1$-$C_6$-alkyl and S(=O)$_2$—$C_1$-$C_6$-alkyl;
$R^b$ represents $C_1$-$C_6$-alkyl or $C_3$-$C_{10}$-cycloalkyl;

or $R^a$ and $R^b$ together with the nitrogen atom form a 5- or 6-membered heterocycle which may optionally be mono- or polysubstituted by identical or different radicals from the group consisting of hydroxy, halogen, cyano, and $C_1$-$C_6$-alkyl;

$R^c$ represents hydroxy, halogen, cyano, $C_1$-$C_3$-alkyl or $C_1$-$C_3$-alkoxy;

$R^d$ represents hydrogen, $C_1$-$C_6$-alkyl or $C_3$-$C_{10}$-cycloalkyl;

$R^2$ represents hydrogen, $C_1$-$C_6$-alkyl or $C_3$-$C_6$-cycloalkyl;

$R^{13}$ represents hydrogen or $C_1$-$C_6$-alkyl;

W represents 5-membered heteroaryl which contains one to three heteroatoms selected from the group consisting of N, O and S and may optionally be monosubstituted by $R^3$ and optionally be mono- or polysubstituted by identical or different radicals $R^4$ or W represents pyridyl, pyrazinyl, pyridazinyl, 1,2,4-triazinyl or 1,3,5-triazinyl which may optionally be monosubstituted by $R^3$ and optionally be mono- or polysubstituted by identical or different radicals $R^4$;

$R^3$ represents hydrogen, halogen, cyano, C(=O)$R^a$, $NH_2$, $NHR^a$, N($R^a$)$R^b$, N(H)C(=O)$R^a$ or $C_1$-$C_6$-alkyl, where
$C_1$-$C_6$-alkyl may optionally be mono- or polysubstituted by identical or different radicals from the group consisting of hydroxy, halogen, cyano, C(=O)$R^a$, C(=O)OH, C(=O)O$R^a$, S(=O)$_2$—$C_1$-$C_6$-alkyl, $NH_2$, $NHR^a$, N($R^a$)$R^b$, $C_1$-$C_6$-alkoxy, $C_3$-$C_8$-cycloalkoxy,
where $C_1$-$C_6$-alkoxy and $C_3$-$C_8$-cycloalkoxy may optionally be mono- or polysubstituted by identical or different halogen radicals;
or $C_1$-$C_6$-alkyl is optionally mono- or polysubstituted by identical or different radicals from the group consisting of $C_3$-$C_6$-cycloalkyl and heterocycloalkyl,
where $C_3$-$C_6$-cycloalkyl and heterocycloalkyl may optionally be mono-, di- or trisubstituted by identical or different radicals from the group consisting of halogen, cyano, $C_1$-$C_3$-alkyl and $C_1$-$C_3$-alkoxy,
or $C_1$-$C_6$-alkyl is optionally mono- or polysubstituted by identical or different radicals from the group consisting of aryl and 5- or 6-membered heteroaryl,
where aryl and 5- or 6-membered heteroaryl may optionally be mono-, di- or trisubstituted by identical or different substituents from the group consisting of halogen, cyano, $C_1$-$C_3$-alkyl and $C_1$-$C_3$-alkoxy, or $R^3$ represents $C_1$-$C_6$-alkoxy, where
$C_1$-$C_6$-alkoxy may optionally be mono- or polysubstituted by identical or different radicals from the group consisting of hydroxy, halogen, cyano, C(=O)O$R^a$, S(=O)$_2$—$C_1$-$C_6$-alkyl, N($R^a$)$R^b$, $C_3$-$C_8$-cycloalkyl, $C_1$-$C_4$-alkoxy, $C_3$-$C_8$-cycloalkoxy,
or represents $C_3$-$C_6$-cycloalkyl, heterocycloalkyl or $C_5$-$C_{11}$-spirocycloalkyl, where cycloalkyl, heterocycloalkyl and spirocycloalkyl may optionally be mono- or polysubstituted by identical or different radicals from the group consisting of hydroxy, halogen, cyano, C(=O)$R^a$, C(=O)OH, C(=O)O$R^a$, $C_1$-$C_6$-alkyl and $C_1$-$C_4$-alkoxy;
or represents aryl or 5- to 10-membered heteroaryl, where aryl and heteroaryl may optionally be mono- or polysubstituted by identical or different radicals from the group consisting of halogen, hydroxy, cyano, C(=O)O$R^a$, S(=O)$_2$—$C_1$-$C_6$-alkyl, $NO_2$, $NH_2$, $NHR^a$, N($R^a$)$R^b$, N(H)C(=O)$R^a$, $C_3$-$C_8$-cycloalkyl, $C_1$-$C_3$-alkoxy and $C_1$-$C_3$-alkyl, where
$C_1$-$C_3$-alkyl may optionally be mono- or polysubstituted by identical or different halogen radicals;

$R^4$ represents halogen, hydroxy, cyano or $C_1$-$C_6$-alkyl, where $C_1$-$C_6$-alkyl may optionally be mono- or polysubstituted by identical or different radicals from the group consisting of halogen, $C_1$-$C_6$-alkoxy, where $C_1$-$C_6$-alkoxy may optionally be mono- or polysubstituted by identical or different radicals from the group consisting of halogen, $C_2$-$C_6$-alkenyl, $C_2$-$C_6$-alkynyl, $C_3$-$C_{10}$-cycloalkyl, 3- to 10-membered heterocycloalkyl and aryl, where aryl may optionally be mono- or poly substituted by identical or different radicals R, or $R^4$ represents aryl or heteroaryl which may optionally be mono- or polysubstituted by identical or different radicals R, or $R^4$ represents C(=O)$R^a$, C(=O)$NH_2$, C(=O)N(H)$R^a$, C(=O)N($R^a$)$R^b$, C(=O)O$R^a$, $NH_2$, $NHR^a$, N($R^a$)$R^b$, N(H)C(=O)$R^a$, N($R^a$)C(=O)$R^a$, N(H)C(=O)$NH_2$, N(H)C(=O)$NHR^a$, N(H)C(=O)N($R^a$)$R^b$, N($R^a$)C(=O)$NH_2$, N($R^a$)C(=O)$NHR^a$, N($R^a$)C(=O)N($R^a$)$R^b$, N(H)C(=O)O$R^a$, N($R^a$)C(=O) O$R^a$, $NO_2$, N(H)S(=O)$R^a$, N($R^a$)S(=O)$R^a$, N(H)S(=O)$_2R^a$, N($R^a$)S(=O)$_2R^a$, N=S(=O)($R^a$)$R^b$, OC(=O)$R^a$, OC(=O)$NH_2$, OC(=O)$NHR^a$, OC(=O)N($R^a$)$R^b$, SH, S$R^a$, S(=O)$R^a$, S(=O)$_2R^a$, S(=O)$_2$$NH_2$, S(=O)$_2$$NHR^a$, S(=O)$_2$N($R^a$)$R^b$ or S(=O)(=N—$R^a$)$R^b$;

R represents halogen, cyano, $C_1$-$C_6$-alkyl, $C_2$-$C_6$-alkenyl, $C_2$-$C_6$-alkynyl, $C_3$-$C_{10}$-cycloalkyl, 3- to 10-membered heterocycloalkyl, aryl, heteroaryl, C(=O)$R^a$, C(=O)$NH_2$, C(=O)N(H)$R^a$, C(=O)N($R^a$)$R^b$, C(=O)O$R^a$, $NH_2$, $NHR^a$, N($R^a$)$R^b$, N(H)C(=O)$R^a$, N($R^a$)C(=O)$R^a$, N(H)C(=O)$NH_2$, N(H)C(=O)$NHR^a$, N(H)C(=O)N($R^a$)$R^b$, N($R^a$)C(=O)$NH_2$, N($R^a$)C(=O)$NHR^a$, N($R^a$)C(=O)N($R^a$)$R^b$, N(H)C(=O)O$R^a$, N($R^a$)C(=O)O$R^a$, $NO_2$, N(H)S(=O)$R^a$, N($R^a$)S(=O)$R^a$, N(H)S(=O)$_2R^a$, N($R^a$)S(=O)$_2R^a$, N=S(=O)($R^a$)$R^b$, OH, $C_1$-$C_6$-alkoxy, OC(=O)$R^a$, OC(=O)$NH_2$, OC(=O)$NHR^a$, OC(=O)N($R^a$)$R^b$, SH, S$R^a$, S(=O)$R^a$, S(=O)$_2R^a$, S(=O)$_2$$NH_2$, S(=O)$_2$$NHR^a$, S(=O)$_2$N($R^a$)$R^b$ or S(=O)(=N$R^a$)$R^b$;

n represents 0 or 1;

Y represents a group selected from:

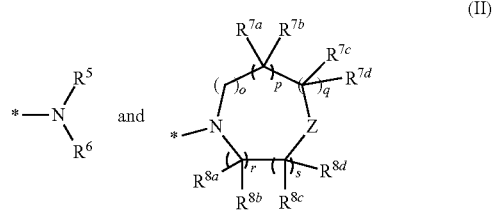

(II)

where * represents the point of attachment of the group to the remainder of the molecule;

$R^5$ represents hydrogen, $C_1$-$C_6$-alkyl or $C_3$-$C_{10}$-cycloalkyl, where
$C_1$-$C_6$-alkyl may optionally be mono- or polysubstituted by identical or different radicals from the group consisting of hydroxy, halogen, cyano, C(=O)OH, C(=O)O$R^a$, S(=O)$_2$—$C_1$-$C_6$-alkyl, N($R^a$)$R^b$, $C_1$-$C_4$-alkoxy and $C_3$-$C_8$-cycloalkyl;

$R^6$ represents hydrogen or $C_1$-$C_6$-alkyl, where
$C_1$-$C_6$-alkyl may optionally be mono- or polysubstituted by identical or different radicals from the group consisting of hydroxy, halogen, cyano, $C_3$-$C_{10}$-cycloalkyl, C(=O)R$^a$, C(=O)OH, C(=O)OR$^a$, S(=O)$_2$—C$_1$-C$_6$-alkyl, N(R$^a$)R$^b$, C$_1$-C$_4$-alkoxy and C$_3$-C$_8$-cycloalkoxy,
or represents C$_3$-C$_{10}$-cycloalkyl, where
C$_3$-C$_{10}$-cycloalkyl may optionally be mono- or polysubstituted by identical or different radicals from the group consisting of hydroxy, halogen, cyano and C$_1$-C$_6$-alkyl, where
C$_1$-C$_6$-alkyl may optionally be substituted by hydroxy,
or represents heterocycloalkyl, where
heterocycloalkyl may optionally be mono- or polysubstituted by identical or different radicals from the group consisting of halogen, cyano, C$_1$-C$_3$-alkyl and C$_1$-C$_3$-alkoxy,
or represents aryl or 5- or 6-membered heteroaryl, where aryl and 5- or 6-membered heteroaryl may optionally be mono- or polysubstituted by identical or different radicals from the group consisting of halogen, cyano, C$_1$-C$_3$-alkyl, C$_1$-C$_3$-alkoxy, S(=O)$_2$NH$_2$, S(=O)$_2$NHR$^a$ and S(=O)$_2$N(R$^a$)R$^b$;

R$^{7a}$ represents hydrogen, halogen, N(R$^a$)R$^b$, C$_1$-C$_6$-alkyl or C$_3$-C$_{10}$-cycloalkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

R$^{7b}$ represents hydrogen, halogen or C$_1$-C$_6$-alkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

or R$^{7a}$ and R$^{7b}$ together with the carbon atom form C$_3$-C$_6$-cycloalkyl which may optionally be mono- or polysubstituted by identical or different radicals from the group consisting of hydroxy, halogen, cyano and C$_1$-C$_6$-alkyl,
or R$^{7a}$ and R$^{7b}$ together represent an oxo group;

R$^{7c}$ represents hydrogen, halogen, N(R$^a$)R$^b$, C$_1$-C$_6$-alkyl or C$_3$-C$_{10}$-cycloalkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

R$^{7d}$ represents hydrogen, halogen or C$_1$-C$_6$-alkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

or R$^{7c}$ and R$^{7d}$ together with the carbon atom form C$_3$-C$_6$-cycloalkyl which may optionally be mono- or polysubstituted by identical or different radicals from the group consisting of hydroxy, halogen, cyano and C$_1$-C$_6$-alkyl,
or R$^{7c}$ and R$^{7d}$ together represent an oxo group;

R$^{8a}$ represents hydrogen, halogen, N(R$^a$)R$^b$, C$_1$-C$_6$-alkyl or C$_3$-C$_{10}$-cycloalkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

R$^{8b}$ represents hydrogen, halogen or C$_1$-C$_6$-alkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

or R$^{8a}$ and R$^{8b}$ together with the carbon atom form C$_3$-C$_6$-cycloalkyl which may optionally be mono- or polysubstituted by identical or different radicals from the group consisting of hydroxy, halogen, cyano and C$_1$-C$_6$-alkyl, R$^8$c represents hydrogen, halogen, N(R$^a$)R$^b$, C$_1$-C$_6$-alkyl or C$_3$-C$_{10}$-cycloalkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

R$^{8d}$ represents hydrogen, halogen or C$_1$-C$_6$-alkyl, where
C$_1$-C$_6$-alkyl may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_1$-C$_4$-alkoxy, C$_3$-C$_8$-cycloalkyl and heterocycloalkyl;

or R$^{8c}$ and R$^{8d}$ together with the carbon atom form C$_3$-C$_6$-cycloalkyl which may optionally be mono- or polysubstituted by identical or different radicals from the group consisting of hydroxy, halogen, cyano and C$_1$-C$_6$-alkyl,
or R$^{8c}$ and R$^{8d}$ together represent an oxo group;

o represents 0, 1 or 2,
p represents 0, 1 or 2,
q represents 0, 1 or 2,
r represents 0, 1 or 2,
s represents 0, 1 or 2,
where o, p, q, r and s do not simultaneously represent 0;

Z represents a group selected from C(=O), CR$^9$R$^{10}$, NR$^{11}$, O, S, S(=O) and S(=O)$_2$;

R$^9$ represents hydrogen or C$_1$-C$_6$-alkyl,

R$^{10}$ represents hydrogen, halogen, cyano, C(=O)R$^a$, C(=O)OH, C(=O)OR$^a$, C(=O)NH$_2$, C(=O)N(H)R$^a$, C(=O)N(R$^a$)R$^b$, N(H)C(=O)R$^a$, N(R$^b$)C(=O)R$^a$, S(=O)$_2$R$^a$, hydroxy, N(R$^a$)R$^b$ and C$_1$-C$_6$-alkyl, where
C$_1$-C$_6$-alkyl may optionally be mono- or polysubstituted by identical or different radicals from the group consisting of hydroxy, halogen, cyano, C(=O)R$^a$, C(=O)OH, C(=O)OR$^a$, S(=O)$_2$—C$_1$-C$_6$-alkyl, N(R$^a$)R$^b$, C$_1$-C$_4$-alkoxy and C$_3$-C$_8$-cycloalkoxy,
or represents C$_1$-C$_6$-alkoxy, where
C$_1$-C$_6$-alkoxy may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, N(R$^a$)R$^b$, C$_3$-C$_8$-cycloalkyl, C$_1$-C$_4$-alkoxy, C$_3$-C$_8$-cycloalkoxy, heterocycloalkyl, aryl and 5- or 6-membered heteroaryl, where
aryl and 5- or 6-membered heteroaryl may optionally be mono- or polysubstituted by identical or different radicals from the group consisting of halogen, cyano, C$_1$-C$_3$-alkyl and C$_1$-C$_3$-alkoxy,
or represents aryloxy or 5- or 6-membered heteroaryloxy in which
aryloxy and 5- or 6-membered heteroaryloxy may optionally be mono- or disubstituted by identical or different radicals from the group consisting of hydroxy, halogen, cyano, C(=O)OH, C(=O)OR$^a$, C$_1$-C$_3$-alkyl and C$_1$-C$_3$-alkoxy,
or represents C$_3$-C$_8$-cycloalkyl, C$_3$-C$_8$-cycloalkyl-C$_1$-C$_4$-alkyl, heterocycloalkyl or heterocycloalkyl-C$_1$-C$_4$-alkyl, which may optionally be mono- or polysubstituted by identical or different radicals from the group consisting of hydroxy, halogen, cyano, $C(=O)R^a$, $C(=O)OH$, $C(=O)OR^a$, $C_1$-$C_6$-alkyl and $C_1$-$C_6$-alkoxy, where
$C_1$-$C_6$-alkoxy may optionally be mono- or polysubstituted by identical or different halogen radicals or an oxo group;
or represents $C_2$-$C_6$-alkenyl or $C_2$-$C_6$-alkynyl,
or represents aryl, 5- to 10-membered heteroaryl, aryl-$C_1$-$C_4$-alkyl or 5- or 6-membered heteroaryl-$C_1$-$C_4$-alkyl, where
aryl and heteroaryl may optionally be mono- or polysubstituted by identical or different radicals from the group consisting of halogen, hydroxy, cyano, $C(=O)OH$, $C(=O)OR^a$, $NHR^a$, $N(R^a)R^b$, $C_3$-$C_8$-cycloalkyl and $C_1$-$C_3$-alkoxy;
or $R^9$ and $R^{10}$ together with the carbon atom form $C_3$-$C_8$-cycloalkyl or a 4- to 6-membered heterocycle, where
the $C_3$-$C_8$-cycloalkyl radical or the 4- to 6-membered heterocycle may optionally be mono- or polysubstituted by identical or different radicals from the group consisting of hydroxy, halogen, cyano, $C_1$-$C_6$-alkyl, $C(=O)R^a$ and an oxo group;
$R^{11}$ represents hydrogen, $C(=O)R^a$, $C(=O)OR^a$, $C(=O)NH_2$, $C(=O)N(H)R^a$, $C(=O)N(R^a)R^b$, $S(=O)_2R^a$, $S(=O)_2N(R^a)R^b$ or $C_1$-$C_6$-alkyl, where
$C_1$-$C_6$-alkyl may optionally be mono- or polysubstituted by identical or different radicals from the group consisting of hydroxy, halogen, cyano, $C(=O)R^a$, $C(=O)OR^a$, $C(=O)NH_2$, $C(=O)N(H)R^a$, $C(=O)N(R^a)R^b$, $S(=O)_2$—$C_1$-$C_6$-alkyl, $N(R^a)R^b$, $C_3$-$C_8$-cycloalkyl, $C_1$-$C_4$-alkoxy and $C_3$-$C_8$-cycloalkoxy, where
$C_3$-$C_8$-cycloalkyl, $C_1$-$C_4$-alkoxy and $C_3$-$C_8$-cycloalkoxy may optionally be mono- or polysubstituted by identical or different radicals from the group consisting of hydroxy and halogen,
or represents $C_3$-$C_8$-cycloalkyl, heterocycloalkyl or heterocycloalkyl-$C_1$-$C_4$-alkyl
which may optionally be mono- or polysubstituted by identical or different radicals from the group consisting of hydroxy, halogen, cyano, $C_1$-$C_6$-alkyl, $C_1$-$C_6$-alkoxy, where alkyl and alkoxy may optionally be mono- or polysubstituted by identical or different radicals from the group consisting of halogen and an oxo group,
or represents $C_2$-$C_6$-alkenyl or $C_2$-$C_6$-alkynyl,
or represents aryl, 5- to 10-membered heteroaryl, aryl-$C_1$-$C_4$-alkyl or 5- or 6-membered heteroaryl-$C_1$-$C_4$-alkyl, where
aryl and heteroaryl may optionally be mono- or polysubstituted by identical or different radicals from the group consisting of halogen, hydroxy, cyano, $C(=O)OH$, $C(=O)OR^a$, $C_1$-$C_3$-alkyl, $C_3$-$C_8$-cycloalkyl and $C_1$-$C_3$-alkoxy;
and their diastereomers, enantiomers, their metabolites, their salts, their solvates or the solvates of their salts.

DETAILED DESCRIPTION

Figure 1:
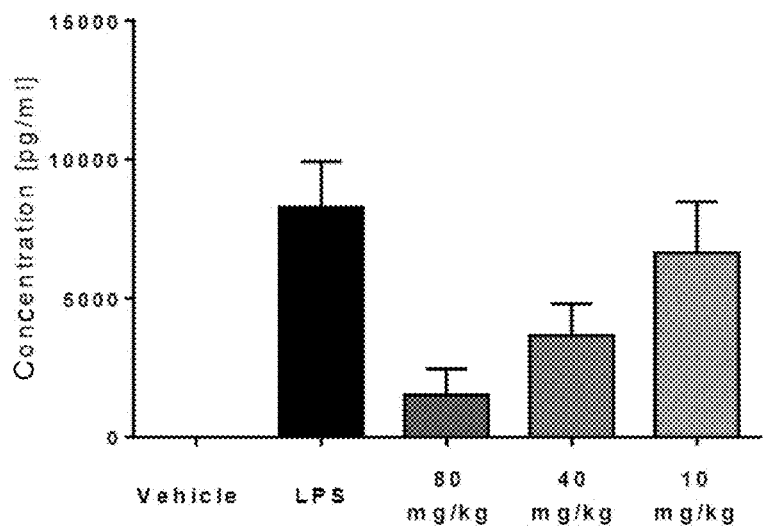
FIG. 1 Treatment of LPS-induced inflammation with Exemplary Compound 64 leads to a reduced amount of secreted TNF-α.

If, in the synthesis intermediates and working examples of the invention described below, a compound is given in the form of a salt of the corresponding base or acid, the exact stoichiometric composition of such a salt as obtained by the respective preparation and/or purification process is generally not known. Unless specified in more detail, additions to names and structural formulae, such as "hydrochloride", "trifluoroacetate", "sodium salt" or "x HCl", "x CF₃COOH", "x Na⁺" are not to be understood stoichiometrically in the case of such salts, but have only descriptive character with regard to the salt-forming components comprised therein.

This applies correspondingly if synthesis intermediates or working examples or salts thereof were obtained by the preparation and/or purification processes described in the form of solvates, for example hydrates, of unknown stoichiometric composition (if of a defined type).

Compounds according to the invention are the compounds of the formula (I) and their salts, solvates and solvates of the salts, the compounds encompassed by formula (I) of the formulae mentioned below and their salts, solvates and solvates of the salts and the compounds encompassed by formula (I) and mentioned below as working examples, and their salts, solvates and solvates of the salts, if the compounds encompassed by formula (I) and mentioned below are not already salts, solvates and solvates of the salts.

Preferred salts in the context of the present invention are physiologically acceptable salts of the compounds according to the invention. The invention also encompasses salts which themselves are unsuitable for pharmaceutical applications but which can be used, for example, for the isolation or purification of the inventive compounds.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of the solvates in which the coordination is with water.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as 2H (deuterium), 3H (tritium), 13C, 14C, 15N, 17O, 18O, 32P, 33P, 33S, 34S, 35S, 36S, 18F, 36Cl, 82Br, 123I, 124I, 129I and 131I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with 3H or 14C isotopes are suitable for this purpose. In addition, the incorporation of isotopes, for example of deuterium, can lead to particular therapeutic benefits as a consequence of greater metabolic stability of the compound, for example to an extension of the half-life in the body or to a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further below and the procedures described in the working examples, by using corresponding isotopic modifications of the respective reagents and/or starting compounds.

The present invention further provides all the possible crystalline and polymorphous forms of the compounds according to the invention, where the polymorphs may be present either as single polymorphs or as a mixture of a plurality of polymorphs in all concentration ranges.

In addition, the present invention also encompasses prodrugs of the compounds according to the invention. The term "prodrugs" here denotes compounds which may themselves be biologically active or inactive, but are converted (for example by metabolic or hydrolytic means) to inventive compounds during their residence time in the body.

In the context of the present invention, unless specified otherwise, the substituents have the following meanings:

Alkyl in the context of the invention is a straight-chain or branched alkyl radical having the particular number of carbon atoms specified. Examples which may be mentioned are methyl, ethyl, n-propyl, isopropyl, n-butyl, isobutyl, 1-methylpropyl, tert-butyl, n-pentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 1-ethylbutyl and 2-ethylbutyl. Preference is given to methyl, ethyl, n-propyl, n-butyl and 1-methylpropyl and also tert-butyl.

Alkenyl in the context of the invention is a straight-chain or branched monovalent hydrocarbon radical having at least one double bond and having the particular number of carbon atoms specified. These are generally 2 to 6 carbon atoms, preferably 2 to 4 and particularly preferably 2 or 3 carbon atoms.

In the case of a plurality of double bonds, these may be isolated or conjugated, with isolated double bonds being preferred.

Examples which may be mentioned are:
vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, methylhexadienyl.

Particular preference is given to vinyl or allyl.

Alkynyl in the context of the invention is a straight-chain or branched monovalent hydrocarbon radical having at least one triple bond and having the particular number of carbon atoms specified. These are generally 2 to 6 carbon atoms, preferably 2 to 4 and particularly preferably 2 or 3 carbon atoms.

Examples which may be mentioned are:
ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl.

Particular preference is given to ethynyl, prop-1-ynyl or prop-2-ynyl.

Cycloalkyl in the context of the invention is a monocyclic saturated alkyl radical having the number of carbon atoms specified in each case. Examples which may be mentioned as being preferred are cyclopropyl, cyclobutyl, cyclopentyl, cyclohexyl and cycloheptyl.

Alkoxy in the context of the invention is a straight-chain or branched alkoxy radical having the particular number of carbon atoms specified. 1 to 6 or 1 to 4 carbon atoms are preferred. Examples which may be mentioned are methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Preference is given to a linear or branched alkoxy radical having 1 to 4 carbon atoms. Examples which may be mentioned as being preferred are methoxy, ethoxy, n-propoxy, 1-methylpropoxy, n-butoxy and isobutoxy.

Cycloalkoxy in the context of the invention is a monocyclic saturated alkyl radical which has the particular number of carbon atoms specified and is attached via an oxygen atom. Examples which may be mentioned as being preferred are: cyclopropoxy, cyclobutoxy, cyclopentoxy, cyclohexoxy and cycloheptoxy.

Aryl in the context of the invention is a monovalent mono- to tricyclic aromatic, carbocyclic ring system having generally 6 to 14 carbon atoms. Examples which may be mentioned are: phenyl, naphthyl and phenanthryl. Preference is given to phenyl.

Heterocyclyl or heterocyclus or heterocycloalkyl in the context of the invention is a mono- or polycyclic, preferably mono- or bicyclic, non-aromatic, saturated or partially unsaturated heterocycle having generally 3 to 10, preferably 3 to 7, ring atoms and up to 3, preferably up to 1 or 2, heteroatoms and/or heterogroups from the group consisting of N, O, S, SO and $SO_2$. Preference is given to 3- to 7-membered, monocyclic saturated heterocyclyl radicals having up to two heteroatoms from the group consisting of O, N and S. Examples which may be mentioned are: azetidinyl, oxetanyl, pyrrolidinyl, pyrazolidinyl, tetrahydrofuranyl, piperidinyl, piperazinyl, tetrahydropyranyl, morpholinyl, thiomorpholinyl, dioxidothiomorpholinyl, dihydroindolyl and dihydroisoindolyl. Preference is given to: azetidinyl, pyrrolidinyl, piperidinyl, piperazinyl and morpholinyl.

Heteroaryl is a monovalent, aromatic mono- or bicyclic ring system having generally 5 to 10, preferably 5 to 6, ring atoms and preferably 1 to 3 heteroatoms. The heteroatoms may be nitrogen atoms, oxygen atoms and/or sulphur atoms. The binding valency can be at any aromatic carbon atom or at a nitrogen atom.

Heteroaryl radicals having 5 ring atoms include, for example, the rings: thienyl, thiazolyl, furyl, pyrrolyl, oxazolyl, imidazolyl, pyrazolyl, isoxazolyl, isothiazolyl, oxadiazolyl, triazolyl, tetrazolyl and thiadiazolyl.

Heteroaryl radicals having 6 ring atoms include, for example, the rings: pyridyl, pyridazinyl, pyrimidinyl, pyrazinyl and triazinyl.

A bicyclic heteroaryl radical in accordance with the present invention has 9 or 10 ring atoms.

Heteroaryl radicals having 9 ring atoms include, for example, the rings: phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, indolinyl.

Heteroaryl radicals having 10 ring atoms include, for example, the rings:
isoquinolinyl, quinolinyl, quinolizinyl, quinazolinyl, quinoxalinyl, cinnolinyl, phthalazinyl, 1,7- or 1,8-naphthyridinyl, pteridinyl, chromanyl.

$C_5$-$C_{11}$-Spirocycloalkyl or heterospirocycloalkyl with replacement of 1-4 carbon atoms by nitrogen, oxygen and/or sulphur, including the two oxidized forms thereof, SO and $SO_2$, and the derivatives thereof modified as the sulphoximine, is understood to mean a fusion of two ring systems which share a common atom. Examples are spiro[2.2]pentane, spiro[2.3]hexane, azaspiro[2.3]hexane, spiro[3.3]heptane, azaspiro[3.3]heptane, oxaspiro[3.3]heptane, thiaazaspiro[3.3]heptane, oxaspiro[3.3]heptane, oxazaspiro[5.3]nonane, oxazaspiro[4.3]octane, oxazaspiro[5.5]undecane, diazaspiro[3.3]heptane, thiazaspiro[3.3]heptane, thiazaspiro[4.3]octane, azaspiro[5.5]decane, and the further homologous spiro[3.4], spiro[4.4], spiro[5.5], spiro[6.6], spiro[2.4], spiro[2.5], spiro[2.6], spiro[3.5], spiro[3.6], spiro[4.5], spiro[4.6] and spiro[5.6] systems including the variants modified by heteroatoms according to the definition.

Halogen in the context of the invention is fluorine, chlorine and bromine Preference is given to fluorine and chlorine.

Hydroxy in the context of the invention is OH.

An oxo group in the context of the invention is an oxygen atom attached to a carbon atom via a double bond.

A symbol * at a bond denotes the point of attachment in the molecule.

When radicals in the compounds according to the invention are substituted, the radicals may be mono- or polysubstituted, unless specified otherwise. In the context of the present invention, it is the case that for all radicals which occur more than once, their meaning is independent of the others. Substitution by one, two or three identical or different substituents is preferred.

Preference is given to compounds of the formula (I) in which
W represents 5-membered heteroaryl which contains one to three heteroatoms selected from the group consisting of N, O and S and may optionally be monosubstituted by $R^3$ and optionally be mono- or poly substituted by identical or different radicals $R^4$, where a ring heteroatom is located next to the ring carbon atom which is the point of attachment to the remainder of the molecule or represents pyridyl, pyrazinyl, pyridazinyl, 1,2,4-triazinyl or 1,3,5-triazinyl which may optionally be monosubstituted by $R^3$ and optionally be mono- or polysubstituted by identical or different radicals $R^4$, where a ring heteroatom is located next to the ring carbon atom which is the point of attachment of the group to the remainder of the molecule.

Preference is furthermore given to compounds of the formula (I) in which
W represents a group selected from the following general formulae (III) to (IX):

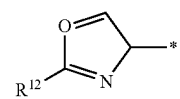

III

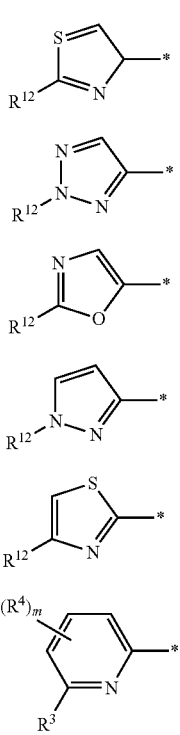

in which
R$^{12}$ represents hydrogen, halogen, C$_1$-C$_6$-alkyl which is optionally mono- or polysubstituted by identical or different halogen radicals, C$_3$-C$_6$-cycloalkyl which is optionally mono- or polysubstituted by identical or different halogen radicals, aryl which is optionally mono- or polysubstituted by identical or different radicals from the group consisting of R$^c$ or 5- or 6-membered heteroaryl which is optionally mono- or polysubstituted by identical or different radicals from the group consisting of R$^c$ or represents NHR$^a$;
m represents 0, 1, 2 or 3 and
R$^3$ and R$^4$ have the meanings given above and
* represents the point of attachment of the group to the remainder of the molecule.

Particular preference is furthermore given to compounds of the general formula (I) in which W represents a group of the general formula (IX)

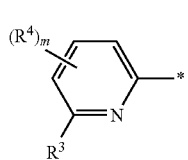

in which m=0 or 1 and
R$^3$ is a C$_1$-C$_6$-alkyl radical which is optionally mono- or polysubstituted by halogen and/or hydroxy, is halogen, cyano or a C$_3$-C$_6$-cycloalkyl radical which is optionally mono- or polysubstituted by halogen and/or hydroxy.

Preferably, R$^3$ is a C$_1$-C$_3$-alkyl radical which is unsubstituted or mono- or polysubstituted by hydroxy and/or halogen.

For the purpose of the invention, particularly preferred C$_1$-C$_3$-alkyls radical for R$^3$ are methyl and ethyl. Preferably, R$^3$ is a C$_1$-C$_6$-alkyl radical which is optionally monosubstituted by hydroxy and/or mono- to trisubstituted by fluorine.

Particularly preferably, R$^3$ is a C$_1$-C$_3$-alkyl radical which is optionally monosubstituted by hydroxy and/or mono- to trisubstituted by fluorine.

Preferred substituted C$_1$-C$_3$-alkyl radicals for R$^3$ are trifluoro-C$_1$-C$_3$-alkyl, hydroxymethyl, 1-hydroxyethyl, 2-hydroxypropan-2-yl and 2,2,2-trifluoro-1-hydroxy ethyl. Here, particular preference is given to a trifluoromethyl radical.

Also preferred for R$^3$ is a cyclopropyl radical.

In an exemplary manner, the following radicals may be mentioned for W:

1-ethyl-1H-pyrazol-3-yl, 2,4'-bipyridin-6-yl, 2-(4-fluorophenyl)-1,3-thiazol-4-yl, 2-(4-methoxyphenyl)-1,3-thiazol-4-yl, 2-(azetidin-3-ylamino)-1,3-thiazol-4-yl, 2-(pyridin-3-yl)-1,3-thiazol-4-yl, 2-(pyridin-4-yl)-1,3-thiazol-4-yl, 2-(trifluoromethyl)-1,3-thiazol-4-yl, 2-bromo-1,3-thiazol-4-yl, 2-cyclopropyl-1,3-oxazol-4-yl, 2-methyl-1,3-oxazol-4-yl, 2-methyl-1,3-oxazol-5-yl, 2-phenyl-2H-1,2,3-triazol-4-yl, 2-{[1-(tert-butoxycarbonyl)azetidin-3-yl]amino}-1,3-thiazol-4-yl, 4'-methyl-2,3'-bipyridin-6-yl, 4-(trifluoromethyl)-1,3-thiazol-2-yl, 5'-methyl-2,3'-bipyridin-6-yl, 5-fluoro-6-(1-methyl-1H-pyrazol-4-yl)pyridin-2-yl, 5-fluoropyridin-2-yl, 6'-acetamido-2,3'-bipyridin-6-yl, 6'-amino-2,3'-bipyridin-6-yl, 6'-methoxy-2,3'-bipyridin-6-yl, 6'-methyl-2,3'-bipyridin-6-yl, 6-(1,3-dimethyl-1H-pyrazol-4-yl)pyridin-2-yl, 6-(1-methyl-1H-pyrazol-4-yl)pyridin-2-yl, 6-(1-methyl-1H-pyrazol-5-yl)pyridin-2-yl, 6-(1H-1,2,4-triazol-1-yl)pyridin-2-yl, 6-(1H-pyrazol-1-yl)pyridin-2-yl, 6-(3-hydroxyazetidin-1-yl)pyridin-2-yl, 6-(3-methyl-1H-pyrazol-4-yl)pyridin-2-yl, 6-(4-chloro-1H-pyrazol-1-yl)pyridin-2-yl, 6-(4H-1,2,4-triazol-4-yl)pyridin-2-yl, 6-(azetidin-3-ylamino)pyridin-2-yl, 6-(cyclopropylmethoxy)pyridin-2-yl, 6-(dimethylamino)pyridin-2-yl, 6-(morpholin-4-yl)pyridin-2-yl, 6-(morpholin-4-yl)pyridin-2-yl, 6-(trifluoromethyl)pyridin-2-yl, 6-[1-hydroxy ethyl]pyridin-2-yl, 6-[(2R,6S)-2,6-dimethylmorpholin-4-yl]pyridin-2-yl, 6-[3-(methylsulphonyl)phenyl]pyridin-2-yl, 6-[3-(trifluoromethyl)-1H-pyrazol-4-yl]pyridin-2-yl, 6-acetamidopyridin-2-yl, 6-aminopyridin-2-yl, 6-bromopyridin-2-yl, 6-chloropyridin-2-yl, 6-cyclopropylpyridin-2-yl, 6-ethoxypyridin-2-yl, 6-ethylpyridin-2-yl, 6-fluoropyridin-2-yl, 6-methoxypyridin-2-yl, 6-methylpyridin-2-yl, 6-{[(2S)-azetidin-2-ylmethyl]amino}pyridin-2-yl and 6-(2-hydroxypropan-2-yl)pyridin-2-yl.

Preferred for W are the following radicals:

2-(4-fluorophenyl)-1,3-thiazol-4-yl, 2-(4-methoxyphenyl)-1,3-thiazol-4-yl, 2-(azetidin-3-ylamino)-1,3-thiazol-4-yl, 2-(pyridin-4-yl)-1,3-thiazol-4-yl, 2-cyclopropyl-1,3-oxazol-4-yl, 5-fluoro-6-(1-methyl-1H-pyrazol-4-yl)pyridin-2-yl, 6-(1-methyl-1H-pyrazol-4-yl)pyridin-2-yl, 6-(1H-1,2,4-triazol-1-yl)pyridin-2-yl, 6-(1H-pyrazol-1-yl)pyridin-2-yl, 6-(3-methyl-1H-pyrazol-4-yl)pyridin-2-yl, 6-(azetidin-3-ylamino)pyridin-2-yl, 6-(dimethylamino)pyridin-2-yl, 6-(morpholin-4-yl)pyridin-2-yl, 6-(trifluoromethyl)pyridin-2-yl, 6-[1-hydroxyethyl]pyridin-2-yl, 6-[3-(trifluoromethyl)-1H-pyrazol-4-yl]pyridin-2-yl, 6-cyclopropylpyridin-2-yl, 6-methylpyridin-2-yl and 6-(2-hydroxypropan-2-yl)pyridin-2-yl.

If W represents a group of the general formula (IX) and m=1, $R^4$ is preferably located in the position ortho to $R^3$:

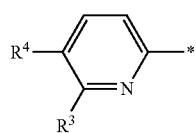

If W represents a group of the general formula (X), $R^4$ is preferably hydrogen, $C_1$-$C_3$-alkyl, fluorine, chlorine, bromine, cyano or trifluoromethyl.

Particularly preferably, W represents a group of the general formula (X) in which $R^4$ is hydrogen.

Particularly preferred for W are the following radicals: 6-(1-methyl-1H-pyrazol-4-yl)pyridin-2-yl, 6-(1H-1,2,4-triazol-1-yl)pyridin-2-yl, 6-(1H-pyrazol-1-yl)pyridin-2-yl, 6-(3-methyl-1H-pyrazol-4-yl)pyridin-2-yl, 6-(azetidin-3-ylamino)pyridin-2-yl, 6-(dimethylamino)pyridin-2-yl, 6-(morpholin-4-yl)pyridin-2-yl, 6-(trifluoromethyl)pyridin-2-yl, 6-[1-hydroxyethyl]pyridin-2-yl, 6-[3-(trifluoromethyl)-1H-pyrazol-4-yl]pyridin-2-yl, 6-cyclopropylpyridin-2-yl, 6-methylpyridin-2-yl and 6-(2-hydroxypropan-2-yl)pyridin-2-yl.

Preference is furthermore given to compounds in which $R^1$ is hydrogen, halogen, hydroxy, cyano, $C_1$-$C_6$-alkoxy, $C_1$-$C_6$-alkyl, $C_3$-$C_8$-cycloalkyl, aryloxy or heteroaryloxy.

In a preferred embodiment, $C_1$-$C_6$-alkoxy in the sense of $R^1$ is methoxy, ethoxy, isopropoxy or else isobutoxy. $C_1$-$C_6$-Alkoxy may be mono- or polysubstituted, preferably by one or more halogens or else by $C_3$-$C_8$-cycloalkyl mono- or polysubstituted by identical or different halogens.

If $R^1$ represents mono- or polyhalogenated $C_1$-$C_6$-alkoxy, preference is given to fluorine. Here, trifluoromethoxy, difluoromethoxy and 2,2,2-trifluoroethoxy may be mentioned by way of example. Trifluoromethoxy and 2,2,2-trifluoroethoxy are very particularly preferred.

If $R^1$ represents a $C_1$-$C_6$-alkoxy radical which is mono- or polysubstituted by $C_3$-$C_8$-cycloalkyl, preference is given to $C_3$-$C_5$-cycloalkyl, in particular to a cyclopropyl radical. Cyclopropylmethoxy may be mentioned as an example thereof.

If $R^1$ is a $C_1$-$C_6$-alkoxy radical substituted by an aryl group, preference is given to aryl groups having 6 carbon atoms, for example benzyloxy.

If $R^1$ is a $C_1$-$C_6$-alkoxy radical substituted by a heteroaryl group, preference is given to 6-membered heteroaryl radicals. Here, a pyrimidylmethoxy radical may be mentioned as an example for $R^1$.

Further preferred embodiments for $R^1$ in the sense of $C_1$-$C_6$-alkyl are methyl or ethyl.

If $R^1$ is a halogen, preference is given to bromine, fluorine or chlorine. Particular preference is given to chlorine.

Furthermore, $R^1$ may be a hydroxy-substituted $C_1$-$C_5$-alkyl radical. Here, particular mention may be made of 2-hydroxypropan-2-yl or 3-hydroxypentan-3-yl. Preference is given to a 2-hydroxypropan-2-yl radical.

If $R^1$ is a halogen, preference is given to fluorine, chlorine and bromine. Particular preference is given to chlorine.

The present invention also provides compounds of the general formula (I) in which W represents a group of the general formula (IX) or (X) and $R^2$ represents hydrogen.

Moreover, the present invention provides compounds of the general formula (I) in which W represents a group of the general formula (IX) or (X) and $R^0$ represents hydrogen or methyl.

Moreover, the present invention provides compounds of the general formula (I) in which W represents a group of the general formula (IX) or (X) and $R^{13}$ represents hydrogen or methyl.

Moreover, the present invention provides compounds of the general formula (I) in which W represents a group of the general formula (IX) or (X) and n represents 0 or 1.

Moreover, the present invention provides compounds of the general formula (I) in which W represents a group of the general formula (IX) or (X) and $R^1$ represents hydrogen, cyano, isopropoxy, trifluoromethoxy, 2,2,2-trifluoroethoxy, isobutoxy, cyclopropylmethoxy, pyridin-2-ylmethoxy, benzyloxy, bromine, chlorine, ethoxy, fluorine, hydroxy, methoxy or 2-hydroxypropan-2-yl.

Moreover, the present invention provides compounds of the general formula (I) in which W represents a group of the general formula (IX)

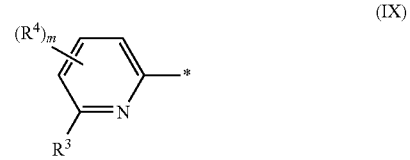

in which m represents 0 or 1, $R^3$ is a $C_1$-$C_6$-alkyl radical which is optionally mono- or polysubstituted by halogen and/or hydroxy, is halogen, cyano or a $C_3$-$C_6$-cycloalkyl radical which is optionally mono- or polysubstituted by halogen and/or hydroxy and $R^4$ is a $C_1$-$C_3$-alkyl radical, fluorine, chlorine, bromine, cyano or trifluoromethyl.

Moreover, the present invention provides compounds of the general formula (I) in which W represents a group of the general formula (X)

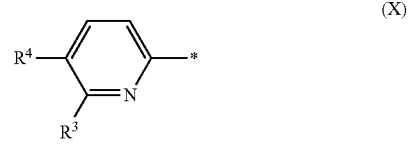

in which $R^4$ is hydrogen, $C_1$-$C_3$-alkyl, fluorine, chlorine, bromine, cyano or trifluoromethyl and $R^3$ is a $C_1$-$C_6$-alkyl radical which is optionally mono- or polysubstituted by halogen and/or hydroxy, is halogen, cyano or a $C_3$-$C_6$-cycloalkyl radical which is optionally mono- or polysubstituted by halogen and/or hydroxy.

Particular preference is given to compounds in which W represents a group of the general formula (X) in which $R^4$ represents hydrogen and $R^3$ is a $C_1$-$C_3$-alkyl radical which is unsubstituted or mono- or polysubstituted by hydroxy and/or halogen.

Very particular preference is given here to compounds in which W represents a group of the general formula (X) in which $R^4$ represents hydrogen and $R^3$ is a $C_1$-$C_3$-alkyl radical which is optionally monosubstituted by hydroxy and/or mono- to trisubstituted by fluorine.

Here, special preference is given to compounds in which $R^4$ represents hydrogen and $R^3$ is methyl, ethyl, trifluoro-$C_1$-$C_3$-alkyl, hydroxymethyl, 1-hydroxyethyl, 2-hydroxypropan-2-yl or 2,2,2-trifluoro-1-hydroxyethyl.

Especially preferably, $R^4$ is hydrogen and $R^3$ is a trifluoromethyl or a cyclopropyl radical.

Y either represents a radical

or represents a group

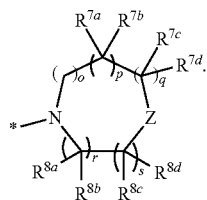

If Y represents $NR^5R^6$ as described above, $R^5$ is preferably $C_1$-$C_6$-alkyl, particularly preferably methyl or ethyl.

$R^6$ is likewise $C_1$-$C_6$-alkyl which may optionally be mono- or polysubstituted, preferably by $C_3$-$C_{10}$-cycloalkyl.

Particularly preferred for $R^6$ are methyl or ethyl which are optionally substituted by $C_3$-$C_{10}$-cycloalkyl. Here, particular preference is given to cyclopropyl.

As an example thereof, mention may be made of cyclopropylmethyl.

Further preferred embodiments for $R^6$ are $C_3$-$C_{10}$-cycloalkyl, heterocycloalkyl, 5- or 6-membered heteroaryl or aryl.

Particular preference is given here to pyridazinyl, phenyl, oxazolyl, piperidinyl and cyclohexyl.

If Y represents $NR^5R^6$, the following radicals may be mentioned as examples for Y: (3-sulphamoylphenyl)amino, [(3R)-piperidin-3-ylamino]ethyl, 1,2-oxazol-4-ylamino, [3-(dimethylsulphamoyl)phenyl]amino, [trans-4-(2-hydroxypropan-2-yl)cyclohexyl]amino, pyridazin-4-ylamino, (cyclopropylmethyl)(methyl)amino.

If Y represents a group of the general formula (II)

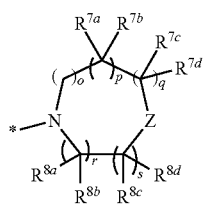

where
o=0, 1 or 2;
p=0, 1, 2 or 3;
q=0 or 1,
where the sum of o, p and q=1, 2 or 3; and
r=0 or 1;
s=0 or 1; and
Z represents $CR^9R^{10}$, $NR^{11}$, O, S or $S(=O)_2$,
then 0 or 1 or 2 is preferred for p.

Here, special preference is given to compounds in which Y represents a group of the general formula (II)

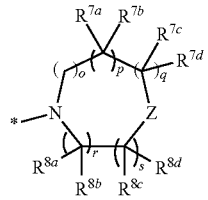

in which
o=0,
p=0 or 1,
q, r and s=1 and
Z represents $CR^9R^{10}$, $NR^{11}$, O, S or $S(=O)_2$.

If Y represents a group of the formula (II) mentioned above, the following groups may be mentioned by way of example:
4-benzoylpiperazin-1-yl, 4-(pyrrolidin-1-yl)piperidin-1-yl, 4-(3-hydroxy-2,2-dimethylpropanoyl)piperazin-1-yl, 4-(methoxyacetyl)piperazin-1-yl, 4-(2-hydroxypropan-2-yl)piperidin-1-yl, 4-(cyclopropylmethyl)piperazin-1-yl, 4-methylpiperazin-1-yl, 4-(cyclopropylcarbonyl)piperazin-1-yl, morpholin-4-yl, 4-(ethoxycarbonyl)piperazin-1-yl, 3-(dimethylamino)azetidin-1-yl, 3-(piperidin-1-yl)azetidin-1-yl, 2-[4-(2-hydroxy-2-methylpropyl)piperidin-1-yl, 4-hydroxy-1,4'-bipiperidin-1'-yl, 4-(dimethylamino)piperidin-1-yl, 4-(2,2,2-trifluoroethyl)piperazin-1-yl, 4-ethyl-3-oxopiperazin-1-yl, 4-(4-fluorobenzoyl)piperazin-1-yl, 4-(pyridin-2-yl)piperazin-1-yl, 4-cyclopentyl-3-oxopiperazin-1-yl, 3-oxo-4-phenylpiperazin-1-yl, 4-(2,2-dimethylpropanoyl)piperazin-1-yl, 4-(2-hydroxy-2-methylpropanoyl)piperazin-1-yl, 4-(1-phenylethyl)piperazin-1-yl]ethyl, 4-(pyridin-3-ylcarbonyl)piperazin-1-yl, 4-isonicotinoylpiperazin-1-yl, 4-(morpholin-4-ylcarbonyl)piperazin-1-yl, 4-[2-(methylamino)-2-oxoethyl]piperazin-1-yl, 4-(pyrazin-2-yl)piperazin-1-yl, 4-(1-hydroxyethyl)piperidin-1-yl, 2-(2-methyl-2,8-diazaspiro[4.5]dec-8-yl, 6-acetyl-2,6-diazaspiro[3.3]hept-2-yl, 3-oxo-2,8-diazaspiro[4.5]dec-8-yl)ethyl, 6-methyl-2,6-diazaspiro[3.5]non-2-yl, 7-oxa-2-azaspiro[3.5]non-2-yl, 1,4'-bipiperidin-1'-yl, 2-[2-(hydroxymethyl)piperidin-1-yl, 3-(hydroxymethyl)piperidin-1-yl, 4-carbamoylpiperidin-1-yl, 3-(dimethylamino)piperidin-1-yl, 3-(morpholin-4-ylmethyl)piperidin-1-yl, 4-[(cyclopropylcarbonyl)amino]piperidin-1-yl, 4-[(5-cyclopropyl-1,2,4-oxadiazol-3-yl)methyl]piperidin-1-yl, 4-(pyrrolidin-1-ylcarbonyl)piperidin-1-yl, 4-(4-methylpiperazin-1-yl)piperidin-1-yl, 4-[2-(morpholin-4-yl)ethyl]piperidin-1-yl, 4-[(5-methyl-1,2,4-oxadiazol-3-yl)methyl]piperidin-1-yl, 3-(pyrrolidin-1-ylmethyl)piperidin-1-yl, 4-(methylsulphonyl)piperidin-1-yl, 4-[2-oxo-2-(pyrrolidin-1-yl)ethyl]piperazin-1-yl, 4-(phenylsulphonyl)piperidin-1-yl, 4-[isonicotinoyl(methyl)amino]piperidin-1-yl, 4-[2-(isopropylamino)-2-oxoethyl]piperazin-1-yl, 4-(1,1-dioxidotetrahydrothiophen-3-yl)piperazin-1-yl, 4-[(methoxyacetyl)(methyl)amino]piperidin-1-yl, 4-(cyclohexylcarbonyl)piperazin-1-yl, 4-[2-(cyclopropylamino)-2-oxoethyl]piperazin-1-yl, 2-hydroxyethyl)piperidin-1-yl, 4-(1H-pyrrol-1-yl)piperidin-1-yl, 4-(3-hydroxypropyl)piperazin-1-yl, 4-carbamoylpiperazin-1-yl, 4-(2-oxopyrrolidin-1-yl)piperidin-1-yl, 4-(2-amino-2-oxoethyl)piperazin-1-yl, 1,1-dioxidothiomorpholin-4-yl, 4-isopropylpiperazin-1-yl, 4-(2-thienylcarbonyl)piperazin-1-yl, 2-cyclopropyl-2-oxoethyl)piperazin-1-yl, 4-[(1-methyl-1H-pyrazol-4-yl)methyl]piperazin-1-yl, 4-[(1,5-dimethyl-1H-pyrazol-3-yl)carbonyl]piperazin-1-yl, 4-(diethylcarbamoyl)piperazin-1-yl, thiomorpholin-4-yl, 4-(2-furylmethyl)piperazin-1-yl, 4-(3-thienylmethyl)piperazin-1-yl, 4'-methyl-1,4'-bipiperidin-1'-yl, 6-methyl-2,6-diazaspiro[3.3]hept-2-yl, 4-cyclopentylpiperazin-1-yl, 4-[2-(2-hydroxyethoxy)ethyl]piperazin-1-yl, 4-(pyridin-4-ylmethyl)piperazin-1-yl, 4-(dimethylsulphamoyl)piperazin-1-yl, 4-(pyridin-4-yl)piperazin-1-yl, 4-(methylsulphonyl)piperazin-1-yl, {4-[2-(1H-imidazol-1-yl)ethyl]piperazin-1-yl, 4-(diethylsulphamoyl)piperazin-1-yl, 4-(pyridin-3-yl)piperazin-1-yl, 4-(piperidin-1-ylsulphonyl)piperazin-1-yl, 4-[(1,5-dimethyl-1H-pyrazol-4-yl)sulphonyl, 4-ethylpiperazin-1-yl, 4-methyl-4-[(4-methylpiperazin-1-yl)carbonyl]piperidin-1-yl, 4-(cyclobutylcarbonyl)piperazin-1-yl, 4-(cyclopentylcarbonyl)piperazin-1-yl, 4-[3-(methylsulphonyl)benzoyl]piperazin-1-yl and 4-[2-methoxy-5-(methylsulphonyl)benzoyl]piperazin-1-yl.

Especially preferably, Y is 4-methylpiperazin-1-yl, 4-ethylpiperazin-1-yl or morpholin-4-yl.

The present invention preferably provides compounds of the general formula (I) in which W represents a group of the general formula (IX)

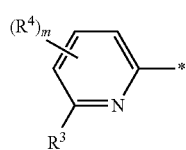

(IX)

in which
m represents 0 and $R^2$, $R^0$ and $R^{13}$ all represent hydrogen and $R^3$ represents trifluoromethyl, ethyl, methyl, cyclopropyl, 2,2,2-trifluoro-1-hydroxyethyl or 1-hydroxyethyl; Y represents 4-methylpiperazin-1-yl, 4-ethylpiperazin-1-yl or morpholin-4-yl, n represents 0 and $R^1$ represents cyclopropylmethoxy, trifluoromethoxy, 2,2,2-trifluoroethoxy, chlorine, ethoxy or methoxy.

Here, $R^1$ particularly preferably represents cyclopropylmethoxy, methoxy or ethoxy.

Here, particular preference is given to compounds in which $R^3$ is a trifluoromethyl or a cyclopropyl radical.

The present invention also provides the following compounds:
N-{2-[2-(4-benzoylpiperazin-1-yl)-2-oxoethyl]-6-methyl-2H-indazol-5-yl}-6-(trifluoromethyl)pyridine-2-carboxamide
6-ethyl-N-(6-methyl-2-{2-oxo-2-[4-(pyrrolidin-1-yl)piperidin-1-yl]ethyl}-2H-indazol-5-yl)pyridine-2-carboxamide
5-fluoro-N-(6-methyl-2-{2-oxo-2-[4-(pyrrolidin-1-yl)piperidin-1-yl]ethyl}-2H-indazol-5-yl)pyridine-2-carboxamide
N-(2-{2-[4-(3-hydroxy-2,2-dimethylpropanoyl)piperazin-1-yl]-2-oxoethyl}-6-methyl-2H-indazol-5-yl)-6-(trifluoromethyl)pyridine-2-carboxamide
N-(2-{2-[4-(methoxyacetyl)piperazin-1-yl]-2-oxoethyl}-6-methyl-2H-indazol-5-yl)-6-(trifluoromethyl)pyridine-2-carboxamide
N-(2-{2-[4-(2-hydroxypropan-2-yl)piperidin-1-yl]-2-oxoethyl}-6-methoxy-2H-indazol-5-yl)-6-(trifluoromethyl)pyridine-2-carboxamide
N-(2-{2-[4-(2-hydroxypropan-2-yl)piperidin-1-yl]-2-oxoethyl}-6-methoxy-2H-indazol-5-yl)-6-methylpyridine-2-carboxamide
N-(2-{2-[4-(cyclopropylmethyl)piperazin-1-yl]-2-oxoethyl}-6-methoxy-2H-indazol-5-yl)-6-(trifluoromethyl)pyridine-2-carboxamide
N-(2-{2-[4-(cyclopropylmethyl)piperazin-1-yl]-2-oxoethyl}-6-methoxy-2H-indazol-5-yl)-6-methylpyridine-2-carboxamide
N-{2-[2-(4-benzoylpiperazin-1-yl)-2-oxoethyl]-6-methoxy-2H-indazol-5-yl}-6-cyclopropylpyridine-2-carboxamide
N-{2-[2-(4-benzoylpiperazin-1-yl)-2-oxoethyl]-6-methoxy-2H-indazol-5-yl}-6-(1-hydroxyethyl)pyridine-2-carboxamide
N-{2-[2-(4-methylpiperazin-1-yl)-2-oxoethyl]-6-(trifluoromethoxy)-2H-indazol-5-yl}-6-(trifluoromethyl)pyridine-2-carboxamide
6-methyl-N-{2-[2-(4-methylpiperazin-1-yl)-2-oxoethyl]-6-(trifluoromethoxy)-2H-indazol-5-yl}pyridine-2-carboxamide
tert-butyl 3-{[4-({2-[2-(4-methylpiperazin-1-yl)-2-oxoethyl]-6-(trifluoromethoxy)-2H-indazol-5-yl}carbamoyl)-1,3-thiazol-2-yl]amino}azetidine-1-carboxylate
N-{6-bromo-2-[2-(4-methylpiperazin-1-yl)-2-oxoethyl]-2H-indazol-5-yl}-6-(trifluoromethyl)pyridine-2-carboxamide
N-{6-bromo-2-[2-(4-methylpiperazin-1-yl)-2-oxoethyl]-2H-indazol-5-yl}-6-methylpyridine-2-carboxamide
N-{6-bromo-2-[2-(4-methylpiperazin-1-yl)-2-oxoethyl]-2H-indazol-5-yl}-2-cyclopropyl-1,3-oxazole-4-carboxamide
tert-butyl 3-{[4-({6-bromo-2-[2-(4-methylpiperazin-1-yl)-2-oxoethyl]-2H-indazol-5-yl}carbamoyl)-1,3-thiazol-2-yl]amino}azetidine-1-carboxylate
2-(azetidin-3-ylamino)-N-{2-[2-(4-methylpiperazin-1-yl)-2-oxoethyl]-6-(trifluoromethoxy)-2H-indazol-5-yl}-1,3-thiazole-4-carboxamide
N-{6-cyano-2-[2-(4-methylpiperazin-1-yl)-2-oxoethyl]-2H-indazol-5-yl}-6-(trifluoromethyl)pyridine-2-carboxamide
6'-methyl-N-{2-[2-(4-methylpiperazin-1-yl)-2-oxoethyl]-2H-indazol-5-yl}-2,3'-bipyridine-6-carboxamide
5'-methyl-N-{2-[2-(4-methylpiperazin-1-yl)-2-oxoethyl]-2H-indazol-5-yl}-2,3'-bipyridine-6-carboxamide
4'-methyl-N-{2-[2-(4-methylpiperazin-1-yl)-2-oxoethyl]-2H-indazol-5-yl}-2,3'-bipyridine-6-carboxamide
6'-methoxy-N-{2-[2-(4-methylpiperazin-1-yl)-2-oxoethyl]-2H-indazol-5-yl}-2,3'-bipyridine-6-carboxamide
6'-acetamido-N-{2-[2-(4-methylpiperazin-1-yl)-2-oxoethyl]-2H-indazol-5-yl}-2,3'-bipyridine-6-carboxamide
N-{2-[2-(4-methylpiperazin-1-yl)-2-oxoethyl]-2H-indazol-5-yl}-6'-nitro-2,3'-bipyridine-6-carboxamide
6'-amino-N-{2-[2-(4-methylpiperazin-1-yl)-2-oxoethyl]-2H-indazol-5-yl}-2,3'-bipyridine-6-carboxamide
N-{2-[2-(4-benzoylpiperazin-1-yl)-2-oxoethyl]-6-fluoro-2H-indazol-5-yl}-6-(trifluoromethyl)pyridine-2-carboxamide
N-(2-{2-[4-(cyclopropylcarbonyl)piperazin-1-yl]-2-oxoethyl}-6-fluoro-2H-indazol-5-yl)-6-(trifluoromethyl)pyridine-2-carboxamide
N-{6-fluoro-2-[2-(4-methylpiperazin-1-yl)-2-oxoethyl]-2H-indazol-5-yl}-6-(trifluoromethyl)pyridine-2-carboxamide
N-(2-{2-[4-(cyclopropylcarbonyl)piperazin-1-yl]-2-oxoethyl}-6-fluoro-2H-indazol-5-yl)-6-methylpyridine-2-carboxamide
N-{6-fluoro-2-[2-(4-methylpiperazin-1-yl)-2-oxoethyl]-2H-indazol-5-yl}-6-methylpyridine-2-carboxamide
N-(2-{2-[4-(cyclopropylcarbonyl)piperazin-1-yl]-2-oxoethyl}-6-fluoro-2H-indazol-5-yl)-6-(1-methyl-1H-pyrazol-4-yl)pyridine-2-carboxamide N-{2-[2-(4-benzoylpiperazin-1-yl)-2-oxoethyl]-6-fluoro-2H-indazol-5-yl}-6-(1-methyl-1H-pyrazol-4-yl)pyridine-2-carboxamide N-{6-fluoro-2-[2-(4-methylpiperazin-1-yl)-2-oxoethyl]-2H-indazol-5-yl}-6-(1-methyl-1H-pyrazol-4-yl)pyridine-2-carboxamide N-{2-[2-(4-benzoylpiperazin-1-yl)-2-oxoethyl]-6-fluoro-2H-indazol-5-yl}-5-fluoro-6-(1-methyl-1H-pyrazol-4-yl)pyridine-2-carboxamide N-(2-{2-[4-(cyclopropylcarbonyl)piperazin-1-yl]-2-oxoethyl}-6-fluoro-2H-indazol-5-yl)-5-fluoro-6-(1-methyl-1H-pyrazol-4-yl)pyridine-2-carboxamide N-{2-[2-(4-benzoylpiperazin-1-yl)-2-oxoethyl]-6-fluoro-2H-indazol-5-yl}-6-(morpholin-4-yl)pyridine-2-carboxamide N-(2-{2-[4-(cyclopropylcarbonyl)piperazin-1-yl]-2-oxoethyl}-6-fluoro-2H-indazol-5-yl)-6-(morpholin-4-yl)pyridine-2-carboxamide N-{6-fluoro-2-[2-(4-methylpiperazin-1-yl)-2-oxoethyl]-2H-indazol-5-yl}-6-(morpholin-4-yl)pyridine-2-carboxamide N-{6-(benzyloxy)-2-[2-(4-methylpiperazin-1-yl)-2-oxoethyl]-2H-indazol-5-yl}-6-(trifluoromethyl)pyridine-2-carboxamide N-{6-isobutoxy-2-[2-(4-methylpiperazin-1-yl)-2-oxoethyl]-2H-indazol-5-yl}-6-(trifluoromethyl)pyridine-2-carboxamide N-{6-isobutoxy-2-[2-(morpholin-4-yl)-2-oxoethyl]-2H-indazol-5-yl}-6-(trifluoromethyl)pyridine-2-carboxamide N-(2-{2-[4-(2-hydroxypropan-2-yl)piperidin-1-yl]-2-oxoethyl}-6-isobutoxy-2H-indazol-5-yl)-6-(trifluoromethyl)pyridine-2-carboxamide N-(2-{2-[(cyclopropylmethyl)(methyl)amino]-2-oxoethyl}-6-isobutoxy-2H-indazol-5-yl)-6-(trifluoromethyl)pyridine-2-carboxamide N-{6-(cyclopropylmethoxy)-2-[2-(4-methylpiperazin-1-yl)-2-oxoethyl]-2H-indazol-5-yl}-6-(trifluoromethyl)pyridine-2-carboxamide N-{6-(cyclopropylmethoxy)-2-[2-(morpholin-4-yl)-2-oxoethyl]-2H-indazol-5-yl}-6-(trifluoromethyl)pyridine-2-carboxamide N-[6-(cyclopropylmethoxy)-2-{2-[4-(2-hydroxypropan-2-yl)piperidin-1-yl]-2-oxoethyl}-2H-indazol-5-yl]-6-(trifluoromethyl)pyridine-2-carboxamide N-(6-(cyclopropylmethoxy)-2-{2-[(cyclopropylmethyl)(methyl)amino]-2-oxoethyl}-2H-indazol-5-yl)-6-(trifluoromethyl)pyridine-2-carboxamide N-{2-[2-(4-methylpiperazin-1-yl)-2-oxoethyl]-6-(pyridin-2-ylmethoxy)-2H-indazol-5-yl}-6-(trifluoromethyl)pyridine-2-carboxamide N-{2-[2-(morpholin-4-yl)-2-oxoethyl]-6-(pyridin-2-ylmethoxy)-2H-indazol-5-yl}-6-(trifluoromethyl)pyridine-2-carboxamide N-[2-{2-[4-(2-hydroxypropan-2-yl)piperidin-1-yl]-2-oxoethyl}-6-(pyridin-2-ylmethoxy)-2H-indazol-5-yl]-6-(trifluoromethyl)pyridine-2-carboxamide N-[2-{2-[(cyclopropylmethyl)(methyl)amino]-2-oxoethyl}-6-(pyridin-2-ylmethoxy)-2H-indazol-5-yl]-6-(trifluoromethyl)pyridine-2-carboxamide N-{2-[2-(4-benzoylpiperazin-1-yl)-2-oxoethyl]-6-chloro-2H-indazol-5-yl}-6-(trifluoromethyl)pyridine-2-carboxamide N-{6-chloro-2-[2-(morpholin-4-yl)-2-oxoethyl]-2H-indazol-5-yl}-6-(trifluoromethyl)pyridine-2-carboxamide ethyl 4-{[6-chloro-5-({[6-(trifluoromethyl)pyridin-2-yl]carbonyl}amino)-2H-indazol-2-yl]acetyl}piperazine-1-carboxylate N-(6-chloro-2-{2-oxo-2-[4-(pyrrolidin-1-yl)piperidin-1-yl]ethyl}-2H-indazol-5-yl)-6-(trifluoromethyl)pyridine-2-carboxamide N-(6-chloro-2-{2-[4-(2-hydroxypropan-2-yl)piperidin-1-yl]-2-oxoethyl}-2H-indazol-5-yl)-6-(trifluoromethyl)pyridine-2-carboxamide N-(6-chloro-2-{2-[4-(3-hydroxy-2,2-dimethylpropanoyl)piperazin-1-yl]-2-oxoethyl}-2H-indazol-5-yl)-6-(trifluoromethyl)pyridine-2-carboxamide N-(6-chloro-2-{2-[3-(dimethylamino)azetidin-1-yl]-2-oxoethyl}-2H-indazol-5-yl)-6-(trifluoromethyl)pyridine-2-carboxamide N-(6-chloro-2-{2-oxo-2-[3-(piperidin-1-yl)azetidin-1-yl]ethyl}-2H-indazol-5-yl)-6-(trifluoromethyl)pyridine-2-carboxamide N-(6-chloro-2-{2-[4-(2-hydroxy-2-methylpropyl)piperidin-1-yl]-2-oxoethyl}-2H-indazol-5-yl)-6-(trifluoromethyl)pyridine-2-carboxamide N-{6-chloro-2-[2-(4-hydroxy-1,4'-bipiperidin-1'-yl)-2-oxoethyl]-2H-indazol-5-yl}-6-(trifluoromethyl)pyridine-2-carboxamide N-{6-methoxy-2-[2-(4-methylpiperazin-1-yl)-2-oxoethyl]-2H-indazol-5-yl}-6-(trifluoromethyl)pyridine-2-carboxamide N-{6-methoxy-2-[2-(morpholin-4-yl)-2-oxoethyl]-2H-indazol-5-yl}-6-(trifluoromethyl)pyridine-2-carboxamide N-(2-{2-[4-(dimethylamino)piperidin-1-yl]-2-oxoethyl}-6-ethoxy-2H-indazol-5-yl)-6-(trifluoromethyl)pyridine-2-carboxamide N-(6-ethoxy-2-{2-oxo-2-[4-(pyrrolidin-1-yl)piperidin-1-yl]ethyl}-2H-indazol-5-yl)-6-(trifluoromethyl)pyridine-2-carboxamide N-{6-ethoxy-2-[2-(4-methylpiperazin-1-yl)-2-oxoethyl]-2H-indazol-5-yl}-6-(trifluoromethyl)pyridine-2-carboxamide N-{2-[2-(4-benzoylpiperazin-1-yl)-2-oxoethyl]-6-ethoxy-2H-indazol-5-yl}-6-(trifluoromethyl)pyridine-2-carboxamide N-(6-ethoxy-2-{2-[4-(2-hydroxypropan-2-yl)piperidin-1-yl]-2-oxoethyl}-2H-indazol-5-yl)-6-(trifluoromethyl)pyridine-2-carboxamide N-{6-ethoxy-2-[2-(morpholin-4-yl)-2-oxoethyl]-2H-indazol-5-yl}-6-(trifluoromethyl)pyridine-2-carboxamide N-{2-[2-(4-benzoylpiperazin-1-yl)-2-oxoethyl]-3-methyl-2H-indazol-5-yl}-6-(trifluoromethyl)pyridine-2-carboxamide N-{2-[3-(4-benzoylpiperazin-1-yl)-3-oxopropyl]-2H-indazol-5-yl}-6-(trifluoromethyl)pyridine-2-carboxamide N-(2-{2-[4-(cyclopropylcarbonyl)piperazin-1-yl]-2-oxoethyl}-2H-indazol-5-yl)-2-(pyridin-3-yl)-1,3-thiazole-4-carboxamide N-(2-{2-[4-(cyclopropylcarbonyl)piperazin-1-yl]-2-oxoethyl}-2H-indazol-5-yl)-2-(pyridin-4-yl)-1,3-thiazole-4-carboxamide N-(2-{2-[4-(cyclopropylcarbonyl)piperazin-1-yl]-2-oxoethyl}-2H-indazol-5-yl)-6-(trifluoromethyl)pyridine-2-carboxamide 6-(azetidin-3-ylamino)-N-(2-{2-[4-(cyclopropylcarbonyl)piperazin-1-yl]-2-oxoethyl}-2H-indazol-5-yl)pyridine-2-carboxamide N-{2-[2-(4-methylpiperazin-1-yl)-2-oxoethyl]-2H-indazol-5-yl}-2-(pyridin-3-yl)-1,3-thiazole-4-carboxamide N-{2-[2-(4-methylpiperazin-1-yl)-2-oxoethyl]-2H-indazol-5-yl}-6-(1-methyl-1H-pyrazol-4-yl)pyridine-2-carboxamide N-{2-[2-(4-methylpiperazin-1-yl)-2-oxoethyl]-2H-indazol-5-yl}-6-(1H-pyrazol-4-yl)pyridine-2-carboxamide 6-(1,3-dimethyl-1H-pyrazol-4-yl)-N-{2-[2-(4-methylpiperazin-1-yl)-2-oxoethyl]-2H-indazol-5-yl}pyridine-2-carboxamide N-{2-[2-(4-methylpiperazin-1-yl)-2-oxoethyl]-2H-indazol-5-yl}-6-[3-(trifluoromethyl)-1H-pyrazol-4-yl]pyridine-2-carboxamide 6-ethyl-N-{2-[2-(4-methylpiperazin-1-yl)-2-oxoethyl]-2H-indazol-5-yl}pyridine-2-carboxamide 6-(1-methyl-1H-pyrazol-4-yl)-N-(2-{2-oxo-2-[4-(2,2,2-trifluoroethyl)piperazin-1-yl]ethyl}-2H-indazol-5-yl)pyridine-2-carboxamide N-(2-{2-oxo-2-[4-(2,2,2-trifluoroethyl)piperazin-1-yl]ethyl}-2H-indazol-5-yl)-6-(trifluoromethyl)pyridine-2-carboxamide N-{2-[2-(4-ethyl-3-oxopiperazin-1-yl)-2-oxoethyl]-2H-indazol-5-yl}-6-(1-methyl-1H-pyrazol-4-yl)pyridine-2-carboxamide N-{2-[2-(4-benzoylpiperazin-1-yl)-2-oxoethyl]-2H-indazol-5-yl}-6-(trifluoromethyl)pyridine-2-carboxamide N-{2-[2-(4-benzoylpiperazin-1-yl)-2-oxoethyl]-2H-indazol-5-yl}-6-methylpyridine-2-carboxamide N-{2-[2-(4-benzoylpiperazin-1-yl)-2-oxoethyl]-2H-indazol-5-yl}-6-(morpholin-4-yl)pyridine-2-carboxamide N-{2-[2-(4-benzoylpiperazin-1-yl)-2-oxoethyl]-2H-indazol-5-yl}-2-(pyridin-4-yl)-1,3-thiazole-4-carboxamide N-{2-[2-(4-benzoylpiperazin-1-yl)-2-oxoethyl]-2H-indazol-5-yl}-6-chloropyridine-2-carboxamide N-{2-[2-(4-benzoylpiperazin-1-yl)-2-oxoethyl]-2H-indazol-5-yl}-2-methyl-1,3-oxazole-5-carboxamide 6-amino-N-{2-[2-(4-benzoylpiperazin-1-yl)-2-oxoethyl]-2H-indazol-5-yl}pyridine-2-carboxamide N-{2-[2-(4-benzoylpiperazin-1-yl)-2-oxoethyl]-2H-indazol-5-yl}-2-methyl-1,3-oxazole-4-carboxamide N-{2-[2-(4-benzoylpiperazin-1-yl)-2-oxoethyl]-2H-indazol-5-yl}-6-methoxypyridine-2-carboxamide N-{2-[2-(4-benzoylpiperazin-1-yl)-2-oxoethyl]-2H-indazol-5-yl}-2-cyclopropyl-1,3-oxazole-4-carboxamide N-{2-[2-(4-benzoylpiperazin-1-yl)-2-oxoethyl]-2H-indazol-5-yl}-6-(4H-1,2,4-triazol-4-yl)pyridine-2-carboxamide N-{2-[2-(4-benzoylpiperazin-1-yl)-2-oxoethyl]-2H-indazol-5-yl}-2-phenyl-2H-1,2,3-triazole-4-carboxamide N-{2-[2-(4-benzoylpiperazin-1-yl)-2-oxoethyl]-2H-indazol-5-yl}-6-(1-methyl-1H-pyrazol-5-yl)pyridine-2-carboxamide N-{2-[2-(4-benzoylpiperazin-1-yl)-2-oxoethyl]-2H-indazol-5-yl}-2-(trifluoromethyl)-1,3-thiazole-4-carboxamide N-{2-[2-(4-benzoylpiperazin-1-yl)-2-oxoethyl]-2H-indazol-5-yl}-6-(1H-pyrazol-1-yl)pyridine-2-carboxamide N-{2-[2-(4-benzoylpiperazin-1-yl)-2-oxoethyl]-2H-indazol-5-yl}-6-(1-methyl-1H-pyrazol-4-yl)pyridine-2-carboxamide N-{2-[2-(4-benzoylpiperazin-1-yl)-2-oxoethyl]-2H-indazol-5-yl}-1-ethyl-1H-pyrazole-3-carboxamide N-{2-[2-(4-benzoylpiperazin-1-yl)-2-oxoethyl]-2H-indazol-5-yl}-6-(4-chloro-1H-pyrazol-1-yl)pyridine-2-carboxamide N-{2-[2-(4-benzoylpiperazin-1-yl)-2-oxoethyl]-2H-indazol-5-yl}-4-(trifluoromethyl)-1,3-thiazole-2-carboxamide N-{2-[2-(4-benzoylpiperazin-1-yl)-2-oxoethyl]-2H-indazol-5-yl}-6-(1,3-dimethyl-1H-pyrazol-4-yl)pyridine-2-carboxamide N-{2-[2-(4-benzoylpiperazin-1-yl)-2-oxoethyl]-2H-indazol-5-yl}-2,4'-bipyridine-6-carboxamide N-{2-[2-(4-benzoylpiperazin-1-yl)-2-oxoethyl]-2H-indazol-5-yl}-6-(1H-pyrazol-4-yl)pyridine-2-carboxamide N-{2-[2-(4-benzoylpiperazin-1-yl)-2-oxoethyl]-2H-indazol-5-yl}-5-fluoro-6-(1-methyl-1H-pyrazol-4-yl)pyridine-2-carboxamide N-{2-[2-(4-benzoylpiperazin-1-yl)-2-oxoethyl]-2H-indazol-5-yl}-6-(3-methyl-1H-pyrazol-4-yl)pyridine-2-carboxamide N-{2-[2-(4-benzoylpiperazin-1-yl)-2-oxoethyl]-2H-indazol-5-yl}-6-(1H-1,2,4-triazol-1-yl)pyridine-2-carboxamide N-{2-[2-(4-benzoylpiperazin-1-yl)-2-oxoethyl]-2H-indazol-5-yl}-6-[3-(trifluoromethyl)-1H-pyrazol-4-yl]pyridine-2-carboxamide N-{2-[2-(4-benzoylpiperazin-1-yl)-2-oxoethyl]-2H-indazol-5-yl}-6-ethoxypyridine-2-carboxamide N-{2-[2-(4-benzoylpiperazin-1-yl)-2-oxoethyl]-2H-indazol-5-yl}-6-(cyclopropylmethoxy)pyridine-2-carboxamide N-{2-[2-(4-benzoylpiperazin-1-yl)-2-oxoethyl]-2H-indazol-5-yl}-6-ethylpyridine-2-carboxamide N-{2-[2-(4-benzoylpiperazin-1-yl)-2-oxoethyl]-2H-indazol-5-yl}-2-(4-methoxyphenyl)-1,3-thiazole-4-carboxamide N-{2-[2-(4-benzoylpiperazin-1-yl)-2-oxoethyl]-2H-indazol-5-yl}-2-bromo-1,3-thiazole-4-carboxamide N-{2-[2-(4-benzoylpiperazin-1-yl)-2-oxoethyl]-2H-indazol-5-yl}-2-(4-fluorophenyl)-1,3-thiazole-4-carboxamide N-{2-[2-(4-benzoylpiperazin-1-yl)-2-oxoethyl]-2H-indazol-5-yl}-6-fluoropyridine-2-carboxamide N-{2-[2-(4-benzoylpiperazin-1-yl)-2-oxoethyl]-2H-indazol-5-yl}-6-bromopyridine-2-carboxamide N-(2-{2-[4-(4-fluorobenzoyl)piperazin-1-yl]-2-oxoethyl}-2H-indazol-5-yl)-6-(trifluoromethyl)pyridine-2-carboxamide N-(2-{2-oxo-2-[4-(pyridin-2-yl)piperazin-1-yl]ethyl}-2H-indazol-5-yl)-6-(trifluoromethyl)pyridine-2-carboxamide N-(2-{2-[4-(methoxyacetyl)piperazin-1-yl]-2-oxoethyl}-2H-indazol-5-yl)-6-(trifluoromethyl)pyridine-2-carboxamide N-{2-[2-(4-cyclopentyl-3-oxopiperazin-1-yl)-2-oxoethyl]-2H-indazol-5-yl}-6-(trifluoromethyl)pyridine-2-carboxamide N-{2-[2-oxo-2-(3-oxo-4-phenylpiperazin-1-yl)ethyl]-2H-indazol-5-yl}-6-(trifluoromethyl)pyridine-2-carboxamide N-(2-{2-[4-(2,2-dimethylpropanoyl)piperazin-1-yl]-2-oxoethyl}-2H-indazol-5-yl)-6-(trifluoromethyl)pyridine-2-carboxamide N-(2-{2-[4-(cyclopropylmethyl)piperazin-1-yl]-2-oxoethyl}-2H-indazol-5-yl)-6-(trifluoromethyl)pyridine-2-carboxamide N-{2-[2-oxo-2-(pyridazin-4-ylamino)ethyl]-2H-indazol-5-yl}-6-(trifluoromethyl)pyridine-2-carboxamide N-(2-{2-[4-(2-hydroxy-2-methylpropanoyl)piperazin-1-yl]-2-oxoethyl}-2H-indazol-5-yl)-6-(trifluoromethyl)pyridine-2-carboxamide N-(2-{2-oxo-2-[4-(1-phenylethyl)piperazin-1-yl]ethyl}-2H-indazol-5-yl)-6-(trifluoromethyl)pyridine-2-carboxamide N-(2-{2-oxo-2-[4-(pyridin-3-ylcarbonyl)piperazin-1-yl]ethyl}-2H-indazol-5-yl)-6-(trifluoromethyl)pyridine-2-carboxamide N-{2-[2-(4-isonicotinoylpiperazin-1-yl)-2-oxoethyl]-2H-indazol-5-yl}-6-(trifluoromethyl)pyridine-2-carboxamide N-(2-{2-[4-(morpholin-4-ylcarbonyl)piperazin-1-yl]-2-oxoethyl}-2H-indazol-5-yl)-6-(trifluoromethyl)pyridine-2-carboxamide N-[2-(2-{4-[2-(methylamino)-2-oxoethyl]piperazin-1-yl}-2-oxoethyl)-2H-indazol-5-yl]-6-(trifluoromethyl)pyridine-2-carboxamide N-(2-{2-oxo-2-[4-(pyrazin-2-yl)piperazin-1-yl]ethyl}-2H-indazol-5-yl)-6-(trifluoromethyl)pyridine-2-carboxamide
N-(2-{2-[4-(1-hydroxyethyl)piperidin-1-yl]-2-oxoethyl}-2H-indazol-5-yl)-6-(trifluoromethyl)pyridine-2-carboxamide
N-{2-[2-(2-methyl-2,8-diazaspiro[4.5]dec-8-yl)-2-oxoethyl]-2H-indazol-5-yl}-6-(trifluoromethyl)pyridine-2-carboxamide
N-{2-[2-(6-acetyl-2,6-diazaspiro[3.3]hept-2-yl)-2-oxoethyl]-2H-indazol-5-yl}-6-(trifluoromethyl)pyridine-2-carboxamide
N-{2-[2-oxo-2-(3-oxo-2,8-diazaspiro[4.5]dec-8-yl)ethyl]-2H-indazol-5-yl}-6-(trifluoromethyl)pyridine-2-carboxamide
N-{2-[2-(6-methyl-2,6-diazaspiro[3.5]non-2-yl)-2-oxoethyl]-2H-indazol-5-yl}-6-(trifluoromethyl)pyridine-2-carboxamide
N-{2-[2-(7-oxa-2-azaspiro[3.5]non-2-yl)-2-oxoethyl]-2H-indazol-5-yl}-6-(trifluoromethyl)pyridine-2-carboxamide
N-{2-[2-(1,4'-bipiperidin-1'-yl)-2-oxoethyl]-2H-indazol-5-yl}-6-(trifluoromethyl)pyridine-2-carboxamide
N-(2-{2-[2-(hydroxymethyl)piperidin-1-yl]-2-oxoethyl}-2H-indazol-5-yl)-6-(trifluoromethyl)pyridine-2-carboxamide
N-(2-{2-[3-(hydroxymethyl)piperidin-1-yl]-2-oxoethyl}-2H-indazol-5-yl)-6-(trifluoromethyl)pyridine-2-carboxamide
N-{2-[2-(4-carbamoylpiperidin-1-yl)-2-oxoethyl]-2H-indazol-5-yl}-6-(trifluoromethyl)pyridine-2-carboxamide
N-(2-{2-[3-(dimethylamino)piperidin-1-yl]-2-oxoethyl}-2H-indazol-5-yl)-6-(trifluoromethyl)pyridine-2-carboxamide
N-{2-[2-[3-(morpholin-4-ylmethyl)piperidin-1-yl]-2-oxoethyl}-2H-indazol-5-yl)-6-(trifluoromethyl)pyridine-2-carboxamide
N-[2-(2-{4-[(cyclopropylcarbonyl)amino]piperidin-1-yl}-2-oxoethyl)-2H-indazol-5-yl]-6-(trifluoromethyl)pyridine-2-carboxamide
N-[2-(2-{4-(3-ethyl-1,2,4-oxadiazol-5-yl)piperidin-1-yl]-2-oxoethyl}-2H-indazol-5-yl)-6-(trifluoromethyl)pyridine-2-carboxamide
N-(2-(2-{4-[(5-cyclopropyl-1,2,4-oxadiazol-3-yl)methyl]piperidin-1-yl}-2-oxoethyl)-2H-indazol-5-yl]-6-(trifluoromethyl)pyridine-2-carboxamide
N-(2-{2-oxo-2-[4-(pyrrolidin-1-ylcarbonyl)piperidin-1-yl]ethyl}-2H-indazol-5-yl)-6-(trifluoromethyl)pyridine-2-carboxamide
N-(2-{2-[4-(4-methylpiperazin-1-yl)piperidin-1-yl]-2-oxoethyl}-2H-indazol-5-yl)-6-(trifluoromethyl)pyridine-2-carboxamide
N-[2-(2-{4-[2-(morpholin-4-yl)ethyl]piperidin-1-yl}-2-oxoethyl)-2H-indazol-5-yl]-6-(trifluoromethyl)pyridine-2-carboxamide
N-[2-(2-{4-[(5-methyl-1,2,4-oxadiazol-3-yl)methyl]piperidin-1-yl}-2-oxoethyl)-2H-indazol-5-yl]-6-(trifluoromethyl)pyridine-2-carboxamide
N-(2-{2-oxo-2-[3-(pyrrolidin-1-ylmethyl)piperidin-1-yl]ethyl}-2H-indazol-5-yl)-6-(trifluoromethyl)pyridine-2-carboxamide
N-[2-(2-{[3-(dimethylsulphamoyl)phenyl]amino}-2-oxoethyl)-2H-indazol-5-yl]-6-(trifluoromethyl)pyridine-2-carboxamide
N-{2-[2-(1,2-oxazol-4-ylamino)-2-oxoethyl]-2H-indazol-5-yl}-6-(trifluoromethyl)pyridine-2-carboxamide
N-(2-{2-[4-(methylsulphonyl)piperidin-1-yl]-2-oxoethyl}-2H-indazol-5-yl)-6-(trifluoromethyl)pyridine-2-carboxamide
N-[2-(2-oxo-2-{4-[2-oxo-2-(pyrrolidin-1-yl)ethyl]piperazin-1-yl}ethyl)-2H-indazol-5-yl]-6-(trifluoromethyl)pyridine-2-carboxamide
N-(2-{2-oxo-2-[4-(phenylsulphonyl)piperidin-1-yl]ethyl}-2H-indazol-5-yl)-6-(trifluoromethyl)pyridine-2-carboxamide
N-(2-{2-oxo-2-[(3-sulphamoylphenyl)amino]ethyl}-2H-indazol-5-yl)-6-(trifluoromethyl)pyridine-2-carboxamide
N-[2-(2-{4-[isonicotinoyl(methyl)amino]piperidin-1-yl}-2-oxoethyl)-2H-indazol-5-yl]-6-(trifluoromethyl)pyridine-2-carboxamide
N-[2-(2-{4-[2-(isopropylamino)-2-oxoethyl]piperazin-1-yl}-2-oxoethyl)-2H-indazol-5-yl]-6-(trifluoromethyl)pyridine-2-carboxamide
N-(2-{2-[4-(1,1-dioxidotetrahydrothiophen-3-yl)piperazin-1-yl]-2-oxoethyl}-2H-indazol-5-yl)-6-(trifluoromethyl)pyridine-2-carboxamide
N-[2-(2-{4-[(methoxyacetyl)(methyl)amino]piperidin-1-yl}-2-oxoethyl)-2H-indazol-5-yl]-6-(trifluoromethyl)pyridine-2-carboxamide
ethyl 4-{[5-({[6-(trifluoromethyl)pyridin-2-yl]carbonyl}amino)-2H-indazol-2-yl]acetyl}piperazine-1-carboxylate
N-(2-{2-[4-(cyclohexylcarbonyl)piperazin-1-yl]-2-oxoethyl}-2H-indazol-5-yl)-6-(trifluoromethyl)pyridine-2-carboxamide
N-[2-(2-{4-[2-(cyclopropylamino)-2-oxoethyl]piperazin-1-yl}-2-oxoethyl)-2H-indazol-5-yl]-6-(trifluoromethyl)pyridine-2-carboxamide
N-(2-{2-[2-(2-hydroxyethyl)piperidin-1-yl]-2-oxoethyl}-2H-indazol-5-yl)-6-(trifluoromethyl)pyridine-2-carboxamide
N-(2-{2-oxo-2-[4-(pyrrolidin-1-yl)piperidin-1-yl]ethyl}-2H-indazol-5-yl)-6-(trifluoromethyl)pyridine-2-carboxamide
N-(2-{2-oxo-2-[4-(1H-pyrrol-1-yl)piperidin-1-yl]ethyl}-2H-indazol-5-yl)-6-(trifluoromethyl)pyridine-2-carboxamide
N-(2-{2-[4-(3-hydroxypropyl)piperazin-1-yl]-2-oxoethyl}-2H-indazol-5-yl)-6-(trifluoromethyl)pyridine-2-carboxamide
4-{[5-({[6-(trifluoromethyl)pyridin-2-yl]carbonyl}amino)-2H-indazol-2-yl]acetyl}piperazine-1-carboxamide
N-(2-{2-oxo-2-[4-(2-oxopyrrolidin-1-yl)piperidin-1-yl]ethyl}-2H-indazol-5-yl)-6-(trifluoromethyl)pyridine-2-carboxamide
N-{2-[2-(morpholin-4-yl)-2-oxoethyl]-2H-indazol-5-yl}-6-(trifluoromethyl)pyridine-2-carboxamide
N-(2-{2-[4-(2-amino-2-oxoethyl)piperazin-1-yl]-2-oxoethyl}-2H-indazol-5-yl)-6-(trifluoromethyl)pyridine-2-carboxamide
N-{2-[2-(1,1-dioxidothiomorpholin-4-yl)-2-oxoethyl]-2H-indazol-5-yl}-6-(trifluoromethyl)pyridine-2-carboxamide
N-{2-[2-(4-isopropylpiperazin-1-yl)-2-oxoethyl]-2H-indazol-5-yl}-6-(trifluoromethyl)pyridine-2-carboxamide
N-(2-{2-oxo-2-[4-(2-thienylcarbonyl)piperazin-1-yl]ethyl}-2H-indazol-5-yl)-6-(trifluoromethyl)pyridine-2-carboxamide
N-(2-{2-[4-(2-cyclopropyl-2-oxoethyl)piperazin-1-yl]-2-oxoethyl}-2H-indazol-5-yl)-6-(trifluoromethyl)pyridine-2-carboxamide
N-[2-(2-{4-[(1-methyl-1H-pyrazol-4-yl)methyl]piperazin-1-yl}-2-oxoethyl)-2H-indazol-5-yl]-6-(trifluoromethyl)pyridine-2-carboxamide
N-[2-(2-{4-[(1,5-dimethyl-1H-pyrazol-3-yl)carbonyl]piperazin-1-yl}-2-oxoethyl)-2H-indazol-5-yl]-6-(trifluoromethyl)pyridine-2-carboxamide N,N-diethyl-4-{[5-({[6-(trifluoromethyl)pyridin-2-yl]carbonyl}amino)-2H-indazol-2-yl]acetyl}piperazine-1-carboxamide N-{2-[2-oxo-2-(thiomorpholin-4-yl)ethyl]-2H-indazol-5-yl}-6-(trifluoromethyl)pyridine-2-carboxamide N-(2-{2-[4-(2-furylmethyl)piperazin-1-yl]-2-oxoethyl}-2H-indazol-5-yl)-6-(trifluoromethyl)pyridine-2-carboxamide N-(2-{2-oxo-2-[4-(3-thienylmethyl)piperazin-1-yl]ethyl}-2H-indazol-5-yl)-6-(trifluoromethyl)pyridine-2-carboxamide N-{2-[2-(4'-methyl-1,4'-bipiperidin-1'-yl)-2-oxoethyl]-2H-indazol-5-yl}-6-(trifluoromethyl)pyridine-2-carboxamide N-{2-[2-(6-methyl-2,6-diazaspiro[3.3]hept-2-yl)-2-oxoethyl]-2H-indazol-5-yl}-6-(trifluoromethyl)pyridine-2-carboxamide N-{2-[2-(4-cyclopentylpiperazin-1-yl)-2-oxoethyl]-2H-indazol-5-yl}-6-(trifluoromethyl)pyridine-2-carboxamide N-[2-(2-{4-[2-(2-hydroxyethoxy)ethyl]piperazin-1-yl}-2-oxoethyl)-2H-indazol-5-yl]-6-(trifluoromethyl)pyridine-2-carboxamide N-(2-{2-oxo-2-[4-(pyridin-4-ylmethyl)piperazin-1-yl]ethyl}-2H-indazol-5-yl)-6-(trifluoromethyl)pyridine-2-carboxamide N-(2-{2-[4-(dimethylsulphamoyl)piperazin-1-yl]-2-oxoethyl}-2H-indazol-5-yl)-6-(trifluoromethyl)pyridine-2-carboxamide N-(2-{2-oxo-2-[4-(pyridin-4-yl)piperazin-1-yl]ethyl}-2H-indazol-5-yl)-6-(trifluoromethyl)pyridine-2-carboxamide N-(2-{2-[4-(methylsulphonyl)piperazin-1-yl]-2-oxoethyl}-2H-indazol-5-yl)-6-(trifluoromethyl)pyridine-2-carboxamide formic acid N-[2-(2-{4-[2-(1H-imidazol-1-yl)ethyl]piperazin-1-yl}-2-oxoethyl)-2H-indazol-5-yl]-6-(trifluoromethyl)pyridine-2-carboxamide (1:1)

N-(2-{2-[4-(diethylsulphamoyl)piperazin-1-yl]-2-oxoethyl}-2H-indazol-5-yl)-6-(trifluoromethyl)pyridine-2-carboxamide N-(2-{2-oxo-2-[4-(pyridin-3-yl)piperazin-1-yl]ethyl}-2H-indazol-5-yl)-6-(trifluoromethyl)pyridine-2-carboxamide N-(2-{2-oxo-2-[4-(piperidin-1-ylsulphonyl)piperazin-1-yl]ethyl}-2H-indazol-5-yl)-6-(trifluoromethyl)pyridine-2-carboxamide N-[2-(2-{4-[(1,5-dimethyl-1H-pyrazol-4-yl)sulphonyl]piperazin-1-yl}-2-oxoethyl)-2H-indazol-5-yl]-6-(trifluoromethyl)pyridine-2-carboxamide N-(2-{2-[4-(cyclopropylmethyl)piperazin-1-yl]-2-oxoethyl}-2H-indazol-5-yl)-6-(1-methyl-1H-pyrazol-4-yl)pyridine-2-carboxamide N-(2-{2-[4-(2-hydroxypropan-2-yl)piperidin-1-yl]-2-oxoethyl}-2H-indazol-5-yl)-6-(1-methyl-1H-pyrazol-4-yl)pyridine-2-carboxamide 6-(1-methyl-1H-pyrazol-4-yl)-N-(2-{2-oxo-2-[4-(pyrrolidin-1-yl)piperidin-1-yl]ethyl}-2H-indazol-5-yl)pyridine-2-carboxamide N-{2-[2-(4-ethylpiperazin-1-yl)-2-oxoethyl]-2H-indazol-5-yl}-6-(1-methyl-1H-pyrazol-4-yl)pyridine-2-carboxamide N-(2-{2-[4-(dimethylamino)piperidin-1-yl]-2-oxoethyl}-2H-indazol-5-yl)-6-(1-methyl-1H-pyrazol-4-yl)pyridine-2-carboxamide N-(2-{2-[(cyclopropylmethyl)(methyl)amino]-2-oxoethyl}-6-methoxy-2H-indazol-5-yl)-6-methylpyridine-2-carboxamide N-(2-{2-[(cyclopropylmethyl)(methyl)amino]-2-oxoethyl}-6-ethoxy-2H-indazol-5-yl)-6-(trifluoromethyl)pyridine-2-carboxamide N-(2-{2-[(cyclopropylmethyl)(methyl)amino]-2-oxoethyl}-6-methoxy-2H-indazol-5-yl)-6-(trifluoromethyl)pyridine-2-carboxamide 6-cyclopropyl-N-(2-{2-[4-(2-hydroxypropan-2-yl)piperidin-1-yl]-2-oxoethyl}-6-methoxy-2H-indazol-5-yl)pyridine-2-carboxamide 6-(1-hydroxyethyl)-N-(2-{2-[4-(2-hydroxypropan-2-yl)piperidin-1-yl]-2-oxoethyl}-6-methoxy-2H-indazol-5-yl)pyridine-2-carboxamide 6-(azetidin-3-ylamino)-N-{2-[2-(4-benzoylpiperazin-1-yl)-2-oxoethyl]-2H-indazol-5-yl}pyridine-2-carboxamide 6-[(azetidin-2-ylmethyl)amino]-N-{2-[2-(4-benzoylpiperazin-1-yl)-2-oxoethyl]-2H-indazol-5-yl}pyridine-2-carboxamide N-{2-[2-(4-benzoylpiperazin-1-yl)-2-oxoethyl]-2H-indazol-5-yl}-6-(3-hydroxyazetidin-1-yl)pyridine-2-carboxamide 6-[(2R,6S)-2,6-dimethylmorpholin-4-yl]-N-(6-methyl-2-{2-oxo-2-[4-(pyrrolidin-1-yl)piperidin-1-yl]ethyl}-2H-indazol-5-yl)pyridine-2-carboxamide N-[2-(2-{4-methyl-4-[(4-methylpiperazin-1-yl)carbonyl]piperidin-1-yl}-2-oxoethyl)-2H-indazol-5-yl]-6-(trifluoromethyl)pyridine-2-carboxamide N-(6-chloro-2-{2-oxo-2-[(3R)-piperidin-3-ylamino]ethyl}-2H-indazol-5-yl)-6-(trifluoromethyl)pyridine-2-carboxamide N-(2-{2-[4-(cyclopropylcarbonyl)piperazin-1-yl]-2-oxoethyl}-6-isopropoxy-2H-indazol-5-yl)-6-methylpyridine-2-carboxamide N-(2-{2-[4-(cyclopropylcarbonyl)piperazin-1-yl]-2-oxoethyl}-6-isopropoxy-2H-indazol-5-yl)-6-(trifluoromethyl)pyridine-2-carboxamide N-{2-[2-(4-benzoylpiperazin-1-yl)-2-oxoethyl]-6-isopropoxy-2H-indazol-5-yl}-6-methylpyridine-2-carboxamide N-{2-[2-(4-benzoylpiperazin-1-yl)-2-oxoethyl]-6-isopropoxy-2H-indazol-5-yl}-6-(trifluoromethyl)pyridine-2-carboxamide N-{6-isopropoxy-2-[2-(4-methylpiperazin-1-yl)-2-oxoethyl]-2H-indazol-5-yl}-6-(trifluoromethyl)pyridine-2-carboxamide N-{6-isopropoxy-2-[2-(4-methylpiperazin-1-yl)-2-oxoethyl]-2H-indazol-5-yl}-6-methylpyridine-2-carboxamide N-(2-{2-[4-(cyclobutylcarbonyl)piperazin-1-yl]-2-oxoethyl}-2H-indazol-5-yl)-6-(trifluoromethyl)pyridine-2-carboxamide N-(2-{2-[4-(cyclopentylcarbonyl)piperazin-1-yl]-2-oxoethyl}-2H-indazol-5-yl)-6-(trifluoromethyl)pyridine-2-carboxamide N-[2-(2-{4-[3-(methylsulphonyl)benzoyl]piperazin-1-yl}-2-oxoethyl)-2H-indazol-5-yl]-6-(trifluoromethyl)pyridine-2-carboxamide N-[2-(2-{4-[2-methoxy-5-(methylsulphonyl)benzoyl]piperazin-1-yl}-2-oxoethyl)-2H-indazol-5-yl]-6-(trifluoromethyl)pyridine-2-carboxamide 6-bromo-N-(6-methyl-2-{2-oxo-2-[4-(pyrrolidin-1-yl)piperidin-1-yl]ethyl}-2H-indazol-5-yl)pyridine-2-carboxamide 2-(4-methoxyphenyl)-N-(6-methyl-2-{2-oxo-2-[4-(pyrrolidin-1-yl)piperidin-1-yl]ethyl}-2H-indazol-5-yl)-1,3-thiazole-4-carboxamide 2-(4-fluorophenyl)-N-(6-methyl-2-{2-oxo-2-[4-(pyrrolidin-1-yl)piperidin-1-yl]ethyl}-2H-indazol-5-yl)-1,3-thiazole-4-carboxamide N-(6-methyl-2-{2-oxo-2-[4-(pyrrolidin-1-yl)piperidin-1-yl]ethyl}-2H-indazol-5-yl)-6-(trifluoromethyl)pyridine-2-carboxamide 6-bromo-N-{2-[2-(4-methylpiperazin-1-yl)-2-oxoethyl]-2H-indazol-5-yl}pyridine-2-carboxamide 6-bromo-N-{2-[2-(4-methylpiperazin-1-yl)-2-oxoethyl]-6-(trifluoromethoxy)-2H-indazol-5-yl}pyridine-2-carboxamide N-{2-[2-(4-methylpiperazin-1-yl)-2-oxoethyl]-6-(trifluoromethoxy)-2H-indazol-5-yl}-6-(4H-1,2,4-triazol-4-yl)pyridine-2-carboxamide 2-bromo-N-{6-bromo-2-[2-(4-methylpiperazin-1-yl)-2-oxoethyl]-2H-indazol-5-yl}-1,3-thiazole-4-carboxamide N-{6-hydroxy-2-[2-(4-methylpiperazin-1-yl)-2-oxoethyl]-2H-indazol-5-yl}-6-(trifluoromethyl)pyridine-2-carboxamide N-[6-(benzyloxy)-2-{2-[4-(2-hydroxypropan-2-yl)piperidin-1-yl]-2-oxoethyl}-2H-indazol-5-yl]-6-methylpyridine-2-carboxamide 6-bromo-N-{6-bromo-2-[2-(4-methylpiperazin-1-yl)-2-oxoethyl]-2H-indazol-5-yl}pyridine-2-carboxamide N-{6-(benzyloxy)-2-[2-(4-methylpiperazin-1-yl)-2-oxoethyl]-2H-indazol-5-yl}-6-methylpyridine-2-carboxamide 2-(azetidin-3-ylamino)-N-{2-[2-(4-benzoylpiperazin-1-yl)-2-oxoethyl]-2H-indazol-5-yl}-1,3-thiazole-4-carboxamide 6-acetamido-N-{6-methoxy-2-[2-(morpholin-4-yl)-2-oxoethyl]-2H-indazol-5-yl}pyridine-2-carboxamide 6-(dimethylamino)-N-(2-{2-[4-(2-hydroxypropan-2-yl)piperidin-1-yl]-2-oxoethyl}-6-methoxy-2H-indazol-5-yl)pyridine-2-carboxamide 6-(dimethylamino)-N-{6-methoxy-2-[2-(morpholin-4-yl)-2-oxoethyl]-2H-indazol-5-yl}pyridine-2-carboxamide 6-acetamido-N-(2-{2-[4-(2-hydroxypropan-2-yl)piperidin-1-yl]-2-oxoethyl}-6-methoxy-2H-indazol-5-yl)pyridine-2-carboxamide 6-(dimethylamino)-N-{6-methoxy-2-[2-(4-methylpiperazin-1-yl)-2-oxoethyl]-2H-indazol-5-yl}pyridine-2-carboxamide N-{2-[2-(4-methylpiperazin-1-yl)-2-oxoethyl]-2H-indazol-5-yl}-6-[3-(methylsulphonyl)phenyl]pyridine-2-carboxamide N-{2-[1-(4-benzoylpiperazin-1-yl)-1-oxopropan-2-yl]-2H-indazol-5-yl}-6-(trifluoromethyl)pyridine-2-carboxamide N-[6-chloro-2-(2-{([trans-4-(2-hydroxypropan-2-yl)cyclohexyl]amino}-2-oxoethyl)-2H-indazol-5-yl]-6-(trifluoromethyl)pyridine-2-carboxamide 6-(2-hydroxypropan-2-yl)-N-{6-methoxy-2-[2-(morpholin-4-yl)-2-oxoethyl]-2H-indazol-5-yl}pyridine-2-carboxamide N-{6-chloro-2-[2-(3,3-difluoropyrrolidin-1-yl)-2-oxoethyl]-2H-indazol-5-yl}-6-(trifluoromethyl)pyridine-2-carboxamide N-{6-chloro-2-[2-oxo-2-(pyrrolidin-1-yl)ethyl]-2H-indazol-5-yl}-6-(trifluoromethyl)pyridine-2-carboxamide N-{6-chloro-2-[2-(2-oxa-7-azaspiro[3.5]non-7-yl)-2-oxoethyl]-2H-indazol-5-yl}-6-(trifluoromethyl)pyridine-2-carboxamide N-(6-chloro-2-{2-[4-(2-hydroxy-2-methylpropyl)piperazin-1-yl]-2-oxoethyl}-2H-indazol-5-yl)-6-(trifluoromethyl)pyridine-2-carboxamide N-{6-methoxy-2-[2-oxo-2-(pyrrolidin-1-yl)ethyl]-2H-indazol-5-yl}-6-(trifluoromethyl)pyridine-2-carboxamide N-{2-[2-(3,3-difluoropyrrolidin-1-yl)-2-oxoethyl]-6-methoxy-2H-indazol-5-yl}-6-(trifluoromethyl)pyridine-2-carboxamide 6-(difluoromethyl)-N-{6-methoxy-2-[2-(morpholin-4-yl)-2-oxoethyl]-2H-indazol-5-yl}pyridine-2-carboxamide N-{2-[2-(3,3-difluoropyrrolidin-1-yl)-2-oxoethyl]-6-methoxy-2H-indazol-5-yl}-6-methylpyridine-2-carboxamide N-{6-methoxy-2-[2-(morpholin-4-yl)-2-oxoethyl]-2H-indazol-5-yl}-6-methylpyridine-2-carboxamide N-{6-methoxy-2-[2-(morpholin-4-yl)-2-oxoethyl]-2H-indazol-5-yl}-2-(tetrahydro-2H-pyran-4-yl)-1,3-oxazole-4-carboxamide N-{2-[2-(1,1-dioxido-1-thia-6-azaspiro[3.3]hept-6-yl)-2-oxoethyl]-6-methoxy-2H-indazol-5-yl}-6-(trifluoromethyl)pyridine-2-carboxamide N-{6-methoxy-2-[2-(2-oxa-6-azaspiro[3.3]hept-6-yl)-2-oxoethyl]-2H-indazol-5-yl}-6-(trifluoromethyl)pyridine-2-carboxamide N-{6-(3-hydroxy-2,2-dimethylpropoxy)-2-[2-(morpholin-4-yl)-2-oxoethyl]-2H-indazol-5-yl}-6-(trifluoromethyl)pyridine-2-carboxamide 6-ethyl-N-{6-methoxy-2-[2-(morpholin-4-yl)-2-oxoethyl]-2H-indazol-5-yl}pyridine-2-carboxamide 6-isobutyl-N-{6-methoxy-2-[2-(morpholin-4-yl)-2-oxoethyl]-2H-indazol-5-yl}pyridine-2-carboxamide methyl 2-[2-(morpholin-4-yl)-2-oxoethyl]-5-({[6-(trifluoromethyl)pyridin-2-yl]carbonyl}amino)-2H-indazole-6-carboxylate methyl 5-{[(6-methylpyridin-2-yl)carbonyl]amino}-2-[2-(morpholin-4-yl)-2-oxoethyl]-2H-indazole-6-carboxylate N-{6-methoxy-2-[2-(morpholin-4-yl)-2-oxoethyl]-2H-indazol-5-yl}-6-(pyrrolidin-1-yl)pyridine-2-carboxamide N-{6-methoxy-2-[2-(morpholin-4-yl)-2-oxoethyl]-2H-indazol-5-yl}-6-(morpholin-4-yl)pyridine-2-carboxamide 6-(cyclopropylamino)-N-{6-methoxy-2-[2-(morpholin-4-yl)-2-oxoethyl]-2H-indazol-5-yl}pyridine-2-carboxamide 6-(butylamino)-N-{6-methoxy-2-[2-(morpholin-4-yl)-2-oxoethyl]-2H-indazol-5-yl}pyridine-2-carboxamide N-{6-methoxy-2-[2-(morpholin-4-yl)-2-oxoethyl]-2H-indazol-5-yl}-6-(propylamino)pyridine-2-carboxamide 6-(isobutylamino)-N-{6-methoxy-2-[2-(morpholin-4-yl)-2-oxoethyl]-2H-indazol-5-yl}pyridine-2-carboxamide R—N-{6-methoxy-2-[2-(morpholin-4-yl)-2-oxoethyl]-2H-indazol-5-yl}-6-(2,2,2-trifluoro-1-hydroxyethyl)pyridine-2-carboxamide S—N-{6-methoxy-2-[2-(morpholin-4-yl)-2-oxoethyl]-2H-indazol-5-yl}-6-(2,2,2-trifluoro-1-hydroxyethyl)pyridine-2-carboxamide 6-(1-hydroxyethyl)-N-{6-methoxy-2-[2-(morpholin-4-yl)-2-oxoethyl]-2H-indazol-5-yl}pyridine-2-carboxamide 6-(cyclopropylamino)-N-{6-methoxy-2-[2-(4-methylpiperazin-1-yl)-2-oxoethyl]-2H-indazol-5-yl}pyridine-2-carboxamide N-{6-methoxy-2-[2-(4-methylpiperazin-1-yl)-2-oxoethyl]-2H-indazol-5-yl}-6-(propylamino)pyridine-2-carboxamide 6-(isobutylamino)-N-{6-methoxy-2-[2-(4-methylpiperazin-1-yl)-2-oxoethyl]-2H-indazol-5-yl}pyridine-2-carboxamide 6-(1-hydroxyethyl)-N-{6-methoxy-2-[2-(4-methylpiperazin-1-yl)-2-oxoethyl]-2H-indazol-5-yl}pyridine-2-carboxamide N-{6-methoxy-2-[2-(4-methylpiperazin-1-yl)-2-oxoethyl]-2H-indazol-5-yl}-4-methyl-6-(trifluoromethyl)pyridine-2-carboxamide N-{6-(benzyloxy)-2-[2-(morpholin-4-yl)-2-oxoethyl]-2H-indazol-5-yl}-6-(trifluoromethyl)pyridine-2-carboxamide 6-(cyclopropylamino)-N-(2-{2-[4-(2-hydroxypropan-2-yl)
  piperidin-1-yl]-2-oxoethyl}-6-methoxy-2H-indazol-5-yl)
  pyridine-2-carboxamide
6-(butylamino)-N-(2-{2-[4-(2-hydroxypropan-2-yl)piperi-
  din-1-yl]-2-oxoethyl}-6-methoxy-2H-indazol-5-yl)pyri-
  dine-2-carboxamide
N-(2-{2-[4-(2-hydroxypropan-2-yl)piperidin-1-yl]-2-oxo-
  ethyl}-6-methoxy-2H-indazol-5-yl)-6-[(2-methoxyethyl)
  amino]pyridine-2-carboxamide
N-(2-{2-[4-(2-hydroxypropan-2-yl)piperidin-1-yl]-2-oxo-
  ethyl}-6-methoxy-2H-indazol-5-yl)-6-(propylamino)
  pyridine-2-carboxamide
N-(2-{2-[4-(2-hydroxypropan-2-yl)piperidin-1-yl]-2-oxo-
  ethyl}-6-methoxy-2H-indazol-5-yl)-6-(isobutylamino)
  pyridine-2-carboxamide
5-fluoro-N-(2-{2-[4-(2-hydroxypropan-2-yl)piperidin-1-
  yl]-2-oxoethyl}-6-methoxy-2H-indazol-5-yl)-6-methyl-
  pyridine-2-carboxamide
N-{6-hydroxy-2-[2-(morpholin-4-yl)-2-oxoethyl]-2H-inda-
  zol-5-yl}-6-(trifluoromethyl)pyridine-2-carboxamide
N-{6-(3-cyanopropoxy)-2-[2-(morpholin-4-yl)-2-oxo-
  ethyl]-2H-indazol-5-yl}-6-(trifluoromethyl)pyridine-2-
  carboxamide
N-{2-[2-(morpholin-4-yl)-2-oxoethyl]-6-(2,2,2-trifluo-
  roethoxy)-2H-indazol-5-yl}-6-(trifluoromethyl)pyridine-
  2-carboxamide
N-{6-(cyclohexylmethoxy)-2-[2-(morpholin-4-yl)-2-oxo-
  ethyl]-2H-indazol-5-yl}-6-(trifluoromethyl)pyridine-2-
  carboxamide
N-{6-(2,2-dimethylpropoxy)-2-[2-(morpholin-4-yl)-2-oxo-
  ethyl]-2H-indazol-5-yl}-6-(trifluoromethyl)pyridine-2-
  carboxamide
N-{2-[2-(morpholin-4-yl)-2-oxoethyl]-6-(tetrahydrofuran-
  2-ylmethoxy)-2H-indazol-5-yl}-6-(trifluoromethyl)pyri-
  dine-2-carboxamide
N-{6-(cyclopentyloxy)-2-[2-(morpholin-4-yl)-2-oxoethyl]-
  2H-indazol-5-yl}-6-(trifluoromethyl)pyridine-2-carbox-
  amide
N-{6-(cyanomethoxy)-2-[2-(morpholin-4-yl)-2-oxoethyl]-
  2H-indazol-5-yl}-6-(trifluoromethyl)pyridine-2-carbox-
  amide
({2-[2-(morpholin-4-yl)-2-oxoethyl]-5-({[6-(trifluorom-
  ethyl)pyridin-2-yl]carbonyl}amino)-2H-indazol-6-
  yl}oxy)acetic acid
N-{6-(cyclobutylmethoxy)-2-[2-(morpholin-4-yl)-2-oxo-
  ethyl]-2H-indazol-5-yl}-6-(trifluoromethyl)pyridine-2-
  carboxamide
N-{2-[2-(morpholin-4-yl)-2-oxoethyl]-6-[2-(pyrrolidin-1-
  yl)ethoxy]-2H-indazol-5-yl}-6-(trifluoromethyl)pyri-
  dine-2-carboxamide
N-{6-[2-(morpholin-4-yl)ethoxy]-2-[2-(morpholin-4-yl)-2-
  oxoethyl]-2H-indazol-5-yl}-6-(trifluoromethyl)pyridine-
  2-carboxamide
N-{2-[2-(morpholin-4-yl)-2-oxoethyl]-6-[2-(piperidin-1-yl)
  ethoxy]-2H-indazol-5-yl}-6-(trifluoromethyl)pyridine-2-
  carboxamide
N-{6-(3-hydroxypropoxy)-2-[2-(morpholin-4-yl)-2-oxo-
  ethyl]-2H-indazol-5-yl}-6-(trifluoromethyl)pyridine-2-
  carboxamide
N-{6-(2-hydroxypropoxy)-2-[2-(morpholin-4-yl)-2-oxo-
  ethyl]-2H-indazol-5-yl}-6-(trifluoromethyl)pyridine-2-
  carboxamide
N-{6-(2-hydroxyethoxy)-2-[2-(morpholin-4-yl)-2-oxo-
  ethyl]-2H-indazol-5-yl}-6-(trifluoromethyl)pyridine-2-
  carboxamide
N-{6-(2-methoxyethoxy)-2-[2-(morpholin-4-yl)-2-oxo-
  ethyl]-2H-indazol-5-yl}-6-(trifluoromethyl)pyridine-2-
  carboxamide
ethyl ({2-[2-(morpholin-4-yl)-2-oxoethyl]-5-({[6-(trifluo-
  romethyl)pyridin-2-yl]carbonyl}amino)-2H-indazol-6-
  yl}oxy)acetate
methyl 4-({2-[2-(morpholin-4-yl)-2-oxoethyl]-5-({[6-(trif-
  luoromethyl)pyridin-2-yl]carbonyl}amino)-2H-indazol-
  6-yl}oxy)butanoate
ethyl 2-({2-[2-(morpholin-4-yl)-2-oxoethyl]-5-({[6-(trifluo-
  romethyl)pyridin-2-yl]carbonyl}amino)-2H-indazol-6-
  yl}oxy)propanoate
ethyl 3-methyl-2-({2-[2-(morpholin-4-yl)-2-oxoethyl]-5-({
  [6-(trifluoromethyl)pyridin-2-yl]carbonyl}amino)-2H-in-
  dazol-6-yl}oxy)butanoate
2-({2-[2-(morpholin-4-yl)-2-oxoethyl]-5-({[6-(trifluorom-
  ethyl)pyridin-2-yl]carbonyl}amino)-2H-indazol-6-
  yl}oxy)propanoic acid
N-{6-(2-hydroxypropan-2-yl)-2-[2-(morpholin-4-yl)-2-
  oxoethyl]-2H-indazol-5-yl}-6-(trifluoromethyl)pyridine-
  2-carboxamide
N-{6-chloro-2-[2-(4-methylpiperazin-1-yl)-2-oxoethyl]-
  2H-indazol-5-yl}-6-(difluoromethyl)pyridine-2-carbox-
  amide
N-{6-chloro-2-[2-(morpholin-4-yl)-2-oxoethyl]-2H-inda-
  zol-5-yl}-6-(difluoromethyl)pyridine-2-carboxamide.

The present invention further provides a process for preparing intermediates of the general formula (III) from the compound of the formula (II)

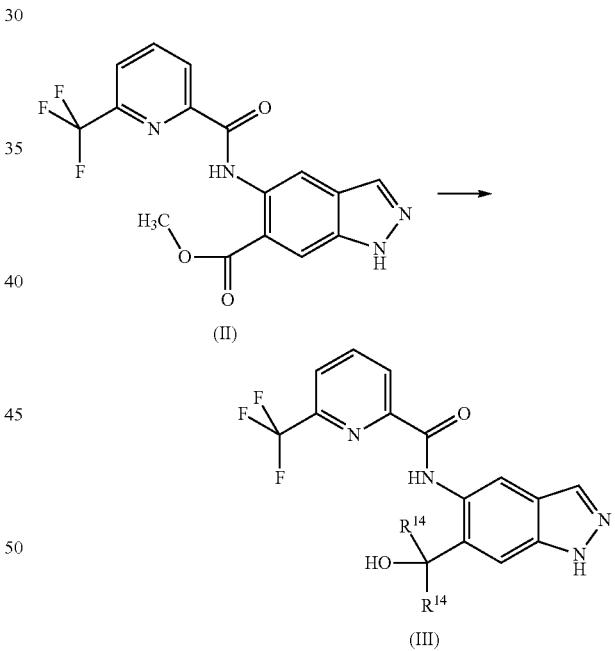

in which $R^{14}$ is either methyl or ethyl.

The conversion of the intermediate of the formula (II) into the intermediates of the formula (III) is carried out by a Grignard reaction. Preferably, the Grignard reaction is carried out using alkylmagnesium bromide. To this end, preference is given to using either methylmagnesium bromide or ethylmagnesium bromide.

Thus, the invention also provides intermediates of the general formula (II).

The invention furthermore provides intermediates of the general formula (III) in which $R^{14}$ represents either methyl or ethyl.

The compounds of the formula (I) according to the invention act as inhibitors of IRAK4 kinase and have an unforeseeable useful pharmacological activity spectrum.

Thus, in addition to the subject matter mentioned above, the present invention also provides the use of the compounds according to the invention for the treatment and/or prophylaxis of diseases in man and animals.

The compounds according to the invention are suitable for the prophylaxis and/or treatment of various disorders and disease-related states, in particular disorders mediated by TLR (except for TLR3) and/or the IL-1 receptor family and/or disorders whose pathology is mediated directly by IRAK4. IRAK4-associated disorders which may be mentioned are multiple sclerosis, atherosclerosis, myocardial infarction, Alzheimer's disease, virus-induced myocarditis, gout, psoriasis and arthritis.

The compounds according to the invention can furthermore be used for the prophylaxis and/or treatment of disorders mediated by MyD88 and TLR (except for TLR3). This includes multiple sclerosis, rheumatoid arthritis, metabolic syndrome, diabetes, osteoarthritis, Sjögren syndrome, sepsis, skin disorders such as psoriasis, atopic dermatitis and acne vulgaris, pulmonary disorders such as pulmonary fibrosis, chronic obstructive pulmonary disease (COPD), acute respiratory distress syndrome (ARDS), acute lung injury (ALI), interstitial lung disease (ILD), sarcoidosis and pulmonary hypertension.

By virtue of the mechanism of action of the compounds according to the invention, they are suitable for the prophylaxis and/or treatment of the TLR-mediated disorders Behçet's disease, gout, endometriosis, graft rejection, lupus erythematosus, adult-onset Still's disease and chronic inflammatory bowel disorders such as ulcerative colitis and Crohn's disease.

In addition to the disorders already listed, the use of the compounds according to the invention is also suitable for the treatment and/or prevention of the following disorders: eye disorders such as ceratitis, allergic conjunctivitis, keratoconjunctivitis sicca, macular degeneration and uveitis; cardiovascular disorders such as arteriosclerosis, myocardial reperfusion damage, myocardial infarction, hypertension and neurological disorders such as Alzheimer's disease, stroke and Parkinson's disease.

Furthermore, the compounds according to the invention can be used for the prophylaxis and/or treatment of pruritus and pain. By virtue of the mechanism of action of the compounds according to the invention, they are suitable for the prophylaxis and/or treatment of oncological disorders such as lymphomas, chronic lymphatic leukaemia, melanomas and liver cell carcinoma and Ras-dependent tumours.

Moreover, the compounds according to the invention are suitable for the treatment and/or prevention of disorders mediated via the IL-1 receptor family. These disorders comprise CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome, FMF (familial mediterranean fever), HIDS (hyper-IgD syndrome), TRAPS (tumour necrosis factor receptor 1-associated periodic syndrome), juvenile idiopathic arthritis, adult-onset Still's disease, Adamantiades-Behçet's disease, rheumatoid arthritis, osteoarthritis, keratoconjunctivitis sicca und Sjögren syndrome, multiple sclerosis, lupus erythematosus, type-1 diabetes, type-2 diabetes and the sequelae of myocardial infarction. Pulmonary disorders such as asthma, COPD, idiopathic interstitial pneumonia and ARDS, endometriosis, chronic-inflammatory bowel disorders such as Crohn's disease and ulcerative colitis are associated with dysregulation of the IL-1 reptor family and suitable for therapeutic and/or prophylactic use of the compounds according to the invention.

The compounds according to the invention can furthermore be employed for the treatment and/or prevention of neurological disorders mediated by the IL-1 receptor family, such as stroke, Alzheimer's disease, stroke, skull-brain trauma, pain disorders such as cancer pain, postoperative pain, inflammation-induced and chronic pain and dermatological disorders such as psoriasis, atopic dermatitis, allergic contact dermatitis.

The treatment and/or prophylaxis of inflammatory skin disorders, cardiovascular disorders, lung disorders, eye disorders, autoimmune disorders and neoplastic disorders with the IRAK4 inhibitors according to the invention is particularly preferred.

The present invention further also provides a method for treatment and/or prevention of disorders, in particular the disorders mentioned above, using an effective amount of at least one of the compounds according to the invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The compounds according to the invention can be used alone or, if required, in combination with other active compounds. The present invention therefore further provides medicaments comprising at least one of the inventive compounds and one or more further active ingredients, especially for treatment and/or prevention of the aforementioned disorders. Preferred examples of active compounds suitable for combinations include:

in general, mention may be made of active compounds such as antibacterial (e.g. penicillins, vancomycin, ciprofloxacin), antiviral (e.g. aciclovir, oseltamivir) and antimycotic (e.g. naftifin, nystatin) substances and gamma globulins, immunomodulatory and immunosuppressive compounds such as cyclosporin, tacrolimus, rapamycin, mycophenolate mofetil, interferons, corticosteroids (e.g. prednisone, prednisolone, methylprednisolone, hydrocortisone, betamethasone), cyclophosphamide, azathioprine and sulfasalazine; paracetamol, non-steroidal anti-inflammatory substances (NSAIDS) (aspirin, ibuprofen, naproxen, etodolac, celecoxib, colchicine).

For tumour therapy, mention may be made of immunotherapy, antiproliferative substances such as, by way of example but not by way of limitation, trastuzumab, rituximab, tositumomab, aromatase inhibitors (e.g. letrozole, anastrozole), antiestrogens (e.g. tamoxifen), topoisomerase I inhibitors (e.g. irinotecan, topotecan), topoisomerase II inhibitors (e.g. daunorubicin, idarubicin, mitoxantrone), microtubuli-active substances (e.g. vinblastine, vincristine), telomerase inhibitors (e.g. imetelstat), alkylating substances and histone deacetylase inhibitors (e.g. vorinostat, romidepsin, panobinostat); substances which modulate cell differentiation processes such as MMP inhibitors (peptide mimetics, non-peptide mimetics and tetracyclins such as, for example, marimastat, BAY 12-9566, BMS-275291, clodronate, prinomastat, doxycycline), mTOR inhibitors (e.g. sirolimus, everolimus, temsirolimus, zotarolimus), antimetabolites (e.g. methotrexate, 5-fluorouracil, cladribine, fludarabine), platinum compounds (e.g. carboplatin, cisplatin, cisplatinum); anti-angiogenic compounds (e.g. bevacizumab), antiandrogenic compounds (e.g. flutamide, nilutamide, bicalutamide, cyproterone acetate), proteasome inhibitors (e.g. bortezomib, carfilzomib, oprozomib, ONYX0914), gonadoliberin agonists and -antagonists (e.g. goserelin, triptorelin, degarelix), methionine aminopeptidase inhibitors (e.g. bengamide derivatives, TNP-470, PPI-2458), heparanase inhibitors (e.g. SST0001, PI-88); inhibitors of genetically modified ras protein (e.g. farnesyl transferase inhibitors such as lonafarnib, tipifarnib), HSP90 inhibitors (e.g.: geldamycin derivatives such as 17-allylaminogeldanamycin, 17-demethoxygeldanamycin (17AAG), 17-DMAG, retaspimycin hydrochloride, IPI-493, AUY922, BIIB028, STA-9090, KW-2478), kinesin spindle protein inhibitors (e.g. SB715992, SB743921, pentamidine/chlorpromazine), MEK (mitogen-activated protein kinase kinase) inhibitors (e.g. trametinib, BAY 86-9766, AZD6244,), kinase inhibitors (e.g.: sorafenib, regorafenib, lapatinib, sutent, dasatinib, cetuximab BMS-908662, GSK2118436, AMG 706), hedgehog signal inhibitors (e.g. cyclopamine, vismodegib), BTK (Bruton's tyrosine kinase) inhibitors (e.g. ibrutinib), JAK/pan-JAK (janus kinase) inhibitor (e.g. SB-1578, baricitinib, tofacitinib, pacritinib, momelotinib, ruxolitinib, VX-509, AZD-1480, TG-101348), PI3K inhibitor (e.g. BAY 1082439, BAY 80-6946, ATU-027, SF-1126, DS-7423, GSK-2126458, buparlisib, PF-4691502, BYL-719, XL-147, XL-765, idelalisib), SYK (spleen tyrosine kinase) inhibitor (e.g. fostamatinib, Excellair, PRT-062607), bisphosphonates (e.g. etridonate, clodronate, tiludronate, pamidronate, alendronic acid, ibandronate, risedronate, zoledronate), rituximab, cyclophosphamide, doxorubicin, vincristine, chlorambucil, fludarabine, dexamethasone, cladribine, prednisone.

Also suitable for tumour therapy is a combination of a non-drug therapy such as chemotherapy, radiotherapy or phototherapy which is accompanied by a drug treatment with the IRAK4 inhibitors according to the invention or which, after the non-drug tumour therapy such as chemotherapy, radiotherapy or phototherapy has ended, are supplemented by a drug treatment with the IRAK4 inhibitors according to the invention.

In addition to those mentioned above, the IRAK4 inhibitors according to the invention can also be combined with the following active compounds:
active compounds for Alzheimer therapy such as, for example, acetylcholinesterase inhibitors (e.g. donepezil, rivastigmine, galantamine, tacrine), NMDA (N-methyl-D-aspartate) receptor antagonists (e.g. memantine); L-DOPA/ carbidopa (L-3,4-dihydroxyphenylalanine), COMT (catechol-O-methyl transferase) inhibitors (e.g. entacapone), dopamine agonists (e.g. ropinrol, pramipexol, bromocriptine), MAO-B (monoaminooxidase-B) inhibitors (e.g. selegiline), anticholinergics (e.g. trihexyphenidyl) and NMDA antagonists (e.g. amantadin) for the treatment of Parkinson's disease; beta-interferon (IFN-beta) (e.g. IFN beta-1b, IFN beta-1a Avonex® and Betaferon®), glatiramer acetate, immunoglobulins, natalizumab, fingolimod and immunosuppressive drugs such as mitoxantrone, azathioprine and cyclophosphamide for the treatment of multiple sclerosis; substances for the treatment of pulmonary disorders such as, for example, beta-2-sympathomimetics (e.g. salbutamol), anticholinergics (e.g. glycopyrronium), methylxanthines (e.g. theophylline), leukotriene receptor antagonists (e.g. montelukast), PDE-4 (phosphodiesterase type 4) inhibitors (e.g. roflumilast), methotrexate, IgE antibodies, azathioprine and cyclophosphamide, cortisol-containing preparations; substances for treating osteoarthritis such as non-steroidal anti-inflammatory substances (NSAIDs). In addition to the two therapies mentioned, methotrexate and biologics for B-cell and T-cell therapy (e.g. rituximab, abatacept) may be mentioned for rheumatoid disorders such as rheumatoid arthritis and juvenile idiopathic arthritis. Neurotrophic substances such as acetylcholinesterase inhibitors (e.g. donepezil), MAO (monoaminooxidase) inhibitors (e.g. selegiline), interferons and anticonvulsive drugs (e.g. gabapentin); active compounds for the treatment of cardiovascular disorders such as beta-blockers (e.g. metoprolol), ACE inhibitors (e.g. benazepril), diuretics (e.g. hydrochlorothiazide), calcium channel blockers (e.g. nifedipine), statins (e.g. simvastatin); anti-diabetics such as, for example, metformin and glibenclamide, sulphonylureas (e.g. tolbutamide) and insulin therapy for the treatment of diabetes and metabolic syndrome. Active compounds such as mesalazine, sulfasalazine, azathioprine, 6-mercaptopurine or methotrexate, probiotic bacteria (Mutaflor, VSL#3®, *Lactobacillus* GG, *Lactobacillus plantarum*, *L. acidophilus*, *L. casei*, *Bifidobacterium infantis* 35624, *Enterococcus fecium* SF68, *Bifidobacterium longum*, *Escherichia coli* Nissle 1917), antibiotics such as, for example, ciprofloxacin and metronidazole, anti-diarrhoeal drugs such as, for example, loperamide, or laxatives (bisacodyl) for the treatment of chronic-inflammatory bowel disorders. Immunosuppressives such as glucocorticoids and non-steroidale anti-inflammatory substances (NSAIDs), cortisone, chloroquin, cyclosporine, azathioprine, belimumab, rituximab, cyclophosphamide for the treatment of lupus erythematosus. By way of example, but not by way of limitation, calcineurin inhibitors (e.g. tacrolimus and ciclosporin), cell division inhibitors (e.g. azathioprine, mycophenolate mofetil, mycophenolic acid, everolimus or sirolimus), rapamycin, basiliximab, daclizumab, anti-CD3 antibodies, anti-T-lymphocyte globulin/anti-lymphocyte globulin for organ transplants. Vitamin D3 analogues such as, for example, calcipotriol, tacalcitol or calcitriol, salicylic acid, urea, ciclosporine, methotrexate, efalizumab for dermatological disorders.

The present invention further provides medicaments which comprise at least one compound according to the invention, typically together with one or more inert, non-toxic, pharmaceutically suitable excipients, and the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in suitable administration forms for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of from about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active compound, nature of the preparation and time or interval over which administration takes place.

Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are in each case based on volume.

Preparation of the Compounds According to the Invention

The preparation of the compounds according to the invention is illustrated by the following synthesis schemes:

The intermediates 0 shown in Synthesis Scheme 1 can be prepared analogously to literature and patent procedures, for example from 4-substituted 2-fluoro-5-nitrobenzaldehydes or 2-chloro-5-nitrobenzaldehydes, or they are commercially available. For the preparation, 4-substituted 2-fluoro-5-nitrobenzaldehydes are reacted with hydrazine (J. Med. Chem., 2013, 56, 4343). The resulting 5-nitroindazoles (Intermediates 0) can be reduced, for example, with palladium on carbon by hydrogenation (US201228984, WO200671940, US2003153596, EP2045253) or transfer hydrogenation (Eur. J. Med. Chem., 2010, 45, 5520) or by reaction with iron (J. Chem. Soc., 1955, 2412) or tin(II) chloride (Bioorg. Med. Chem., 2004, 12, 2115, US201215962) to give the corresponding 5-aminoindazoles. The Intermediates 1a can be converted into Intermediates 1b. The radical $R^2$ can be introduced by various routes, for example via alkylation with alkyl halides (Bioorg. Med. Chem., 2010, 18, 4801) or alkylsulphonates or via reductive amination by reaction with aldehydes (WO2009102498) or ketones (EP140325). Suitable for use as reducing agents are various hyride donors such as, for example, sodium borohydride, sodium cyanoborohydride or sodium trisacetoxyborohydride. Alternatively, it is also possible to acylate the anilinic nitrogen of the Intermediates 1a first using an acyl halide or a carboxylic anhydride, and then to reduce the amide using a suitable reducing agent to give the corresponding amine, which also affords Intermediates 1b. Suitable for use as reducing agents are, for example, lithium aluminium hydride (J. Am. Chem. Soc., 1954, 76, 1384), borane as complex with dimethyl sulphide (Synthetic Communications, 1991, 21, 1579) or tetrahydrofuran (Org. and Biomol. Chem., 2012, 10, 8692) or sodium bis(2-methoxyethoxy)aluminium hydride (WO200873461).

The Intermediates 1a and 1b can be provided at the anilinic nitrogen with a known protective group described in the literature (Protecting Groups, Philip J. Kocienski, 3rd Revised Edition (9 Feb. 2005), Thieme, Chapter 8; Greene's Protective Groups in Organic Synthesis, Peter G. M. Wuts, Theodora W. Greene, 4th Edition (8 Dec. 2006), Wiley-Interscience, Chapter 7), giving the Intermediates 2. The preferred protective group is the tert-butyloxycarbonyl group (BOC protective group). The BOC protective group is preferably introduced with di-tert-butyl dicarbonate in the presence of a base such as, for example, N,N-diisopropylethylamine or triethylamine.

The Intermediates 2 can be reacted with carboxylic esters halogenated in the carboxylic acid moiety such as, for example, methyl bromoacetate, ethyl bromoacetate, tert-butyl bromoacetate, benzyl bromoacetate, ethyl 3-bromopropanoate or ethyl 2-bromopropanoate under basic conditions to give a mixture of the corresponding regioisomeric 1- and 2-alkylated indazole compounds (Organic Letters, 2009, 11, 5054; WO200474284; US2009286800; WO200919167; WO201297744; J. Med. Chem., 2007, 50, 3101; Molecules, 2006, 11, 86). Here, preference is given to the reaction with N,N-dicyclohexylmethylamine in tetrahydrofuran or N,N-dimethylformamide between 25° C. and 100° C. (J. Org. Chem. 2006, 71, 5392). Likewise preferred is the reaction in the presence of potassium carbonate in N,N-dimethylformamide. The mixtures of the regioisomeric 1- and 2-alkylated indazole compounds can be separated by column chromatography or preparative HPLC, which gives access to the 2-alkylated indazole compounds (Intermediates 3).

The conversion of the Intermediates 3 into the Intermediates 4 can be carried out under known conditions (Protecting Groups, Philip J. Kocienski, 3rd Revised Edition (9 Feb. 2005), Thieme, Chapter 6; Greene's Protective Groups in Organic Synthesis, Peter G. M. Wuts, Theodora W. Greene, 4th Edition (8 Dec. 2006), Wiley-Interscience, Chapter 5; WO200919167 A1). Here, preference is given to hydrolysis with lithium hydroxide or lithium hydroxide monohydrate in a mixture of tetrahydrofuran and water (J. Med. Chem., 2012, 55, 1318, Bioorg. Med. Chem., 2009, 17, 7113). Optionally, ethanol or methanol may also be added.

The Intermediates 4 can be reacted with amines to give the corresponding Intermediates 5. Here, use may be made of various coupling reagents known from the literature (Amino Acids, Peptides and Proteins in Organic Chemistry. Vol. 3—Building Blocks, Catalysis and Coupling Chemistry, Andrew B. Hughes, Wiley, Chapter 12—Peptide-Coupling Reagents, 407-442; Chem. Soc. Rev., 2009, 38, 606). The use of 1-(3-dimethylaminopropyl)-3-ethylcarbodiimide hydrochloride in combination with 1-hydroxy-1H-benzotriazole hydrate is preferred (WO2012107475; Bioorg. Med. Chem. Let., 2008, 18, 2093).

The Intermediates 5 obtained in this manner can be converted into Intermediates 6. The removal of the protective group at the anilinic nitrogen can be carried out under known reaction conditions (Protecting Groups, Philip J. Kocienski, 3rd Revised Edition (9 Feb. 2005), Thieme, Chapter 8; Greene's Protective Groups in Organic Synthesis, Peter G. M. Wuts, Theodora W. Greene, 4th Edition (8 Dec. 2006), Wiley-Interscience, Chapter 7). Preferred is the removal of the tert-butyloxycarbonyl protective group with trifluoroacetic acid in dichloromethane (Bioorg. Med. Chem. Lett., 2011, 21, 6274; J. Med. Chem., 2008, 51, 1904; WO201353051).

Using the coupling reagents known from the literature which were already mentioned for the preparation of the Intermediates 5, the Intermediates 6 can be reacted with heterocyclic carboxylic acids to give compounds of the general formula (I). Here, too, preference is given to using 1-(3-dimethylaminopropyl)-3-ethylcarbodiimide hydrochloride in combination with 1-hydroxy-1H-benzotriazole hydrate (US2006194801)

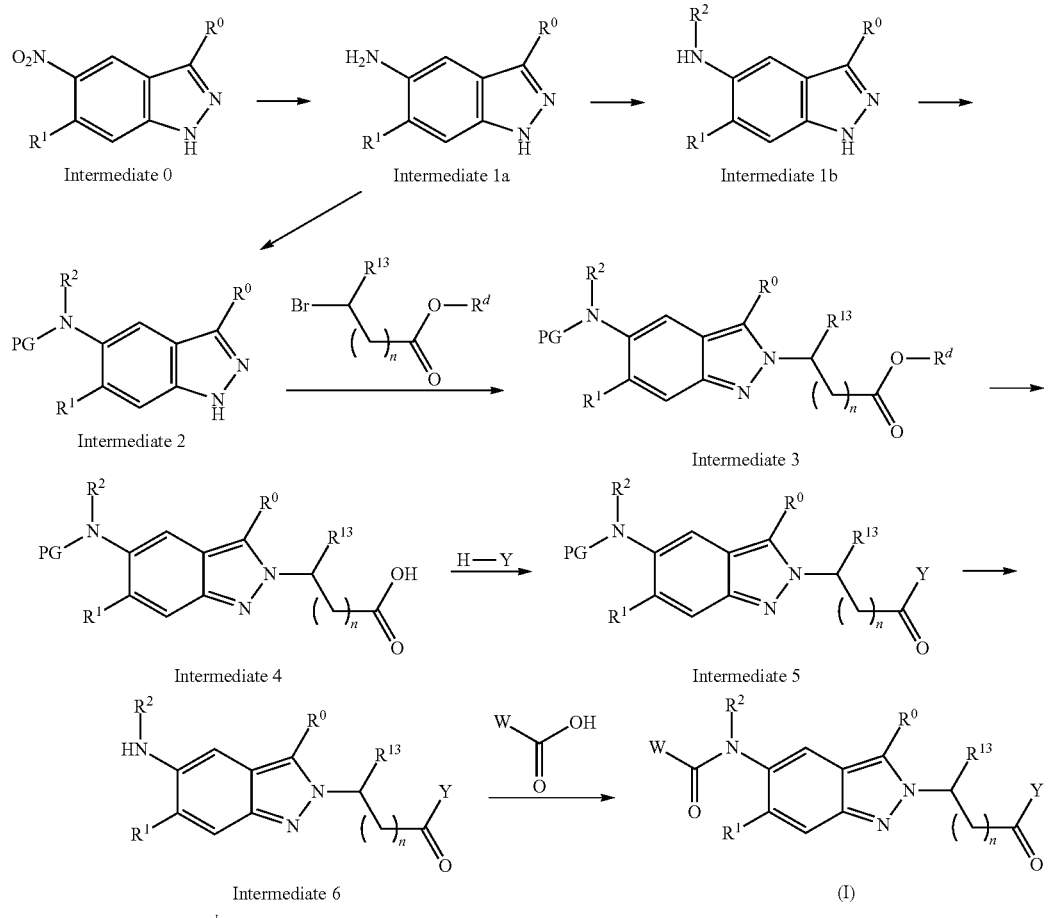

Synthesis Scheme 1:

(PG means protective group; $R^d$ represents $C_1$-$C_6$-alkyl or benzyl.)

Alternatively, the Intermediates 5 can also be obtained directly from Intermediates 2, as illustrated in Synthesis Scheme 1a. The reagents used are halogenated carboxamides. The reaction conditions are identical to those of the preparation of Intermediate 3 from Intermediate 2. Preference is given to the reaction with 2-bromoacetamides in the presence of the base N,N-dicyclohexylmethylamine. Particular preference is given to the reaction with 2-bromo-1-(morpholin-4-yl)ethanone.

Synthesis Scheme 1a:

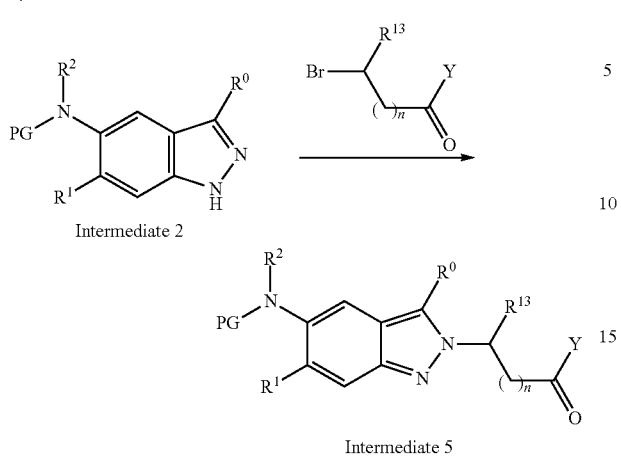

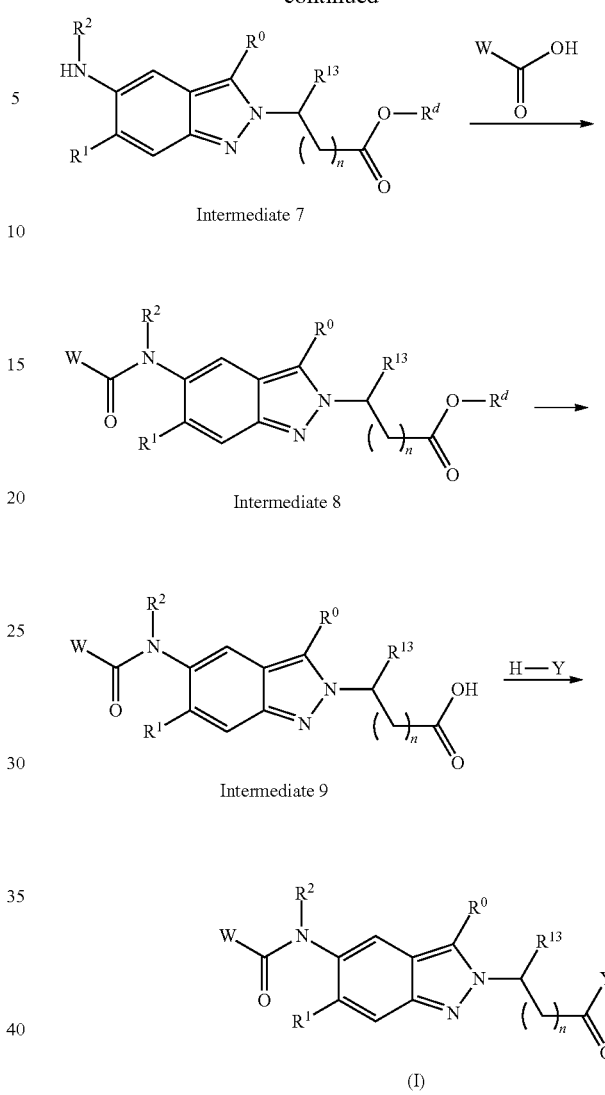

(PG means protective group; $R^d$ represents $C_1$-$C_6$-alkyl or benzyl.)

As illustrated in Synthesis Scheme 2, the Intermediates 3 can also be converted first into the Intermediates 7 (J. Am. Chem. Soc., 2009, 131, 3342; EP2522657). If PG denotes tert-butyloxycarbonyl, it is preferred to use trifluoroacetic acid in dichloromethane (WO201062171). The Intermediates 7 can be reacted with heterocyclic carboxylic acids to give the Intermediates 8. Here, as in Synthesis Scheme 1, coupling reagents are used. The preferred coupling reagent used is 1-(3-dimethylaminopropyl)-3-ethylcarbodiimide hydrochloride in combination with 1-hydroxy-1H-benzotriazole hydrate.

The Intermediates 8 can be hydrolysed analogously to Synthesis Scheme 1, the hydrolysis with lithium hydroxide or lithium hydroxide monohydrate in a mixture of tetrahydrofuran and water being preferred. Optionally, ethanol or methanol may also be added.

The Intermediates 9 formed in this manner can be converted into the compounds of the general formula (I). The coupling with amines is carried out analogously to Synthesis Scheme 1 using coupling reagents known from the literature. The use of 1-(3-dimethylaminopropyl)-3-ethylcarbodiimide hydrochloride in combination with 1-hydroxy-1H-benzotriazole hydrate is preferred.

Synthesis Scheme 2:

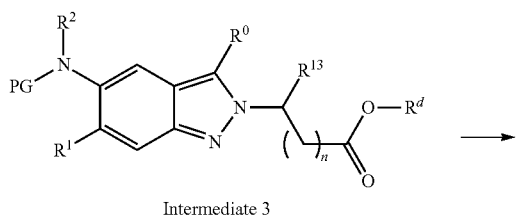

Synthesis Scheme 3:

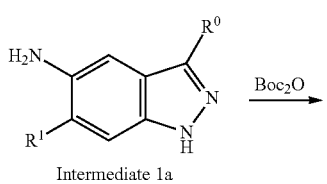

The Intermediates 2b can be prepared as illustrated in Synthesis Scheme 3. Reaction of the Intermediates 1a with an excess of di-tert-butyl dicarbonate gives a mixture of Intermediates 10 and 11 which can be hydrolysed selectively at positions 1 and 2, respectively, thereby giving the Intermediates 2b. The hydrolysis is preferably carried out using sodium carbonate in a mixture of N,N-dimethylformamide and water between 50° C. and 100° C. for 12-36 hours (Tet. Lett., 2006, 47, 8575).

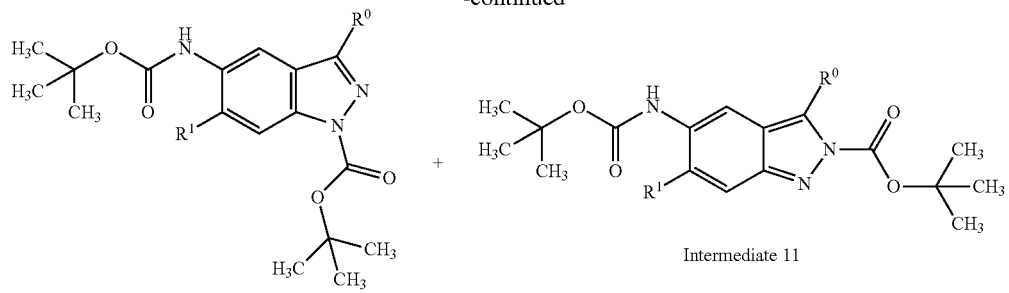

Intermediate 10 + Intermediate 11

↓ Na₂CO₃, DMF, H₂O

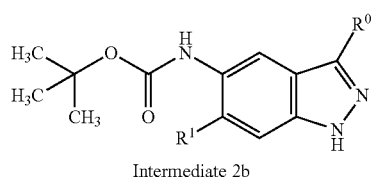

Intermediate 2b

The Intermediates 8a can be prepared as described in Synthesis Scheme 4 Intermediates 1a for example with the meaning $R^1$=Cl in a multistep synthesis sequence. To this end, initially one of the nitrogen atoms in the indazole ring is protected, preferably the nitrogen atom in position 1 (WO200958924). The preferred protective group is the tert-butyloxycarbonyl group (BOC protective group). The BOC protective group is preferably introduced with di-tert-butyl dicarbonate in the presence of a base such as, for example, N,N-diisopropylethylamine or triethylamine.

Under the coupling conditions mentioned above, the Intermediates 12 can be acylated with heterocyclic carboxylic acids, thus giving the Intermediates 13. The use of 1-(3-dimethylaminopropyl)-3-ethylcarbodiimide hydrochloride in combination with 1-hydroxy-1H-benzotriazole hydrate is preferred.

The protective group of the Intermediates 13 at the indazole ring can be removed under reaction conditions known from the literature (Protecting Groups, Philip J. Kocienski, 3rd Revised Edition (9 Feb. 2005), Thieme, Chapter 8; Greene's Protective Groups in Organic Synthesis, Peter G. M. Wuts, Theodora W. Greene, 4th Edition (8 Dec. 2006), Wiley-Interscience, Chapter 7). Preferred is the use of trifluoroacetic acid in dichloromethane for the removal of a BOC protective group. The Intermediates 14 can be converted into a mixture of the corresponding regioisomeric 1- and 2-alkylated indazole compounds. Separation of the regioisomers gives the desired 2-alkylated indazole derivatives (Intermediates 8a) (J. Org. Chem. 2006, 71, 5392). Here, the same reaction conditions as for the preparation of the Intermediates 3 from the Intermediates 2 are employed (Synthesis Scheme 1). The use of N,N-dicyclohexylmethylamine in tetrahydrofuran or N,N-dimethylformamide is preferred.

Synthesis Scheme 4:

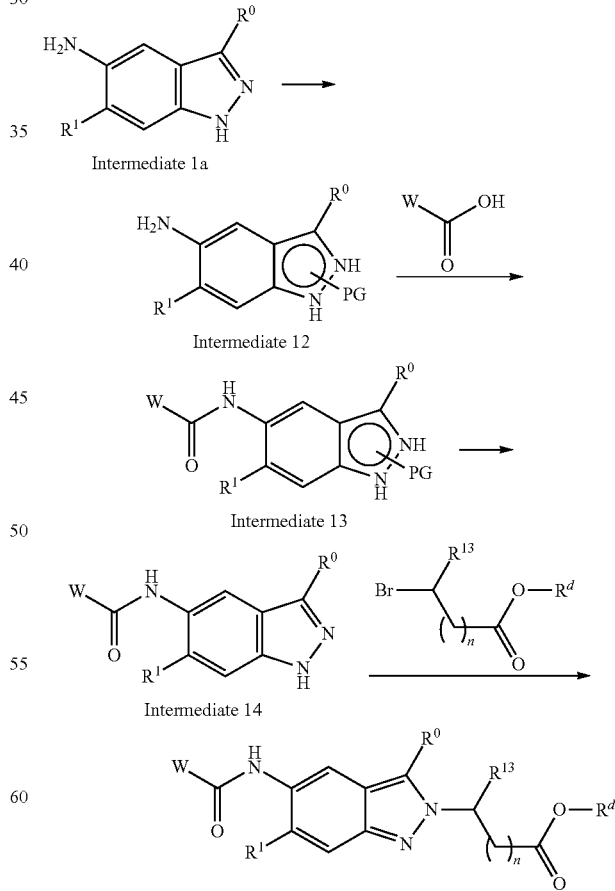

(PG means protective group; $R^d$ represents $C_1$-$C_6$-alkyl or benzyl.)

In some cases, the Intermediates 14 can also be prepared as described in Synthesis Scheme 5. The Intermediates 1a are acylated regioselectively at the anilic nitrogen with heterocyclic carboxylic acids. Here, the coupling reagents mentioned above are employed. Preference is given to the combination of 1-(3-dimethylaminopropyl)-3-ethylcarbodiimide hydrochloride and 1-hydroxy-1H-benzotriazole hydrate using the base triethylamine (EP1403255; WO2005 82890; US2006194801; Bioorg. Med. Chem. Lett., 2007, 17, 3550).

Synthesis Scheme 5:

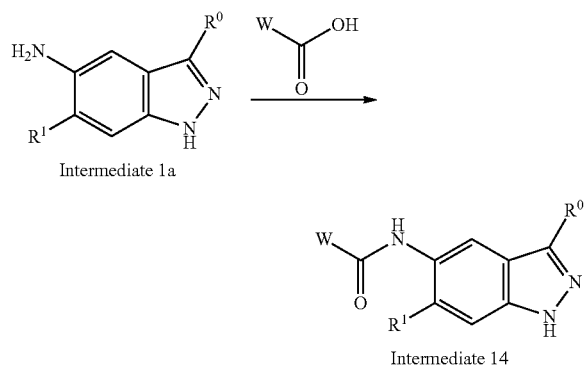

Intermediate 1a

Intermediate 14

According to Synthesis Scheme 5-1, it is possible to obtain, from Intermediates 14a where $R^{1c}=$—$CO_2Me$ or —$CO_2Et$, preferably —$CO_2Me$, in a Grignard reaction (Organikum, 19$^{th}$ Edition, Johann Ambrosius Barth Leipzig, pp. 515-520) by using methylmagnesium bromide, methylmagnesium chloride, ethylmagnesium bromide or ethylmagnesium chloride, Intermediates 14b where $R^{1d}=$—$C(CH_3)_2OH$ or —$C(CH_2CH_3)_2OH$. The reaction with methylmagnesium bromide is preferred to obtain Intermediates where $R^{1d}=$—$C(CH_3)_2OH$. The intermediates of the formula 14b can then be converted analogously to Synthesis Scheme 4 and then according to Synthesis Schema 2 into compounds according to the invention where $R^1=$—$C(CH_3)_2OH$ or —$C(CH_2CH_3)_2OH$. Alternatively and preferably, the Intermediates 14b can also be converted by reaction with 2-chloroacetamides or 2-bromoacetamides into compounds of the formula (I) according to the invention where $R^1=$—$C(CH_3)_2OH$ or —$C(CH_2CH_3)_2OH$. Here, the same reaction conditions as in Synthesis Scheme 1a may be employed. The use of N,N-dicyclohexylmethylamine in tetrahydrofuran or N,N-dimethylformamide is preferred. Particular preference is given to the use of 2-bromo-1-(morpholin-4-yl)ethanone.

Synthesis Scheme 5-1:

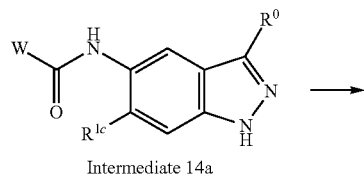

Intermediate 14a

-continued

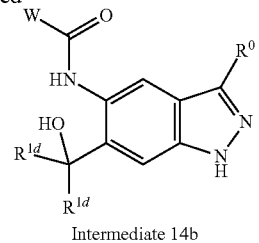

Intermediate 14b ($R^{1c}$ represents —$CO_2Me$ or —$CO_2Et$
$R^{1d}$ represents methyl or ethyl)

A subset of the compounds according to the invention can be prepared as illustrated in Scheme 6. The starting materials of the general formula (Ia) are reacted in the presence of a palladium catalyst with an organometallic compound which transfers the radical $R^{1b}$. The radical $R^{1b}$ represents $C_1$-$C_6$-alkyl, $C_3$-$C_8$-cycloalkyl, heterocycloalkyl, $C_3$-$C_8$-cycloalkyl-$C_1$-$C_4$-alkyl, heterocycloalkyl-$C_1$-$C_4$-alkyl, $C_2$-$C_6$-alkenyl, $C_2$-$C_6$-alkynyl, aryl, 5- to 10-membered heteroaryl, aryl-$C_1$-$C_4$-alkyl or 5- or 6-membered heteroaryl-$C_1$-$C_4$-alkyl which may optionally be mono- or polysubstituted by identical or different substituents from the group consisting of protected hydroxy, halogen, cyano, $C(=O)OR^a$, $S(=O)_2$—$C_1$-$C_6$-alkyl, protected $NH_2$, protected $NHR^a$ or $N(R^a)R^b$. Suitable for the reaction are the known coupling reactions using organomagnesium compounds (Kumada reaction: J. Organomet. Chem., 2002, 653, 288; Handbook of Organopalladium Chemistry for Organic Synthesis, 2002, 1, 335; Top. Curr. Chem., 2002, 219, 1), organoboron compounds (Suzuki reaction: Pure Appl. Chem., 1985, 57, 1749; Chem. Rev., 1995, 95, 2457; Advances in Metal-Organic Chemistry, 1998, 6, 187; Angew. Chem., Int. Ed. Engl., 2004, 43, 2201, Top. Curr. Chem., 2002, Vol. 219, 248), organotin compounds (Stille reaction: Angew. Chem., 1986, 98, 504; Synthesis, 1992, 803; Org. React., 1997, 50, 1; Angew. Chem., Int. Ed. Engl., 2004, 43, 4704; J. Organomet. Chem., 2002, 653, 50) or organozinc compounds (Negishi reaction: Acc. Chem. Res., 1982, 15, 340; Metal-Catalyzed Cross-coupling Reactions, F. Diedrich, P. J. Stang, Wiley-VCH, 1998, 1; Aust. J. Chem. 2004, 57, 107; Handbook of Organopalladium Chemistry for Organic Synthesis, E.-I. Negishi, Y. Dumond, 2002, Vol. 1, 767) in the presence of a palladium compound (e.g. palladium(II) acetate, tetrakis(triphenylphosphine)palladium, allylchloro(1,3-bis(2,6-di-isopropylphenyl)imidazol-2-ylidene)palladium, tris(dibenzylideneacetone)dipalladium(0), a ligand (e.g. 2,2'-bis(diphenylphosphino)-1, 1'-binaphthyl, triphenylphosphine, 1,1'-bis(diphenylphosphino)ferrocene, 2-dicyclohexylphosphino-2',4',6'-triisopropylbiphenyl, 4,5-bis(diphenylphosphino)-9,9-dimethylxanthene, 2-(dicyclohexylphosphino)3,6-dimethoxy-2',4',6'-triisopropyl-1,1'-biphenyl, 1,1'-bis(di-o-tolylphosphino)ferrocene) in a solvent (e.g. N,N-dimethylformamide, toluene, xylene, tetrahydrofuran, dioxane, dimethoxyethane, tert-butyl methyl ether) using a base (e.g. sodium tert-butoxide, potassium tert-butoxide, sodium hydride, potassium hydride, potassium hexamethyldisilazide, tripotassium phosphate, caesium carbonate) at a temperature of 40-200° C. The temperature depends inter alia on the solvent. Alternatively to the palladium compounds mentioned above, it is also possible to use other palladium compounds which are so-called pre-catalysts (e.g. chloro[2-(dicyclohexylphosphino)-3,6-dimethoxy-2',4',6'-triisopropyl-1,1'-biphenyl][2-(2-aminoethyl)phenyl]palladium(II) or (2-dicyclohexylphosphino-2',4',6'-triisopropyl-1,1'-biphenyl) [2-(2-aminoethyl)phenyl)]palladium(II) chloride. Preferred for use in the reactions are tetrakis(triphenylphosphine)palladium, palladium(II) acetate with 2,2'-bis(diphenylphosphino)-1, 1'-binaphthyl or 4,5-bis(diphenylphosphino)-9,9-dimethylxanthene or allylchloro(1,3-bis(2,6-di-isopropylphenyl) imidazol-2-ylidene)palladium. The use of tetrakis (triphenylphosphine)palladium is particularly preferred. Here, the radicals $R^a$ and $R^b$ can assume the definitions described for the general formula (I). In the case that the electrophiles carry protected hydroxyl functions or protected $NH_2$ or $NHR^a$, this protective group can be removed again in an additional synthesis step by a customary literature process (Protecting Groups, Philip J. Kocienski, 3rd Revised Edition (9 Feb. 2005), Thieme; Greene's Protective Groups in Organic Synthesis, Peter G. M. Wuts, Theodora W. Greene, 4th Edition (8 Dec. 2006), Wiley-Interscience).

In the case that $R^{1b}$ represents cyanide, the reaction of the starting materials of the general formula (Ia) can be carried out in the presence of one of the palladium compounds described above and in the presence of zinc cyanide in one of the solvents described above at a temperature of 40-200° C. Here, heating of the reaction mixture may be either by thermal heating or in the microwave. Particular preference is given here to using tetrakis(triphenylphosphine)palladium in N,N-dimethylformamide at a temperature of 150° C. in the microwave.

In addition, the starting materials of the general formula (Ia) can also be reacted with primary or secondary amines or with alkoxides (Buchwald-Hartwig reaction: Chemtracts: Inorg. Chem., 1996, 8, 1; Chem. Org. Chem. 1997, 1, 287; Synlett 1997, 329; Angew. Chem., Int. Ed. Engl., 1998, 37, 2046; Pure Appl. Chem. 1999, 71, 1425; Top. Curr. Chem. 2002, 219, 131), which allows compounds of the general formula (Ib) where $R^{1b}$=$NHR^a$, $NR^aR^b$, $NHC(=O)R^a$ or $OR^a$ to be obtained. The reaction is carried out in the presence of a palladium compound (e.g. palladium(II) acetate, tris(dibenzylideneacetone)dipalladium(0)), a ligand (e.g. 2,2'-bis(diphenylphosphino)-1,1'-binaphthyl, triphenylphosphine, 1,1'-bis(diphenylphosphino)ferrocene, 2-dicyclohexylphosphino-2',4',6'-triisopropylbiphenyl, 4,5-bis (diphenylphosphino)-9,9-dimethylxanthene, 2-(dicyclohexylphosphino)3,6-dimethoxy-2',4',6'-triisopropyl-1,1'-biphenyl, 1,1'-bis(di-o-tolylphosphino)ferrocen) in a solvent (e.g. N,N-dimethylformamide, toluene, xylene, tetrahydrofuran, dioxane, dimethoxyethane, tert-butyl methyl ether) using a base (e.g. sodium tert-butoxide, potassium tert-butoxide, lithium hexamethyldisilazide, sodium hexamethyldisilazide, potassium hexamethyldisilazide, potassium carbonate, caesium carbonate) at a temperature of 40-200° C. The temperature depends inter alia on the solvent. Alternatively to the palladium compounds mentioned above, it is also possible to use other palladium compounds which are so-called pre-catalysts (e.g. chloro[2-(dicyclohexylphosphino)-3,6-dimethoxy-2',4',6'-triisopropyl-1,1'-biphenyl][2-(2-aminoethyl)phenyl]palladium(II) or (2-dicyclohexylphosphino-2',4',6'-triisopropyl-1,1'-biphenyl) [2-(2-aminoethyl)phenyl)]palladium(II) chloride). Here, the reaction with the last-mentioned pre-catalysts is preferred.

Synthesis Scheme 6:

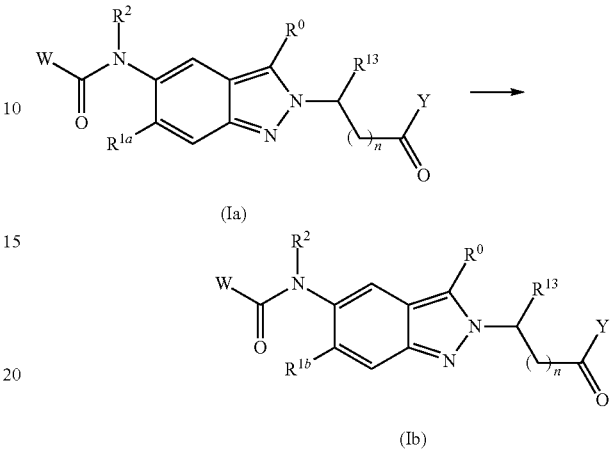

($R^{1a}$ represents chlorine, bromine, iodine, [(trifluoromethyl)sulphonyl]oxy or [(nonafluorobutyl)sulphonyl]oxy.

$R^{1b}$ represents a) $C_1$-$C_6$-alkyl, $C_3$-$C_8$-cycloalkyl, heterocycloalkyl, $C_3$-$C_8$-cycloalkyl-$C_1$-$C_4$-alkyl, heterocycloalkyl-$C_1$-$C_4$-alkyl, $C_2$-$C_6$-alkenyl, $C_2$-$C_6$-alkynyl, aryl, 5- to 10-membered heteroaryl, aryl-$C_1$-$C_4$-alkyl or 5- or 6-membered heteroaryl-$C_1$-$C_4$-alkyl which may optionally be mono- or polysubstituted by identical or different substituents from the group consisting of protected hydroxy, halogen, cyano, $C(=O)OR^a$, $S(=O)_2$-$C_1$-$C_6$-alkyl, protected $NH_2$, protected $NHR^a$ or $N(R^a)R^b$, b) cyanide, c) $NHR^a$, $NR^aR^b$, $NHC(=O)R^a$ or $OR^a$.)

A subset of the compounds according to the invention can be prepared as shown in Synthesis Scheme 7 by reacting starting materials of the general formula (Ic) with electrophiles $R^e$—X such as alkyl halides, alkylsulphonates, aryl halides, arylsulphonates, hetaryl halides or hetarylsulphonates. X has the meaning chlorine, bromine, iodine, $O(S=O)_2CH_3$, $O(S=O)_2C_6H_4CH_3$ or $O(S=O)_2CF_3$, with X preferably being chlorine, bromine or iodine and particularly preferably bromine.

$R^e$ represents $C_1$-$C_6$-alkyl, $C_3$-$C_8$-cycloalkyl, heterocycloalkyl, $C_3$-$C_8$-cycloalkyl-$C_1$-$C_4$-alkyl, heterocycloalkyl-$C_1$-$C_4$-alkyl, $C_2$-$C_6$-alkenyl, $C_2$-$C_6$-alkynyl, aryl, 5- to 10-membered heteroaryl, aryl-$C_1$-$C_4$-alkyl or 5- or 6-membered heteroaryl-$C_1$-$C_4$-alkyl which may optionally be mono- or polysubstituted by identical or different substituents from the group consisting of hydroxy (optionally protected), halogen, cyano, $C(=O)OR^a$, $S(=O)_2$—$C_1$-$C_6$-alkyl, protected $NH_2$, protected $NHR^a$ or $NR^aR^b$. Here, the radicals $R^a$ and $R^b$ can assume the definitions described for the general formula (I). In the case that the electrophiles carry protected hydroxyl functions or protected $NH_2$ or $NHR^a$, this protective group can be removed again in an additional synthesis step by a customary literature process (Protecting Groups, Philip J. Kocienski, 3rd Revised Edition (9 Feb. 2005), Thieme; Greene's Protective Groups in Organic Synthesis, Peter G. M. Wuts, Theodora W. Greene, 4th Edition (8 Dec. 2006), Wiley-Interscience). If $R^e$—X has the meaning alkyl halide or alkylsulphonate, it is possible to use suitable bases such as, for example, sodium tert-butoxide, potassium tert-butoxide, sodium hydride, potassium hydride, potassium hexamethyldisilazide, tripotassium phosphate, sodium carbonate, potassium carbonate, caesium carbonate (WO2003101379 A2; Bioor. Med. Chem., 2008, 16, 1966; J. Med. Chem., 2012, 55, 7141). Furthermore, it is possible to use further additives such as, for example, sodium iodide, potassium iodide, caesium iodide for the alkylation. The reaction with activated aryl halides, arylsulphonates, hetaryl halides or hetarylsulphonates (electron-withdrawing radicals or heteroatoms in the ortho- and/or para-position to the halide or sulphonate) can take place by nucleophilic aromatic substitution at the activated aryl halide, arylsulphonate, hetaryl halide or hetarylsulphonate, it being likewise possible to employ suitable bases such as, for example, sodium tert-butoxide, potassium tert-butoxide, sodium hydride, potassium hydride, potassium hexamethyldisilazide, tripotassium phosphate, sodium carbonate, potassium carbonate or caesium carbonate for the reaction (WO200795124 A2, EP2103620 A1). Furthermore, the arylation or heteroarylation of the starting materials of the general formula (Ic) in Synthesis Scheme 7 can be carried out by reaction with aryl halides, arylsulphonates, hetaryl halides or hetarylsulphonates using a copper-based transition metal catalyst known from the literature (e.g. copper(I) iodide, copper(I) oxide, copper(II) acetate) (Russ. Chem. Rev., 1974, 43, 1443; Tetrahedron, 2000, 56, 5054; Synlett, 2003, 2428; Angew. Chem., Int. Ed. Engl., 2003, 42, 5400; Angew. Chem., Int. Ed. Engl., 2004, 43, 1043) or palladium (e.g. palladium(II) acetate, tris(dibenzylideneacetone)dipalladium(0)) (Acc. Chem. Res., 1998, 31, 852; Angew. Chem., Int. Ed. Engl., 1998, 37, 2046; Top. Cur. Chem., 2002, 219, 131) in the presence of a suitable base (e.g. sodium tert-butoxide, potassium tert-butoxide, sodium hydride, potassium hydride, potassium hexamethyldisilazide, tripotassium phosphate, sodium carbonate, potassium carbonate, caesium carbonate) and a ligand (e.g. 2,2'-bis(diphenylphosphino)-1,1'-binaphthyl, 4,5-bis(diphenylphosphino)-9,9-dimethylxanthene, triphenylphosphine, 1,1'-bis(diphenylphosphino)ferrocene, 1,1'-bis(di-o-tolylphosphino)ferrocene, 1,3-di-tert-butyl-2-chloro-1,3,2-diazaphospholidine, 2'-(dicyclohexylphosphino)-N,N-dimethylbiphenyl-2-amine) in a solvent (e.g. N,N-dimethylformamide, toluene, xylene, tetrahydrofuran, dioxane, dimethoxyethane, tert-butyl methyl ether) at a temperature of 40-200° C. Preferably, the 6-hydroxyindazoles are reacted with alkyl halides using the base potassium carbonate and the solvent N,N-dimethylformamide. The reactions are preferably carried out at 70-150° C. in the microwave over a period of 1-24 hours.

Synthesis Scheme 7:

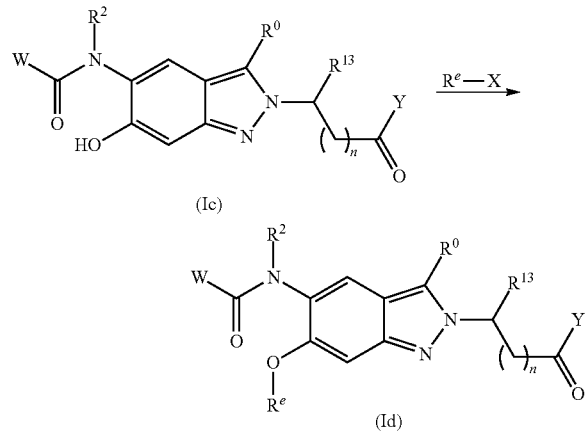

(Ic)

(Id)

(R$^e$ represents C$_1$-C$_6$-alkyl, C$_3$-C$_8$-cycloalkyl, heterocycloalkyl, C$_3$-C$_8$-cycloalkyl-C$_1$-C$_4$-alkyl, heterocycloalkyl-C$_1$-C$_4$-alkyl, C$_2$-C$_6$-alkenyl, C$_2$-C$_6$-alkynyl, aryl, 5- to 10-membered heteroaryl, aryl-C$_1$-C$_4$-alkyl or 5- or 6-membered heteroaryl-C$_1$-C$_4$-alkyl which may optionally be mono- or polysubstituted by identical or different substituents from the group consisting of hydroxy (optionally protected), halogen, cyano, C(=O)OR$^a$, S(=O)$_2$-C$_1$-C$_6$-alkyl, protected NH$_2$, protected NHR$^a$ or NR$^a$R$^b$.)

The pyridinecarboxylic acids (Intermediate 19) used as starting material for the synthesis of a subset of the compounds according to the invention are commercially available or can be prepared by routes known from the literature in accordance with Synthesis Scheme 8. Some of the Intermediates 19 can be prepared from carboxylic esters (Intermediate 17) by hydrolysis or—in the case that it is a tert-butyl ester—by reaction with an acid such as, for example, hydrogen chloride or trifluoroacetic acid. The Intermediates 19 may optionally be produced as salts (for example as potassium salt). The Intermediates 17 are commercially available, can be prepared by routes known from the literature or are available from the Intermediates 16 which, as X$^1$, carry chlorine, bromine or iodine, by reaction in a carbon monoxide atmosphere, optionally under superatmospheric pressure in the presence of a phosphine ligand such as, for example, 1,3-bis(diphenylphoshino)propane, a palladium compound such as, for example, palladium(II) acetate and a base such as, for example, triethylamine with addition of ethanol or methanol in a solvent such as, for example, dimethyl sulphoxide.

Here, the radical R$^3$ represents cyano, substituted or unsubstituted C$_1$-C$_6$-alkyl, substituted or unsubstituted C$_1$-C$_6$-alkoxy, substituted or unsubstituted C$_3$-C$_6$-cycloalkyl, heterocycloalkyl, C$_5$-C$_{11}$-spirocycloalkyl, substituted or unsubstituted C$_3$-C$_6$-cycloalkyl-C$_1$-C$_4$-alkyl, substituted or unsubstituted aryl, 5- to 10-membered heteroaryl, NH$_2$, NHR$^a$, N(R$^a$)R$^b$ or N(H)C(=O)R$^a$.

In the special case that R$^3$ has the meaning substituted or unsubstituted C$_1$-C$_6$-alkoxy, NH$_2$, NHR$^a$ or N(R$^a$)R$^b$, R$^3$ can be introduced by heating the corresponding bishalogenated Intermediates 15 in which X$^1$ and X$^2$ independently of one another represent chlorine, bromine or iodine with alcohols or amines, which yields the Intermediates 16.

If R$^3$ represents substituted or unsubstituted C$_1$-C$_6$-alkyl (Eur. J. of Org. Chem., 2002, 327), substituted or unsubstituted C$_3$-C$_6$-cycloalkyl, heterocycloalkyl, C$_5$-C$_{11}$-spirocycloalkyl or substituted or unsubstituted C$_3$-C$_6$-cycloalkyl-C$_1$-C$_4$-alkyl, R$^3$ can be introduced by reacting the Intermediates 15 with the appropriate organometal compounds. Suitable for this purpose are organolithium compounds (Green Chemistry, 2011, 13, 1110), organomagnesium compounds or organocopper compounds (Angew. Chem., 2013, 125, 6397). In the case of amino- or hydroxy-substituted radicals R$^3$, the functional group in the organometal compound carries a protective group which is known in the literature and, according to the opinion of the person skilled in the art, suitable (Protecting Groups, Philip J. Kocienski, 3rd Revised Edition (9 Feb. 2005), Thieme; Greene's Protective Groups in Organic Synthesis, Peter G. M. Wuts, Theodora W. Greene, 4th Edition (8 Dec. 2006), Wiley-Interscience). This protective group can be removed again in an additional synthesis step by a customary literature process (Protecting Groups, Philip J. Kocienski, 3rd Revised Edition (9 Feb. 2005), Thieme; Greene's Protective Groups in Organic Synthesis, Peter G. M. Wuts, Theodora W. Greene, 4th Edition (8 Dec. 2006), Wiley-Interscience). Alternatively, the radical R$^3$ can also be introduced via a palladium-catalysed Suzuki coupling (Pure Appl. Chem., 1985, 57, 1749; Chem. Rev., 1995, 95, 2457; Advances in Metal-Organic Chemistry, 1998, 6, 187; Angew. Chem., Int. Ed. Engl., 2004, 43, 2201, Top. Curr. Chem., 2002, Vol. 219, 248) if R$^3$ is substituted or unsubstituted aryl or a 5- to 10-membered heteroaryl. Here, R$^3$ is introduced via a corresponding organoboron compound in the presence of a palladium compound (e.g. palladium(II) acetate, tris(dibenzylideneacetone)dipalladium(0), tetrakis(triphenylphosphine)palladium), a ligand (e.g. 2,2'-bis(diphenylphosphino)-1,1'-binaphthyl, triphenylphosphine, 1,1'-bis (diphenylphosphino)ferrocene, 2-dicyclohexylphosphino-2', 4',6'-triisopropylbiphenyl, 4,5-bis(diphenylphosphino)-9,9-dimethylxanthene, 2-(dicyclohexylphosphino)3,6-dimethoxy-2',4',6'-triisopropyl-1,1'-biphenyl, 1,1'-bis(di-o-tolylphosphino)ferrocene) in a solvent (e.g. N,N-dimethylformamide, acetonitrile, toluene, xylene, tetrahydrofuran, dioxane, dimethoxyethane, methanol, ethanol, water) using a base (e.g. sodium carbonate, potassium carbonate, caesium carbonate, tripotassium phosphate, potassium fluoride, sodium hydroxide) and optionally added lithium chloride at a temperature of 25-200° C. The use of tetrakis(triphenylphosphine)palladium is preferred.

Alternatively, the Intermediates 17 can also be prepared from Intermediates 18. To introduce the radical $R^3$, the above-described Suzuki reaction with appropriate organoboron compounds is employed.

Synthesis Scheme 8:

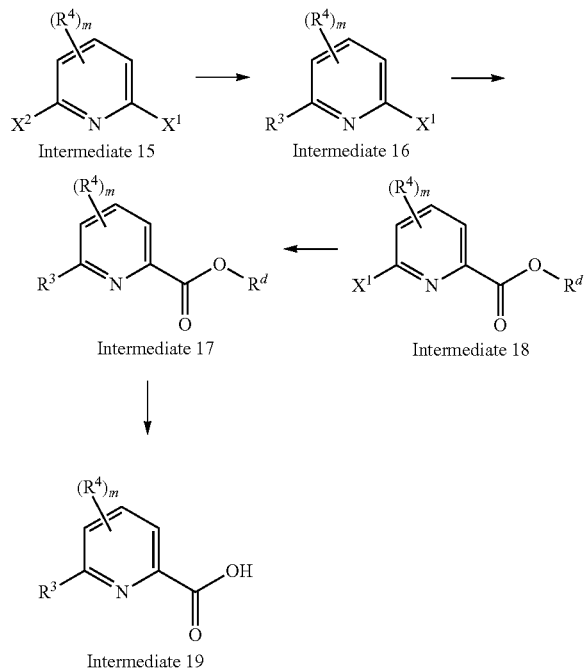

($X^1$ represents chlorine, bromine or iodine.
$X^2$ represents chlorine, bromine or iodine.
$R^d$ represents $C_1$-$C_6$-alkyl or benzyl.
$R^3$, $R^4$ and m have the definitions described in the general formula (I).)

In accordance with Synthesis Scheme 9, Intermediates 20, which can be prepared according to Synthesis Scheme 2, can be reacted in a Negishi reaction (Acc. Chem. Res., 1982, 15, 340; Metal-Catalyzed Cross-coupling Reactions, F. Diedrich, P. J. Stang, Wiley-VCH, 1998, 1; Aust. J. Chem. 2004, 57, 107; Handbook of Organopalladium Chemistry for Organic Synthesis, E.-I. Negishi, Y. Dumond, 2002, Vol. 1, 767) with primary and secondary alkylzinc reagents in the presence of a palladium catalyst, which allows the preparation of a subset (Ie) of the compounds according to the invention where $R^g$=primary or secondary $C_1$-$C_6$-alkyl. Preference is given to the reaction with diethylzinc or 2-methylpropylzinc bromide.

Synthesis Scheme 9:

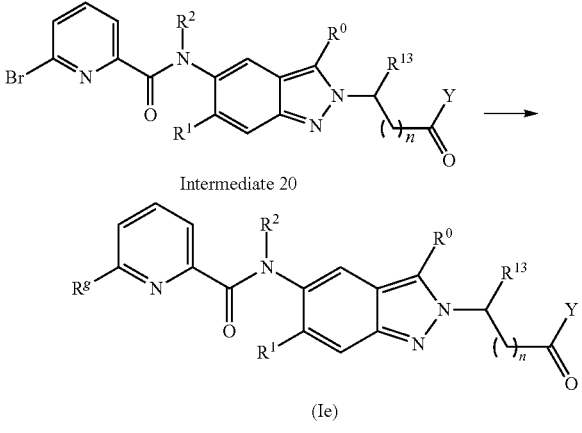

($R^g$ represents primary or secondary $C_1$-$C_6$-alkyl)

Further intermediates can be obtained according to Synthesis Scheme 10: The Intermediates 9 can be reacted in an amide coupling as described in Synthesis Scheme 1 to give the Intermediates 21. The use of 1-(3-dimethylaminopropyl)-3-ethylcarbodiimide hydrochloride in combination with 1-hydroxy-1H-benzotriazole hydrate is preferred. Intermediates 21 can then be converted by reaction with trifluoroacetic acid into Intermediates 22 which, in an amide coupling reaction, can be reacted analogously to the methods described in Synthesis Scheme 1 to afford Exemplary Compounds.

Synthesis Scheme 10:

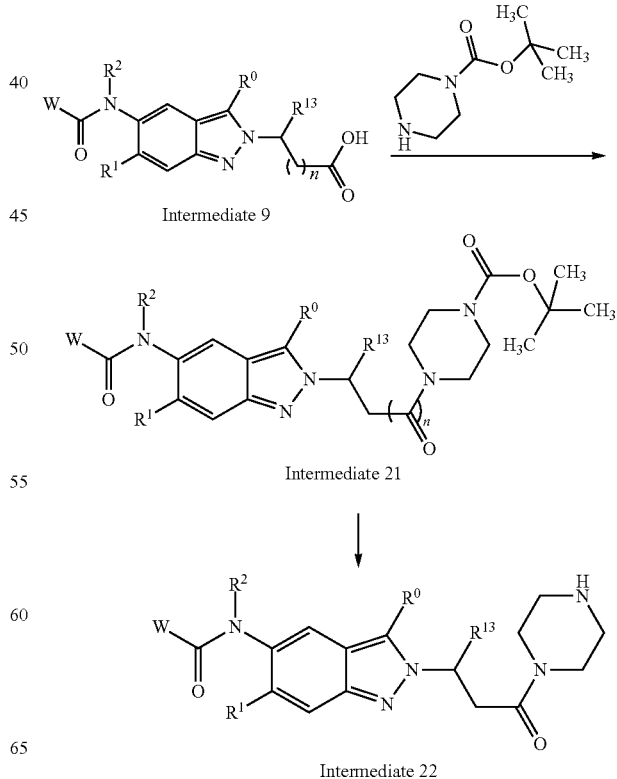

Intermediates of type 2b can be obtained according to Synthesis Scheme 11: Intermediates 12b are reacted with benzyl carbonochloridate and N-ethyl-N-isopropylpropane-2-amine in THF to give Intermediates 23. The reaction with trifluoroacetic acid in dichloromethane then leads to the Intermediates 2b which are reacted further according to Synthesis Scheme 1 to give the compounds according to the invention.

Synthesis Scheme 11:

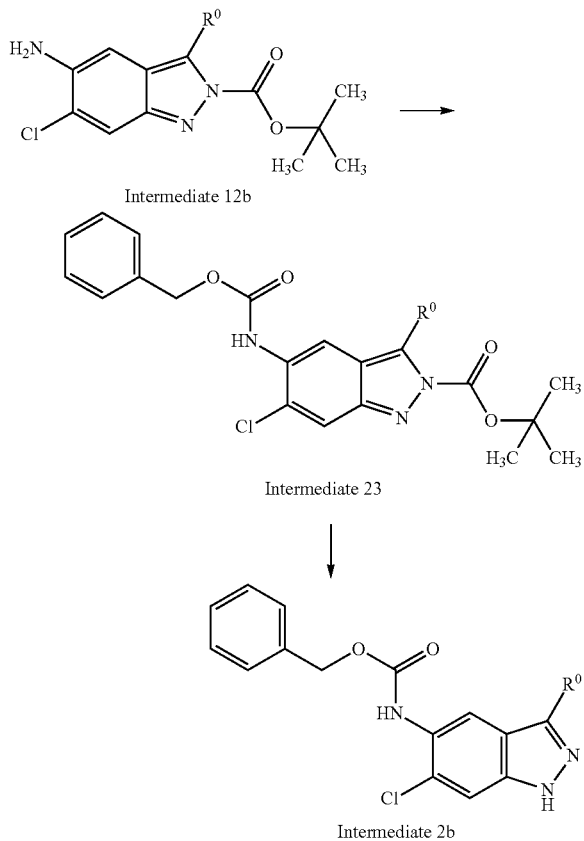

Intermediate 12b

Intermediate 23

Intermediate 2b

Abbreviations

| | |
|---|---|
| DMF | N,N-dimethylformamide |
| HPLC | high-performance liquid chromatography |
| HOBt | 1-hydroxy-1H-benzotriazole hydrate |
| UPLC | ultra-performance liquid chromatography |
| DAD | diode array detector |
| EDC | 1-(3-dimethylaminopropyl)-3-ethylcarbodiimide hydrochloride |
| ELSD | evaporating light scattering detector |
| ESI | electrospray ionization |
| SQD | single quadrupole detector |
| PTFE | polytetrafluoroethylene |
| CV | column volume(s) |
| BOC | tert-butyloxycarbonyl |
| PG | protecting group |
| LG | leaving group |

Methods

Analytical HPLC methods:
Method A1: UPLC (ACN—HCOOH):
Instrument: Waters Acquity UPLC-MS SQD 3001; column: Acquity UPLC BEH C18 1.7 50×2.1 mm; mobile phase A: water +0.1% by volume of formic acid (99%), mobile phase B: acetonitrile; gradient: 0-1.6 min 1-99% B, 1.6-2.0 min 99% B; flow rate 0.8 ml/min; temperature: 60° C.; injection: 2 µl; DAD scan: 210-400 nm; ELSD.

Method A2: UPLC (ACN—NH3):
Instrument: Waters Acquity UPLC-MS SQD 3001; column: Acquity UPLC BEH C18 1.7 50×2.1 mm; mobile phase A: water+0.2% by volume of ammonia (32%), mobile phase B: acetonitrile; gradient: 0-1.6 min 1-99% B, 1.6-2.0 min 99% B; flow rate 0.8 ml/min; temperature: 60° C.; injection: 2 µl; DAD scan: 210-400 nm; ELSD.

Method A3: (LC-MS)
Instrument: Agilent 1290 Infinity LC; column: Acquity UPLC BEH C18 1.7 50×2.1 mm; mobile phase A: water+0.05% by volume of formic acid, mobile phase B: acetonitrile+0.05% by volume of formic acid; gradient: 0-1.7 min 2-90% B, 1.7-2.0 min 90% B; flow rate 1.2 ml/min; temperature: 60° C.; injection: 2 µl; DAD scan: 190-390 nm; MS: Agilent TOF 6230.

Method A4: (LC-MS)
Instrument: Waters Acquity; column: Kinetex (Phenomenex), 50×2 mm; mobile phase A: water+0.05% by volume of formic acid, mobile phase B: acetonitrile+0.05% by volume of formic acid; gradient: 0-1.9 min 1-99% B, 1.9-2.1 min 99% B; flow rate 1.5 ml/min; temperature: 60° C.; injection: 0.5 µl; DAD scan: 200-400 nm.

Preparative HPLC Methods:
Method P1: System: Waters autopurification system: Pump 2545, Sample Manager 2767, CFO, DAD 2996, ELSD 2424, SQD; column: XBridge C18 5 µm 100×30 mm; mobile phase:A:water+0.1% by volume of formic acid, mobile phase B: acetonitrile; gradient: 0-8 min 10-100% B, 8-10 min 100% B; flow rate: 50 ml/min; temperature: room temp.; solution: max. 250 mg/max. 2.5 ml DMSO or DMF; injection: 1×2.5 ml; detection: DAD scan range 210-400 nm; MS ESI+, ESI−, scan range 160-1000 m/z.

Method P2: System: Waters autopurification system: Pump 254, Sample Manager 2767, CFO, DAD 2996, ELSD 2424, SQD 3100; column: XBridge C18 5 µm 100×30 mm; mobile phase: A: water+0.2% by volume of ammonia (32%), mobile phase B: methanol; gradient: 0-8 min 30-70% B; flow rate: 50 ml/min; temperature: room temp.; detection: DAD scan range 210-400 nm; MS ESI+, ESI−, scan range 160-1000 m/z; ELSD.

Method P3: System: Labomatic, pump: HD-5000, fraction collector: LABOCOL Vario-4000, UV detector: Knauer UVD 2.1S; column: XBridge C18 5 µm 100×30 mm; mobile phase A: water+0.2% by volume of ammonia (25%), mobile phase B: acetonitrile; gradient: 0-1 min 15% B, 1-6.3 min 15-55% B, 6.3-6.4 min 55-100% B, 6.4-7.4 min 100% B; flow rate: 60 ml/min; temperature: room temp.; solution: max. 250 mg/2 ml DMSO; injection: 2×2 ml; detection: UV 218 nm; software: SCPA PrepCon5.

Method P4: System: Agilent: Prep 1200, 2×Prep Pump, DLA, MWD, Prep FC; column: Chiralpak IA 5 µm 250×20 mm; mobile phase A: methanol, mobile phase B: ethanol; gradient: isocratic 50% B; flow rate: 15 ml/min; temperature: room temp.; detection: UV 254 nm Method P5: System: Labomatic, pump: HD-5000, fraction collector: LABOCOL Vario-4000, UV detector: Knauer UVD 2.1S; column: Chromatorex RP C18 10 µm 125×30 mm, mobile phase: A: water+0.1% by volume of formic acid, mobile phase B: acetonitrile; gradient: 0-15 min 65-100% B; flow rate: 60 ml/min; temperature: room temp.; solution: max. 250 mg/2 ml DMSO; injection: 2×2 ml; detection: UV 254 nm; software: SCPA PrepCon5.

Microwave

CEM Discover S-Class; autosampler: CEM Explorer; software: CEM Synergy; method: Dynamic heating mode, 300 W, 18 bar max.

Intermediates

2-Fluoro-5-nitro-4-(trifluoromethoxy)benzaldehyde

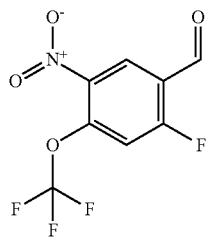 [SMILES: O=Cc1cc([N+](=O)[O-])c(OC(F)(F)F)cc1F]

20.9 g (100.4 mmol) of 2-fluoro-4-(trifluoromethoxy)benzaldehyde were dissolved in 100 ml of sulphuric acid (w=96%) and, in a three-necked flask fitted with mechanical stirrer, dropping funnel and internal thermometer, cooled to −15° C. Over a period of 60 min, the nitrating acid (28 ml of sulphuric acid (w=96%) in 14 ml of nitric acid (w=65%)), which had been prepared and cooled beforehand, was added dropwise to this solution. During the addition, the internal temperature fluctuated between −15° C. and −12° C. After the end of the dropwise addition, stirring was continued for another hour (internal temperature −13° C.). The reaction mixture was added to ice and extracted three times with in each case 150 ml of ethyl acetate. The combined org. phases were washed with saturated sodium chloride solution, dried over sodium sulphate, filtered and concentrated. This gave 25.4 g (100% of theory) of the title compound.

$^1$H NMR (400 MHz, CHLOROFORM-d) δ=7.34 (dd, 1H), 8.57 (d, 1H), 10.34 (s, 1H).

Intermediate 0-2

5-Nitro-6-(trifluoromethoxy)-1H-indazole

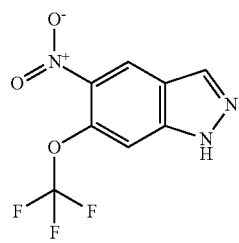 [SMILES: O=[N+]([O-])c1cc2cn[nH]c2cc1OC(F)(F)F]

25.4 g (100.4 mmol) of 2-fluoro-5-nitro-4-(trifluoromethoxy)benzaldehyde were initially charged in 200 ml of absolute ethanol, and 25 ml (513.6 mmol) of hydrazine hydrate were added. The colour of the solution darkened. The reaction mixture was heated under reflux for 2 h. The reaction mixture was then added to 1.4 l of water and stirred vigorously for 10 minutes. The precipitate formed was filtered off with suction and washed three times with in each case 40 ml of water. The resulting solid was dried in a vacuum drying cabinet at +50° C. overnight. This gave 19.4 g (78% of theory) of the title compound.

UPLC-MS (Method A1): $R_t$=1.03 min

MS (ESIpos): m/z=248 (M+H)$^+$ $^1$H-NMR (400 MHz, DMSO-d6) δ=7.86 (s, 1H), 8.46 (s, 1H), 8.82 (s, 1H), 13.87 (br. s., 1H).

Intermediate 0-3

6-(Benzyloxy)-5-nitro-1H-indazole

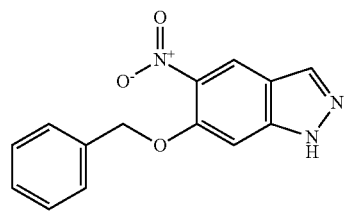 [SMILES: O=[N+]([O-])c1cc2cn[nH]c2cc1OCc1ccccc1]

20.0 g (111.6 mmol) of 5-nitro-1H-indazol-6-ol (CAS No. 1082041-56-2) were initially charged in 750 ml of tetrahydrofuran, and 13.9 ml (134.0 mmol) of benzyl alcohol and 35.1 g (134.0 mmol) of triphenylphosphine were added. The solution was cooled to 0° C., and 26.03 ml (134.0 mmol) of diisopropylazo dicarboxylate were added. The reaction mixture was stirred at 0° C. for 1 h and then at 25° C. for 24 h. Water was then added, and the reaction mixture was extracted with ethyl acetate. The combined organic phases were washed with saturated sodium chloride solution and concentrated. The residue was taken up in dichloromethane, Isolute® HM-N (Biotage) was added and during concentration the residue was adsorbed on Isolute. The Isolute was applied to a cartridge (750 g; KP-Sil) pre-equilibrated with hexane and chromatography was carried out using the Isolera® flash purification system (Biotage) (mobile phase: hexane/ethyl acetate; flow rate: 200 ml/min; gradient: isocratic 88:12 (1 CV), 88:12→20:80 (10 CV), isocratic 20:80 (2 CV)). The combined product fractions were concentrated and dried. This gave 18.908 g (63% of theory) of the title compound.

UPLC-MS (Method A1): $R_t$=1.09 min

MS (ESIpos): m/z=270 (M+H)$^+$ $^1$H-NMR (300 MHz, DMSO-d6) δ=5.35 (s, 2H), 7.25-7.57 (m, 6H), 8.20 (s, 1H), 8.45 (s, 1H), 13.38 (br. s., 1H).

Intermediate 0-4

6-Ethoxy-5-nitro-1H-indazole

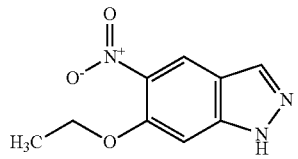

100 mg (0.56 mmol) of 5-nitro-1H-indazol-6-ol (CAS No. 1082041-56-2) were initially charged in 668 µl of N,N- dimethylformamide, and 93 mg (0.67 mmol) of potassium carbonate and 54 µl (0.67 mmol) of iodoethane were added. The solution was heated in a microwave at 60° C. for 1 h. Water was then added, and the reaction mixture was extracted with ethyl acetate. The combined organic phases were washed with saturated sodium chloride solution, filtered through a hydrophobic filter and concentrated. The residue was taken up in dichloromethane, Isolute® HM-N (Biotage) was added and during concentration the residue was adsorbed on Isolute. The Isolute was applied to a cartridge (25 g; KP-Sil) pre-equilibrated with hexane and chromatography was carried out using the Isolera® flash purification system (Biotage) (mobile phase: hexane/ethyl acetate; flow rate: 25 ml/min; gradient: isocratic 88:12 (1 CV), 88:12→0:100 (10 CV), isocratic 0:100 (2 CV)). The combined product fractions were concentrated and dried. This gave 89 mg (77% of theory) of the title compound.

UPLC-MS (Method A1): $R_t$=0.89 min

MS (ESIpos): m/z=208 (M+H)$^+$ $^1$H NMR (300 MHz, DMSO-d6) δ=1.37 (t, 3H), 4.23 (q, 2H), 7.19 (s, 1H), 8.17 (s, 1H), 8.40 (s, 1H), 13.31 (br. s., 1H).

Intermediate 0-5

Methyl 5-nitro-1H-indazole-6-carboxylate

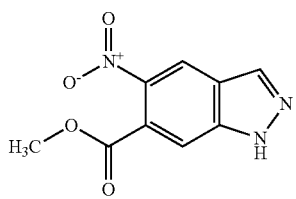 [SMILES: COC(=O)c1cc2[nH]ncc2cc1[N+](=O)[O-]]

4.60 g (26.1 mmol) of methyl 1H-indazole-6-carboxylate were dissolved in 120 ml of sulphuric acid (W=96%) and, in a three-necked flask fitted with mechanical stirrer, dropping funnel and internal thermometer, cooled to −15° C. Over a period of 15 minutes, the nitrating acid (9.2 ml of sulphuric acid (w=96%) in 4 ml of nitric acid (w=65%)), which had been prepared and cooled beforehand, was added dropwise to this solution. During the addition, the internal temperature fluctuated between −15° C. and −12° C. After the end of the dropwise addition, stirring was continued for another hour (internal temperature −5° C.). The reaction mixture was added to ice, and the precipitate formed was filtered off with suction, washed with water and dried in a drying cabinet at 50° C. under reduced pressure. This gave 5.49 g (91% of theory) of the title compound.

UPLC-MS (Method A1): $R_t$=1.21 min

MS (ESIpos): m/z=471 (M+H)$^+$ $^1$H NMR (400 MHz, DMSO-d6): δ=3.85 (s, 3H) 6.01 (s, 2H) 6.98 (s, 1H) 7.79-7.91 (m, 1H) 7.99 (s, 1H) 12.84 (br. s., 1H).

Intermediate 1-1

6-(Trifluoromethoxy)-1H-indazole-5-amine

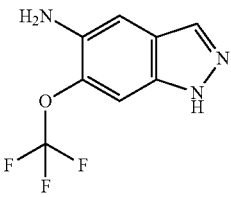 [SMILES: Nc1cc2cn[nH]c2cc1OC(F)(F)F]

10.0 g (40.5 mmol) of 5-nitro-6-(trifluoromethoxy)-1H-indazole (Intermediate 0-2) were dissolved in 400 ml of methanol. The solution was then degassed and flushed with nitrogen (this was repeated twice). 2.48 g (2.0 mmol) of palladium on activated carbon were added. The flask was evacuated and flushed with hydrogen. The reaction mixture was hydrogenated under standard hydrogen pressure at room temperature for 5 hours. The reaction mixture was filtered through a PTFE filter with Celite and concentrated. This gave 7.2 g (74% of theory) of the title compound.

UPLC-MS (Method A1): $R_t$=0.75 min

MS (ESIpos): m/z=218 (M+H)$^+$

1H NMR (400 MHz, DMSO-d6) δ=4.91 (s, 2H), 7.04 (s, 1H), 7.32 (s, 1H), 7.83 (s, 1H), 12.72 (br. s., 1H).

Intermediate 1-2

5-Amino-1H-indazol-6-ol

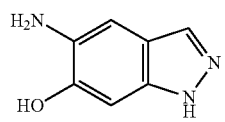

Analogously to Intermediate 1-1, 6.5 g (36.3 mmol) of 5-nitro-1H-indazol-6-ol (CAS No. 1082041-56-2) were dissolved in 1.5 l of methanol and hydrogenated with 193 mg (1.8 mmol) of palladium on activated carbon under standard hydrogen pressure at 25° C. for 5 h. This gave 5.28 g (98% of theory) of the title compound.

UPLC-MS (Method A1): $R_t$=0.26 min

MS (ESIpos): m/z=150 (M+H)$^+$ $^1$H NMR (400 MHz, DMSO-d6): δ=4.37 (br. s., 2H) 6.71-6.78 (m, 2H) 7.59 (s, 1H) 12.17 (br. s., 1H).

Intermediate 1-3

6-(Benzyloxy)-1H-indazole-5-amine

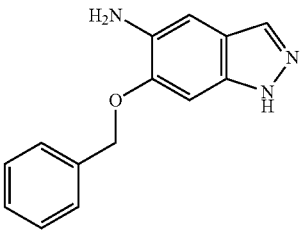 [SMILES: Nc1cc2cn[nH]c2cc1OCc1ccccc1]

18.5 g (68.7 mmol) of 6-(benzyloxy)-5-nitro-1H-indazole (Intermediate 0-3) were dissolved in 500 ml of ethanol and initially charged in a 1 l three-necked flask with mechanical stirrer and reflux condenser, and 100 ml of water were added. 19.2 g (343.5 mmol) of iron powder and 1.84 g (34.35 mmol) of ammonium chloride were then added. The brown suspension was heated at reflux for 4 h. The reaction mixture was cooled to 25° C. using a water bath and filtered through Celite (clear filtrate). The filter cake was washed with ethanol. The filtrate was concentrated until about 200 ml of solvent were left. The reaction mixture was added to 2 l of water. The suspension was cooled and the resulting precipitate was then filtered off with suction. The filter cake was washed twice with in each case 150 ml of water and twice with in each case 100 ml of diethyl ether. The precipitate was dried in a vacuum drying cabinet at 50° C. for 5 h and then re-hydrogenated for 5 h using 193 mg (1.81 mmol) of palladium on activated carbon at 25° C. under standard hydrogen pressure. This gave 15.28 g (92% of theory) of the title compound.

UPLC-MS (Method A1): $R_t$=0.66 min
MS (ESIpos): m/z=240 (M+H)$^+$
$^1$H-NMR (300 MHz, DMSO-d6): δ=4.54 (s, 2H), 5.19 (s, 2H), 6.84 (s, 1H), 6.91 (s, 1H), 7.22-7.45 (m, 3H), 7.48-7.57 (m, 2H), 7.66 (s, 1H), 12.43 (br. s., 1H).

Intermediate 1-4

6-Isopropoxy-1H-indazole-5-amine

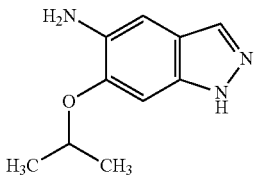

10 g (45.2 mmol) of 6-isopropoxy-5-nitro-1H-indazole (CAS No. 1082041-56-2) were dissolved in 200 ml of ethanol and hydrogenated with 1.20 g (1.13 mmol) of palladium on activated carbon under standard hydrogen pressure at 25° C. for 24 h. The reaction mixture was filtered off through Celite, the filter cake was washed with ethanol and the filtrate was concentrated. The residue was subjected to incipient dissolution with a little ethanol in an ultrasonic bath, diethyl ether was added and the residue was digested further in the ultrasonic bath. The solid was filtered off with suction and washed with a little diethyl ether and hexane, giving 4.69 g (54%) of product. The filtrate was concentrated and applied to a Biotage SNAP cartridge (100 g; KP-Sil) pre-equilibrated with hexane and chromatography was carried out using the Isolera® flash purification system (mobile phase: hexane/ethyl acetate; gradient: 90:10→35:65 (9.2 CV), isocratic 35:65 (1 CV)). The combined product fractions were concentrated and the residue was digested with a mixture of hexane and dichloromethane (2:1) in an ultrasonic bath. The solid formed was filtered off. This gave an additional 2.36 g (27% of theory) of the title compound.

UPLC-MS (Method A1): $R_t$=0.75 min
MS (ESIpos): m/z=192 (M+H)$^+$
$^1$H NMR (400 MHz, DMSO-d6): δ=1.31 (s, 3H), 1.33 (s, 3H), 4.43 (s, 2H), 4.57-4.68 (m, 1H), 6.81 (s, 1H), 6.83 (s, 1H), 7.64 (s, 1H), 12.34 (br. s., 1H).

Intermediate 1-5

6-Ethoxy-1H-indazole-5-amine

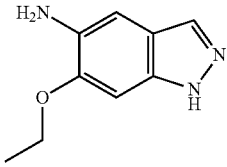

Analogously to Intermediate 1-1, 65 mg (0.31 mmol) of 6-ethoxy-5-nitro-1H-indazole (Intermediate 0-4) were dissolved in 4.1 ml of methanol and hydrogenated with 33 mg (0.03 mmol) of palladium on activated carbon under standard hydrogen pressure at 25° C. for 5 h. This gave 54 mg (97% of theory) of the title compound.

UPLC-MS (Method A1): $R_t$=0.64 min
MS (ESIpos): m/z=178 (M+H)$^+$
$^1$H NMR (400 MHz, DMSO-d6): δ=1.40 (t, 3H), 4.07 (q, 2H), 4.47 (br. s., 2H), 6.81 (s, 2H), 7.65 (s, 1H), 12.39 (br. s., 1H).

Intermediate 1-6

Methyl 5-amino-1H-indazole-6-carboxylate

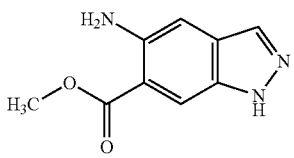

Analogously to Intermediate 1-1, 5.48 g (24.8 mmol) of methyl 5-nitro-1H-indazole-6-carboxylate (Intermediate 0-9) were dissolved in 293 ml of methanol and hydrogenated with 1.32 g (1.24 mmol) of palladium on activated carbon under standard hydrogen pressure at 25° C. for 3 h. This gave 4.52 g (91% of theory) of the title compound.

UPLC-MS (Method A1): $R_t$=0.75 min
MS (ESIpos): m/z=222 (M+H)$^+$
$^1$H NMR (500 MHz, DMSO-d6): δ=3.85 (s, 3H), 6.05 (br. s., 2H), 6.99 (d, 1H), 7.85 (d, 1H), 8.00 (s, 1H), 12.83 (br. s., 1H).

Intermediate 2-1 tert-Butyl (6-methyl-1H-indazol-5-yl)carbamate

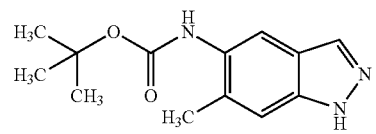 [SMILES: Cc1cc2[nH]ncc2cc1NC(=O)OC(C)(C)C]

10.3 g (70.0 mmol) of 6-methyl-1H-indazole-5-amine (CAS No: 81115-45-9) were suspended in 150 ml of tetrahydrofuran, 13.4 ml (80.0 mmol) of N,N-diisopropylethylamine were added and the mixture was cooled to 0° C. After addition of 5.52 g (25.3 mmol) of di-tert-butyl dicarbonate at 0° C., the mixture was then stirred at 25° C. for 18 h. The mixture was concentrated, giving 17.6 g of a crude product which was used without purification.

UPLC-MS (Method A1): $R_t$=1.01 min
MS (ESIpos): m/z=248 (M+H)$^+$

Intermediate 2-2 tert-Butyl (6-methoxy-1H-indazol-5-yl)carbamate

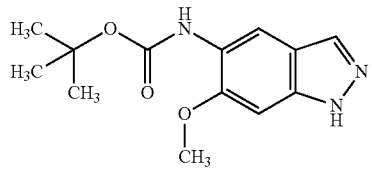 [SMILES: COc1cc2[nH]ncc2cc1NC(=O)OC(C)(C)C]

4.0 g (24.5 mmol) of 6-methoxy-1H-indazol-5-amine (CAS No. 749223-61-8) were dissolved in 30 ml of tetrahydrofuran, and 5.35 g (24.5 mmol) of di-tert-butyl dicarbonate were added. The reaction mixture was stirred at 25° C. for 18 h. The mixture was then concentrated and the residue was suspended in 20 ml of dichloromethane 200 ml of hexane were added and the resulting suspension was stirred with ice bath cooling for 25 minutes. The precipitate was filtered off with suction, washed twice with 25 ml of hexane and dried. This gave 4.83 g (75% of theory) of the title compound.

UPLC-MS (Method A2): $R_t$=1.08 min
MS (ESIpos): m/z=264 (M+H)$^+$
$^1$H NMR (400 MHz, CHLOROFORM-d) δ=1.56 (s, 9H), 3.95 (s, 3H), 6.88 (s, 1H), 7.12 (br. s., 1H), 7.94 (d, 1H), 8.40 (br. s., 1H).

Intermediate 2-3 tert-Butyl [6-(trifluoromethoxy)-1H-indazol-5-yl]carbamate

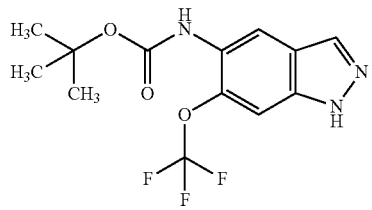 [SMILES: CC(C)(C)OC(=O)Nc1cc2cn[nH]c2cc1OC(F)(F)F]

5.0 g (23.0 mmol) of 6-(trifluoromethoxy)-1H-indazole-5-amine (Intermediate 1-1) were suspended in 100 ml of tetrahydrofuran, 4.81 ml (27.6 mmol) of N,N-diisopropylethylamine were added and the mixture was cooled to 0° C. After addition of 5.52 g (25.3 mmol) of di-tert-butyl dicarbonate at 0° C., the mixture was then stirred at 25° C. for 18 h. A further 3.52 g (16.1 mmol) of di-tert-butyl dicarbonate were added, and the mixture was stirred at 25° C. for a further 24 h. The reaction mixture was heated at reflux for a further 24 h. The reaction mixture was then concentrated, taken up in ethyl acetate and washed with 0.5 M hydrochloric acid, saturated sodium bicarbonate solution and saturated sodium chloride solution. The combined organic phases were dried over sodium sulphate and the solution was, after filtration, concentrated. The residue was taken up in dichloromethane, Isolute® HM-N (Biotage) was added and during concentration the residue was adsorbed on Isolute. The Isolute was applied to a Biotage SNAP cartridge (340 g; KP-Sil) pre-equilibrated with hexane and chromatography was carried out using the Isolera® flash purification system (Biotage) (mobile phase: hexane/ethyl acetate; gradient: isocratic 90:10 (3 CV), 90:10→80:20 (2 CV), isocratic 80:20 (7 CV), 80:20→75:25 (1 CV), isocratic 75:25 (7 CV)). The combined product fractions were concentrated and the brownish solid was dried under reduced pressure. This gave 3.48 g (48% of theory) of the title compound.

UPLC-MS (Method A2): $R_t$=1.15 min
MS (ESIpos): m/z=318 (M+H)$^+$
1H NMR (300 MHz, DMSO-d6) δ=1.44 (s, 9H), 7.51 (s, 1H), 7.83 (s, 1H), 8.11 (s, 1H), 8.80 (s, 1H).

Intermediate 2-4 tert-Butyl (6-hydroxy-1H-indazol-5-yl)carbamate

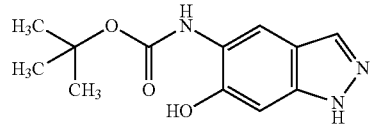 [SMILES: CC(C)(C)OC(=O)Nc1cc2cn[nH]c2cc1O]

8.05 g (36.8 mmol) of di-tert-butyl dicarbonate were suspended in 125 ml of tetrahydrofuran and 5.0 g (33.5 mmol) of 5-amino-1H-indazol-6-ol (Intermediate 1-2) were added a little at a time with stirring. The reaction mixture was stirred at 25° C. for 24 h. The reaction mixture was subsequently concentrated, the residue was taken up in methanol and 2 ml of 1 M aqueous sodium hydroxide solution and 2 ml of water were added. The mixture was stirred for another 30 min and the methanol was then distilled off 1 M hydrochloric acid was added to the residue until a pH of 7 had been reached. The mixture was then extracted with dichloromethane and the combined org. phases were dried over sodium sulphate, filtered and concentrated. This gave 7.50 g (90% of theory) of the title compound.

UPLC-MS (Method A2): $R_t$=0.95 min
MS (ESIpos): m/z=250 (M+H)$^+$
$^1$H NMR (300 MHz, DMSO-d6): δ=1.47 (s, 9H) 6.88 (s, 1H) 7.66 (s, 1H) 7.82 (s, 1H) 7.91 (s, 1H) 10.19 (br. s., 1H) 12.50 (s, 1H).

Intermediate 2-5 tert-Butyl (6-fluoro-1H-indazol-5-yl)carbamate

Analogously to Intermediate 2-2, 4.96 g (32.8 mmol) of 6-fluoro-1H-indazole-5-amine (CAS No.: 709046-14-0), 7.16 g (32.8 mmol) of di-tert-butyl dicarbonate and 6.28 ml (36 mmol) of N,N-diisopropylethylamine were dissolved in 51 ml of tetrahydrofuran and stirred at 25° C. for 20 h. This gave 5.72 g (69% of theory) of the title compound.

UPLC-MS (Method A1): $R_t$=1.01 min

MS (ESIpos): m/z=252 (M+H)$^+$ $^1$H-NMR (300 MHz, DMSO-d6): δ=1.45 (s, 9H), 7.35 (d, 1H), 7.81 (m, 1H), 8.03 (s, 1H), 8.80 (s, 1H), 13.08 (s, 1H).

Intermediate 2-6 tert-Butyl (6-bromo-1H-indazol-5-yl)carbamate

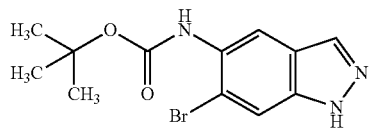 [SMILES: CC(C)(C)OC(=O)Nc1cc2cn[nH]c2cc1Br]

7.05 g (17.1 mmol) of the mixture of tert-butyl 6-bromo-5-[(tert-butoxycarbonyl)amino]-1H-indazole-1-carboxylate and tert-butyl 6-bromo-5-[(tert-butoxycarbonyl)amino]-2H-indazole-2-carboxy late (Intermediates 10 and 11) were dissolved in 141 ml of dimethylformamide, and 2.17 g (20.5 mmol) of sodium carbonate in 71 ml of water were added. The reaction mixture was heated at 85° C. for 24 h. Dichloromethane was added and the reaction mixture was washed with 0.5 M hydrochloric acid and saturated sodium chloride solution, dried over sodium sulphate and concentrated. The product was dried under reduced pressure. This gave 5.35 g (98% of theory) of product.

UPLC-MS (Method A2): $R_t$=1.09 min

MS (ESIneg): m/z=310 (M($^{79}$Br)—H)$^+$ $^1$H NMR (400 MHz, CHLOROFORM-d) δ=1.57 (s, 9H) 7.01 (br. s., 1H) 7.83 (s, 1H) 8.07 (s, 1H) 8.50 (s, 1H).

Intermediate 2-7 tert-Butyl [6-(benzyloxy)-1H-indazol-5-yl]carbamate

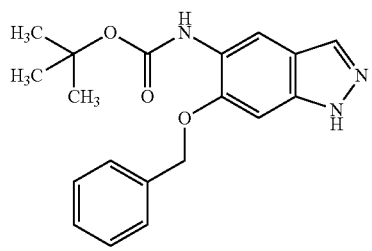 [SMILES: CC(C)(C)OC(=O)Nc1cc2cn[nH]c2cc1OCc1ccccc1]

7.50 g (30.1 mmol) of tert-butyl (6-hydroxy-1H-indazol-5-yl)carbamate (Intermediate 2-4) were dissolved in 150 ml of N,N-dimethylformamide, and 5.66 g (33.1 mmol) of benzyl bromide and 8.32 g (60.2 mmol) of potassium carbonate were added with stirring. The reaction mixture was stirred at 25° C. for 24 h. The reaction mixture was then diluted with water and extracted with ethyl acetate. The combined organic phases were washed with saturated sodium chloride solution, the phases were separated and filtered through a hydrophobic filter. The residue was taken up in dichloromethane and during concentration adsorbed on Isolute. The Isolute was applied to a Biotage SNAP cartridge (340 g; KP-Sil) pre-equilibrated with hexane and chromatography was carried out using the Isolera® flash purification system (Biotage) (mobile phase: hexane/ethyl acetate; gradient 100:0→60:40 (10 CV), isoratic 60:40 (9 CV)). The combined product fractions were concentrated and dried under reduced pressure. This gave 3.46 g (34% of theory) of product.

UPLC-MS (Method A2): $R_t$=1.27 min

MS (ESIpos): m/z=340 (M+H)$^+$

1H NMR (300 MHz, CHLOROFORM-d): δ=1.55 (s, 9H) 5.20 (s, 2H) 6.92 (s, 1H) 7.14 (s, 1H) 7.36-7.49 (m, 5H) 7.94 (d, J=0.75 Hz, 1H) 8.44 (s, 1H).

Intermediate 2-8 tert-Butyl-1H-indazol-5-ylcarbamate

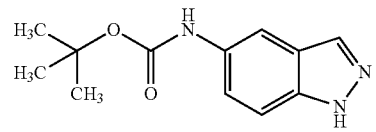 [SMILES: CC(C)(C)OC(=O)Nc1ccc2[nH]ncc2c1]

25.5 g (191.5 mmol) of 1H-indazole-5-amine (CAS No. 19335-11-6) were initially charged in 300 ml of tetrahydrofuran, 37 ml of N,N-diisopropylethylamine were added, 41.8 g (191.5 mmol) of di-tert-butyl dicarbonate were added a little at a time and the mixture was stirred at 25° C. for 24 h. The mixture was concentrated, giving 44.6 g (95% of theory) of the title compound.

UPLC-MS (METHOD A1): $R_t$=0.96 min

MS (ESIpos): m/z=234 (M+H)$^+$ $^1$H-NMR (300 MHz, DMSO-d6): δ=1.44 (s, 9H), 7.24-7.46 (m, 2H), 7.84 (s, 1H), 7.92 (s, 1H), 9.24 (br. s., 1H), 12.86 (br. s., 1H).

Intermediate 2-9 tert-Butyl (3-methyl-1H-indazol-5-yl)carbamate

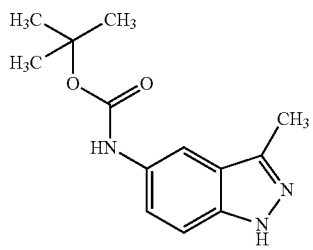 [SMILES: Cc1n[nH]c2ccc(NC(=O)OC(C)(C)C)cc12]

1.00 g (6.8 mmol) of 3-methyl-1H-indazole-5-amine were reacted analogously with 1.48 g (6.8 mmol) of di-tert-butyl carbonate and 1.3 ml (7.5 mmol) of N,N-diisopropylethylamine in 15 ml of THF overnight. Concentration gave 1.70 g of the title compound as a crude product.

UPLC-MS (METHOD A1): Rt=1.01 min

MS (ESIpos): m/z=248 (M+H)+.

Intermediate 2-10 tert-Butyl (6-isopropoxy-1H-indazol-5-yl)carbamate

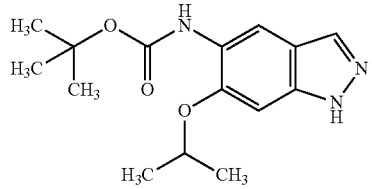 [SMILES: CC(C)Oc1cc2[nH]ncc2cc1NC(=O)OC(C)(C)C]

Analogously to Intermediate 2-2, 2.2 g (11.6 mmol) of 6-isopropoxy-1H-indazole-5-amine (Intermediate 1-4) were reacted with 2.52 g (11.6 mmol) of di-tert-butyl dicarbonate and 2.21 ml (12.7 mmol) of N,N-diisopropylethylamine. This gave 2.72 g (81% of theory) of the title compound.
UPLC-MS (Method A1): Rt=1.20
MS (ESIpos): m/z=292 (M+H)$^+$
1H-NMR (300 MHz, DMSO-d6): δ=1.34 (d, 6H), 1.47 (s, 9H), 4.63-4.74 (m, 1H), 6.98 (s, 1H), 7.68 (s, 1H), 7.88 (s, 1H), 7.94 (s, 1H), 12.68 (s, 1H).

Intermediate 2-11

Benzyl (6-chloro-1H-indazol-5-yl)carbamate

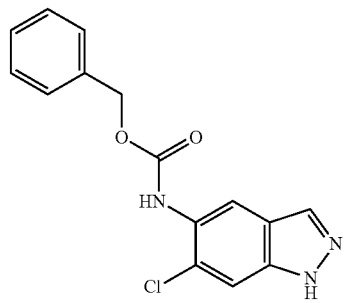 [SMILES: O=C(Nc1cc2cn[nH]c2cc1Cl)OCc1ccccc1]

6.1 ml of trifluoroacetic acid were added to 4.61 g of tert-butyl-5-{[(benzyloxy)carbonyl]amino}-6-chloro-2H-indazole-2-carboxylate (Intermediate 23-1, crude product) in 40 ml of dichloromethane, and the mixture was stirred at room temperature overnight. Saturated aqueous sodium bicarbonate solution was added and the solid was filtered off with suction, washed with water and diethyl ether and dried. This gave 2.11 g of a light-brown solid (crude product).
$^1$H-NMR (400 MHz, DMSO-d$_6$, selected signals): δ [ppm]=5.13 (s, 2H), 7.69 (s, 1H), 7.83 (s, 1H), 8.07 (s, 1H), 9.13 (br. s., 1H), 13.15 (br. s., 1H).

Intermediate 3-1

Ethyl {5-[(tert-butoxycarbonyl)amino]-6-methyl-2H-indazol-2-yl}acetate

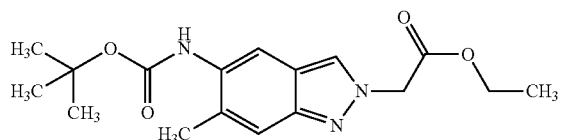

10.0 g (40.4 mmol) of tert-butyl (6-methyl-1H-indazol-5-yl)carbamate (Intermediate 2-1) were stirred with 9.00 ml (80.9 mmol) of ethyl bromoacetate in 75 ml of tetrahydrofuran in the presence of 17.1 ml (80.9 mmol) of N,N-dicyclohexylmethylamine at 70° C. for 24 h. The precipitated solid was filtered off and washed twice with ethyl acetate. Water was added to the filtrate and the organic phase was separated off and extracted twice with ethyl acetate. The combined organic phases were washed with 1 M hydrochloric acid solution, saturated sodium bicarbonate solution and saturated sodium chloride solution and concentrated. The residue was taken up in dichloromethane, Isolute® HM-N (Biotage) was added and during concentration the residue was adsorbed on Isolute. The Isolute was applied to a Biotage SNAP cartridge (340 g; KP-Sil) pre-equilibrated with hexane and chromatography was carried out using the Isolera® flash purification system (Biotage) (mobile phase: hexane/ethyl acetate; flow rate: 100 ml/min; gradient: isocratic 100:10 (1 CV), 100:0→50:50 (20 CV), isocratic 50:50 (0.2 CV)). The combined product fractions were concentrated and dried. This gave 8.90 g (42% of theory) of the title compound.

In a second experiment, 213 mg of the title compound were obtained analogously from 2.00 g of tert-butyl (6-methyl-1H-indazol-5-yl)carbamate using 2.24 g of potassium carbonate instead of N,N-dicyclohexylmethylamine at 80° C. in N,N-dimethylformamide, with two successive purifications on silica gel (hexane/ethyl acetate).
UPLC-MS (Method A1): R$_t$=1.14 min
MS (ESIpos): m/z=334 (M+H)$^+$
$^1$H-NMR (600 MHz, DMSO-d6): δ=1.21 (t, 3H), 1.46 (s, 9H), 2.28 (s, 3H), 4.16 (q, 2H), 5.34 (s, 2H), 7.38 (d, 1H), 7.57 (s, 1H), 8.25 (d, 1H), 8.40 (s, 1H).

Intermediate 3-2

Benzyl {5-[(tert-butoxycarbonyl)amino]-6-methoxy-2H-indazol-2-yl}acetate

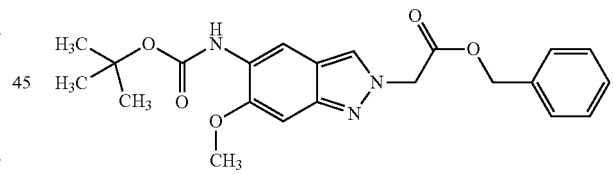

Analogously to Intermediate 3-1, 4.17 g (15.8 mmol) of tert-butyl (6-methoxy-1H-indazol-5-yl)carbamate (Intermediate 2-2) in 50 ml of THF were stirred with 2.51 ml (15.8 mmol) of benzyl bromoacetate and 3.36 ml (15.8 mmol) of N,N-dicyclohexylmethylamine at 65° C. for 4 h, 2.51 ml (15.8 mmol) of benzyl bromoacetate and 3.36 ml (15.8 mmol) of N,N-dicyclohexylmethylamine were then added and the mixture was stirred at 65° C. for a further 18 h. Work-up and purification by column chromatography using the Isolera® flash purification system (Biotage) (mobile phase: hexane/ethyl acetate; flow rate: 100 ml/min; gradient: isocratic 100:10 (5 min), 100:0→75:25 (20 min), isocratic 75:25 (5 min), 75:25→50:50 (15 min), isocratic 50:50 (5 min), 50:50→20:80 (6 min)) gave 3.22 g (47% of theory) of the title compound.
UPLC-MS (Method A1): R$_t$=1.37 min
MS (ESIpos): m/z=412 (M+H)$^+$ ¹H-NMR (500 MHz, DMSO-d6): δ=1.47 (s, 9H), 3.86 (s, 3H), 5.20 (s, 2H), 5.37 (s, 2H), 6.97 (s, 1H), 7.28-7.42 (m), 7.79 (s, 1H), 7.94 (br. s., 1H), 8.21 (s, 1H).

Intermediate 3-3

Ethyl {5-[(tert-butoxycarbonyl)amino]-6-(trifluoromethoxy)-2H-indazol-2-yl}acetate

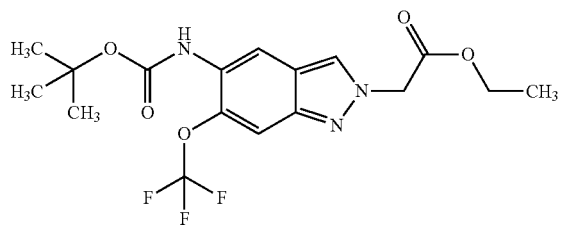 [SMILES: CCOC(=O)Cn1cc2cc(NC(=O)OC(C)(C)C)c(OC(F)(F)F)cc2n1]

Analogously to Intermediate 3-1, 3.17 g (10.0 mmol) of tert-butyl [6-(trifluoromethoxy)-1H-indazol-5-yl]carbamate (Intermediate 2-3), 5.54 ml (50 mmol) of ethyl bromoacetate and 10.7 ml (50 mmol) of N,N-dicyclohexylmethylamine in 20 ml of tetrahydrofuran were heated at 70° C. for 24 h. Work-up and purification by column chromatography using the Isolera® flash purification system (Biotage) (mobile phase: hexane/dichloromethane/ethyl acetate; gradient: isocratic 90:5:5 (5 CV), 90:5:5→85:7.5:7.5 (5 CV), isocratic 85:7.5:7.5 (11 CV), 85:7.5:7.5→80:10:10 (3 CV), isocratic 80:10:10 (9 CV)) gave 512 mg (13% of theory) of product.

UPLC-MS (Method A2): R$_t$=1.29 min
MS (ESIpos): m/z=404 (M+H)$^+$
¹H NMR (400 MHz, DMSO-d6) δ=1.22 (t, 3H), 1.44 (s, 9H), 4.18 (q, 2H), 5.42 (s, 2H), 7.58 (s, 1H), 7.82 (s, 1H), 8.44 (d, 1H), 8.75 (s, 1H).

Intermediate 3-4

Ethyl {6-(benzyloxy)-5-[(tert-butoxycarbonyl)amino]-2H-indazol-2-yl}acetate

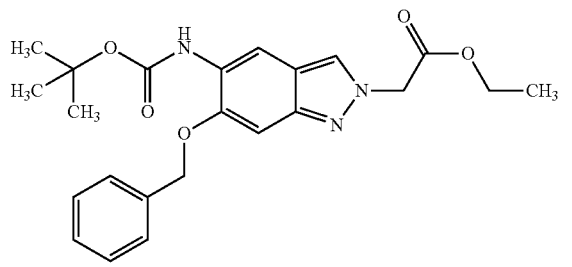 [SMILES: CCOC(=O)Cn1cc2cc(NC(=O)OC(C)(C)C)c(OCc3ccccc3)cc2n1]

Analogously to Intermediate 3-1, 3.46 g (10.2 mmol) of tert-butyl [6-(benzyloxy)-1H-indazol-5-yl]carbamate (Intermediate 2-7), 2.26 ml (20.3 mmol) of ethyl bromoacetate and 4.36 ml (20.3 mmol) of N,N-dicyclohexylmethylamine in 50 ml of tetrahydrofuran were heated at 70° C. for 2 h. Another 2.26 ml (20.3 mmol) of ethyl bromoacetate and 4.36 ml (20.3 mmol) of N,N-dicyclohexylamine were added, and the mixture was stirred at 70° C. for a further 22 h. Work-up and purification by column chromatography using the Isolera® flash purification system (Biotage) (mobile phase: hexane/ethyl acetate; gradient: 90:10→65:35 (10 CV), isoratic 65:35 (5 CV), 65:35->50:50 (5 CV), isocratic 50:50 (5 CV)) gave 2.37 g (55% of theory) of the title compound.

UPLC-MS (Method A1): R$_t$=1.43 min
MS (ESIpos): m/z=426 (M+H)$^+$
1H NMR (400 MHz, CHLOROFORM-d): δ=1.28 (t, 3H), 1.54 (s, 9H), 4.25 (q, 2H), 5.09 (s, 2H), 5.19 (s, 2H), 7.03 (s, 1H), 7.25 (s, 1H), 7.32-7.49 (m, 5H), 7.82 (s, 1H), 8.30 (s, 1H).

Intermediate 3-5

Ethyl {5-[(tert-butoxycarbonyl)amino]-6-fluoro-2H-indazol-2-yl}acetate

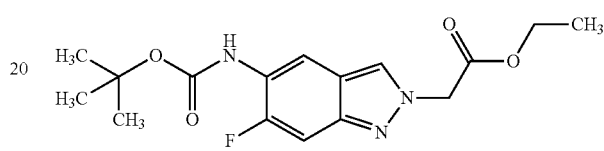

Analogously to Intermediate 3-1, 5.44 g (21.6 mmol) of tert-butyl (6-fluoro-1H-indazol-5-yl)carbamate (Intermediate 2-5), 4.80 ml (43.3 mmol) of ethyl bromoacetate and 9.18 ml (43.3 mmol) of N,N-dicyclohexylmethylamine in 30 ml of tetrahydrofuran were stirred for 72 h, with an additional 0.96 ml (8.6 mmol) of ethyl bromoacetate and 1.84 ml (8.6 mmol) of N,N-dicyclohexylmethylamine being added after 24 h and 48 h, respectively. The mixture was concentrated, taken up in dichloromethane, washed with water, dried and concentrated. Work-up and purification by column chromatography using the Isolera® flash purification system (Biotage) (mobile phase: hexane/dichloromethane/ethyl acetate; isocratic 40:48:12 (8 CV)) gave 3.75 g (47% of theory) of the title compound.

UPLC-MS (Method A1): R$_t$=1.15 min
MS (ESIpos): m/z=338 (M+H)$^+$
¹H-NMR (300 MHz, DMSO-d6): δ=1.21 (t, 3H), 1.46 (s, 9H), 4.17 (q, 2H), 5.36 (s, 2H), 7.37 (d, 1H), 7.84 (d, 1H), 8.36 (s, 1H), 8.80 (s, 1H).

Intermediate 3-6

Ethyl {6-bromo-5-[(tert-butoxycarbonyl)amino]-2H-indazol-2-yl}acetate

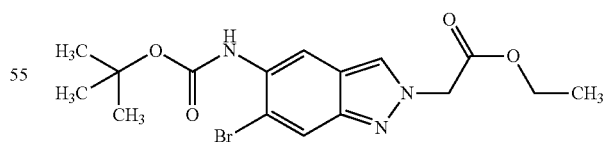

Analogously to Intermediate 3-1, 4.85 g (15.5 mmol) of tert-butyl (6-bromo-1H-indazol-5-yl)carbamate (Intermediate 2-6), 6.89 ml (62.1 mmol) of ethyl bromoacetate and 13.3 ml (62.1 mmol) of N,N-dicyclohexylmethylamine in 50 ml of tetrahydrofuran were stirred at 70° C. for 24 h. Work-up and purification by column chromatography using the Isolera® flash purification system (Biotage) (mobile phase: hexane/dichloromethane/ethyl acetate; gradient: isocratic 80:10:10 (16 CV), 80:10:10→75:12.5:12.5 (1 CV), isocratic 75:12.5:12.5 (8 CV)) gave 2.01 g (32% of theory) of the title compound.

UPLC-MS (Method A2): $R_t$=1.27 min
MS (ESIpos): m/z=398 (M($^{79}$Br)+H)$^+$
$^1$H-NMR (400 MHz, DMSO-d6): δ=1.21 (t, 3H), 1.45 (s, 9H), 4.17 (q, 2H), 5.40 (s, 2H), 7.78 (s, 1H), 7.96 (s, 1H), 8.41 (d, 1H), 8.54 (s, 1H).

Intermediate 3-7

Ethyl {5-[(tert-butoxycarbonyl)amino]-2H-indazol-2-yl}acetate

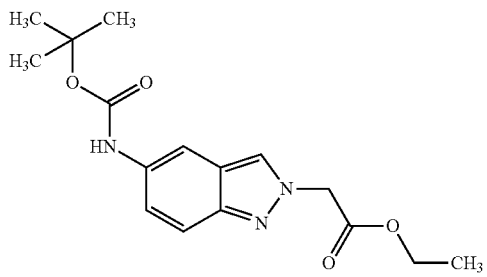 [SMILES: CCOC(=O)Cn1cc2cc(NC(=O)OC(C)(C)C)ccc2n1]

10.5 g (76.3 mmol) of potassium carbonate and 4.67 ml (42.0 mmol) of ethyl bromoacetate were added to 8.90 g (38.1 mmol) of tert-butyl 1H-indazol-5-ylcarbamate (Intermediate 2-8) in 80 ml of N,N-dimethylformamide and the mixture was stirred at 80° C. for 24 h. The mixture was diluted with water and extracted with ethyl acetate, the organic phase was washed with water and saturated sodium chloride solution, dried and concentrated and the residue was purified by column chromatography on silica gel (hexane/ethyl acetate). This gave 2.4 g of the title compound as main component as a mixture with tert-butyl 1H-indazol-5-ylcarbamate (starting material).

$^1$H-NMR (500 MHz, CHLOROFORM-d, selected signals): δ=1.28 (t, 3H), 4.25 (q, 1H), 5.16 (s, 2H), 7.03 (dd, 1H), 7.62 (d, 1H).

Intermediate 3-8

Ethyl {5-[(tert-butoxycarbonyl)amino]-3-methyl-2H-indazol-2-yl}acetate

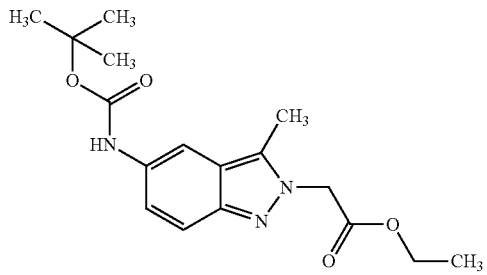 [SMILES: CCOC(=O)Cn1nc2ccc(NC(=O)OC(C)(C)C)cc2c1C]

A mixture of 1.70 g of tert-butyl (3-methyl-1H-indazol-5-yl)carbamate (Intermediate 2-9) (crude product) and 842 μl (7.6 mmol) of ethyl bromoacetate and 1.90 g (13.7 mmol) of potassium carbonate in 10 ml of N,N-dimethylformamide was stirred at 80° C. for 5 h. The mixture was diluted with water and extracted three times with ethyl acetate and the extract was washed with water and saturated sodium chloride solution, dried and concentrated. The residue was purified by column chromatography purification on silica gel (hexane/ethyl acetate). This gave 436 mg of the title compound as a crude product.

UPLC-MS (METHOD A1): $R_t$=1.12 min
MS (ESIpos): m/z=334 (M+H)$^+$.

Intermediate 3-9

Ethyl 3-{5-[(tert-butoxycarbonyl)amino]-2H-indazol-2-yl}propanoate

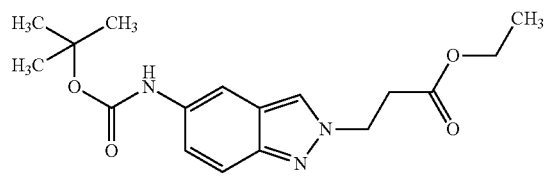 [SMILES: CCOC(=O)CCn1cc2cc(NC(=O)OC(C)(C)C)ccc2n1]

1.0 g (4.3 mmol) of tert-butyl 1H-indazol-5-ylcarbamate (Intermediate 2-8), 656 μl (5.1 mmol) of ethyl bromopropionate and 1.30 g (9.4 mmol) of potassium carbonate in 6.4 ml of N,N-dimethylformamide were heated at 80° C. for 90 min Work-up and purification by column chromatography using the Isolera® flash purification system (Biotage) (mobile phase: hexane/ethyl acetate; gradient 100:0→80:20 (5 CV), 80:20→70:30 (5 CV), 70:30→60:40 (5 CV)) gave 640 mg (45% of theory) of the product.

UPLC-MS (Method A1): $R_t$=1.12 min
MS (ESIpos): m/z=334 (M+H)$^+$
$^1$H-NMR (300 MHz, DMSO-d6): δ=1.13 (t, 3H), 1.48 (s, 9H), 3.00 (t, 2H), 4.04 (q, 2H), 4.60 (t, 2H), 7.17-7.24 (m, 1H), 7.43-7.50 (m, 1H), 7.82 (s, 1H), 8.21 (s, 1H), 9.23 (s, 1H).

Intermediate 3-10

Ethyl {5-[(tert-butoxycarbonyl)amino]-6-isopropoxy-2H-indazol-2-yl}acetate

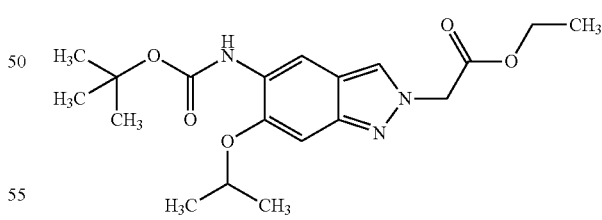

Analogously to Intermediate 3-5, 2.72 g (9.3 mmol) of tert-butyl (6-isopropoxy-1H-indazol-5-yl)carbamate (Intermediate 2-10) were reacted with 3.10 ml (28.0 mmol) of ethyl bromoacetate. This gave 1.84 g (52% of theory) of the title compound.

UPLC-MS (Method A1): Rt=1.32 min
MS (ESIpos): m/z=378 (M+H)$^+$
$^1$H NMR (600 MHz, DMSO-d6): δ=1.21 (t, 3H), 1.34 (d, 6H), 1.48 (s, 9H), 4.16 (q, 2H), 4.68-4.75 (m, 1H), 5.27 (s, 2H), 6.98 (s, 1H), 7.63 (s, 1H), 7.97 (s, 1H), 8.17 (s, 1H).

Intermediate 3-11

Ethyl 2-{5-[(tert-butoxycarbonyl)amino]-2H-indazol-2-yl}propanoate

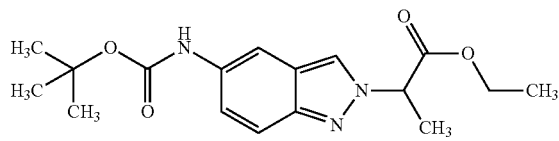

A mixture of 15.0 g (64.3 mmol) of tert-butyl 1H-indazol-5-ylcarbamate (Intermediate 2-8), 9.21 ml (70.7 mmol) of ethyl 2-bromopropanoate and 17.8 g (128.6 mmol) of potassium carbonate in 100 ml of N,N-dimethylformamide was stirred at 80° C. for 24 h. The mixture was diluted with water and extracted with ethyl acetate, and the extract was washed with saturated sodium chloride solution and concentrated. The residue was purified by column chromatography on silica gel (hexane/ethyl acetate). This gave 6.10 g (28% of theory) of the title compound.

$^1$H-NMR (400 MHz, DMSO-d6): δ=1.14 (t, 3H), 1.49 (s, 9H), 1.77 (d, 3H), 4.07-4.17 (m, 2H), 5.52 (q, 1H), 7.23 (dd, 1H), 7.49 (d, 1H), 7.85 (br. s., 1H), 8.32 (s, 1H), 9.22 (s, 1H).

Intermediate 3-12 tert-Butyl (5-{[(benzyloxy)carbonyl]amino}-6-chloro-2H-indazol-2-yl)acetate

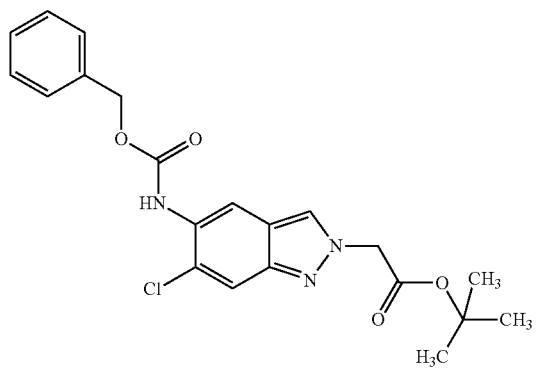 [SMILES: CC(C)(C)OC(=O)Cn1cc2cc(NC(=O)OCc3ccccc3)c(Cl)cc2n1]

2.11 g of benzyl (6-chloro-1H-indazol-5-yl)carbamate (Intermediate 2-11) were initially charged in 20 ml of THF, 1.5 ml of tert-butyl bromoacetate and 2.2 ml of N,N-dicyclohexylmethylamine were added and the mixture was stirred at 65° C. overnight. Another 0.75 ml of tert-butyl bromoacetate and 1.1 ml of N,N-dicyclohexylmethylamine were added, and the mixture was stirred at 70° C. overnight. The solid was filtered off, the filter cake was washed with ethyl acetate, water was added to the filtrate, the mixture was extracted with ethyl acetate and the extract was washed with 1M aqueous hydrochloric acid solution, saturated sodium bicarbonate solution and sodium chloride solution, filtered through a hydrophobic filter and concentrated. The residue was purified by column chromatography on silica gel. This gave 950 mg of the title compound as a yellow foam.

$^1$H NMR (400 MHz, DMSO-d6): δ=1.43 (s, 9H), 5.14 (s, 2H), 5.29 (s, 2H), 7.29-7.47 (m, 5H), 7.80 (s, 1H), 7.84 (s, 1H), 8.41 (s, 1H), 9.09 (s, 1H).

Intermediate 4-1

{5-[(tert-Butoxycarbonyl)amino]-6-methyl-2H-indazol-2-yl}acetic acid

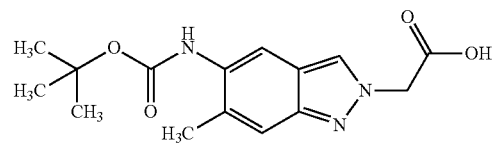 [SMILES: Cc1cc2nn(CC(=O)O)cc2cc1NC(=O)OC(C)(C)C]

10.7 g (254 mmol) of lithium hydroxide monohydrate dissolved in 50 ml of water were added to 10.6 g (25.4 mmol, 80%) of ethyl {5-[(tert-butoxycarbonyl)amino]-6-methyl-2H-indazol-2-yl}acetate (Intermediate 3-1) in 100 ml of tetrahydrofuran and 10 ml of ethanol, and the mixture was stirred. This resulted in the precipitation of a solid. After 18 h, the reaction mixture was diluted with water and acidified to pH 4 using 2M hydrochloric acid, and the solid was filtered off, washed with water and diethyl ether and dried. This gave 6.98 g (87% of theory) of the title compound.

UPLC-MS (Method A1): $R_t$=0.92 min

MS (ESIpos): m/z=306 (M+H)$^+$ $^1$H-NMR (300 MHz, DMSO-d6): δ=1.44 (s, 9H), 2.25 (s, 3H), 4.78 (s, 2H), 7.32 (s, 1H), 7.49 (s, 1H), 8.10 (s, 1H), 8.35 (s, 1H).

Intermediate 4-2

{5-[(tert-Butoxycarbonyl)amino]-6-methoxy-2H-indazol-2-yl}acetic acid

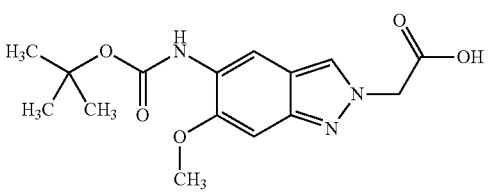 [SMILES: COc1cc2nn(CC(=O)O)cc2cc1NC(=O)OC(C)(C)C]

Analogously to Intermediate 4-1, 3.2 g of benzyl {5-[(tert-butoxycarbonyl)amino]-6-methoxy-2H-indazol-2-yl}acetate (Intermediate 3-2) gave 1.91 g of the title compound.

UPLC-MS (Method A1): $R_t$=1.04 min

MS (ESIpos): m/z=322 (M+H)$^+$ $^1$H-NMR (500 MHz, DMSO-d6): δ=1.47 (s, 9H), 3.86 (s, 3H), 5.16 (s, 2H), 6.96 (s, 1H), 7.78 (s, 1H), 7.93 (br. s., 1H), 8.16 (d, 1H), 13.13 (br. s., 1H).

Intermediate 4-3

{5-[(tert-Butoxycarbonyl)amino]-6-(trifluoromethoxy)-2H-indazol-2-yl}acetic acid

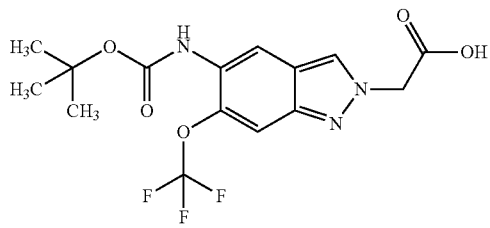 [SMILES: CC(C)(C)OC(=O)Nc1cc2cn(CC(=O)O)nc2cc1OC(F)(F)F]

Analogously to Intermediate 4-1, 530 mg (1.31 mmol) of ethyl {5-[(tert-butoxycarbonyl)amino]-6-(trifluoromethoxy)-2H-indazol-2-yl}acetate (Intermediate 3-3) were suspended in 20 ml of tetrahydrofuran, a solution of 157 mg (6.57 mmol) of lithium hydroxide monohydrate in 2.4 ml of water was then added and the mixture was stirred at 25° C. for 24 h. Work-up gave 437 mg (81% of theory) of the title compound.

UPLC-MS (Method A1): $R_t$=1.10 min

MS (ESIpos): m/z=376 (M+H)$^+$ $^1$H-NMR (400 MHz, DMSO-d6): δ=1.44 (s, 9H), 5.29 (s, 2H), 7.57 (s, 1H), 7.81 (s, 1H), 8.41 (d, 1H), 8.74 (s, 1H).

Intermediate 4-4

{6-Bromo-5-[(tert-butoxycarbonyl)amino]-2H-indazol-2-yl}acetic acid

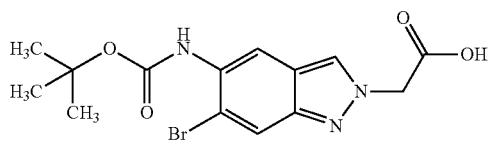 [SMILES: CC(C)(C)OC(=O)Nc1cc2cn(CC(=O)O)nc2cc1Br]

Analogously to Intermediate 4-1, 1.00 g (2.5 mmol) of ethyl {6-bromo-5-[(tert-butoxycarbonyl)amino]-2H-indazol-2-yl}acetate (Intermediate 3-6) was dissolved in 50 ml of tetrahydrofuran, a solution of 301 mg (12.6 mmol) of lithium hydroxide monohydrate in 4.5 ml of water was then added and the mixture was stirred at 25° C. for 24 h. Work-up gave 844 mg (82% of theory) of the title compound.

UPLC-MS (Method A1): $R_t$=0.64 min

MS (ESIpos): m/z=370 (M($^{79}$Br)+H)$^+$ $^1$H-NMR (300 MHz, DMSO-d6): δ=1.45 (s, 9H), 3.35 (s br, 1H), 5.28 (s, 2H), 7.76 (s, 1H), 7.95 (s, 1H), 8.38 (s, 1H), 8.52 (s, 1H).

Intermediate 4-5

{5-[(tert-Butoxycarbonyl)amino]-2H-indazol-2-yl}acetic acid

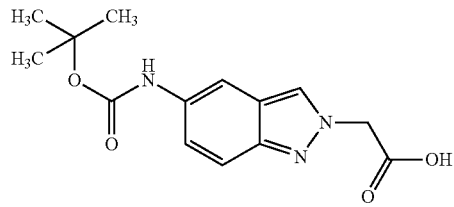 [SMILES: CC(C)(C)OC(=O)Nc1ccc2nn(CC(=O)O)cc2c1]

Analogously to Intermediate 4-1, 5.00 g (15.6 mmol) of ethyl {5-[(tert-butoxycarbonyl)amino]-2H-indazol-2-yl}acetate (Intermediate 3-7) were dissolved in 50 ml of tetrahydrofuran and 5 ml of ethanol, a solution of 6.57 g (15.6 mmol) of lithium hydroxide monohydrate in 20 ml of water was then added and the mixture was stirred at 25° C. for 24 h. Work-up gave 4.1 g (89% of theory) of the title compound.

UPLC-MS (Method A1): $R_t$=0.90 min

MS (ESIpos): m/z=292 (M+H)+.

Intermediate 4-6

{5-[(tert-Butoxycarbonyl)amino]-3-methyl-2H-indazol-2-yl}acetic acid

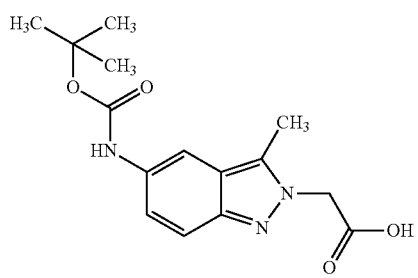 [SMILES: Cc1c2cc(NC(=O)OC(C)(C)C)ccc2nn1CC(=O)O]

Analogously to Intermediate 4-1, 436 mg (1.3 mmol) of ethyl {5-[(tert-butoxycarbonyl)amino]-3-methyl-2H-indazol-2-yl}acetate (Intermediate 3-8) were dissolved in 5 ml of tetrahydrofuran and 1 ml of ethanol, a solution of 549 mg (13.1 mmol) of lithium hydroxide monohydrate in 2.5 ml of water was then added and the mixture was stirred at 25° C. for 24 h. This gave, after addition of citric acid, a solid which was filtered off, washed with water and diethyl ether and dried. This gave 320 mg (70% of theory) of the title compound.

UPLC-MS (Method A1): $R_t$=0.92 min

MS (ESIpos): m/z=306 (M+H)$^+$.

Intermediate 4-7

2-{5-[(tert-Butoxycarbonyl)amino]-2H-indazol-2-yl}propanoic acid

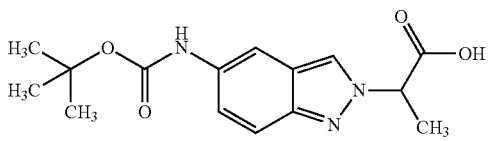 [SMILES: CC(C(=O)O)n1cc2cc(NC(=O)OC(C)(C)C)ccc2n1]

Analogously to Intermediate 4-1, 5.77 g (17.3 mmol) of ethyl 2-{5-[(tert-butoxycarbonyl)amino]-2H-indazol-2-yl}propanoate (Intermediate 3-8) were dissolved in 50 ml of tetrahydrofuran and 5 ml of ethanol, a solution of 7.26 g (17.3 mmol) of lithium hydroxide monohydrate in 40 ml of water was then added and the mixture was stirred at 25° C. for 24 h. Acidification with 1 M hydrochloric acid solution gave a solid which was filtered off, washed with water and diethyl ether and dried. This gave 4.2 g (79% of theory) of the title compound.

$^1$H-NMR (300 MHz, DMSO-d6): δ=1.45 (s, 9H), 1.72 (d, 3H), 5.33-5.41 (m, 1H), 7.18 (dd, 1H), 7.45 (d, 1H), 7.82 (s, 1H), 8.26 (s, 1H), 9.20 (s, 1H), 13.13 (br. s., 1H).

Intermediate 4-8

{6-(Benzyloxy)-5-[(tert-butoxycarbonyl)amino]-2H-indazol-2-yl}acetic acid

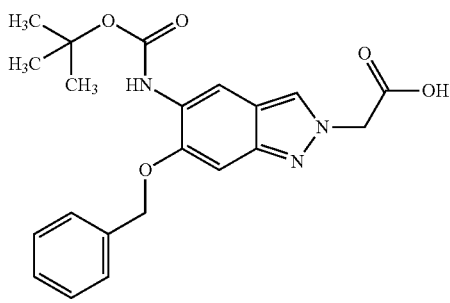 [SMILES: CC(C)(C)OC(=O)Nc1cc2cn(CC(=O)O)nc2cc1OCc1ccccc1]

Analogously to Intermediate 4-1, 14.15 g (33.3 mmol) of ethyl {6-(benzyloxy)-5-[(tert-butoxycarbonyl)amino]-2H-indazol-2-yl}acetate (Intermediate 3-4) were dissolved in 250 ml of tetrahydrofuran and 25 ml of ethanol, a solution of 3.98 g (166.3 mmol) of lithium hydroxide monohydrate in 30 ml of water was then added and the mixture was stirred at 25° C. for 72 h. After acidification with 1 M hydrochloric acid solution to pH 3 the reaction mixture was concentrated, water was added and the resulting solid was filtered off, washed with water and diethyl ether and dried. This gave 13.05 g (33% of theory) of the title compound.

UPLC-MS (Method A1): $R_t$=1.25 min

MS (ESIpos): m/z=398 (M+H)$^+$ $^1$H-NMR (300 MHz, DMSO-d6): δ=1.45 (s, 9H), 4.93 (s, 2H), 5.20 (s, 2H), 7.01 (s, 1H), 7.26-7.45 (m, 3H), 7.53 (d, 2H), 7.80-7.91 (m, 2H), 8.11 (s, 1H).

Intermediate 4-9

(5-{[(Benzyloxy)carbonyl]amino}-6-chloro-2H-indazol-2-yl)acetic acid

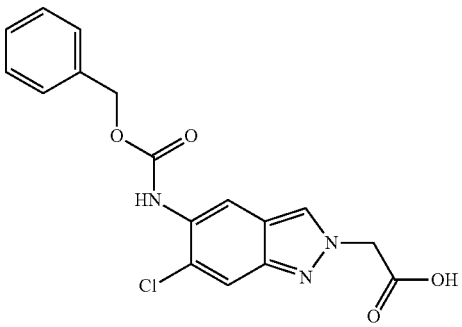 [SMILES: O=C(O)Cn1cc2cc(NC(=O)OCc3ccccc3)c(Cl)cc2n1]

1.7 ml of trifluoroacetic acid were added to a mixture of 940 g of tert-butyl (5-{[(benzyloxy)carbonyl]amino}-6-chloro-2H-indazol-2-yl)acetate (Intermediate 3-12) in 10 ml of dichloromethane, and the mixture was stirred at room temperature overnight. Saturated aqueous sodium bicarbonate solution was added and the precipitate was filtered off with suction, washed with water and ethyl acetate and dried. This gave 766 mg of the title compound.

$^1$H-NMR (400 MHz, DMSO-d$_6$): δ [ppm]=4.66 (s, 2H), 5.12 (s, 2H), 7.26-7.45 (m, 5H), 7.69 (s, 1H), 7.75 (s, 1H), 8.22 (s, 1H), 9.01 (s, 1H).

Intermediate 5-1 tert-Butyl {2-[2-(4-benzoylpiperazin-1-yl)-2-oxoethyl]-6-methyl-2H-indazol-5-yl}carbamate

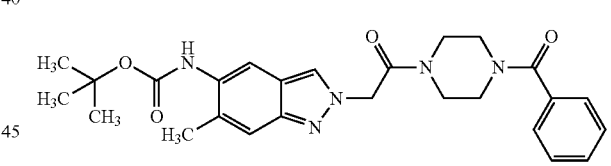

181 mg (0.59 mmol) of {5-[(tert-butoxycarbonyl)amino]-6-methyl-2H-indazol-2-yl}acetic acid (Intermediate 4-1) and 169 mg (0.89 mmol) of phenyl(piperazin-1-yl)methanone were initially charged in 5 ml of tetrahydrofuran and 0.5 ml of N,N-dimethylformamide 91 mg (0.59 mmol) of 1-hydroxy-1H-benzotriazole hydrate, 227 mg (1.19 mmol) of 1-(3-dimethylaminopropyl)-3-ethylcarbodiimide hydrochloride and 0.25 ml (1.79 mmol) of triethylamine were added and the mixture was stirred at 25° C. for 18 h. The mixture was diluted with water and ethyl acetate and the precipitated solid was filtered off, washed with water and diethyl ether and dried under reduced pressure. This gave 248 mg (85% of theory) of the title compound.

UPLC-MS (Method A1): $R_t$=1.07 min

MS (ESIpos): m/z=478 (M+H)$^+$ $^1$H NMR (400 MHz, DMSO-d6): δ=1.42 (s, 9H), 2.24 (s, 3H), 3.32-3.82 (m, 8H), 5.41 (br. s., 2H), 7.33 (s, 1H), 7.38-7.48 (m, 5H), 7.52 (s, 1H), 8.12-8.16 (m, 1H), 8.35 (s, 1H).

Intermediate 5-2 tert-Butyl (6-methyl-2-{2-oxo-2-[4-(pyrrolidin-1-yl)piperidin-1-yl]ethyl}-2H-indazol-5-yl)carbamate

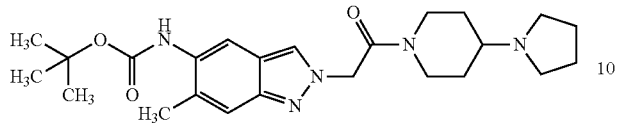

Analogously to Intermediate 5-1, 2.00 g (6.55 mmol) of {5-[(tert-butoxycarbonyl)amino]-6-methyl-2H-indazol-2-yl}acetic acid (Intermediate 4-1) were reacted with 1.31 g (8.52 mmol) of 4-(pyrrolidin-1-yl)piperidine. This gave 2.59 g (90% of theory) of the title compound.
UPLC-MS (Method A1): $R_t$=0.77 min
MS (ESIpos): m/z=442 (M+H)$^+$
$^1$H-NMR (300 MHz, DMSO-d6): δ=1.18-1.52 (m, 11H, contains singlet at 1.45 ppm), 1.66 (br. s., 4H), 1.83 (t, 2H), 2.16-2.30 (m, 4H), 2.76-2.90 (m, 1H), 3.08-3.22 (m, 1H), 3.80-3.92 (m, 1H), 4.01-4.14 (m, 1H), 5.31-5.46 (m, 2H), 7.35 (s, 1H), 7.53 (s, 1H), 8.15 (s, 1H), 8.39 (s, 1H).

Intermediate 5-3 tert-Butyl (2-{2-[4-(3-hydroxy-2,2-dimethylpropanoyl)piperazin-1-yl]-2-oxoethyl}-6-methyl-2H-indazol-5-yl)carbamate

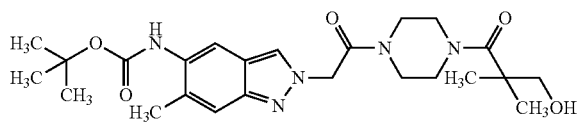

Analogously to Intermediate 5-1, 300 mg (0.98 mmol) of {5-[(tert-butoxycarbonyl)amino]-6-methyl-2H-indazol-2-yl}acetic acid (Intermediate 4-1) were reacted with 238 mg (1.28 mmol) of 3-hydroxy-2,2-dimethyl-1-(piperazin-1-yl)propan-1-one. This gave 216 mg (46% of theory) of the title compound.
UPLC-MS (Method A2): $R_t$=0.96 min
MS (ESIpos): m/z=474 (M+H)$^+$
$^1$H-NMR (400 MHz, DMSO-d6): δ=1.16 (s, 6H), 1.45 (s, 9H), 2.26 (s, 3H), 3.39-3.68 (m, 10H), 4.59 (t, 1H), 5.42 (s, 2H), 7.35 (s, 1H), 7.54 (s, 1H), 8.15 (s, 1H), 8.37 (s, 1H).

Intermediate 5-4 tert-Butyl (2-{2-[4-(methoxyacetyl)piperazin-1-yl]-2-oxoethyl}-6-methyl-2H-indazol-5-yl)carbamate

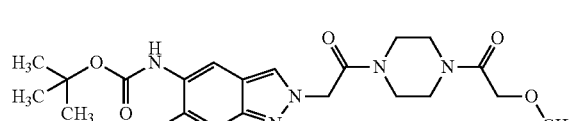

Analogously to Intermediate 5-1, 300 mg (0.98 mmol) of {5-[(tert-butoxycarbonyl)amino]-6-methyl-2H-indazol-2-yl}acetic acid (Intermediate 4-1) were reacted with 248 mg (1.28 mmol) of 2-methoxy-1-(piperazin-1-yl)ethanone hydrochloride (1:1). This gave 144 mg of the title compound as a crude product.
UPLC-MS (Method A2): $R_t$=0.93 min
MS (ESIpos): m/z=446 (M+H)$^+$.

Intermediate 5-5 tert-Butyl (2-{2-[4-(2-hydroxypropan-2-yl)piperidin-1-yl]-2-oxoethyl}-6-methoxy-2H-indazol-5-yl)carbamate

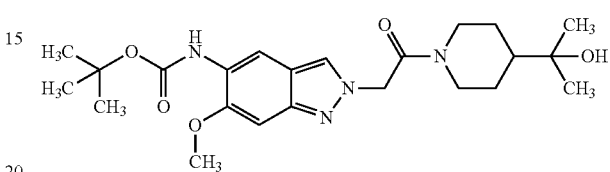

Analogously to Intermediate 5-1, 266 mg (0.83 mmol) of {5-[(tert-butoxycarbonyl)amino]-6-methoxy-2H-indazol-2-yl}acetic acid (Intermediate 4-2) were reacted with 154 mg (1.08 mmol) of 2-(piperidin-4-yl)propan-2-ol in 10 ml of tetrahydrofuran. This gave 382 mg of the title compound as a crude product.
UPLC-MS (Method A1): $R_t$=1.10 min
MS (ESIpos): m/z=447 (M+H)$^+$.

Intermediate 5-6 tert-Butyl (2-{2-[4-(cyclopropylmethyl)piperazin-1-yl]-2-oxoethyl}-6-methoxy-2H-indazol-5-yl)carbamate

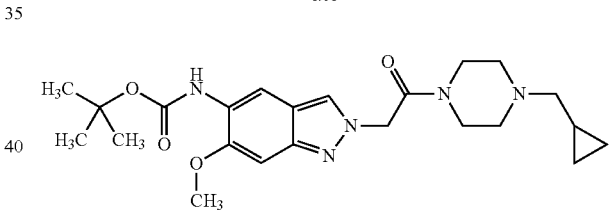

Analogously to Intermediate 5-1, 250 mg (0.78 mmol) of {5-[(tert-butoxycarbonyl)amino]-6-methoxy-2H-indazol-2-yl}acetic acid (Intermediate 4-2) were reacted with 164 mg (1.17 mmol) of 1-(cyclopropylmethyl)piperazine. This gave 402 mg of the title compound as a crude product.
UPLC-MS (Method A1): $R_t$=0.85 min
MS (ESIpos): m/z=444 (M+H)$^+$

Intermediate 5-7 tert-Butyl {2-[2-(4-benzoylpiperazin-1-yl)-2-oxoethyl]-6-methoxy-2H-indazol-5-yl}carbamate

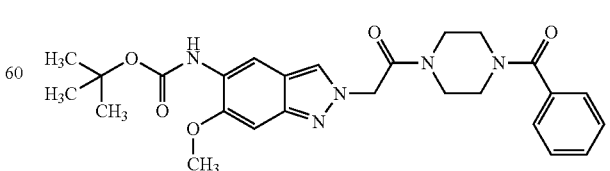

Analogously to Intermediate 5-1, 548 mg (1.71 mmol) of {5-[(tert-butoxycarbonyl)amino]-6-methoxy-2H-indazol-2- yl}acetic acid (Intermediate 4-2) were reacted with 389 mg (2.05 mmol) of phenyl(piperazin-1-yl)methanone. This gave 808 mg of the title compound as a crude product.
UPLC-MS (Method A1): $R_t$=1.14 min
MS (ESIpos): m/z=494 (M+H)$^+$ Intermediate 5-8 tert-Butyl {2-[2-(4-methylpiperazin-1-yl)-2-oxo-ethyl]-6-(trifluoromethoxy)-2H-indazol-5-yl}carbamate

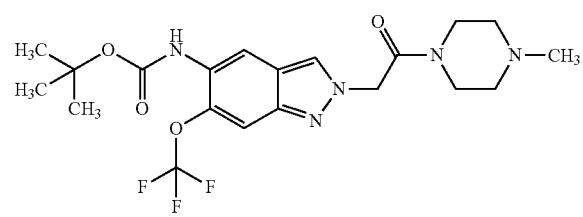 [SMILES: CN1CCN(C(=O)Cn2cc3cc(NC(=O)OC(C)(C)C)c(OC(F)(F)F)cc3n2)CC1]

350 mg (0.85 mmol) of tert-butyl {2-[2-(4-methylpiperazin-1-yl)-2-oxoethyl]-6-(trifluoromethoxy)-2H-indazol-5-yl}carbamate (Intermediate 4-3), 130 mg (0.85 mmol) of 1-hydroxy-1H-benzotriazole hydrate and 325 mg (1.70 mmol) of 1-(3-dimethylaminopropyl)-3-ethylcarbodiimide hydrochloride in 3.5 ml of N,N-dimethylformamide and 473 µl (3.40 mmol) of triethylamine were stirred at 25° C. for 30 min 103 µl (0.93 mmol) of 1-methylpiperazine (CAS No.: 109-01-3) were then added and the mixture was stirred at 25° C. for 24 h. The mixture was poured into 50 ml of water, filtered off with suction, washed with water and dried. This gave 305 mg (78% of theory) of the title compound.
UPLC-MS (Method A2): $R_t$=1.12 min
MS (ESIpos): m/z=376 (M+H)$^+$
$^1$H-NMR (400 MHz, DMSO-d6): δ=1.44 (s, 9H), 2.23 (s, 3H), 2.28-2.38 (m, 2H), 2.41 (br. s., 2H), 3.47 (br. s., 2H), 3.55 (br. s., 2H), 5.49 (s, 2H), 7.54 (s, 1H), 7.80 (s, 1H), 8.34 (d, 1H), 8.73 (s, 1H), 9.93 (br. s., 1H).

Intermediate 5-9 tert-Butyl {6-bromo-2-[2-(4-methylpiperazin-1-yl)-2-oxoethyl]-2H-indazol-5-yl}carbamate Analogously to Intermediate 5-8, 800 mg (1.97 mmol) of {6-bromo-5-[(tert-butoxycarbonyl)amino]-2H-indazol-2-yl}acetic acid (Intermediate 4-4) were reacted with 246 mg (2.17 mmol) of 1-methylpiperazine. This gave 824 mg (93% of theory) of the title compound.
UPLC-MS (Method A2): $R_t$=1.07 min
MS (ESIpos): m/z=452 (M($^{79}$Br)+H)$^+$
$^1$H-NMR (300 MHz, DMSO-d6): δ=1.45 (s, 9H), 2.20 (s, 3H), 2.25-2.34 (m, 2H), 2.34-2.40 (m, 2H), 3.43-3.49 (m, 2H), 3.50-3.55 (m, 2H), 5.47 (s, 2H), 7.75 (s, 1H), 7.93 (s, 1H), 8.31 (s, 1H), 8.54 (s, 1H).

Intermediate 5-10 tert-Butyl (2-{2-[4-(cyclopropylcarbonyl)piperazin-1-yl]-2-oxoethyl}-2H-indazol-5-yl)carbamate Analogously to Intermediate 5-1, 2.00 g (4.3 mmol, 62%) of {5-[(tert-butoxycarbonyl)amino]-2H-indazol-2-yl}acetic acid (Intermediate 4-5) were reacted with 1.14 g (6.0 mmol) of cyclopropyl(piperazin-1-yl)methanone hydrochloride (1:1). This gave 2.3 g of the title compound as a crude product.
UPLC-MS (Method A1): $R_t$=0.97 min
MS (ESIpos): m/z=428 (M+H)$^+$.

Intermediate 5-11 tert-Butyl {2-[2-(4-benzoylpiperazin-1-yl)-2-oxoethyl]-2H-indazol-5-yl}carbamate Analogously to Intermediate 5-1, 2.53 mg (8.7 mmol) of {5-[(tert-butoxycarbonyl)amino]-2H-indazol-2-yl}acetic acid (Intermediate 4-5) were reacted with 1.98 g (10.4 mmol) of phenyl(piperazin-1-yl)methanone to give 3.8 g (93% of theory) of the title compound.
UPLC-MS (Method A1): $R_t$=1.05 min
MS (ESIpos): m/z=464 (M+H)+.
$^1$H-NMR (400 MHz, DMSO-d$_6$): δ=1.45 (s, 9H), 3.30-3.78 (m, 8H), 5.41 (br. s., 2H), 7.18 (dd, 1H), 7.35-7.50 (m, 6H), 7.82 (br. s., 1H), 8.11 (s, 1H), 9.18 (s, 1H).

Intermediate 5-12 tert-Butyl {2-[2-(4-methylpiperazin-1-yl)-2-oxoethyl]-2H-indazol-5-yl}carbamate

Analogously to Intermediate 5-1, 1.00 g (3.4 mmol) of {5-[(tert-butoxycarbonyl)amino]-2H-indazol-2-yl}acetic acid (Intermediate 4-5) was reacted with 0.41 g (4.1 mmol) of 1-methylpiperazine to give 916 mg (71% of theory) of the title compound.

UPLC-MS (Method A1): Rt=0.73 min
MS (ESIpos): m/z=374 (M+H)+.

Intermediate 5-13 tert-Butyl (2-{2-oxo-2-[4-(2,2,2-trifluoroethyl)piperazin-1-yl]ethyl}-2H-indazol-5-yl)carbamate

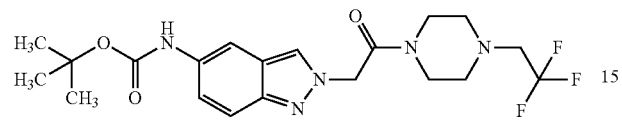

Analogously to Intermediate 5-1, 1.01 g (3.5 mmol) of {5-[(tert-butoxycarbonyl)amino]-2H-indazol-2-yl}acetic acid (Intermediate 4-5) were reacted with 1.00 g (4.2 mmol) of 1-(2,2,2-trifluoroethyl)piperazine dihydrochloride to give 634 g (42% of theory) of the title compound.

UPLC-MS (Method A1): $R_t$=1.11 min
MS (ESIpos): m/z=442 (M+H)$^+$.

Intermediate 5-14 tert-Butyl {2-[2-(4-ethyl-3-oxopiperazin-1-yl)-2-oxoethyl]-2H-indazol-5-yl}carbamate

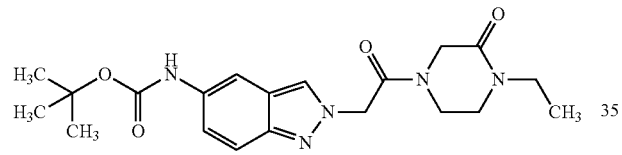

Analogously to Intermediate 5-1, 2.38 g (3.5 mmol, 62%) of {5-[(tert-butoxycarbonyl)amino]-2H-indazol-2-yl}acetic acid (Intermediate 4-5) were reacted with 1.00 g (6.1 mmol) of 1-ethylpiperazin-2-one hydrochloride (1:1) to give 1.92 g (71% of theory) of the title compound as a crude product.

UPLC-MS (Method A1): $R_t$=0.92 min
MS (ESIpos): m/z=402 (M+H)$^+$.

Intermediate 5-15 tert-Butyl {2-[2-(4-benzoylpiperazin-1-yl)-2-oxoethyl]-3-methyl-2H-indazol-5-yl}carbamate

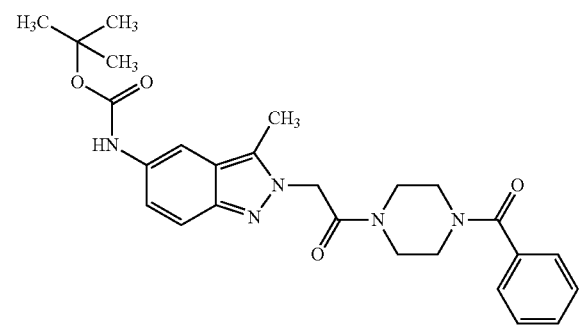 [SMILES: Cc1c2cc(NC(=O)OC(C)(C)C)ccc2nn1CC(=O)N1CCN(C(=O)c2ccccc2)CC1]

Analogously to Intermediate 5-1, 160 mg (0.52 mmol) of {5-[(tert-butoxycarbonyl)amino]-3-methyl-2H-indazol-2-yl}acetic acid (crude product) (Intermediate 4-6) were reacted with 150 mg (0.79 mmol) of phenyl(piperazin-1-yl)methanone. Addition of water and ethyl acetate resulted in the precipitation of a solid which was washed with water and diethyl ether and dried. This gave 130 mg (52% of theory) of the title compound.

UPLC-MS (Method A1): $R_t$=1.07 min
MS (ESIpos): m/z=478 (M+H)$^+$.

Intermediate 5-16 tert-Butyl {6-methoxy-2-[2-(morpholin-4-yl)-2-oxoethyl]-2H-indazol-5-yl}carbamate

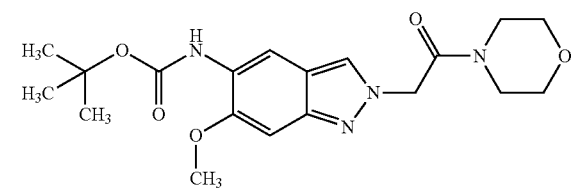

Analogously to Intermediate 5-1, 1.00 g (3.11 mmol) of {5-[(tert-butoxycarbonyl)amino]-6-methoxy-2H-indazol-2-yl}acetic acid (Intermediate 4-2) was reacted with 407 µl (4.67 mmol) of 1-methylpiperazine. The reaction mixture was added to water and extracted with ethyl acetate. The combined organic phases were washed with saturated sodium chloride solution, dried over sodium sulphate, filtered, concentrated and dried. This gave 1.16 g (95% of theory) of the title compound.

UPLC-MS (Method A2): $R_t$=1.03 min
MS (ESIpos): m/z=391 (M+H)$^+$
$^1$H NMR (300 MHz, CHLOROFORM-d): δ=1.55 (s, 9H), 3.58 (s, 4H), 3.66 (s, 4H), 3.93 (s, 3H), 5.18 (s, 2H), 6.94 (s, 1H), 7.22 (s, 1H), 7.81-7.90 (m, 1H), 8.25 (s, 1H).

Intermediate 5-17 tert-Butyl {6-methoxy-2-[2-(4-methylpiperazin-1-yl)-2-oxoethyl]-2H-indazol-5-yl}carbamate

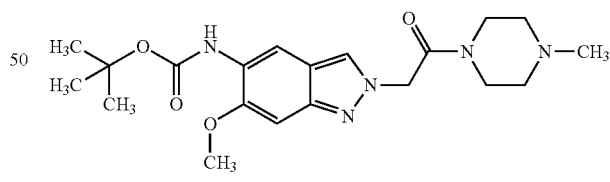

Analogously to Intermediate 5-16, 1.00 g (3.11 mmol) of {5-[(tert-butoxycarbonyl)amino]-6-methoxy-2H-indazol-2-yl}acetic acid (Intermediate 4-2) was reacted with 530 µl (4.67 mmol) of 1-methylpiperazine. Work-up gave 1.21 g (96% of theory) of the title compound.

UPLC-MS (Method A1): $R_t$=0.82 min
MS (ESIpos): m/z=404 (M+H)$^+$
$^1$H NMR (300 MHz, CHLOROFORM-d): δ=1.55 (s, 9H), 2.28 (s, 3H), 2.30-2.34 (m, 2H), 2.34-2.41 (m, 3H), 3.52-3.61 (m, 2H), 3.62-3.71 (m, 2H), 3.93 (s, 3H), 5.18 (s, 2H), 6.94 (s, 1H), 7.22 (s, 1H), 7.85 (s, 1H), 8.24 (s, 1H).

Intermediate 5-18 tert-Butyl (2-{2-[(cyclopropylmethyl)(methyl)amino]-2-oxoethyl}-6-methoxy-2H-indazol-5-yl)carbamate

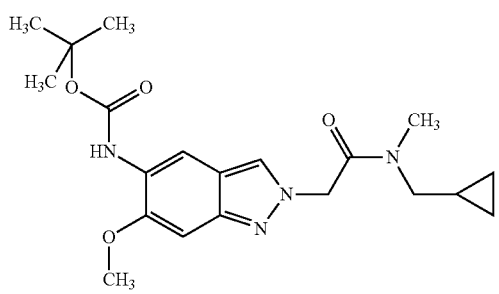 [SMILES: COc1cc2nn(CC(=O)N(C)CC3CC3)cc2cc1NC(=O)OC(C)(C)C]

Analogously to Intermediate 5-1, 250 mg (0.78 mmol) of {5-[(tert-butoxycarbonyl)amino]-6-methoxy-2H-indazol-2-yl}acetic acid (Intermediate 4-2) were stirred with 86 mg (1.01 mmol) of 1-cyclopropyl-N-methylmethanamine at 25° C. for 24 h. The mixture was diluted with water and extracted three times with ethyl acetate, and the extracts were washed with saturated sodium chloride solution and concentrated. This gave 353 mg of a crude product.
UPLC-MS (Method A1): $R_t$=1.19 min
MS (ESIpos): m/z=389 (M+H)$^+$.

Intermediate 5-19 tert-Butyl 2-[1-(4-benzoylpiperazin-1-yl)-1-oxopropan-2-yl]-2H-indazol-5-yl}carbamate

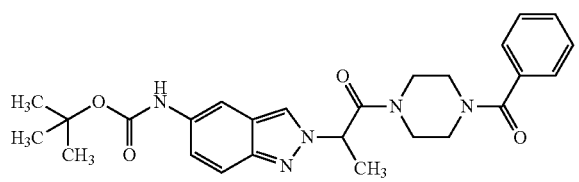 [SMILES: CC(C(=O)N1CCN(C(=O)c2ccccc2)CC1)n1cc2cc(NC(=O)OC(C)(C)C)ccc2n1]

Analogously to Intermediate 5-1, 2.00 g (6.55 mmol) of {5-[(tert-butoxycarbonyl)amino]-2H-indazol-2-yl}propanoic acid (Intermediate 4-6) and 1.50 g (7.86 mmol) of phenyl(piperazin-1-yl)methanone were stirred at 25° C. for 24 h. This gave 3.7 g of the title compound as a crude product.
UPLC-MS (Method A1): $R_t$=1.11 min
MS (ESIpos): m/z=448 (M+H)$^+$.

Intermediate 5-20 tert-Butyl {6-(benzyloxy)-2-[2-(morpholin-4-yl)-2-oxoethyl]-2H-indazol-5-yl}carbamate

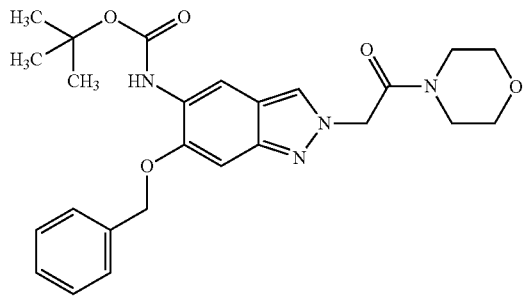 [SMILES: CC(C)(C)OC(=O)Nc1cc2cn(CC(=O)N3CCOCC3)nc2cc1OCc1ccccc1]

Analogously to Intermediate 5-1, 3.50 g (8.81 mmol) of {6-(benzyloxy)-5-[(tert-butoxycarbonyl)amino]-2H-indazol-2-yl}acetic acid (Intermediate 4-8) and 1.14 ml (13.2 mmol) of morpholine were reacted at 25° C. for 24 h. Work-up gave 3.67 g (89% of theory) of the title compound.
UPLC-MS (Method A1): $R_t$=1.25 min
MS (ESIpos): m/z=467 (M+H)$^+$
$^1$H-NMR (400 MHz, DMSO-d6): δ=1.45 (s, 9H), 3.41-3.48 (m, 2H), 3.51-3.60 (m, 4H), 3.61-3.66 (m, 2H), 5.21 (s, 2H), 5.35 (s, 2H), 7.01 (s, 1H), 7.29-7.37 (m, 1H), 7.38-7.44 (m, 2H), 7.50-7.57 (m, 2H), 7.87 (s, 2H), 8.11 (s, 1H).

Intermediate 5-21

Benzyl {6-chloro-2-[2-(4-methylpiperazin-1-yl)-2-oxoethyl]-2H-indazol-5-yl}carbamate

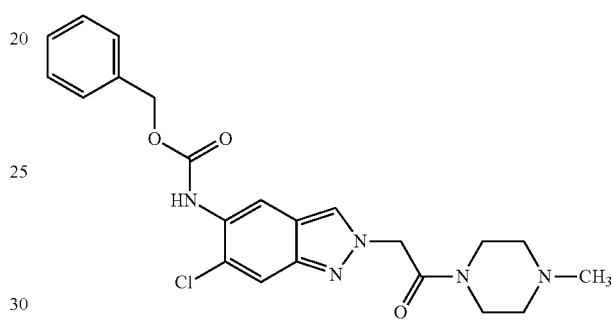

387 mg of (5-{[(benzyloxy)carbonyl]amino}-6-chloro-2H-indazol-2-yl)acetic acid (Intermediate 4-9) were reacted analogously to the preparation of Intermediate 5-1 with 140 mg of 1-methylpiperazine. After the reaction, the mixture was diluted with water and ethyl acetate and saturated sodium chloride solution were added. The precipitated solid was filtered off, washed with water and diethyl ether and dried. This gave 302 mg of the title compound.
$^1$H-NMR (400 MHz, DMSO-d$_6$): δ [ppm]=2.19 (s, 3H), 2.23-2.41 (m, 4H), 3.41-3.48 (m, 2H), 3.48-3.56 (m, 2H), 5.13 (s, 2H), 5.46 (s, 2H), 7.28-7.45 (m, 5H), 7.75 (s, 1H), 7.81 (s, 1H), 8.32 (d, 1H), 9.07 (s, 1H).

Intermediate 5-22

Benzyl {6-chloro-2-[2-(morpholin-4-yl)-2-oxoethyl]-2H-indazol-5-yl}carbamate

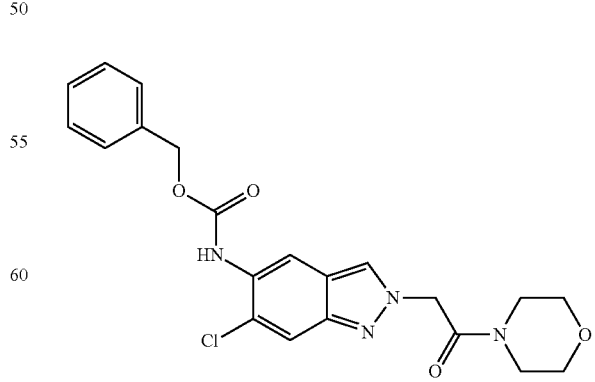

400 mg of benzyl (6-chloro-1H-indazol-5-yl)carbamate (Intermediate 2-11) were initially charged in 5.0 ml of cyclopentyl methyl ether. 265 mg of 2-bromo-1-(morpholin-4-yl)ethanone and 0.22 ml of N-ethyl-N-isopropylpropane-2-amine were added and the mixture was stirred at 100° C. for 20 h. Water was added and a solid was obtained by removing oily residues from the rim of the flask by scratching. The solid was filtered off with suction, washed with water and diethyl ether, triturated with ethyl acetate and dried. This gave 254 mg of the title compound.

1H-NMR (500 MHz, DMSO-d6): δ [ppm]=3.47 (d, 2H), 3.56 (d, 2H), 3.58-3.61 (m, 2H), 3.65 (d, 2H), 5.15 (s, 2H), 5.49 (s, 2H), 7.28-7.48 (m, 5H), 7.76 (s, 1H), 7.83 (s, 1H), 8.33 (s, 1H), 9.07 (s, 1H).

Intermediate 6-1

2-(5-Amino-6-methyl-2H-indazol-2-yl)-1-(4-benzoylpiperazin-1-yl)ethanone

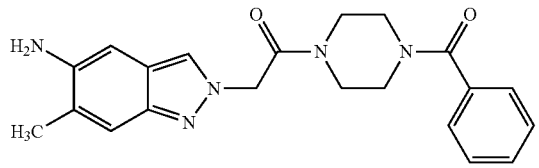 [SMILES: Cc1cc2nn(CC(=O)N3CCN(C(=O)c4ccccc4)CC3)cc2cc1N]

0.3 ml (3.89 mmol) of trifluoroacetic acid was added to 247 mg (0.52 mmol) of tert-butyl {2-[2-(4-benzoylpiperazin-1-yl)-2-oxoethyl]-6-methyl-2H-indazol-5-yl}carbamate (Intermediate 5-1) in 5 ml of dichloromethane and the mixture was stirred at 25° C. for 18 h. Another 0.3 ml (3.89 mmol) of trifluoroacetic acid was then added and the mixture was stirred for 18 h, poured into saturated sodium bicarbonate solution and extracted times with dichloromethane. Concentration gave 223 mg of the title compound as a crude product.

UPLC-MS (Method A1): $R_t$=0.61 min
MS (ESIpos): m/z=378 (M+H)$^+$
$^1$H NMR (400 MHz, DMSO-d6): δ=2.15 (s, 3H), 3.29-3.75 (m, 8H), 4.53 (s, 2H), 5.28 (br. s., 2H), 6.63 (s, 1H), 7.17 (s, 1H), 7.37-7.47 (m, 5H), 7.75-7.79 (m, 1H).

Intermediate 6-2

2-(5-Amino-6-methyl-2H-indazol-2-yl)-1-[4-(pyrrolidin-1-yl)piperidin-1-yl]ethanone

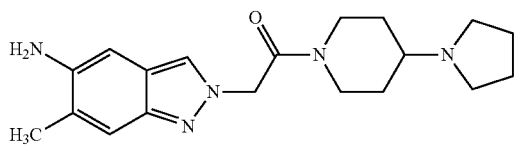

2.59 g (5.87 mmol) of tert-butyl (6-methyl-2-{2-oxo-2-[4-(pyrrolidin-1-yl)piperidin-1-yl]ethyl}-2H-indazol-5-yl) carbamate (Intermediate 5-2) were initially charged in 30 ml of dichloromethane, 4.5 ml (58.7 mmol) of trifluoroacetic acid were added and the mixture was stirred at 25° C. for 78 h. The reaction mixture was concentrated and twice toluene was added and in each case the mixture was concentrated again. The residue was purified by HPLC according to Method P2 (gradient: 0-0.5 min 25 ml/min to 70 ml/min 25% B; 0.5-5.5 min 25-55% B; flow rate: 70 ml/min). This gave 1.04 g (52% of theory) of the title compound.

UPLC-MS (Method A2): $R_t$=0.81 min
MS (ESIpos): m/z=342 (M+H)$^+$
$^1$H-NMR (300 MHz, DMSO-d6): δ=1.16-1.47 (m, 2H), 1.66 (br. s., 4H), 1.82 (br. s., 2H), 2.12-2.28 (m, 4H), 2.74-2.89 (m, 1H), 3.05-3.20 (m, 1H), 3.79-3.92 (m, 1H), 4.02-4.14 (m, 1H), 4.58 (br. s., 2H), 5.18-5.33 (m, 2H), 6.65 (s, 1H), 7.19 (s, 1H), 7.78 (d, 1H).

Intermediate 6-3

1-{4-[(5-Amino-6-methyl-2H-indazol-2-yl)acetyl]piperazin-1-yl}-3-hydroxy-2,2-dimethylpropan-1-one

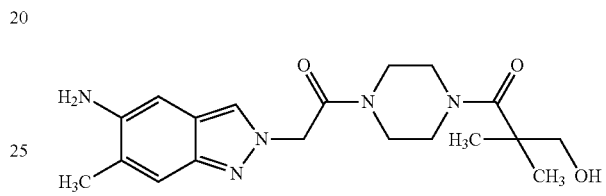

0.34 ml (4.37 mmol) of trifluoroacetic acid was added to 207 mg (0.44 mmol) of tert-butyl (2-{2-[4-(3-hydroxy-2,2-dimethylpropanoyl)piperazin-1-yl]-2-oxoethyl}-6-methyl-2H-indazol-5-yl)carbamate (Intermediate 5-3) in 5 ml of dichloromethane, and the mixture was stirred at 25° C. for 2 days. The mixture was poured into saturated sodium bicarbonate solution and extracted three times with dichloromethane, and the extracts were concentrated. This gave 184 mg of the title compound as a crude product.

UPLC-MS (Method A1): $R_t$=0.52 min
MS (ESIpos): m/z=374 (M+H)$^+$

Intermediate 6-4

2-(5-Amino-6-methyl-2H-indazol-2-yl)-1-[4-(methoxyacetyl)piperazin-1-yl]ethanone

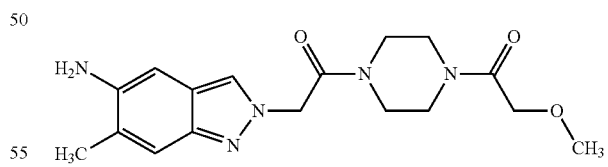

0.25 ml (3.23 mmol) of trifluoroacetic acid were added to 144 mg (0.32 mmol) of tert-butyl (2-{2-[4-(methoxyacetyl)piperazin-1-yl]-2-oxoethyl}-6-methyl-2H-indazol-5-yl)carbamate (Intermediate 5-4) in 3 ml of dichloromethane, and the mixture was stirred at 25° C. for 24 h. The mixture was concentrated, giving 219 mg of the title compound as a crude product.

UPLC-MS (Method A1): $R_t$=0.46 min
MS (ESIpos): m/z=346 (M+H)$^+$

Intermediate 6-5

2-(5-Amino-6-methoxy-2H-indazol-2-yl)-1-[4-(2-hydroxypropan-2-yl)piperidin-1-yl]ethanone

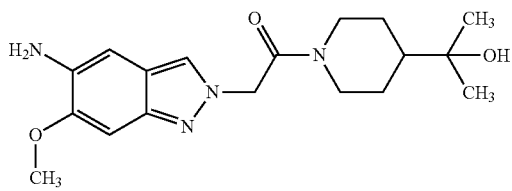 [SMILES: COc1cc2nn(CC(=O)N3CCC(C(C)(C)O)CC3)cc2cc1N]

261 µl (3.38 mmol) of trifluoroacetic acid were added to 382 mg (0.86 mmol) of tert-butyl (2-{2-[4-(2-hydroxypropan-2-yl)piperidin-1-yl]-2-oxoethyl}-6-methoxy-2H-indazol-5-yl)carbamate (Intermediate 5-5) in 5 ml of dichloromethane, and the mixture was stirred at 25° C. for 18 h. Another 609 µl (7.90 mmol) of trifluoroacetic acid were added, and stirring was continued at 25° C. until the reaction had gone to completion. The mixture was concentrated and three times toluene was added and in each case removed again under reduced pressure. This gave 735 mg of the title compound as a crude product.

UPLC-MS (Method A1): $R_t$=0.57 min
MS (ESIpos): m/z=347 (M+H)$^+$.

Intermediate 6-6

2-(5-Amino-6-methoxy-2H-indazol-2-yl)-1-[4-(cyclopropylmethyl)piperazin-1-yl]ethanone

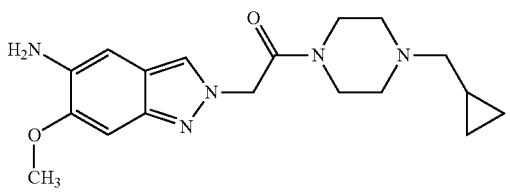 [SMILES: COc1cc2nn(CC(=O)N3CCN(CC4CC4)CC3)cc2cc1N]

Analogously to Intermediate 6-5, 402 mg (0.86 mmol) of tert-butyl (2-{2-[4-(cyclopropylmethyl)piperazin-1-yl]-2-oxoethyl}-6-methoxy-2H-indazol-5-yl)carbamate (Intermediate 5-6) were reacted with 663 µl (8.61 mmol) of trifluoroacetic acid in 5 ml of dichloromethane. This gave 822 mg of the title compound as a crude product.

Intermediate 6-7

2-(5-Amino-6-methoxy-2H-indazol-2-yl)-1-(4-benzoylpiperazin-1-yl)ethanone

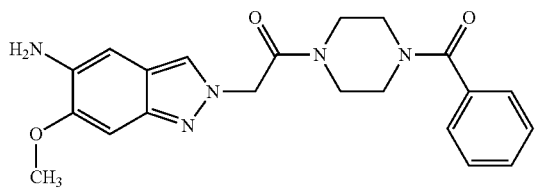 [SMILES: COc1cc2nn(CC(=O)N3CCN(C(=O)c4ccccc4)CC3)cc2cc1N]

Analogously to Intermediate 6-3, 808 mg (1.64 mmol) of tert-butyl {2-[2-(4-benzoylpiperazin-1-yl)-2-oxoethyl]-6-methoxy-2H-indazol-5-yl}carbamate (Intermediate 5-7) were stirred with 1.26 ml (16.37 mmol) of trifluoroacetic acid in 10 ml of dichloromethane at 25° C. for 18 h. Work-up gave 649 mg (99% of theory) of the title compound.

UPLC-MS (Method A1): $R_t$=0.63 min
MS (ESIpos): m/z=394 (M+H)$^+$
$^1$H-NMR (400 MHz, DMSO-d6): δ=3.33-3.79 (8H), 3.81 (s, 3H), 4.60 (s, 2H), 5.27 (br. s., 2H), 6.62 (s, 1H), 6.78 (s, 1H), 7.39-7.50 (m, 5H), 7.76 (s, 1H).

Intermediate 6-8

2-[5-Amino-6-(trifluoromethoxy)-2H-indazol-2-yl]-1-(4-methylpiperazin-1-yl)ethanone

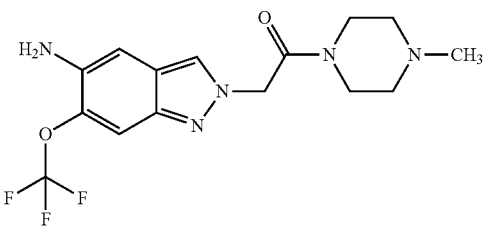 [SMILES: CN1CCN(C(=O)Cn2cc3cc(N)c(OC(F)(F)F)cc3n2)CC1]

Analogously to Intermediate 6-4, 484 mg (1.06 mmol) of tert-butyl {2-[2-(4-methylpiperazin-1-yl)-2-oxoethyl]-6-(trifluoromethoxy)-2H-indazol-5-yl}carbamate (Intermediate 5-8) were reacted with 815 µl of trifluoroacetic acid in 5 ml of dichloromethane Work-up gave 320 mg (85% of theory) of the title compound.

UPLC-MS (Method A2): $R_t$=0.79 min
MS (ESIpos): m/z=357 (M+H)$^+$
$^1$H NMR (400 MHz, DMSO-d6): δ=2.16-2.24 (m, 3H), 2.28 (t, 2H), 2.32-2.40 (m, 2H), 3.41-3.49 (m, 2H), 3.49-3.56 (m, 2H), 4.95 (s, 2H), 5.36 (s, 2H), 6.88 (s, 1H), 7.39 (s, 1H), 7.98 (s, 1H).

Intermediate 6-9

2-(5-Amino-6-bromo-2H-indazol-2-yl)-1-(4-methylpiperazin-1-yl)ethanone

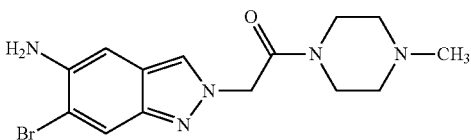 [SMILES: CN1CCN(C(=O)Cn2cc3cc(N)c(Br)cc3n2)CC1]

Analogously to Intermediate 6-4, 293 mg (0.65 mmol) of tert-butyl {6-bromo-2-[2-(4-methylpiperazin-1-yl)-2-oxoethyl]-2H-indazol-5-yl}carbamate (Intermediate 5-9) were reacted with 499 µl (6.48 mmol) of trifluoroacetic acid in 3 ml of dichloromethane Work-up gave 210 mg (92% of theory) of the title compound.

UPLC-MS (Method A2): $R_t$=0.70 min
MS (ESIpos): m/z=352 (M($^{79}$Br)+H)$^+$
$^1$H-NMR (400 MHz, DMSO-d6): δ=2.20 (s, 3H), 2.27 (t, 2H), 2.31-2.40 (m, 2H), 3.41-3.48 (m, 2H), 3.49-3.56 (m, 2H), 4.91 (s, 2H), 5.34 (s, 2H), 6.92 (s, 1H), 7.77 (s, 1H), 7.95 (d, 1H).

Intermediate 6-10

2-(5-Amino-2H-indazol-2-yl)-1-[4-(cyclopropylcarbonyl)piperazin-1-yl]ethanone

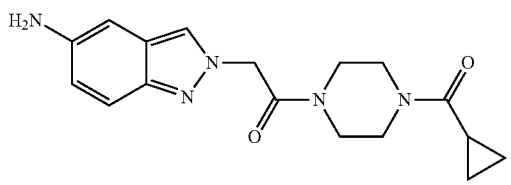 [SMILES: Nc1ccc2nn(CC(=O)N3CCN(C(=O)C4CC4)CC3)cc2c1]

Analogously to Intermediate 6-4, 2.3 g (5.38 mmol) of tert-butyl (2-{2-[4-(cyclopropylcarbonyl)piperazin-1-yl]-2-oxoethyl}-2H-indazol-5-yl)carbamate (Intermediate 5-10) were reacted with 4.1 ml (53.8 mmol) of trifluoroacetic acid in 25 ml of dichloromethane to give 1.09 g (62% of theory) of the title compound as a crude product.
UPLC-MS (Method A1): Rt=0.47 min
MS (ESIpos): m/z=328 (M+H)$^+$.

Intermediate 6-11

2-(5-Amino-2H-indazol-2-yl)-1-(4-benzoylpiperazin-1-yl)ethanone

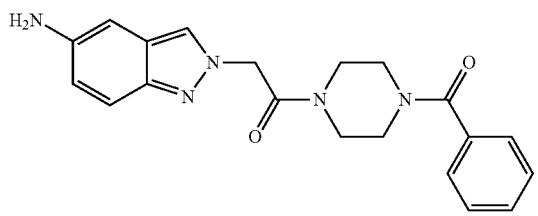 [SMILES: Nc1ccc2nn(CC(=O)N3CCN(C(=O)c4ccccc4)CC3)cc2c1]

Analogously to Intermediate 6-4, 4.20 g (9.06 mmol) of tert-butyl {2-[2-(4-benzoylpiperazin-1-yl)-2-oxoethyl]-2H-indazol-5-yl}carbamate (Intermediate 5-11) were reacted with 6.98 ml (90.6 mmol) of trifluoroacetic acid to give 3.27 g (99% of theory) of the title compound.
UPLC-MS (Method A1): $R_t$=0.57 min
MS (ESIpos): m/z=364 (M+H)$^+$
$^1$H-NMR (300 MHz, DMSO-$d_6$): δ=3.36-3.80 (m, 8H), 4.78 (s, 2H), 5.33 (br. s., 2H), 6.55 (d, 1H), 6.74 (dd, 1H), 7.30 (d, 1H), 7.38-7.53 (m, 5H), 7.81 (s, 1H).

Intermediate 6-12

2-(5-Amino-2H-indazol-2-yl)-1-(4-methylpiperazin-1-yl)ethanone

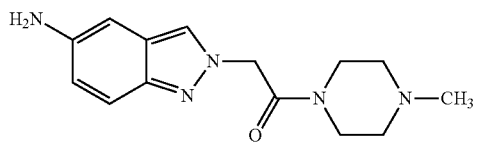 [SMILES: CN1CCN(C(=O)Cn2cc3cc(N)ccc3n2)CC1]

Analogously to Intermediate 6-4, 916 mg (2.45 mmol) of tert-butyl {2-[2-(4-methylpiperazin-1-yl)-2-oxoethyl]-2H-indazol-5-yl}carbamate (Intermediate 5-12) were stirred with 1.89 ml (24.5 mmol) of trifluoroacetic acid in dichloromethane at 25° C. for 24 h. The mixture was concentrated and the crude product was dissolved in 10 ml of tetrahydrofuran and 1 ml of N,N-dimethylformamide. The precipitated solid was filtered off and washed with diethyl ether. The solid was dissolved in methanol and the solution was concentrated to dryness. This gave 1.2 g of the title compound as a crude product.

Intermediate 6-13

2-(5-Amino-2H-indazol-2-yl)-1-[4-(2,2,2-trifluoroethyl)piperazin-1-yl]ethanone

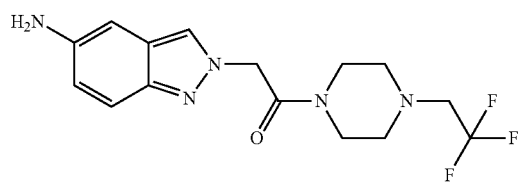 [SMILES: Nc1ccc2nn(CC(=O)N3CCN(CC(F)(F)F)CC3)cc2c1]

Analogously to Intermediate 6-4, 1.1 ml (14.4 mmol) of trifluoroacetic acid were added to 634 mg (1.43 mmol) of tert-butyl (2-{2-oxo-2-[4-(2,2,2-trifluoroethyl)piperazin-1-yl]ethyl}-2H-indazol-5-yl)carbamate (Intermediate 5-13) in 5 ml of dichloromethane and the mixture was stirred at 25° C. for 24 h. The mixture was concentrated and twice toluene was added and evaporated. This gave 1.0 g of a crude product.
UPLC-MS (Method A1): $R_t$=0.59 min
MS (ESIpos): m/z=342 (M+H)$^+$.

Intermediate 6-14

4-[(5-Amino-2H-indazol-2-yl)acetyl]-1-ethylpiperazin-2-one

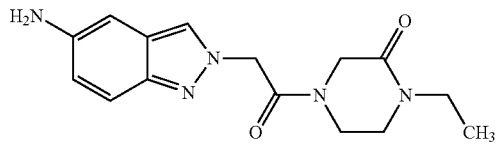 [SMILES: CCN1CCN(C(=O)Cn2cc3cc(N)ccc3n2)CC1=O]

Analogously to Intermediate 6-4, 2.8 ml (35.9 mmol) of trifluoroacetic acid were added to 1.92 g (3.59 mmol, 75%) of tert-butyl {2-[2-(4-ethyl-3-oxopiperazin-1-yl)-2-oxoethyl]-2H-indazol-5-yl}carbamate (Intermediate 5-14) in 15 ml of dichloromethane and the mixture was stirred at 25° C. for 24 h. Saturated sodium bicarbonate solution was added, the mixture was filtered, the organic phase was separated off and the aqueous phase was extracted with dichloromethane. A precipitate formed in the aqueous phase; this precipitate was filtered off with suction and washed with water and diethyl ether. Drying gave 636 mg (44% of theory) of the title compound as a crude product.

Intermediate 6-15

2-(5-Amino-3-methyl-2H-indazol-2-yl)-1-(4-benzoylpiperazin-1-yl)ethanone

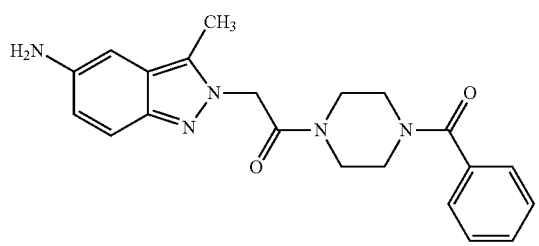 [SMILES: Cc1c2cc(N)ccc2nn1CC(=O)N1CCN(C(=O)c2ccccc2)CC1]

0.21 ml (2.72 mmol) of trifluoroacetic acid was added to 130 mg (0.27 mmol) of tert-butyl {2-[2-(4-benzoylpiperazin-1-yl)-2-oxoethyl]-3-methyl-2H-indazol-5-yl}carbamate in 3 ml of dichloromethane, and the mixture was stirred at 25° C. for 24 h and concentrated. This gave 204 mg of the title compound as a crude product.

UPLC-MS (Method A1): $R_t$=0.61 min

MS (ESIpos): m/z=378 (M+H)$^+$.

Intermediate 6-16

2-(5-Amino-6-methoxy-2H-indazol-2-yl)-1-(morpholin-4-yl)ethanone

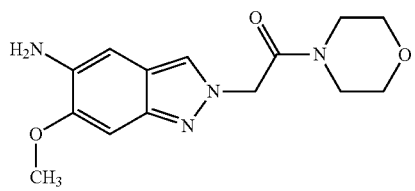 [SMILES: COc1cc2nn(CC(=O)N3CCOCC3)cc2cc1N]

Analogously to Intermediate 6-4, 1.16 g (2.97 mmol) of tert-butyl {6-methoxy-2-[2-(morpholin-4-yl)-2-oxoethyl]-2H-indazol-5-yl}carbamate (Intermediate 5-16) were stirred with 2.29 ml (29.7 mmol) of trifluoroacetic acid in 20 ml of dichloromethane at 25° C. for 24 h. A further 1.15 ml (14.9 mmol) of trifluoroacetic acid were added, and the mixture was stirred at 25° C. for a further 24 h. Three times, the reaction mixture was concentrated with toluene. The residue was dissolved in tetrahydrofuran and diethyl ether was added. The resulting precipitate was filtered off with suction, washed with diethyl ether and dried. This gave 759 mg (88% of theory) of the title compound.

UPLC-MS (Method A2): $R_t$=0.60 min

MS (ESIpos): m/z=291 (M+H)$^+$ $^1$H-NMR (400 MHz, DMSO-d6): δ=3.45 (br. s., 2H), 3.51-3.71 (m, 6H), 3.93 (s, 3H), 5.40 (s, 2H), 7.10 (s, 1H), 7.52 (s, 1H), 8.21 (s, 1H).

Intermediate 6-17

2-(5-Amino-6-methoxy-2H-indazol-2-yl)-1-(4-methylpiperazin-1-yl)ethanone

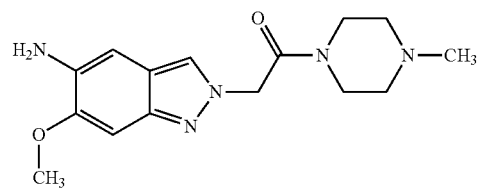 [SMILES: COc1cc2nn(CC(=O)N3CCN(C)CC3)cc2cc1N]

Analogously to Intermediate 6-16, 1.25 g (3.10 mmol) of tert-butyl {6-methoxy-2-[2-(4-methylpiperazin-1-yl)-2-oxoethyl]-2H-indazol-5-yl}carbamate (Intermediate 5-17) were stirred with 2.39 ml (31.0 mmol) of trifluoroacetic acid in 25 ml of dichloromethane at 25° C. for 5 h. Work-up gave 534 mg (57% of theory) of the title compound.

UPLC-MS (Method A2): $R_t$=0.61 min

MS (ESIpos): m/z=304 (M+H)$^+$ $^1$H-NMR (400 MHz, DMSO-d6): δ=2.19 (s, 3H), 2.24-2.30 (m, 2H), 2.30-2.37 (m, 2H), 3.41-3.48 (m, 2H), 3.49-3.54 (m, 2H), 3.82 (s, 3H), 4.61 (br. s., 2H), 5.23 (s, 2H), 6.63 (s, 1H), 6.79 (s, 1H), 7.76 (s, 1H).

Intermediate 6-18

2-(5-Amino-6-methoxy-2H-indazol-2-yl)-N-(cyclopropylmethyl)-N-methylacetamide

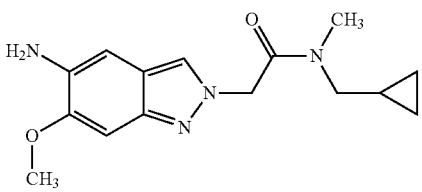 [SMILES: COc1cc2nn(CC(=O)N(C)CC3CC3)cc2cc1N]

Analogously to Intermediate 6-4, 353 mg (0.86 mmol, 95%) of tert-butyl (2-{2-[(cyclopropylmethyl)(methyl)amino]-2-oxoethyl}-6-methoxy-2H-indazol-5-yl)carbamate (Intermediate 5-18) were initially charged in 10 ml of dichloromethane 665 μl (8.63 mmol) of trifluoroacetic acid were added, the mixture was stirred at 25° C. for 24 h, another 200 μl of trifluoroacetic acid were added and the mixture was stirred for 3 h. The mixture was concentrated and twice toluene was added and in each case the mixture was concentrated again. This gave 750 mg of a crude product.

UPLC-MS (Method A1): $R_t$=0.61 min

MS (ESIpos): m/z=289 (M+H)$^+$

Intermediate 6-19

2-(5-Amino-2H-indazol-2-yl)-1-(4-benzoylpiperazin-1-yl)propan-1-one

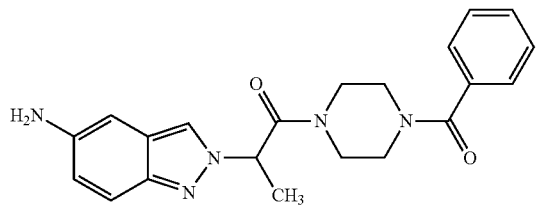 [SMILES: CC(C(=O)N1CCN(C(=O)c2ccccc2)CC1)n1cc2cc(N)ccc2n1]

Analogously to Intermediate 6-4, 3.70 g (7.75 mmol) of tert-butyl {2-[1-(4-benzoylpiperazin-1-yl)-1-oxopropan-2-yl]-2H-indazol-5-yl}carbamate (Intermediate 5-19) (crude product) were initially charged in 40 ml of dichloromethane 6.0 ml (77.4 mmol) of trifluoroacetic acid were added and the mixture was stirred at 25° C. for 24 h. The mixture was carefully poured into saturated sodium bicarbonate solution, extracted with dichloromethane and concentrated. The crude product was triturated with diethyl ether. This gave 2.4 g (75% of theory) of the title compound as a light-brown solid.

$^1$H-NMR (300 MHz, DMSO-d6): δ=1.59 (d, 3H), 2.9-3.7 (broad signals, superimposed), 4.78 (s, 2H), 5.74 (br. s, 1H), 6.52 (s, 1H), 6.71 (dd, 1H), 7.25-7.47 (m), 7.91 (s, 1H).

Intermediate 6-20

2-[5-Amino-6-(benzyloxy)-2H-indazol-2-yl]-1-(morpholin-4-yl)ethanone

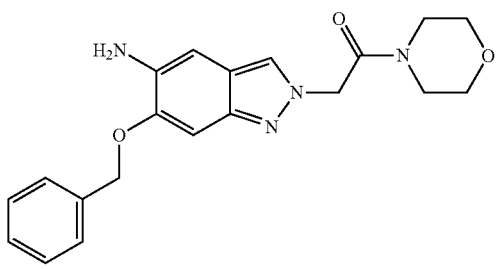 [SMILES: Nc1cc2cn(CC(=O)N3CCOCC3)nc2cc1OCc1ccccc1]

Analogously to Intermediate 6-4, 3.65 g (7.82 mmol) of tert-butyl {6-(benzyloxy)-2-[2-(morpholin-4-yl)-2-oxoethyl]-2H-indazol-5-yl}carbamate (Intermediate 5-20) were initially charged in 50 ml of dichloromethane 6.0 ml (78.2 mmol) of trifluoroacetic acid were added and the mixture was stirred at 25° C. for 24 h. The mixture was carefully poured into saturated sodium bicarbonate solution and extracted with dichloromethane, and the combined organic phases were washed with saturated sodium chloride solution and concentrated. This gave 2.72 g (95% of theory) of the title compound.

UPLC-MS (Method A1): $R_t$=0.85 min

MS (ESIpos): m/z=312 (M+H)$^+$ $^1$H-NMR (400 MHz, CHLOROFORM-d): δ=3.59 (s, 4H), 3.65 (d, 4H), 5.15 (s, 4H), 6.78 (s, 1H), 6.98 (s, 1H), 7.34-7.44 (m, 3H), 7.46-7.50 (m, 2H), 7.71-7.74 (m, 1H).

Intermediate 6-21

2-(5-Amino-6-chloro-2H-indazol-2-yl)-1-(4-methylpiperazin-1-yl)ethanone

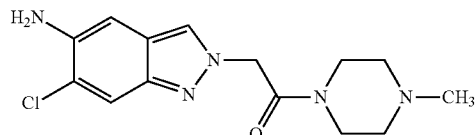

5.0 ml of ice-cold trifluoroacetic acid were added to 299 mg of benzyl {6-chloro-2-[2-(4-methylpiperazin-1-yl)-2-oxoethyl]-2H-indazol-5-yl}carbamate (Intermediate 5-21), and the mixture was stirred at room temperature for 3 days. The mixture was poured into saturated aqueous sodium bicarbonate solution and extracted with ethyl acetate and the extract was washed with sodium chloride solution, filtered through a hydrophobic filter and concentrated. Purification by preparative HPLC (Method P2) gave a solid which was triturated with diethyl ether. Drying gave 101 mg of the title compound.

$^1$H-NMR (300 MHz, DMSO-d$_6$): δ [ppm]=2.18 (s, 3H), 2.22-2.39 (m, 4H), 3.38-3.56 (m), 4.96 (s, 2H), 5.33 (s, 2H), 6.88 (s, 1H), 7.57 (s, 1H), 7.94 (d, 1H).

Intermediate 6-22

2-(5-Amino-6-chloro-2H-indazol-2-yl)-1-(morpholin-4-yl)ethanone

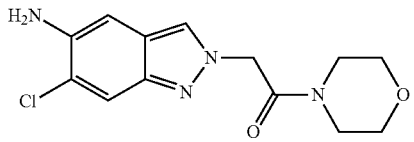 [SMILES: Nc1cc2cn(CC(=O)N3CCOCC3)nc2cc1Cl]

Analogously to the preparation of Intermediate 6-21, 254 mg of benzyl {6-chloro-2-[2-(morpholin-4-yl)-2-oxoethyl]-2H-indazol-5-yl}carbamate (Intermediate 5-22) were stirred with 3 ml of trifluoroacetic acid at room temperature for 6 days. Analogous aqueous work-up gave 137 mg of the title compound as a crude product.

UPLC-MS (Method A1): Rt=0.60 min (UV detector: TIC). Mass found 294.00.

Intermediate 7-1

Ethyl (5-amino-6-fluoro-2H-indazol-2-yl)acetate

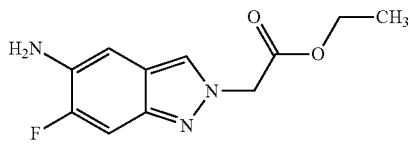 [SMILES: CCOC(=O)Cn1cc2cc(N)c(F)cc2n1]

Analogously to Intermediate 6-4, 1.1 g (3.3 mmol) of ethyl {5-[(tert-butoxycarbonyl)amino]-6-fluoro-2H-indazol-2-yl}acetate (Intermediate 3-5) were reacted with 1.92 ml (24.9 mmol) of trifluoroacetic acid in 11 ml of dichloromethane Work-up gave 790 mg (100% of theory) of the title compound.

UPLC-MS (Method A1): $R_t$=0.67 min
MS (ESIpos): m/z=238 (M+H)$^+$
1H-NMR (300 MHz, DMSO-d6): δ=1.21 (t, 3H), 4.16 (q, 2H), 4.93 (s, 2H), 5.24 (s, 2H), 6.81 (d, 1H), 7.21 (d, 1H), 8.80 (s, 1H).

Intermediate 7-2

Ethyl [5-amino-6-(benzyloxy)-2H-indazol-2-yl]acetate

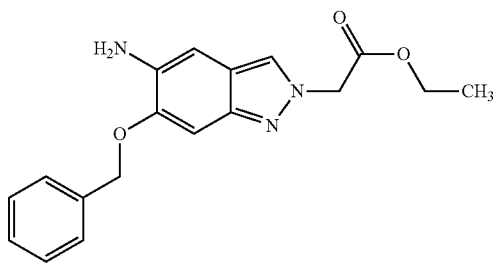 [SMILES: CCOC(=O)Cn1cc2cc(N)c(OCc3ccccc3)cc2n1]

Analogously to Intermediate 6-4, 2.37 g (5.56 mmol) of ethyl {6-(benzyloxy)-5-[(tert-butoxycarbonyl)amino]-2H-indazol-2-yl}acetate (Intermediate 3-4) were reacted with 3.24 ml (41.8 mmol) of trifluoroacetic acid in 25 ml of dichloromethane Work-up gave 1.79 g (99% of theory) of the title compound.

UPLC-MS (Method A1): $R_t$=0.91 min
MS (ESIpos): m/z=326 (M+H)$^+$
$^1$H NMR (400 MHz, CHLOROFORM-d): δ=1.29 (t, 3H), 4.25 (q, 2H), 5.07 (s, 2H), 5.15 (s, 2H), 6.81 (s, 1H), 7.01 (s, 1H), 7.31-7.45 (m, 3H), 7.45-7.52 (m, 2H), 7.67 (s, 1H).

Intermediate 7-3

Ethyl (5-amino-2H-indazol-2-yl)acetate

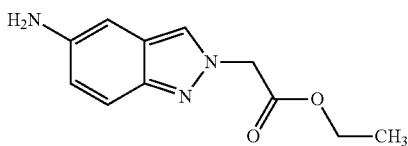 [SMILES: CCOC(=O)Cn1cc2cc(N)ccc2n1]

Analogously to Intermediate 6-4, 9.0 ml (117.4 mmol) of trifluoroacetic acid were added to 5.00 g (15.7 mmol) of tert-butyl {5-[(tert-butoxycarbonyl)amino]-2H-indazol-2-yl}acetate (Intermediate 3-7) in 75 ml of dichloromethane and the mixture was stirred at 25° C. for 24 h. The mixture was poured into saturated sodium bicarbonate solution, the organic phase was separated off and the aqueous phase was extracted three times with dichloromethane. The combined organic phases were washed with sodium chloride solution, dried and concentrated. This gave 3.4 g of the title compound as a brown solid.

UPLC-MS (METHOD A1): Rt=0.47 min
MS (ESIpos): m/z=220 (M+H)$^+$
$^1$H-NMR (400 MHz, DMSO-d$_6$): δ=1.18 (t, 3H), 2.49 (br. s., 1H), 4.12 (q, 2H), 4.80 (s, 2H), 5.20 (s, 2H), 6.52 (dd, 1H), 6.73 (dd, 1H), 7.26-7.32 (m, 1H), 7.87 (d, 1H).

Intermediate 7-4

Ethyl 3-(5-amino-2H-indazol-2-yl)propanoate

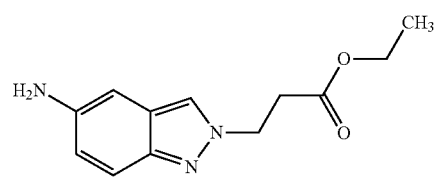 [SMILES: CCOC(=O)CCn1cc2cc(N)ccc2n1]

Analogously to Intermediate 7-1, 640 mg (1.92 mmol) of ethyl 3-{5-[(tert-butoxycarbonyl)amino]-2H-indazol-2-yl}propanoate (Intermediate 3-9) were reacted with 1.1 ml (14.4 mmol) of trifluoroacetic acid. This gave 391 mg (87% of theory) of the title compound.

UPLC-MS (Method A1): Rt=0.50 min
MS (ESIpos): m/z=234 (M+H)$^+$

Intermediate 7-5

Ethyl (5-amino-6-isopropoxy-2H-indazol-2-yl)acetate

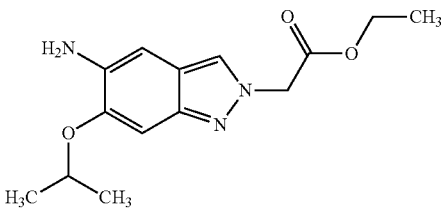 [SMILES: CCOC(=O)Cn1cc2cc(N)c(OC(C)C)cc2n1]

Analogously to Intermediate 7-1, 1.8 g (4.84 mmol) of ethyl {5-[(tert-butoxycarbonyl)amino]-6-isopropoxy-2H-indazol-2-yl}acetate (Intermediate 3-10) were reacted with 2.8 ml (36.3 mmol) of trifluoroacetic acid. This gave 1.3 g (100% of theory) of the title compound.

UPLC-MS (Method A1): $R_t$=0.69 min
MS (ESIpos): m/z=278 (M+H)$^+$
$^1$H-NMR (300 MHz, DMSO-d6): δ=1.21 (t, 3H), 1.32 (d, 6H), 4.15 (q, 2H), 4.59 (s, 1H), 4.60-4.69 (m, 1H), 5.16 (s, 2H), 6.64 (s, 1H), 6.81 (d, 1H), 7.83 (s, 1H).

Intermediate 7-6

Benzyl (5-amino-6-methoxy-2H-indazol-2-yl)acetate

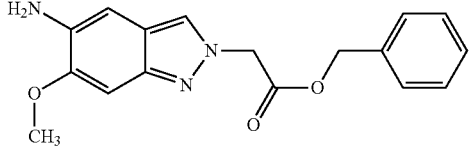 [SMILES: COc1cc2nn(CC(=O)OCc3ccccc3)cc2cc1N]

Analogously to Intermediate 7-1, 25.7 g (60.1 mmol) of benzyl {5-[(tert-butoxycarbonyl)amino]-6-methoxy-2H-indazol-2-yl}acetate (Intermediate 3-2) were reacted with 23.1 ml (300.3 mmol) of trifluoroacetic acid. This gave 20.5 g (98% of theory) of the title compound.

UPLC-MS (Method A1): $R_t$=0.85 min

MS (ESIpos): m/z=312 (M+H)$^+$

Intermediate 8-1

Ethyl [6-fluoro-5-({[6-(trifluoromethyl)pyridin-2-yl]carbonyl}amino)-2H-indazol-2-yl]acetate

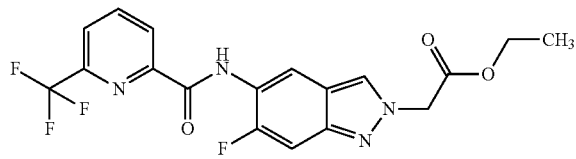 [SMILES: CCOC(=O)Cn1cc2cc(NC(=O)c3cccc(C(F)(F)F)n3)c(F)cc2n1]

221 mg (1.16 mmol) of 6-(trifluoromethyl)pyridine-2-carboxylic acid, 177 mg (1.16 mmol) of 1-hydroxy-1H-benzotriazole hydrate and 444 mg (2.32 mmol) of 1-(3-dimethylaminopropyl)-3-ethylcarbodiimide hydrochloride in 5.5 ml of dimethylformamide were stirred at 25° C. for 30 min 250 mg (1.05 mmol) of ethyl (5-amino-6-fluoro-2H-indazol-2-yl)acetate (Intermediate 7-1) were added and the mixture was stirred at 25° C. for 30 min. The mixture was poured into 150 ml of water, filtered off with suction, washed with water and dried. This gave 366 mg (84% of theory) of the title compound.

UPLC-MS (Method A1): $R_t$=1.23 min

MS (ESIpos): m/z=411 (M+H)$^+$ $^1$H-NMR (300 MHz, DMSO-d6): δ=1.22 (t, 3H), 4.18 (q, 2H), 5.41 (s, 2H), 7.55 (d, 1H), 8.21 (m, 1H), 8.36-8.51 (m, 4H), 10.27 (m, 1H).

Intermediate 8-2

Ethyl (6-fluoro-5-{[(6-methylpyridin-2-yl)carbonyl]amino}-2H-indazol-2-yl)acetate

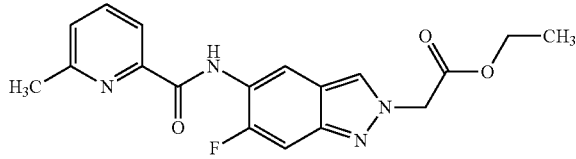 [SMILES: CCOC(=O)Cn1cc2cc(NC(=O)c3cccc(C)n3)c(F)cc2n1]

Analogously to Intermediate 8-1, 159 mg (1.16 mmol) of 6-methylpyridine-2-carboxylic acid were reacted with 250 mg (1.05 mmol) of ethyl (5-amino-6-fluoro-2H-indazol-2-yl)acetate (Intermediate 7-1). Work-up gave 316 mg (84% of theory) of the title compound.

UPLC-MS (Method A1): $R_t$=1.17 min

MS (ESIpos): m/z=357 (M+H)$^+$.

Intermediate 8-3

Ethyl [6-fluoro-5-({[6-(1-methyl-1H-pyrazol-4-yl)pyridin-2-yl]carbonyl}amino)-2H-indazol-2-yl]acetate

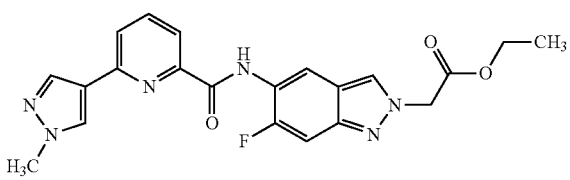 [SMILES: CCOC(=O)Cn1cc2cc(NC(=O)c3cccc(-c4cnn(C)c4)n3)c(F)cc2n1]

Analogously to Intermediate 8-1, 235 mg (1.16 mmol) of 6-(1-methyl-1H-pyrazol-4-yl)pyridine-2-carboxylic acid were reacted with 250 mg (1.05 mmol) of ethyl (5-amino-6-fluoro-2H-indazol-2-yl)acetate (Intermediate 7-1). Work-up gave 364 mg (82% of theory) of the title compound.

UPLC-MS (Method A1): $R_t$=1.05 min

MS (ESIpos): m/z=423 (M+H)$^+$.

Intermediate 8-4

Ethyl [6-fluoro-5-({[5-fluoro-6-(1-methyl-1H-pyrazol-4-yl)pyridin-2-yl]carbonyl}amino)-2H-indazol-2-yl]acetate

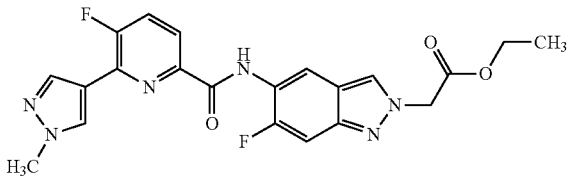 [SMILES: CCOC(=O)Cn1cc2cc(NC(=O)c3ccc(F)c(-c4cnn(C)c4)n3)c(F)cc2n1]

Analogously to Intermediate 8-1, 235 mg (1.0 mmol) of 5-fluoro-6-(1-methyl-1H-pyrazol-4-yl)pyridine-2-carboxylic acid (Intermediate 19-5) were reacted with 250 mg (1.05 mmol) of ethyl (5-amino-6-fluoro-2H-indazol-2-yl)acetate (Intermediate 7-1). Work-up gave 326 mg (76% of theory) of the title compound.

UPLC-MS (Method A1): $R_t$=1.13 min

MS (ESIpos): m/z=442 (M+H)$^+$.

Intermediate 8-5

Ethyl [6-fluoro-5-({[6-(morpholin-4-yl)pyridin-2-yl]carbonyl}amino)-2H-indazol-2-yl]acetate

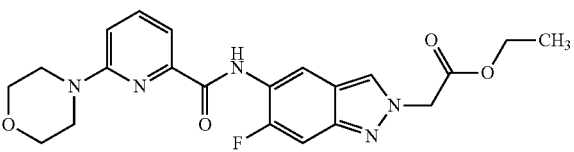 [SMILES: CCOC(=O)Cn1cc2cc(NC(=O)c3cccc(N4CCOCC4)n3)c(F)cc2n1]

Analogously to Intermediate 8-1, 222 mg (0.97 mmol) of 6-(morpholin-4-yl)pyridine-2-carboxylic acid were reacted with 230 mg (0.97 mmol) of ethyl (5-amino-6-fluoro-2H- indazol-2-yl)acetate (Intermediate 7-1). Work-up gave 414 mg (100% of theory) of the title compound.
UPLC-MS (Method A1): R$_t$=1.12 min
MS (ESIpos): m/z=428 (M+H)$^+$.

Intermediate 8-6

Ethyl [6-(benzyloxy)-5-({[6-(trifluoromethyl)pyridin-2-yl]carbonyl}amino)-2H-indazol-2-yl]acetate

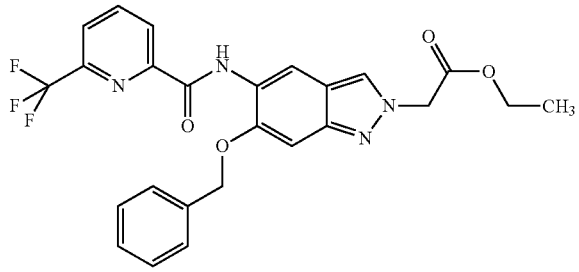 [SMILES: CCOC(=O)Cn1cc2cc(NC(=O)c3cccc(C(F)(F)F)n3)c(OCc3ccccc3)cc2n1]

1.79 g (5.5 mmol) of ethyl [5-amino-6-(benzyloxy)-2H-indazol-2-yl]acetate (Intermediate 7-2), 1.26 g (6.6 mmol) of 6-(trifluoromethyl)pyridine-2-carboxylic acid, 842 mg (5.5 mmol) of 1-hydroxy-1H-benzotriazole hydrate, 2.11 g (11.0 mmol) of 1-(3-dimethylaminopropyl)-3-ethylcarbodiimide hydrochloride and 2.3 ml (16.5 mmol) of triethylamine were stirred in 75 ml of tetrahydrofuran at 25° C. for 24 h. The reaction mixture was concentrated and water was added to the residue. The resulting solid was filtered off with suction and washed twice with water and twice with diethyl ether. The yellow solid was dried under reduced pressure. This gave 2.44 g (89% of theory) of product.
UPLC-MS (Method A1): R$_t$=1.42 min
MS (ESIpos): m/z=499 (M+H)$^+$
$^1$H-NMR (400 MHz, DMSO-d6): δ=1.23 (t, 3H), 4.18 (q, 2H), 5.31 (s, 2H), 5.33 (s, 2H), 7.32 (s, 1H), 7.34-7.47 (m, 3H), 7.54-7.61 (m, 2H), 8.18 (d, 1H), 8.32-8.42 (m, 2H), 8.43-8.52 (m, 1H), 8.81 (s, 1H), 10.47 (s, 1H).

Intermediate 8-7

Ethyl [6-hydroxy-5-({[6-(trifluoromethyl)pyridin-2-yl]carbonyl}amino)-2H-indazol-2-yl]acetate

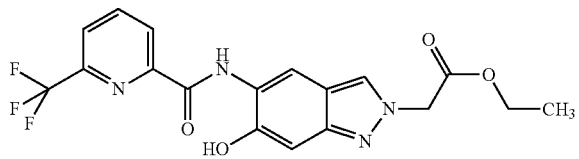 [SMILES: CCOC(=O)Cn1cc2cc(NC(=O)c3cccc(C(F)(F)F)n3)c(O)cc2n1]

1.0 g (2.01 mmol) of ethyl [6-(benzyloxy)-5-({[6-(trifluoromethyl)pyridin-2-yl]carbonyl}amino)-2H-indazol-2-yl] acetate (Intermediate 8-6) was dissolved in 40 ml of ethanol, and the flask was evacuated and then flushed with nitrogen (this procedure was repeated two more times). 213 mg (0.2 mmol) of palladium on carbon were added and the flask was evacuated and flushed with hydrogen. The reaction mixture was hydrogenated under standard hydrogen pressure at 25° C. for 6 h. The reaction mixture was then filtered through a PTFE filter with Celite and concentrated. This gave 783 mg (96% of theory) of product.

UPLC-MS (Method A1): Rt=1.08 min
MS (ESIpos): m/z=409 (M+H)$^+$
$^1$H-NMR (400 MHz, DMSO-d6): δ=1.22 (t, 3H), 4.17 (q, 2H), 5.28 (s, 2H) 6.92 (s, 1H) 8.21 (d, 1H), 8.27 (s, 1H), 8.40 (t, 1H), 8.47 (d, 1H), 8.70 (s, 1H), 10.55 (s, 1H), 10.72 (s, 1H).

Intermediate 8-8

Ethyl [6-isobutoxy-5-({[6-(trifluoromethyl)pyridin-2-yl]carbonyl}amino)-2H-indazol-2-yl]acetate

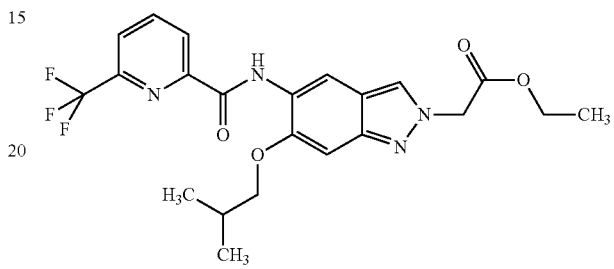

200 mg (0.49 mmol) of ethyl [6-hydroxy-5-({[6-(trifluoromethyl)pyridin-2-yl]carbonyl}amino)-2H-indazol-2-yl] acetate (Intermediate 8-7) were dissolved in 1.5 ml of N,N-dimethylformamide, and 203 mg (1.47 mmol) of potassium carbonate were added with stirring. The suspension was stirred at 25° C. for 10 minutes, and 80 µl (0.73 mmol) of 1-bromo-2-methylpropane were then added. The reaction mixture was stirred in the microwave at 100° C. for 1 h. The reaction mixture was then diluted with water, and ethyl acetate was added. A solid was formed, which was filtered off with suction and washed twice with water and twice with diethyl ether. The greenish solid was dried in a drying cabinet for 3 h. This gave 200 mg (88% of theory) of product.
UPLC-MS (Method A1): R$_t$=1.45 min
MS (ESIpos): m/z=465 (M+H)$^+$
$^1$H-NMR (300 MHz, DMSO-d6): δ=1.12 (d, 6H), 1.22 (t, 3H), 2.19 (dt, 1H), 3.96 (d, 2H), 4.17 (q, 2H), 5.32 (s, 2H), 7.09 (s, 1H), 8.22 (d, 1H), 8.32 (s, 1H), 8.37-8.45 (m, 1H), 8.46-8.51 (m, 1H), 8.78 (s, 1H), 10.58 (s, 1H).

Intermediate 8-9

Ethyl [6-(cyclopropylmethoxy)-5-({[6-(trifluoromethyl)pyridin-2-yl]carbonyl}amino)-2H-indazol-2-yl]acetate

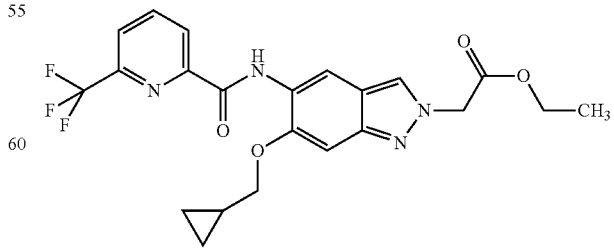

Analogously to Intermediate 8-5, 200 mg (0.49 mmol) of ethyl [6-hydroxy-5-({[6-(trifluoromethyl)pyridin-2-yl]

carbonyl}amino)-2H-indazol-2-yl]acetate (Intermediate 8-7) were reacted with 71 µl (0.73 mmol) of (bromomethyl)cyclopropane. Work-up gave 223 mg (99% of theory) of the title compound.

UPLC-MS (Method A1): R$_t$=1.38 min
MS (ESIpos): m/z=463 (M+H)$^+$
$^1$H-NMR (300 MHz, CHLOROFORM-d): δ=0.38-0.50 (m, 2H), 0.69-0.84 (m, 2H), 1.30 (t, 3H), 1.45 (br. s., 1H), 3.98 (d, 2H), 4.27 (q, 2H), 5.15 (s, 2H), 6.98 (s, 1H), 7.87 (d, 1H), 7.93 (s, 1H), 8.13 (t, 1H), 8.51 (d, 1H), 8.88 (s, 1H), 10.91 (s, 1H).

Intermediate 8-10

Ethyl [6-(pyridin-2-ylmethoxy)-5-({[6-(trifluoromethyl)pyridin-2-yl]carbonyl}amino)-2H-indazol-2-yl]acetate

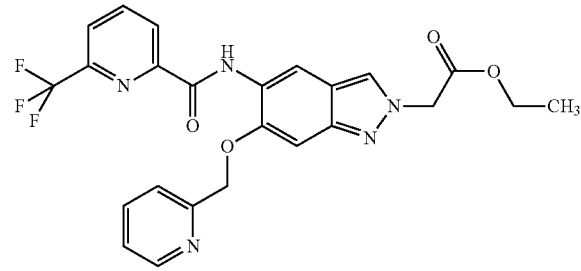 [SMILES: CCOC(=O)Cn1cc2cc(NC(=O)c3cccc(C(F)(F)F)n3)c(OCc3ccccn3)cc2n1]

200 mg (0.49 mmol) of ethyl [6-hydroxy-5-({[6-(trifluoromethyl)pyridin-2-yl]carbonyl}amino)-2H-indazol-2-yl]acetate (Intermediate 8-7) were dissolved in 6.6 ml of N,N-dimethylformamide, and 270 mg (1.96 mmol) of potassium carbonate were added with stirring. The suspension was stirred at 25° C. for 10 minutes, and 185 mg (0.73 mmol) of 2-(bromomethyl)pyridine hydrobromide were then added. The reaction mixture was stirred in the microwave at 100° C. for 1 h. The reaction mixture was then diluted with water, and ethyl acetate was added. A solid was formed, which was filtered off with suction and washed twice with water and twice with diethyl ether. The greenish solid was dried in a drying cabinet for 3 h. This gave 160 mg (65% of theory) of the title compound.

UPLC-MS (Method A1): R$_t$=1.24 min
MS (ESIpos): m/z=500 (M+H)$^+$
1H NMR (400 MHz, DMSO-d6): δ=1.23 (t, 3H), 4.18 (q, 2H), 5.34 (s, 2H), 5.36 (s, 2H), 7.70 (d, 1H), 7.82-7.91 (m, 1H), 8.15-8.21 (m, 1H), 8.36 (s, 1H), 8.37-8.43 (m, 1H), 8.45-8.50 (m, 1H), 8.62 (d, 1H), 8.82 (s, 1H), 10.50 (s, 1H).

Intermediate 8-11

Ethyl [5-({[6-(1-methyl-1H-pyrazol-4-yl)pyridin-2-yl]carbonyl}amino)-2H-indazol-2-yl]acetate

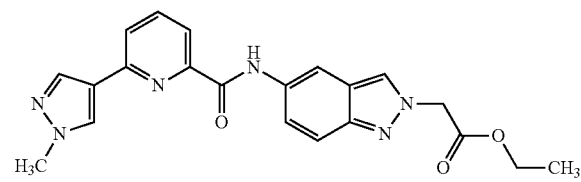 [SMILES: CCOC(=O)Cn1cc2cc(NC(=O)c3cccc(-c4cnn(C)c4)n3)ccc2n1]

Analogously to Intermediate 8-1, 1.00 g of 6-(1-methyl-1H-pyrazol-4-yl)pyridine-2-carboxylic acid (Intermediate 19-2) (crude product) and 961 mg (4.39 mmol) of ethyl (5-amino-2H-indazol-2-yl)acetate (Intermediate 7-3) were stirred in 10 ml of tetrahydrofuran at 25° C. for 24 h. Water was added, the mixture was concentrated and the precipitated solid was filtered off with suction, washed with water and diethyl ether and dried under reduced pressure. This gave 1.45 g (80% of theory) of the title compound.

UPLC-MS (Method A1): Rt=1.01 min
MS (ESIpos): m/z=405 (M+H)$^+$.

Intermediate 8-12

Ethyl [6-ethoxy-5-({[6-(trifluoromethyl)pyridin-2-yl]carbonyl}amino)-2H-indazol-2-yl]acetate

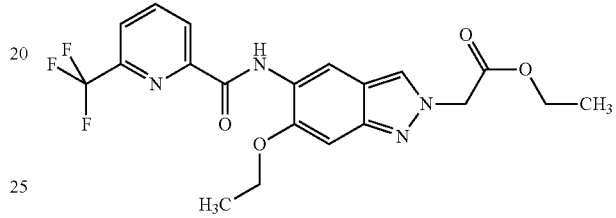

Analogously to Intermediate 3-1, 1.30 g (3.71 mmol) of N-(6-ethoxy-1H-indazol-5-yl)-6-(trifluoromethyl)pyridine-2-carboxamide (Intermediate 14-3), 826 µl (7.42 mmol) of ethyl bromoacetate and 1.54 ml (7.42 mmol) of N,N-dicyclohexylmethylamine in 20 ml of tetrahydrofuran were stirred at 65° C. for 18 h. Another 413 µl (3.71 mmol) of ethyl bromoacetate and 770 µl (3.71 mmol) of N,N-dicyclohexylmethylamine were added, and the mixture was stirred at 65° C. for a further 6 h. Work-up gave 143 mg of the title compound as a crude product.

A further 637 mg of the title compound were obtained by addition of water to the reaction filtrate, extraction with ethyl acetate, washing the organic phase with 1M hydrochloric acid solution, saturated sodium bicarbonate solution, saturated sodium chloride solution, drying, concentration and trituration of the residue with ethyl acetate.

UPLC-MS (Method A1): R$_t$=1.31 min
MS (ESIpos): m/z=437 (M+H)$^+$
$^1$H NMR (400 MHz, DMSO-d6): δ=1.23 (t, 3H), 1.51 (t, 3H), 4.14-4.27 (m, 4H), 5.31 (s, 2H), 7.10 (s, 1H), 8.18-8.23 (m, 1H), 8.31 (s, 1H), 8.37-8.44 (m, 1H), 8.45-8.49 (m, 1H), 8.73 (s, 1H), 10.74 (s, 1H).

Intermediate 8-13

Ethyl 3-[5-({[6-(trifluoromethyl)pyridin-2-yl]carbonyl}amino)-2H-indazol-2-yl]propanoate

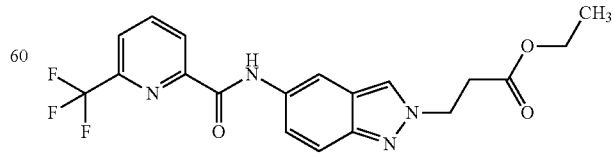

Analogously to Intermediate 8-1, 194 mg (0.83 mmol) of ethyl 3-(5-amino-2H-indazol-2-yl)propanoate (Intermediate 7-4) were reacted with 175 mg (0.91 mmol) of 6-(trifluoromethyl)pyridine-2-carboxylic acid. This gave 285 mg (84% of theory) of the title compound.
UPLC-MS (Method A1): $R_t$=1.17 min
MS (ESIpos): m/z=407 (M+H)$^+$.

Intermediate 8-14 tert-Butyl [6-chloro-5-({[6-(trifluoromethyl)pyridin-2-yl]carbonyl}amino)-2H-indazol-2-yl]acetate

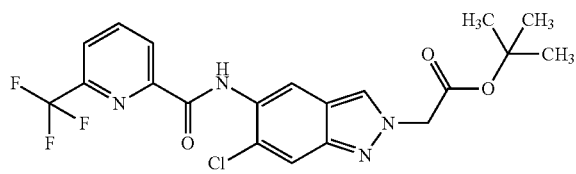 [SMILES: CC(C)(C)OC(=O)Cn1cc2cc(NC(=O)c3cccc(C(F)(F)F)n3)c(Cl)cc2n1]

4.48 g (12.2 mmol) of N-(6-chloro-1H-indazol-5-yl)-6-(trifluoromethyl)pyridine-2-carboxamide (Intermediate 14-1) were initially charged in 40 ml of tetrahydrofuran. 3.61 ml (24.5 mmol) of tert-butyl bromoacetate and 5.19 ml (24.5 mmol) of N,N-dicyclohexylmethylamine were added and the mixture was stirred at 70° C. for 5.5 h. Another 3.61 ml (24.5 mmol) of tert-butyl bromoacetate and 5.19 ml (24.5 mmol) of N,N-dicyclohexylmethylamine were added, the mixture was stirred at 65° C. for 18 h, another 1.81 ml (12.3 mmol) of tert-butyl bromoacetate and 2.60 ml (12.3 mmol) of N,N-dicyclohexylmethylamine were added and the mixture was stirred at 65° C. for a further 6 h. The mixture was filtered, water was added to the filtrate, the mixture was extracted three times with ethyl acetate and the combined organic phases were washed with 1M hydrochloric acid, saturated sodium bicarbonate solution and saturated sodium chloride solution and concentrated. Trituration of the crude product with ethyl acetate gave, after drying, 1.45 g (26% of theory) of the title compound.
UPLC-MS (Method A1): $R_t$=1.43 min
MS (ESIpos): m/z=455 (M+H)$^+$
1H-NMR (400 MHz, DMSO-d6): δ=1.45 (s, 9H), 5.32 (s, 2H), 7.95 (s, 1H), 8.23 (d, 1H), 8.38-8.44 (m, 1H), 8.45-8.49 (m, 1H), 8.49 (s, 1H), 8.66 (s, 1H), 10.5 (s, 1H).

Intermediate 8-15 tert-Butyl [6-methoxy-5-({[6-(trifluoromethyl)pyridin-2-yl]carbonyl}amino)-2H-indazol-2-yl]acetate

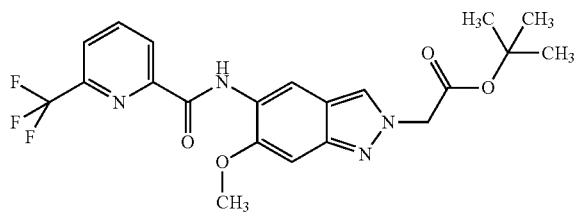 [SMILES: COc1cc2nn(CC(=O)OC(C)(C)C)cc2cc1NC(=O)c1cccc(C(F)(F)F)n1]

2.00 g (5.95 mmol) of N-(6-methoxy-1H-indazol-5-yl)-6-(trifluoromethyl)pyridine-2-carboxamide (Intermediate 14-2) were dissolved in 40 ml of tetrahydrofuran and 4.39 ml (29.7 mmol) of tert-butyl bromoacetate and 6.37 ml (29.7 mmol) of N,N-dicyclohexylmethylamine were added at 25° C. The solution was stirred at 70° C. for 3 h. Another 0.87 ml (5.95 mmol) of tert-butyl bromoacetate and 1.27 ml (5.95 mmol) of N,N-dicyclohexylmethylamine were added, and the mixture was stirred at 70° C. for a further 24 h. The solid in the reaction mixture was filtered off and washed twice with tetrahydrofuran. The regioisomerically pure crystals were dried in a vacuum drying cabinet at 50° C. for 3 h. This gave 1.58 g (59% of theory) of product.
UPLC-MS (Method A1): $R_t$=1.36 min
MS (ESIpos): m/z=451 (M+H)$^+$
$^1$H NMR (400 MHz, CHLOROFORM-d): δ=1.50 (s, 9H), 4.04 (s, 3H), 5.04 (s, 2H), 7.06 (s, 1H), 7.86 (d, 1H), 7.92 (s, 1H), 8.12 (t, 1H), 8.50 (d, 1H), 8.84 (s, 1H), 10.72 (s, 1H).

Intermediate 8-16 tert-Butyl [5-({[6-(trifluoromethyl)pyridin-2-yl]carbonyl}amino)-2H-indazol-2-yl]acetate

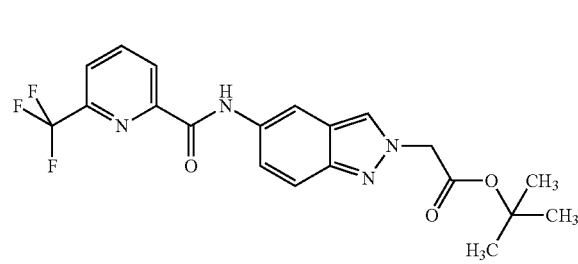 [SMILES: CC(C)(C)OC(=O)Cn1cc2cc(NC(=O)c3cccc(C(F)(F)F)n3)ccc2n1]

525 mg (3.80 mmol) of potassium carbonate were added to a solution of 582 mg (1.90 mmol) of N-(1H-indazol-5-yl)-6-(trifluoromethyl)pyridine-2-carboxamide (Intermediate 14-4) and 309 µl (2.09 mmol) of tert-butyl bromoacetate in 5 ml of N,N-dimethylformamide, and the mixture was stirred at 80° C. for 24 h. Water was added, and the mixture was extracted three times with ethyl acetate. A solid precipitated from the ethyl acetate phase; this solid was filtered off with suction and washed with ethyl acetate. Drying under reduced pressure gave 72 mg (8% of theory) of the title compound. The ethyl acetate phase was concentrated and the residue was purified by preparative HPLC. This gave a further 151 g (19% of theory) of the title compound.
$^1$H-NMR (500 MHz, DMSO-d6): δ=1.45 (s, 9H), 5.27 (s, 2H), 7.56-7.61 (m, 1H), 7.61-7.64 (m, 1H), 8.17 (dd, 1H), 8.30-8.39 (m), 8.39-8.43 (m, 1H), 10.38 (s, 1H).

Intermediate 8-17

Ethyl [6-isopropoxy-5-({[6-(trifluoromethyl)pyridin-2-yl]carbonyl}amino)-2H-indazol-2-yl]acetate

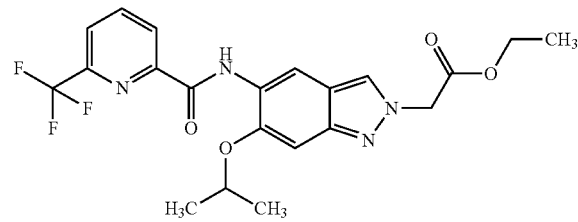 [SMILES: CCOC(=O)Cn1cc2cc(NC(=O)c3cccc(C(F)(F)F)n3)c(OC(C)C)cc2n1]

Analogously to Intermediate 8-1, 300 mg (1.08 mmol) of ethyl (5-amino-6-isopropoxy-2H-indazol-2-yl)acetate (Intermediate 7-5) were reacted with 227 mg (1.19 mmol) of 6-(trifluoromethyl)pyridine-2-carboxylic acid. This gave 487 mg (100% of theory) of the title compound.

UPLC-MS (Method A1): R$_t$=1.34 min

MS (ESIpos): m/z=451 (M+H)$^+$

1H-NMR (300 MHz, DMSO-d6): δ=1.23 (t, 3H), 1.41 (d, 6H), 4.18 (q, 2H), 4.79-4.92 (m, 1H), 5.32 (s, 2H), 7.18 (s, 1H), 8.22 (d, 1H), 8.33 (s, 1H), 8.37-8.50 (m, 2H), 8.75 (s, 1H), 10.75 (s, 1H).

Intermediate 8-18

Ethyl (6-isopropoxy-5-{[(6-methylpyridin-2-yl)carbonyl]amino}-2H-indazol-2-yl)acetate

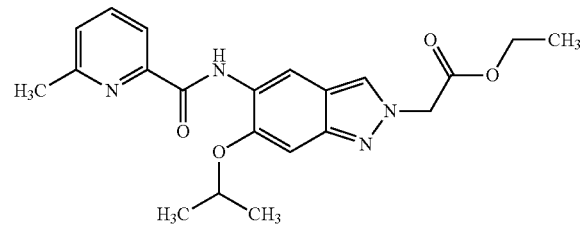 [SMILES: CCOC(=O)Cn1cc2cc(NC(=O)c3cccc(C)n3)c(OC(C)C)cc2n1]

Analogously to Intermediate 8-2, 0.3 g (1 mmol) of ethyl (5-amino-6-isopropoxy-2H-indazol-2-yl)acetate (Intermediate 7-5) were reacted with 137 mg (1.2 mmol) of 6-methylpyridine-2-carboxylic acid. This gave 380 mg (89% of theory) of the title compound.

UPLC-MS (Method A1): R$_t$=1.28 min

MS (ESIpos): m/z=397 (M+H)$^+$

1H-NMR (300 MHz, DMSO-d6): δ=1.22 (t, 3H), 1.45 (d, 6H), 2.62 (s, 3H), 4.18 (q, 2H), 4.78-4.89 (m, 1H), 5.31 (s, 2H), 7.15 (s, 1H), 7.52-7.60 (m, 1H), 7.95-8.01 (m, 2H), 8.29 (s, 1H), 8.72 (s, 1H), 10.99 (s, 1H).

Intermediate 8-19 tert-Butyl [6-(benzyloxy)-5-{[(6-methylpyridin-2-yl)carbonyl]amino}-2H-indazol-2-yl]acetate

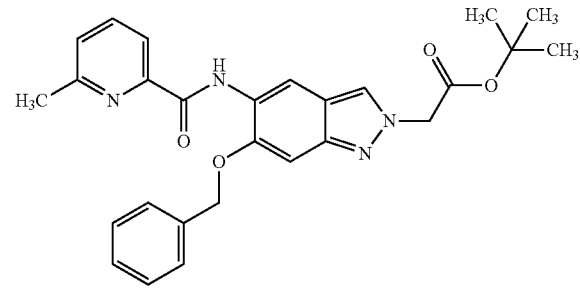 [SMILES: Cc1cccc(C(=O)Nc2cc3cn(CC(=O)OC(C)(C)C)nc3cc2OCc2ccccc2)n1]

Analogously to Intermediate 8-15, 1.00 g (2.79 mmol) of N-[6-(benzyloxy)-1H-indazol-5-yl]-6-methylpyridine-2-carboxamide (Intermediate 14-5) was dissolved in 20 ml of tetrahydrofuran and 1.64 ml (11.2 mmol) of tert-butyl bromoacetate and 2.39 ml (11.2 mmol) of N,N-dicyclohexylmethylamine were added at 25° C. After 3 h at 70° C., another 1.64 ml (11.2 mmol) of tert-butyl bromoacetate and 2.39 ml (11.2 mmol) of N,N-dicyclohexylmethylamine were added, and the mixture was stirred at 70° C. for a further 24 h. The solid in the reaction mixture was filtered off and washed twice with tetrahydrofuran. The regioisomerically pure crystals were dried in a vacuum drying cabinet at 50° C. for 3 h. This gave 971 mg (74% of theory) of product.

UPLC-MS (Method A1): R$_t$=1.47 min

MS (ESIpos): m/z=473 (M+H)$^+$

1H-NMR (500 MHz, DMSO-d6): δ=1.45 (s, 9H), 2.43 (s, 3H), 5.20 (s, 2H), 5.31 (s, 2H), 7.29 (s, 1H), 7.39-7.43 (m, 1H), 7.45-7.53 (m, 3H), 7.63-7.68 (m, 2H), 7.93-7.97 (m, 1H), 7.97-8.00 (m, 1H), 8.29 (d, 1H), 8.78 (s, 1H), 10.87 (s, 1H).

Intermediate 8-20

Methyl 3-[6-methoxy-5-({[6-(trifluoromethyl)pyridin-2-yl]carbonyl}amino)-2H-indazol-2-yl]-2-methylpropanoate

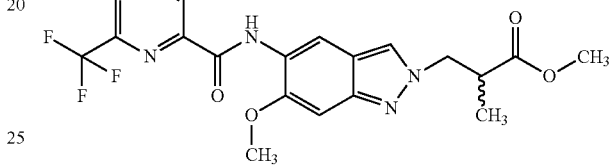

164 mg (1.19 mmol) of potassium carbonate and 83 μl (0.65 mmol) of methyl (2R)-3-bromo-2-methylpropanoate were added to 200 mg (0.60 mmol) of N-(6-methoxy-1H-indazol-5-yl)-6-(trifluoromethyl)pyridine-2-carboxamide (Intermediate 14-2) in 5 ml of acetonitrile, and then mixture was stirred at 85° C. for 24 h. The mixture was diluted with water and extracted with ethyl acetate and the extract was washed with saturated sodium chloride solution, filtered through a hydrophobic filter and concentrated. The crude product was dissolved in 2.0 ml of dimethyl sulphoxide and purified by preparative HPLC. The product fraction was lyophilized. This gave 25 mg (56% of theory) of the title compound.

UPLC-MS (Method A1): R$_t$=1.23 min

MS (ESIpos): m/z=437 (M+H)$^+$

1H-NMR (300 MHz, DMSO-d6): δ=1.08 (d, 3H), 3.13 (q, 1H), 3.55 (s, 3H), 4.04 (s, 3H), 4.48 (dd, 1H), 4.62 (dd, 1H), 7.40 (s, 1H), 8.02 (s, 1H), 8.17-8.26 (m, 1H), 8.40 (t, 1H), 8.47 (d, 1H), 8.71 (s, 1H), 10.42 (s, 1H).

Intermediate 8-21

Benzyl [5-({[6-(difluoromethyl)pyridin-2-yl]carbonyl}amino)-6-methoxy-2H-indazol-2-yl]acetate

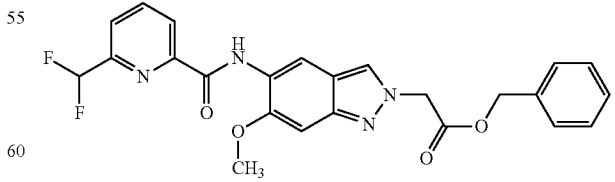

Analogously to Intermediate 8-6, 400 mg (1.29 mmol) of benzyl (5-amino-6-methoxy-2H-indazol-2-yl)acetate (Intermediate 7-6) were stirred with 245 mg (1.41 mmol) of 6-(difluoromethyl)pyridine-2-carboxylic acid (CAS No: 1256824-41-5), 197 mg (1.29 mmol) of 1-hydroxy-1H- benzotriazole hydrate and 493 mg (2.57 mmol) of 1-(3-dimethylaminopropyl)-3-ethylcarbodiimide hydrochloride and 537 µl (3.85 mmol) of triethylamine in 10 ml of tetrahydrofuran at 25° C. for 24 h. The reaction mixture was diluted with water and extracted three times with ethyl acetate. The combined organic phases were washed with saturated sodium chloride solution and concentrated. The crude product was taken up in diethyl ether and a little water and stirred for 30 minutes. The solid was filtered off with suction, washed three times with diethyl ether and dried in a drying cabinet. This gave 401 mg (48% of theory) of the title compound.

UPLC-MS (Method A1): $R_t$=1.29 min
MS (ESIpos): m/z=467 (M+H)$^+$.

Intermediate 8-22

Benzyl [5-({[6-(2-hydroxypropan-2-yl)pyridin-2-yl]carbonyl}amino)-6-methoxy-2H-indazol-2-yl]acetate

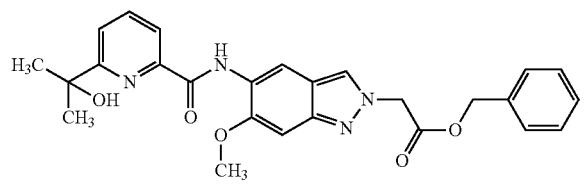 [SMILES: COc1cc2nn(CC(=O)OCc3ccccc3)cc2cc1NC(=O)c1cccc(C(C)(C)O)n1]

Analogously to Intermediate 8-6, 300 mg (0.96 mmol) of benzyl (5-amino-6-methoxy-2H-indazol-2-yl)acetate (Intermediate 7-6), 295 mg (1.16 mmol) of potassium 6-(2-hydroxypropan-2-yl)pyridine-2-carboxylate (Intermediate 19-11), 148 mg (0.96 mmol) of 1-hydroxy-1H-benzotriazole hydrate, 277 mg (1.45 mmol) of 1-(3-dimethylaminopropyl)-3-ethylcarbodiimide hydrochloride and 403 µl (2.89 mmol) of triethylamine in 10 ml of tetrahydrofuran were stirred at 25° C. for 24 h. The reaction mixture was diluted with water and extracted three times with ethyl acetate. The combined organic phases were washed with saturated sodium chloride solution and concentrated. The crude product was dissolved in 4 ml of dimethyl sulphoxide and purified by preparative HPLC according to Method P5 (gradient: 0-15 min 30-70% B; flow rate: 150 ml/min) The product fractions were lyophilized. This gave 209 mg (46% of theory) of the title compound.

UPLC-MS (Method A1): $R_t$=1.19 min
MS (ESIpos): m/z=475 (M+H)$^+$
$^1$H-NMR (300 MHz, DMSO-d6): δ 1.57 (s, 6H), 4.00 (s, 3H), 5.21 (s, 2H), 5.41 (s, 2H), 5.47 (s, 1H), 7.13 (s, 1H), 7.34-7.41 (m, 5H), 7.94 (dd, 1H), 7.99-8.12 (m, 2H), 8.33 (s, 1H), 8.69 (s, 1H), 10.94 (s, 1H).

Intermediate 8-23

Benzyl (6-methoxy-5-{[(6-methylpyridin-2-yl)carbonyl]amino}-2H-indazol-2-yl)acetate

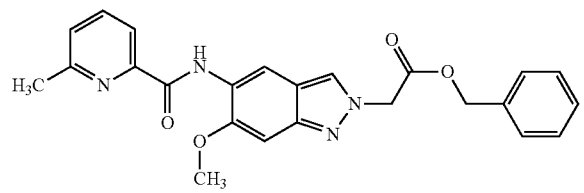 [SMILES: COc1cc2nn(CC(=O)OCc3ccccc3)cc2cc1NC(=O)c1cccc(C)n1]

7.57 g (19.0 mmol) of N-(6-methoxy-1H-indazol-5-yl)-6-methylpyridine-2-carboxamide (Intermediate 14-6) were stirred with 6.03 ml (38.1 mmol) of benzyl bromoacetate in 100 ml of tetrahydrofuran in the presence of 8.01 ml (38.1 mmol) of N,N-dicyclohexylmethylamine at 70° C. for 2.5 h and at 60° C. for 17 h. Another 3.02 ml (19.1 mmol) of benzyl bromoacetate and 4.01 ml (19.1 mmol) of N,N-dicyclohexylmethylamine were added and the mixture was stirred at 70° C. for a further 24 h. The solid was filtered off with suction and washed with ethyl acetate. The filtrate was filtered once more and washed twice with ethyl acetate and the solid was dried. Water was added to the filtrate, and after phase separation the aqueous phase was washed once more with ethyl acetate. The combined organic phases were washed with saturated sodium chloride solution, filtered through a hydrophobic filter and concentrated. Ethyl acetate was added to the crude product, and the mixture was stirred for 15 minutes. The solid was filtered off with suction, washed three times with ethyl acetate and dried in a drying cabinet. This gave a total of 6.02 g (63% of theory) of the title compound.

LC-MS (Method A3): $R_t$=1.25 min
MS (ESIpos): m/z=431 (M+H)$^+$
$^1$H-NMR (500 MHz, DMSO-d6): δ=2.63 (s, 3H), 4.01 (s, 3H), 5.21 (s, 2H), 5.40 (s, 2H), 7.11 (s, 1H), 7.34-7.40 (m, 5H), 7.55 (dd, 1H), 7.93-8.02 (m, 2H), 8.30-8.33 (m, 1H), 8.73 (s, 1H), 10.72 (s, 1H).

Intermediate 8-24 tert-Butyl [6-methoxy-5-({[2-(tetrahydro-2H-pyran-4-yl)-1,3-oxazol-4-yl]carbonyl}amino)-2H-indazol-2-yl]acetate

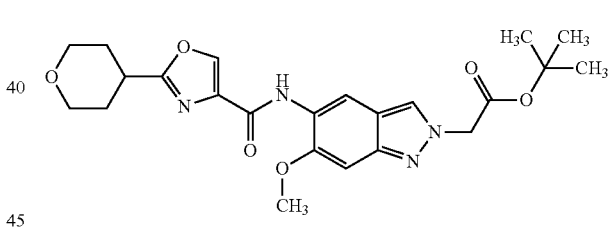

1.19 g (1.77 mmol) of N-(6-methoxy-1H-indazol-5-yl)-2-(tetrahydro-2H-pyran-4-yl)-1,3-oxazole-4-carboxamide (Intermediate 14-7) were stirred with 524 µl (3.55 mmol) of tert-butyl bromoacetate in 10 ml of tetrahydrofuran in the presence of 752 µl (3.55 mmol) of N,N-dicyclohexylmethylamine at 70° C. for 2.5 h and at 60° C. for 17 h. Another 1.51 ml (9.5 mmol) of tert-butyl bromoacetate and 2.00 ml (9.5 mmol) of N,N-dicyclohexylmethylamine were added and the mixture was stirred at 70° C. for a further 6 h. The solid was filtered off with suction and washed three times with ethyl acetate. Water was added to the filtrate, and after phase separation the aqueous phase was washed once more with ethyl acetate. The combined organic phases were washed with saturated sodium chloride solution, filtered through a hydrophobic filter and concentrated. Ethyl acetate was added to the crude product and the solid was filtered off with suction, washed three times with ethyl acetate and dried in a drying cabinet. This gave a total of 330 mg (41% of theory) of the title compound.

UPLC-MS (Method A1): $R_t$=1.23 min
MS (ESIpos): m/z=457 (M+H)$^+$

¹H-NMR (500 MHz, DMSO-d6): δ=1.44 (s, 9H), 1.72-1.86 (m, 2H), 1.91-2.02 (m, 2H), 3.17-3.27 (m, 1H), 3.48 (td, 2H), 3.92 (dt, 2H), 3.97 (s, 3H), 5.18 (s, 2H), 7.10 (s, 1H), 8.26 (d, 1H), 8.57 (s, 1H), 8.74 (s, 1H), 9.41 (s, 1H).

Intermediate 8-25 tert-Butyl (5-{[(6-bromopyridin-2-yl)carbonyl]amino}-6-methoxy-2H-indazol-2-yl)acetate

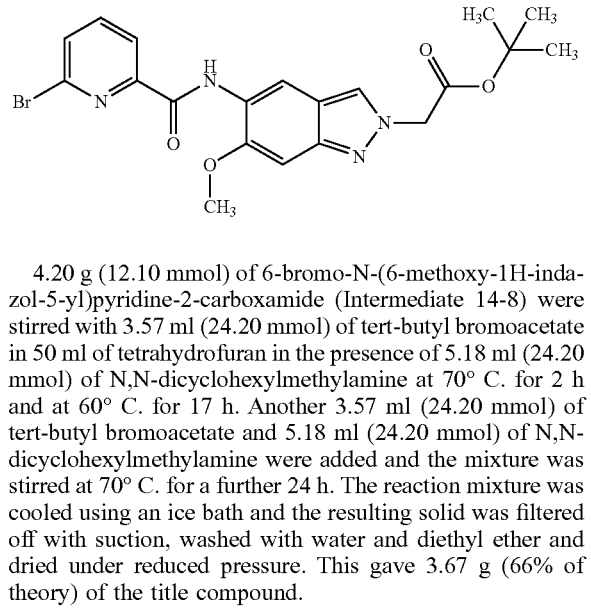

4.20 g (12.10 mmol) of 6-bromo-N-(6-methoxy-1H-indazol-5-yl)pyridine-2-carboxamide (Intermediate 14-8) were stirred with 3.57 ml (24.20 mmol) of tert-butyl bromoacetate in 50 ml of tetrahydrofuran in the presence of 5.18 ml (24.20 mmol) of N,N-dicyclohexylmethylamine at 70° C. for 2 h and at 60° C. for 17 h. Another 3.57 ml (24.20 mmol) of tert-butyl bromoacetate and 5.18 ml (24.20 mmol) of N,N-dicyclohexylmethylamine were added and the mixture was stirred at 70° C. for a further 24 h. The reaction mixture was cooled using an ice bath and the resulting solid was filtered off with suction, washed with water and diethyl ether and dried under reduced pressure. This gave 3.67 g (66% of theory) of the title compound.

UPLC-MS (Method A1): $R_t$=1.33 min

MS (ESIpos): m/z=461 (M+H)⁺

¹H-NMR (500 MHz, DMSO-d6): δ=1.44 (s, 9H) 4.00 (s, 3H) 5.20 (s, 2H) 7.14 (s, 1H) 7.90-8.10 (m, 2H) 8.20 (dd, 1H) 8.29 (s, 1H) 8.68 (s, 1H) 10.31 (s, 1H).

Intermediate 9-1

[6-Fluoro-5-({[6-(trifluoromethyl)pyridin-2-yl]carbonyl}amino)-2H-indazol-2-yl]acetic acid

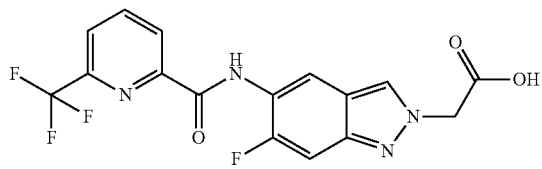 [SMILES: O=C(O)Cn1cc2cc(NC(=O)c3cccc(C(F)(F)F)n3)c(F)cc2n1]

381 mg (0.93 mmol) of ethyl [6-fluoro-5-({[6-(trifluoromethyl)pyridin-2-yl]carbonyl}amino)-2H-indazol-2-yl]acetate (Intermediate 8-1) were suspended in 9.2 ml of tetrahydrofuran and 0.45 ml of ethanol, and a solution of 222 mg (9.3 mmol) of lithium hydroxide in 2.3 ml of water was then added. The mixture was stirred at 25° C. for 30 min and then acidified to pH 2 with ice cooling using 2N hydrochloric acid. 10 ml of water were added and the precipitate was filtered off with suction. This gave 332 mg (93% of theory) of the title compound.

UPLC-MS (Method A1): $R_t$=1.04 min

MS (ESIpos): m/z=383 (M+H)⁺

1H-NMR (300 MHz, DMSO-d6): δ=5.30 (s, 2H), 7.55 (d, 1H), 8.22 (m, 1H), 8.34-8.54 (m, 4H), 10.26 (m, 1H), 13.30 (s br, 1H).

Intermediate 9-2

(6-Fluoro-5-{[(6-methylpyridin-2-yl)carbonyl]amino}-2H-indazol-2-yl)acetic acid

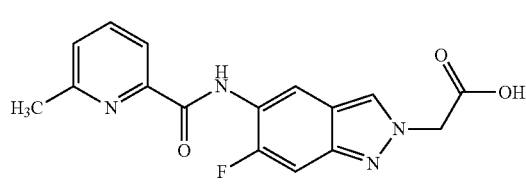 [SMILES: Cc1cccc(C(=O)Nc2cc3cn(CC(=O)O)nc3cc2F)n1]

Analogously to Intermediate 9-1, 316 mg (0.89 mmol) of ethyl (6-fluoro-5-{[(6-methylpyridin-2-yl)carbonyl]amino}-2H-indazol-2-yl)acetate (Intermediate 8-2) were reacted with 212 mg (8.87 mmol) of lithium hydroxide in 2.2 ml of water, 8.8 ml of tetrahydrofuran and 0.44 ml of ethanol. Work-up gave 302 mg of the title compound as a crude product.

UPLC-MS (Method A1): $R_t$=0.99 min

MS (ESIpos): m/z=329 (M+H)⁺

¹H NMR (400 MHz, DMSO-d6) δ=2.62 (s, 3H), 5.28 (s, 2H), 7.44-7.63 (m, 2H), 7.90-8.06 (m, 2H), 8.45 (s, 1H), 8.56 (d, 1H), 10.38 (d, J=1H).

Intermediate 9-3

[6-Fluoro-5-({[6-(1-methyl-1H-pyrazol-4-yl)pyridin-2-yl]carbonyl}amino)-2H-indazol-2-yl]acetic acid

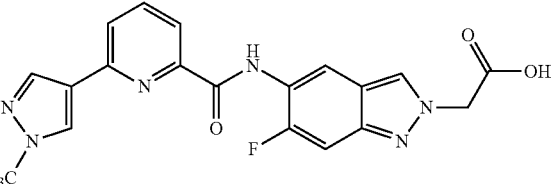

Analogously to Intermediate 9-1, 364 mg (0.86 mmol) of ethyl [6-fluoro-5-({[6-(1-methyl-1H-pyrazol-4-yl)pyridin-2-yl]carbonyl}amino)-2H-indazol-2-yl]acetate (Intermediate 8-3) were reacted with 206 mg (8.6 mmol) of lithium hydroxide in 2.1 ml of water, 8.5 ml of tetrahydrofuran and 0.42 ml of ethanol Work-up gave 302 mg (89% of theory) of the title compound as a crude product.

UPLC-MS (Method A1): $R_t$=0.87 min

MS (ESIpos): m/z=395 (M+H)⁺

¹H-NMR (300 MHz, DMSO-d6): δ=3.93 (s, 3H), 5.30 (s, 2H), 7.55 (d, 1H), 7.92 (t, 2H), 8.03 (t, 1H), 8.21 (s, 1H), 8.39 (d, 1H), 8.46 (s, 1H), 8.52 (s, 1H), 10.51 (s, 1H), 13.26 (s br, 1H).

Intermediate 9-4

[6-Fluoro-5-({[5-fluoro-6-(1-methyl-1H-pyrazol-4-yl)pyridin-2-yl]carbonyl}amino)-2H-indazol-2-yl]acetic acid

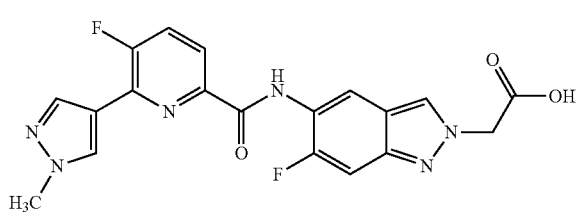 [SMILES: Cn1cc(-c2nc(C(=O)Nc3cc4cn(CC(=O)O)nc4cc3F)ccc2F)cn1]

Analogously to Intermediate 9-1, 326 mg (0.74 mmol) of ethyl [6-fluoro-5-({[5-fluoro-6-(1-methyl-1H-pyrazol-4-yl)pyridin-2-yl]carbonyl}amino)-2H-indazol-2-yl]acetate (Intermediate 8-4) were reacted with 177 mg (7.4 mmol) of lithium hydroxide in 1.8 ml of water, 7.3 ml of tetrahydrofuran and 0.36 ml of ethanol Work-up gave 305 mg (100% of theory) of the title compound as a crude product.

UPLC-MS (Method A1): $R_t$=0.95 min

MS (ESIpos): m/z=413 (M+H)$^+$ $^1$H-NMR (300 MHz, DMSO-d6): δ=3.96 (s, 3H), 5.30 (s, 2H), 7.54 (d, 1H), 7.98 (m, 2H), 8.27 (m, 2H), 8.46 (s, 1H), 8.53 (s, 1H), 10.42 (s, 1H), 13.29 (s br, 1H).

Intermediate 9-5

[6-Fluoro-5-({[6-(morpholin-4-yl)pyridin-2-yl]carbonyl}amino)-2H-indazol-2-yl]acetic acid

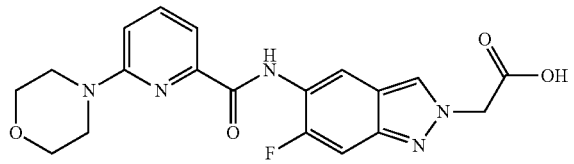 [SMILES: O=C(O)Cn1cc2cc(NC(=O)c3cccc(N4CCOCC4)n3)c(F)cc2n1]

Analogously to Intermediate 9-1, 436 mg (1.02 mmol) of ethyl [6-fluoro-5-({[6-(morpholin-4-yl)pyridin-2-yl]carbonyl}amino)-2H-indazol-2-yl]acetate (Intermediate 8-5) were reacted with 244 mg (10.2 mmol) of lithium hydroxide in 2.5 ml of water, 10 ml of tetrahydrofuran and 0.5 ml of ethanol. Work-up gave 295 mg (72% of theory) of the title compound as a crude product.

UPLC-MS (Method A1): $R_t$=0.95 min

MS (ESIpos): m/z=400 (M+H)$^+$ $^1$H-NMR (300 MHz, DMSO-d6): δ=3.59 (m, 4H), 3.75 (m, 4H), 5.26 (s, 2H), 7.15 (d, 1H), 7.42-7.59 (m, 2H), 7.82 (t, 1H), 8.40-8.51 (m, 2H), 10.28 (m, 1H).

Intermediate 9-6

[6-(Benzyloxy)-5-({[6-(trifluoromethyl)pyridin-2-yl]carbonyl}amino)-2H-indazol-2-yl]acetic acid

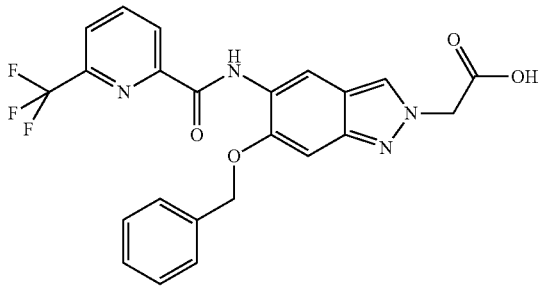 [SMILES: O=C(O)Cn1cc2cc(NC(=O)c3cccc(C(F)(F)F)n3)c(OCc3ccccc3)cc2n1]

Analogously to Intermediate 9-1, 75 mg (0.15 mmol) of ethyl [6-(benzyloxy)-5-({[6-(trifluoromethyl)pyridin-2-yl]carbonyl}amino)-2H-indazol-2-yl]acetate (Intermediate 8-6) were reacted with 18 mg (0.75 mmol) of lithium hydroxide in 271 μl of water and 2.5 ml of tetrahydrofuran. Work-up gave 59 mg (83% of theory) of the title compound.

UPLC-MS (Method A1): $R_t$=1.26 min

MS (ESIpos): m/z=471 (M+H)$^+$ $^1$H-NMR (400 MHz, DMSO-d6): δ=7.31 (s, 1H), 7.33-7.47 (m, 3H), 7.54-7.63 (m, 2H), 8.12-8.22 (m, 1H), 8.31 (s, 1H), 8.39 (s, 1H), 8.46-8.51 (m, 1H), 8.80 (s, 1H), 10.47 (s, 1H).

Intermediate 9-7

[6-Isobutoxy-5-({[6-(trifluoromethyl)pyridin-2-yl]carbonyl}amino)-2H-indazol-2-yl]acetic acid

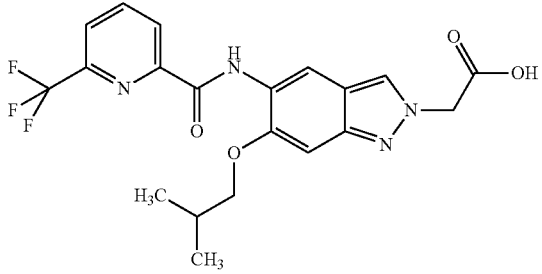 [SMILES: CC(C)COc1cc2nn(CC(=O)O)cc2cc1NC(=O)c1cccc(C(F)(F)F)n1]

Analogously to Intermediate 9-1, 200 mg (0.43 mmol) of ethyl [6-isobutoxy-5-({[6-(trifluoromethyl)pyridin-2-yl]carbonyl}amino)-2H-indazol-2-yl]acetate (Intermediate 8-8) were reacted with 51 mg (2.15 mmol) of lithium hydroxide in 776 μl of water and 10 ml of tetrahydrofuran. Work-up gave 64 mg (87% of theory) of the title compound.

UPLC-MS (Method A1): $R_t$=1.22 min

MS (ESIpos): m/z=437 (M+H)$^+$ $^1$H-NMR (300 MHz, DMSO-d6): δ=1.11 (s, 3H), 1.13 (s, 3H), 2.19 (dt, 1H), 3.96 (d, 2H), 5.21 (s, 2H), 7.09 (s, 1H), 8.22 (dd, 1H), 8.31 (s, 1H), 8.37-8.46 (m, 1H), 8.46-8.52 (m, 1H), 8.78 (s, 1H), 10.58 (s, 1H).

Intermediate 9-8

[6-(Cyclopropylmethoxy)-5-({[6-(trifluoromethyl)pyridin-2-yl]carbonyl}amino)-2H-indazol-2-yl]acetic acid

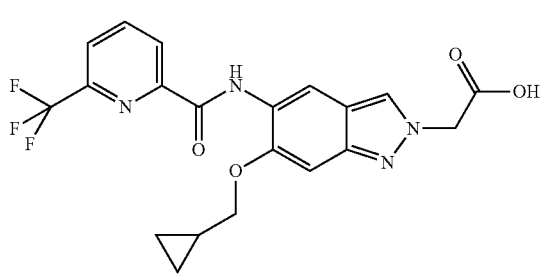 [SMILES: O=C(O)Cn1cc2cc(NC(=O)c3cccc(C(F)(F)F)n3)c(OCC3CC3)cc2n1]

Analogously to Intermediate 9-1, 220 mg (0.48 mmol) of ethyl [6-(cyclopropylmethoxy)-5-({[6-(trifluoromethyl)pyridin-2-yl]carbonyl}amino)-2H-indazol-2-yl]acetate (Intermediate 8-9) were reacted with 57 mg (2.38 mmol) of lithium hydroxide in 857 μl of water and 10 ml of tetrahydrofuran. Work-up gave 181 mg (88% of theory) of the title compound.

UPLC-MS (Method A1): $R_t$=1.21 min
MS (ESIpos): m/z=435 (M+H)$^+$
$^1$H NMR (400 MHz, DMSO-d6): δ=0.42-0.48 (m, 2H), 0.63-0.69 (m, 2H), 1.29-1.41 (m, 1H), 4.03 (d, 2H), 5.20 (s, 2H), 7.07 (s, 1H), 8.21 (dd, 1H), 8.29 (s, 1H), 8.37-8.44 (m, 1H), 8.46-8.50 (m, 1H), 8.76 (s, 1H), 10.71 (s, 1H).

Intermediate 9-9

[6-(Pyridin-2-ylmethoxy)-5-({[6-(trifluoromethyl)pyridin-2-yl]carbonyl}amino)-2H-indazol-2-yl]acetic acid

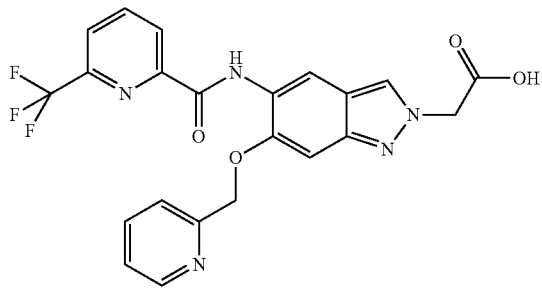 [SMILES: O=C(O)Cn1cc2cc(NC(=O)c3cccc(C(F)(F)F)n3)c(OCc3ccccn3)cc2n1]

Analogously to Intermediate 9-1, 160 mg (0.32 mmol) of ethyl [6-(pyridin-2-ylmethoxy)-5-({[6-(trifluoromethyl)pyridin-2-yl]carbonyl}amino)-2H-indazol-2-yl]acetate (Intermediate 8-10) were reacted with 38 mg (1.60 mmol) of lithium hydroxide in 577 μl of water and 6.7 ml of tetrahydrofuran. Work-up gave 129 mg (85% of theory) of the title compound.

UPLC-MS (Method A1): $R_t$=1.02 min
MS (ESIpos): m/z=472 (M+H)$^+$
$^1$H-NMR (300 MHz, DMSO-d6): δ=5.02 (s, 2H), 5.34 (s, 2H), 7.30 (s, 1H), 7.42 (dd, 1H), 7.70 (d, 1H), 7.80-7.92 (m, 1H), 8.18 (d, 1H), 8.27 (s, 1H), 8.39 (t, 1H), 8.44-8.53 (m, 1H), 8.62 (d, 1H), 8.80 (s, 1H), 10.49 (s, 1H).

Intermediate 9-10

[5-({[6-(1-Methyl-1H-pyrazol-4-yl)pyridin-2-yl]carbonyl}amino)-2H-indazol-2-yl]acetic acid

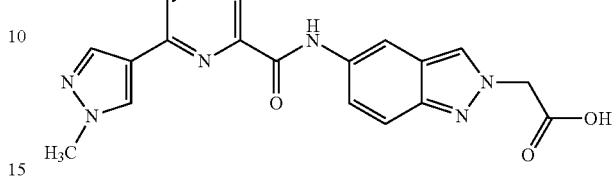

Analogously to Intermediate 9-1, 1.2 g (3.11 mmol) of ethyl [5-({[6-(1-methyl-1H-pyrazol-4-yl)pyridin-2-yl]carbonyl}amino)-2H-indazol-2-yl]acetate (Intermediate 8-11) (crude product) were initially charged in 10 ml of tetrahydrofuran, and 1.25 g (29.7 mmol) of lithium hydroxide monohydrate in 3 ml of water and 2 ml of ethanol were added. The mixture was stirred at 25° C. for 5 h. Water was added, followed by 10% strength citric acid down to a pH of 4. The mixture was extracted three times with ethyl acetate, and saturated sodium chloride solution was added to the aqueous phase. A solid precipitated from the aqueous phase; this solid was filtered off with suction, washed with water and ethyl acetate and dried. This gave 850 mg (54% of theory) of the title compound as a brown solid.

UPLC-MS (Method A1): $R_t$=0.82 min
MS (ESIpos): m/z=37 (M+H)+.
$^1$H-NMR (300 MHz, DMSO-d$_6$): δ=3.93 (s), 4.98 (s, 2H), 7.60 (s, 2H), 7.83-8.05 (m, 3H), 8.23-8.40 (m, 3H), 8.67 (s, 1H), 10.42 (s, 1H).

Intermediate 9-11

([6-Chloro-5-({[6-(trifluoromethyl)pyridin-2-yl]carbonyl}amino)-2H-indazol-2-yl]acetic acid

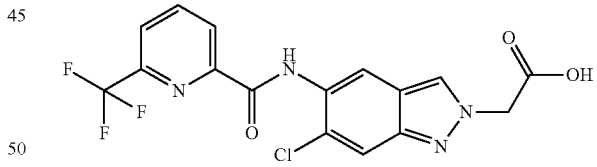

1.45 g (3.19 mmol) of tert-butyl [6-chloro-5-({[6-(trifluoromethyl)pyridin-2-yl]carbonyl}amino)-2H-indazol-2-yl]acetate (Intermediate 8-14) were dissolved in 15 ml of dichloromethane, and 2.46 ml (31.9 mmol) of trifluoroacetic acid were added at 25° C. The solution was stirred at 25° C. for 18 h. Water was added, the resulting precipitate was filtered off with suction, washed three times with water and twice with diethyl ether and the solid was dried under reduced pressure. This gave 1.28 g (98% of theory) of the title compound.

UPLC-MS (Method A1): $R_t$=1.11 min
MS (ESIpos): m/z=399 (M+H)$^+$
1H-NMR (400 MHz, DMSO-d6): δ=5.31 (s, 2H), 7.93 (s, 1H), 8.22 (dd, 1H), 8.37-8.50 (m, 3H), 8.64 (s, 1H), 10.52 (s, 1H), 13.28 (br. s., 1H).

Intermediate 9-12

[6-Methoxy-5-({[6-(trifluoromethyl)pyridin-2-yl]carbonyl}amino)-2H-indazol-2-yl]acetic acid

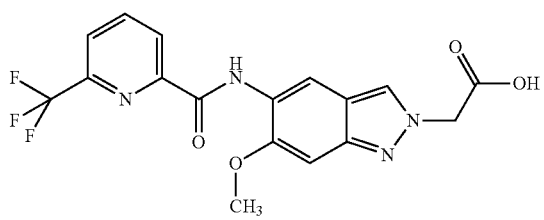 [SMILES: COc1cc2nn(CC(=O)O)cc2cc1NC(=O)c1cccc(C(F)(F)F)n1]

Analogously to Intermediate 9-11, 1.1 g (2.44 mmol) of tert-butyl [6-methoxy-5-({[6-(trifluoromethyl)pyridin-2-yl]carbonyl}amino)-2H-indazol-2-yl]acetate (Intermediate 8-15) were stirred with 3.76 ml (48.8 mmol) of trifluoroacetic acid in 20 ml of dichloromethane at 25° C. for 24 h. Work-up gave 1.20 g (96% of theory) of the title compound.

UPLC-MS (Method A1): $R_t$=1.09 min

MS (ESIpos): m/z=395 (M+H)$^+$ $^1$H-NMR (300 MHz, DMSO-d6): δ=3.99 (s, 3H), 5.22 (s, 2H), 7.14 (s, 1H), 8.22 (dd, 1H), 8.31 (s, 1H), 8.42 (d, 1H), 8.46 (s, 1H), 8.71 (s, 1H), 10.51 (s, 1H).

Intermediate 9-13

[6-Ethoxy-5-({[6-(trifluoromethyl)pyridin-2-yl]carbonyl}amino)-2H-indazol-2-yl]acetic acid

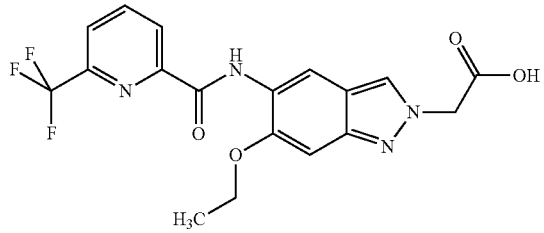 [SMILES: CCOc1cc2nn(CC(=O)O)cc2cc1NC(=O)c1cccc(C(F)(F)F)n1]

Analogously to Intermediate 9-1, 774 mg (1.77 mmol) of ethyl {[6-ethoxy-5-({[6-(trifluoromethyl)pyridin-2-yl]carbonyl}amino)-2H-indazol-2-yl]acetate (Intermediate 8-12) were initially charged in 1 ml of ethanol and 25 ml of tetrahydrofuran, a solution of 745 mg (17.74 mmol) of lithium hydroxide monohydrate dissolved in 5 ml of water was then added and the mixture was stirred at 25° C. for 3 days. Work-up gave 698 mg (94% of theory) of the title compound.

UPLC-MS (Method A1): $R_t$=1.13 min

MS (ESIpos): m/z=409 (M+H)$^+$ $^1$H-NMR (300 MHz, DMSO-d6): δ=1.49 (t, 3H), 4.20 (q, 2H), 5.17 (s, 2H), 7.09 (s, 1H), 8.21 (dd, 1H), 8.28 (s, 1H), 8.36-8.48 (m, 2H), 8.71 (s, 1H), 10.73 (s, 1H).

Intermediate 9-14

[5-({[6-(Trifluoromethyl)pyridin-2-yl]carbonyl}amino)-2H-indazol-2-yl]acetic acid

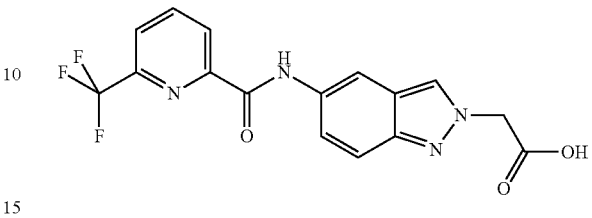

197 μl (2.57 mmol) of trifluoroacetic acid were added to a mixture of 216 mg (2.02 mmol) of tert-butyl [5-({[6-(trifluoromethyl)pyridin-2-yl]carbonyl}amino)-2H-indazol-2-yl]acetate (Intermediate 8-16) in 3 ml of dichloromethane. The mixture was stirred at 25° C. for 3 days, another 197 μl (2.57 mmol) of trifluoroacetic acid were added and the mixture was stirred at 25° C. Water was added to the reaction mixture. The mixture was stirred for 10 min and the solid was filtered off with suction, washed with water and dried. This gave 142 mg (76% of theory) of the title compound.

$^1$H-NMR (300 MHz, DMSO-d$_6$): δ=5.25 (s, 2H), 7.52-7.62 (m, 2H), 8.14 (dd, 1H), 8.26-8.41 (m, 4H), 10.37 (s, 1H).

Intermediate 9-15

3-[5-({[6-(Trifluormethyl)pyridin-2-yl]carbonyl}amino)-2H-indazol-2-yl]propanoic acid

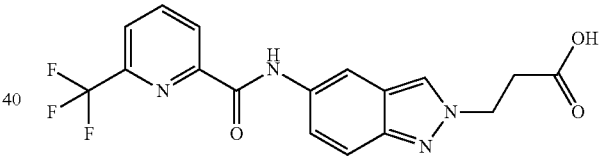

Analogously to Intermediate 9-1, 285 mg (0.70 mmol) of ethyl 3-[5-({[6-(trifluoromethyl)pyridin-2-yl]carbonyl}amino)-2H-indazol-2-yl]propanoate (Intermediate 8-13) were reacted with 168 mg (7.0 mmol) of lithium hydroxide. This gave 253 mg (95% of theory) of the title compound.

UPLC-MS (Method A1): $R_t$=0.99 min

MS (ESIpos): m/z=379 (M+H)$^+$.

Intermediate 9-16

[6-Isopropoxy-5-({[6-(trifluoromethyl)pyridin-2-yl]carbonyl}amino)-2H-indazol-2-yl]acetic acid

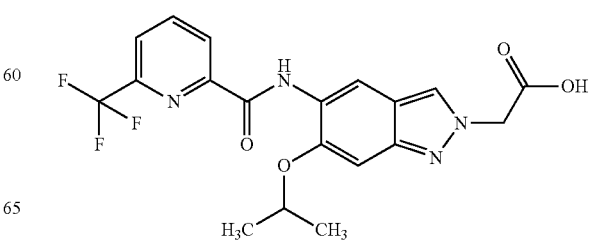

Analogously to Intermediate 9-1, 490 mg (1.1 mmol) of ethyl [6-isopropoxy-5-({[6-(trifluoromethyl)pyridin-2-yl]carbonyl}amino)-2H-indazol-2-yl]acetate (Intermediate 8-17) were reacted with 260 mg (11 mmol) of lithium hydroxide. This gave 367 mg (80% of theory) of the title compound.

UPLC-MS (Method A1): Rt=1.17 min
MS (ESIpos): m/z=423 (M+H)+
1H-NMR (300 MHz, DMSO-d6): δ=1.45 (d, 6H), 4.80-4.92 (m, 1H), 5.21 (s, 2H), 7.17 (s, 1H), 8.19-8.25 (m, 1H), 8.30 (s, 1H), 8.36-8.49 (m, 2H), 8.74 (s, 1H), 10.75 (s, 1H), 13.21 (s, 1H).

Intermediate 9-17

(6-Isopropoxy-5-{[(6-methylpyridin-2-yl)carbonyl]amino}-2H-indazol-2-yl)acetic acid

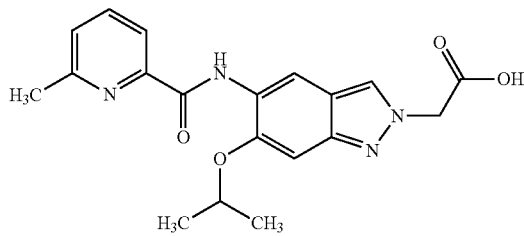 [SMILES: Cc1cccc(C(=O)Nc2cc3cn(CC(=O)O)nc3cc2OC(C)C)n1]

Analogously to Intermediate 9-1, 370 mg (0.93 mmol) of ethyl (6-isopropoxy-5-{[(6-methylpyridin-2-yl)carbonyl]amino}-2H-indazol-2-yl)acetate (Intermediate 8-18) were reacted with 223 mg (9.33 mmol) of lithium hydroxide. This gave 280 mg (81% of theory) of the title compound.

UPLC-MS (Method A1): Rt=1.11 min
MS (ESIpos): m/z=369 (M+H)+
1H-NMR (300 MHz, DMSO-d6): δ=1.45 (d, 6H), 2.62 (s, 3H), 4.78-4.89 (m, 1H), 5.19 (s, 2H), 7.14 (s, 1H), 7.52-7.60 (m, 1H), 7.93-8.02 (m, 2H), 8.27 (s, 1H), 8.72 (s, 1H), 10.99 (s, 1H), 13.19 (sbr, 1H).

Intermediate 9-18

[6-(Benzyloxy)-5-{[(6-methylpyridin-2-yl)carbonyl]amino}-2H-indazol-2-yl]acetic acid

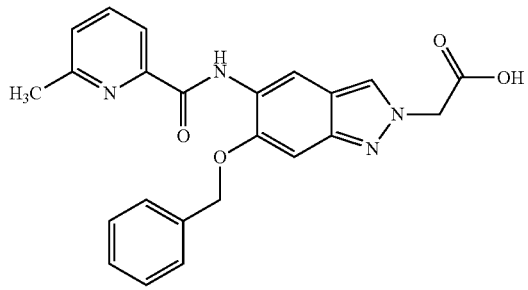 [SMILES: Cc1cccc(C(=O)Nc2cc3cn(CC(=O)O)nc3cc2OCc2ccccc2)n1]

Analogously to Intermediate 9-14, 100 mg (0.21 mmol) of tert-butyl [6-(benzyloxy)-5-{[(6-methylpyridin-2-yl)carbonyl]amino}-2H-indazol-2-yl]acetate (Intermediate 8-19) were dissolved in 6.7 ml of dichloromethane and stirred with 326 μl (4.23 mmol) of trifluoroacetic acid at 25° C. for 24 h. Work-up gave 67 mg (76% of theory) of the title compound.

UPLC-MS (Method A1): Rt=1.20 min
MS (ESIpos): m/z=417 (M+H)+
1H NMR (400 MHz, DMSO-d6): δ=2.43 (s, 3H), 5.22 (s, 2H), 5.31 (s, 2H), 7.29 (s, 1H), 7.42 (d, 1H), 7.44-7.54 (m, 3H), 7.65 (d, 2H), 7.91-8.02 (m, 2H), 8.30 (s, 1H), 8.78 (s, 1H), 10.87 (s, 1H).

Intermediate 9-19

(6-Methoxy-5-{[(6-methylpyridin-2-yl)carbonyl]amino}-2H-indazol-2-yl)acetic acid

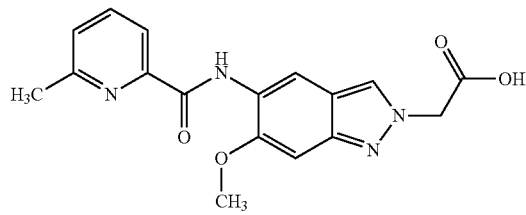 [SMILES: COc1cc2nn(CC(=O)O)cc2cc1NC(=O)c1cccc(C)n1]

Analogously to Intermediate 9-1, 2.28 g (3.92 mmol, 74%) of benzyl (6-methoxy-5-{[(6-methylpyridin-2-yl)carbonyl]amino}-2H-indazol-2-yl)acetate (Intermediate 8-23) were dissolved in 20 ml of tetrahydrofuran and 3.0 ml of methanol, a solution of 1.65 g (39.2 mmol) of lithium hydroxide monohydrate in 3.0 ml of water was then added. The mixture was diluted with water and acidified to pH 4 using 10% strength citric acid. The precipitated solid was filtered off, washed three times with water and three times with diethyl ether and dried under reduced pressure. This gave 2.43 g of the title compound as a crude product.

UPLC-MS (Method A1): Rt=1.00 min
MS (ESIpos): m/z=341 (M+H)+

Intermediate 9-20

[6-Methoxy-5-({[2-(tetrahydro-2H-pyran-4-yl)-1,3-oxazol-4-yl]carbonyl}amino)-2H-indazol-2-yl]acetic acid

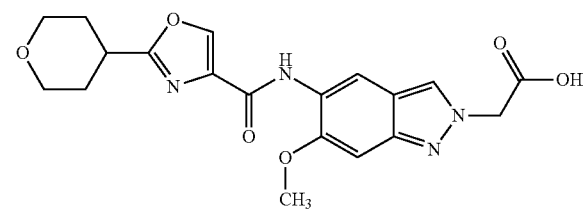 [SMILES: COc1cc2nn(CC(=O)O)cc2cc1NC(=O)c1coc(C2CCOCC2)n1]

Analogously to Intermediate 9-11, 325 mg (0.71 mmol) of tert-butyl [6-methoxy-5-({[2-(tetrahydro-2H-pyran-4-yl)-1,3-oxazol-4-yl]carbonyl}amino)-2H-indazol-2-yl]acetate (Intermediate 8-24) were dissolved in 5 ml of dichloromethane and stirred with 549 μl (7.12 mmol) of trifluoroacetic acid at 25° C. for 21 h. Another 275 μl (3.56 mmol) of trifluoroacetic acid were added and the mixture was stirred at 25° C. for a further 70 h. Water was added, the resulting precipitate was filtered off with suction, washed three times with water and three times with diethyl ether and the solid was dried under reduced pressure. This gave 313 mg of the title compound as a crude product.

UPLC-MS (Method A1): $R_t$=0.91 min
MS (ESIpos): m/z=401 (M+H)$^+$
$^1$H-NMR (300 MHz, DMSO-d6): δ=1.67-1.90 (m, 2H), 1.98 (d, 2H), 3.22 (ddd, 1H), 3.40-3.54 (m, 2H), 3.87-4.01 (m, 6H), 5.20 (s, 2H), 7.10 (s, 1H), 8.27 (s, 1H), 8.56 (s, 1H), 8.75 (s, 1H), 9.42 (s, 1H).

Intermediate 9-21

(5-{[(6-Bromopyridin-2-yl)carbonyl]amino}-6-methoxy-2H-indazol-2-yl)acetic acid

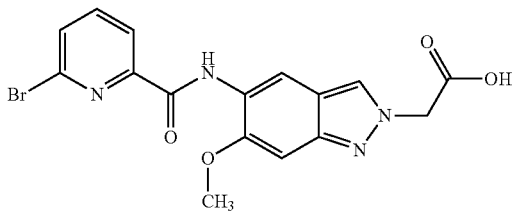 [SMILES: COc1cc2nn(CC(=O)O)cc2cc1NC(=O)c1cccc(Br)n1]

Analogously to Intermediate 9-11, 3.50 g (7.59 mmol) of tert-butyl (5-{[(6-bromopyridin-2-yl)carbonyl]amino}-6-methoxy-2H-indazol-2-yl)acetate (Intermediate 8-25) were dissolved in 100 ml of dichloromethane and stirred with 11.7 ml (15.54 mmol) of trifluoroacetic acid at 25° C. for 24 h. The reaction mixture was carefully added to saturated sodium bicarbonate solution and stirred briefly, and the resulting precipitate was filtered off with suction and dried at 50° C. in a vacuum drying cabinet. This gave 3.10 g of the title compound as a crude product.
UPLC-MS (Method A1): $R_t$=1.02 min
MS (ESIpos): m/z=405 (M+H)$^+$
$^1$H-NMR (300 MHz, DMSO-d6): δ=4.00 (s, 3H) 5.21 (s, 2H) 7.13 (s, 1H) 7.95 (dd, 1H) 8.04 (t, 1H) 8.20 (dd, 1H) 8.28-8.31 (m, 1H) 8.68 (s, 1H) 10.30 (s, 1H).

Intermediate 9-22

3-[6-Methoxy-5-({[6-(trifluoromethyl)pyridin-2-yl]carbonyl}amino)-2H-indazol-2-yl]-2-methylpropanoic acid

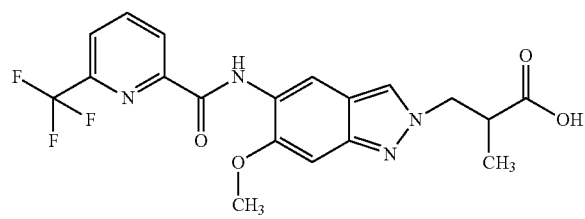 [SMILES: COc1cc2nn(CC(C)C(=O)O)cc2cc1NC(=O)c1cccc(C(F)(F)F)n1]

Analogously to Intermediate 4-1, 37 mg (0.09 mmol) of methyl 3-[6-methoxy-5-({[6-(trifluoromethyl)pyridin-2-yl]carbonyl}amino)-2H-indazol-2-yl]-2-methylpropanoate (Intermediate 8-20) were dissolved in 2 ml of tetrahydrofuran and 0.1 ml of methanol, a solution of 36 mg (0.85 mmol) of lithium hydroxide monohydrate in 0.1 ml of water was then added and the mixture was stirred at 25° C. for 23.5 h. The mixture was diluted with water, acidified to pH 4 using 10% strength citric acid and extracted three times with ethyl acetate. The combined organic phases were washed with saturated sodium chloride solution, filtered through a hydrophobic filter, concentrated and dried under reduced pressure. This gave 34 mg (94% of theory) of the title compound.
UPLC-MS (Method A1): $R_t$=1.13 min
MS (ESIpos): m/z=423 (M+H)$^+$
$^1$H-NMR (300 MHz, DMSO-d6): δ=1.04 (d, 3H), 3.00-3.13 (m, 2H), 3.98 (s, 3H), 4.37 (dd, 1H), 4.59 (dd, 1H), 7.15 (s, 1H), 8.22 (dd, 1H), 8.29 (s, 1H), 8.35-8.44 (m, 1H), 8.44-8.49 (m, 1H), 8.68 (s, 1H), 10.49 (s, 1H).

Intermediate 9-23

3-[6-Methoxy-5-({[6-(trifluoromethyl)pyridin-2-yl]carbonyl}amino)-2H-indazol-2-yl]-2-methylpropanoic acid

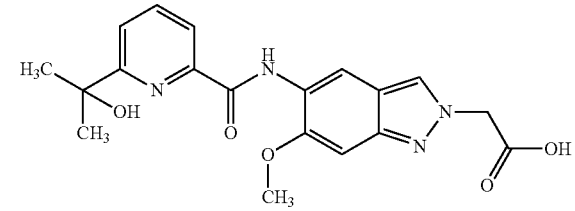 [SMILES: COc1cc2nn(CC(=O)O)cc2cc1NC(=O)c1cccc(C(C)(C)O)n1]

Analogously to Intermediate 4-1, 206 mg (0.43 mmol) of benzyl [5-({[6-(2-hydroxypropan-2-yl)pyridin-2-yl]carbonyl}amino)-6-methoxy-2H-indazol-2-yl]acetate (Intermediate 8-22) were suspended in 10 ml of tetrahydrofuran and 1.0 ml of methanol, a solution of 182 mg (4.33 mmol) of lithium hydroxide monohydrate in 1.5 ml of water was then added and the mixture was stirred at 25° C. for 24 h. The mixture was diluted with water, acidified to pH 4 using 10% strength citric acid and concentrated. The precipitated solid was filtered off, washed once with water and three times with diethyl ether and dried under reduced pressure. This gave 155 mg (93% of theory) of the title compound.
UPLC-MS (Method A1): $R_t$=1.20 min
MS (ESIpos): m/z=421 (M+H)$^+$
$^1$H NMR (400 MHz, DMSO-d6): δ=1.57 (s, 6H), 3.99 (s, 3H), 5.20 (s, 2H), 5.47 (s, 1H), 7.12 (s, 1H), 7.93 (dd, J=7.5, 1.3 Hz, 1H), 7.98-8.11 (m, 2H), 8.28 (s, 1H), 8.68 (s, 1H), 10.93 (s, 1H).

Intermediate 9-24

[5-({[6-(Difluoromethyl)pyridin-2-yl]carbonyl}amino)-6-methoxy-2H-indazol-2-yl]acetic acid

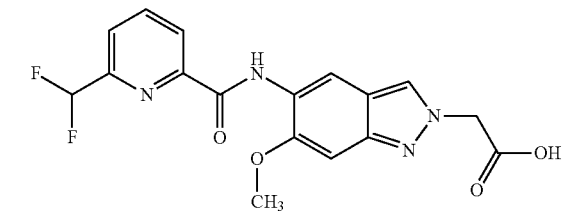 [SMILES: COc1cc2nn(CC(=O)O)cc2cc1NC(=O)c1cccc(C(F)F)n1]

Analogously to Intermediate 4-1, 613 mg of benzyl [5-({[6-(difluoromethyl)pyridin-2-yl]carbonyl}amino)-6-methoxy-2H-indazol-2-yl]acetate (Intermediate 8-21) were stirred at room temperature with 469 mg of lithium hydroxide monohydrate in 3 ml of water, 15 ml of THF and 1 ml of methanol for 3 h. This gave, after analogous work-up, 378 mg of the title compound.

UPLC-MS (Method A1): Rt=0.98 min, mass found (UV Detector TIC) 376.00.

Intermediate 10 and Intermediate 11 tert-Butyl 6-bromo-5-[(tert-butoxycarbonyl)amino]-1H-indazole-1-carboxylate and tert-butyl 6-bromo-5-[(tert-butoxycarbonyl)amino]-2H-indazol-2-carboxylate

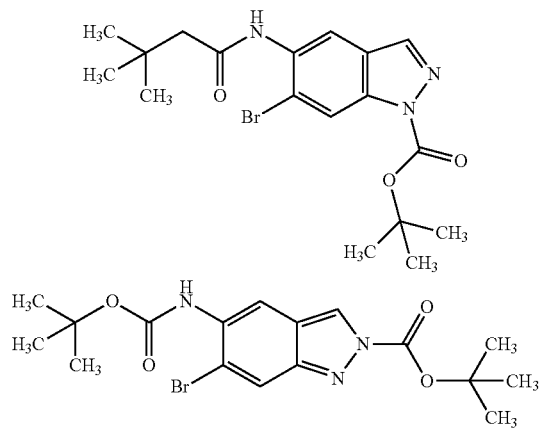

27.5 g (126.1 mmol) of di-tert-butyl dicarbonate were dissolved in 53.5 ml of tetrahydrofuran and cooled to 0° C. After addition of 5.35 g (25.2 mmol) of 6-bromo-1H-indazole-5-amine (CAS No: 1360928-41-1) at 0° C., the mixture was then stirred at 80° C. for 24 h. The reaction mixture was concentrated, dichloromethane was added and the reaction mixture was washed with 0.5 M hydrochloric acid and saturated sodium chloride solution, dried over sodium sulphate and, during concentration, adsorbed on Isolute® HM-N (Biotage). The Isolute was applied to a Biotage SNAP cartridge (340 g; KP-Sil) pre-equilibrated with hexane and chromatography was carried out using the Isolera® flash purification system (Biotage) (mobile phase: hexane/ethyl acetate; gradient: isocratic 80:20 (9 CV)). This gave 7.07 g (68% of theory) of the regioisomeric product mixture.

(Ratio: 1-isomer/2-isomer: 85%/15%)
UPLC-MS (Method A2): R$_t$=1.48 min
MS (ESIneg): m/z=410 (M($^{79}$Br)—H)$^+$ Intermediate 12-1 tert-Butyl 5-amino-6-chloro-1H-indazole-1-carboxylate

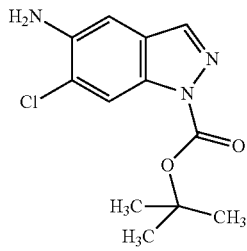 [SMILES: CC(C)(C)OC(=O)n1ncc2cc(N)c(Cl)cc21]

2.1 ml (11.8 mmol) of N,N-diisopropylethylamine and 2.34 g (10.7 mmol) of di-tert-butyl dicarbonate were added to 1.80 g (10.7 mmol) of 6-chloro-1H-indazole-5-amine (CAS No. 221681-75-0) in 18 ml of tetrahydrofuran, and the mixture was stirred at 25° C. for 18 h. The mixture was concentrated and the residue was taken up in ethyl acetate and, during concentration, adsorbed on Isolute. The Isolute was applied to a Biotage SNAP cartridge (100 g; KP-Sil) pre-equilibrated with hexane and chromatography was carried out using the Isolera® flash purification system (Biotage) (mobile phase: hexane/ethyl acetate; flow rate: 50 ml/min; gradient: isocratic 100:0 (5 min), 100:0→75:25 (20 min), isocratic 75:25 (5 min), 75:25→50:50 (15 min), isocratic 50:50 (5 min), 50:50→0:100 (15 min)) The combined product fractions were concentrated and dried under reduced pressure. This gave 1.23 g (43% of theory) of the title compound.

UPLC-MS (Method A1): R$_t$=1.16 min
MS (ESIpos): m/z=268 (M+H)$^+$

Intermediate 12-2 tert-Butyl 5-amino-6-chloro-2H-indazole-2-carboxylate

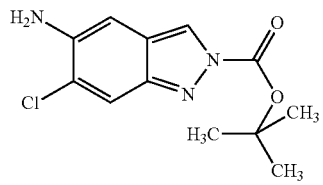

7.5 g of 6-chloro-1H-indazole-5-amine (CAS No. 221681-75-0) were converted analogously to the preparation of Intermediate 12-1. Purification by column-chromatographic purification on silica gel (hexane/ethyl acetate) gave 1.0 g of the title compound.

$^1$H-NMR (500 MHz, DMSO-d6): δ=1.62 (s, 9H), 5.33 (s, 2H), 6.79 (s, 1H), 7.74 (s, 1H), 8.50 (d, 1H).

Intermediate 13 tert-Butyl 6-chloro-5-({[6-(trifluoromethyl)pyridin-2-yl]carbonyl}amino)-1H-indazole-1-carboxylate

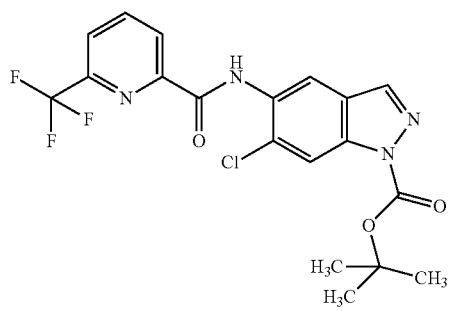 [SMILES: CC(C)(C)OC(=O)n1ncc2cc(NC(=O)c3cccc(C(F)(F)F)n3)c(Cl)cc21]

Analogously to Intermediate 5-1, 1.23 g (4.59 mmol) of tert-butyl 5-amino-6-chloro-1H-indazole-1-carboxylate (Intermediate 12-1) in 20 ml of N,N-dimethylformamide were stirred with 1.14 g (5.97 mmol) of 6-(trifluoromethyl)pyridine-2-carboxylic acid at 25° C. for 72 h. Water was added, the mixture was stirred for 15 min and the solid was filtered off with suction, washed three times with water and dried under reduced pressure. This gave 2.02 g (98% of theory) of the title compound.

UPLC-MS (Method A1): R$_t$=1.57 min
MS (ESIpos): m/z=441 (M+H)$^+$
$^1$H-NMR (300 MHz, DMSO-d6): δ=1.65 (s, 9H), 8.19-8.27 (m, 2H), 8.37-8.53 (m, 3H), 8.75 (s, 1H), 10.59 (s, 1H).

Intermediate 14-1

N-(6-Chloro-1H-indazol-5-yl)-6-(trifluoromethyl)pyridine-2-carboxamide

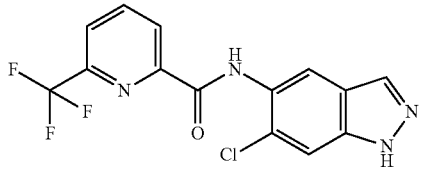 [SMILES: O=C(Nc1cc2cn[nH]c2cc1Cl)c1cccc(C(F)(F)F)n1]

Analogously to Intermediate 6-1, 6.7 ml (8.73 mmol) of trifluoroacetic acid were added to 3.85 g (8.73 mmol) of tert-butyl 6-chloro-5-({[6-(trifluoromethyl)pyridin-2-yl]carbonyl}amino)-1H-indazole-1-carboxylate (Intermediate 13) in 40 ml of dichloromethane, and the mixture was stirred at 25° C. for 18 h. Work-up gave 2.98 g (100% of theory) of the title compound.

UPLC-MS (Method A1): R$_t$=1.18 min
MS (ESIpos): m/z=341 (M+H)$^+$
$^1$H-NMR (300 MHz, DMSO-d6): δ=7.83 (s, 1H), 8.14-8.27 (m, 2H), 8.36-8.49 (m, 2H), 8.60 (s, 1H), 10.50 (br. s., 1H), 13.25 (br. s., 1H).

Intermediate 14-2

N-(6-Methoxy-1H-indazol-5-yl)-6-(trifluoromethyl)pyridine-2-carboxamide

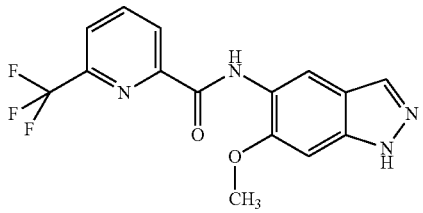 [SMILES: COc1cc2[nH]ncc2cc1NC(=O)c1cccc(C(F)(F)F)n1]

3.84 g (23.5 mmol) of 6-methoxy-1H-indazole-5-amine (CAS No.: 749223-61-8) and 4.95 g (25.9 mmol) of 6-(trifluoromethyl)pyridine-2-carboxylic acid were dissolved in 150 ml of tetrahydrofuran, and mit 3.60 g (23.5 mmol) of 1-hydroxy-1H-benzotriazole hydrate, 9.02 g (47.1 mmol) of 1-(3-dimethylaminopropyl)-3-ethylcarbodiimide hydrochloride and 9.84 ml (70.6 mmol) of triethylamine were added at 25° C. The solution was stirred at 25° C. for 24 h. After concentration of the solution, the residue was taken up in ethyl acetate, water was added and the aqueous phase was extracted three times with ethyl acetate. The combined organic phases were washed with saturated sodium chloride solution and dried over sodium sulphate and, after filtration, the solution was concentrated. The residue was taken up in dichloromethane, Isolute® HM-N (Biotage) was added and during concentration the residue was adsorbed on Isolute. The Isolute was applied to a Biotage SNAP cartridge (340 g; KP-Sil) pre-equilibrated with hexane and chromatography was carried out using the Isolera® flash purification system (Biotage) (mobile phase: hexane/ethyl acetate; gradient 100:0→50:50 (9 CV), isocratic 50:50 (4 CV)). The combined product fractions were concentrated and the beige solid was dried under reduced pressure. This gave 3.75 g (47% of theory) of the title compound.

UPLC-MS (Method A1): R$_t$=1.12 min
MS (ESIpos): m/z=337 (M+H)$^+$
$^1$H-NMR (400 MHz, DMSO-d6): δ=4.01 (s, 3H), 7.13 (s, 1H), 8.02 (s, 1H), 8.21 (dd, 1H), 8.40 (t, 1H), 8.47 (d, 1H), 8.74 (s, 1H), 10.42 (s, 1H), 12.91 (s, 1H).

Intermediate 14-3

N-(6-Ethoxy-1H-indazol-5-yl)-6-(trifluoromethyl)pyridine-2-carboxamide

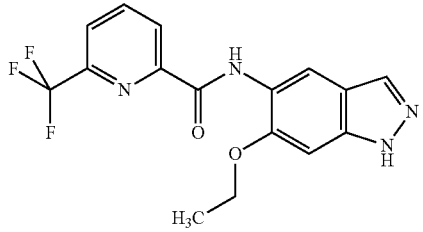 [SMILES: CCOc1cc2[nH]ncc2cc1NC(=O)c1cccc(C(F)(F)F)n1]

Analogously to Intermediate 5-1, 1.00 g (5.64 mmol) of 6-ethoxy-1H-indazole-5-amine and 1.29 g (6.77 mmol) of 6-(trifluoromethyl)pyridine-2-carboxylic acid were reacted in 50 ml of tetrahydrofuran at room temperature for 18 h. Work-up and purification by column chromatography using the Isolera® flash purification system (Biotage) (SNAP cartridge (100 g; KP-Sil), mobile phase: hexane/ethyl acetate; gradient: isocratic 100:0 (1 CV), 100:0→50:50 (10 CV), isocratic 50:50 (4.7 CV), 50:50→3:97 (9.4 CV)) gave 1.30 g (64% of theory) of the title compound.

UPLC-MS (Method A1): R$_t$=1.18 min
MS (ESIpos): m/z=351 (M+H)$^+$
$^1$H-NMR (500 MHz, DMSO-d6): δ=1.51 (t, 3H), 4.24 (q, 2H), 7.10 (s, 1H), 8.00 (s, 1H), 8.20 (dd, 1H), 8.39-8.43 (m, 1H), 8.46-8.48 (m, 1H), 8.79 (s, 1H), 10.67 (s, 1H), 12.87 (s, 1H).

Intermediate 14-4

N-(1H-Indazol-5-yl)-6-(trifluoromethyl)pyridine-2-carboxamide

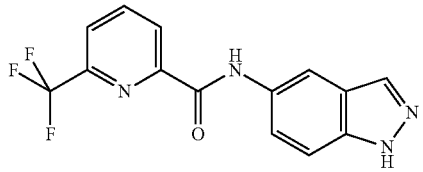 [SMILES: O=C(Nc1ccc2[nH]ncc2c1)c1cccc(C(F)(F)F)n1]

Analogously to Intermediate 5-1, 4.43 g (33.3 mmol) of 1H-indazole-5-amine (CAS No.: 19335-11-6) were reacted analogously with 7.00 g (36.6 mmol) of 6-(trifluoromethyl)pyridine-2-carboxylic acid. This gave, after purification by column chromatography on silica gel (hexane/ethyl acetate), 7.8 g (73% of theory) of the title compound.

$^1$H-NMR (300 MHz, DMSO-d$_6$): δ=7.51 (d, 1H), 7.68 (dd, 1H), 8.05 (s, 1H), 8.14 (dd, 1H), 8.25-8.41 (m, 3H), 10.42 (s, 1H), 13.04 (br. s., 1H).

Intermediate 14-5

N-[6-(Benzyloxy)-1H-indazol-5-yl]-6-methylpyridine-2-carboxamide

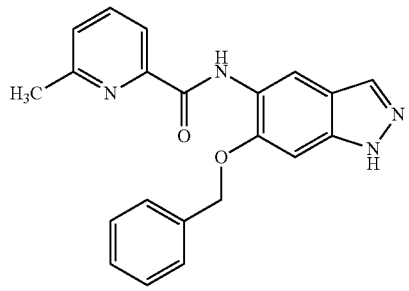 [SMILES: Cc1cccc(C(=O)Nc2cc3cn[nH]c3cc2OCc2ccccc2)n1]

Analogously to Intermediate 14-2, 1.00 g (4.18 mmol) of 6-(benzyloxy)-1H-indazole-5-amine (Intermediate 1-3) and 688 mg (5.02 mmol) of 6-methylpyridine-2-carboxylic acid were dissolved in 50 ml of tetrahydrofuran and stirred with 640 mg (4.18 mmol) of 1-hydroxy-1H-benzotriazole hydrate, 1.60 g (8.36 mmol) of 1-(3-dimethylaminopropyl)-3-ethylcarbodiimide hydrochloride and 1.75 ml (12.54 mmol) of triethylamin at 25° C. for 24 h. After concentration of the solution, water was added to the precipitate formed and the precipitate was filtered off with suction, washed with water and diethyl ether and dried under reduced pressure. This gave 1.13 g (76% of theory) of the title compound.

UPLC-MS (Method A1): R$_t$=1.26 min
MS (ESIpos): m/z=359 (M+H)$^+$ $^1$H-NMR (300 MHz, DMSO-d6): δ=2.43 (s, 3H), 5.34 (s, 2H), 7.29 (s, 1H), 7.35-7.57 (m, 4H), 7.65 (d, 2H), 7.86-8.07 (m, 3H), 8.84 (s, 1H), 10.82 (s, 1H), 12.95 (s, 1H).

Intermediate 14-6

N-(6-Methoxy-1H-indazol-5-yl)-6-methylpyridine-2-carboxamide

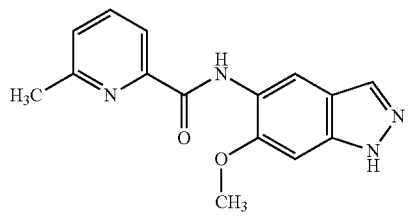 [SMILES: COc1cc2[nH]ncc2cc1NC(=O)c1cccc(C)n1]

Analogously to Intermediate 14-2, 5.00 g (30.64 mmol) of 6-methoxy-1H-indazole-5-amine (CAS No. 749223-61-8) and 4.62 g (33.70 mmol) of 6-methylpyridine-2-carboxylic acid were dissolved in 100 ml of tetrahydrofuran and stirred with 4.69 g (30.64 mmol) of 1-hydroxy-1H-benzotriazole hydrate, 11.74 g (61.28 mmol) of 1-(3-dimethylaminopropyl)-3-ethylcarbodiimide hydrochloride and 21.35 ml (153.2 mmol) of triethylamine at 25° C. for 20 h. Water was added, and the reaction mixture was concentrated. The resulting precipitate was filtered off with suction, washed three times with water and three times with diethyl ether and dried in a drying cabinet. This gave 7.89 g (65% of theory) of the title compound.

UPLC-MS (Method A1): R$_t$=0.49 min
MS (ESIpos): m/z=283 (M+H)$^+$

Intermediate 14-7

N-(6-Methoxy-1H-indazol-5-yl)-2-(tetrahydro-2H-pyran-4-yl)-1,3-oxazole-4-carboxamide

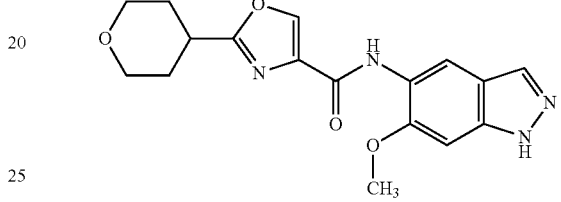

Analogously to Intermediate 14-2, 782 mg (4.80 mmol) of 6-methoxy-1H-indazole-5-amine (CAS No. 749223-61-8) and 1.04 g (5.27 mmol) of 2-(tetrahydro-2H-pyran-4-yl)-1,3-oxazole-4-carboxylic acid (CAS No. 955401-82-8) were dissolved in 15 ml of tetrahydrofuran and stirred with 734 mg (4.80 mmol) of 1-hydroxy-1H-benzotriazole hydrate, 1.84 g (9.59 mmol) of 1-(3-dimethylaminopropyl)-3-ethylcarbodiimide hydrochloride and 3.34 ml (24.0 mmol) of triethylamine at 25° C. for 26 h. Water was added, and the reaction mixture was concentrated. The resulting precipitate was filtered off with suction, washed three times with water and three times with diethyl ether and dried in a drying cabinet. This gave 1.19 g (37% of theory) of the title compound.

UPLC-MS (Method A1): R$_t$=0.94 min
MS (ESIpos): m/z=343 (M+H)$^+$

Intermediate 14-8

6-Bromo-N-(6-methoxy-1H-indazol-5-yl)pyridine-2-carboxamide

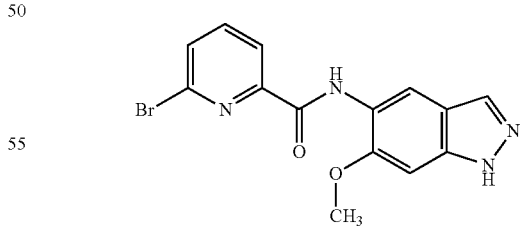

2.0 g (12.26 mmol) of 6-methoxy-1H-indazole-5-amine (CAS No. 749223-61-8) were dissolved in 50 ml of tetrahydrofuran, 4.72 g (14.71 mmol) of 0-(benzotriazol-1-yl)-N,N,N',N'-tetramethyluronium tetrafluoroborate and 2.56 ml (14.71 mmol) of N,N-diisopropylethylamine were added and the mixture was stirred at 25° C. for 30 minutes. 2.56 ml (14.71 mmol) of 6-bromopyridine-2-carboxylic acid (CAS No. 21190-87-4) were added, and the mixture was stirred at 25° C. for a further 24 h. The reaction mixture was concentrated and the residue was added to 400 ml of water. The resulting precipitate was filtered off with suction, washed twice with water and twice with diethyl ether and dried at 50° C. in a vacuum drying cabinet for 4 h. This gave 4.18 g (98% of theory) of the title compound.

UPLC-MS (Method A1): $R_t$=0.93 min

MS (ESIpos): m/z=347 (M+H)$^+$ $^1$H-NMR (300 MHz, DMSO-d6): δ=4.02 (s, 3H) 7.13 (s, 1H) 7.89-8.10 (m, 3H) 8.20 (dd, 1H) 8.71 (s, 1H) 10.22 (s, 1H) 12.90 (br. s., 1H).

Intermediate 14-9

Methyl 5-({[6-(trifluoromethyl)pyridin-2-yl]carbonyl}amino)-1H-indazole-6-carboxylate

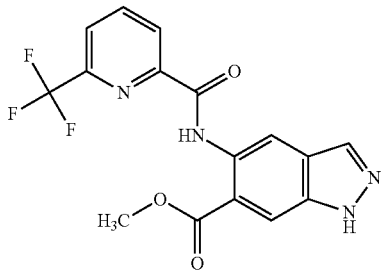 [SMILES: COC(=O)c1cc2[nH]ncc2cc1NC(=O)c1cccc(C(F)(F)F)n1]

4.5 g (23.53 mmol) of methyl 5-amino-1H-indazole-6-carboxylate (Intermediate 1-6) were dissolved in 45 ml of tetrahydrofuran, 9.07 g (28.24 mmol) of O-(benzotriazol-1-yl)-N,N,N',N'-tetramethyluronium tetrafluoroborate and 4.92 ml (28.24 mmol) of N,N-diisopropylethylamine were added and the mixture was stirred at 25° C. for 30 minutes. 4.95 g (25.89 mmol) of 6-(trifluoromethyl)pyridine-2-carboxylic acid (CAS No. 21190-87-4) were added, and the mixture was stirred at 25° C. for a further 24 h. The reaction mixture was filtered off with suction through a membrane filter, washed with tetrahydrofuran and water and dried at 50° C. in a vacuum drying cabinet for 24 h. The filtrate was concentrated with acetonitrile and the resulting precipitate was filtered off with suction, washed and dried. This gave 8.60 g (84% of theory) of the title compound.

UPLC-MS (Method A1): $R_t$=1.21 min

MS (ESIpos): m/z=365 (M+H)$^+$ $^1$H-NMR (300 MHz, DMSO-d6): δ=3.97 (s, 3H), 8.13-8.27 (m, 2H), 8.30 (s, 1H), 8.33-8.45 (m, 1H), 8.45-8.51 (m, 1H), 9.15 (s, 1H), 12.57 (s, 1H), 13.44 (s, 1H).

Intermediate 14-10

Methyl 5-{[(6-methylpyridin-2-yl)carbonyl]amino}-1H-indazole-6-carboxylate

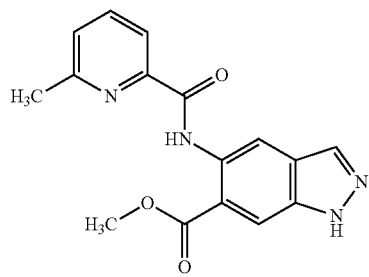 [SMILES: COC(=O)c1cc2[nH]ncc2cc1NC(=O)c1cccc(C)n1]

500 mg (2.62 mmol) of methyl 5-amino-1H-indazole-6-carboxylate (Intermediate 1-6) were dissolved in 5 ml of tetrahydrofuran, 1.01 g (3.14 mmol) of O-(benzotriazol-1-yl)-N,N,N',N'-tetramethyluronium tetrafluoroborate and 547 µl (3.14 mmol) of N,N-diisopropylethylamine were added and the mixture was stirred at 25° C. for 30 minutes. 395 mg (2.88 mmol) of 6-methylpyridine-2-carboxylic acid (CAS No. 21190-87-4) were added, and the mixture was stirred at 25° C. for a further 8 h. The reaction mixture was added to water and stirred vigorously for 10 minutes and the precipitate was filtered off with suction through a nylon filter. The precipitate was washed twice with water and twice with diethyl ether. The solid was dried in a vacuum drying cabinet at 50° C. for 3 h. This gave 790 mg (92% of theory) of the title compound.

UPLC-MS (Method A1): $R_t$=1.05 min

MS (ESIpos): m/z=311 (M+H)$^+$ $^1$H-NMR (300 MHz, DMSO-d6): δ=2.65 (s, 3H), 4.00 (s, 3H), 7.55 (dd, 1H), 7.91-7.99 (m, 1H), 7.99-8.04 (m, 1H), 8.23 (s, 1H), 8.29 (s, 1H), 9.18 (s, 1H), 12.65 (s, 1H), 13.41 (s, 1H).

Intermediate 14-11

N-[6-(2-Hydroxypropan-2-yl)-1H-indazol-5-yl]-6-(trifluoromethyl)pyridine-2-carboxamide

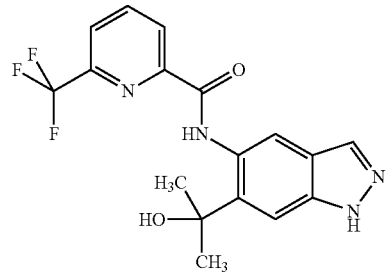 [SMILES: CC(C)(O)c1cc2[nH]ncc2cc1NC(=O)c1cccc(C(F)(F)F)n1]

6.9 ml (5 equiv.) of a 3M methylmagnesium bromide solution in diethyl ether were added carefully to an ice-cold solution of 1.50 g (4.12 mmol) of methyl 5-({[6-(trifluoromethyl)pyridin-2-yl]carbonyl}amino)-1H-indazole-6-carboxylate (Intermediate 14-9) in 20 ml of THF. The mixture was stirred with ice bath cooling for 1 h and at room temperature for 19.5 h. Another 2 equiv. of methylmagnesium bromide solution were added and the mixture was stirred at room temperature for a further 24 h. Saturated aqueous ammonium chloride solution was added and the mixture was stirred and extracted three times with ethyl acetate. The combined organic phases were washed with sodium chloride solution, filtered through a hydrophobic filter and concentrated. The residue was purified by column chromatography on silica gel (hexane/ethyl acetate gradient). This gave 763 mg (45% of theory) of the title compound.

$^1$H-NMR (400 MHz, DMSO-d$_6$): δ [ppm]=1.63 (s, 6H), 5.99 (s, 1H), 7.49 (s, 1H), 8.06 (s, 1H), 8.14-8.19 (m, 1H), 8.37 (t, 1H), 8.46 (d, 1H), 8.78 (s, 1H), 12.32 (s, 1H), 12.97 (s, 1H).

Intermediate 16-1

6-Bromo-N-isobutylpyridine-2-amine

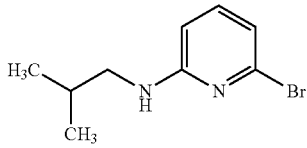

In a pressure reactor, 1.0 g of 2,6-dibromopyridine and 340 mg of 2-methylpropane-1-amine and 1.43 ml of 2,2,6,6-tetramethylpiperidine were stirred at 190° C. for 16 h. The mixture was poured into saturated sodium bicarbonate solution, extracted with dichloromethane, washed with saturated sodium chloride solution, dried over sodium sulphate and concentrated. The residue was purified by column chromatography on silica gel. This gave 920 mg of the title compound.

$^1$H-NMR (300 MHz, CHLOROFORM-d): δ=[ppm]=1.00 (d, 6H), 1.81-1.98 (m, 1H), 3.05 (t, 2H), 4.76 (br. s., 1H), 6.29 (d, 1H), 6.72 (d, 1H), 7.22-7.35 (m, 2H).

Intermediate 17-1

Methyl 6-(1-hydroxyethyl)pyridine-2-carboxylate

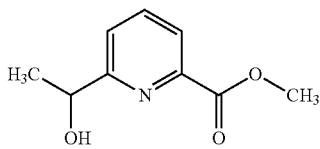

2.00 g of 1-(6-bromopyridin-2-yl)ethanol (Telfer, Shane G.; Kuroda, Reiko, *Chemistry A European Journal*, 2005, 11, 57-68) were suspended in 20 ml of methanol and 30 ml of dimethyl sulphoxide. 265 mg of 1,3-bis(diphenylphoshino)propane, 140 mg of palladium(II) acetate and 3.2 ml of triethylamine were added, the mixture was flushed three times with carbon monoxide and stirred in a carbon monoxide atmosphere (12 bar 0.5 h, then at 16 bar overnight). Water was added, the mixture was extracted with ethyl acetate and the extract was concentrated. This gave 1.7 g of methyl 6-(1-hydroxyethyl)pyridine-2-carboxylate as an oil (crude product).

$^1$H-NMR (400 MHz, CHLOROFORM-d): δ=1.57 (d, 3H), 4.02 (s, 3H), 5.03 (q, 1H), 7.56 (d, 1H), 7.88 (t, 1H), 8.05 (d, 1H).

Intermediate 17-2

Methyl 6-(2,2,2-trifluoro-1-hydroxyethyl)pyridine-2-carboxylate

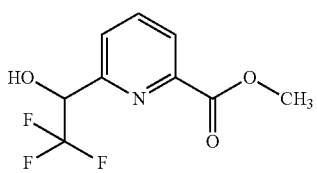 [SMILES: COC(=O)c1cccc(C(O)C(F)(F)F)n1]

1.04 g (4.06 mmol) of 1-(6-bromopyridin-2-yl)-2,2,2-trifluoroethanol (CAS 1093880-21-7) were reacted analogously to Intermediate 17-1 in a carbon monoxide atmosphere. After analogous work-up, the crude product was purified by preparative HPLC. This gave 696 mg of the title compound.

$^1$H-NMR (300 MHz, DMSO-d$_6$): δ=3.89 (s, 3H), 5.15-5.28 (m, 1H), 7.18-7.25 (m, 1H), 7.86 (dd, 1H), 8.05-8.14 (m, 2H).

Intermediate 17-3

Methyl 6-(2-hydroxypropan-2-yl)pyridine-2-carboxylate

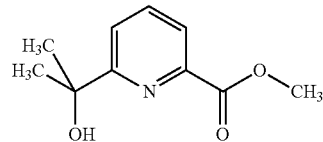

1.00 g of 2-(6-bromopyridin-2-yl)propan-2-ol was reacted analogously to Intermediate 17-1 in a carbon monoxide atmosphere. After analogous work-up, the crude product was purified by preparative HPLC. This gave 540 mg of the title compound.

$^1$H-NMR (400 MHz, DMSO-d$_6$): δ [ppm]=1.44 (s, 6H), 3.86 (s, 3H), 5.34 (s, 1H), 7.86-7.99 (m, 3H).

Intermediate 17-4

Methyl 6-{[1-(tert-butoxycarbonyl)azetidin-3-yl]amino}pyridine-2-carboxylate

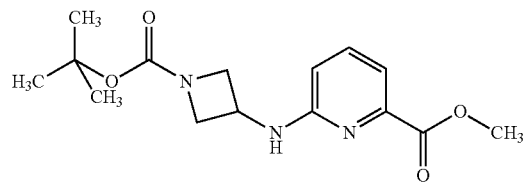 [SMILES: COC(=O)c1cccc(NC2CN(C(=O)OC(C)(C)C)C2)n1]

A mixture of 250 mg of methyl 6-fluoropyridine-2-carboxylate, 361 mg of tert-butyl 3-aminoazetidine-1-carboxylate (1.3 equivalents) and 0.84 ml of N-ethyl-N-isopropylpropane-2-amine in 3.0 ml of 1-methylpyrrolidin-2-one was stirred at 80° C. Another 0.5 equivalent of tert-butyl 3-aminoazetidine-1-carboxylate was added and the mixture was stirred at 100° C. overnight. Another 0.5 equivalent of tert-butyl 3-aminoazetidine-1-carboxylate was added and the mixture was stirred at room temperature for 3 days. Water was added, the mixture was extracted with ethyl acetate, the organic phases were concentrated and the residue was purified by preparative HPLC. This gave 230 mg of the title compound.

UPLC-MS (Method A1): Rt=1.07 min (UV detector TIC), mass found 307.15.

Intermediate 17-5

Methyl 6-({[1-(tert-butoxycarbonyl)azetidin-2-yl]methyl}amino)pyridine-2-carboxylate

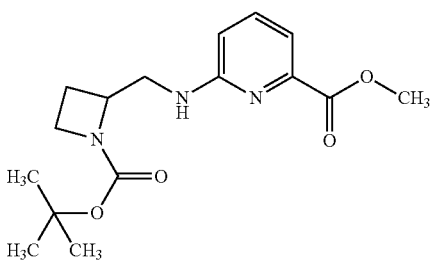 [SMILES: COC(=O)c1cccc(NCC2CCN2C(=O)OC(C)(C)C)n1]

A mixture of 500 mg of methyl 6-fluoropyridine-2-carboxylate, 720 mg of tert-butyl 2-(aminomethyl)azetidine-1-carboxylate and 2.2 ml of N-ethyl-N-isopropylpropane-2-amine in 7.5 ml of 1-methylpyrrolidin-2-one was stirred at 100° C. for 30 min, at 120° C. for 4 h and at 140° C. for 3 h. The mixture was concentrated and the product was purified by preparative HPLC (column: Reprospher C18-DE 5 μm 125×30 mm, solvent system: A=water+0.1% by volume of formic acid (99%), B=acetonitrile, gradient 0-5.5 min 40-80% B). This gave 230 mg of the title compound as a crude product. Mass found (UV detector TIC) 321.17.

Intermediate 17-6

Methyl 6-[(2R,6S)-2,6-dimethylmorpholin-4-yl]pyridine-2-carboxylate

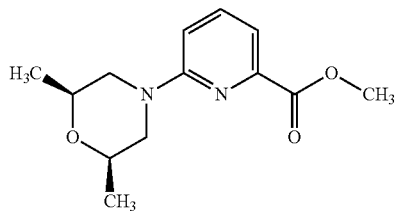

300 mg of methyl 6-fluoropyridine-2-carboxylate were reacted analogously with 334 mg of (2R,6S)-2,6-dimethylmorpholine analogously to Intermediate 17-4 at 80° C. overnight. Another 0.5 equivalent of (2R,6S)-2,6-dimethylmorpholine was added and the mixture was stirred at 100° C. for 7 h. Aqueous work-up gave 875 mg of a crude product which still contained 1-methylpyrrolidin-2-one. UPLC-MS (Method A1): Rt=1.05 min (UV detector TIC), mass found 250.00.

Intermediate 17-7

Methyl 6-(isobutylamino)pyridine-2-carboxylate

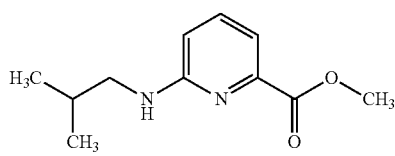

900 mg of 6-bromo-N-isobutylpyridine-2-amine (Intermediate 16-1) were reacted analogously to Intermediate 17-1 in a carbon monoxide atmosphere. The crude product was purified by column chromatographic purification on silica gel. This gave 796 mg of the title compound.

$^1$H-NMR (300 MHz, CHLOROFORM-d): d [ppm]=1.02 (d, 3H), 1.83-1.98 (m, 1H), 3.08 (t, 2H), 3.97 (s, 3H), 4.97 (br. s., 1H), 6.58 (d, 1H), 7.42 (d, 1H), 7.58 (t, 1H).

Intermediate 19-1

Potassium 6-(1-hydroxyethyl)pyridine-2-carboxylate

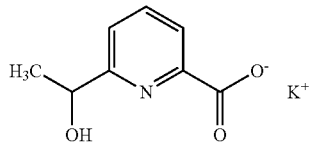

541 mg of methyl 6-(1-hydroxyethyl)pyridine-2-carboxylate (Intermediate 17-1, crude product) were initially charged in 5 ml of methanol, 120 mg of potassium hydroxide were added and the mixture was stirred at 50° C. overnight. More potassium hydroxide was added and the mixture was stirred at 50° C. for 5 h. The mixture was concentrated, giving 625 mg of potassium 6-(1-hydroxyethyl)pyridine-2-carboxylate as a crude product.

Intermediate 19-2

6-(1-Methyl-1H-pyrazol-4-yl)pyridine-2-carboxylic acid

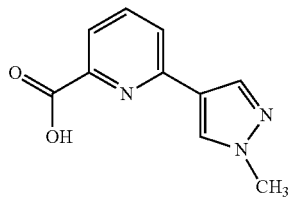

500 mg (2.31 mmol) of methyl 6-bromopyridine-2-carboxylate, 578 mg (1.2 equiv.) of 1-methyl-4-(4,4,5,5-tetramethyl-1,3,2-dioxaborolan-2-yl)-1H-pyrazole and 192 mg of lithium chloride were initially charged in 5 ml of toluene and 3 ml of ethanol 162 mg of bis(triphenylphosphine)palladium (II) chloride and 3.5 ml of aqueous sodium carbonate solution (2 M) were added and the mixture was heated in the microwave at 120° C. The mixture was acidified to pH 5 with 10% strength citric acid solution and extracted three times with ethyl acetate, and the extract was washed with sodium chloride solution, filtered and concentrated. The residue was purified by preparative HPLC (column XBridge C18 5 μm 100×30 mm) This gave 70 mg (15% of theory) of the title compound.

$^1$H-NMR (400 MHz, DMSO-d$_6$): δ=3.89 (s, 3H), 7.79-7.94 (m, 3H), 8.09 (s, 1H), 8.39 (s, 1H), (12.9 br. s, 1H).

Intermediate 19-3

6-(1-methyl-1H-pyrazol-5-yl)pyridine-2-carboxylic acid

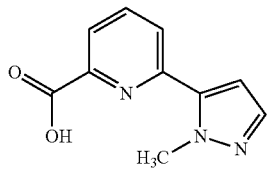

Analogously to the synthesis of Intermediate 19-2, 500 mg (2.31 mmol) of methyl 6-bromopyridine-2-carboxylate were reacted with 1-methyl-5-(4,4,5,5-tetramethyl-1,3,2-dioxaborolan-2-yl)-1H-pyrazole in the microwave at 120° C. for 90 min Purification by preparative HPLC according to Method P1 gave 34 mg (15% of theory) of the title compound.

$^1$H-NMR (400 MHz, DMSO-$d_6$): δ=4.22 (s, 3H), 6.89 (d, 1H), 7.50 (d, 1H), 7.96-8.10 (m, 3H), 13.29 (br. s., 1H).

Intermediate 19-4

6-(1H-Pyrazol-4-yl)pyridine-2-carboxylic acid

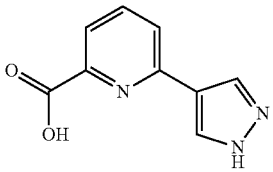 [SMILES: O=C(O)c1cccc(-c2cn[nH]c2)n1]

Analogously to the synthesis of Intermediate 19-2, 1 g (2.31 mmol) of 6-bromopyridine-2-carboxylic acid and 1.15 g of 4-(4,4,5,5-tetramethyl-1,3,2-dioxaborolan-2-yl)-1H-pyrazole were reacted in the microwave at 120° C. for 90 min Ethyl acetate and water were added, the mixture was filtered and the organic phase was separated off and extracted twice with ethyl acetate. The ethyl acetate phases were discarded. 10% strength citric acid solution was added to the aqueous phase until a pH of 4 was reached, the mixture was extracted three times with ethyl acetate and the ethyl acetate phases were concentrated. This gave a residue which was purified by preparative HPLC (column XBridge C18). This gave 110 mg (12% of theory) of the title compound.

$^1$H-NMR (300 MHz, DMSO-$d_6$): δ=7.77-7.98 (m, 3H), 8.31 (s, 2H), 13.03 (br. s., 2H).

Intermediate 19-5

5-Fluoro-6-(1-methyl-1H-pyrazol-4-yl)pyridine-2-carboxylic acid

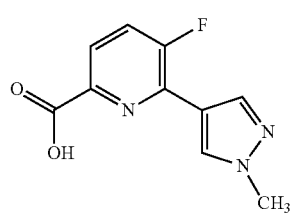 [SMILES: Cn1cc(-c2nc(C(=O)O)ccc2F)cn1]

500 mg of methyl 6-bromo-5-fluoropyridine-2-carboxylate were reacted analogously with 533 mg (1.2 equiv.) of 1-methyl-4-(4,4,5,5-tetramethyl-1,3,2-dioxaborolan-2-yl)-1H-pyrazole in the microwave at 120° C. for 90 min. This gave 380 mg (80% of theory) of the title compound as a crude product.

UPLC-MS (Method A1): $R_t$=0.72 min

MS (ESIpos): m/z=222 (M+H)$^+$

Intermediate 19-6

6-(1,3-Dimethyl-1H-pyrazol-4-yl)pyridine-2-carboxylic acid

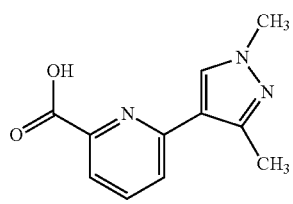 [SMILES: Cc1nn(C)cc1-c1cccc(C(=O)O)n1]

Analogously to the synthesis of Intermediate 19-2, 500 mg (2.31 mmol) of methyl 6-bromopyridine-2-carboxylate were reacted with 617 mg of 1,3-dimethyl-4-(4,4,5,5-tetramethyl-1,3,2-dioxaborolan-2-yl)-1H-pyrazole in the microwave at 120° C. for 90 min Purification by HPLC gave 66 mg (13% of theory) of the title compound.

$^1$H-NMR (400 MHz, DMSO-$d_6$): δ=2.47 (s), 3.80 (s, 3H), 7.71-7.81 (m, 2H), 7.88-7.94 (m, 1H), 8.27 (s, 1H), 12.95 (br. s., 1H).

Intermediate 19-7

6-(3-Methyl-1H-pyrazol-4-yl)pyridine-2-carboxylic acid

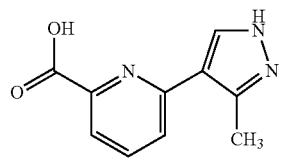

Analogously to the synthesis of Intermediate 19-2, 216 mg of methyl 6-bromopyridine-2-carboxylate were reacted with 250 mg of 3-methyl-4-(4,4,5,5-tetramethyl-1,3,2-dioxaborolan-2-yl)-1H-pyrazole in the microwave at 120° C. for 90 min. This gave, after purification by HPLC, 68 mg (33% of theory) of the title compound mixed with methyl 6-(3-methyl-1H-pyrazol-4-yl)pyridine-2-carboxylate.

UPLC-MS (Method A1): $R_t$=0.50 min

MS (ESIpos): m/z=204 (M+H)$^+$

Intermediate 19-8

6-[3-(Methylsulphonyl)phenyl]pyridine-2-carboxylic acid

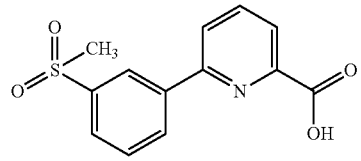 [SMILES: CS(=O)(=O)c1cccc(-c2cccc(C(=O)O)n2)c1]

500 mg (2.31 mmol) of methyl 6-bromopyridine-2-carboxylate, 694 mg (1.5 equiv.) of [3-(methylsulphonyl)phenyl]boronic acid and were initially charged in 10 ml of DMSO. 267 mg of tetrakis(triphenylphosphine)palladium (0), 736 mg of sodium carbonate and 2 ml of water were added and the mixture was heated in the microwave at 110° C. for 2 h. The mixture was diluted with water and acidified to pH 4 with 10% strength citric acid solution, ethyl acetate was added, the mixture was filtered, the phases of the filtrate were separated, the aqueous phase was extracted with ethyl acetate and the extract was washed with sodium chloride solution and concentrated. 2.5 ml of methanol and 917 mg of lithium hydroxide monohydrate in 10 ml of water were added and the mixture was stirred at room temperature for 5 h. The mixture was diluted with water, acidified to pH 4 with 10% strength citric acid solution and extracted with ethyl acetate and the extracts were washed with sodium chloride solution and concentrated. This gave 776 mg of the title compound as a crude product.

UPLC-MS (Method A1): $R_t$=0.75 min

MS (ESIpos): m/z=278 (M+H)$^+$

Intermediate 19-9

6-[3-(Trifluoromethyl)-1H-pyrazol-4-yl]pyridine-2-carboxylic acid

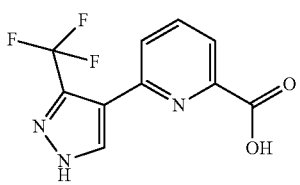

Analogously to the preparation of Intermediate 19-8, 250 mg of methyl 6-bromopyridine-2-carboxylate were reacted with 394 mg of 4-(4,4,5,5-tetramethyl-1,3,2-dioxaborolan-2-yl)-3-(trifluoromethyl)-1H-pyrazole. This gave 442 mg of the title compound as a crude product.

UPLC-MS (Method A1): $R_t$=0.82 min

MS (ESIpos): m/z=258 (M+H)$^+$

Intermediate 19-10

Potassium 6-(2,2,2-trifluoro-1-hydroxyethyl)pyridine-2-carboxylate

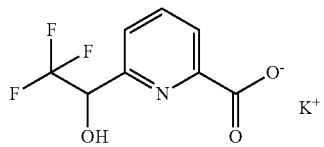 [SMILES: O=C([O-])c1cccc(C(O)C(F)(F)F)n1 ; [K+]]

165 mg of potassium hydroxide were added to 693 mg of methyl 6-(2,2,2-trifluoro-1-hydroxyethyl)pyridine-2-carboxylate (Intermediate 17-2) in 5.0 ml of methanol, and the mixture was stirred at 50° C. for 20 h. Concentration gave 787 mg of a solid which was processed further without any further purification.

Intermediate 19-11

Potassium 6-(2-hydroxypropan-3-yl)pyridine-2-carboxylate

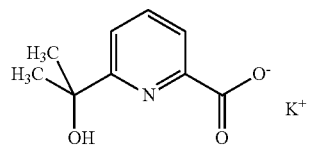

Analogously to Intermediate 19-10, 535 mg of methyl 6-(2-hydroxypropan-2-yl)pyridine-2-carboxylate (Intermediate 17-3) were reacted with 0.28 g of potassium hydroxide in 6.0 ml of methanol at 50° C. This gave, after concentration, 876 mg of the title compound as a crude product.

Intermediate 19-12

6-{[1-(tert-Butoxycarbonyl)azetidin-3-yl]amino}pyridine-2-carboxylic acid

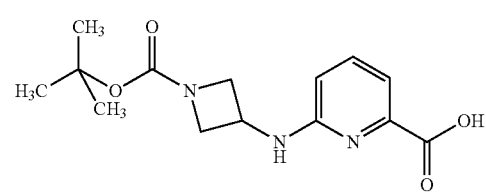 [SMILES: CC(C)(C)OC(=O)N1CC(Nc2cccc(C(=O)O)n2)C1]

0.31 g of lithium hydroxide monohydrate dissolved in 1.0 ml of water and 0.5 ml of ethanol was added to a mixture of 230 mg of methyl 6-{[1-(tert-butoxycarbonyl)azetidin-3-yl]amino}pyridine-2-carboxylate (Intermediate 17-4) in 4.0 ml of THF, and the mixture was stirred at room temperature overnight. The mixture was diluted with water, acidified to pH 6 with citric acid solution and extracted with ethyl acetate, and the extract was washed with saturated sodium chloride solution, filtered through a hydrophobic filter and concentrated. This gave 202 mg of an oil which was used without further purification.

Intermediate 19-13

Potassium 6-({[1-(tert-butoxy carbonyl)azetidin-2-yl]methyl}amino)pyridine-2-carboxylate

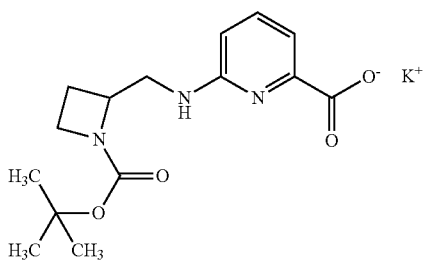 [SMILES: CC(C)(C)OC(=O)N1CCC1CNc1cccc(C(=O)[O-])n1 ; [K+]]

24 mg of potassium hydroxide were added to 230 mg of methyl 6-({[1-(tert-butoxycarbonyl)azetidin-2-yl]methyl}amino)pyridine-2-carboxylate (Intermediate 17-5) in 3.0 ml of ethanol, and the mixture was stirred at 50° C. overnight. The mixture was concentrated, giving 265 mg of a crude product which was used further without purification.

Intermediate 19-14

6-[(2R,6S)-2,6-Dimethylmorpholin-4-yl]pyridine-2-carboxylic acid

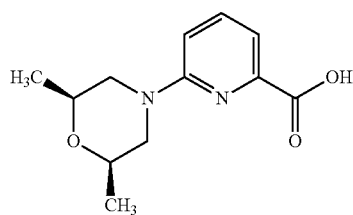 [SMILES: C[C@@H]1CN(c2cccc(C(=O)O)n2)C[C@H](C)O1]

875 mg of methyl 6-[(2R,6S)-2,6-dimethylmorpholin-4-yl]pyridine-2-carboxylate (Intermediate 17-6) were initially charged in 5 ml of THF and 1 ml of methanol, 698 mg of lithium hydroxide monohydrate in 2.5 ml of water were added and the mixture was stirred at room temperature overnight. Twice, toluene was added and the mixture was in each case concentrated again. Methanol was added, the mixture was stirred, the solid was filtered off and washed with diethyl ether and the filtrate was concentrated and purified by preparative HPLC (Method P1). This gave 224 mg of the title compound.

UPLC-MS (Method A1): Rt=0.66 min (UV detector TIC), mass found 236.12.

Intermediate 19-15

Potassium 6-(isobutylamino)pyridine-2-carboxylate

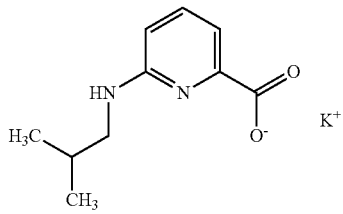

454 mg of lithium hydroxide were added to a solution of 790 mg of methyl 6-(isobutylamino)pyridine-2-carboxylate (Intermediate 17-7) in 3.4 ml of water, 32 ml of THF and 3.2 ml of methanol, and the mixture was stirred at room temperature overnight. This gave, after concentration, 1.15 g of a solid which was used without further purification.

UPLC-MS (Method A1): Rt=0.58 min (UV detector TIC), mass found 194.00.

Intermediate 20-1

6-Bromo-N-{6-methoxy-2-[2-(morpholin-4-yl)-2-oxoethyl]-2H-indazol-5-yl}pyridine-2-carboxamide

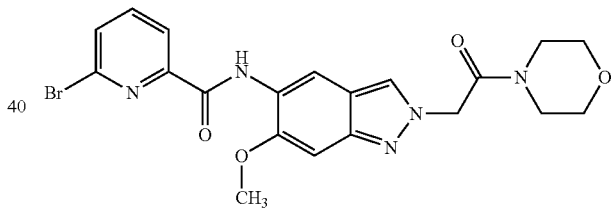

Analogously to Intermediate 8-6, 1.00 g (2.47 mmol) of (5-{[(6-bromopyridin-2-yl)carbonyl]amino}-6-methoxy-2H-indazol-2-yl)acetic acid (Intermediate 9-21), 258 µl (2.96 mmol) of morpholine, 378 mg (2.47 mmol) of 1-hydroxy-1H-benzotriazole hydrate, 946 mg (4.94 mmol) of 1-(3-dimethylaminopropyl)-3-ethylcarbodiimide hydrochloride and 1.03 ml (7.40 mmol) of triethylamine in 35 ml of tetrahydrofuran were stirred at 25° C. for 24 h. The reaction mixture was concentrated, water was added and the resulting precipitate was filtered off with suction, washed with water and diethyl ether and concentrated under reduced pressure. This gave 586 mg (50% of theory) of the title compound.

UPLC-MS (Method A1): $R_t$=1.07 min

MS (ESIpos): m/z=474 (M+H)$^+$ $^1$H NMR (400 MHz, DMSO-d6): δ=3.47 (d, 2H), 3.58 (br. s., 4H), 3.64 (d, 2H), 4.00 (s, 3H), 5.40 (s, 2H), 7.93-7.99 (m, 1H), 8.05 (t, 1H), 8.14-8.29 (m, 2H), 8.68 (s, 1H), 10.31 (s, 1H).

Intermediate 21-1 tert-Butyl 4-{[5-({[6-(trifluoromethyl)pyridin-2-yl]carbonyl}amino)-2H-indazol-2-yl]acetyl}piperazine-1-carboxylate

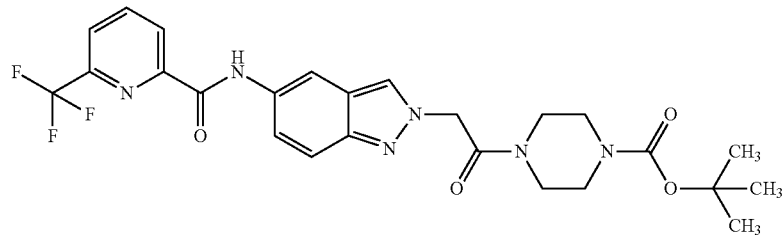 [SMILES: CC(C)(C)OC(=O)N1CCN(C(=O)Cn2cc3cc(NC(=O)c4cccc(C(F)(F)F)n4)ccc3n2)CC1]

1.30 g (3.57 mmol) of [5-({[6-(trifluoromethyl)pyridin-2-yl]carbonyl}amino)-2H-indazol-2-yl]acetic acid (Intermediate 9-14) was in 50 ml of tetrahydrofuran and 5.4 ml of N,N-dimethylformamide, and the mixture was stirred at 25° C. for 30 minutes. 997 mg (5.35 mmol) of tert-butyl piperazine-1-carboxylate, 546 mg (3.57 mmol) of 1-hydroxy-1H-benzotriazole hydrate and 1.37 g (7.14 mmol) of 1-(3-dimethylaminopropyl)-3-ethylcarbodiimide hydrochloride were then added, and the mixture was stirred at 25° C. for a further 24 h. The reaction mixture was added to water. The resulting solid was filtered off with suction and washed twice with water. The solid was taken up in dichloromethane and the solution was dried over sodium sulphate, filtered and concentrated. The yellow solid was dried under reduced pressure. This gave 1.78 g (94% of theory) of tert-butyl 4-{[5-({[6-(trifluoromethyl)pyridin-2-yl]carbonyl}amino)-2H-indazol-2-yl]acetyl}piperazine-1-carboxylate.

UPLC-MS (Method A1): $R_t$=1.21 min
MS (ESIpos): m/z=533 (M+H)$^+$

Intermediate 22-1

N-{2-[2-Oxo-2-(piperazin-1-yl)ethyl]-2H-indazol-5-yl}-6-(trifluoromethyl)pyridine-2-carboxamide

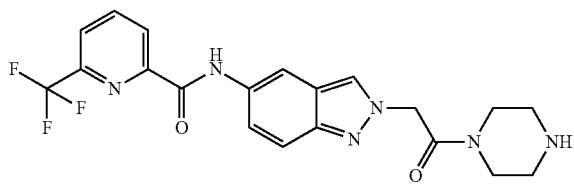 [SMILES: O=C(Nc1ccc2nn(CC(=O)N3CCNCC3)cc2c1)c1cccc(C(F)(F)F)n1]

1.93 ml (25.08 mmol) of trifluoroacetic acid were added to 1.78 g (3.34 mmol) of tert-butyl 4-{[5-({[6-(trifluoromethyl)pyridin-2-yl]carbonyl}amino)-2H-indazol-2-yl]acetyl}piperazine-1-carboxylate (Intermediate 21-1) in 11 ml of dichloromethane, and the mixture was stirred at 25° C. for 24 h. The mixture was then poured into saturated sodium bicarbonate solution. The resulting suspension was filtered and the filter cake was washed with 30 ml of water and 10 ml of diethyl ether. Drying under reduced pressure gave 1.41 g (97% of theory) of N-{2-[2-oxo-2-(piperazin-1-yl)ethyl]-2H-indazol-5-yl}-6-(trifluoromethyl)pyridine-2-carboxamide as a crude product.

UPLC-MS (Method A1): $R_t$=0.80 min
MS (ESIpos): m/z=433 (M+H)$^+$
$^1$H NMR (400 MHz, DMSO-d6): δ=2.66 (br. s., 2H), 2.73 (br. s., 2H), 3.39 (br. s., 2H), 3.47 (br. s., 2H), 5.44 (s, 2H), 7.47-7.68 (m, 2H), 8.17 (d, J=7.1 Hz, 1H), 8.30 (s, 2H), 8.33-8.43 (m, 2H), 10.37 (s, 1H).

Intermediate 23-1 tert-Butyl 5-{[(benzyloxy)carbonyl]amino}-6-chloro-2H-indazole-2-carboxylate

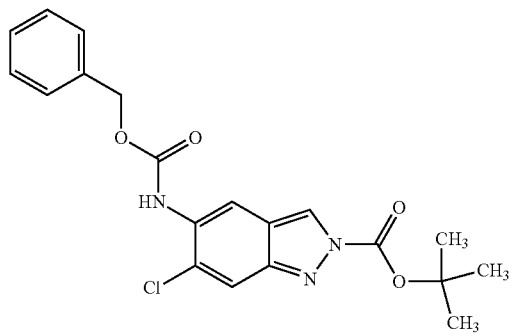 [SMILES: CC(C)(C)OC(=O)n1cc2cc(NC(=O)OCc3ccccc3)c(Cl)cc2n1]

1.50 ml of N-ethyl-N-isopropylpropane-2-amine and 1.11 ml of benzyl carbonochloridate were added to 2.09 g of tert-butyl 5-amino-6-chloro-2H-indazole-2-carboxylate (Intermediate 12-2) in 15 ml of THF, and the mixture was stirred at room temperature overnight. Another 1.50 ml of N-ethyl-N-isopropylpropane-2-amine and 1.11 ml of benzyl carbonochloridate were added, and the mixture was stirred at room temperature for 3 days. Another 1.50 ml of N-ethyl-N-isopropylpropane-2-amine and 1.11 ml of benzyl carbonochloridate were added, and the mixture was stirred at room temperature overnight. Water was added, the mixture was extracted with ethyl acetate and the extract was washed with sodium chloride solution and concentrated. This gave 4.61 mg of a crude product which was processed further without further purification.

UPLC-MS (Method A1): Rt=1.40 min (UV-TIC), mass found 401.00.

The chemical names of the examples were generated using the ACD/LABS (Batch Version 12.01.) software.

EXAMPLES

General Procedure 1a 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 5.0 equivalents of triethylamine and 1.5 equivalents of the carboxylic acid in question were stirred in tetrahydrofuran at 25° C. for 24 h. Water and ethyl acetate were added to the reaction mixture. The resulting precipitate was filtered off, washed with water and diethyl ether and dried.

General Procedure 1b 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 3.0 equivalents of triethylamine and 1.5 equivalents of the carboxylic acid in question were stirred in N,N-dimethylformamide at 25° C. for 24 h, giving a suspension. The resulting precipitate was filtered off, washed twice with N,N-dimethylformamide and diethyl ether and dried.

General Procedure 1c 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 5.0 equivalents of triethylamine and 1.3 equivalents of the carboxylic acid in question were stirred in tetrahydrofuran at 25° C. for 24 h. Water was added and the reaction mixture was extracted repeatedly with ethyl acetate. The combined organic phases were concentrated and the residue was purified by preparative HPLC according to Method P1.

General Procedure 1d 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 3.0 equivalents of triethylamine and 1.2 equivalents of the carboxylic acid in question were stirred in 1 ml of N,N-dimethylformamide at 25° C. for 24 h. The reaction mixture was diluted with a further 1.5 ml of N,N-dimethylformamide and purified by preparative HPLC according to Method P1.

General Procedure 1e 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 4.0 equivalents of triethylamine and 1.2 equivalents of the carboxylic acid in question were stirred in 1 ml of tetrahydrofuran at 25° C. for 24 h. The reaction mixture was poured into 25 ml of water. The precipitate formed was filtered off, washed twice with diethyl ether and dried in a drying cabinet.

TABLE 1

Examples 1-18
The exemplary compounds were prepared by the general experimental procedures 1a-1e from the appropriate intermediates and carboxylic acids.

| Ex. No. | Structure/Name | Prepared from | * see key | $^1$H-NMR/LC-MS |
|---|---|---|---|---|
| 1 | 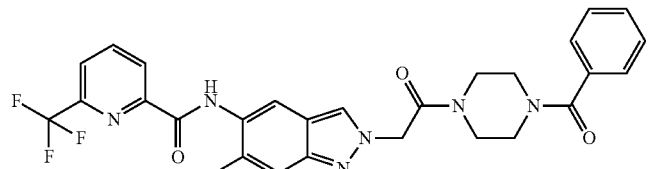<br>N-{2-[2-(4-benzoylpiperazin-1-yl)-2-oxoethyl]-6-methyl-2H-indazol-5-yl}-6-(trifluoromethyl)pyridine-2-carboxamide | Intermediate 6-1 and 6-(trifluoromethyl)pyridine-2-carboxylic acid | 1a [a] (68%) | (400 MHz, DMSO-d6): δ = 2.38 (s, 3H), 3.32-3.77 (8H), 5.45 (br. s., 2H), 7.39-7.49 (m, 6H), 8.15-8.21 (m, 2H), 8.24 (s, 1H), 8.33-8.43 (m, 2H), 10.11 (s, 1H). UPLC-MS (Method A1): Rt = 1.16 min MS (ESIpos): m/z = 551 (M + H)+ |
| 2 | 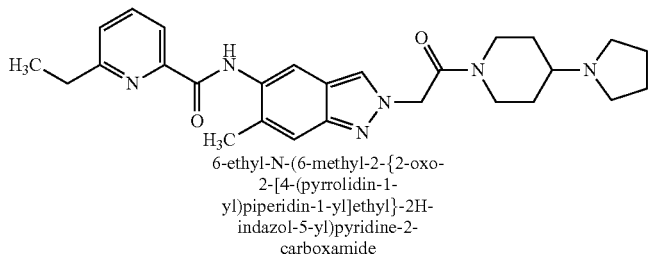<br>6-ethyl-N-(6-methyl-2-{2-oxo-2-[4-(pyrrolidin-1-yl)piperidin-1-yl]ethyl}-2H-indazol-5-yl)pyridine-2-carboxamide | Intermediate 6-2 and 6-ethyl-pyridine-2-carboxylic acid | 1a (91%) | (300 MHz, DMSO-d6): δ = 1.21-1.49 (m, 5H), 1.67 (br. s., 4H), 1.84 (t, 2H), 2.14-2.31 (m, 1H), 2.79-2.95 (m, 3H), 3.17 (t, 1H), 3.80-3.93 (m, 1H), 4.03-4.16 (m, 1H), 5.34-5.49 (m, 2H), 7.49 (s, 1H), 7.53-7.59 (m, 1H), 7.94-8.01 (m, 2H), 8.24 (s, 1H), 8.39 (s, 1H), 10.37 (s, 1H). UPLC-MS (Method A2): Rt = 1.18 min MS (ESIpos): m/z = 475 (M + H)+ |
| 3 | 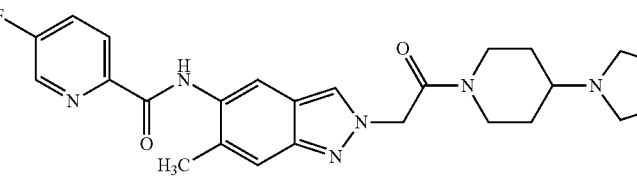<br>5-fluoro-N-(6-methyl-2-{2-oxo-2-[4-(pyrrolidin-1-yl)piperidin-1-yl]ethyl}-2H-indazol-5-yl)pyridine-2-carboxamide | Intermediate 6-2 and 5-fluoro-pyridine-2-carboxylic acid | 1b (36%) | (400 MHz, DMSO-d6): δ = 1.18-1.37 (m, 1 H), 1.37-1.51 (m, 1 H), 1.68 (br. s., 4 H), 1.76-1.94 (m, 2 H), 2.14-2.30 (m, 1 H), 2.39 (s, 3 H), 2.78-2.94 (m, 1 H), 3.18 (t, 1 H), 3.82-3.95 (m, 1 H), 4.03-4.16 (m, 1 H), 5.44 (d, 1 H), 5.39 (d, 1 H), 7.44-7.50 (m, 1 H), 7.99 (td, 1 H), 8.12 (s, 1 H), 8.20-8.29 (m, 2 H), 8.75 (d, 1 H), 10.15 (s, 1 H). LC-MS (Method A3): Rt = 0.79 min MS (ESIpos): m/z = 465 (M + H)+ |

TABLE 1-continued

Examples 1-18
The exemplary compounds were prepared by the general experimental procedures 1a-1e from the appropriate intermediates and carboxylic acids.

| Ex. No. | Structure/Name | Prepared from | * see key | $^1$H-NMR/LC-MS |
|---|---|---|---|---|
| 4 | 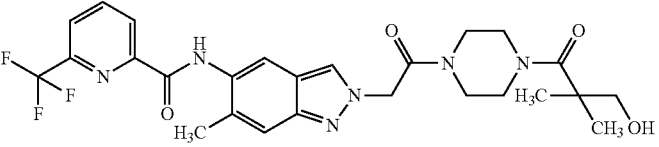 [SMILES: Cc1cc2nn(CC(=O)N3CCN(C(=O)C(C)(C)CO)CC3)cc2cc1NC(=O)c1cccc(C(F)(F)F)n1]<br>N-(2-{2-[4-(3-hydroxy-2,2-dimethylpropanoyl)piperazin-1-yl]-2-oxoethyl}-6-methyl-2H-indazol-5-yl)-6-(trifluoromethyl)pyridine-2-carboxamide | Intermediate 6-3 and 6-(trifluoromethyl)pyridine-2-carboxylic acid | 1a (53%) | (300 MHz, DMSO-d6): δ = 1.16 (s, 6H), 2.40 (s, 3H), 3.39-3.52 (m, 4H), 3.52-3.70 (m, 6H), 4.62 (t, 1H), 5.47 (s, 2H), 7.49 (s, 1H), 8.17-8.29 (m, 3H), 8.34-8.45 (m, 2H), 10.15 (s, 1H). UPLC-MS (Method A1): Rt = 1.06 min MS (ESIpos): m/z = 547 (M + H)+ |
| 5 | 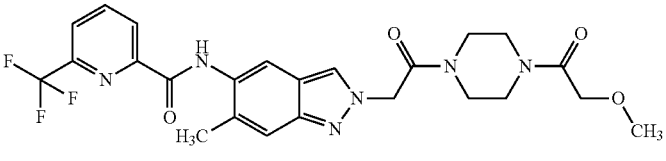 [SMILES: COCC(=O)N1CCN(C(=O)Cn2cc3cc(NC(=O)c4cccc(C(F)(F)F)n4)c(C)cc3n2)CC1]<br>N-(2-{2-[4-(methoxyacetyl)piperazin-1-yl]-2-oxoethyl}-6-methyl-2H-indazol-5-yl)-6-(trifluoromethyl)pyridine-2-carboxamide | Intermediate 6-4 and 6-(trifluoromethyl)pyridine-2-carboxylic acid | 1a (12%) | (400 MHz, DMSO-d6): δ = 2.40 (s, 3H), 3.36-3.64 (m, 8H), 4.12 (br. s., 2H), 5.47 (s, 2H), 7.49 (s, 1H), 8.18-8.28 (m, 3H), 8.35-8.45 (m, 2H), 10.13 (s, 1H). UPLC-MS (Method A1): Rt = 1.02 min MS (ESIpos): m/z = 519 (M + H)+ |
| 6 | 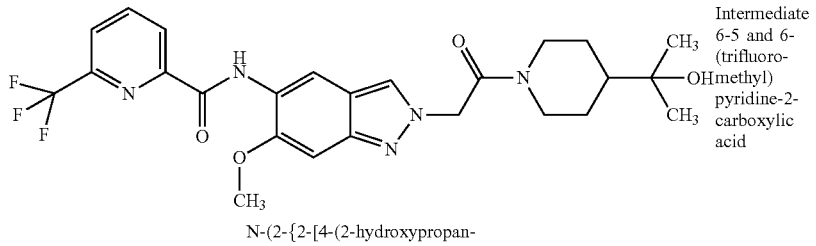<br>N-(2-{2-[4-(2-hydroxypropan-2-yl)piperidin-1-yl]-2-oxoethyl}-6-methoxy-2H-indazol-5-yl)-6-(trifluoromethyl)pyridine-2-carboxamide | Intermediate 6-5 and 6-(trifluoromethyl)pyridine-2-carboxylic acid | 1c (51%) | (300 MHz, DMSO-d6): δ = 0.94-1.29 (m, 8H, contains singlet at 1.04 ppm), 1.35-1.51 (m, 1H), 1.74 (t, 2H), 2.53 (s, 1H), 2.98 (t, 1H), 3.91-4.10 (m, 4H), 4.17 (s, 1H), 4.41 (d, 1H), 5.28-5.44 (m, 2H), 7.10 (s, 1H), 8.18-8.27 (m, 2H), 8.35-8.50 (m, 2H), 8.69 (s, 1H), 10.50 (s, 1H). UPLC-MS (Method A1): Rt = 1.13 min MS (ESIpos): m/z = 520 (M + H)+ |
| 7 | 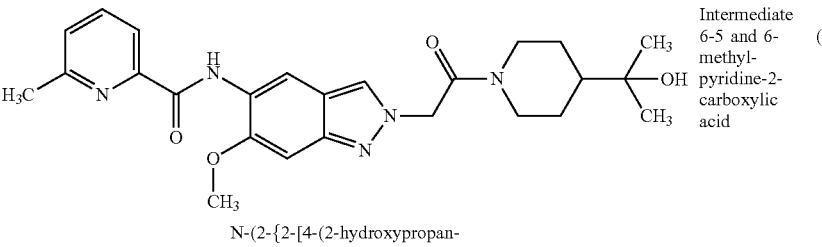<br>N-(2-{2-[4-(2-hydroxypropan-2-yl)piperidin-1-yl]-2-oxoethyl}-6-methoxy-2H-indazol-5-yl)-6-methylpyridine-2-carboxamide | Intermediate 6-5 and 6-methylpyridine-2-carboxylic acid | 1c (41%) | (300 MHz, DMSO-d6): δ = 0.97-1.29 (m, 8H, contains singlet at 1.04 ppm), 1.36-1.50 (m, 1H), 1.74 (t, 2H), 2.53 (s, 1H), 2.61 (s, 3H), 2.98 (t, 1H), 3.95-4.08 (m, 4H), 4.17 (s, 1H), 4.41 (d, 1H), 5.28-5.42 (m, 2H), 7.08 (s, 1H), 7.51-7.59 (m, 1H), 7.92-8.02 (m, 2H), 8.20 (s, 1H), 8.70 (s, 1H), 10.70 (s, 1H). UPLC-MS (Method A1): Rt = 1.06 min MS (ESIpos): m/z = 466 (M + H)+ |

TABLE 1-continued

Examples 1-18
The exemplary compounds were prepared by the general experimental procedures 1a-1e from the appropriate intermediates and carboxylic acids.

| Ex. No. | Structure/Name | Prepared from | * see key | ¹H-NMR/LC-MS |
|---|---|---|---|---|
| 8 | N-(2-{2-[4-(cyclopropylmethyl)piperazin-1-yl]-2-oxoethyl}-6-methoxy-2H-indazol-5-yl)-6-(trifluoromethyl)pyridine-2-carboxamide hydrochloride | Intermediate 6-6 and 6-(trifluoromethyl)pyridine-2-carboxylic acid | 1a (17%) [b] | (400 MHz, DMSO-d6): δ = 0.41 (br. s., 2H), 0.66 (d, 2H), 1.12 (br. s., 1H), 2.89-3.26 (m, 5H), 3.60 (br. s., 3H), 4.00 (s, 3H), 4.21 (d, 1H), 4.42 (d, 1H), 5.48 (d, 2H), 7.11 (s, 1H), 8.19-8.25 (m, 2H), 8.36-8.49 (m, 2H), 8.72 (s, 1H), 10.5 (s, 1H), 10.7 (s). UPLC-MS (Method A1): Rt = 0.94 min MS (ESIpos): m/z = 517 (M + H)+ |
| 9 | N-(2-{2-[4-(cyclopropylmethyl)piperazin-1-yl]-2-oxoethyl]-6-methoxy-2H-indazol-5-yl)-6-methylpyridine-2-carboxamide | Intermediate 6-6 and 6-methylpyridine-2-carboxylic acid | 1c (26%) [c] | (300 MHz, DMSO-d6, selected signals, sample contained a proportion of formic acid): δ = 0.27 (br. s., 2H), 0.59 (br. s., 2H), 0.97 (br. s., 1H), 2.62 (s), 3.05 (br. s.), 3.53 (br. s.), 4.00 (s, 3H), 5.43 (br. s., 2H), 7.08 (s, 1H), 7.55 (dd, 1H), 7.93-8.01 (m, 2H), 8.19 (s, 1H), 8.72 (s, 1H), 10.71 (s, 1H). UPLC-MS (Method A1): Rt = 0.85 min MS (ESIpos): m/z = 463 (M + H)+ |
| 10 | N-{2-[2-(4-benzoylpiperazin-1-yl)-2-oxoethyl]-6-methoxy-2H-indazol-5-yl}-6-cyclopropylpyridine-2-carboxamide | Intermediate 6-7 and 6-cyclopropylpyridine-2-carboxylic acid | 1a (50%) [d] | (300 MHz, DMSO-d6): δ = 1.04-1.15 (m, 4H), 2.21-2.33 (m, 1H), 3.39-3.87 (8H), 4.00 (s, 3H), 5.41 (br. s., 2H), 7.09 (s, 1H), 7.41-7.52 (m, 5H), 7.58-7.65 (m, 1H), 7.87-7.96 (m, 2H), 8.20 (s, 1H), 8.66 (s, 1H), 10.80 (s, 1H). UPLC-MS (Method A1): Rt = 1.18 min MS (ESIpos): m/z = 539 (M + H)+ |
| 11 | N-{2-[2-(4-benzoylpiperazin-1-yl)-2-oxoethyl]-6-methoxy-2H-indazol-5-yl}-6-(1-hydroxyethyl)pyridine-2-carboxamide | Intermediate 6-7 and Intermediate 19-1 | 1c (49%) | (300 MHz, DMSO-d6): δ = 1.51 (d, 3H), 3.38-3.91 (8H), 3.99 (s, 3H), 4.81-4.90 (m, 1H), 5.41 (br. s., 2H), 5.60 (d, 1H), 7.09 (s, 1H), 7.35-7.56 (m, 5H), 7.76-7.82 (m, 1H), 8.01-8.11 (m, 2H), 8.21 (s, 1H), 8.68 (s, 1H), 10.78 (s, 1H). UPLC-MS (Method A1): Rt = 0.93 min MS (ESIpos): m/z = 534 (M + H)+ |

TABLE 1-continued

Examples 1-18
The exemplary compounds were prepared by the general experimental procedures 1a-1e from the appropriate intermediates and carboxylic acids.

| Ex. No. | Structure/Name | Prepared from | * see key | $^1$H-NMR/LC-MS |
|---|---|---|---|---|
| 12 | 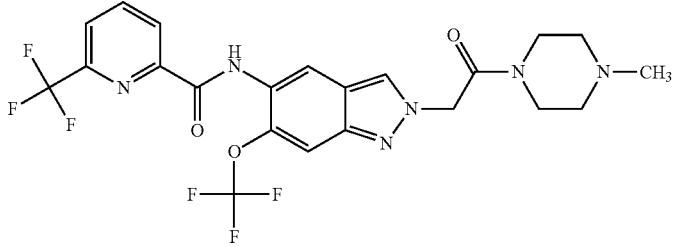 [SMILES: CN1CCN(C(=O)Cn2cc3cc(NC(=O)c4cccc(C(F)(F)F)n4)c(OC(F)(F)F)cc3n2)CC1]<br>N-{2-[2-(4-methylpiperazin-1-yl)-2-oxoethyl]-6-(trifluoromethoxy)-2H-indazol-5-yl}-6-(trifluoromethyl)pyridine-2-carboxamide | Intermediate 6-8 and 6-(trifluoromethyl)pyridine-2-carboxylic acid | 1d (47%) | (400 MHz, DMSO-d6) δ = 2.22 (s, 3 H) 2.27-2.36 (m, 2 H) 2.37-2.44 (m, 2 H) 3.44-3.52 (m, 2 H) 3.52-3.60 (m, 2 H) 5.52 (s, 2 H) 7.75 (s, 1 H) 8.23 (dd, 1 H) 8.38-8.50 (m, 3 H) 8.71 (s, 1 H) 10.40 (s, 1 H). UPLC-MS (Method A1): Rt = 0.96 min MS (ESIpos): m/z = 531 (M + H)+ |
| 13 | 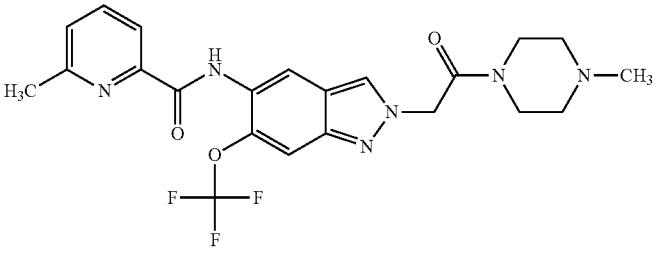<br>6-methyl-N-{2-[2-(4-methylpiperazin-1-yl)-2-oxoethyl]-6-(trifluoromethoxy)-2H-indazol-5-yl}pyridine-2-carboxamide | Intermediate 6-8 and 6-methylpyridine-2-carboxylic acid | 1d (49%) | (300 MHz, DMSO-d6) δ = 2.21 (s, 3 H), 2.25-2.34 (m, 2 H), 2.39 (br. s., 2 H), 2.61 (s, 3 H), 3.44-3.51 (m, 2 H), 3.51-3.61 (m, 2 H), 5.52 (s, 2 H), 7.59 (dd, 1 H), 7.76 (s, 1 H), 7.96-8.04 (m, 2 H), 8.45 (s, 1 H), 8.72 (s, 1 H), 10.65 (s, 1 H). UPLC-MS (Method A1): Rt = 0.92 min MS (ESIpos): m/z = 477 (M + H)+ |
| 14 | 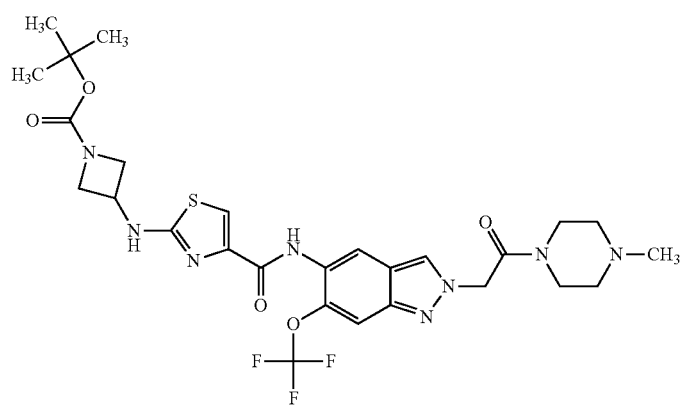 [SMILES: CN1CCN(C(=O)Cn2cc3cc(NC(=O)c4csc(NC5CN(C(=O)OC(C)(C)C)C5)n4)c(OC(F)(F)F)cc3n2)CC1]<br>tert-butyl 3-{[4-({2-[2-[4-methylpiperazin-1-yl]-2-oxoethyl]-6-(trifluoromethoxy)-2H-indazol-5-yl}carbamoyl)-1,3-thiazol-2-yl]amino}azetidine-1-carboxylate | Intermediate 6-8 and 2-{[1-(tert-butoxycarbonyl)azetidin-3-yl]amino}-1,3-thiazole-4-carboxylic acid** | 1d (39%) | (300 MHz, DMSO-d6) δ = 1.39 (s, 9 H), 2.21 (s, 3 H), 2.26-2.34 (m, 2 H), 2.38 (br. s., 2 H), 3.46 (br. s., 2 H), 3.54 (br. s., 2 H), 3.77 (dd, 2 H), 4.20 (t, 2 H), 4.46 (d, 1 H), 5.50 (s, 2 H), 7.56 (s, 1 H), 7.73 (s, 1 H), 8.42 (s, 1 H), 8.57 (d, 1 H), 8.62 (s, 1 H), 9.54 (s, 1 H). UPLC-MS (Method A1): Rt = 0.63 min MS (ESIpos): m/z = 639 (M + H)+ |

TABLE 1-continued

Examples 1-18
The exemplary compounds were prepared by the general experimental procedures 1a-1e from the appropriate intermediates and carboxylic acids.

| Ex. No. | Structure/Name | Prepared from | * see key | ¹H-NMR/LC-MS |
|---|---|---|---|---|
| 15 | 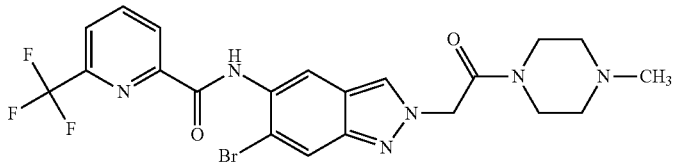 [SMILES: CN1CCN(C(=O)Cn2cc3cc(NC(=O)c4cccc(C(F)(F)F)n4)c(Br)cc3n2)CC1]<br>N-{6-bromo-2-[2-(4-methylpiperazin-1-yl)-2-oxoethyl]-2H-indazol-5-yl}-6-(trifluoromethyl)pyridine-2-carboxamide | Intermediate 6-9 and 6-(trifluoromethyl)pyridine-2-carboxylic acid | 1e (76%) | (300 MHz, DMSO-d6) δ = 2.21 (s, 3 H), 2.29 (br. s., 2 H), 2.38 (br. s., 2 H), 3.47 (br. s., 2 H), 3.54 (br. s., 2 H), 5.50 (s, 2 H), 8.09 (s, 1 H), 8.24 (d, 1 H), 8.35-8.50 (m, 3 H), 8.64 (s, 1 H), 10.54 (s, 1 H).<br>LC-MS (Method A3): Rt = 0.93 min<br>MS (ESIpos): m/z = 525 (M(79Br) + H)+ |
| 16 | 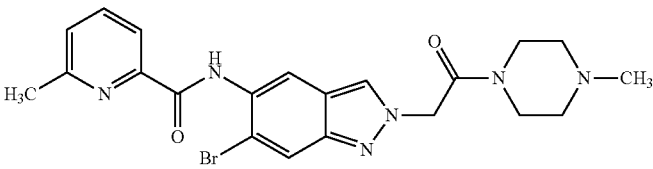<br>N-{6-bromo-2-[2-(4-methylpiperazin-1-yl)-2-oxoethyl]-2H-indazol-5-yl}-6-methylpyridine-2-carboxamide | Intermediate 6-9 and 6-methyl pyridine-2-carboxylic acid | 1e (93%) | (300 MHz, DMSO-d6) δ = 2.21 (s, 3 H), 2.25-2.35 (m, 2 H), 2.38 (br. s., 2 H), 2.64 (s, 3 H), 3.47 (br. s., 2 H), 3.54 (br. s., 2 H), 5.49 (s, 2 H), 7.58 (dd, 1 H), 7.97-8.04 (m, 2 H), 8.08 (s, 1 H), 8.39 (s, 1 H), 8.71 (s, 1 H), 10.77 (s, 1 H).<br>LC-MS (Method A3): Rt = 0.88 min<br>MS (ESIpos): m/z = 471 (M(79Br) + H)+ |
| 17 | 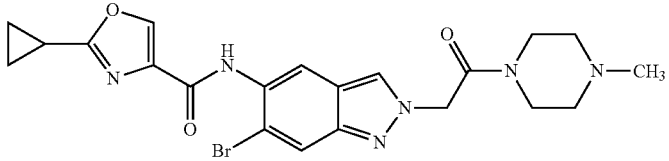 [SMILES: CN1CCN(C(=O)Cn2cc3cc(NC(=O)c4coc(C5CC5)n4)c(Br)cc3n2)CC1]<br>N-{6-bromo-2-[2-(4-methylpiperazin-1-yl)-2-oxoethyl]-2H-indazol-5-yl}-2-cyclopropyl-1,3-oxazole-4-carboxamide | Intermediate 6-9 and 2-cyclopropyl-1,3-oxazole-4-carboxylic acid | 1e (55%) | (300 MHz, DMSO-d6) δ = 1.01-1.07 (m, 2 H), 1.07-1.16 (m, 2 H), 2.17-2.26 (m, 4 H), 2.27-2.34 (m, 2 H), 2.37 (br. s., 2 H), 3.46 (br. s., 2 H), 3.54 (br. s., 2 H), 5.49 (s, 2 H), 8.03 (s, 1 H), 8.29 (s, 1 H), 8.37 (s, 1 H), 8.63 (s, 1 H), 9.61 (s, 1 H).<br>LC-MS (Method A3): Rt = 0.83 min<br>MS (ESIpos): m/z = 487 (M(79Br) + H)+ |
| 18 | 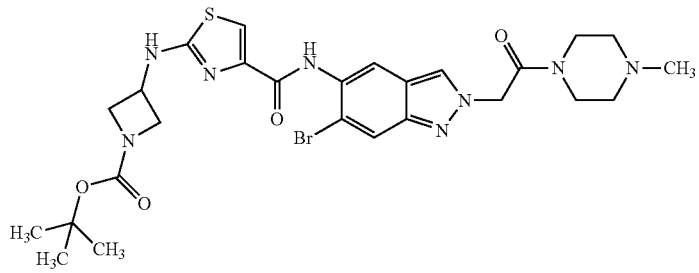 [SMILES: CN1CCN(C(=O)Cn2cc3cc(NC(=O)c4csc(NC5CN(C(=O)OC(C)(C)C)C5)n4)c(Br)cc3n2)CC1]<br>tert-butyl 3-{[4-({6-bromo-2-[2-(4-methylpiperazin-1-yl)-2-oxoethyl]-2H-indazol-5-yl}carbamoyl)-1,3-thiazol-2-yl]amino}azetidine-1-carboxylate | Intermediate 6-9 and 2-{[1-(tert-butoxycarbonyl)azetidin-3-yl]amino}-1,3-thiazole-4-carboxylic acid** | 1e (41%) | (300 MHz, DMSO-d6) δ = 1.39 (s, 9 H), 2.21 (s, 3 H), 2.25-2.33 (m, 2 H), 2.37 (br. s., 2 H), 3.46 (br. s., 2 H), 3.54 (br. s., 2 H), 3.79 (dd, J = 8.6, 5.4 Hz, 2 H), 4.23 (t, 2 H), 4.50 (d, 1 H), 5.47 (s, 2 H), 7.54 (s, 1 H), 8.05 (s, 1 H), 8.31-8.41 (m, 1 H), 8.54 (d, 1 H), 8.64 (s, 1 H), 9.82 (s, 1 H).<br>UPLC-MS (Method A2): Rt = 1.09 min<br>MS (ESIpos): m/z = 633 (M(79Br) + H)+ |

* Prepared according to the stated procedure, the yield in % is indicated in brackets
[a]: The reaction was carried out in a mixture of tetrahydrofuran/N,N-dimethylformamide (5:1). 3 equivalents of triethlamine were used.
[b]: 1.3 equivalents of the pyridinecarboxylic acid were used.
[c]: 1.5 equivalents of the pyridinecarboxylic acid were used. The product was in the aqueous phase.
[d]: Preparative HPLC was carried out according to Method P1.
[e]: The product precipitated directly from the reaction mixture, was filtered off, washed repeatedly with water and dried in a drying cabinet.
**2-{[1-tert-Butoxycarbonyl)azetidin-3-yl]amino}-1,3-aminoazetidine-1-carboxylate analogously to *Bioorganic and Medicinal Chemistry Letters*, 1996, 6, 12, 1409-1414 and *Chemical and Pharmaceutical Bulletin*, 2005, 53, 4, 437-440.

Example 19

2-(Azetidin-3-ylamino)-N-{2-[2-(4-methylpiperazin-1-yl)-2-oxoethyl]-6-(trifluoromethoxy)-2H-indazol-5-yl}-1,3-thiazole-4-carboxamide

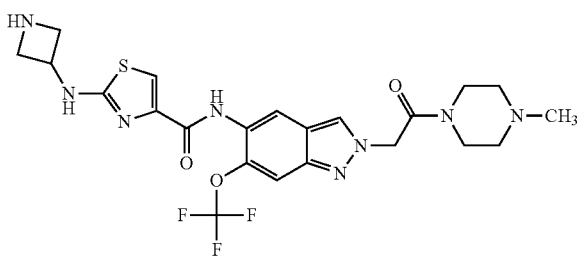 [SMILES: CN1CCN(C(=O)Cn2cc3cc(NC(=O)c4csc(NC5CNC5)n4)c(OC(F)(F)F)cc3n2)CC1]

21 mg (0.03 mmol) of tert-butyl 3-{[4-({2-[2-(4-methyl-piperazin-1-yl)-2-oxoethyl]-6-(trifluoromethoxy)-2H-indazol-5-yl}carbamoyl)-1,3-thiazol-2-yl]amino}azetidine-1-carboxylate (Example 18) were dissolved in 1 ml of dichloromethane, and 25 µl (0.03 mmol) of trifluoroacetic acid were added. The reaction mixture was stirred at 25° C. for 24 h. The mixture was then diluted with more dichloromethane and washed with saturated sodium bicarbonate solution and with saturated sodium chloride solution. The mixture was then filtered through a hydrophobic filter and concentrated. The residue was dried under reduced pressure. This gave 7 mg (31% of theory) of the title compound.

UPLC-MS (Method A2): $R_t$=0.86 min
MS (ESIpos): m/z=539 (M+H)$^+$
$^1$H-NMR (400 MHz, DMSO-d6): δ=2.21 (s, 3H), 2.29 (br. s., 2H), 2.38 (br. s., 2H), 3.42-3.49 (m, 4H), 3.54 (br. s., 2H), 3.69-3.73 (m, 1H), 5.50 (s, 2H), 7.49 (s, 1H), 7.72 (s, 1H), 8.42 (s, 1H), 8.64 (s, 1H), 9.58 (s, 1H).

Example 20

N-{6-Cyano-2-[2-(4-methylpiperazin-1-yl)-2-oxoethyl]-2H-indazol-5-yl}-6-(trifluoromethyl)pyridine-2-carboxamide

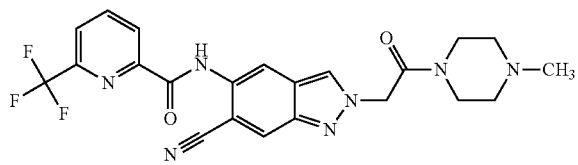 [SMILES: CN1CCN(C(=O)Cn2cc3cc(NC(=O)c4cccc(C(F)(F)F)n4)c(C#N)cc3n2)CC1]

50 mg (0.10 mmol) of N-{6-bromo-2-[2-(4-methylpiperazin-1-yl)-2-oxoethyl]-2H-indazol-5-yl}-6-(trifluoromethyl)pyridine-2-carboxamide (Example 15), 5 mg (0.005 mmol) of tetrakis(triphenylphosphine)palladium(0) and 12 mg (0.10 mmol) of zinc cyanide were initially charged in a microwave vessel and suspended in 1 ml of N,N-dimethylformamide. The reaction mixture was stirred in the microwave at 150° C. for 15 minutes. Since the reaction was still incomplete, another 5 mg (0.005 mmol) of tetrakis(triphenylphosphine)palladium(0) and 5.5 mg (0.05 mmol) of zinc cyanide were added and the mixture was stirred in the microwave at 150° C. for a further 30 minutes. The reaction mixture was diluted with ethyl acetate and washed with water and saturated sodium chloride solution. The solution was then filtered through a hydrophobic filter and concentrated. The crude product was dissolved in 2.5 ml of N,N-dimethylformamide and purified by preparative HPLC according to Method P1. The product fraction was lyophilized. This gave 25 mg (56% of theory) of the title compound.

LC-MS (Method A3): $R_t$=1.07 min
MS (ESIpos): m/z=472 (M+H)$^+$
$^1$H-NMR (400 MHz, DMSO-d6): δ=2.22 (s, 3H), 2.27-2.33 (m, 2H), 2.36-2.42 (m, 2H), 3.44-3.50 (m, 2H), 3.52-3.58 (m, 2H), 5.59 (s, 2H), 8.21-8.26 (m, 2H), 8.37-8.43 (m, 2H), 8.43-8.47 (m, 1H), 8.51 (d, 1H), 10.66 (s, 1H).

Example 21

6'-Methyl-N-{2-[2-(4-methylpiperazin-1-yl)-2-oxoethyl]-2H-indazol-5-yl}-2,3'-bipyridine-6-carboxamide

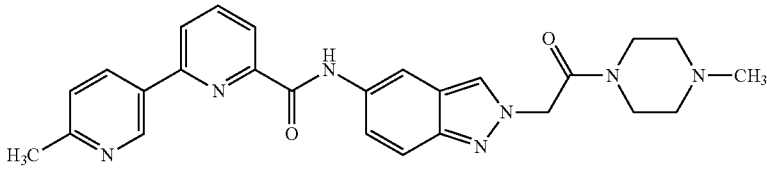

75 mg (0.16 mmol) of 6-bromo-N-{2-[2-(4-methylpiperazin-1-yl)-2-oxoethyl]-2H-indazol-5-yl}pyridine-2-carboxamide (Example 231) were dissolved in a degassed mixture of 1.73 ml of dioxane and 0.25 ml of water, and 45 mg (0.33 mmol) of (6-methylpyridin-3-yl)boronic acid, 13 mg (0.02 mmol) of 1,1'-bis(diphenylphosphino)ferrocenepalladium(II) dichloride and 52 mg (0.49 mmol) of sodium carbonate were added. The reaction mixture was stirred in the microwave at 105° C. for 90 minutes. The reaction mixture was then filtered and saturated ammonium chloride solution and dichloromethane were added to the filtrate. The phases were separated and the organic phase was washed with saturated sodium chloride solution, filtered through a hydrophobic filter and concentrated. The crude product was dissolved in 2.5 ml of N,N-dimethylformamide and purified by preparative HPLC according to Method P1. The product fraction was lyophilized. This gave 40 mg (52% of theory) of the title compound.

LC-MS (Method A3): $R_t$=0.46 min
MS (ESIpos): m/z=470 (M+H)$^+$
$^1$H NMR (300 MHz, DMSO-d6): δ=2.22 (s, 3H), 2.31 (br. s., 2H), 2.39 (br. s., 2H), 2.57 (s, 3H), 3.48 (br. s., 2H), 3.55 (d, 2H), 5.47 (s, 2H) 7.44 (d, 1H), 7.62 (s, 2H), 8.08-8.20 (m, 2H), 8.26-8.32 (m, 2H), 8.34 (s, 1H), 8.68 (dd, 1H), 9.43 (d, 1H), 10.54 (s, 1H).

Example 22

5'-Methyl-N-{2-[2-(4-methylpiperazin-1-yl)-2-oxo-ethyl]-2H-indazol-5-yl}-2,3'-bipyridine-6-carboxamide

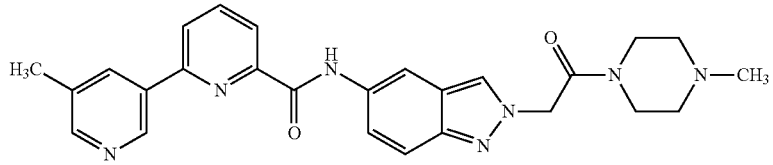

Analogously to Example 21, 75 mg (0.16 mmol) of 6-bromo-N-{2-[2-(4-methylpiperazin-1-yl)-2-oxoethyl]-2H-indazol-5-yl}pyridine-2-carboxamide were stirred with 45 mg (0.33 mmol) of (5-methylpyridin-3-yl)boronic acid, 13 mg (0.02 mmol) of 1,1'-bis(diphenylphosphino)ferrocenepalladium(II) dichloride and 52 mg (0.49 mmol) of sodium carbonate in a degassed mixture of 1.73 ml of dioxane and 0.25 ml of water in the microwave at 105° C. for 90 minutes. Work-up and preparative HPLC according to Method P1 gave 41 mg (53% of theory) of the title compound.

LC-MS (Method A3): $R_t$=0.51 min
MS (ESIpos): m/z=470 (M+H)$^+$
$^1$H NMR (300 MHz, DMSO-d6): δ=2.23 (s, 3H), 2.32 (br. s., 2H), 2.41 (br. s., 2H), 2.45 (s, 3H), 3.48 (br. s., 2H), 3.56 (br. s., 2H), 5.47 (s, 2H), 7.62 (s, 2H), 8.11-8.23 (m, 2H), 8.27-8.37 (m, 3H), 8.55 (s, 1H), 8.60 (s, 1H), 9.38 (d, 1H), 10.55 (s, 1H).

Example 23

4'-Methyl-N-{2-[2-(4-methylpiperazin-1-yl)-2-oxo-ethyl]-2H-indazol-5-yl}-2,3'-bipyridine-6-carboxamide

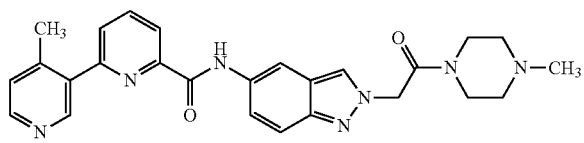 [SMILES: Cc1ccncc1-c1cccc(C(=O)Nc2ccc3nn(CC(=O)N4CCN(C)CC4)cc3c2)n1]

Analogously to Example 21, 75 mg (0.16 mmol) of 6-bromo-N-{2-[2-(4-methylpiperazin-1-yl)-2-oxoethyl]-2H-indazol-5-yl}pyridine-2-carboxamide were stirred with 45 mg (0.33 mmol) of (4-methylpyridin-3-yl)boronic acid, 13 mg (0.02 mmol) of 1,1'-bis(diphenylphosphino)ferrocenepalladium(II) dichloride and 52 mg (0.49 mmol) of sodium carbonate in a degassed mixture of 1.73 ml of dioxane and 0.25 ml of water in the microwave at 105° C. for 90 minutes. Work-up and preparative HPLC according to Method P1 gave 16 mg (21% of theory) of the title compound.

LC-MS (Method A3): $R_t$=0.45 min
MS (ESIpos): m/z=470 (M+H)$^+$
$^1$H-NMR (300 MHz, DMSO-d6): δ=2.21 (s, 3H), 2.30 (br. s., 2H), 2.38 (br. s., 2H), 3.47 (br. s., 2H), 3.54 (d, 2H), 5.45 (s, 2H), 7.42 (d, 1H), 7.57 (d, 2H), 7.91 (t, 1H), 8.19 (d, 2H), 8.28 (s, 1H), 8.34 (s, 1H), 8.54 (d, 1H), 8.78 (s, 1H), 10.41 (s, 1H).

Example 24

6'-Methoxy-N-{2-[2-(4-methylpiperazin-1-yl)-2-oxoethyl]-2H-indazol-5-yl}-2,3'-bipyridine-6-carboxamide

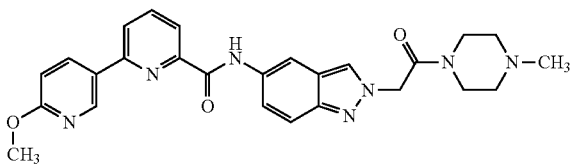 [SMILES: COc1ccc(-c2cccc(C(=O)Nc3ccc4nn(CC(=O)N5CCN(C)CC5)cc4c3)n2)cn1]

Analogously to Example 21, 50 mg (0.11 mmol) of 6-bromo-N-{2-[2-(4-methylpiperazin-1-yl)-2-oxoethyl]-2H-indazol-5-yl}pyridine-2-carboxamide were stirred with 33 mg (0.22 mmol) of (6-methoxypyridin-3-yl)boronic acid, 9 mg (0.01 mmol) of 1,1'-bis(diphenylphosphino)ferrocenepalladium(II) dichloride and 35 mg (0.33 mmol) of sodium carbonate in a degassed mixture of 1.15 ml of dioxane and 0.17 ml of water in the microwave at 105° C. for 90 minutes. Work-up and preparative HPLC according to Method P1 gave 28 mg (52% of theory) of the title compound.

LC-MS (Method A3): $R_t$=0.74 min
MS (ESIpos): m/z=486 (M+H)$^+$
$^1$H-NMR (400 MHz, DMSO-d6): δ=2.21 (s, 3H), 2.30 (t, 2H), 2.38 (t, 2H), 3.45-3.52 (m, 2H), 3.52-3.60 (m, 2H), 3.96 (s, 3H), 5.46 (s, 2H), 6.96-7.01 (m, 1H), 7.58-7.66 (m, 2H), 8.07-8.11 (m, 1H), 8.11-8.16 (m, 1H), 8.24 (dd, 1H), 8.30 (s, 1H), 8.32-8.34 (m, 1H), 8.74 (dd, 1H), 9.22 (d, 1H), 10.52 (s, 1H).

Example 25

6'-Acetamido-N-{2-[2-(4-methylpiperazin-1-yl)-2-oxoethyl]-2H-indazol-5-yl}-2,3'-bipyridine-6-carboxamide

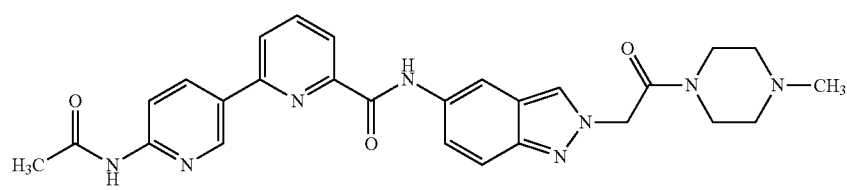 [SMILES: CC(=O)Nc1ccc(-c2cccc(C(=O)Nc3ccc4nn(CC(=O)N5CCN(C)CC5)cc4c3)n2)cn1]

Analogously to Example 21, 50 mg (0.11 mmol) of 6-bromo-N-{2-[2-(4-methylpiperazin-1-yl)-2-oxoethyl]-2H-indazol-5-yl}pyridine-2-carboxamide were stirred with 57 mg (0.22 mmol) of N-[5-(4,4,5,5-tetramethyl-1,3,2-dioxaborolan-2-yl)pyridin-2-yl]acetamide, 9 mg (0.01 mmol) of 1,1'-bis(diphenylphosphino)ferrocenepalladium(II) dichloride and 35 mg (0.33 mmol) of sodium carbonate in a degassed mixture of 1.15 ml of dioxane and 0.17 ml of water in the microwave at 105° C. for 90 minutes. Work-up and preparative HPLC according to Method P1 gave 21 mg (37% of theory) of the title compound.

LC-MS (Method A3): $R_t$=0.59 min
MS (ESIpos): m/z=513 (M+H)$^+$
1H NMR (400 MHz, DMSO-d6): δ=2.15 (s, 3H), 2.21 (s, 3H), 2.27-2.34 (m, 2H), 2.35-2.41 (m, 2H), 3.44-3.51 (m, 2H), 3.52-3.58 (m, 2H), 5.46 (s, 2H), 7.58-7.68 (m, 2H), 8.09-8.12 (m, 1H), 8.12-8.17 (m, 1H), 8.23-8.29 (m, 2H), 8.30 (s, 1H), 8.34 (s, 1H), 8.79 (dd, 1H), 9.32 (dd, 1H), 10.53 (s, 1H), 10.69 (s, 1H).

Example 26

N-{2-[2-(4-Methylpiperazin-1-yl)-2-oxoethyl]-2H-indazol-5-yl}-6'-nitro-2,3'-bipyridine-6-carboxamide

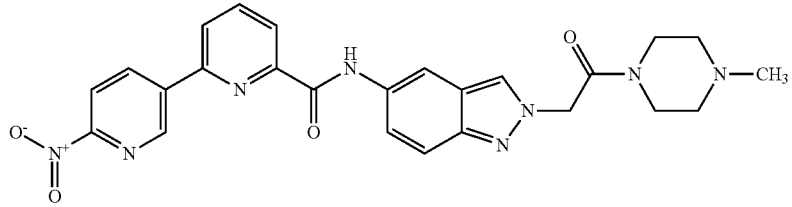 [SMILES: CN1CCN(C(=O)Cn2cc3cc(NC(=O)c4cccc(-c5ccc([N+](=O)[O-])nc5)n4)ccc3n2)CC1]

Analogously to Example 21, 75 mg (0.16 mmol) of 6-bromo-N-{2-[2-(4-methylpiperazin-1-yl)-2-oxoethyl]-2H-indazol-5-yl}pyridine-2-carboxamide were stirred with 82 mg (0.33 mmol) of 2-nitro-5-(4,4,5,5-tetramethyl-1,3,2-dioxaborolan-2-yl)pyridine, 13 mg (0.02 mmol) of 1,1'-bis(diphenylphosphino)ferrocenepalladium(II) dichloride and 52 mg (0.49 mmol) of sodium carbonate in a degassed mixture of 1.73 ml of dioxane and 0.25 ml of water in the microwave at 105° C. for 90 minutes. Work-up and preparative HPLC according to Method P1 gave 26 mg (32% of theory) of the title compound.

UPLC-MS (Method A1): Rt=0.78 min
MS (ESIpos): m/z=501 (M+H)$^+$
$^1$H-NMR (300 MHz, DMSO-d6): δ=2.22 (s, 3H), 2.31 (br. s., 2H), 2.39 (br. s., 2H), 3.48 (br. s., 2H), 3.56 (br. s., 2H), 5.47 (s, 2H), 7.63 (s, 2H), 8.22-8.38 (m, 4H), 8.45-8.55 (m, 2H), 9.22 (dd, 1H), 9.72 (d, 1H), 10.63 (s, 1H).

Example 27

6'-Amino-N-{2-[2-(4-methylpiperazin-1-yl)-2-oxoethyl]-2H-indazol-5-yl}-2,3'-bipyridine-6-carboxamide 20 mg (0.04 mmol) of N-{2-[2-(4-methylpiperazin-1-yl)-2-oxoethyl]-2H-indazol-5-yl}-6'-nitro-2,3'-bipyridine-6-carboxamide were dissolved in 2.5 ml of methanol, 4 mg (0.004 mmol, 10%) of palladium on carbon were added and the mixture was hydrogenated under a hydrogen atmosphere of 1 bar for 4 h. The reaction mixture was filtered off through Celite, the filter cake was washed repeatedly with methanol and the filtrate was concentrated and dried under reduced pressure. This gave 8 mg (43% of theory) of the title compound.

UPLC-MS (Method A1): Rt=0.81 min
MS (ESIpos): m/z=471 (M+H)$^+$
$^1$H NMR (400 MHz, METHANOL-d4): δ=2.34 (s, 3H), 2.43-2.49 (m, 2H), 2.53 (br. s., 2H), 3.66 (br. s., 4H), 5.46 (s, 2H), 6.73 (d, 1H), 7.51-7.58 (m, 1H), 7.60-7.67 (m, 1H), 7.94-8.04 (m, 2H), 8.07 (d, 1H), 8.21 (s, 1H), 8.34 (br. s., 2H), 8.55 (s, 1H), 8.77 (s, 1H).

General Procedure 2a 1.0 equivalent of the respective intermediate, 1.0 equivalent of 1-hydroxy-1H-benzotriazole hydrate and 2.0 equivalents of 1-(3-dimethylaminopropyl)-3-ethylcarbodiimide hydrochloride were stirred in 3 ml of tetrahydrofuran and 0.33 ml of dimethylformamide at 25° C. for 30 min. 1.5 equivalents of the amine were then added and the mixture was stirred at 25° C. for 30 min. The mixture was poured into 50 ml of water, filtered off with suction, washed with water and dried.

General Procedure 2b 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride and 3.0 equivalents of triethylamine were stirred in 1.5 ml of N,N-dimethylformamide at 25° C. for 30 min 1.2 equivalents of the amine were then added. The reaction mixture was diluted with a further 1.0 ml of N,N-dimethylformamide and purified by preparative HPLC according to Method P1.

General Procedure 2c 1.0 equivalent of the respective intermediate, 1.0 equivalent of 1-hydroxy-1H-benzotriazole hydrate, 2.0 equivalents

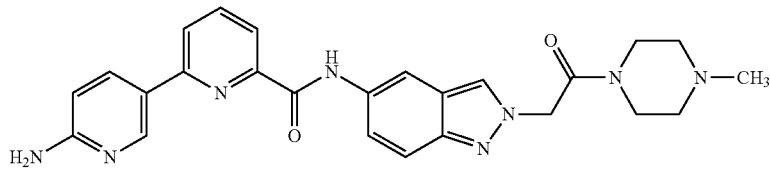

of 1-(3-dimethylaminopropyl)-3-ethylcarbodiimide hydrochloride, 3.0 equivalents of triethylamine and 1.2 equivalents of the amine were stirred in tetrahydrofuran at 25° C. for 18 h. Water was added to the reaction mixture. The solid was filtered off with suction, washed with water and diethyl ether and dried.

General Procedure 2d 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 3.0 equivalents of triethylamine and 1.5 equivalents of the amine were stirred in tetrahydrofuran at 25° C. for 18 h. The reaction solution was diluted with water and extracted with ethyl acetate. The combined organic phases were concentrated and the crude product was purified by preparative HPLC according to Method P4.

General Procedure 2e 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 3.0 equivalents of triethylamine and 1.3 equivalents of the amine were stirred in tetrahydrofuran at 25° C. for 18 h. The reaction mixture was diluted with water and extracted with ethyl acetate. The combined organic phases were concentrated, and 1 ml of dimethyl sulphoxide was added. The solid was filtered off with suction, washed three times with in each case 0.5 ml of dimethyl sulphoxide and three times with diethyl ether and dried. The filtrate was concentrated and purified by preparative HPLC according to Method P2. The resulting product fraction was combined with the solid.

General Procedure 2f 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 4.0 equivalents of triethylamine and 1.2 equivalents of the amine were stirred in tetrahydrofuran at 25° C. for 18 h. The precipitate formed was filtered off and washed with tetrahydrofuran. The solid was triturated with methyl tert-butyl ether and ethyl acetate and then dissolved in dichloromethane, and water was added. The aqueous phase was extracted with dichloromethane and the combined organic phases were washed with saturated sodium chloride solution and dried over sodium sulphate. After filtration, the solution was concentrated and the resulting product was dried.

General Procedure 2g 1.0 equivalent of the respective intermediate, 1.0 equivalent of 1-hydroxy-1H-benzotriazole hydrate, 2.0 equivalents of 1-(3-dimethylaminopropyl)-3-ethylcarbodiimide hydrochloride, 3.0 equivalents of triethylamine and 1.3 equivalents of the amine were stirred in tetrahydrofuran at 50° C. for 18 h. Water and ethyl acetate were added to the reaction mixture. The solid was filtered off with suction, washed with water and diethyl ether and dried.

TABLE 2

Examples 28-71
The exemplary compounds were prepared by the general experimental procedures 2a-2g from the appropriate intermediates and amines.

| Ex. No. | Structure/Name | Prepared from | * see key | 1H-NMR/LC-MS |
|---|---|---|---|---|
| 28 | 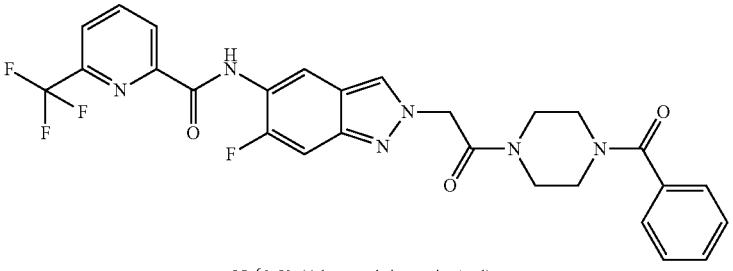<br>N-{2-[2-(4-benzoylpiperazin-1-yl)-2-oxoethyl]-6-fluoro-2H-indazol-5-yl}-6-(trifluoromethyl)pyridine-2-carboxamide | 9-1 and phenyl (piperazin-1-yl)methanone | 2a (94%) | (300 MHz, DMSO-d6): δ = 3.38-3.75 (m, 8H), 5.51 (s, 2H), 7.40-7.56 (m, 6H), 8.19-8.26 (m, 1H), 8.35-8.49 (m, 4H), 10.24 (m, 1H). UPLC-MS (Method A1): Rt = 1.15 min MS (ESIpos): m/z = 555 (M + H)+ |
| 29 | 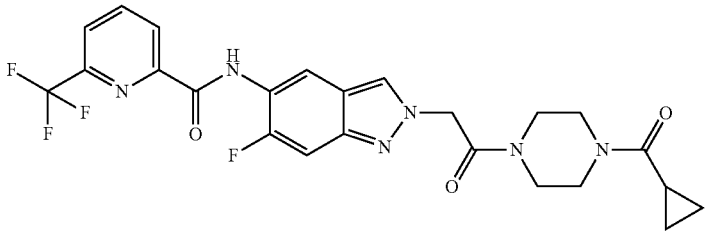 [SMILES: O=C(Nc1cc2cn(CC(=O)N3CCN(C(=O)C4CC4)CC3)nc2cc1F)c1cccc(C(F)(F)F)n1]<br>N-(2-{2-[4-(cyclopropylcarbonyl)piperazin-1-yl]-2-oxoethyl}-6-fluoro-2H-indazol-5-yl)-6-(trifluoromethyl)pyridine-2-carboxamide | 9-1 and cyclopropyl (piperazin-1-yl)methanone | 2a (95%) [a] | (300 MHz, DMSO-d6): δ = 0.69-0.81 (m, 4H), 2.00 (s br, 1H), 3.40-3.82 (m, 8H), 5.52 (s, 2H), 7.53 (d, 1H), 8.22 (m, 1H), 8.36-8.49 (m, 4H), 10.25 (m, 1H). UPLC-MS (Method A1): Rt = 1.09 min MS (ESIpos): m/z = 519 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | 1H-NMR/LC-MS |
|---|---|---|---|---|
| 30 | 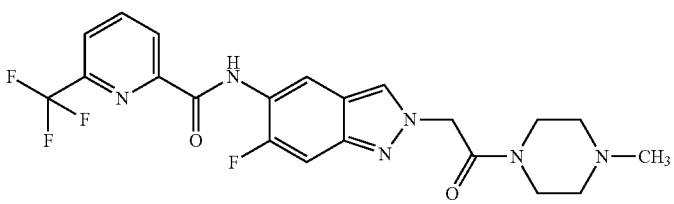 [SMILES: CN1CCN(C(=O)Cn2cc3cc(NC(=O)c4cccc(C(F)(F)F)n4)c(F)cc3n2)CC1]<br>N-{6-fluoro-2-[2-(4-methylpiperazin-1-yl)-2-oxoethyl]-2H-indazol-5-yl}-6-(trifluoromethyl)pyridine-2-carboxamide | 9-1 and 1-methylpiperazine | 2a (41%) | (300 MHz, DMSO-d6): δ = 2.21 (s, 3H), 2.29 (m, 2H), 2.38 (m, 2H), 3.47 (m, 2H), 3.55 (m, 2H), 5.47 (s, 2H), 7.52 (d, 1H), 8.22 (m, 1H), 8.34-8.48 (m, 4H), 10.24 (m, 1H).<br>UPLC-MS (Method A1): Rt = 0.93 min<br>MS (ESIpos): m/z = 465 (M + H)+ |
| 31 | 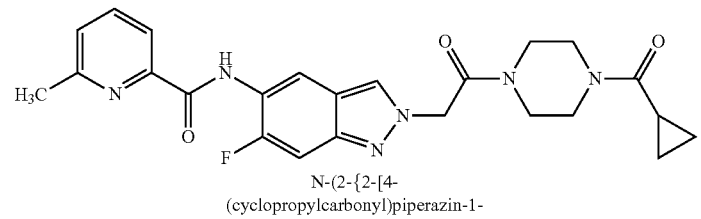<br>N-(2-{2-[4-(cyclopropylcarbonyl)piperazin-1-yl]-2-oxoethyl}-6-fluoro-2H-indazol-5-yl)-6-methylpyridine-2-carboxamide | 9-2 and cyclopropyl(piperazin-1-yl)methanone | 2a (88%) [a] | (300 MHz, DMSO-d6): δ = 0.68-0.82 (m, 4H), 2.01 (s br, 1H), 2.63 (s, 3H), 3.40-3.82 (m, 8H), 5.52 (s, 2H), 7.49-7.62 (m, 2H), 7.95-8.05 (m, 2H), 8.38 (s, 1H), 8.55 (d, 1H), 10.39 (d, 1H).<br>UPLC-MS (Method A1): Rt = 1.02 min<br>MS (ESIpos): m/z = 465 (M + H)+ |
| 32 | 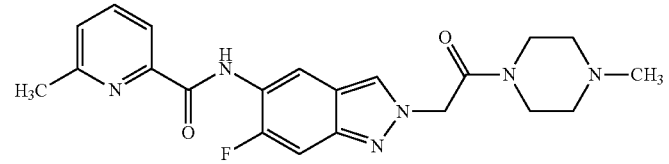<br>N-{6-fluoro-2-[2-(4-methylpiperazin-1-yl)-2-oxoethyl]-2H-indazol-5-yl}-6-methylpyridine-2-carboxamide | 9-2 and 1-methylpiperazine | 2a (68%) | (300 MHz, DMSO-d6): δ = 2.21 (s, 3H), 2.29 (m, 2H), 2.38 (m, 2H), 2.63 (s, 3H), 3.46 (m, 2H), 3.53 (m, 2H), 5.45 (s, 2H), 7.47-7.62 (m, 2H), 7.93 (m, 2H), 8.36 (s, 1H), 8.55 (d, 1H), 10.55 (s, 1H).<br>UPLC-MS (Method A1): Rt = 0.81 min<br>MS (ESIpos): m/z = 411 (M + H)+ |
| 33 | 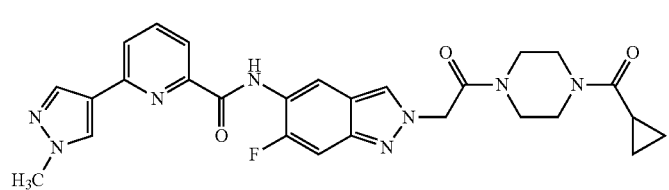 [SMILES: Cn1cc(-c2cccc(C(=O)Nc3cc4cn(CC(=O)N5CCN(C(=O)C6CC6)CC5)nc4cc3F)n2)cn1]<br>N-(2-{2-[4-(cyclopropylcarbonyl)piperazin-1-yl]-2-oxoethyl}-6-fluoro-2H-indazol-5-yl)-6-(1-methyl-1H-pyrazol-4-yl)pyridine-2-carboxamide | 9-3 and cyclopropyl(piperazin-1-yl)methanone | 2a (82%) [a] | (300 MHz, DMSO-d6): δ = 0.68-0.83 (m, 4H), 2.02 (s br, 1H), 3.42-3.85 (m, 8H), 3.93 (s, 3H), 5.53 (s, 2H), 7.54 (d, 1H), 7.87-8.09 (m, 3H), 8.23 (s, 1H), 8.38 (m, 2H), 8.54 (s, 1H), 10.52 (s, 1H).<br>UPLC-MS (Method A1): Rt = 0.93 min<br>MS (ESIpos): m/z = 531 (M + H)+ |
| 34 | 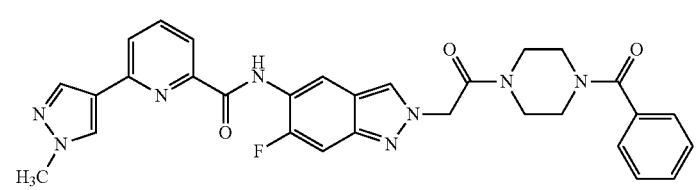<br>N-{2-[2-(4-benzoylpiperazin-1-yl)-2-oxoethyl]-6-fluoro-2H-indazol-5-yl}-6-(1-methyl-1H-pyrazol-4-yl)pyridine-2-carboxamide | 9-3 and phenyl(piperazin-1-yl)methanone | 2a (47%) [b] | (300 MHz, DMSO-d6): δ = 3.40-3.79 (m, 8H), 3.94 (s, 3H), 5.51 (s, 2H), 7.41-7.57 (m, 6H), 7.93 (t, 2H), 8.04 (t, 1H), 8.22 (s, 1H), 8.39 (m, 2H), 8.52 (s, 1H), 10.51 (s, 1H).<br>UPLC-MS (Method A1): Rt = 1.00 min (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 35 | N-{6-fluoro-2-[2-(4-methylpiperazin-1-yl)-2-oxoethyl]-2H-indazol-5-yl}-6-(1-methyl-1H-pyrazol-4-yl)pyridine-2-carboxamide | 9-3 and 1-methyl-piperazine | 2a (14%) [b] | (300 MHz, DMSO-d6): δ = 2.21 (s, 3H), 2.30 (m, 2H), 2.38 (m, 2H), 3.47 (m, 2H), 3.55 (m, 2H), 3.93 (s, 3H), 5.47 (s, 2H), 7.52 (d, 1H), 7.93 (t, 2H), 8.04 (t, 1H), 8.22 (s, 1H), 8.39 (m, 2H), 8.52 (s, 1H), 10.50 (s, 1H). UPLC-MS (Method A1): Rt = 0.74 min MS (ESIpos): m/z = 477 (M + H)+ |
| 36 | N-{2-[2-(4-benzoylpiperazin-1-yl)-2-oxoethyl]-6-fluoro-2H-indazol-5-yl}-5-fluoro-6-(1-methyl-1H-pyrazol-4-yl)pyridine-2-carboxamide | 9-4 and phenyl (piperazin-1-yl)methanone | 2a (64%) | (300 MHz, DMSO-d6): δ = 3.38-3.76 (m, 8H), 3.96 (s, 3H), 5.51 (s, 2H), 7.41-7.56 (m, 6H), 7.93-8.05 (m, 2H), 8.25-8.31 (m, 2H), 8.40 (s, 1H), 8.53 (m, 1H), 10.40 (s, 1H). UPLC-MS (Method A1): Rt = 1.07 min MS (ESIpos): m/z = 585 (M + H)+ |
| 37 | N-(2-{2-[4-(cyclopropylcarbonyl)piperazin-1-yl]-2-oxoethyl}-6-fluoro-2H-indazol-5-yl)-5-fluoro-6-(1-methyl-1H-pyrazol-4-yl)pyridine-2-carboxamide | 9-4 and cyclopropyl (piperazin-1-[a]yl) methanone | 2a (59%) | (300 MHz, DMSO-d6): δ = 0.69-0.83 (m, 4H), 2.01 (s br, 1H), 3.41-3.85 (m, 8H), 3.97 (s, 3H), 5.52 (s, 2H), 7.52 (d, 1H), 7.93-8.06 (m, 2H), 8.28 (m, 2H), 8.39 (s, 1H), 8.53 (s, 1H), 10.40 (s, 1H). UPLC-MS (Method A1): Rt = 1.00 min MS (ESIpos): m/z = 549 (M + H)+ |
| 38 | N-{2-[2-(4-benzoylpiperazin-1-yl)-2-oxoethyl]-6-fluoro-2H-indazol-5-yl}-6-(morpholin-4-yl)pyridine-2-carboxamide | 9-5 and phenyl (piperazin-1-yl)methanone | 2a (78%) | (300 MHz, DMSO-d6): δ = 3.41-3.82 (m, 16H), 5.50 (s, 2H), 7.15 (d, 1H), 7.47 (m, 7H), 7.81 (t, 1H), 8.37 (s, 1H), 8.48 (d, 1H), 10.27 (m, 1H). UPLC-MS (Method A1): Rt = 1.06 min MS (ESIpos): m/z = 572 (M + H)+ |
| 39 | N-(2-{2-[4-(cyclopropylcarbonyl)piperazin-1-yl]-2-oxoethyl}-6-fluoro-2H-indazol-5-yl)-6-(morpholin-4-yl)pyridine-2-carboxamide | 9-5 and cyclopropyl (piperazin-1-yl)methanone | 2a (91%) [a] | (300 MHz, DMSO-d6): δ = 0.67-0.83 (m, 4H), 2.01 (s br, 1H), 3.44-3.81 (m, 16H), 5.50 (s, 2H), 7.15 (d, 1H), 7.44-7.55 (m, 2H), 7.81 (t, 1H), 8.37 (s, 1H), 8.48 (d, 1H), 10.27 (m, 1H). UPLC-MS (Method A1): Rt = 1.01 min MS (ESIpos): m/z = 536 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | $^1$H-NMR/LC-MS |
|---|---|---|---|---|
| 40 | 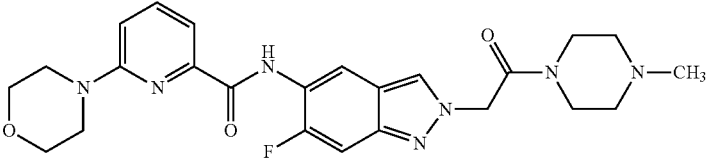 [SMILES: CN1CCN(C(=O)Cn2cc3cc(NC(=O)c4cccc(N5CCOCC5)n4)c(F)cc3n2)CC1]<br>N-{6-fluoro-2-[2-(4-methylpiperazin-1-yl)-2-oxoethyl]-2H-indazol-5-yl}-6-(morpholin-4-yl)pyridine-2-carboxamide | 9-5 and 1-methyl-piperazine | 2a (64%) | (300 MHz, DMSO-d6): δ = 2.21 (s, 3H), 2.30 (m, 2H), 2.38 (m, 2H), 3.47 (m, 2H), 3.55 (m, 2H), 3.59 (m, 4H), 3.76 (m, 4H), 5.45 (s, 2H), 7.15 (d, 1H), 7.44-7.53 (m, 2H), 7.81 (tr, 1H), 8.36 (s, 1H), 8.47 (d, 1H), 10.27 (m, 1H).<br>UPLC-MS (Method A1): Rt = 0.79 min<br>MS (ESIpos): m/z = 482 (M + H)+ |
| 41 | 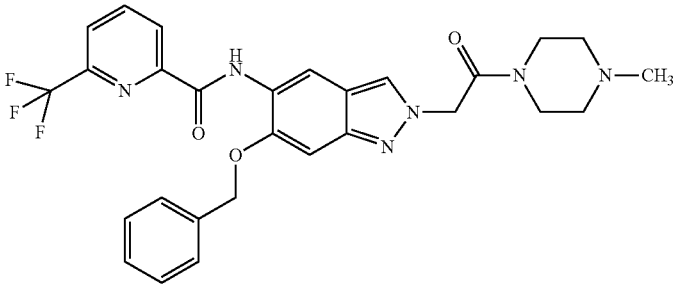 [SMILES: CN1CCN(C(=O)Cn2cc3cc(NC(=O)c4cccc(C(F)(F)F)n4)c(OCc4ccccc4)cc3n2)CC1]<br>N-{6-(benzyloxy)-2-[2-(4-methylpiperazin-1-yl)-2-oxoethyl]-2H-indazol-5-yl}-6-(trifluoromethyl)pyridine-2-carboxamide | 9-6 and 1-methyl-piperazine | 2b (72%) | (400 MHz, DMSO-d6): δ = 2.21 (s, 3 H), 2.26-2.33 (m, 2 H), 2.34-2.43 (m, 2 H), 3.43-3.50 (m, 2 H), 3.51-3.59 (m, 2 H), 5.31 (s, 2 H), 5.39 (s, 2 H), 7.30 (s, 1 H), 7.34-7.45 (m, 3 H), 7.58 (dd, 2 H), 8.18 (dd, 1 H), 8.25 (s, 1 H), 8.35-8.44 (m, 1 H), 8.44-8.50 (m, 1 H), 8.80 (s, 1 H), 10.47 (s, 1 H).<br>LC-MS (Method A3): Rt = 0.96 min<br>MS (ESIpos): m/z = 553 (M + H)+ |
| 42 | 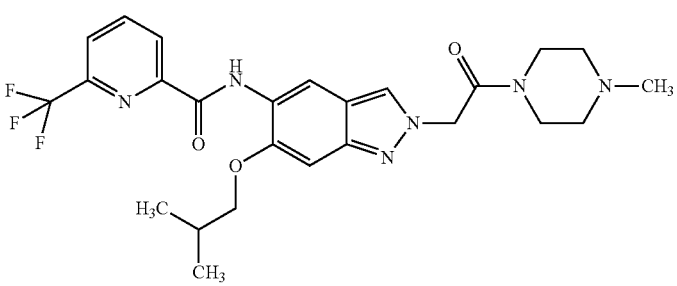 [SMILES: CC(C)COc1cc2nn(CC(=O)N3CCN(C)CC3)cc2cc1NC(=O)c1cccc(C(F)(F)F)n1]<br>N-{6-isobutoxy-2-[2-(4-methylpiperazin-1-yl)-2-oxoethyl]-2H-indazol-5-yl}-6-(trifluoromethyl)pyridine-2-carboxamide | 9-7 and 1-methyl-piperazine | 2b (53%) | (300 MHz, DMSO-d6): δ = 1.11 (s, 3 H), 1.13 (s, 3 H), 2.17-2.23 (m, 1 H), 2.21 (s, 3 H), 2.25-2.33 (m, 2 H), 2.37 (br. s., 2 H), 3.46 (br. s., 2 H), 3.54 (br. s., 2 H), 3.96 (d, 2 H), 5.38 (s, 2 H), 7.07 (s, 1 H), 8.14-8.26 (m, 2 H), 8.34-8.45 (m, 1 H), 8.45-8.53 (m, 1 H), 8.78 (s, 1 H), 10.58 (s, 1 H).<br>LC-MS (Method A3): Rt = 1.06 min<br>MS (ESIpos): m/z = 519 (M + H)+ |
| 43 | 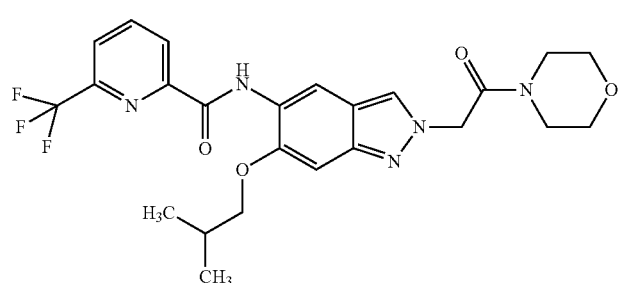<br>N-{6-isobutoxy-2[2-(morpholin-4-yl)-2-oxoethyl]-2H-indazol-5-yl}-6-(trifluoromethyl)pyridine-2-carboxamide | 9-7 and morpholine | 2b (54%) | (300 MHz, DMSO-d6): δ = 3.47 (d, 2 H), 3.52-3.68 (m, 6 H), 3.96 (d, 2 H), 5.40 (s, 2 H), 7.07 (s, 1 H), 8.19-8.25 (m, 2 H), 8.36-8.45 (m, 1 H), 8.46-8.52 (m, 1 H), 8.78 (s, 1 H), 10.58 (s, 1 H).<br>LC-MS (Method A3): Rt = 1.32 min<br>MS (ESIpos): m/z = 506 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 44 | N-(2-{2-[4-(2-hydroxypropan-2-yl)piperidin-1-yl]-2-oxoethyl}-6-isobutoxy-2H-indazol-5-yl)-6-(trifluoromethyl)pyridine-2-carboxamide | 9-7 and 2-(piperidin-4-yl)propan-2-ol | 2b (49%) | (300 MHz, DMSO-d6): δ = 1.05 (s, 6 H), 1.11 (s, 3 H), 1.13 (s, 3 H), 1.19-1.33 (m, 3 H), 1.36-1.52 (m, 1 H), 1.75 (t, 2 H), 2.11-2.25 (m, 1 H), 2.90-3.09 (m, 1 H), 3.96 (d, 2 H), 4.02 (d, 1 H), 4.18 (s, 1 H), 4.42 (d, 1 H), 5.27-5.45 (m, 2 H), 7.07 (s, 1 H), 8.18-8.25 (m, 2 H), 8.35-8.45 (m, 1 H), 8.45-8.52 (m, 1 H), 8.77 (s, 1 H), 10.58 (s, 1 H). LC-MS (Method A3): Rt = 1.34 min MS (ESIpos): m/z = 562 (M + H)+ |
| 45 | N-(2-{2-[(cyclopropylmethyl)(methyl)amino]-2-oxoethyl}-6-isobutoxy-2H-indazol-5-yl)-6-(trifluoromethyl)pyridine-2-carboxamide | 9-7 and 1-cyclopropyl-N-methyl-methanamine | 2b (54%) | (400 MHz, DMSO-d6): δ = 0.18-0.25 (m, 1 H), 0.33 (q, 1 H), 0.41-0.49 (m, 1 H), 0.50-0.58 (m, 1 H), 0.92-1.02 (m, 1 H), 1.11 (s, 3 H), 1.13 (s, 3 H), 2.19 (dt, 1 H), 2.92 (s, 1 H) +30 3.13 (s, 2 H), 3.20 (d, 1 H), 3.34 (d, 1 H), 3.96 (d, 2 H), 5.33-5.42 (m, 2 H), 7.07 (s, 1 H), 8.16-8.28 (m, 2 H), 8.41 (t, 1 H), 8.49 (d, 1 H), 8.78 (s, 1 H), 10.57 (s, 1 H). LC-MS (Method A3): Rt = 1.45 min MS (ESIpos): m/z = 504 (M + H)+ |
| 46 | N-{6-(cyclopropylmethoxy)-2-[2-(4-methylpiperazin-1-yl)-2-oxoethyl]-2H-indazol-5-yl}-6-(trifluoromethyl)pyridine-2-carboxamide | 9-8 and 1-methyl-piperazine | 2b (75%) | (400 MHz, DMSO-d6): δ = 0.39-0.51 (m, 2 H), 0.57-0.70 (m, 2 H), 1.27-1.43 (m, 1 H), 2.21 (s, 3 H), 2.29 (t, 2 H), 2.34-2.39 (m, 2 H), 3.43-3.49 (m, 2 H), 3.51-3.57 (m, 2 H), 4.03 (d, 2 H), 5.37 (s, 2 H), 7.05 (s, 1 H), 8.19-8.23 (m, 2 H), 8.41 (t, 1 H), 8.48 (d, 1 H), 8.76 (s, 1 H), 10.71 (s, 1 H). LC-MS (Method A3): Rt = 1.01 min MS (ESIpos): m/z = 517 (M + H)+ |
| 47 | N-{6-(cyclopropylmethoxy)-2-[2-(morpholin-4-yl)-2-oxoethyl]-2H-indazol-5-yl}-6-(trifluoromethyl)pyridine-2-carboxamide | 9-8 and morpholine | 2b (73%) | (400 MHz, DMSO-d6): δ = 0.40-0.48 (m, 2 H), 0.66 (dd, 2 H), 1.31-1.40 (m, 1 H), 3.43-3.50 (m, 2 H), 3.53-3.68 (m, 6 H), 4.03 (d, 2 H), 5.39 (s, 2 H), 7.05 (s, 1 H), 8.19-8.23 (m, 2 H), 8.38-8.44 (m, 1 H), 8.45-8.50 (m, 1 H), 8.76 (s, 1 H), 10.71 (s, 1 H). LC-MS (Method A3): Rt = 1.25 min MS (ESIpos): m/z = 504 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | *see key | 1H-NMR/LC-MS |
|---|---|---|---|---|
| 48 | 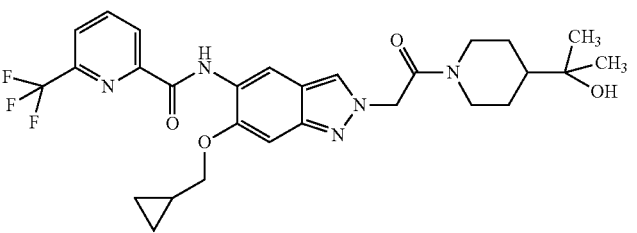 [SMILES: CC(C)(O)C1CCN(C(=O)Cn2cc3cc(NC(=O)c4cccc(C(F)(F)F)n4)c(OCC4CC4)cc3n2)CC1]<br>N-[6-(cyclopropylmethoxy)-2-{2-[4-(2-hydroxypropan-2-yl)piperidin-1-yl]-2-oxoethyl}-2H-indazol-5-yl]-6-(trifluoromethyl)pyridine-2-carboxamide | 9-8 and 2-(piperidin-4-yl)propan-2-ol | 2b (78%) | (400 MHz, DMSO-d6): δ = 0.41-0.48 (m, 2 H), 0.62-0.69 (m, 2 H), 1.05 (s, 6 H), 1.09 (d, 1 H), 1.18-1.29 (m, 2 H), 1.29-1.40 (m, 1 H), 1.40-1.51 (m, 1 H), 1.75 (t, 2 H), 2.99 (t, 1 H), 4.02 (d, 3 H), 4.16 (s, 1 H), 4.42 (d, 1 H), 5.25-5.45 (m, 2 H), 7.04 (s, 1 H), 8.17-8.24 (m, 2 H), 8.41 (t, 1 H), 8.48 (d, 1 H), 8.75 (s, 1 H), 10.70 (s, 1 H). LC-MS (Method A3): Rt = 1.27 min MS (ESIpos): m/z = 560 (M + H)+ |
| 49 | 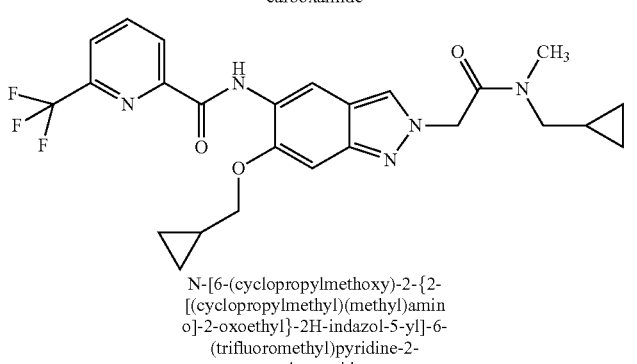<br>N-[6-(cyclopropylmethoxy)-2-{2-[(cyclopropylmethyl)(methyl)amino]-2-oxoethyl}-2H-indazol-5-yl]-6-(trifluoromethyl)pyridine-2-carboxamide | 9-8 and 1-cyclopropyl-N-methyl-methanamine | 2b (54%) | (400 MHz, DMSO-d6): δ = 0.22 (q, 1 H), 0.33 (d, 1 H), 0.41-0.48 (m, 3 H), 0.50-0.57 (m, 1 H), 0.62-0.69 (m, 2 H), 0.97 (br. s., 1 H), 1.30-1.41 (m, 1 H), 2.92 (s, 1 H) + 3.13 (s, 2 H), 3.20 (d, 1 H), 3.34 (d, 1 H), 4.03 (d, 2 H), 5.29-5.43 (m, 2 H), 7.05 (s, 1 H), 8.19-8.25 (m, 2 H), 8.41 (t, 1H), 8.48 (d, 1 H), 8.76 (s, 1H), 10.70 (s, 1 H). LC-MS (Method A3): Rt = 1.38 min MS (ESIpos): m/z = 502 (M + H)+ |
| 50 | 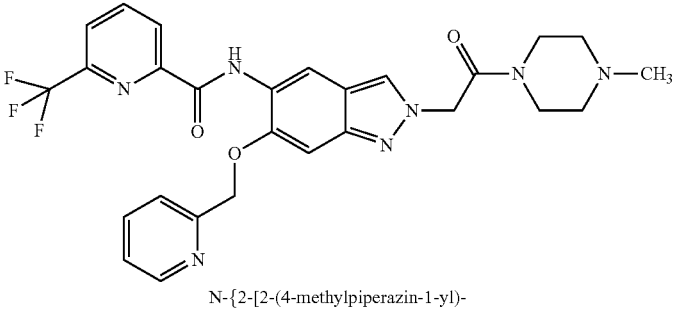<br>N-{2-[2-(4-methylpiperazin-1-yl)-2-oxoethyl]-6-(pyridin-2-ylmethoxy)-2H-indazol-5-yl}-6-(trifluoromethyl)pyridine-2-carboxamide | 9-9 and 1-methyl-piperazine | 2b (75%) | (300 MHz, DMSO-d6): δ = 2.21 (s, 3 H), 2.24-2.33 (m, 2 H), 2.37 (br. s., 2 H), 3.47 (br. s., 2 H), 3.55 (br. s., 2 H), 5.36 (s, 2 H), 5.40 (s, 2 H), 7.30 (s, 1 H), 7.36-7.47 (m, 1 H), 7.71 (d, 1 H), 7.79-7.90 (m, 1 H) 8.19 (dd, 1 H), 8.26 (s, 1 H), 8.34-8.44 (m, 1 H), 8.45-8.52 (m, 1 H), 8.62 (d, 1 H), 8.81 (s, 1 H), 10.50 (s, 1 H). LC-MS (Method A3): Rt = 0.92 min MS (ESIpos): m/z = 554 (M + H)+ |
| 51 | 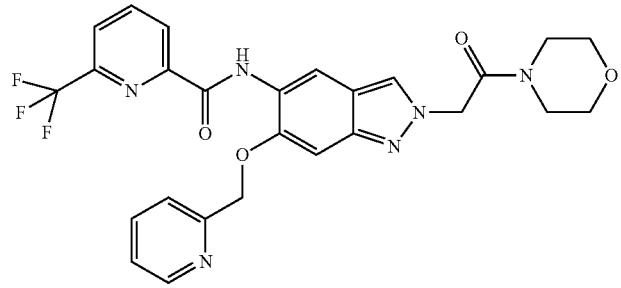 [SMILES: O=C(Nc1cc2cn(CC(=O)N3CCOCC3)nc2cc1OCc1ccccn1)c1cccc(C(F)(F)F)n1]<br>N-{2-[2-(morpholin-4-yl)-2-oxoethyl]-6-(pyridin-2-ylmethoxy)-2H-indazol-5-yl}-6-(trifluoromethyl)pyridine-2-carboxamide | 9-9 and morpholine | 2b (23%) | (400 MHz, DMSO-d6): δ = 3.40-3.52 (m, 2 H), 3.59 (d, 4 H), 3.62-3.68 (m, 2 H), 5.36 (s, 2 H), 5.41 (s, 2 H), 7.30 (s, 1 H), 7.42 (dd, 1 H), 7.70 (d, 1 H), 7.86 (td, 1 H), 8.15-8.23 (m, 1 H), 8.27 (s, 1 H), 8.39 (t, 1 H), 8.48 (d, 1 H), 8.62 (d, 1 H), 8.81 (s, 1 H), 10.50 (s, 1 H). LC-MS (Method A3): Rt = 1.11 min MS (ESIpos): m/z = 541 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 52 | 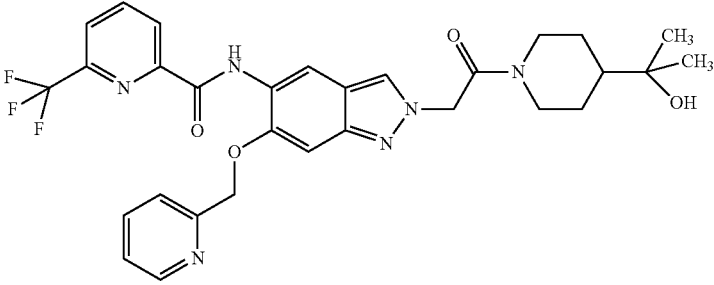 [SMILES: CC(C)(O)C1CCN(C(=O)Cn2cc3cc(NC(=O)c4cccc(C(F)(F)F)n4)c(OCc4ccccn4)cc3n2)CC1]<br>N-[2-{2-[4-(2-hydroxypropan-2-yl)piperidin-1-yl]-2-oxoethyl}-6-(pyridin-2-ylmethoxy)-2H-indazol-5-yl]-6-(trifluoromethyl)pyridine-2-carboxamide | 9-9 and 2-(piperidin-4-yl)propan-2-ol | 2b (29%) | (400 MHz, DMSO-d6): δ = 1.05 (s, 6 H), 1.17-1.34 (m, 3 H), 1.37-1.52 (m, 1 H), 1.76 (t, 2 H), 2.91-3.08 (m, 1 H), 4.04 (d, 1 H), 4.17 (s, 1 H), 4.42 (d, 1 H), 5.28-5.45 (m, 4 H), 7.29 (s, 1 H), 7.36-7.47 (m, 1 H), 7.70 (d, 1 H), 7.86 (td, 1 H), 8.19 (dd, 1 H), 8.26 (s, 1 H), 8.40 (t, 1 H), 8.48 (d, 1 H), 8.58-8.65 (m, 1 H), 8.81 (s, 1 H), 10.50 (s, 1 H).<br>LC-MS (Method A3): Rt = 1.15 min<br>MS (ESIpos): m/z = 597 (M + H)+ |
| 53 | 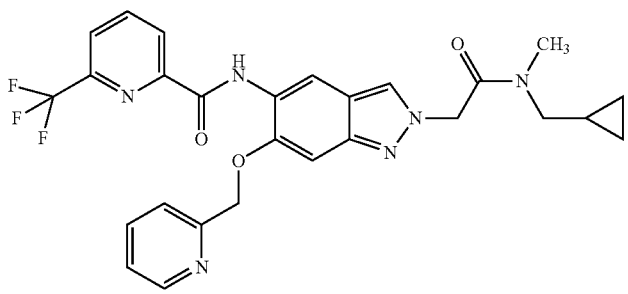 [SMILES: CN(CC1CC1)C(=O)Cn1cc2cc(NC(=O)c3cccc(C(F)(F)F)n3)c(OCc3ccccn3)cc2n1]<br>N-[2-{2-[(cyclopropylmethyl)(methyl)amino]-2-oxoethyl}-6-(pyridin-2-ylmethoxy)-2H-indazol-5-yl]-6-(trifluoromethyl)pyridine-2-carboxamide | 9-9 and 1-cyclopropyl-N-methyl-methanamine | 2b (44%) | (400 MHz, DMSO-d6): δ = 0.19-0.26 (m, 1 H), 0.30-0.37 (m, 1 H), 0.40-0.49 (m, 1 H), 0.51-0.60 (m, 1 H), 0.91-1.02 (m, 1 H), 2.93 (s, 1 H)+3.14 (s, 2 H), 3.21 (d, 1 H), 3.35 (d, 1 H), 5.36 (s, 2 H), 5.39 (s, 2 H), 7.30 (s, 1 H), 7.37-7.45 (m, 1 H), 7.70 (d, 1 H), 7.86 (td, 1 H), 8.19 (dd, 1 H), 8.27 (d, 1 H), 8.40 (t, 1 H), 8.48 (d, 1 H), 8.62 (d, 1 H), 8.81 (s, 1 H), 10.50 (s, 1 H).<br>LC-MS (Method A3): Rt = 1.24 min<br>MS (ESIpos): m/z = 539 (M + H)+ |
| 54 | 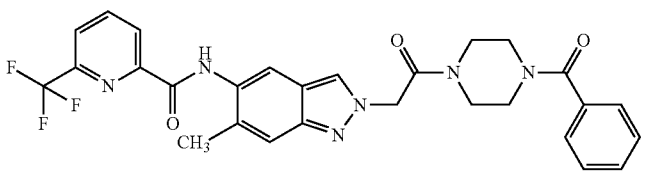<br>N-{2-[2-(4-benzoylpiperazin-1-yl)-2-oxoethyl]-6-chlor-2H-indazol-5-yl}-6-(trifluoromethyl)pyridine-2-carboxamide | 9-11 and phenyl(piperazin-1-yl)methanone | 2c (95%) | (300 MHz, DMSO-d6): δ= 3.40-3.82 (m, 8H), 5.54 (br. s., 2H), 7.41-7.52 (m, 5H), 7.91 (s, 1H), 8.23 (dd, 1H), 8.37-8.49 (m, 3H), 8.64 (s, 1H), 10.5 (s, 1H).<br>UPLC-MS (Method A1): Rt = 1.22 min<br>MS (ESIpos): m/z = 571 (M + H)+ |
| 55 | 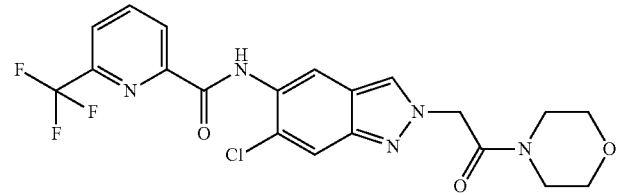 [SMILES: O=C(Nc1cc2cn(CC(=O)N3CCOCC3)nc2cc1Cl)c1cccc(C(F)(F)F)n1]<br>N-{6-chloro-2-[2-(morpholin-4-yl)-2-oxoethyl]-2H-indazol-5-yl}-6-(trifluoromethyl)pyridine-2-carboxamide | 9-11 and morpholine | 2d (44%) | (400 MHz, DMSO-d6): δ = 3.48 (d, 2H), 3.53-3.63 (m, 4H), 3.66 (d, 2H), 5.52 (s, 2H), 7.92 (s, 1H), 8.24 (d, 1H), 8.38-8.44 (m, 2H), 8.45-8.49 (m, 1H), 8.66 (s, 1H), 10.5 (br. s., 1H).<br>UPLC-MS (Method A1): Rt = 1.16 min<br>MS (ESIpos): m/z = 468 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 56 | ethyl 4-{[6-chloro-5-({[6-(trifluoromethyl)pyridin-2-yl]carbonyl}amino)-2H-indazol-2-yl]acetyl}piperazine-1-carboxylate | 9-11 and ethyl-piperazine-1-carboxylate | 2d (41%) | (500 MHz, DMSO-d6): δ = 1.21 (t, 3H), 3.37-3.63 (m, 9H), 4.08 (q, 2H), 5.54 (s, 2H), 7.92 (s, 1H), 8.24 (dd, 1H), 8.39-8.44 (m, 2H), 8.45-8.49 (m, 1H), 8.66 (s, 1H), 10.5 (s, 1H). UPLC-MS (Method A1): Rt = 1.24 min MS (ESIpos): m/z = 538 (M + H)+ |
| 57 | N-(6-chloro-2-{2-oxo-2-[4-(pyrrolidin-1-yl)piperidin-1-yl]ethyl}-2H-indazol-5-yl)-6-(trifluoromethyl)pyridine-2-carboxamide | 9-11 and 4-(pyrrolidin-1-yl)piperidine | 2d (31%) [c] | (400 MHz, DMSO-d6): δ = 1.25-1.37 (m, 1H), 1.39-1.53 (m, 1H), 1.68 (br. s., 4H), 1.78-1.95 (m, 2H), 2.19-2.30 (m, 1H), 2.87 (t, 1H), 3.19 (t, 1H), 3.88 (d, 1H), 4.10 (d, 1H), 5.49 (d, 2H), 7.91 (s, 1H), 8.23 (d, 1H), 8.38-8.44 (m, 2H), 8.45-8.49 (m, 1H), 8.66 (s, 1H), 10.5 (br. s., 1H). UPLC-MS (Method A1): Rt = 1.00 min MS (ESIpos): m/z = 535 (M + H)+ |
| 58 | N-(6-chloro-2-{2-[4-(2-hydroxypropan-2-yl)piperidin-1-yl]-2-oxoethyl}-2H-indazol-5-yl)-6-(trifluoromethyl)pyridine-2-carboxamide | 9-11 and 2-(piperidin-4-yl)propan-2-ol | 2d (32%) [d] | (400 MHz, DMSO-d6, selected signals): δ = 1.05 (s, 6H), 1.68-1.85 (m, 2H), 3.02 (t, 1H), 4.02 (d, 1H), 4.17 (s, 1H), 4.42 (d, 1H), 5.42-5.55 (m, 2H), 7.91 (s, 1H), 8.23 (d, 1H), 8.38-8.51 (m, 3H), 8.65 (s, 1H), 10.5 (s, 1H). UPLC-MS (Method A1): Rt = 1.18 min MS (ESIpos): m/z = 524 (M + H)+ |
| 59 | N-(6-chloro-2-{2-[4-(3-hydroxy-2,2-dimethylpropanoyl)piperazin-1-yl]-2-oxoethyl}-2H-indazol-5-yl)-6-(trifluoromethyl)pyridine-2-carboxamide | 9-11 and 3-hydroxy-2,2-dimethyl-1-(piperazin-1-yl)propan-1-one | 2d (39%) [e] | (400 MHz, DMSO-d6): δ = 1.18 (s, 6H), 3.39-3.72 (m, 10H), 4.61 (t, 1H), 5.54 (s, 2H), 7.92 (s, 1H), 8.24 (d, 1H), 8.38-8.44 (m, 2H), 8.45-8.50 (m, 1H), 8.66 (s, 1H), 10.5 (s, 1H). UPLC-MS (Method A1): Rt = 1.13 min MS (ESIpos): m/z = 567 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 60 | N-(6-chloro-2-{2[3-(dimethylamino)azetidin-1-yl]-2-oxoethyl}-2H-indazol-5-yl)-6-(trifluoromethyl)pyridine-2-carboxamide | 9-11 and N,N-dimethyl-azetidine-3-amine | 2e (31%) | (400 MHz, DMSO-d6): δ = 2.08 (s, 6H), 3.07-3.14 (m, 1H), 3.70 (dd, 1H), 3.92 (dd, 1H), 4.02 (dd, 1H), 4.19 (t, 1H), 5.21 (s, 2H), 7.92 (s, 1H), 8.23 (dd, 1H), 8.37-8.49 (m, 3H), 8.64 (s, 1H), 10.5 (s, 1H). UPLC-MS (Method A2): Rt = 1.13 min MS (ESIpos): m/z = 481 (M + H)+ |
| 61 | N-(6-chloro-2-{2-oxo-2-[3-(piperidin-1-yl)azetidin-1-yl]ethyl}-2H-indazol-5-yl)-6-(trifluoromethyl)pyridine-2-carboxamide | 9-11 and 1-(azetidin-3-yl)piperidine | 2e (53%) [f] | (400 MHz, CHLOROFORM-d): δ = 1.69 (br. s., 4H), 2.36 (br. s., 4H), 3.19 (br. s., 1H), 4.01-4.21 (m, 4H), 4.99-5.14 (m, 2H), 7.29 (s, 3H), 7.85 (s, 1H), 7.90-7.95 (m, 1H), 8.11-8.21 (m, 2H), 8.53 (d, 1H), 8.94 (s, 1H), 10.69-10.78 (m, 1H). UPLC-MS (Method A2): Rt = 1.28 min MS (ESIpos): m/z = 521 (M + H)+ |
| 62 | N-(6-chloro-2-{2-[4-(2-hydroxy-2-methylpropyl)piperidin-1-yl]-2-oxoethyl}-2H-indazol-5-yl)-6-(trifluoromethyl)pyridine-2-carboxamide | 9-11 and 2-methyl-1-(piperidin-4-yl)propan-2-ol | 2d (75%) [g] | (300 MHz, DMSO-d6): δ = 0.88-1.36 (m, 10H, contains singlet at 1.11 ppm), 1.64-1.90 (m, 3H), 2.59-2.74 (m, superimposed by DMSO-d6 signal), 3.09 (t, 1H), 3.89 (d, 1H), 4.11 (s, 1H), 4.23 (d, 1H), 5.38-5.55 (m, 2H), 7.90 (s, 1H), 8.23 (dd, 1H), 8.37-8.49 (m, 3H), 8.63 (s, 1H), 10.5 (s, 1H). UPLC-MS (Method A1): Rt = 1.23 min MS (ESIpos): m/z = 538 (M + H)+ |
| 63 | N-{6-chloro-2-[2-(4-hydroxy-1,4'-bipiperidin-1'-yl)-2-oxoethyl]-2H-indazol-5-yl}-6-(trifluoromethyl)pyridine-2-carboxamide | 9-11 and 1,4'-bipiperidin-4-ol | 2g (85%) [h] | (300 MHz, DMSO-d6): δ = 1.18-1.53 (m, 4H), 1.64-1.83 (m, 4H), 2.18 (t, 2H), 2.53-2.80 (m, 4H, superimposed by DMSO signal), 3.06 (t, 1H), 3.36-3.46 (m, superimposed by water signal), 3.97 (d, 1H), 4.32 (d, 1H), 4.51 (d, 1H), 5.40-5.58 (m, 2H), 7.90 (s, 1H), 8.20-8.26 (m, 1H), 8.37-8.49 (m, 3H), 8.63 (s, 1H), 10.52 (s, 1H). UPLC-MS (Method A1): Rt = 0.93 min MS (ESIpos): m/z = 564 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 64 | N-{6-methoxy-2-[2-(4-methylpiperazin-1-yl)-2-oxoethyl]-2H-indazol-5-yl}-6-(trifluoromethyl)pyridine-2-carboxamide | 9-12 and 1-methyl-piperazine | 2f (57%) | (400 MHz, DMSO-d6): δ = 2.21 (s, 3H), 2.30 (t, 2H), 2.37 (d, 2H), 3.47 (d, 2H), 3.51-3.59 (m, 2H), 3.99 (s, 3H), 5.39 (s, 2H), 7.11 (s, 1H), 8.18-8.26 (m, 2H), 8.37-8.43 (m, 1H), 8.44-8.49 (m, 1H), 8.71 (s, 1H), 10.51 (s, 1H). UPLC-MS (Method A1): Rt = 0.91 min MS (ESIpos): m/z = 477 (M + H)+ |
| 65 | N-{6-methoxy-2-[2-(morpholin-4-yl)-2-oxoethyl]-2H-indazol-5-yl}-6-(trifluoromethyl)pyridine-2-carboxamide | 9-12 and morpholine | 2b (85%) | (300 MHz, DMSO-d6): δ = 3.42-3.51 (m, 2 H), 3.53-3.62 (m, 4 H), 3.62-3.68 (m, 2 H), 3.99 (s, 3 H), 5.40 (s, 2 H), 7.12 (s, 1 H), 8.19-8.25 (m, 2H), 8.36-8.44 (m, 1 H), 8.44-8.50 (m, 1 H), 8.71 (s, 1 H), 10.51 (s, 1 H). LC-MS (Method A3): Rt = 1.14 min MS (ESIpos): m/z = 464 (M + H)+ |
| 66 | N-(2-{2-[4-(dimethylamino)piperidin-1-yl]-2-oxoethyl}-6-ethoxy-2H-indazol-5-yl)-6-(trifluoromethyl)pyridine-2-carboxamide | 9-13 and N,N-dimethyl-piperidine-4-amine | 2g (63%) | (400 MHz, DMSO-d6): δ = 1.17-1.29 (m, 1H), 1.31-1.45 (m, 1H), 1.49 (t, 3H), 1.69-1.83 (m, 2H), 2.17 (s, 6H), 2.28-2.38 (m, 1H), 2.66 (t, 1H), 3.08 (t, 1H), 3.96 (d, 1H), 4.15-4.31 (m, 3H), 5.30-5.41 (m, 2H), 7.07 (s, 1H), 8.18-8.24 (m, 2H), 8.37-8.47 (m, 2H), 8.71 (s, 1H), 10.7 (s, 1H). UPLC-MS (Method A1): Rt = 0.93 min MS (ESIpos): m/z = 519 (M + H)+ |
| 67 | N-(6-ethoxy-2-{2-oxo-2-[4-(pyrrolidin-1-yl)piperidin-1-yl]ethyl}-2H-indazol-5-yl)-6-(trifluoromethyl)pyridine-2-carboxamide | 9-13 and 4-(pyrrolidin-1-yl)piperidine | 2g (43%) [i] | (400 MHz, DMSO-d6): δ = 1.22-1.35 (m, 1H), 1.37-1.54 (m, 4H), 1.67 (br. s., 4H), 1.84 (t, 2H), 2.19-2.26 (m, 1H), 2.43-2.58 (superimposed by DMSO-d6 signal), 2.84 (t, 1H), 3.16 (t, 1H), 3.87 (d, 1H), 4.09 (d, 1H), 4.20 (q, 2H), 5.30-5.42 (m, 2H), 7.07 (s, 1H), 8.19-8.24 (m, 2H), 8.37-8.48 (m, 2H), 8.70-8.73 (m, 1H), 10.7 (s, 1H). UPLC-MS (Method A1): Rt = 0.96 min MS (ESIpos): m/z = 545 (M + H)+ |

TABLE 2-continued

Examples 28-71

The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 68 | 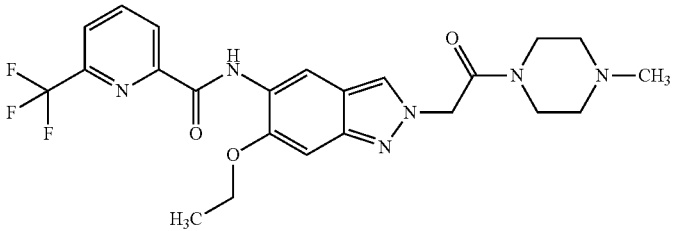 [SMILES: CCOc1cc2nn(CC(=O)N3CCN(C)CC3)cc2cc1NC(=O)c1cccc(C(F)(F)F)n1]<br>N-{6-ethoxy-2-[2-(4-methylpiperazin-1-yl)-2-oxoethyl]-2H-indazol-5-yl}-6-(trifluoromethyl)pyridine-2-carboxamide | 9-13 and 1-methyl-piperazine | 2g (51%) [i] | (400 MHz, DMSO-d6): δ = 1.49 (t, 3H), 2.20 (s, 3H), 2.26-2.41 (m, 4H), 3.42-3.58 (m, 4H), 4.20 (q, 2H), 5.37 (s, 2H), 7.07 (s, 1H), 8.18-8.24 (m, 2H), 8.37-8.47 (m, 2H), 8.71 (s, 1H), 10.7 (s, 1H).<br>UPLC-MS (Method A1): Rt = 0.92 min<br>MS (ESIpos): m/z = 491 (M + H)+ |
| 69 | 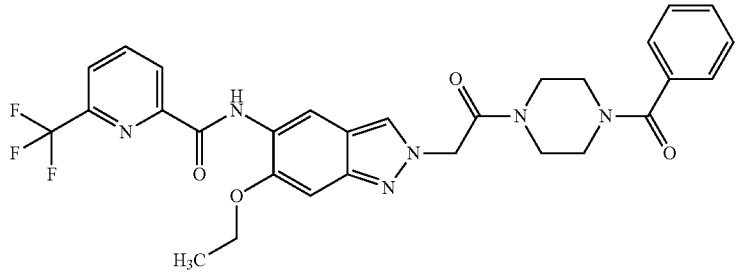 [SMILES: CCOc1cc2nn(CC(=O)N3CCN(C(=O)c4ccccc4)CC3)cc2cc1NC(=O)c1cccc(C(F)(F)F)n1]<br>N-{2-[2-(4-benzoylpiperazin-1-yl)-2-oxoethyl]-6-ethoxy-2H-indazol-5-yl}-6-(trifluoromethyl)pyridine-2-carboxamide | 9-13 and phenyl(piperazin-1-yl)methanone | 2g (71%) | (400 MHz, DMSO-d6): δ = 1.49 (t, 3H), 3.33-3.79 (m, 8H), 4.20 (q, 2H), 5.41 (br. s., 2H), 7.08 (s, 1H), 7.41-7.50 (m, 5H), 8.19-8.24 (m, 2H), 8.37-8.47 (m, 2H), 8.72 (s, 1H), 10.7 (s, 1H).<br>UPLC-MS (Method A1): Rt = 1.23 min<br>MS (ESIpos): m/z = 581 (M + H)+ |
| 70 | 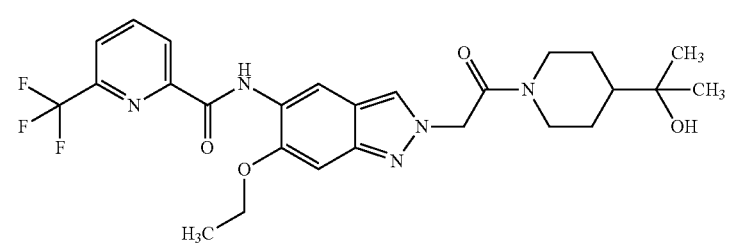 [SMILES: CCOc1cc2nn(CC(=O)N3CCC(C(C)(C)O)CC3)cc2cc1NC(=O)c1cccc(C(F)(F)F)n1]<br>N-(6-ethoxy-2-{2-[4-(2-hydroxypropan-2-yl)piperidin-1-yl]-2-oxoethyl}-2H-indazol-5-yl)-6-(trifluoromethyl)pyridine-2-carboxamide | 9-13 and 2-(piperidin-4-yl)propan-2-ol | 2g (79%) | (300 MHz, DMSO-d6): δ = 0.97-1.29 (m, 8H, contains s at 1.03), 1.37-1.56 (m, 4H), 1.74 (t, 2H), 2.42 ?+0 2.63 (signal obscured by DMSO-d6 signal) 2.98 (t, 1H), 4.02 (d, 1H), 4.14-4.25 (m, 3H), 4.40 (d, 1H), 5.27-5.43 (m, 2H), 7.07 (s, 1H), 8.17-8.24 (m, 2H), 8.36-8.48 (m, 2H), 8.71 (s, 1H), 10.7 (s, 1H).<br>UPLC-MS (Method A1): Rt = 1.19 min<br>MS (ESIpos): m/z = 534 (M + H)+ |

TABLE 2-continued

Examples 28-71
The exemplary compounds were prepared by the general experimental procedures 2a-2g from the appropriate intermediates and amines.

| Ex. No. | Structure/Name | Prepared from | * see key | ¹H-NMR/LC-MS |
|---|---|---|---|---|
| 71 | 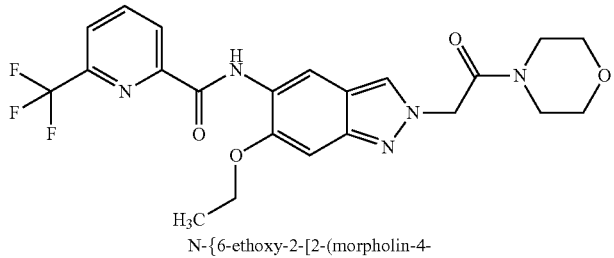 N-{6-ethoxy-2-[2-(morpholin-4-yl)-2-oxoethyl]-2H-indazol-5-yl}-6-(trifluoromethyl)pyridine-2-carboxamide | 9-13 and morpholine | 2g (89%) | (300 MHz, DMSO-d6): δ = 1.49 (t, 3H), 3.41-3.70 (m, 8H), 4.20 (q, 2H), 5.38 (s, 2H), 7.07 (s, 1H), 8.18-8.26 (m, 2H), 8.36-8.48 (m, 2H), 8.71 (s, 1H), 10.73 (s, 1H). UPLC-MS (Method A1): Rt = 1.16 min MS (ESIpos): m/z = 478 (M + H)+ |

* Prepared according to the stated procedure, the yield in % is indicated in brackets
[a]: The piperazine was used as hydrochloride. In addition to the piperazine, 1.6 equivalents of triethylamine were added to the reaction mixture.
[b]: The product was purified by preparative HPLC according to Method P1.
[c]: Gradient for the preparative HPLC: iso. ethanol/methanol/diethylamine 50:50:0.1; flow rate: 35 ml/min
[d]: Gradient for the preparative HPLC: iso. hexane/ethanol/diethylamine 70:30:0.1; flow rate: 40 ml/min
[e]: Gradient for the preparative HPLC: iso. hexane/ethanol/diethylamine 70:30:0.1; flow rate: 31 ml/min
[f]: N,N-Dimethylformamide was used instead of dimethyl sulphoxide.
[g]: HPLC was carried out according to Method P1.
[h]: 1.5 equivalents of piperazine were used.
[i]: The product was triturated with N,N-dimethylformamide and dimethyl sulphoxide.

Example 72

N-{2-[2-(4-Benzoylpiperazin-1-yl)-2-oxoethyl]-3-methyl-2H-indazol-5-yl}-6-(trifluoromethyl)pyridine-2-carboxamide

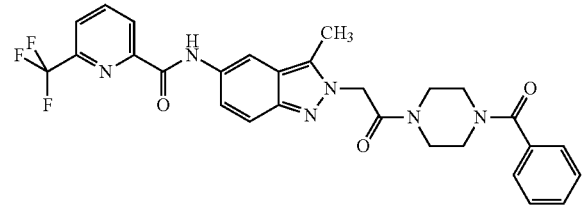 [SMILES: Cc1c2cc(NC(=O)c3cccc(C(F)(F)F)n3)ccc2nn1CC(=O)N1CCN(C(=O)c2ccccc2)CC1]

Analogously to Intermediate 8-1, 103 mg (0.27 mmol) of 2-(5-amino-3-methyl-2H-indazol-2-yl)-1-(4-benzoylpiperazin-1-yl)ethanone (Intermediate 6-15, crude product) were reacted with 78 mg (0.41 mmol) of 6-(trifluoromethyl)pyridine-2-carboxylic acid. After 24 h at 25° C., water was added. The solid was filtered off, washed with water and diethyl ether and dried under reduced pressure. This gave 43 mg (29% of theory) of the title compound.

UPLC-MS (Method A1): Rt=1.12 min

MS (ESIpos): m/z=551 (M+H)+.

¹H-NMR (300 MHz, DMSO-d₆): δ=3.34-3.73 (m, 8H), 5.48 (br. s., 2H), 7.42-7.58 (m, 7H), 8.14-8.23 (m, 2H), 8.32-8.43 (m, 2H), 10.35 (s, 1H).

Example 73

N-{2-[3-(4-Benzoylpiperazin-1-yl)-3-oxopropyl]-2H-indazol-5-yl}-6-(trifluoromethyl)pyridine-2-carboxamide

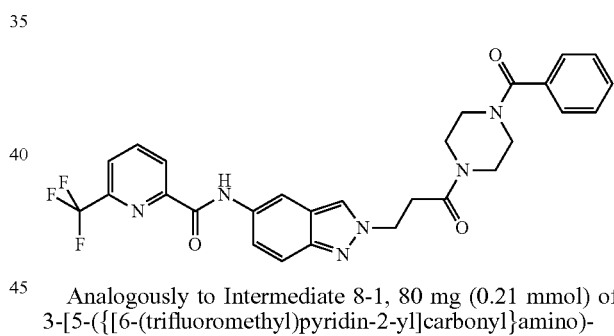

Analogously to Intermediate 8-1, 80 mg (0.21 mmol) of 3-[5-({[6-(trifluoromethyl)pyridin-2-yl]carbonyl}amino)-2H-indazol-2-yl]propanoic acid (Intermediate 9-15) in 0.3 ml of N,N-dimethylformamide and 2.9 ml of tetrahydrofuran were stirred with 32 mg (0.21 mmol) of 1-hydroxy-1H-benzotriazole hydrate and 81 mg (0.42 mmol) 1-(3-dimethylaminopropyl)-3-ethylcarbodiimide hydrochloride for 30 minutes. 60 mg (0.32 mmol) of phenyl(piperazin-1-yl)methanone were added. The reaction mixture was stirred at 25° C. for 2.5 h and added dropwise to 50 ml of water. The aqueous phase was extracted three times with ethyl acetate. The combined organic phases were washed with saturated sodium chloride solution, dried over sodium sulphate, filtered and concentrated. The crude product was stirred in 2 ml of dimethyl sulphoxide for 30 min, filtered and washed with 30 ml of water. The solid was purified by preparative HPLC according to Method P1. This gave 5 mg (4% of theory) of the title compound.

UPLC-MS (Method A1): $R_t$=1.10 min

MS (ESIpos): m/z=551 (M+H)+

¹H-NMR (400 MHz, DMSO-d6): δ=3.10 (br. s., 2H), 3.50 (br. s., 6H), 4.65 (t, 2H), 7.36-7.42 (m, 2H), 7.42-7.47 (m, 3H), 7.53-7.63 (m, 2H), 8.17 (dd, 1H), 8.28 (s, 1H), 8.32-8.42 (m, 3H), 10.35 (s, 1H).

The exemplary compounds of Tables 3-17 were synthesized in an amide synthesis analogously to Experimental Procedures 1a-1g and 2a-2g or by a method indicated in the table and analysed by analytical LC-MS (Method A4).

TABLE 3

Examples 74-77
The exemplary compounds were prepared from 2-(5-amino-2H-indazol-2-yl)-1-[4-(cyclopropyl-1-carbonyl)piperazin-1-yl]ethanone (Intermediate 6-10) and the starting material indicated in the table.

| Example | Structure and name | Starting material and notes | LC-MS retention time [min] |
|---|---|---|---|
| 74 | 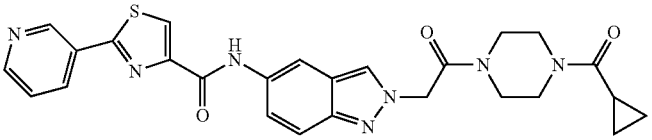 [SMILES: O=C(Nc1ccc2nn(CC(=O)N3CCN(C(=O)C4CC4)CC3)cc2c1)c1csc(-c2cccnc2)n1] N-(2-{2-[4-(cyclopropylcarbonyl)piperazin-1-yl]-2-oxoethyl}-2H-indazol-5-yl)-2-(pyridin-3-yl)-1,3-thiazole-4-carboxamide | 2-(pyridin-3-yl)-1,3-thiazole-4-carboxylic acid | 0.78 |
| 75 | 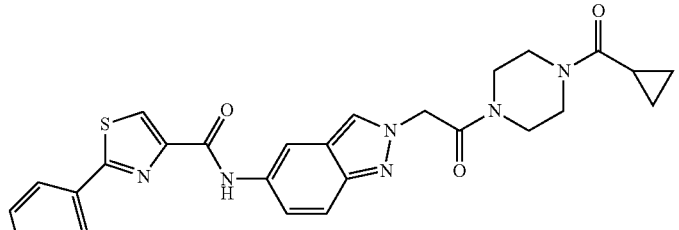 N-(2-{2-[4-(cyclopropylcarbonyl)piperazin-1-yl]-2-oxoethyl}-2H-indazol-5-yl)-2-(pyridin-4-yl)-1,3-thiazole-4-carboxamide | 2-(pyridin-4-yl)-1,3-thiazole-4-carboxylic acid | 0.70 |
| 76 | 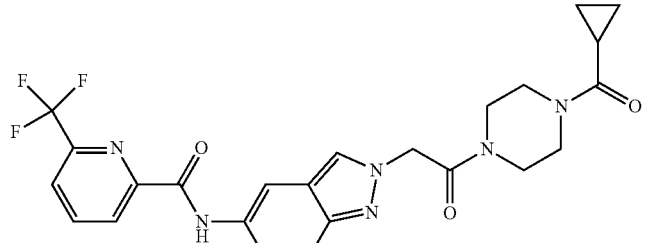 N-(2-{2-[4-(cyclopropyl-1-carbonyl)piperazin-1-yl]-2-oxoethyl}-2H-indazol-5-yl)-6-(trifluoromethyl)pyridine-2-carboxamide | 6-(trifluoromethyl)pyridine-2-carboxylic acid | 0.94 |
| 77 | 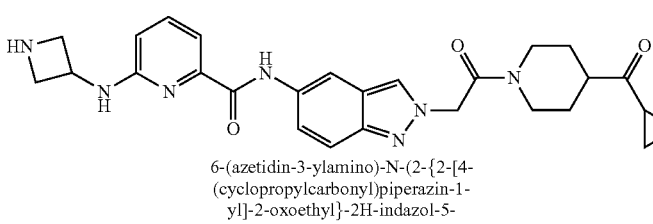 6-(azetidin-3-ylamino)-N-(2-{2-[4-(cyclopropylcarbonyl)piperazin-1-yl]-2-oxoethyl}-2H-indazol-5-yl)pyridine-2-carboxamide | The 2-(5-amino-2H-indazol-2-yl)-1-[4-(cyclopropylcarbonyl)piperazin-1-yl]ethanone starting material was reacted with 6-fluoropyridine-2-carboxylic acid. This gave N-(2-{2-[4-(cyclopropylcarbonyl)piperazin-1-yl]-2-oxoethyl}-2H-indazol-5-yl)-6-fluoropyridine-2-carboxamide, which was reacted with 2 equiv. of tert-butyl 3-aminoazetidine-1-carboxylate and N-ethyl-N-isopropylpropane-2-amine in NMP at 100° C. The crude product obtained was then reacted with trifluoroacetic acid in dichloromethane Purification by preparative HPLC gave 14 mg of the exemplary compound. | 0.54 |

TABLE 4

Examples 78-83
The exemplary compounds were prepared from 2-(5-amino-2H-indazol-2-yl)-1-(4-methylpiperazin-1-yl)ethanone
and the starting material indicated in the table.

| Example | Structure and name | Starting material and notes | LC-MS retention time [min] |
|---|---|---|---|
| 78 | 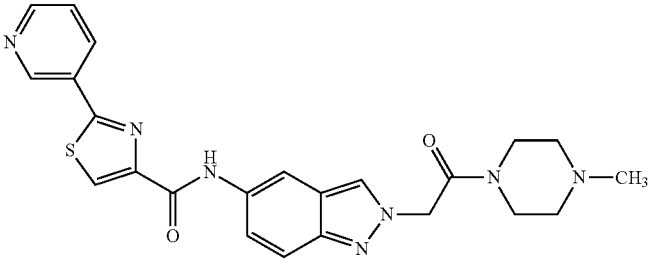 [SMILES: CN1CCN(C(=O)Cn2cc3cc(NC(=O)c4csc(-c5cccnc5)n4)ccc3n2)CC1]<br>N-{2-[2-(4-methylpiperazin-1-yl)-2-oxoethyl]-2H-indazol-5-yl}-2-(pyridin-3-yl)-1,3-thiazole-4-carboxamide | 2-(pyridin-3-yl)-1,3-thiazole-4-carboxylic acid | 0.55 |
| 79 | 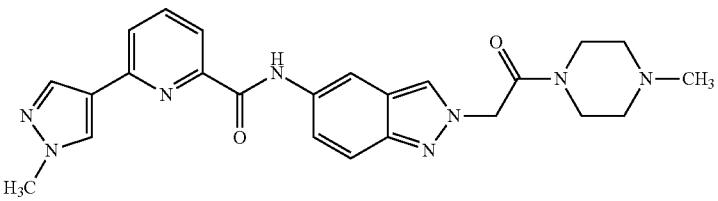 [SMILES: CN1CCN(C(=O)Cn2cc3cc(NC(=O)c4cccc(-c5cnn(C)c5)n4)ccc3n2)CC1]<br>N-{2-[2-(4-methylpiperazin-1-yl)-2-oxoethyl]-2H-indazol-5-yl}-6-(1-methyl-1H-pyrazol-4-yl)pyridine-2-carboxamide | 6-(1-methyl-1H-pyrazol-4-yl)pyridine-2-carboxylic acid | 0.60 |
| 80 | 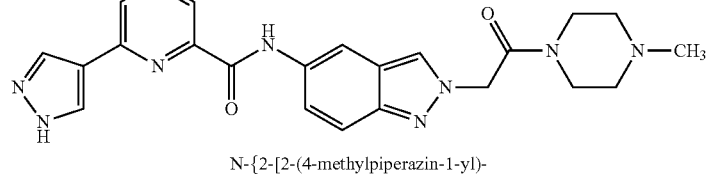<br>N-{2-[2-(4-methylpiperazin-1-yl)-2-oxoethyl]-2H-indazol-5-yl}-6-(1H-pyrazol-4-yl)pyridine-2-carboxamide | 6-(1H-pyrazol-4-yl)pyridine-2-carboxylic acid | 0.54 |
| 81 | 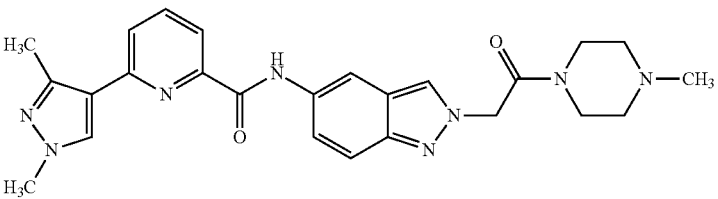 [SMILES: Cc1nn(C)cc1-c1cccc(C(=O)Nc2ccc3nn(CC(=O)N4CCN(C)CC4)cc3c2)n1]<br>6-(1,3-dimethyl-1H-pyrazol-4-yl)-N-{2-[2-(4-methylpiperazin-1-yl)-2-oxoethyl]-2H-indazol-5-yl}pyridine-2-carboxamide | 6-(1,3-dimethyl-1H-pyrazol-4-yl)pyridine-2-carboxylic acid | 0.64 |

TABLE 4-continued

Examples 78-83
The exemplary compounds were prepared from 2-(5-amino-2H-indazol-2-yl)-1-(4-methylpiperazin-1-yl)ethanone and the starting material indicated in the table.

| Example | Structure and name | Starting material and notes | LC-MS retention time [min] |
|---|---|---|---|
| 82 | 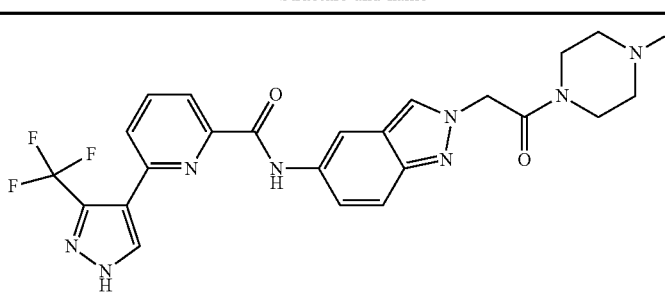<br>N-{2-[2-(4-methylpiperazin-1-yl)-2-oxoethyl]-2H-indazol-5-yl}-6-[3-(trifluoromethyl)-1H-pyrazol-4-yl]pyridine-2-carboxamide | 6-[3-(trifluoromethyl)-1H-pyrazol-4-yl]pyridine-2-carboxylic acid | 0.66 |
| 83 | 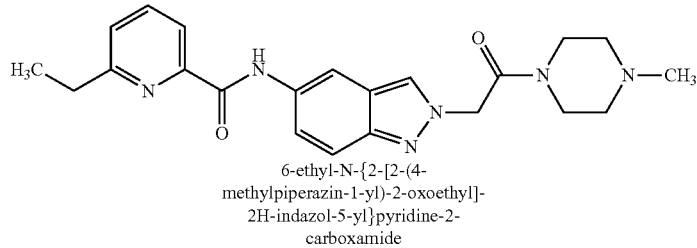<br>6-ethyl-N-{2-[2-(4-methylpiperazin-1-yl)-2-oxoethyl]-2H-indazol-5-yl}pyridine-2-carboxamide | 6-ethylpyridine-2-carboxylic acid | 0.66 |

TABLE 5

Examples 84-85
The exemplary compounds were prepared from 2-(5-amino-2H-indazol-2-yl)-1-[4-(2,2,2-trifluoroethyl)piperazin-1-yl]ethanone (Intermediate 6-13) and the starting material indicated in the table.

| Example | Structure and name | Starting material and notes | LC-MS retention time [min] |
|---|---|---|---|
| 84 | 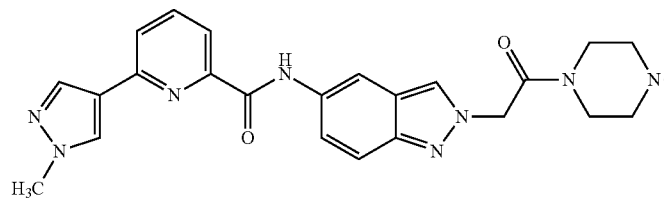<br>6-(1-methyl-1H-pyrazol-4-yl)-N-(2-{2-oxo-2-[4-(2,2,2-trifluoroethyl)piperazin-1-yl]ethyl}-2H-indazol-5-yl)pyridine-2-carboxamide | 6-(1-methyl-1H-pyrazol-4-yl)pyridine-2-carboxylic acid | 0.97 |
| 85 | 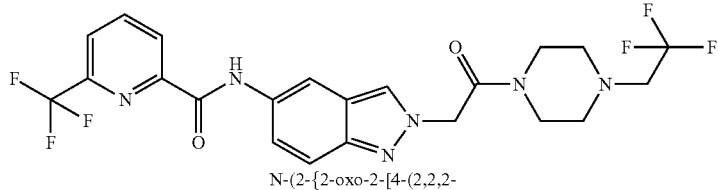<br>N-(2-{2-oxo-2-[4-(2,2,2-trifluoroethyl)piperazin-1-yl]ethyl}-2H-indazol-5-yl)-6-(trifluoromethyl)pyridine-2-carboxamide | 6-(trifluoromethyl)pyridine-2-carboxylic acid | 1.10 |

TABLE 6

Example 86
The exemplary compounds were prepared from 4-[(5-amino-2H-indazol-2-yl)acetyl]-1-ethylpiperazin-2-one and the starting material indicated in the table.

| Example | Name and structure | Starting material and notes | LC-MS retention time [min] |
|---|---|---|---|
| 86 | N-{2-[2-(4-ethyl-3-oxopiperazin-1-yl)-2-oxoethyl]-2H-indazol-5-yl}-6-(1-methyl-1H-pyrazol-4-yl)pyridine-2-carboxamide | 6-(1-methyl-1H-pyrazol-4-yl)pyridine-2-carboxylic acid | 0.79 |

TABLE 7

Examples 87-121
The exemplary compounds were prepared from 2-(5-amino-2H-indazol-2-yl)-1-(4-benzoylpiperazin-1-yl)ethanone (Intermediate 6-11) and the starting material indicated in the table.

| Example | Name and structure | Starting material and notes | LC-MS retention time [min] |
|---|---|---|---|
| 87 | N-{2-[2-(4-benzoylpiperazin-1-yl)-2-oxoethyl]-2H-indazol-5-yl}-6-(trifluoromethyl)pyridine-2-carboxamide | 6-(trifluoromethyl)pyridine-2-carboxylic acid | 1.02 |
| 88 | N-{2-[2-(4-benzoylpiperazin-1-yl)-2-oxoethyl]-2H-indazol-5-yl}-6-methylpyridine-2-carboxamide | 6-methylpyridine-2-carboxlic acid | 0.93 |
| 89 | N-{2-[2-(4-benzoylpiperazin-1-yl)-2-oxoethyl]-2H-indazol-5-yl}-6-(morpholin-4-yl)pyridine-2-carboxamide | 6-(morpholin-4-yl)pyridine-2-carboxylic acid | 0.94 |

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
|---|---|---|---|
| 90 | 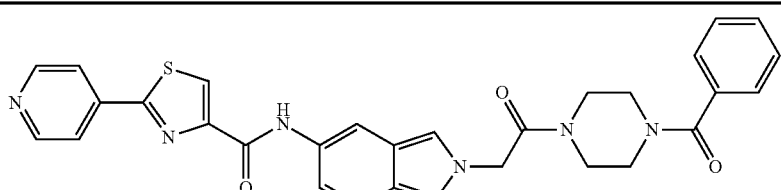<br>N-{2-[2-(4-benzoylpiperazin-1-yl)-2-oxoethyl]-2H-indazol-5-yl}-2-(pyridin-4-yl)-1,3-thiazole-4-carboxamide | 2-(pyridin-4-yl)-1,3-thiazole-4-carboxylic acid | 0.79 |
| 91 | 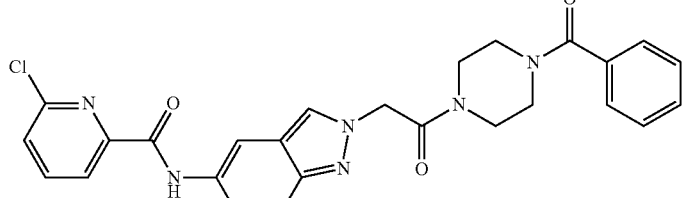<br>N-{2-[2-(4-benzoylpiperazin-1-yl)-2-oxoethyl]-2H-indazol-5-yl}-6-chloropyridine-2-carboxamide | 6-chloropyridine-2-carboxylic acid | 0.96 |
| 92 | 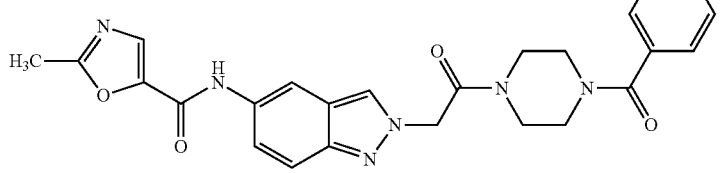<br>N-{2-[2-(4-benzoylpiperazin-1-yl)-2-oxoethyl]-2H-indazol-5-yl}-2-methyl-1,3-oxazole-5-carboxamide | 2-methyl-1,3-oxazol-5-carboxylic acid | 0.77 |
| 93 | 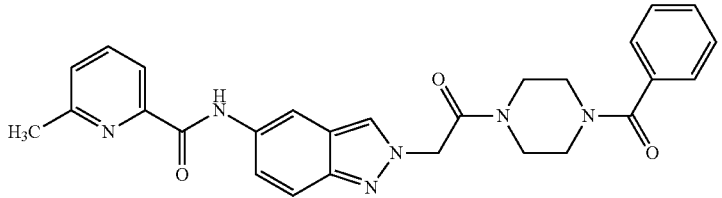<br>6-amino-N-{2-[2-(4-benzoylpiperazin-1-yl)-2-oxoethyl]-2H-indazol-5-yl}pyridine-2-carboxamide | 6-aminopyridine-2-carboxylic acid | 0.69 |
| 94 | 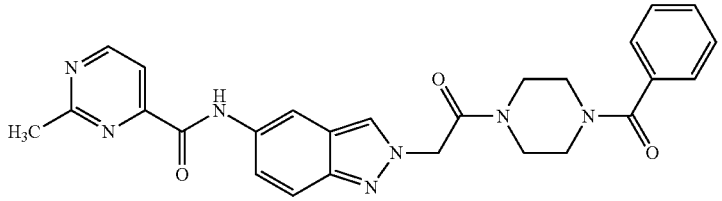 [SMILES: Cc1cccc(C(=O)Nc2ccc3nn(CC(=O)N4CCN(C(=O)c5ccccc5)CC4)cc3c2)n1]<br>2-amino-N-{2-[2-(4-benzoylpiperazin-1-yl)-2-oxoethyl]-2H-indazol-5-yl}pyrimidin-4-carboxamide | 2-aminopyrimidin-4-carboxylic acid | 0.71 |

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
|---|---|---|---|
| 95 | 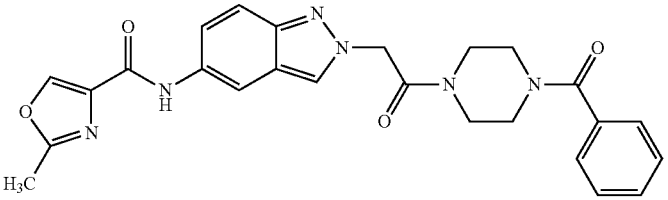 [SMILES: Cc1nc(C(=O)Nc2ccc3nn(CC(=O)N4CCN(C(=O)c5ccccc5)CC4)cc3c2)co1]<br>N-{2-[2-(4-benzoylpiperazin-1-yl)-2-oxoethyl]-2H-indazol-5-yl}-2-methyl-1,3-oxazole-4-carboxamide | 2-methyl-1,3-oxazole-4-carboxylic acid | 0.77 |
| 96 | 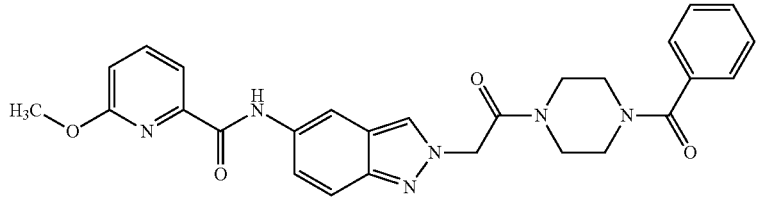 [SMILES: COc1cccc(C(=O)Nc2ccc3nn(CC(=O)N4CCN(C(=O)c5ccccc5)CC4)cc3c2)n1]<br>N-{2-[2-(4-benzoylpiperazin-1-yl)-2-oxoethyl]-2H-indazol-5-yl}-6-methoxypyridine-2-carboxamide | 6-methoxypyridine-2-carboxylic acid | 0.96 |
| 97 | 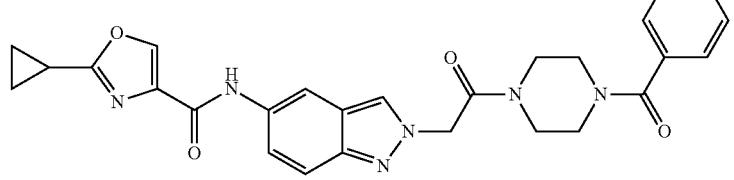<br>N-{2-[2-(4-benzoylpiperazin-1-yl)-2-oxoethyl]-2H-indazol-5-yl}-2-cyclopropyl-1,3-oxazole-4-carboxamide | 2-cyclopropyl-1,3-oxazole-4-carboxylic acid | 0.89 |
| 98 | 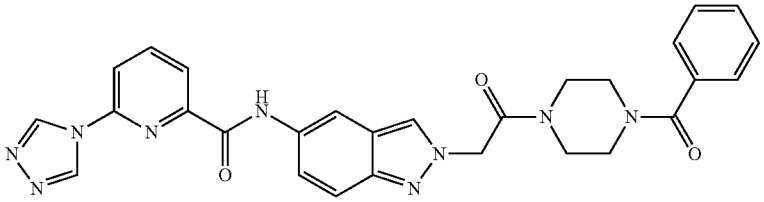<br>N-{2-[2-(4-benzoylpiperazin-1-yl)-2-oxoethyl]-2H-indazol-5-yl}-6-(4H-1,2,4-triazol-4-yl)pyridine-2-carboxamide | 6-(4H-1,2,4-triazol-4-yl)pyridine-2-carboxylic acid | 0.74 |
| 99 | 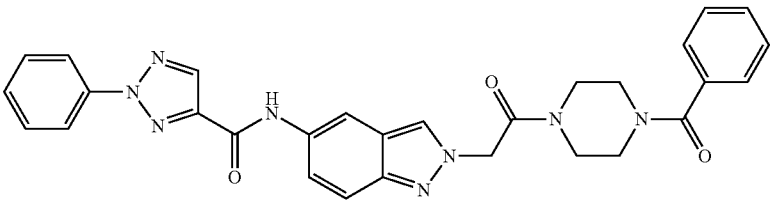 [SMILES: O=C(Nc1ccc2nn(CC(=O)N3CCN(C(=O)c4ccccc4)CC3)cc2c1)c1cnn(-c2ccccc2)n1]<br>N-{2-[2-(4-benzoylpiperazin-1-yl)-2-oxoethyl]-2H-indazol-5-yl}-2-phenyl-2H-1,2,3-triazole-4-carboxamide | 2-phenyl-2H-1,2,3-triazole-4-carboxylic acid | 1.04 |

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
| --- | --- | --- | --- |
| 100 | 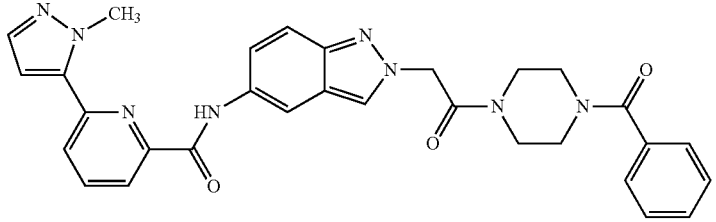 [SMILES: Cn1nccc1-c1cccc(C(=O)Nc2ccc3nn(CC(=O)N4CCN(C(=O)c5ccccc5)CC4)cc3c2)n1]<br>N-{2-[2-(4-benzoylpiperazin-1-yl)-2-oxoethyl]-2H-indazol-5-yl}-6-(1-methyl-1H-pyrazol-5-yl)pyridine-2-carboxamide | 6-(1-(1-1H-pyrazol-5-yl)pyridine-2-carboxylic acid | 0.93 |
| 101 | 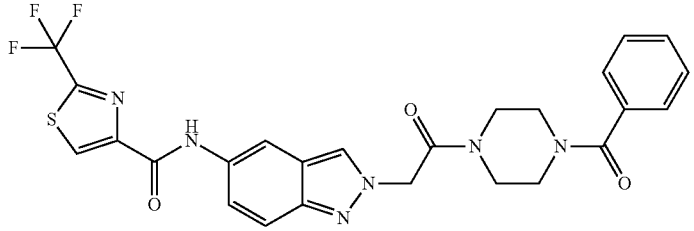 [SMILES: O=C(Nc1ccc2nn(CC(=O)N3CCN(C(=O)c4ccccc4)CC3)cc2c1)c1csc(C(F)(F)F)n1]<br>N-{2-[2-(4-benzoylpiperazin-1-yl)-2-oxoethyl]-2H-indazol-5-yl}-2-(trifluoromethyl)-1,3-thiazole-4-carboxamide | 2-(trifluoromethyl)-1,3-thiazole-4-carboxylic acid | 0.99 |
| 102 | 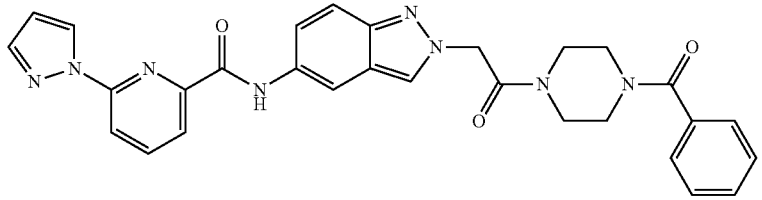 [SMILES: O=C(Nc1ccc2nn(CC(=O)N3CCN(C(=O)c4ccccc4)CC3)cc2c1)c1cccc(-n2cccn2)n1]<br>N-{2-[2-(4-benzoylpiperazin-1-yl)-2-oxoethyl]-2H-indazol-5-yl}-6-(1H-pyrazol-1-yl)pyridine-2-carboxamide | 6-(1H-pyrazol-1-yl)pyridine-2-carboxylic acid | 0.97 |
| 103 | 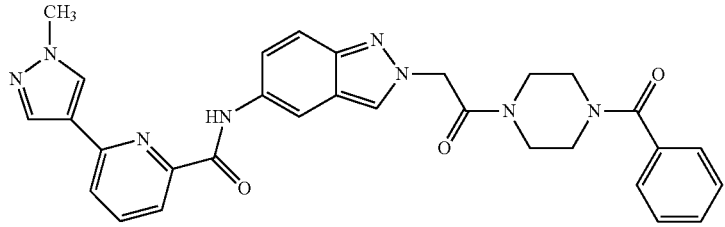 [SMILES: Cn1cc(-c2cccc(C(=O)Nc3ccc4nn(CC(=O)N5CCN(C(=O)c6ccccc6)CC5)cc4c3)n2)cn1]<br>N-{2-[2-(4-benzoylpiperazin-1-yl)-2-oxoethyl]-2H-indazol-5-yl}-6-(1-methyl-1H-pyrazol-4-yl)pyridine-2-carboxamide | 6-(1-methyl-1H-pyrazol-4-yl)pyridine-2-carboxylic acid | 0.91 |

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
|---|---|---|---|
| 104 | 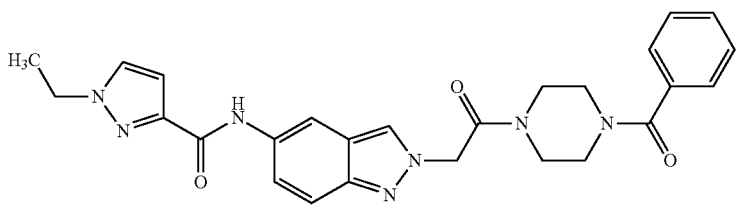 [SMILES: CCn1ccc(C(=O)Nc2ccc3nn(CC(=O)N4CCN(C(=O)c5ccccc5)CC4)cc3c2)n1]<br>N-{2-[2-(4-benzoylpiperazin-1-yl)-2-oxoethyl]-2H-indazol-5-yl}-1-ethyl-1H-pyrazole-3-carboxamide | 1-ethyl-1H-pyrazol-3-carboxylic acid | 0.81 |
| 105 | 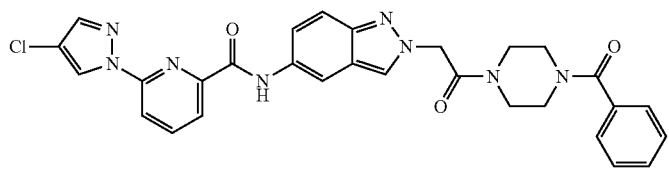 [SMILES: O=C(Nc1ccc2nn(CC(=O)N3CCN(C(=O)c4ccccc4)CC3)cc2c1)c1cccc(-n2cc(Cl)cn2)n1]<br>N-{2-[2-(4-benzoylpiperazin-1-yl)-2-oxoethyl]-2H-indazol-5-yl}-6-(4-chloro-1H-pyrazol-1-yl)pyridine-2-carboxamide | 6-(4-chloro-1H-pyrazol-1-yl)pyridine-2-carboxylic acid | 1.11 |
| 106 | 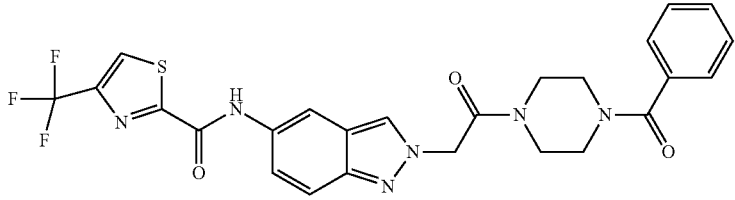 [SMILES: O=C(Nc1ccc2nn(CC(=O)N3CCN(C(=O)c4ccccc4)CC3)cc2c1)c1nc(C(F)(F)F)cs1]<br>N-{2-[2-(4-benzoylpiperazin-1-yl)-2-oxoethyl]-2H-indazol-5-yl}-4-(trifluoromethyl)-1,3-thiazole-2-carboxamide | 4-(trifluoromethyl)-1,3-thiazol-2-carboxylic acid | 1.02 |
| 107 | 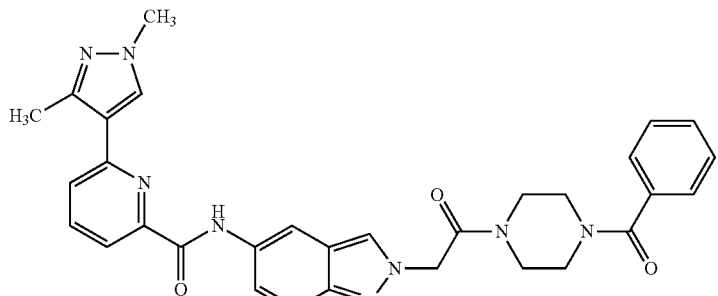<br>N-{2-[2-(4-benzoylpiperazin-1-yl)-2-oxoethyl]-2H-indazol-5-yl}-6-(1,3-dimethyl-1H-pyrazol-4-yl)pyridine-2-carboxamide | 6-(1,3-dimethyl-1H-pyrazol-4-yl)pyridine-2-carboxylic acid | 0.95 |

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
|---|---|---|---|
| 108 | 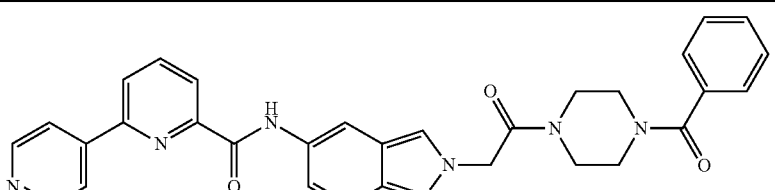<br>N-{2-[2-(4-benzoylpiperazin-1-yl)-2-oxoethyl]-2H-indazol-5-yl}-2,4'-bipyridine-6-carboxamide | 2,4'-bipyridine-6-carboxylic acid | 0.73 |
| 109 | 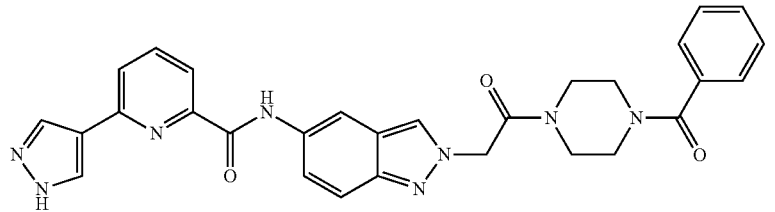 [SMILES: O=C(Nc1ccc2nn(CC(=O)N3CCN(C(=O)c4ccccc4)CC3)cc2c1)c1cccc(-c2cn[nH]c2)n1]<br>N-{2-[2-(4-benzoylpiperazin-1-yl)-2-oxoethyl]-2H-indazol-5-yl}-6-(1H-pyrazol-4-yl)pyridine-2-carboxamide | 6-(1H-pyrazol-4-yl)pyridine-2-carboxylic acid | 0.84 |
| 110 | 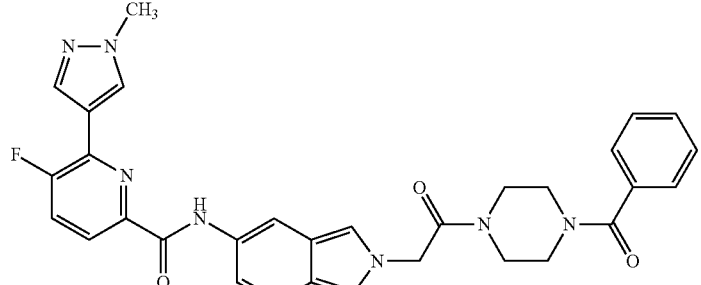<br>N-{2-[2-(4-benzoylpiperazin-1-yl)-2-oxoethyl]-2H-indazol-5-yl}-5-fluoro-6-(1-methyl-1H-pyrazol-4-yl)pyridine-2-carboxamide | 5-fluoro-6-(1-methyl-1H-pyrazol-4-yl)pyridine-2-carboxylic acid | 0.96 |
| 111 | 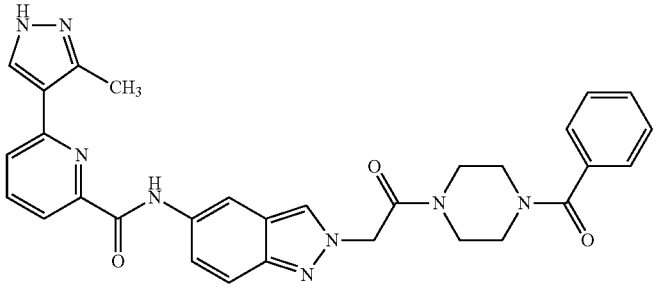 [SMILES: Cc1n[nH]cc1-c1cccc(C(=O)Nc2ccc3nn(CC(=O)N4CCN(C(=O)c5ccccc5)CC4)cc3c2)n1]<br>N-{2-[2-(4-benzoylpiperazin-1-yl)-2-oxoethyl]-2H-indazol-5-yl}-6-(3-methyl-1H-pyrazol-4-yl)pyridine-2-carboxamide | 6-(3-methyl-1H-pyrazol-4-yl)pyridine-2-carboxylic acid | 0.88 |

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
|---|---|---|---|
| 112 | 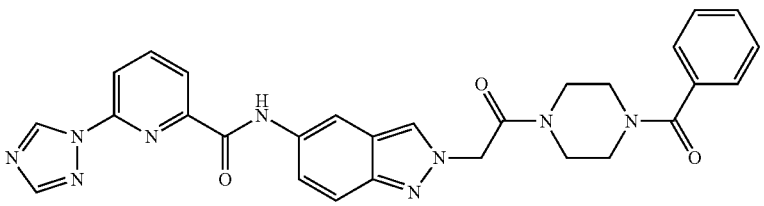<br>N-{2-[2-(4-benzoylpiperazin-1-yl)-2-oxoethyl]-2H-indazol-5-yl}-6-(1H-1,2,4-triazol-1-yl)pyridine-2-carboxamide | 6-(1H-1,2,4-triazol-1-yl)pyridine-2-carboxylic acid | 0.85 |
| 113 | 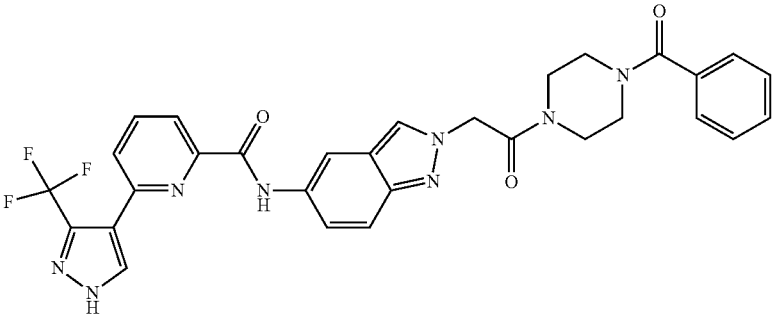 [SMILES: O=C(Nc1ccc2nn(CC(=O)N3CCN(C(=O)c4ccccc4)CC3)cc2c1)c1cccc(-c2c[nH]nc2C(F)(F)F)n1]<br>N-{2-[2-(4-benzoylpiperazin-1-yl)-2-oxoethyl]-2H-indazol-5-yl}-6-[3-(trifluoromethyl)-1H-pyrazol-4-yl]pyridine-2-carboxamide | 6-[3-(trifluoromethyl)-1H-pyrazol-4-yl]pyridine-2-carboxylic acid | 0.97 |
| 114 | 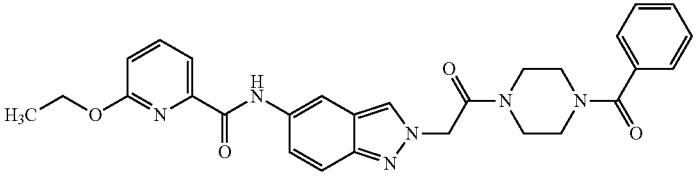 [SMILES: CCOc1cccc(C(=O)Nc2ccc3nn(CC(=O)N4CCN(C(=O)c5ccccc5)CC4)cc3c2)n1]<br>N-{2-[2-(4-benzoylpiperazin-1-yl)-2-oxoethyl]-2H-indazol-5-yl}-6-ethoxypyridine-2-carboxamide | 6-ethoxypyridine-2-carboxylic acid | 1.04 |
| 115 | 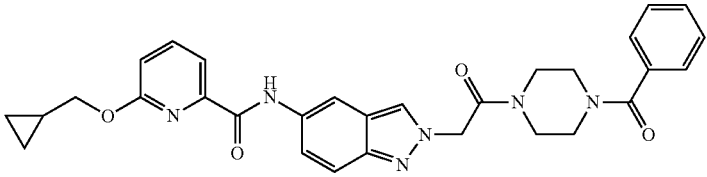 [SMILES: O=C(Nc1ccc2nn(CC(=O)N3CCN(C(=O)c4ccccc4)CC3)cc2c1)c1cccc(OCC2CC2)n1]<br>N-{2-[2-(4-benzoylpiperazin-1-yl)-2-oxoethyl]-2H-indazol-5-yl}-6-(cyclopropylmethoxy)pyridine-2-carboxamide | 6-(cyclopropylmethoxy)pyridine-2-carboxylic acid | 1.11 |

US 9,951,086 B2

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
|---|---|---|---|
| 116 | 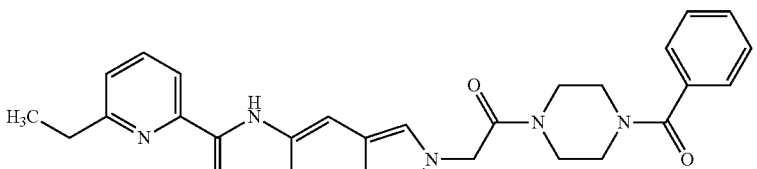<br>N-{2-[2-(4-benzoylpiperazin-1-yl)-2-oxoethyl]-2H-indazol-5-yl}-6-ethylpyridine-2-carboxamide | 6-ethylpyridine-2-carboxylic acid | 1.03 |
| 117 | 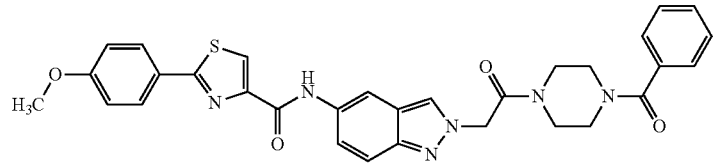 [SMILES: COc1ccc(-c2nc(C(=O)Nc3ccc4nn(CC(=O)N5CCN(C(=O)c6ccccc6)CC5)cc4c3)cs2)cc1]<br>N-{2-[2-(4-benzoylpiperazin-1-yl)-2-oxoethyl]-2H-indazol-5-yl}-2-(4-methoxyphenyl)-1,3-thiazole-4-carboxamide | 2-(4-methoxyphenyl)-1,3-thiazole-4-carboxylic acid | 1.12 |
| 118 | 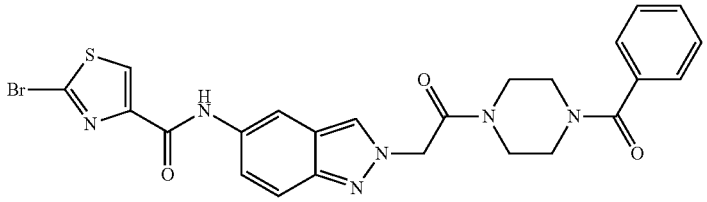 [SMILES: O=C(Nc1ccc2nn(CC(=O)N3CCN(C(=O)c4ccccc4)CC3)cc2c1)c1csc(Br)n1]<br>N-{2-[2-(4-benzoylpiperazin-1-yl)-2-oxoethyl]-2H-indazol-5-yl}-2-bromo-1,3-thiazole-4-carboxamide | 2-bromo-1,3-thiazole-4-carboxylic acid | 0.93 |
| 119 | 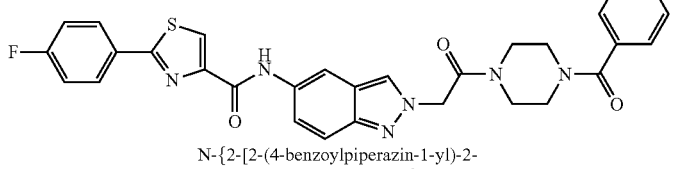<br>N-{2-[2-(4-benzoylpiperazin-1-yl)-2-oxoethyl]-2H-indazol-5-yl}-2-(4-fluorophenyl)-1,3-thiazole-4-carboxamide | 2-(4-fluorophenyl)-1,3-thiazole-4-carboxylic acid | 1.13 |
| 120 | 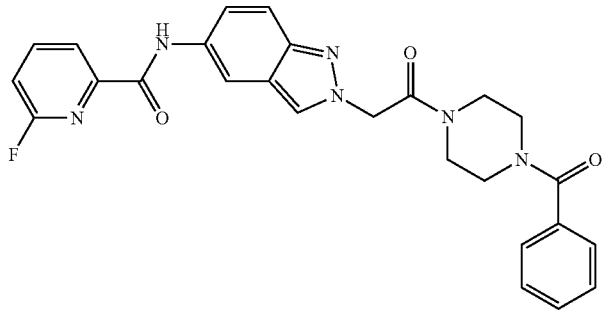 [SMILES: O=C(Nc1ccc2nn(CC(=O)N3CCN(C(=O)c4ccccc4)CC3)cc2c1)c1cccc(F)n1]<br>N-{2-[2-(4-benzoylpiperazin-1-yl)-2-oxoethyl]-2H-indazol-5-yl}-6-fluoropyridine-2-carboxamide | 6-fluoropyridine-2-carboxylic acid | 0.89 |

TABLE 7-continued

Examples 87-121
The exemplary compounds were prepared from 2-(5-amino-2H-indazol-2-yl)-1-(4-benzoylpiperazin-1-yl)ethanone
(Intermediate 6-11) and the starting material indicated in the table.

| Example | Name and structure | Starting material and notes | LC-MS retention time [min] |
|---|---|---|---|
| 121 | 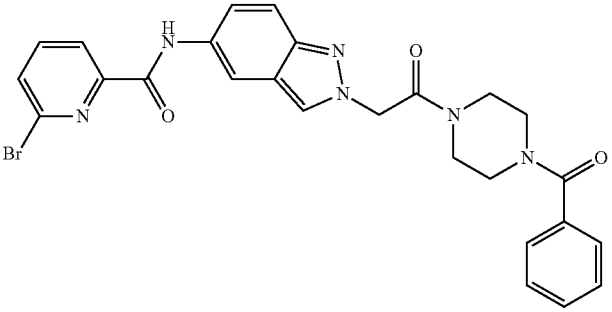 [SMILES: O=C(Nc1ccc2nn(CC(=O)N3CCN(C(=O)c4ccccc4)CC3)cc2c1)c1cccc(Br)n1]<br>N-{2-[2-(4-benzoylpiperazin-1-yl)-2-oxoethyl]-2H-indazol-5-yl}-6-bromopyridine-2-carboxamide | 6-bromopyridine-2-carboxylic acid | 0.98 |

TABLE 8

Examples 122-200
The exemplary compounds were prepared from [5-({[6-(trifluoromethyl)pyridin-2-yl]carbonyl}amino)-2H-indazol-2-yl]acetic
acid (Intermediate 9-14) and the starting material indicated in the table.

| Example | Structure and name | Starting material and notes | LC-MS retention time [min] |
|---|---|---|---|
| 122 | 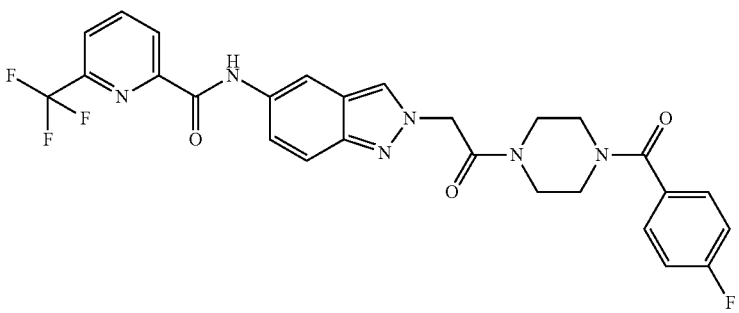 [SMILES: O=C(Nc1ccc2nn(CC(=O)N3CCN(C(=O)c4ccc(F)cc4)CC3)cc2c1)c1cccc(C(F)(F)F)n1]<br>N-(2-{2-[4-(4-fluorobenzoyl)piperazin-1-yl]-2-oxoethyl}-2H-indazol-5-yl)-6-(trifluoromethyl)pyridine-2-carboxamide | (4-fluorophenyl)(piperazin-1-yl)methanone | 1.05 |
| 123 | 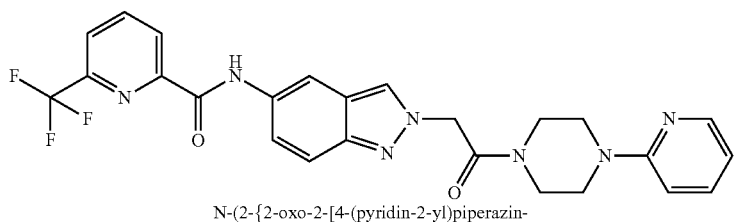<br>N-(2-{2-oxo-2-[4-(pyridin-2-yl)piperazin-1-yl]ethyl}-2H-indazol-5-yl)-6-(trifluoromethyl)pyridine-2-carboxamide | 1-(pyridin-2-yl)piperazine | 0.75 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 124 | 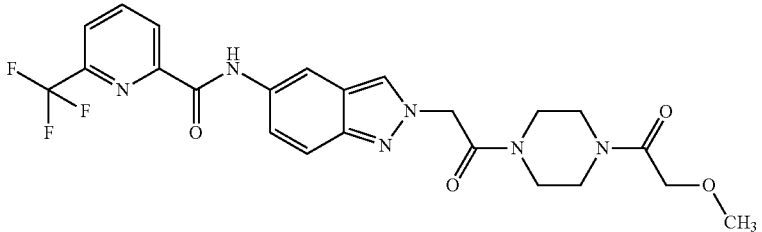 [SMILES: COCC(=O)N1CCN(C(=O)Cn2cc3cc(NC(=O)c4cccc(C(F)(F)F)n4)ccc3n2)CC1]<br>N-(2-{2-[4-(methoxyacetyl)piperazin-1-yl]-2-oxoethyl}-2H-indazol-5-yl)-6-(trifluoromethyl)pyridine-2-carboxamide | 2-methoxy-1-(piperazin-1-yl)ethanone | 0.86 |
| 125 | 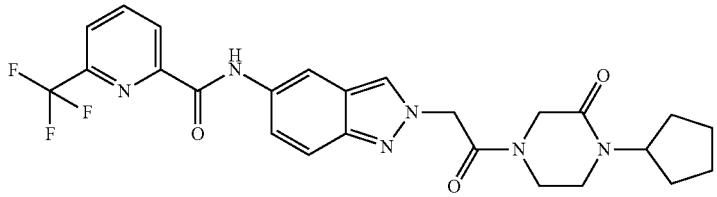 [SMILES: O=C(Nc1ccc2nn(CC(=O)N3CCN(C4CCCC4)C(=O)C3)cc2c1)c1cccc(C(F)(F)F)n1]<br>N-{2-[2-(4-cyclopentyl-3-oxopiperazin-1-yl)-2-oxoethyl]-2H-indazol-5-yl}-6-(trifluoromethyl)pyridine-2-carboxamide | 1-cyclopentylpiperazin-2-one | 1.03 |
| 126 | 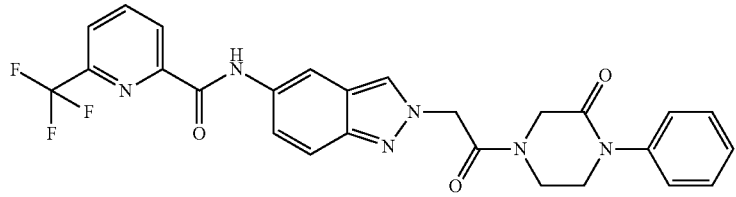 [SMILES: O=C(Nc1ccc2nn(CC(=O)N3CCN(c4ccccc4)C(=O)C3)cc2c1)c1cccc(C(F)(F)F)n1]<br>N-{2-[2-oxo-2-(3-oxo-4-phenylpiperazin-1-yl)ethyl]-2H-indazol-5-yl}-6-(trifluoromethyl)pyridine-2-carboxamide | 1-phenylpiperazin-2-one | 1.01 |
| 127 | 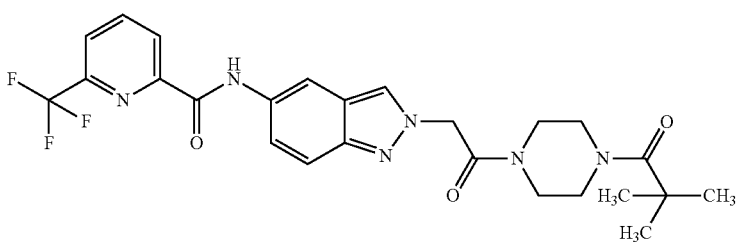 [SMILES: CC(C)(C)C(=O)N1CCN(C(=O)Cn2cc3cc(NC(=O)c4cccc(C(F)(F)F)n4)ccc3n2)CC1]<br>N-(2-{2-[4-(2,2-dimethylpropanoyl)piperazin-1-yl]-2-oxoethyl}-2H-indazol-5-yl)-6-(trifluoromethyl)pyridine-2-carboxamide | 2,2-dimethyl-1-(piperazin-1-yl)propan-1-one | 1.03 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
| --- | --- | --- | --- |
| 128 | N-(2-{2-[4-(cyclopropylmethyl)piperazin-1-yl]-2-oxoethyl}-2H-indazol-5-yl)-6-(trifluoromethyl)pyridine-2-carboxamide | 1-(cyclopropylmethyl)piperazine | 0.70 |
| 129 | N-{2-[2-oxo-2-(pyridazin-4-ylamino)ethyl]-2H-indazol-5-yl}-6-(trifluoromethyl)pyridine-2-carboxamide | pyridazine-4-amin | 0.86 |
| 130 | N-(2-{2-[4-(2-hydroxy-2-methylpropanoyl)piperazin-1-yl]-2-oxoethyl}-2H-indazol-5-yl)-6-(trifluoromethyl)pyridine-2-carboxamide | 2-hydroxy-2-methyl-1-(piperazin-1-yl)propan-1-one | 0.89 |
| 131 | N-(2-{2-oxo-2-[4-(1-phenylethyl)piperazin-1-yl]ethyl}-2H-indazol-5-yl)-6-(trifluoromethyl)pyridine-2-carboxamide | 1-(1-phenylethyl)piperazine | 0.79 |

TABLE 8-continued

Examples 122-200

The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 132 | 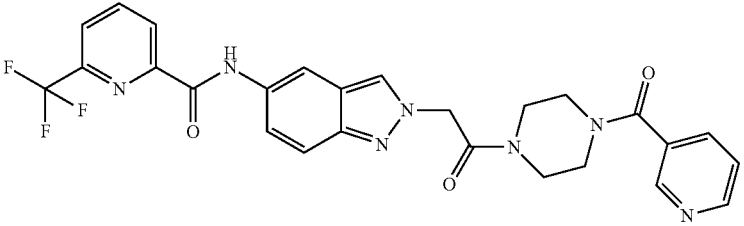 [SMILES: O=C(Nc1ccc2nn(CC(=O)N3CCN(C(=O)c4cccnc4)CC3)cc2c1)c1cccc(C(F)(F)F)n1]<br>N-(2-{2-oxo-2-[4-(pyridin-3-ylcarbonyl)piperazin-1-yl]ethyl}-2H-indazol-5-yl)-6-(trifluoromethyl)pyridine-2-carboxamide | piperazin-1-yl(pyridin-3-yl)methanone | 0.86 |
| 133 | 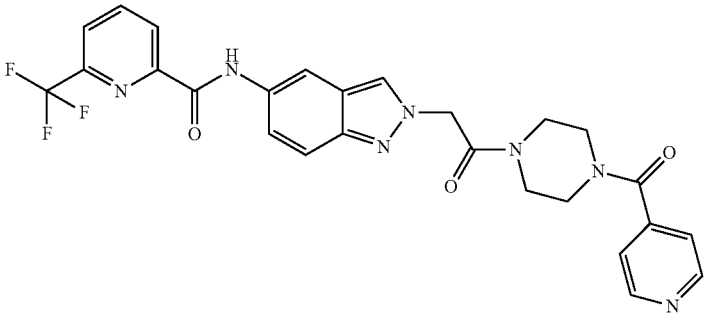 [SMILES: O=C(Nc1ccc2nn(CC(=O)N3CCN(C(=O)c4ccncc4)CC3)cc2c1)c1cccc(C(F)(F)F)n1]<br>N-{2-[2-(4-isonicotinoylpiperazin-1-yl)-2-oxoethyl]-2H-indazol-5-yl}-6-(trifluoromethyl)pyridine-2-carboxamide | piperazin-1-yl(pyridin-4-yl)methanone | 0.83 |
| 134 | 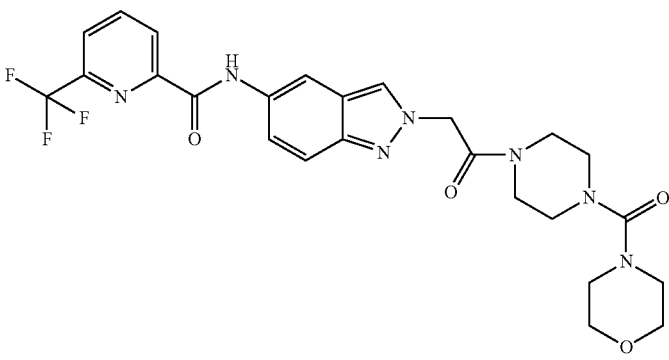 [SMILES: O=C(Nc1ccc2nn(CC(=O)N3CCN(C(=O)N4CCOCC4)CC3)cc2c1)c1cccc(C(F)(F)F)n1]<br>N-(2-{2-[4-(morpholin-4-ylcarbonyl)piperazin-1-yl]-2-oxoethyl}-2H-indazol-5-yl)-6-(trifluoromethyl)pyridine-2-carboxamide | morpholin-4-yl(piperazin-1-yl)methanone | 0.90 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 135 | 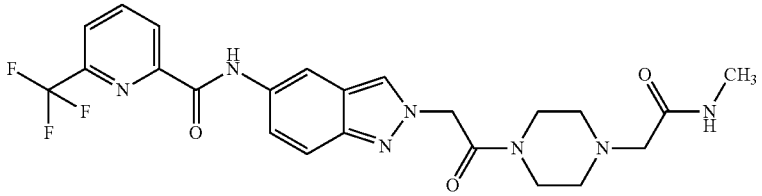 [SMILES: CNC(=O)CN1CCN(C(=O)Cn2cc3cc(NC(=O)c4cccc(C(F)(F)F)n4)ccc3n2)CC1]<br>N-[2-(2-{4-[2-(methylamino)-2-oxoethyl]piperazin-1-yl}-2-oxoethyl)-2H-indazol-5-yl]-6-(trifluoromethyl)pyridine-2-carboxamide | N-methyl-2-(piperazin-1-yl)acetamide | 0.69 |
| 136 | 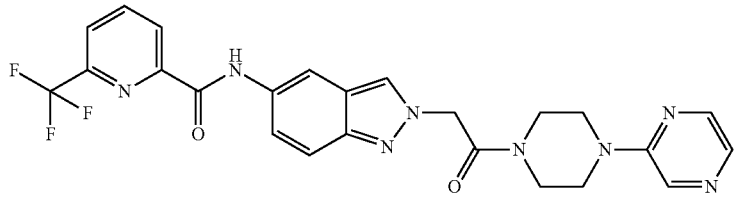<br>N-(2-{2-oxo-2-[4-(pyrazin-2-yl)piperazin-1-yl]ethyl]-2H-indazol-5-yl)-6-(trifluoromethyl)pyridine-2-carboxamide | 2-(piperazin-1-yl)pyrazine | 0.97 |
| 137 | 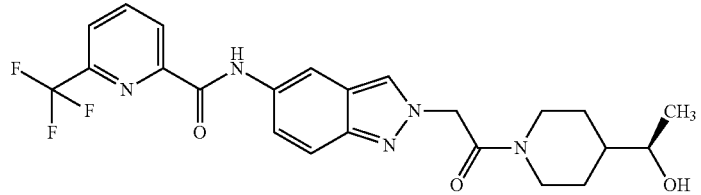 [SMILES: C[C@@H](O)C1CCN(C(=O)Cn2cc3cc(NC(=O)c4cccc(C(F)(F)F)n4)ccc3n2)CC1]<br>N-(2-{2-[4-(1-hydroxyethyl)piperidin-1-yl]-2-oxoethyl}-2H-indazol-5-yl)-6-(trifluoromethyl)pyridine-2-carboxamide | (1R)-1-(piperidin-4-yl)ethanol | 0.92 |
| 138 | 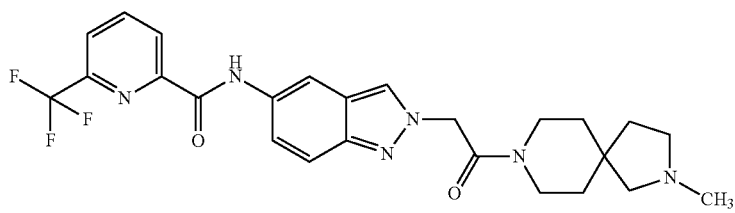 [SMILES: CN1CCC2(CCN(C(=O)Cn3cc4cc(NC(=O)c5cccc(C(F)(F)F)n5)ccc4n3)CC2)C1]<br>N-{2-[2-(2-methyl-2,8-diazaspiro[4.5]dec-8-yl)-2-oxoethyl]-2H-indazol-5-yl}-6-(trifluoromethyl)pyridine-2-carboxamide | 2-methyl-2,8-diazaspiro[4.5]decane | 0.69 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 139 | 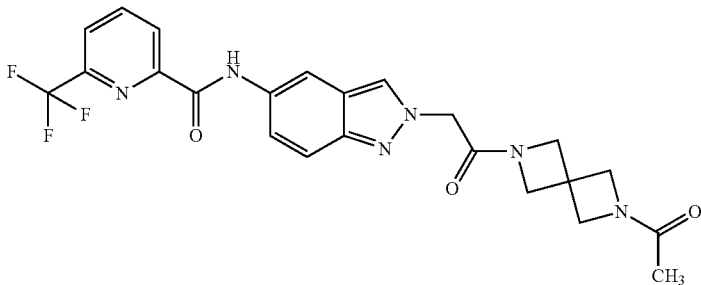 [SMILES: CC(=O)N1CC2(C1)CN(C(=O)Cn1cc3cc(NC(=O)c4cccc(C(F)(F)F)n4)ccc3n1)C2]<br>N-{2-[2-(6-acetyl-2,6-diazaspiro[3.3]hept-2-yl)-2-oxoethyl]-2H-indazol-5-yl}-6-(trifluoromethyl)pyridine-2-carboxamide | 1-(2,6-diazaspiro[3.3]hept-2-yl)ethanone | 0.84 |
| 140 | 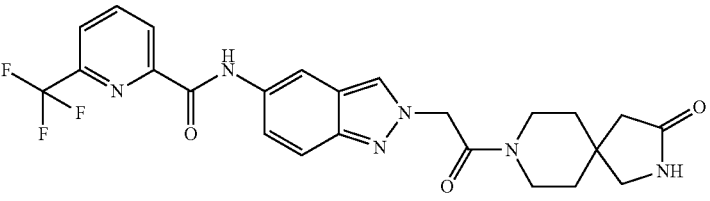 [SMILES: O=C1CC2(CCN(C(=O)Cn3cc4cc(NC(=O)c5cccc(C(F)(F)F)n5)ccc4n3)CC2)CN1]<br>N-{2-[2-oxo-2-(3-oxo-2,8-diazaspiro[4.5]dec-8-yl)ethyl]-2H-indazol-5-yl}-6-(trifluoromethyl)pyridine-2-carboxamide | 2,8-diazaspiro[4.5]decan-3-one | 0.85 |
| 141 | 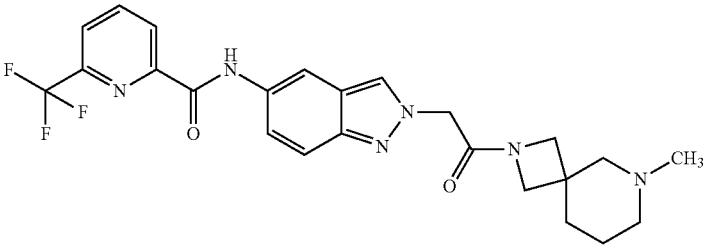 [SMILES: CN1CCCC2(C1)CN(C(=O)Cn1cc3cc(NC(=O)c4cccc(C(F)(F)F)n4)ccc3n1)C2]<br>N-{2-[2-(6-methyl-2,6-diazaspiro[3.5]non-2-yl)-2-oxoethyl]-2H-indazol-5-yl}-6-(trifluoromethyl)pyridine-2-carboxamide | 6-methyl-2,6-diazaspiro[3.5]nonane | 0.67 |
| 142 | 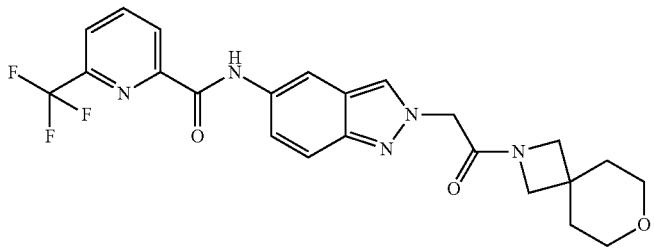 [SMILES: O=C(Nc1ccc2nn(CC(=O)N3CC4(CCOCC4)C3)cc2c1)c1cccc(C(F)(F)F)n1]<br>N-{2-[2-(7-oxa-2-azaspiro[3.5]non-2-yl)-2-oxoethyl]-2H-indazol-5-yl}-6-(trifluoromethyl)pyridine-2-carboxamide | 7-oxa-2-azaspiro[3.5]nonane | 0.94 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 143 | 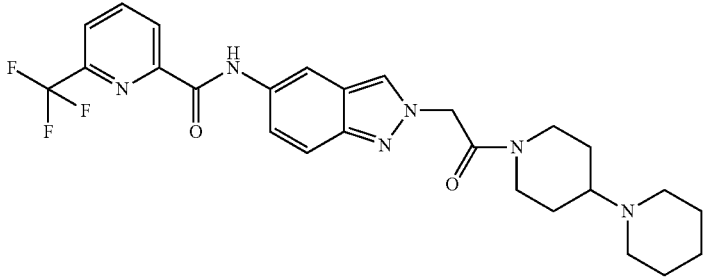 [SMILES: O=C(Nc1ccc2nn(CC(=O)N3CCC(N4CCCCC4)CC3)cc2c1)c1cccc(C(F)(F)F)n1]<br>N-{2-[2-(1,4'-bipiperidin-1-yl)-2-oxoethyl]-2H-indazol-5-yl)-6-(trifluoromethyl)pyridine-2-carboxamide | 1,4'-bipiperidine | 0.71 |
| 144 | 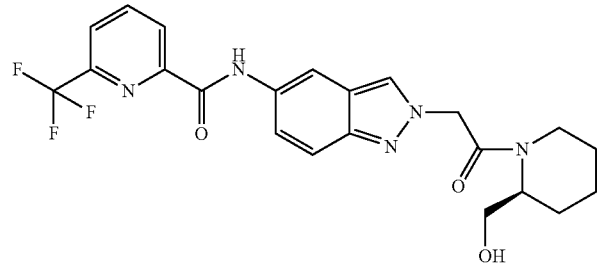 [SMILES: O=C(Nc1ccc2nn(CC(=O)N3CCCC[C@H]3CO)cc2c1)c1cccc(C(F)(F)F)n1]<br>N-(2-{2-[2-(hydroxymethyl)piperidin-1-yl]-2-oxoethyl}-2H-indazol-5-yl)-6-(trifluoromethyl)pyridine-2-carboxamide | (2S)-piperidin-2-ylmethanol | 0.94 |
| 145 | 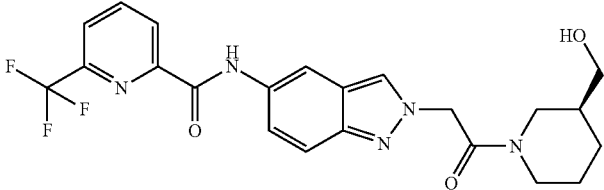 [SMILES: O=C(Nc1ccc2nn(CC(=O)N3CCC[C@H](CO)C3)cc2c1)c1cccc(C(F)(F)F)n1]<br>N-(2-{2-[3-(hydroxymethyl)piperidin-1-yl]-2-oxoethyl}-2H-indazol-5-yl)-6-(trifluoromethyl)pyridine-2-carboxamide | (3S)-piperidin-3-ylmethanol | 0.91 |
| 146 | 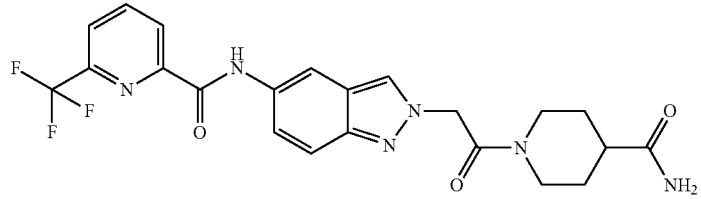 [SMILES: NC(=O)C1CCN(C(=O)Cn2cc3cc(NC(=O)c4cccc(C(F)(F)F)n4)ccc3n2)CC1]<br>N-{2-[2-(4-carbamoylpiperidin-1-yl)-2-oxoethyl]-2H-indazol-5-yl}-6-(trifluoromethyl)pyridine-2-carboxamide | piperidine-4-carboxamide | 0.82 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 147 | 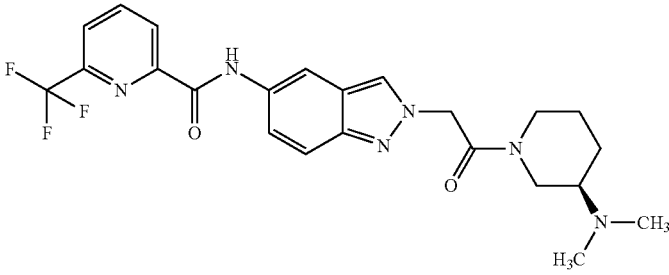 [SMILES: CN(C)[C@@H]1CCCN(C(=O)Cn2cc3cc(NC(=O)c4cccc(C(F)(F)F)n4)ccc3n2)C1]<br>N-(2-{2-[3-(dimethylamino)piperidin-1-yl]-2-oxoethyl}-2H-indazol-5-yl)-6-(trifluoromethyl)pyridine-2-carboxamide | (3R)-N,N-dimethylpiperidine-3-amine | 0.68 |
| 148 | 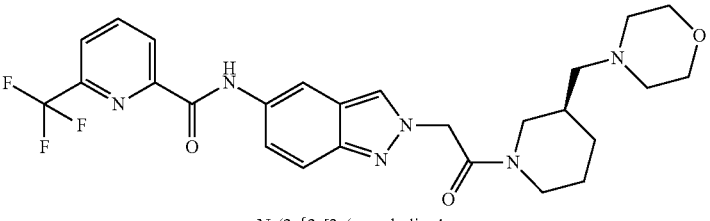<br>N-(2-{2-[3-(morpholin-4-ylmethyl)piperidin-1-yl]-2-oxoethyl}-2H-indazol-5-yl)-6-(trifluoromethyl)pyridine-2-carboxamide | 4-[(3S)-piperidin-3-ylmethyl]morpholine | 0.71 |
| 149 | 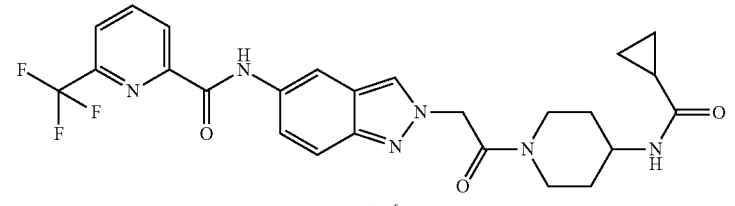<br>N-[2-(2-{4-[(cyclopropylcarbonyl)amino]piperidin-1-yl}-2-oxoethyl)-2H-indazol-5-yl]-6-(trifluoromethyl)pyridine-2-carboxamide | N-(piperidin-4-yl)cyclopropanecarboxamide | 0.94 |
| 150 | 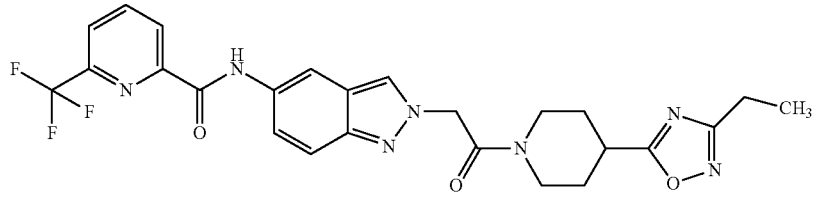 [SMILES: CCc1noc(C2CCN(C(=O)Cn3cc4cc(NC(=O)c5cccc(C(F)(F)F)n5)ccc4n3)CC2)n1]<br>N-(2-{2-[4-(3-ethyl-1,2,4-oxadiazol-5-yl)piperidin-1-yl]-2-oxoethyl}-2H-indazol-5-yl)-6-(trifluoromethyl)pyridine-2-carboxamide | 4-(3-ethyl-1,2,4-oxadiazol-5-yl)piperidine | 1.08 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 151 | 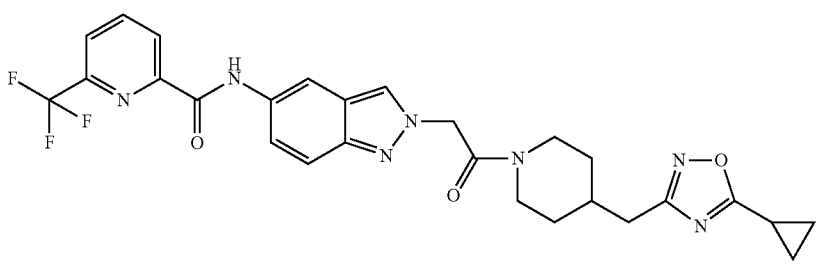 [SMILES: O=C(Nc1ccc2nn(CC(=O)N3CCC(Cc4noc(C5CC5)n4)CC3)cc2c1)c1cccc(C(F)(F)F)n1]<br>N-[2-(2-{4-[(5-cyclopropyl-1,2,4-oxadiazol-3-yl)methyl]piperidin-1-yl}-2-oxoethyl)-2H-indazol-5-yl]-6-(trifluoromethyl)pyridine-2-carboxamide | 4-[(5-cyclopropyl-1,2,4-oxadiazol-3-yl)methyl]piperidine | 1.12 |
| 152 | 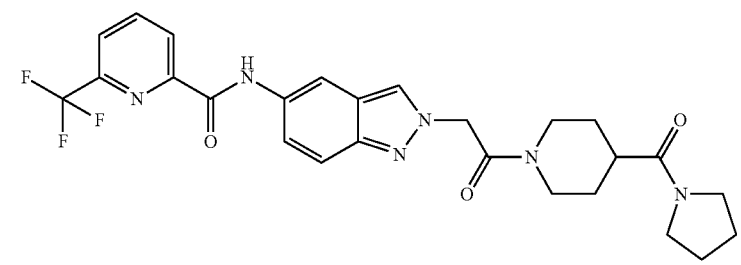 [SMILES: O=C(Nc1ccc2nn(CC(=O)N3CCC(C(=O)N4CCCC4)CC3)cc2c1)c1cccc(C(F)(F)F)n1]<br>N-(2-{2-oxo-2-[4-(pyrrolidin-1-ylcarbonyl)piperidin-1-yl]ethyl}-2H-indazol-5-yl)-6-(trifluoromethyl)pyridine-2-carboxamide | piperidin-4-yl(pyrrolidin-1-yl)methanone | 0.96 |
| 153 | 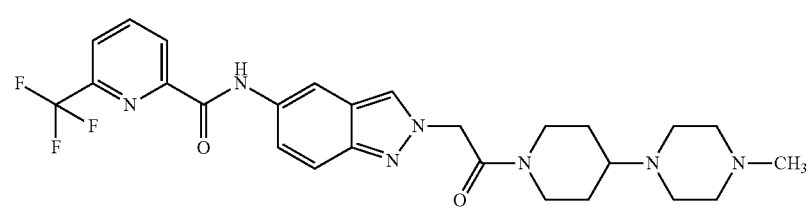 [SMILES: CN1CCN(C2CCN(C(=O)Cn3cc4cc(NC(=O)c5cccc(C(F)(F)F)n5)ccc4n3)CC2)CC1]<br>N-(2-{2-[4-(4-methylpiperazin-1-yl)piperidin-1-yl]-2-oxoethyl}-2H-indazol-5-yl)-6-(trifluoromethyl)pyridine-2-carboxamide | 1-methyl-4-(piperidin-4-yl)piperazine | 0.64 |
| 154 | 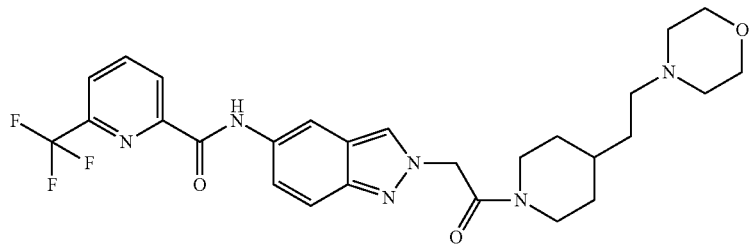 [SMILES: O=C(Nc1ccc2nn(CC(=O)N3CCC(CCN4CCOCC4)CC3)cc2c1)c1cccc(C(F)(F)F)n1]<br>N-[2-(2-{4-[2-(morpholin-4-yl)ethyl]piperidin-1-yl}-2-oxoethyl)-2H-indazol-5-yl]-6-(trifluoromethyl)pyridine-2-carboxamide | 4-[2-(piperidin-4-yl)ethyl]morpholine | 0.71 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 155 | 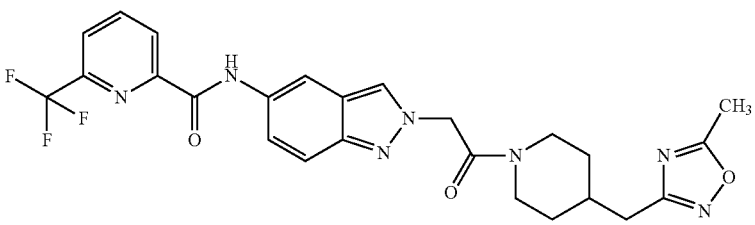 [SMILES: Cc1nc(CC2CCN(C(=O)Cn3cc4cc(NC(=O)c5cccc(C(F)(F)F)n5)ccc4n3)CC2)no1]<br>N-[2-(2-{4-[(5-methyl-1,2,4-oxadiazol-3-yl)methyl]piperidin-1-yl}-2-oxoethyl)-2H-indazol-5-yl]-6-(trifluoromethyl)pyridine-2-carboxamide | 4-[(5-methyl-1,2,4-oxadiazol-3-yl)methyl]piperidine | 1.03 |
| 156 | 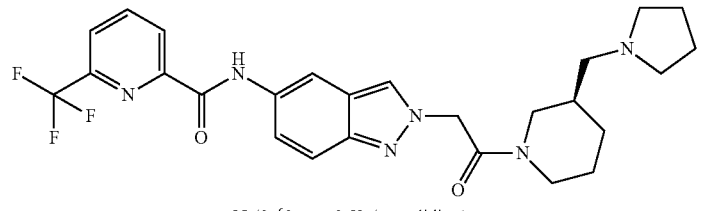<br>N-(2-{2-oxo-2-[3-(pyrrolidin-1-ylmethyl)piperidin-1-yl]ethyl}-2H-indazol-5-yl)-6-(trifluoromethyl)pyridine-2-carboxamide | (3S)-3-(pyrrolidin-1-ylmethyl)piperidine | 0.72 |
| 157 | 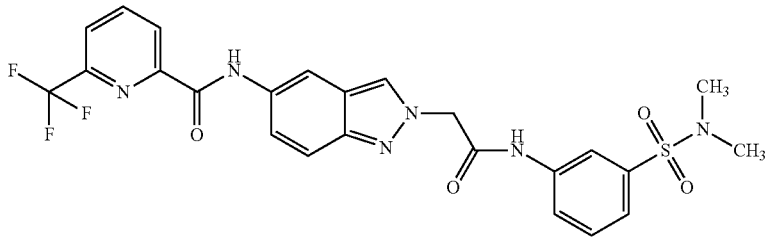 [SMILES: CN(C)S(=O)(=O)c1cccc(NC(=O)Cn2cc3cc(NC(=O)c4cccc(C(F)(F)F)n4)ccc3n2)c1]<br>N-[2-(2-{[3-(dimethylsulphamoyl]phenyl]amino}-2-oxoethyl)-2H-indazol-5-yl]-6-(trifluoromethyl)pyridine-2-carboxamide | 3-amino-N,N-dimethylbenzenesulphonamide | 1.11 |
| 158 | 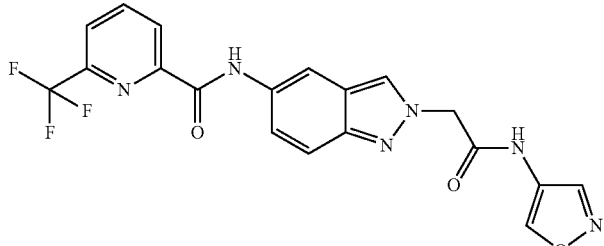<br>N-{2-[2-(1,2-oxazol-4-ylamino)-2-oxoethyl]-2H-indazol-5-yl}-6-(trifluoromethyl)pyridine-2-carboxamide | 1,2-oxazole-4-amine | 0.97 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 159 | 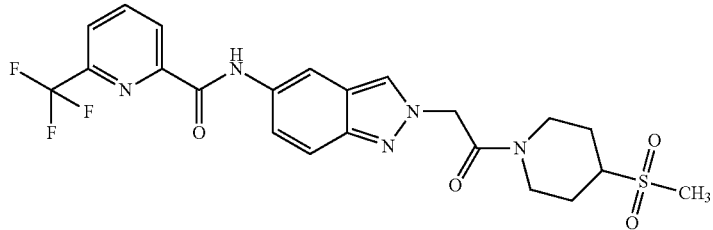 [SMILES: CS(=O)(=O)C1CCN(C(=O)Cn2cc3cc(NC(=O)c4cccc(C(F)(F)F)n4)ccc3n2)CC1]<br>N-(2-{2-[4-(methylsulphonyl)piperidin-1-yl]-2-oxoethyl}-2H-indazol-5-yl)-6-(trifluoromethyl)pyridine-2-carboxamide | 4-(methylsulphonyl)piperidine | 0.89 |
| 160 | 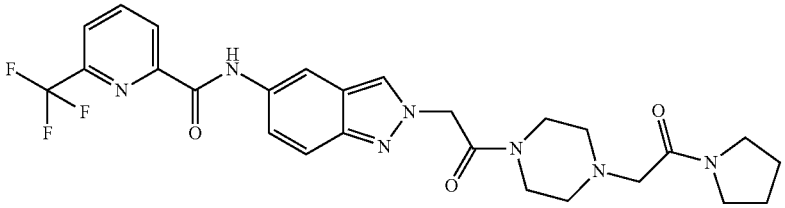 [SMILES: O=C(Nc1ccc2nn(CC(=O)N3CCN(CC(=O)N4CCCC4)CC3)cc2c1)c1cccc(C(F)(F)F)n1]<br>N-[2-(2-oxo-2-{4-[2-oxo-2-(pyrrolidin-1-yl)ethyl]piperazin-1-yl}ethyl)-2H-indazol-5-yl]-6-(trifluoromethyl)pyridine-2-carboxamide | 2-(piperazin-1-yl)-1-(pyrrolidin-1-yl)ethanone | 0.71 |
| 161 | 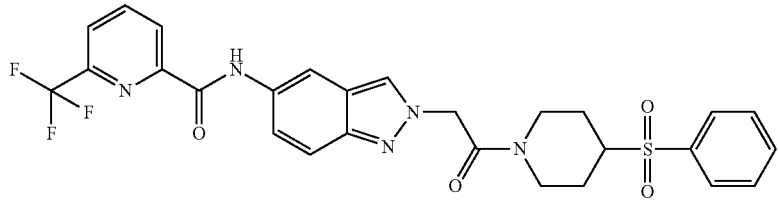 [SMILES: O=C(Nc1ccc2nn(CC(=O)N3CCC(S(=O)(=O)c4ccccc4)CC3)cc2c1)c1cccc(C(F)(F)F)n1]<br>N-(2-{2-oxo-2-[4-(phenylsulphonyl)piperidin-1-yl]ethyl}-2H-indazol-5-yl)-6-(trifluoromethyl)pyridine-2-carboxamide | 4-(phenylsulphonyl)piperidine | 1.08 |
| 162 | 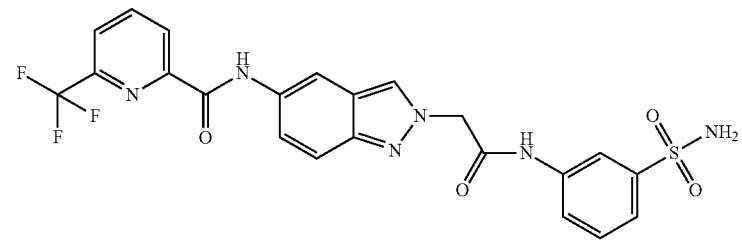 [SMILES: NS(=O)(=O)c1cccc(NC(=O)Cn2cc3cc(NC(=O)c4cccc(C(F)(F)F)n4)ccc3n2)c1]<br>N-(2-{2-oxo-2-[(3-sulphamoylphenyl)aminolethyl}-2H-indazol-5-yl)-6-(trifluoromethyl)pyridine-2-carboxamide | 3-aminobenzenesulphonamide | 0.96 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
| --- | --- | --- | --- |
| 163 | 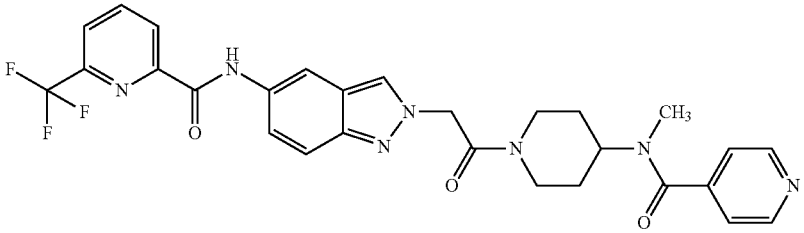 [SMILES: CN(C(=O)c1ccncc1)C1CCN(C(=O)Cn2cc3cc(NC(=O)c4cccc(C(F)(F)F)n4)ccc3n2)CC1]<br>N-[2-(2-{4-[isonicotinoyl(methyl)amino]piperidin-1-yl}-2-oxoethyl)-2H-indazol-5-yl]-6-(trifluoromethyl)pyridine-2-carboxamide | N-methyl-N-(piperidin-4-yl)isonicotinamide | 0.85 |
| 164 | 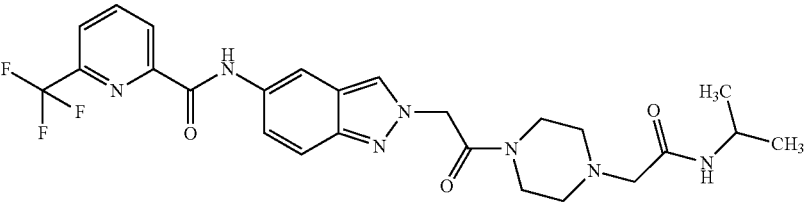 [SMILES: CC(C)NC(=O)CN1CCN(C(=O)Cn2cc3cc(NC(=O)c4cccc(C(F)(F)F)n4)ccc3n2)CC1]<br>N-[2-(2-{4-[2-(isopropylamino)-2-oxoethyl]piperazin-1-yl}-2-oxoethyl)-2H-indazol-5-yl]-6-(trifluoromethyl)pyridine-2-carboxamide | N-isopropyl-2-(piperazin-1-yl)acetamide | 0.74 |
| 165 | 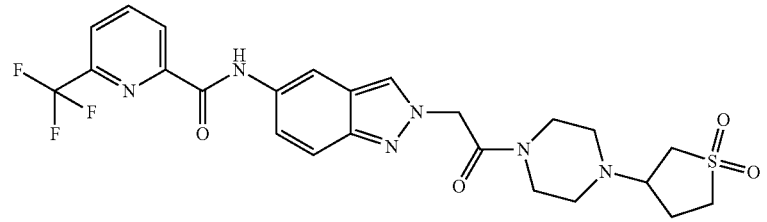 [SMILES: O=C(Nc1ccc2nn(CC(=O)N3CCN(C4CCS(=O)(=O)C4)CC3)cc2c1)c1cccc(C(F)(F)F)n1]<br>N-(2-{2-[4-(1,1-dioxidotetrahydrothiophen-3-yl)piperazin-1-yl]-2-oxoethyl}-2H-indazol-5-yl)-6-(trifluoromethyl)pyridine-2-carboxamide | 1-(1,1-dioxidotetrahydrothiophen-3-yl)piperazine | 0.82 |
| 166 | 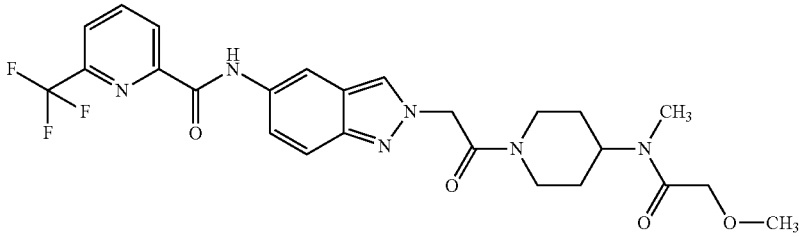 [SMILES: COCC(=O)N(C)C1CCN(C(=O)Cn2cc3cc(NC(=O)c4cccc(C(F)(F)F)n4)ccc3n2)CC1]<br>N-[2-(2-{4-[(methoxyacetyl)(methyl)amino]piperidin-1-yl}-2-oxoethyl)-2H-indazol-5-yl]-6-(trifluoromethyl)pyridine-2-carboxamide | 2-methoxy-N-methyl-N-(piperidin-4-yl)acetamide | 0.90 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 167 | 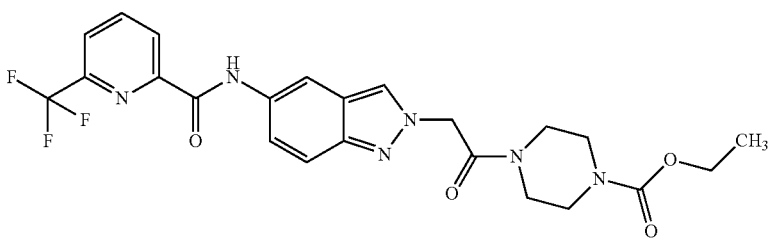 [SMILES: CCOC(=O)N1CCN(C(=O)Cn2cc3cc(NC(=O)c4cccc(C(F)(F)F)n4)ccc3n2)CC1] ethyl 4-{[5-({[6-(trifluoromethyl]pyridin-2-yl]carbonyl}amino)-2H-indazol-2-yl]acetyl}piperazine-1-carboxylate | ethyl piperazine-1-carboxylate | 1.01 |
| 168 | 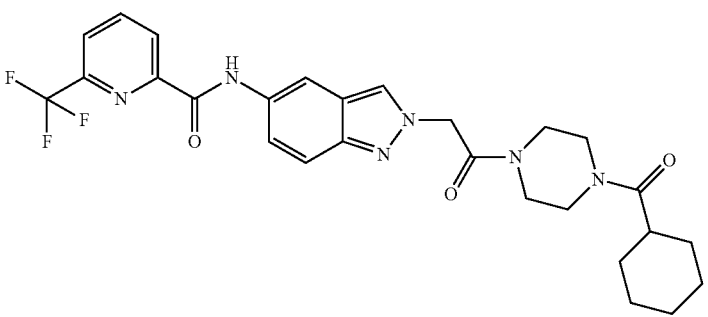 [SMILES: O=C(Nc1ccc2nn(CC(=O)N3CCN(C(=O)C4CCCCC4)CC3)cc2c1)c1cccc(C(F)(F)F)n1] N-(2-{2-[4-(cyclohexylcarbonyl)piperazin-1-yl]-2-oxoethyl}-2H-indazol-5-yl)-6-(trifluoromethyl)pyridine-2-carboxamide | cyclohexyl(piperazin-1-yl)methanone | 1.10 |
| 169 | 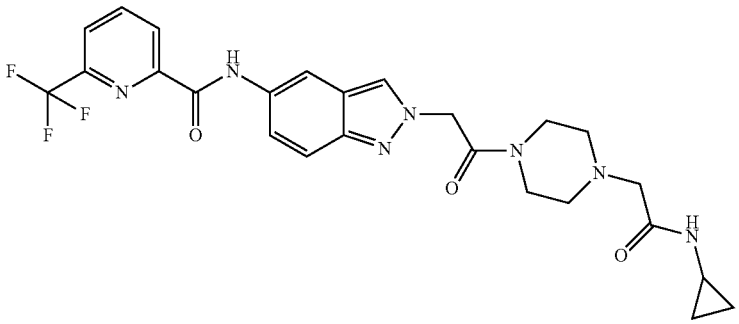 [SMILES: O=C(CN1CCN(C(=O)Cn2cc3cc(NC(=O)c4cccc(C(F)(F)F)n4)ccc3n2)CC1)NC1CC1] N-[2-(2-{4-[2-(cyclopropylamino)-2-oxoethyl]piperazin-1-yl}-2-oxoethyl)-2H-indazol-5-yl]-6-(trifluoromethyl)pyridine-2-carboxamide | N-cyclopropyl-2-(piperazin-1-yl)acetamide | 0.72 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 170 | 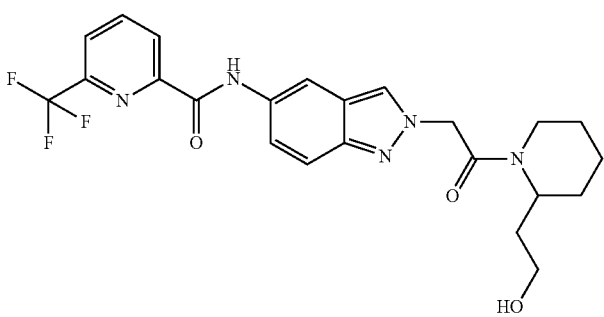 [SMILES: O=C(Nc1ccc2nn(CC(=O)N3CCCCC3CCO)cc2c1)c1cccc(C(F)(F)F)n1]<br>N-(2-{2-[2-(2-hydroxyethyl)piperidin-1-yl]-2-oxoethyl}-2H-indazol-5-yl)-6-(trifluoromethyl)pyridine-2-carboxamide | 2-(piperidin-2-yl)ethanol | 0.98 |
| 171 | 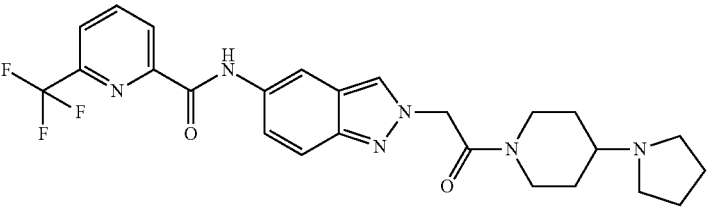 [SMILES: O=C(Nc1ccc2nn(CC(=O)N3CCC(N4CCCC4)CC3)cc2c1)c1cccc(C(F)(F)F)n1]<br>N-(2-{2-oxo-2-[4-(pyrrolidin-1-yl)piperidin-1-yl]ethyl}-2H-indazol-5-yl)-6-(trifluoromethyl)pyridine-2-carboxamide | 4-(pyrrolidin-1-yl)piperidine | 0.69 |
| 172 | 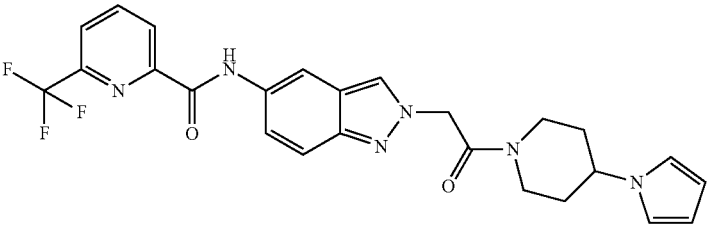 [SMILES: O=C(Nc1ccc2nn(CC(=O)N3CCC(n4cccc4)CC3)cc2c1)c1cccc(C(F)(F)F)n1]<br>N-(2-{2-oxo-2-[4-(1H-pyrrol-1-yl)piperidin-1-yl]ethyl}-2H-indazol-5-yl)-6-(trifluoromethyl)pyridine-2-carboxamide | 4-(1H-pyrrol-1-yl)piperidine | 1.13 |
| 173 | 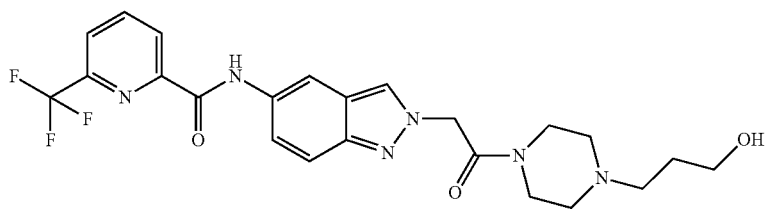 [SMILES: O=C(Nc1ccc2nn(CC(=O)N3CCN(CCCO)CC3)cc2c1)c1cccc(C(F)(F)F)n1]<br>N-(2-{2-[4-(3-hydroxypropyl)piperazin-1-yl]-2-oxoethyl}-2H-indazol-5-yl)-6-(trifluoromethyl)pyridine-2-carboxamide | 3-(piperazin-1-yl)propan-1-ol | 0.65 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 174 | 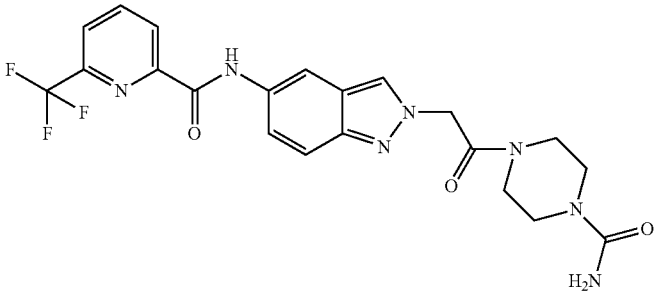 [SMILES: NC(=O)N1CCN(C(=O)Cn2cc3cc(NC(=O)c4cccc(C(F)(F)F)n4)ccc3n2)CC1]<br>4-{[5-({[6-(trifluoromethyl)pyridin-2-yl]carbonyl}amino)-2H-indazol-2-yl]acetyl}piperazine-1-carboxamide | piperazine-1-carboxamide | 0.81 |
| 175 | 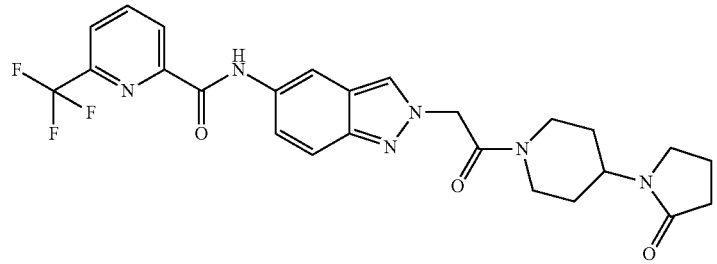 [SMILES: O=C(Nc1ccc2nn(CC(=O)N3CCC(N4CCCC4=O)CC3)cc2c1)c1cccc(C(F)(F)F)n1]<br>N-(2-{2-oxo-2-[4-(2-oxopyrrolidin-1-yl)piperidin-1-yl]ethyl}-2H-indazol-5-yl)-6-(trifluoromethyl)pyridine-2-carboxamide | 1-(piperidin-4-yl)pyrrolidin-2-one | 0.92 |
| 176 | 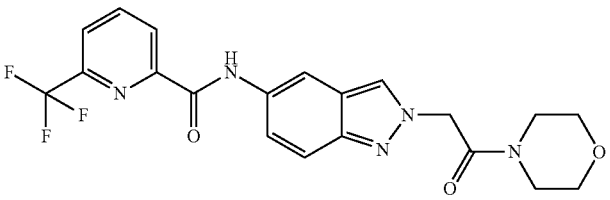 [SMILES: O=C(Nc1ccc2nn(CC(=O)N3CCOCC3)cc2c1)c1cccc(C(F)(F)F)n1]<br>N-{2-[2-(morpholin-4-yl)-2-oxoethyl]-2H-indazol-5-yl}-6-(trifluoromethyl)pyridine-2-carboxamide | morpholine | 0.90 |
| 177 | 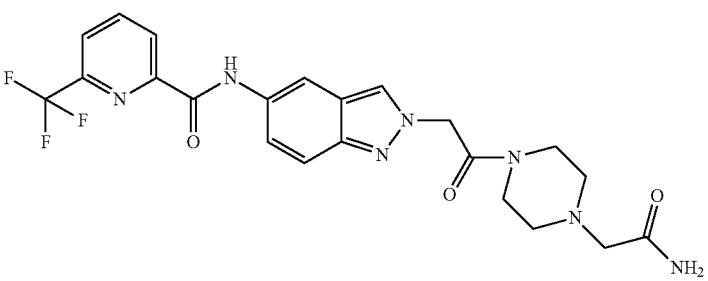 [SMILES: NC(=O)CN1CCN(C(=O)Cn2cc3cc(NC(=O)c4cccc(C(F)(F)F)n4)ccc3n2)CC1]<br>N-(2-{2-[4-(2-amino-2-oxoethyl)piperazin-1-yl]-2-oxoethyl}-2H-indazol-5-yl)-6-(trifluoromethyl)pyridine-2-carboxamide | 2-(piperazin-1-yl)acetamide | 0.67 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 178 | 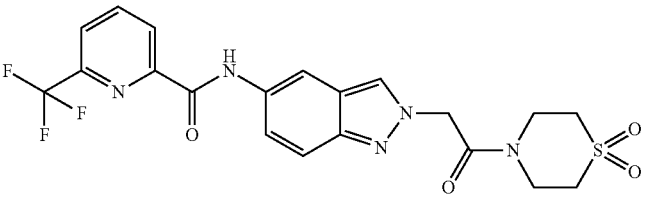 [SMILES: O=C(Nc1ccc2nn(CC(=O)N3CCS(=O)(=O)CC3)cc2c1)c1cccc(C(F)(F)F)n1]  N-{2-[2-(1,1-dioxidothiomorpholin-4-yl)-2-oxoethyl]-2H-indazol-5-yl}-6-(trifluoromethyl)pyridine-2-carboxamide | thiomorpholine 1,1-dioxide | 0.89 |
| 179 | 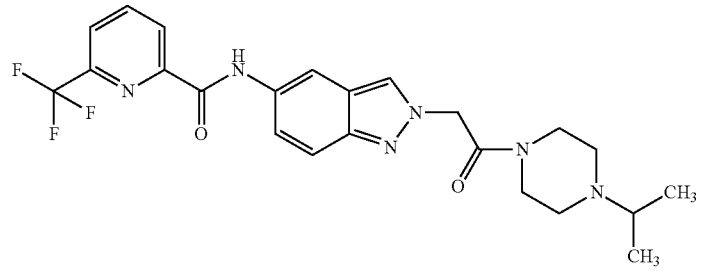 [SMILES: CC(C)N1CCN(C(=O)Cn2cc3cc(NC(=O)c4cccc(C(F)(F)F)n4)ccc3n2)CC1]  N-{2-[2-(4-isopropylpiperazin-1-yl)-2-oxoethyl]-2H-indazol-5-yl}-6-(trifluoromethyl)pyridine-2-carboxamide | 1-isopropylpiperazine | 0.69 |
| 180 | 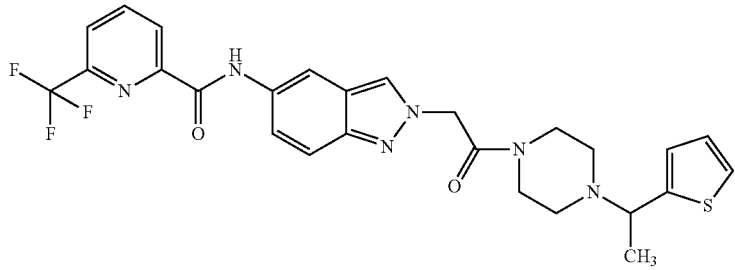 [SMILES: CC(c1cccs1)N1CCN(C(=O)Cn2cc3cc(NC(=O)c4cccc(C(F)(F)F)n4)ccc3n2)CC1]  N-(2-{2-oxo-2-[4-(2-thienylcarbonyl)piperazin-1-yl]ethyl}-2H-indazol-5-yl)-6-(trifluoromethyl)pyridine-2-carboxamide | piperazin-1-yl(2-thienyl)methanone | 1.01 |
| 181 | 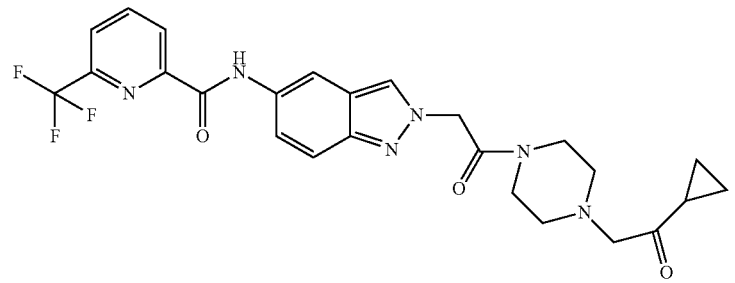 [SMILES: O=C(Nc1ccc2nn(CC(=O)N3CCN(CC(=O)C4CC4)CC3)cc2c1)c1cccc(C(F)(F)F)n1]  N-(2-{2-[4-(2-cyclopropyl-2-oxoethyl)piperazin-1-yl]-2-oxoethyl}-2H-indazol-5-yl)-6-(trifluoromethyl)pyridine-2-carboxamide | 1-cyclopropyl-2-(piperazin-1-yl)ethanone | 0.72 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 182 | 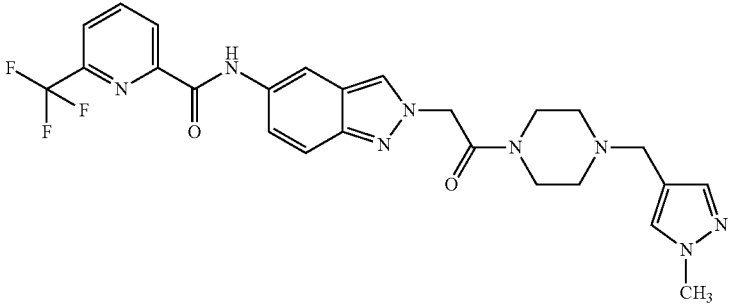 [SMILES: Cn1cc(CN2CCN(C(=O)Cn3cc4cc(NC(=O)c5cccc(C(F)(F)F)n5)ccc4n3)CC2)cn1]<br>N-[2-(2-{4-[(1-methyl-1H-pyrazol-4-yl)methyl]piperazin-1-yl}-2-oxoethyl)-2H-indazol-5-yl]-6-(trifluoromethyl)pyridine-2-carboxamide | 1-[(1-methyl-1H-pyrazol-4-yl)methyl]piperazine | 0.68 |
| 183 | 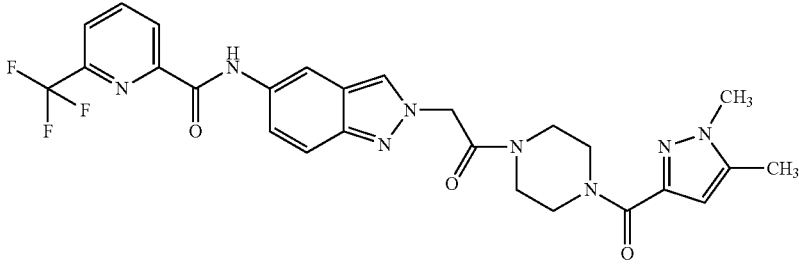 [SMILES: Cc1cc(C(=O)N2CCN(C(=O)Cn3cc4cc(NC(=O)c5cccc(C(F)(F)F)n5)ccc4n3)CC2)nn1C]<br>N-[2-(2-{4-[(1,5-dimethyl-1H-pyrazol-3-yl)carbonyl]piperazin-1-yl}-2-oxoethyl)-2H-indazol-5-yl]-6-(trifluoromethyl)pyridine-2-carboxamide | (1,5-dimethyl-1H-pyrazol-3-yl)(piperazin-1-yl)methanone | 0.95 |
| 184 | 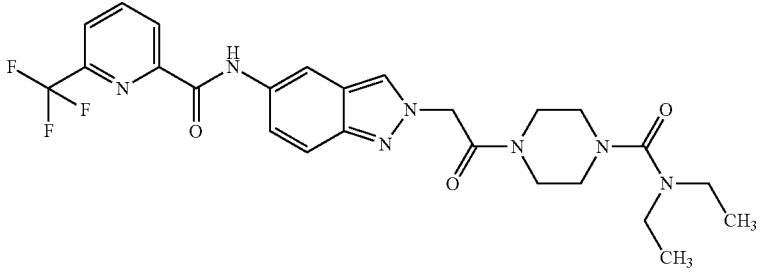 [SMILES: CCN(CC)C(=O)N1CCN(C(=O)Cn2cc3cc(NC(=O)c4cccc(C(F)(F)F)n4)ccc3n2)CC1]<br>N,N-diethyl-4-{[5-({[6-(trifluoromethyl)pyridin-2-yl]carbonyl}amino)-2H-indazol-2-yl]acetyl}piperazine-1-carboxamide | N,N-diethylpiperazine-1-carboxamide | 1.04 |
| 185 | 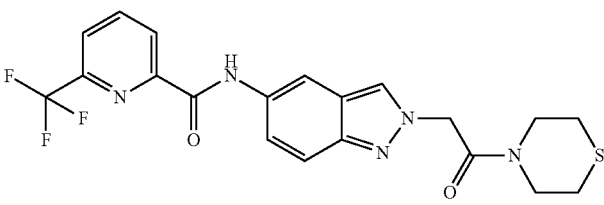 [SMILES: O=C(Nc1ccc2nn(CC(=O)N3CCSCC3)cc2c1)c1cccc(C(F)(F)F)n1]<br>N-{2-[2-oxo-2-(thiomorpholin-4-yl)ethyl]-2H-indazol-5-yl}-6-(trifluoromethyl)pyridine-2-carboxamide | thiomorpholine | 1.01 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 186 | 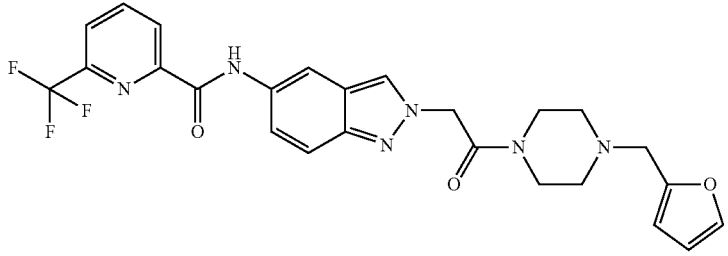 [SMILES: O=C(Nc1ccc2nn(CC(=O)N3CCN(Cc4ccco4)CC3)cc2c1)c1cccc(C(F)(F)F)n1]<br>N-(2-{2-[4-(2-furylmethyl)piperazin-1-yl]-2-oxoethyl}-2H-indazol-5-yl)-6-(trifluoromethyl)pyridine-2-carboxamide | 1-(2-furylmethyl)piperazine | 0.74 |
| 187 | 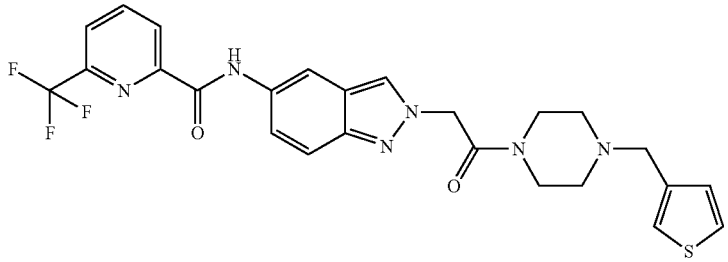 [SMILES: O=C(Nc1ccc2nn(CC(=O)N3CCN(Cc4ccsc4)CC3)cc2c1)c1cccc(C(F)(F)F)n1]<br>N-(2-{2-oxo-2-[4-(3-thienylmethyl)piperazin-1-yl]ethyl}-2H-indazol-5-yl)-6-(trifluoromethyl)pyridine-2-carboxamide | 1-(3-thienylmethyl)piperazine | 0.76 |
| 188 | 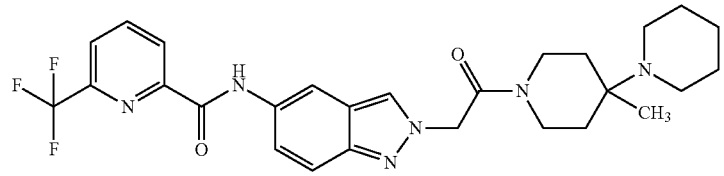 [SMILES: CC1(N2CCCCC2)CCN(C(=O)Cn2cc3cc(NC(=O)c4cccc(C(F)(F)F)n4)ccc3n2)CC1]<br>N-{2-[2-(4'-methyl-1,4'-bipiperidin-1'-yl)-2-oxoethyl]-2H-indazol-5-yl}-6-(trifluoromethyl)pyridine-2-carboxamide | 4'-methyl-1,4'-bipiperidine | 0.72 |
| 189 | 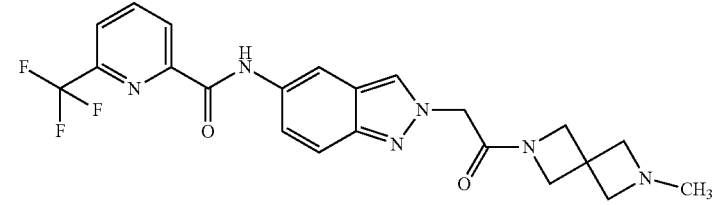 [SMILES: CN1CC2(C1)CN(C(=O)Cn1cc3cc(NC(=O)c4cccc(C(F)(F)F)n4)ccc3n1)C2]<br>N-{2-[2-(6-methyl-2,6-diazaspiro[3.3]hept-2-yl)-2-oxoethyl]-2H-indazol-5-yl}-6-(trifluoromethyl)pyridine-2-carboxamide | 2-methyl-2,6-diazaspiro [3.3]heptane | 0.65 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 190 | 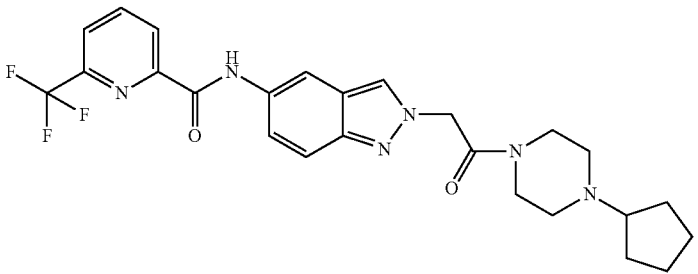 [SMILES: O=C(Nc1ccc2nn(CC(=O)N3CCN(C4CCCC4)CC3)cc2c1)c1cccc(C(F)(F)F)n1]<br>N-{2-[2-(4-cyclopentylpiperazin-1-yl)-2-oxoethyl]-2H-indazol-5-yl}-6-(trifluoromethyl)pyridine-2-carboxamide | 1-cyclopentylpiperazine | 0.72 |
| 191 | 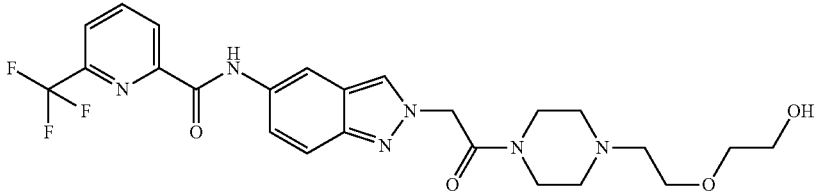 [SMILES: O=C(Nc1ccc2nn(CC(=O)N3CCN(CCOCCO)CC3)cc2c1)c1cccc(C(F)(F)F)n1]<br>N-[2-[2-{4-[2-(2-hydroxyethoxy)ethyl]piperazin-1-yl}-2-oxoethyl)-2H-indazol-5-yl]-6-(trifluoromethyl)pyridine-2-carboxamide | 2-[2-(piperazin-1-yl)ethoxy]ethanol | 0.66 |
| 192 | 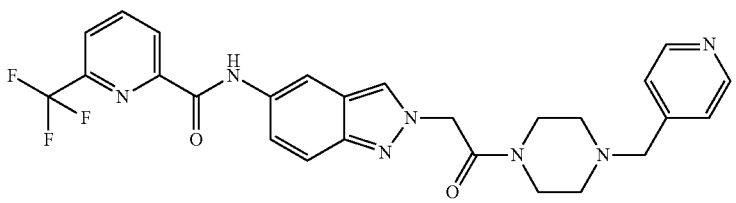 [SMILES: O=C(Nc1ccc2nn(CC(=O)N3CCN(Cc4ccncc4)CC3)cc2c1)c1cccc(C(F)(F)F)n1]<br>N-(2-{2-oxo-2-[4-(pyridin-4-ylmethyl)piperazin-1-yl]ethyl}-2H-indazol-5-yl)-6-(trifluoromethyl]pyridine-2-carboxamide | 1-(pyridin-4-ylmethyl)piperazine | 0.70 |
| 193 | 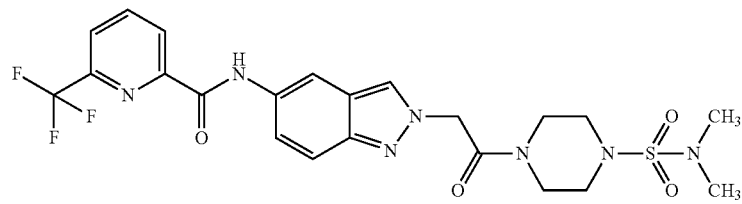 [SMILES: CN(C)S(=O)(=O)N1CCN(C(=O)Cn2cc3cc(NC(=O)c4cccc(C(F)(F)F)n4)ccc3n2)CC1]<br>N-(2-{2-[4-(dimethylsulphamoyl]piperazin-1-yl]-2-oxoethyl}-2H-indazol-5-yl)-6-(trifluoromethyl)pyridine-2-carboxamide | N,N-dimethylpiperazine-1-sulphonamide | 1.01 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 194 | 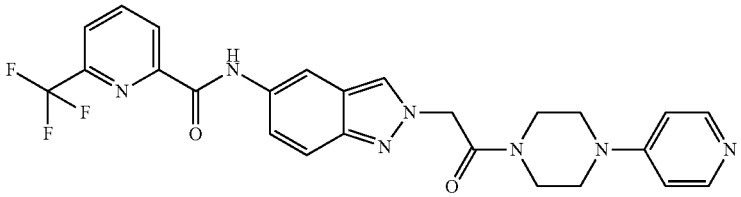 [SMILES: O=C(Nc1ccc2nn(CC(=O)N3CCN(c4ccncc4)CC3)cc2c1)c1cccc(C(F)(F)F)n1]<br>N-(2-{2-oxo-2-[4-(pyridin-4-yl]piperazin-1-yl]ethyl}-2H-indazol-5-yl)-6-(trifluoromethyl)pyridine-2-carboxamide | 1-(pyridin-4-yl)piperazine | 0.70 |
| 195 | 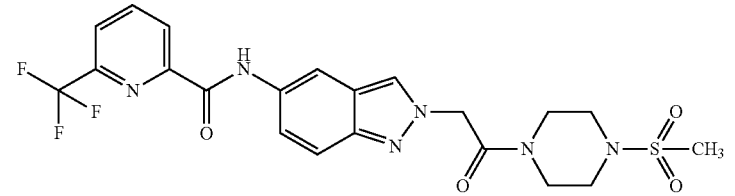 [SMILES: CS(=O)(=O)N1CCN(C(=O)Cn2cc3cc(NC(=O)c4cccc(C(F)(F)F)n4)ccc3n2)CC1]<br>N-(2-{2-[4-(methylsulphonyl]piperazin-1-yl]-2-oxoethyl}-2H-indazol-5-yl)-6-(trifluoromethyl)pyridine-2-carboxamide | 1-(methylsulphonyl)piperazine | 0.92 |
| 196 | 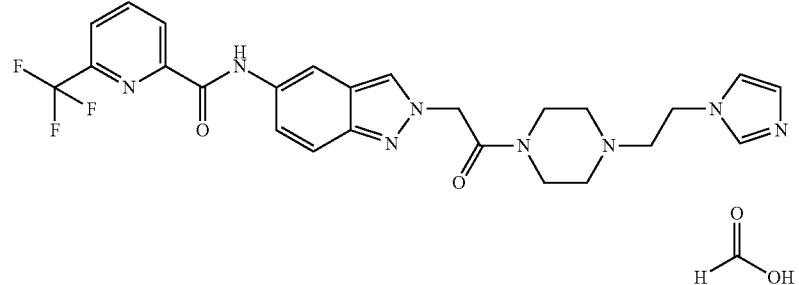 [SMILES: O=C(Nc1ccc2nn(CC(=O)N3CCN(CCn4ccnc4)CC3)cc2c1)c1cccc(C(F)(F)F)n1 ; O=CO]<br>formic acid N-[2-(2-{4-[2-(1H-imidazol-1-yl)ethyl]piperazin-1-yl}-2-oxoethyl)-2H-indazol-5-yl]-6-(trifluoromethyl)pyridine-2-carboxamide (1:1) | 1-[2-(1H-imidazol-1-yl)ethyl]piperazine | 0.64 |
| 197 | 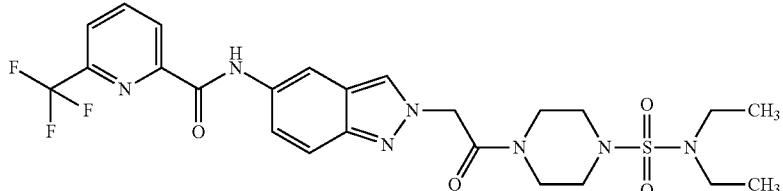<br>N-(2-{2-[4-(diethylsulphamoyl)piperazin-1-yl]-2-oxoethyl}-2H-indazol-5-yl)-6-(trifluoromethyl)pyridine-2-carboxamide | N,N-diethylpiperazine-1-sulphonamide | 1.11 |

TABLE 8-continued

Examples 122-200
The exemplary compounds were prepared from [5-({[6-(trifluoromethylpyridin-2-yl]carbonyl}amino)-2H-indazol-2-yl]acetic acid (Intermediate 9-14) and the starting material indicated in the table.

| Example | Structure and name | Starting material and notes | LC-MS retention time [min] |
|---|---|---|---|
| 198 | 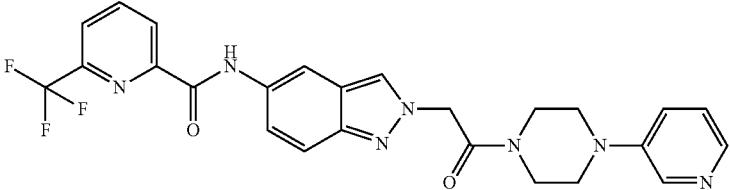 [SMILES: O=C(Nc1ccc2nn(CC(=O)N3CCN(c4cccnc4)CC3)cc2c1)c1cccc(C(F)(F)F)n1]<br>N-(2-{2-oxo-2-[4-(pyridin-3-yl)piperazin-1-yl]ethyl}-2H-indazol-5-yl)-6-(trifluoromethyl)pyridine-2-carboxamide | 1-(pyridin-3-yl)piperazine | 0.72 |
| 199 | 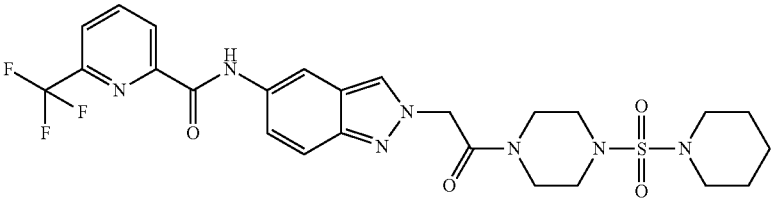 [SMILES: O=C(Nc1ccc2nn(CC(=O)N3CCN(S(=O)(=O)N4CCCCC4)CC3)cc2c1)c1cccc(C(F)(F)F)n1]<br>N-(2-{2-oxo-2-[4-(piperidin-1-ylsulphonyl)piperazin-1-yl]ethyl}-2H-indazol-5-yl)-6-(trifluoromethyl)pyridine-2-carboxamide | 1-(piperidin-1-ylsulphonyl)piperazine | 1.14 |
| 200 | 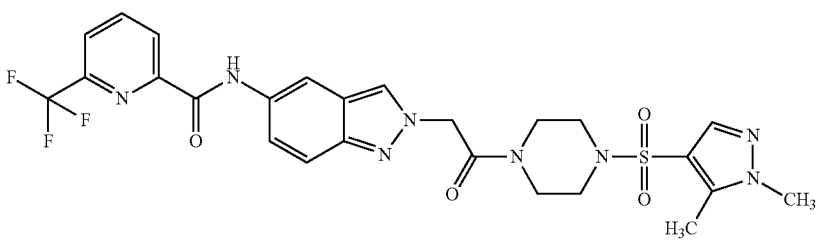 [SMILES: Cc1c(S(=O)(=O)N2CCN(C(=O)Cn3cc4cc(NC(=O)c5cccc(C(F)(F)F)n5)ccc4n3)CC2)cnn1C]<br>N-[2-(2-{4-[(1,5-dimethyl-1H-pyrazol-4-yl)sulphonyl]piperazin-1-yl}-2-oxoethyl)-2H-indazol-5-yl]-6-(trifluoromethyl)pyridine-2-carboxamide | 1-[(1,5-dimethyl-1H-pyrazol-4-yl)sulphonyl]piperazine | 1.00 |

TABLE 9

Examples 201-205
The exemplary compounds were prepared from [5-({[6-(1-methyl-1H-pyrazol-4-yl)pyridin-2-yl]carbonyl}amino)-2H-indazol-2-yl]acetic acid (Intermediate 9-10) and the starting material indicated in the table.

| Example | Name and structure | Starting material and notes | LC-MS retention time [min] |
|---|---|---|---|
| 201 | 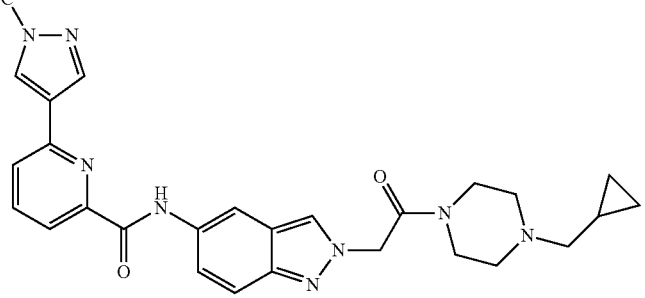  N-(2-{2-[4-(cyclopropylmethyl)piperazin-1-yl]-2-oxoethyl}-2H-indazol-5-yl)-6-(1-methyl-1H-pyrazol-4-yl)pyridine-2-carboxamide | 1-(cyclopropylmethyl)piperazine | 0.64 |
| 202 | 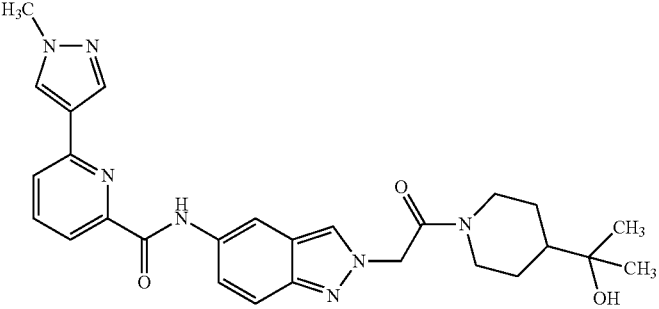 [SMILES: Cn1cc(-c2cccc(C(=O)Nc3ccc4nn(CC(=O)N5CCC(C(C)(C)O)CC5)cc4c3)n2)cn1]  N-(2-{2-[4-(2-hydroxypropan-2-yl)piperidin-1-yl]-2-oxoethyl}-2H-indazol-5-yl)-6-(1-methyl-1H-pyrazol-4-yl)pyridine-2-carboxamide | 2-(piperidin-4-yl)propan-2-ol | 0.85 |
| 203 | 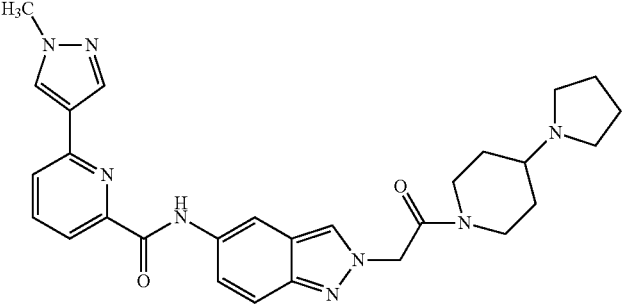 [SMILES: Cn1cc(-c2cccc(C(=O)Nc3ccc4nn(CC(=O)N5CCC(N6CCCC6)CC5)cc4c3)n2)cn1]  6-(1-methyl-1H-pyrazol-4-yl)-N-(2-{2-oxo-2-[4-(pyrrolidin-1-yl)piperidin-1-yl]ethyl}-2H-indazol-5-yl)pyridine-2-carboxamide | 4-(pyrrolidin-1-yl)piperidine | 0.63 |

TABLE 9-continued

Examples 201-205
The exemplary compounds were prepared from [5-({[6-(1-methyl-1H-pyrazol-4-yl)pyridin-2-yl]carbonyl}amino)-2H-indazol-2-yl]acetic acid (Intermediate 9-10) and the starting material indicated in the table.

| Example | Name and structure | Starting material and notes | LC-MS retention time [min] |
|---|---|---|---|
| 204 | 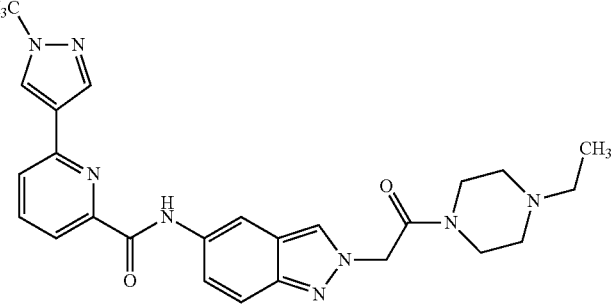<br>N-{2-[2-(4-ethylpiperazin-1-yl)-2-oxoethyl]-2H-indazol-5-yl}-6-(1-methyl-1H-pyrazol-4-yl)pyridine-2-carboxamide | 1-ethylpiperazine | 0.61 |
| 205 | 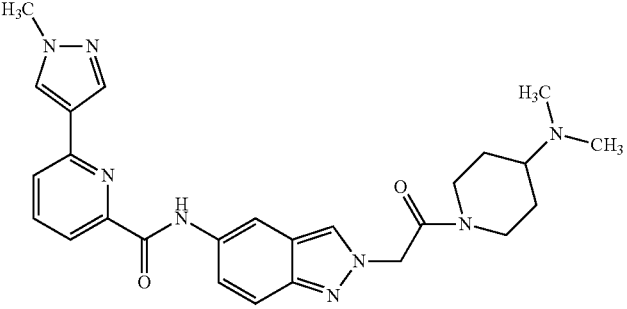<br>N-(2-{2-[4-(dimethylamino)piperidin-1-yl]-2-oxoethyl}-2H-indazol-5-yl)-6-(1-methyl-1H-pyrazol-4-yl)pyridine-2-carboxamide | N,N-dimethylpiperidine-4-amine | 0.61 |

TABLE 10

Examples 206-208
The exemplary compounds were prepared from the intermediates indicated in the table.

| Example | Name and structure | Starting materials and notes | LC-MS retention time [min] |
|---|---|---|---|
| 206 | 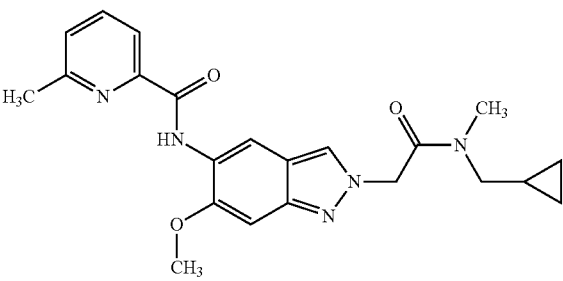<br>N-(2-{2-[(cyclopropylmethyl)(methyl)amino]-2-oxoethyl}-6-methoxy-2H-indazol-5-yl)-6-methylpyridine-2-carboxamide | The exemplary compound was prepared from 2-(5-amino-6-methoxy-2H-indazol-2-yl)-N-(cyclopropylmethyl)-N-methylacetamide and 6-methylpyridine-2-carboxylic acid. $^1$H-NMR (300 MHz, DMSO-d6): δ = 0.17-0.57 (m, 4H), 0.91-1.11 (m, 1H), 2.61 (s), 2.91 (s), 3.12 (s), 3.19 (d), 3. (s, 3H), 5.33-5.40 (m, 2H), 7.09 (s, 1H), 7.55 (dd, 1H), 7.93-8.02 (m, 2H), 8.18-8.24 (m, 1H), 8.71 (s, 1H), 10.71 (s, 1H). | 1.07 |

TABLE 10-continued

Examples 206-208
The exemplary compounds were prepared from the intermediates indicated in the table.

| Example | Name and structure | Starting materials and notes | LC-MS retention time [min] |
|---|---|---|---|
| 207 | 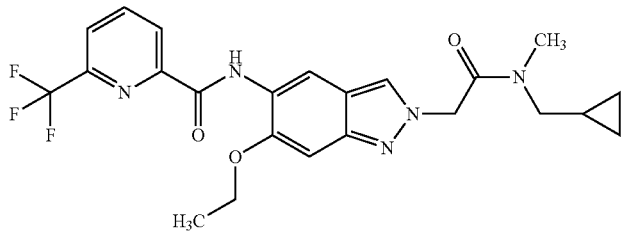<br>N-(2-{2-[(cyclopropylmethyl)(methyl)amino]-2-oxoethyl}-6-ethoxy-2H-indazol-5-yl)-6-(trifluoromethyl)pyridine-2-carboxamide | The exemplary compound was prepared from 105 mg (0.26 mmol) of [6-ethoxy-5-({[6-(trifluoromethyl)pyridin-2-yl]carbonyl}amino)-2H-indazol-2-yl]acetic acid and 33 mg (1.5 eq.) of 1-cyclopropyl-N-methylmethanamine. This gave 87 mg of the exemplary compound.<br>$^1$H-NMR (300 MHz, DMSO-d6): δ = 0.17-0.57 (m, 4H), 0.88-1.12 (m, 1H), 1.49 (t, 3H), 2.91 (s, 1H), 3.09-3.24 (m, 3H), 3.34 (br. s., 1H), 4.20 (q, 2H), 5.32-5.40 (m, 2H), 7.08 (s, 1H), 8.17-8.26 (m, 2H), 8.36-8.48 (m, 2H), 8.71 (s, 1H), 10.7 (s, 1H). | 1.24 |
| 208 | 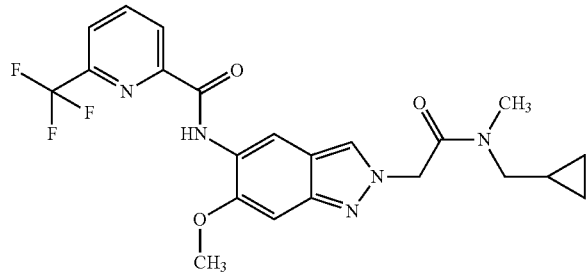<br>N-(2-{2-[(cyclopropylmethyl)(methyl)amino]-2-oxoethyl}-6-methoxy-2H-indazol-5-yl)-6-(trifluoromethyl)pyridine-2-carboxamide | The exemplary compound was prepared from 2-(5-amino-6-methoxy-2H-indazol-2-yl)-N-(cyclopropylmethyl)-N-methylacetamide and 6-(trifluoromethyl)pyridine-2-carboxylic acid.<br>1H-NMR (300 MHz, DMSO-d6): δ = 0.16-0.59 (m, 4H), 0.88-1.14 (m, 1H), 2.91 (s, 1H), 3.10-3.23 (m, 3H), 3.98 (s, 3H), 5.33-5.42 (m, 2H), 7.11 (s, 1H), 8.17-8.28 (m, 2H), 8.35-8.49 (m, 2H), 8.70 (s, 1H), 10.50 (s, 1H). | 1.16 |

TABLE 11

Examples 209-210
The exemplary compounds (Ex.) were prepared from 2-(5-amino-6-methoxy-2H-indazol-2-yl)-1-[4-(2-hydroxypropan-2-yl)piperidin-1-yl]ethanone (Intermediate 6-5).

| Ex. | Name and structure | Starting materials and notes | LC-MS retention time [min] |
|---|---|---|---|
| 209 | 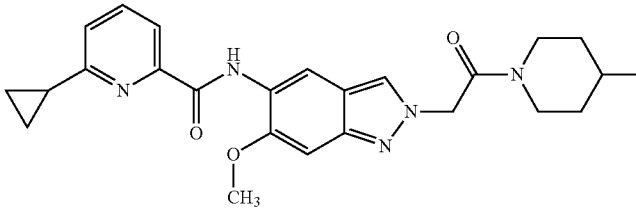<br>6-cyclopropyl-N-(2-{2-[4-(2-hydroxypropan-2-yl)piperidin-1-yl]-2-oxoethyl}-6-methoxy-2H-indazol-5-yl)pyridine-2-carboxamide | prepared from 100 mg of 2-(5-amino-6-methoxy-2H-indazol-2-yl)-1-[4-(2-hydroxypropan-2-yl)piperidin-1-yl]ethanone and 6-cyclopropylpyridine-2-carboxylic acid.<br>1H-NMR (400 MHz, DMSO-d6): δ = 0.99-1.14 (m, 11H), 1.14-1.28 (m, 1H), 1.38-1.49 (m, 1H), 1.74 (t, 2H), 2.21-2.30 (m, 1H), 2.98 (t, 1H), 3.97-4.08 (m, 4H), 4.15 (s, 1H), 4.41 (d, 1H), 5.26-5.43 (m, 2H), 7.08 (s, 1H), 7.58-7.64 (m, 1H), 7.87-7.96 (m, 2H), 8.17-8.23 (m, 1H), 8.65 (s, 1H), 10.80 (s, 1H). | 1.08 |

TABLE 11-continued

Examples 209-210
The exemplary compounds (Ex.) were prepared from 2-(5-amino-6-methoxy-2H-indazol-2-yl)-1-
[4-(2-hydroxypropan-2-yl)piperidin-1-yl]ethanone (Intermediate 6-5).

| Ex. | Name and structure | Starting materials and notes | LC-MS retention time [min] |
|---|---|---|---|
| 210 | 6-(1-hydroxyethyl)-N-(2-{2-[4-(2-hydroxypropan-2-yl)piperidin-1-yl]-2-oxoethyl}-6-methoxy-2H-indazol-5-yl)pyridine-2-carboxamide | prepared from 150 mg of 2-(5-amino-6-methoxy-2H-indazol-2-yl)-1-[4-(2-hydroxypropan-2-yl)piperidin-1-yl]etanone and 133 mg of potassium 6-(1-hydroxyethyl)pyridine-2-carboxylate (Intermediate 19-1). 1H-NMR (400 MHz, DMSO-d6): δ = 0.99-1.13 (m, 7H), 1.15-1.29 (m, 1H), 1.34-1.48 (m, 1H), 1.51 (d, 3H), 1.74 (t, 2H), 2.99 (t, 1H), 3.95-4.07 (m, 4H), 4.16 (s, 1H), 4.41 (d, 1H), 4.81-4.90 (m, 1H), 5.28-5.43 (m, 2H), 5.58 (d, 1H), 7.08 (s, 1H), 7.79 (dd, 1H), 8.01-8.10 (m, 2H), 8.20 (s, 1H), 8.67 (s, 1H), 10.78 (s, 1H). | 0.82 |

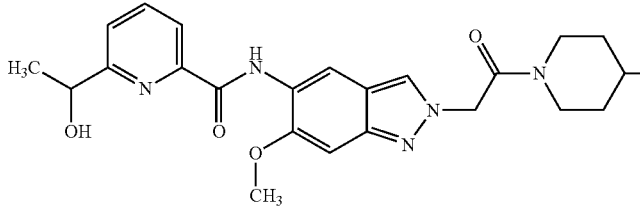

TABLE 12

Examples 211-213
The exemplary compounds were prepared from 2-(5-amino-2H-indazol-2-yl)-1-(4-
benzoylpiperazin-1-yl)ethanone (Intermediate 6-11).

| Ex. | Name and structure | Preparation and notes | LC-MS retention time [min] |
|---|---|---|---|
| 211 | 6-(azetidin-3-ylamino)-N-{2-[2-(4-benzoylpiperazin-1-yl)-2-oxoethyl]-2H-indazol-5-yl}pyridine-2-carboxamide | 96 mg of 2-(5-amino-2H-indazol-2-yl)-1-(4-benzoylpiperazin-1-yl)ethanone and 202 mg of 6-{[1-(tert-butoxycarbonyl)azetidin-3-yl]amino}pyridine-2-carboxylic acid (Intermediate 19-12) were reacted with EDC, HOBt and triethylamine. Aqueous work-up gave 252 mg of tert-butyl 3-{[6-({2-[2-(4-benzoylpiperazin-1-yl)-2-oxoethyl]-2H-indazol-5-yl}carbamoyl)pyridin-2-yl]amino}azetidine-1-carboxylate as crude product which was reacted with trifluoroacetic acid in dichloromethane. Purification by HPLC according to Method P2 gave 19 mg of the title compound. | 0.60 |
| 212 | 6-[(azetidin-2-ylmethyl)amino]-N-{2-[2-(4-benzoylpiperazin-1-yl)-2-oxoethyl]-2H-indazol-5-yl}pyridine-2-carboxamide | 100 mg of 2-(5-amino-2H-indazol-2-yl)-1-(4-benzoylpiperazin-1-yl)ethanone and 265 mg of potassium 6-({[1-(tert-butoxycarbonyl)azetidin-2-yl]methyl}amino)pyridine-2-carboxylate (Intermediate 19-13) were reacted with EDC, HOBt and triethylamine. Aqueous work-up and HPLC gave 93 mg of tert-butyl 2-({[6-({2-[2-(4-benzoyl-piperazin-1-yl)-2-oxoethyl]-2H-indazol-5-yl}carbamoyl)pyridin-2-yl]amino}methyl)azetidine-1-carboxylate which was reacted with trifluoroacetic acid in dichloromethane. HPLC purification gave 50 mg of the title compound. $^1$H-NMR (400 | 0.61 |

TABLE 12-continued

Examples 211-213
The exemplary compounds were prepared from 2-(5-amino-2H-indazol-2-yl)-1-(4-benzoylpiperazin-1-yl)ethanone (Intermediate 6-11).

| Ex. | Name and structure | Preparation and notes | LC-MS retention time [min] |
|---|---|---|---|
| | | MHz, DMSO-d6, selected signals): δ = 2.20-2.42 (m, 2H), 4.37-4.49 (m, 1H), 5.48 (br. s., 2H), 6.77 (d, 1H), 7.24 (t, 1H), 7.32 (d, 1H), 7.39-7.53 (m, 6H), 7.53-7.65 (m, 2H), 8.28 (d, 2H), 10.17 (br. s., 1H). | |
| 213 | 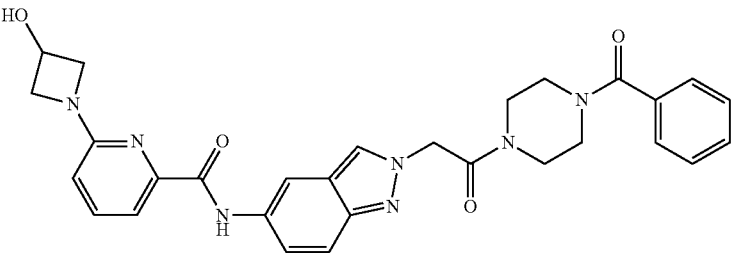<br>N-{2-[2-(4-benzoylpiperazin-1-yl)-2-oxoethyl]-2H-indazol-5-yl}-6-(3-hydroxyazetidin-1-yl)pyridine-2-carboxamide | 85 mg of N-{2-[2-(4-benzoylpiperazin-1-yl)-2-oxoethyl]-2H-indazol-5-yl}-6-chloropyridine-2-carboxamide (Example 91) were reacted with 3 equiv. of azetidin-3-ol hydrochloride (1:1) and 115 μl of N-ethyl-N-isopropylpropane-2-amine in 2 ml NMP at 100° C. Purification by HPLC gave 2 mg of the title compound. $^1$H-NMR (400 MHz, DMSO-d6, selected signals): δ = 3.82 (dd, 2H), 4.30 (t, 2H), 4.58-4.66 (m, 1H), 5.49 (br. s., 2H), 5.70 (d, 1H), 6.63 (d, 1H), 7.38 (d, 1H), 7.42-7.52 (m), 7.56-7.61 (m, 1H), 7.71 (t, 1H), 8.27 (s, 1H), 8.31 (s, 1H), 10.11 (s, 1H). | 0.81 |

TABLE 13

Examples 214-216

| Ex. | Name and structure | Preparation and notes | LC-MS retention time [min] |
|---|---|---|---|
| 214 | 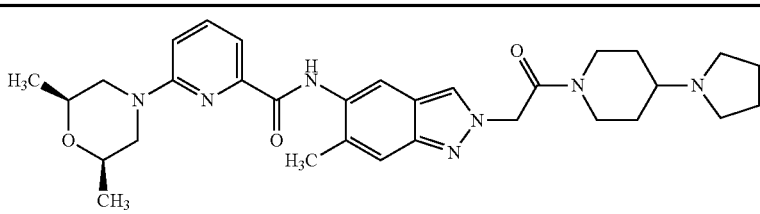<br>6-[(2R,6S)-2,6-dimethylmorpholin-4-yl]-N-(6-methyl-2-{2-oxo-2-[4-(pyrrolidin-1-yl)piperidin-1-yl]ethyl}-2H-indazol-5-yl)pyridine-2-carboxamide | 75 mg of 6-[(2R,6S)-2,6-dimethylmorpholin-4-yl]pyridine-2-carboxylic acid (Intermediate 19-14) were reacted with 118 mg of 2-(5-amino-6-methyl-2H-indazol-2-yl)-1-[4-(pyrrolidin-1-yl)piperidin-1-yl]ethanone (Intermediate 6-2). $^1$H-NMR (400 MHz, DMSO-d6): δ = 1.18 (d, 6H), 1.21-1.48 (m, 2H), 1.67 (br. s., 4H), 1.84 (t, 2H), 2.20-2.28 (m, 1H), 2.28-2.39 (m, 1H), 2.84 (t, 1H), 3.17 (t), 3.61-3.71 (m, 2H), 3.88 (d, 1H), 4.10 (d, 1H), 4.29 (d, 2H), 5.34-5.46 (m, 2H), 7.14 (d, 1H), 7.41-7.50 (m, 2H), 7.77 (dd, 1H), 8.22 (s, 1H), 8.36 (s, 1H), 10.18 (s, 1H). | 0.78 |

TABLE 13-continued

Examples 214-216

| Ex. | Name and structure | Preparation and notes | LC-MS retention time [min] |
|---|---|---|---|
| 215 | 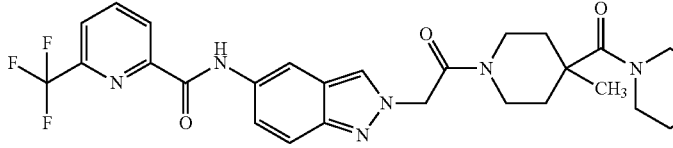<br>N-[2-(2-{4-methyl-4-[(4-methylpiperazin-1-yl)carbonyl]piperidin-1-yl}-2-oxoethyl)-2H-indazol-5-yl]-6-(trifluoromethyl)pyridine-2-carboxamide | 400 mg of [5-({[6-(trifluoromethyl)pyridin-2-yl]carbonyl}amino)-2H-indazol-2-yl]acetic acid were reacted with 296 mg of ethyl 4-methylpiperidine-4-carboxylate hydrochloride (1:1) in the presence of EDC, HOBt and triethylamine. This gave 544 mg of ethyl 4-methyl-1-{[5-({[6-(trifluoromethyl)pyridin-2-yl]carbonyl}amino)-2H-indazol-2-yl]acetyl}piperidine-4-carboxylate as a crude product. Ethanol and THF and 348 mg of lithium hydroxide monohydrate in water were added, and the mixture was stirred overnight and acidified with citric acid solution. Extraction with ethyl acetate and purification by HPLC gave 89 mg of 4-methyl-1-{[5-({[6-(trifluoromethyl)pyridin-2-yl]carbonyl}amino)-2H-indazol-2-yl]acetyl}piperidine-4-carboxylic acid. 49 mg of this were reacted with 15 mg of 1-methylpiperazine in the presence of EDC, HOBt and triethylamine in THF. Purification by HPLC gave 29 mg of N-[2-(2-{4-methyl-4-[(4-methylpiperazin-1-yl)carbonyl]piperidin-1-yl}-2-oxoethyl)-2H-indazol-5-yl]-6-(trifluoromethyl)pyridine-2-carboxamide.<br>$^1$H-NMR (300 MHz, DMSO-d6, selected signals): δ = 1.25 (s, 3H), 1.36-1.57 (m, 2H), 1.98-2.22 (m, 5H), 2.27 (br. s., 4H), 3.13 (t), 3.54 (s), 3.60-3.80 (m, 2H), 5.35-5.50 (m, 2H), 7.51-7.63 (m, 2H), 8.17 (dd, 1H), 8.26-8.42 (m, 4H), 10.37 (s, 1H). | 0.71 |
| 216 | 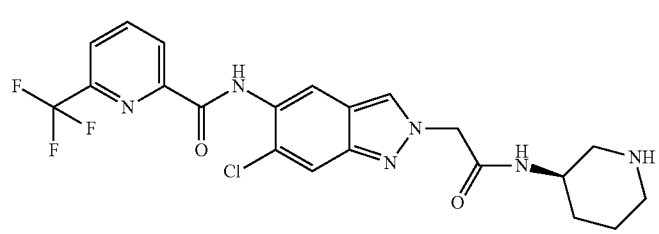<br>N-(6-chloro-2-{2-oxo-2-[(3R)-piperidin-3-ylamino]ethyl}-2H-indazol-5-yl)-6-(trifluoromethyl)pyridine-2-carboxamide | 100 mg of ([6-chloro-5-({[6-(trifluoromethyl)pyridin-2-yl]carbonyl}amino)-2H-indazol-2-yl]acetic acid (Intermediate 9-11) were reacted with 65 mg of tert-butyl (3R)-3-aminopiperidine-1-carboxylate in the presence of EDC, HOBt and triethylamine in THF. Addition of water and extraction with ethyl acetate gave, after concentration, 148 mg of tert-butyl (3R)-3-({[6-chloro-5-({[6-(trifluoromethyl)pyridin-2-yl]carbonyl}amino)-2H-indazol-2-yl]acetyl}amino)piperidine-1-carboxylate as a crude product. After addition of dichloromethane and trifluoroacetic acid, the mixture was stirred | 0.79 |

TABLE 13-continued

Examples 214-216

| Ex. | Name and structure | Preparation and notes | LC-MS retention time [min] |
|---|---|---|---|
| | | overnight, concentrated and purified by HPLC. This gave 105 mg of N-(6-chloro-2-{2-oxo-2-((3R)-piperidin-3-ylamino]ethyl}-2H-indazol-5-yl)-6-(trifluoromethyl)pyridine-2-carboxamide. <br> $^1$H-NMR (300 MHz, DMSO-d6, selected signals): δ = 1.39-1.64 (m, 2H), 1.74-1.90 (m, 2H), 2.56-2.67 (m, 1H), 2.68-2.80 (m, 1H), 2.98-3.21 (m, superimposed), 3.10-3.21 (m, 2H), 5.07-5.22 (m, 2H), 7.92 (s, 1H), 8.18-8.27 (m, 1H), 8.36-8.53 (m, 4H), 8.64 (s, 1H), 10.53 (s, 1H). | |

TABLE 14

Examples 217-222
The exemplary compounds were prepared from [6-isopropoxy-5-({[6-(trifluoromethyl)pyridin-2-yl]carbonyl}amino)-2H-indazol-2-yl]acetic acid (Intermediate 9-16) or (6-isopropoxy-5-{[(6-methylpyridin-2-yl)carbonyl]amino}-2H-indazol-2-yl)acetic acid (Intermediate 9-17) and starting material indicated in the table according to General Procedure 2a.

| Ex. | Structure/Name | Prepared from | Yield [%] | $^1$H-NMR/LC-MS |
|---|---|---|---|---|
| 217 | 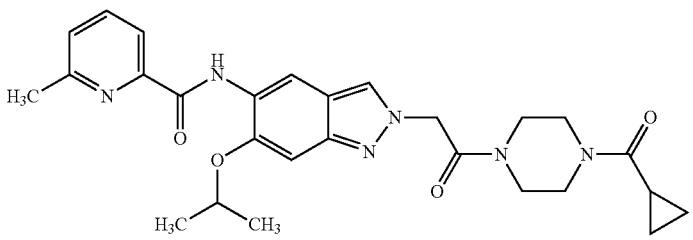 <br> N-(2-{2-[4-(cyclopropylcarbonyl)piperazin-1-yl]-2-oxoethyl}-6-isopropoxy-2H-indazol-5-yl)-6-methylpyridine-2-carboxamide | cyclopropyl (piperazin-1-yl) methanone | 91 | (300 MHz, DMSO-d6): δ = 0.67-0.82 (m, 4H), 1.45 (d, 6H), 1.92-2.09 (m, 1H), 2.62 (s, 3H), 3.38-3.86 (m, 8H), 4.76-4.90 (m, 1H), 5.42 (s, 2H), 7.13 (s, 1H), 7.53-7.60 (m, 1H), 7.93-8.02 (m, 2H), 8.21 (s, 1H), 8.72 (s, 1H), 10.99 (s, 1H), UPLC-MS (Method A1): Rt = 1.14 min <br> MS (ESIpos): m/z = 505 (M + H)+ |
| 218 | 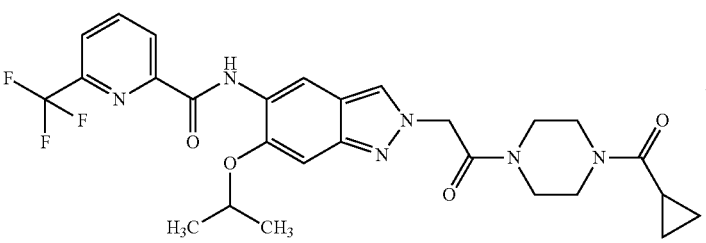 <br> N-(2-{2-[4-(cyclopropylcarbonyl)piperazin-1-yl]-2-oxoethyl}-6-isopropoxy-2H-indazol-5-yl)-6-(trifluoromethyl)pyridine-2-carboxamide | cyclopropyl (piperazin-1-yl) methanone | 75 | (300 MHz, DMSO-d6): δ = 0.67-0.82 (m, 4H), 1.41 (d, 6H), 1.92-2.08 (m, 1H), 3.38-3.88 (m, 8H), 4.79-4.93 (m, 1H), 5.43 (s, 2H), 7.16 (s, 1H), 8.18-8.27 (m, 2H), 8.36-8.51 (m, 2H), 8.75 (s, 1H), 10.75 (s, 1H). UPLC-MS (Method A1): Rt = 1.20 min <br> MS (ESIpos): m/z = 559 (M + H)+ |

TABLE 14-continued

Examples 217-222

The exemplary compounds were prepared from [6-isopropoxy-5-({[6-(trifluoromethyl)pyridin-2-yl]carbonyl}amino)-2H-indazol-2-yl]acetic acid (Intermediate 9-16) or (6-isopropoxy-5-{[(6-methylpyridin-2-yl)carbonyl]amino}-2H-indazol-2-yl)acetic acid (Intermediate 9-17) and starting material indicated in the table according to General Procedure 2a.

| Ex. | Structure/Name | Prepared from | Yield [%] | $^1$H-NMR/LC-MS |
|---|---|---|---|---|
| 219 | 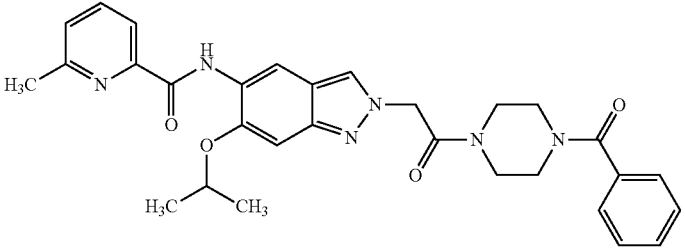<br>N-{2-[2-(4-benzoylpiperazin-1-yl)-2-oxoethyl]-6-isopropoxy-2H-indazol-5-yl}-6-methylpyridine-2-carboxamide | phenyl (piperazin-1-yl) methanone | 82 | (300 MHz, DMSO-d6): δ = 1.45 (d, 6H), 2.62 (s, 3H), 3.37-3.86 (m, 8H), 4.76-4.92 (m, 1H), 5.41 (s, 2H), 7.13 (s, 1H), 7.39-7.51 (m, 5H), 7.53-7.61 (m, 1H), 7.92-8.04 (m, 2H), 8.20 (s, 1H), 8.72 (s, 1H), 10.98 (s, 1H). UPLC-MS (Method A1): Rt = 1.21 min MS (ESIpos): m/z = 541 (M + H)+ |
| 220 | 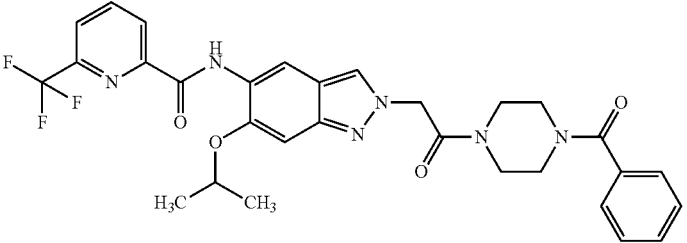<br>N-{2-[2-(4-benzoylpiperazin-1-yl)-2-oxoethyl]-6-isopropoxy-2H-indazol-5-yl}-6-trifluoromethyl)pyridine-2-carboxamide | phenyl (piperazin-1-yl) methanone | 98 | (300 MHz, DMSO-d6): δ = 1.41 (d, 6H), 3.38-3.93 (m, 8H), 4.79-4.93 (m, 1H), 5.42 (s, 2H), 7.15 (s, 1H), 7.40-7.53 (m, 5H), 8.17-8.26 (m, 2H), 8.35-8.51 (m, 2H), 8.75 (s, 1H), 10.74 (s, 1H). UPLC-MS (Method A1): Rt = 1.26 min MS (ESIpos): m/z = 595 (M + H)+ |
| 221 | 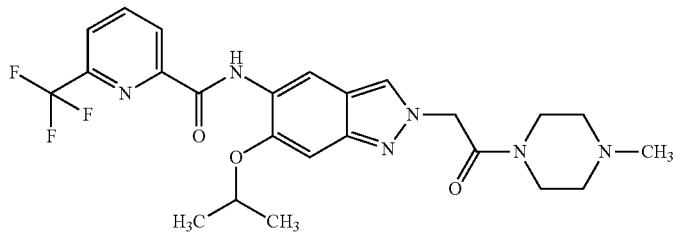<br>N-{6-isopropoxy-2-[2-(4-methylpiperazin-1-yl)-2-oxoethyl]-2H-indazol-5-yl}-6-(trifluoromethyl)pyridine-2-carboxamide | 1-methyl-piperazine | 36 | (300 MHz, DMSO-d6): δ = 1.41 (d, 6H), 2.12-2.70 (m, 4H), 3.37-3.78 (m, 4H), 4.80-4.91 (m, 1H), 5.40 (s, 2H), 7.15 (s, 1H), 8.18-8.26 (m, 2H), 8.36-8.49 (m, 2H), 8.74 (s, 1H), 10.75 (s, 1H). UPLC-MS (Method A1): Rt = 1.01 min MS (ESIpos): m/z = 505 (M + H)+ |
| 222 | 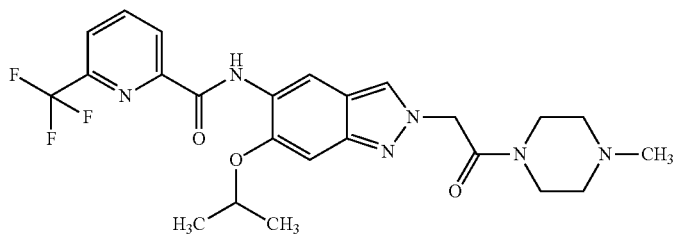<br>N-{6-isopropoxy-2-[2-(4-methylpiperazin-1-yl)-2-oxoethyl]-2H-indazol-5-yl}-6-methylpyridine-2-carboxamide | 1-methyl-piperazine | 63 | (300 MHz, DMSO-d6): δ = 1.45 (d, 6H), 2.18-2.70 (m, 4H), 2.62 (s, 3H), 3.34-3.87 (m, 4H), 4.77-4.89 (m, 1H), 5.39 (s, 2H), 7.12 (s, 1H), 7.53-7.58 (m, 1H), 7.93-8.02 (m, 2H), 8.20 (s, 1H), 8.72 (s, 1H), 10.98 (s, 1H). UPLC-MS (Method A1): Rt = 0.95 min MS (ESIpos): m/z = 451 (M + H)+ |

TABLE 15

Examples 223-226
The exemplary compounds were prepared from N-{2-[2-oxo-2-(piperazin-1-yl)ethyl]-2H-indazol-5-yl}-6-(trifluoromethyl)pyridin-2-carboxamide (Intermediate 22-1) and the starting material indicated in the table analogously to the examples above via an amide synthesis.

| Example | Name and structure | Starting material and notes | LC-MS retention time [min] |
|---|---|---|---|
| 223 | 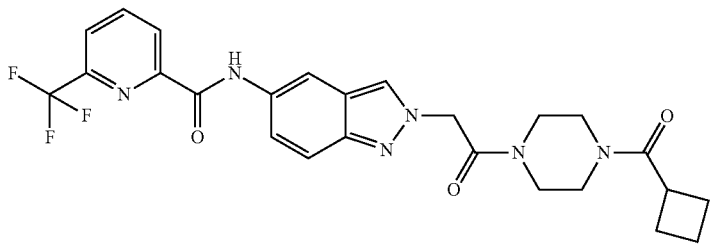<br>N-(2-{2-[4-(cyclobutylcarbonyl)piperazin-1-yl]-2-oxoethyl}-2H-indazol-5-yl)-6-(trifluoromethyl)pyridine-2-carboxamide | cyclobutanecarboxylic acid | 1.0 |
| 224 | 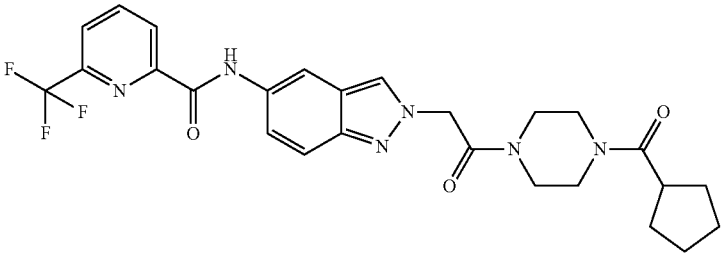<br>N-(2-{2-[4-(cyclopentylcarbonyl)piperazin-1-yl]-2-oxoethyl}-2H-indazol-5-yl)-6-(trifluoromethyl)pyridine-2-carboxamide | cyclopentane-carboxylic acid | 1.06 |
| 225 | 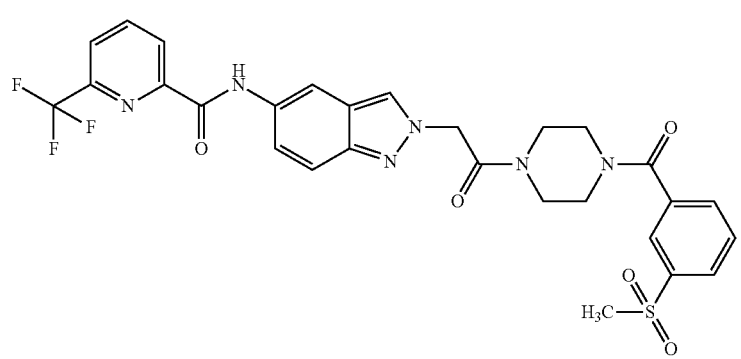<br>N-[2-(2-{4-[3-(methylsulphonyl)benzoyl]piperazin-1-yl}-2-oxoethyl)-2H-indazol-5-yl]-6-(trifluoromethyl)pyridine-2-carboxamide | 3-(methylsulphonyl)benzoic acid | 0.95 |

TABLE 15-continued

Examples 223-226

The exemplary compounds were prepared from N-{2-[2-oxo-2-(piperazin-1-yl)ethyl]-2H-indazol-5-yl}-6-(trifluoromethyl)pyridin-2-carboxamide (Intermediate 22-1) and the starting material indicated in the table analogously to the examples above via an amide synthesis.

| Example | Name and structure | Starting material and notes | LC-MS retention time [min] |
| --- | --- | --- | --- |
| 226 | N-[2-(2-{4-[2-methoxy-5-(methylsulphonyl)benzoyl]piperazin-1-yl}-2-oxoethyl)-2H-indazol-5-yl]-6-(trifluoromethyl)pyridine-2-carboxamide | 2-methoxy-5-(methylsulphonyl)benzoic acid | 0.7 |

TABLE 16

Examples 227-244

The exemplary compounds were prepared from the intermediates and starting materials indicated in the table.

| Ex. | Name and structure | Intermediate | Starting material, preparation and 1H NMR | LC-MS retention time [min] |
| --- | --- | --- | --- | --- |
| 227 | 6-bromo-N-(6-methyl-2-{2-oxo-2-[4-(pyrrolidin-1-yl)piperidin-1-yl]ethyl}-2H-indazol-5-yl)pyridine-2-carboxamide | 6-2 | 6-bromopyridine-2-carboxylic acid $^1$H NMR (400 MHz, DMSO-d6, selected signals): δ = 1.21-1.36 (m, 1 H), 1.38-1.52 (m, 1 H), 1.69 (br. s., 4 H), 1.78-1.95 (m, 2 H), 2.21-2.36 (m, 1 H), 2.39 (s, 3 H), 2.80-2.91 (m, 1 H), 3.18 (t, 1 H), 3.82-3.96 (m, 1 H), 4.04-4.18 (m, 1 H), 5.45 (d, 1 H), 5.40 (d, 1 H), 7.48 (s, 1 H), 7.91-7.97 (m, 1 H), 8.02 (t, 1 H), 8.09 (s, 1 H), 8.17 (dd, 1 H), 8.23-8.27 (m, 1 H), 10.05 (s, 1 H). | 0.7 |

TABLE 16-continued

Examples 227-244
The exemplary compounds were prepared from the intermediates and starting materials indicated in the table.

| Ex. | Name and structure | Intermediate | Starting material, preparation and 1H NMR | LC-MS retention time [min] |
|---|---|---|---|---|
| 228 | 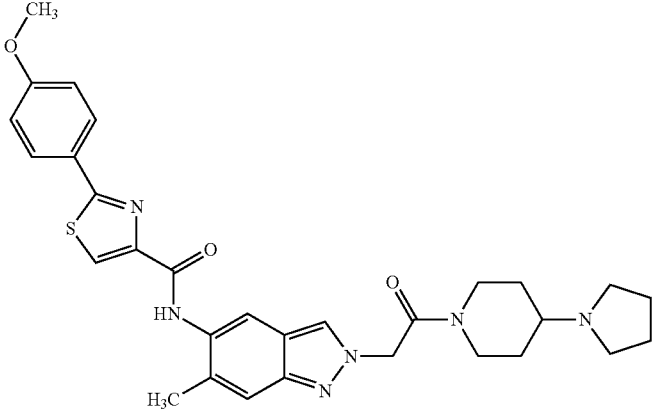<br>2-(4-methoxyphenyl)-N-(6-methyl-2-{2-oxo-2-[4-(pyrrolidin-1-yl)piperidin-1-yl]ethyl}-2H-indazol-5-yl)-1,3-thiazole-4-carboxamide | 6-2 | 2-(4-methoxyphenyl)-1,3-thiazole-4-carboxylic acid<br>$^1$H NMR (400 MHz, DMSO-d6, selected signals): δ = 1.21-1.36 (m, 1 H), 1.37-1.52 (m, 1 H), 1.68 (br. s., 4 H), 1.85 (t, 2 H), 2.18-2.28 (m, 1 H), 2.42 (s, 3 H), 2.80-2.92 (m, 1 H), 3.18 (t, 1 H), 3.85 (s, 3 H), 3.88-3.94 (m, 1 H), 4.05-4.15 (m, 1 H), 5.40 (d, 1 H), 5.45 (d, 1 H), 7.06-7.15 (m, 2 H), 7.49 (s, 1 H), 8.02-8.09 (m, 3 H), 8.25 (s, 1 H), 8.36 (s, 1 H), 9.86 (s, 1 H). | 0.82 |
| 229 | 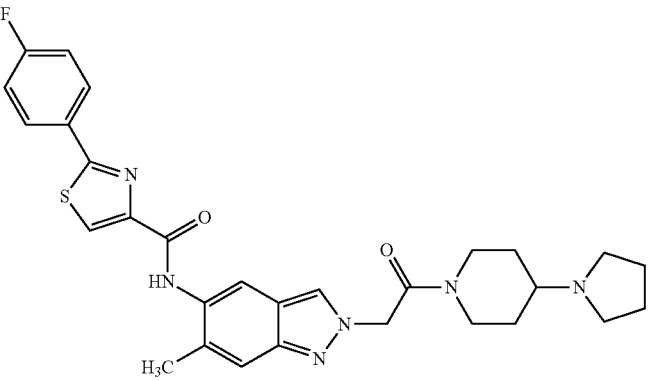<br>2-(4-fluorophenyl)-N-(6-methyl-2-{2-oxo-2-[4-(pyrrolidin-1-yl)piperidin-1-yl]ethyl}-2H-indazol-5-yl)-1,3-thiazole-4-carboxamide | 6-2 | 2-(4-fluorophenyl)-1,3-thiazole-4-carboxylic acid<br>$^1$H NMR (400 MHz, CHLOROFORM-d): δ = 1.26 (s, 1 H), 1.36 (t, 1 H), 1.44-1.59 (m, 1 H), 1.82 (br. s., 2 H), 1.94 (d, 2 H), 2.33 (br s., 1 H), 2.56 (s, 3 H), 2.63 (br. s., 4 H), 2.81-2.92 (m, 1 H), 3.01 (d, 1 H), 3.16 (t, 1 H), 3.98 (d, 1 H), 4.44 (d, 1 H), 5.23-5.29 (m, 2 H), 7.16-7.24 (m, 2 H), 7.53-7.58 (m, 1 H), 7.96-8.04 (m, 3 H), 8.20 (s, 1H), 8.55 (s, 1 H), 9.44 (s, 1 H). | 0.83 |
| 230 | 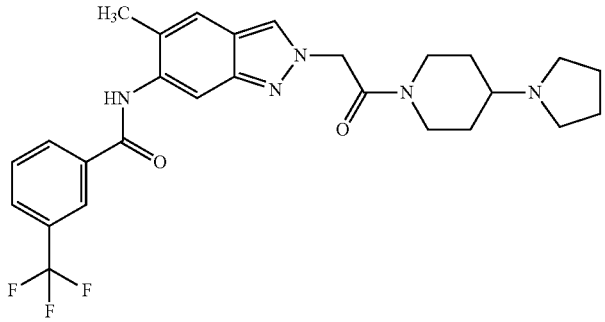<br>N-(6-methyl-2-{2-oxo-2-[4-(pyrrolidin-1-yl)piperidin-1-yl]ethyl}-2H-indazol-5-yl)-6-(trifluoromethyl)pyridine-2-carboxamide | 6-2 | 6-(trifluoromethyl)pyridine-2-carboxylic acid<br>$^1$H NMR (300 MHz, DMSO-d6): δ = 1.15-1.36 (m, 1 H), 1.42-1.45 (m, 1 H), 1.68 (br. s., 4H), 1.86 (t, 2 H), 2.19-2.32 (m, 1 H), 2.41 (s, 3 H), 2.85 (t, 1 H), 3.10-3.24 (m, 1 H), 3.89 (d, 1 H), 4.11 (d, 1 H), 5.43 (s, 2 H), 7.49 (s, 1 H), 8.16-8.24 (m, 2 H), 8.26 (s, 1 H), 8.33-8.49 (m, 2 H), 10.15 (s, 1 H). | 0.75 |

TABLE 16-continued

Examples 227-244
The exemplary compounds were prepared from the intermediates and starting materials indicated in the table.

| Ex. | Name and structure | Intermediate | Starting material, preparation and 1H NMR | LC-MS retention time [min] |
|---|---|---|---|---|
| 231 | 6-bromo-N-{2-[2-(4-methylpiperazin-1-yl)-2-oxoethyl]-2H-indazol-5-yl}pyridine-2-carboxamide | 6-12 | 6-bromopyridine-2-carboxylic acid<br>$^1$H NMR (300 MHz, DMSO-d6): δ = 2.21 (s, 3 H), 2.24-2.34 (m, 2 H), 2.34-2.42 (m, 2 H), 3.43-3.52 (m, 2 H), 3.54 (d, 2 H), 5.45 (s, 2 H), 7.52-7.63 (m, 2 H), 7.84-7.96 (m, 1 H), 8.01 (t, 1 H), 8.15 (dd, 1 H), 8.26-8.36 (m, 2 H), 10.38 (s, 1 H). | 0.61 |
| 232 | 6-bromo-N-{2-[2-(4-methylpiperazin-1-yl)-2-oxoethyl]-6-(trifluoromethoxy)-2H-indazol-5-yl}pyridine-2-carboxamide | 6-8 | 6-bromopyridine-2-carboxylic acid<br>$^1$H NMR (300 MHz, DMSO-d6): δ = 2.21 (s, 3 H), 2.25-2.33 (m, 2 H), 2.39 (br. s., 2 H), 3.47 (br. s., 2 H), 3.54 (d, 2 H), 5.52 (s, 2 H), 7.74 (s, 1 H), 7.94-8.01 (m, 1 H), 8.01-8.10 (m, 1 H), 8.19 (d, 1 H), 8.45 (s, 1 H), 8.55 (s, 1 H), 10.28 (s, 1 H) | 0.82 |
| 233 | N-{2-[2-(4-methylpiperazin-1-yl)-2-oxoethyl]-6-(trifluoromethoxy)-2H-indazol-5-yl}-6-(4H-1,2,4-triazol-4-yl)pyridine-2-carboxamide | 6-8 | 6-(4H-1,2,4-triazol-4-yl)pyridine-2-carboxylic acid<br>$^1$H NMR (400 MHz, DMSO-d6): δ = 2.22 (s, 3 H), 2.27-2.35 (m, 2 H), 2.39 (br. s., 2 H), 3.43-3.52 (m, 2 H), 3.52-3.60 (m, 2 H), 5.53 (s, 2 H), 7.72 (s, 1 H), 8.18 (dd, 2 H), 8.28 (s, 1 H), 8.34 (d, 1 H), 8.47 (s, 1 H), 9.62 (s, 2 H), 10.56 (s, 1 H). | 0.56 |
| 234 | 2-bromo-N-{6-bromo-2-[2-(4-methylpiperazin-1-yl)-2-oxoethyl]-2H-indazol-5-yl}-1,3-thiazole-4-carboxamide | 6-9 | 2-bromo-1,3-thiazole-4-carboxylic acid<br>$^1$H NMR (300 MHz, DMSO-d6): δ = 2.21 (s, 3 H), 2.25-2.34 (m, 2 H), 2.38 (br. s., 2 H), 3.47 (br. s., 2 H), 3.54 (br. s., 2H), 5.49 (s, 2 H), 8.03 (s, 1 H), 8.25 (s, 1 H), 8.35-8.42 (m, 1 H), 8.49 (s, 1 H), 9.96 (s, 1 H). | 0.72 |
| 235 | N-{6-hydroxy-2-[2-(4-methylpiperazin-1-yl)-2-oxoethyl]-2H-indazol-5-yl}-6-(trifluoromethyl)pyridine-2-carboxamide | — | Analogously to Intermediate 8-7, 25 mg (0.05 mmol) of N-{6-(benzyloxy)-2-[2-(4-methylpiperazin-1-yl)-2-oxoethyl]-2H-indazol-5-yl}-6-(trifluoromethyl)pyridine-2-carboxaimide (Example 41) were dissolved in 7 ml of ethanol, 4.8 mg of palladium on carbon were added and the mixture was hydrogenated under standard hydrogen pressure for 6 h. Work-up gave 5 mg (34% of theory) of the product.<br>$^1$H NMR (400 MHz, DMSO-d6): δ = 2.20 (s, 3 H), 2.28 (br. s., 2 H), 2.35 | 0.67 |

TABLE 16-continued

Examples 227-244
The exemplary compounds were prepared from the intermediates and starting materials indicated in the table.

| Ex. | Name and structure | Intermediate | Starting material, preparation and 1H NMR | LC-MS retention time [min] |
|---|---|---|---|---|
| | | | (br. s., 2 H), 3.46 (br. s., 2 H), 3.53 (br. s., 2 H), 5.31 (s, 2 H), 6.88 (s, 1 H), 8.13 (s, 1 H), 8.20 (d, 1 H), 8.40 (t, 1 H), 8.47 (d, 1 H), 8.66 (s, 1 H), 10.64 (br. s., 1H). | |
| 236 | 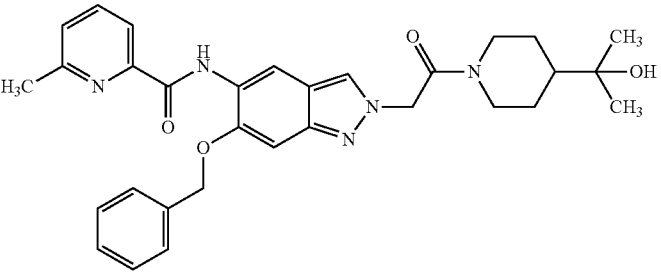<br>N-[6-(benzyloxy)-2-{2-[4-(2-hydroxypropan-2-yl)piperidin-1-yl]-2-oxoethyl}-2H-indazol-5-yl]-6-methylpyridine-2-carboxamide | 9-18 | 2-(piperidin-4-yl)propan-2-ol<br>$^1$H NMR (300 MHz, DMSO-d6): δ = 0.96-1.17 (m, 1 H), 1.05 (s, 6 H), 1.18-1.34 (m, 2 H), 1.36-1.54 (m, 1 H), 1.76 (t, 2 H), 2.43 (s, 3 H), 3.00 (t, 1 H), 4.04 (d, 1 H), 4.19 (s, 1 H), 4.42 (d, 1 H), 5.30 (s, 2 H), 5.38 (s, 1 H), 5.37 (s, 1 H), 7.27 (s, 1 H), 7.37-7.54 (m, 4 H), 7.66 (d, 2 H), 7.87-8.02 (m, 2 H), 8.23 (s, 1 H) 8.78 (s, 1 H) 10.87 (s, 1 H). | 1.19 |
| 237 | 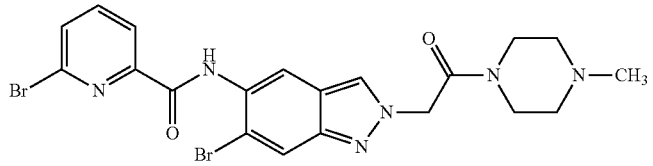<br>6-bromo-N-{6-bromo-2-[2-(4-methylpiperazin-1-yl)-2-oxoethyl]-2H-indazol-5-yl}pyridine-2-carboxamide | 6-9 | 6-bromopyridine-2-carboxylic acid<br>$^1$H NMR (300 MHz, DMSO-d6): δ = 2.20 (s, 3 H), 2.23-2.33 (m, 2 H), 2.37 (br. s., 2 H), 3.46 (d, 2 H), 3.53 (br. s., 2 H), 5.49 (s, 2 H), 7.94-7.99 (m, 1 H), 8.01-8.08 (m, 2 H), 8.16-8.23 (m, 1 H), 8.39 (s, 1 H), 8.51 (s, 1 H), 10.38 (s, 1 H). | 0.77 |
| 238 | 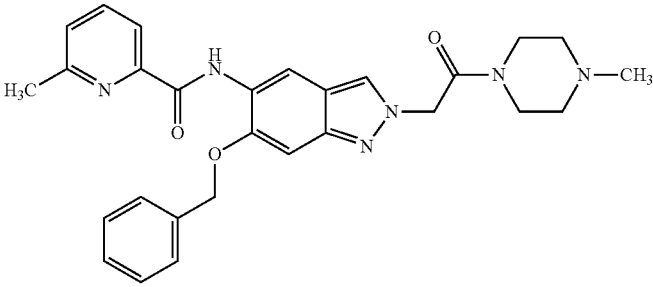<br>N-{6-(benzyloxy)-2-[2-(4-methylpiperazine-1-yl)-2-oxoethyl]-2H-indazol-5-yl}-6-methylpyridine-2-carboxamide | 9-18 | 1-methylpiperazine<br>$^1$H NMR (300 MHz, DMSO-d6): δ = 2.21 (s, 3 H), 2.23-2.33 (m, 2 H), 2.37 (br. s., 2 H), 2.42 (s, 3 H), 3.47 (br. s., 2 H), 3.55 (br. s., 2 H), 5.30 (s, 2 H), 5.39 (s, 2 H), 7.27 (s, 1 H), 7.36-7.56 (m, 4 H), 7.62-7.69 (m, 2 H), 7.90-8.02 (m, 2 H), 8.23 (s, 1 H), 8.78 (s, 1 H), 10.87 (s, 1 H). | 0.87 |
| 239 | 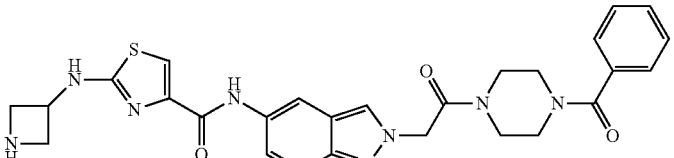<br>2-(azetidin-3-ylamino)-N-{2-[2-(4-benzoylpiperazin-1-yl)-2-oxoethyl]-2H-indazol-5-yl}-1,3-thiazole-4-carboxamide | 6-11 | According to General Procedure 1c, 35 mg (0.09 mmol) of the Intermediate 6-11 were reacted with 32 mg (0.1 mmol) of 2-{[1-(tert-butoxycarbonyl)azetidin-3-yl]amino}-1,3-thiazole-4-carboxylic acid. This gave 10 mg (0.01 mmol) of tert-butyl 3-{[4-({2-[2-(4-benzoylpiperazin-1-yl)-2-oxoethyl]-2H-indazol-5-yl}carbamoyl)-1,3-thiazol-2-yl]amino}azetidine-1-carboxylate.<br>$^1$H NMR (400 MHz, DMSO-d6): δ = 1.39 (s, 9 H), 3.55 (br. s., 4 H), 3.64 (br. s., 4 H), 3.78 (dd, 2 H), 4.25 (t, 2 H), 4.57-4.69 (m, 1 H), 5.48 (br. s., 2 H), 7.39-7.52 (m, 7 H), 7.54-7.59 (m, 1 H), 8.22 (d, 1 H), 8.25- | 0.56 |

TABLE 16-continued

Examples 227-244
The exemplary compounds were prepared from the intermediates and starting materials indicated in the table.

| Ex. | Name and structure | Intermediate | Starting material, preparation and 1H NMR | LC-MS retention time [min] |
|---|---|---|---|---|
| | | | 8.29 (m, 1 H), 8.43 (d, 1 H), 9.55 (s, 1H).<br>50 mg (0.07 mmol) of tert-butyl 3-{[4-({2-[2-(4-benzoylpiperazin-1-yl)-2-oxoethyl]-2H-indazol-5-yl}carbamoyl)-1,3-thiazol-2-yl]amino}azetidine-1-carboxylate were dissolved in 200 µl of 4 M hydrogen chloride in dioxane and the mixture was stirred at room temperature for 24 h. The reaction mixture was concentrated and taken up in dichloromethane, washed with saturated sodium bicarbonate solution and saturated sodium chloride solution, dried over sodium sulphate, filtered and concentrated. Drying gave 11 mg (0.02 mmol) of 2-(azetidin-3-ylamino)-N-{2-[2-(4-benzoylpiperazin-1-yl)-2-oxoethyl]-2H-indazol-5-yl}-1,3-thiazole-4-carboxamide. | |
| 240 | 6-acetamido-N-{6-methoxy-2-[2-(morpholin-4-yl)-2-oxoethyl]-2H-indazol-5-yl}pyridine-2-carboxamide | 6-16 | 6-acetamidopyridine-2-carboxylic acid<br>$^1$H NMR (400 MHz, DMSO-d6): δ = 2.21 (s, 3 H), 3.47 (d, 2 H), 3.51-3.62 (m, 4 H), 3.64 (d, 2 H), 4.03 (s, 3 H), 5.39 (s, 2 H), 7.10 (s, 1 H), 7.87 (dd, 1 H), 8.04 (t, 1 H), 8.22 (s, 1 H), 8.28 (d, 1 H), 8.69 (s, 1 H), 10.34 (s, 1 H), 10.65 (s, 1 H). | 0.76 |
| 241 | 6-(dimethylamino)-N-(2-{2-[4-(2-hydroxypropan-2-yl)-piperidin-1-yl]-2-oxoethyl}-6-methoxy-2H-indazol-5-yl)pyridine-2-carboxamide | 6-5 | 6-(dimethylamino)pyridine-2-carboxylic acid $^1$H NMR (400 MHz, DMSO-d6): δ = 1.01-1.14 (m, 1 H), 1.05 (s, 6 H), 1.18-1.30 (m, 1 H), 2.50-2.52 (m, 1 H) (signal under DMSO), 1.44 (t, 1 H), 1.75 (t, 2 H), 2.99 (t, 1 H), 3.16 (s, 6 H), 3.97 (s, 3 H), 4.03 (d, 1 H), 4.16 (s, 1 H), 4.42 (d, 1 H), 5.27-5.41 (m, 2 H), 6.94 (d, 1 H), 7.07 (s, 1 H), 7.36 (d, 1 H), 7.74 (dd, 1 H), 8.19 (s, 1 H), 8.67 (s, 1 H), 10.88 (s, 1 H). | 1.03 |
| 242 | 6-(dimethylamino)-N-{6-methoxy-2-[2-(morpholin-4-yl)-2-oxoethyl]-2H-indazol-5-yl}pyridine-2-carboxamide | 6-16 | 6-(dimethylamino)pyridine-2-carboxylic acid $^1$H NMR (400 MHz, DMSO-d6): δ = 3.16 (s, 6 H), 3.47 (d, 2 H), 3.53-3.61 (m, 4 H), 3.64 (d, 2 H), 3.98 (s, 3 H), 5.38 (s, 2 H), 6.94 (d, 1 H), 7.08 (s, 1 H), 7.36 (d, 1 H), 7.74 (dd, 1 H), 8.17-8.21 (m, 1 H), 8.67 (s, 1 H), 10.88 (s, 1 H). | 0.99 |

TABLE 16-continued

Examples 227-244

The exemplary compounds were prepared from the intermediates and starting materials indicated in the table.

| Ex. | Name and structure | Intermediate | Starting material, preparation and 1H NMR | LC-MS retention time [min] |
|---|---|---|---|---|
| 243 | 6-acetamido-N-(2-{2-[4-(2-hydroxypropan-2-yl)piperidin-1-yl]-2-oxoethyl}-6-methoxy-2H-indazol-5-yl)pyridine-2-carboxamide | 6-5 | 6-acetamidopyridine-2-carboxylic acid ¹H NMR (400 MHz, DMSO-d6): δ = 0.98-1.12 (m, 1 H), 1.05 (s, 6 H), 1.15-1.31 (m, 1 H), 1.39-1.50 (m, 1 H), 1.75 (t, 2 H), 2.21 (s, 3 H), 2.52-2.57 (m, 1 H), 2.99 (br. s., 1 H), 3.98-4.08 (m, 1 H), 4.03 (s, 3 H), 4.16 (s, 1 H), 4.42 (d, 1 H), 5.36 (d, 2 H), 7.09 (s, 1 H), 7.87 (dd, 1 H), 8.04 (t, 1 H), 8.19-8.23 (m, 1 H), 8.28 (d, 1 H), 8.69 (s, 1 H), 10.34 (s, 1 H), 10.65 (s, 1 H). | 0.83 |
| 244 | 6-(dimethylamino)-N-{6-methoxy-2-[2-(4-methylpiperazin-1-yl)-2-oxoethyl]-2H-indazol-5-yl}pyridine-2-carboxamide | 6-17 | 6-(dimethylamino)pyridine-2-carboxylic acid ¹H NMR (400 MHz, DMSO-d6): δ = 2.21 (s, 3 H), 2.27-2.31 (m, 2 H), 2.34-2.39 (m, 2 H), 3.16 (s, 6 H), 3.43-3.51 (m, 2 H), 3.51-3.58 (m, 2 H), 3.97 (s, 3 H), 5.36 (s, 2 H), 6.94 (d, 1 H), 7.08 (s, 1 H), 7.36 (d, 1 H), 7.74 (dd, 1 H), 8.19 (s, 1 H), 8.67 (s, 1 H), 10.88 (s, 1 H). | 0.74 |

TABLE 17

Examples 245-247

| Ex. | Name and structure | Preparation and notes | LC-MS retention time [min] |
|---|---|---|---|
| 245 | N-{2-[2-(4-methylpiperazin-1-yl)-2-oxoethyl]-2H-indazol-5-yl}-6-[3-(methylsulphonyl)phenyl]pyridine-2-carboxamide | 80 mg of 6-[3-(methylsulphonyl)phenyl]pyridine-2-carboxylic acid (Intermediate 19-8) and 95 mg of 2-(5-amino-2H-indazol-2-yl)-1-(4-methylpiperazin-1-yl)ethanone (Intermediate 6-12, crude product) were reacted with EDC, HOBt and triethylamine in THF at room temperature overnight. The residue was diluted with water and ethyl acetate. The solid was filtered off with suction, washed with water and diethyl ether and dried. This gave 48 mg of the exemplary compound. ¹H NMR (400 MHz, DMSO-d6): δ = 2.20 (s, 3H), 2.24-2.42 (m, 4H), 3.36 (s, 3H), 3.42-3.51 (m, 2H), 3.51-3.61 (m, 2H), 5.45 (s, 2H), 7.56-7.64 (m, 2H), 7.84 (t, 1H), 8.05 (d, 1H), 8.16-8.24 (m, 2H), 8.30 (s, 1H), 8.34-8.40 (m, 2H), 8.75-8.80 (m, 2H), 10.56 (s, 1H). | 0.65 |

TABLE 17-continued

Examples 245-247

| Ex. | Name and structure | Preparation and notes | LC-MS retention time [min] |
|---|---|---|---|
| 246 | 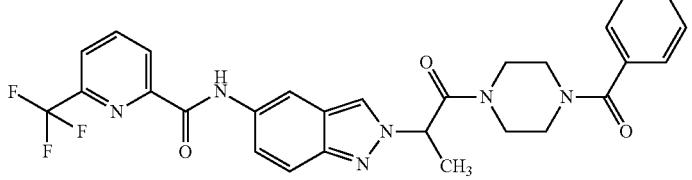<br>N-{2-[1-(4-benzoylpiperazin-1-yl)-1-oxopropan-2-yl]-2H-indazol-5-yl}-6-(trifluoromethyl)pyridine-2-carboxamide | 100 mg of 2-(5-amino-2H-indazol-2-yl)-1-(4-benzoylpiperazin-1-yl)propan-1-one (Intermediate 6-19) and 76 mg of 6-(trifluoromethyl)pyridine-2-carboxylic acid were reacted with EDC, HOBt and triethylamine in THF at room temperature overnight. After addition of water, extraction with ethyl acetate and concentration, the product was purified by preparative HPLC according to Method P1. This gave 98 mg of the exemplary compound.<br>$^1$H NMR (400 MHz, DMSO-d6): δ = 1.68 (d, 3H), 3.1-3.7 (broad signals, superimposed), 5.91 (br. s., 1H), 7.34-7.45 (m, 5H), 7.52-7.61 (m, 2H), 8.14 (dd, 1H), 8.26-8.39 (m, 3H), 8.43 (s, 1H), 10.34 (s, 1H). | 1.08 |
| 247 | 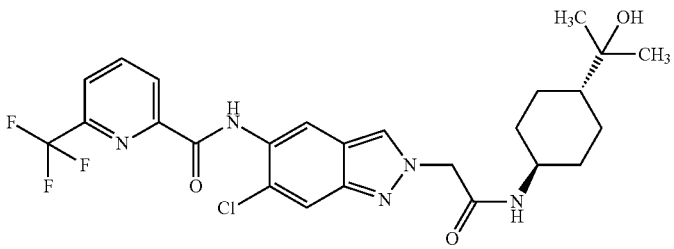<br>N-[6-chloro-2-(2-{[trans-4-(2-hydroxypropan-2-yl)cyclohexyl]amino}-2-oxoethyl)-2H-indazol-5-yl]-6-(trifluoromethyl)pyridine-2-carboxamide | 80 mg of [6-chloro-5-({[6-(trifluoromethyl)pyridin-2-yl]carbonyl}amino)-2H-indazol-2-yl]acetic acid and 41 mg of 2-(trans-4-aminocyclohexyl)propan-2-ol were reacted with EDC, HOBt and triethylamine in THF at room temperature overnight and at 50° C. for 7 h. Water and ethyl acetate were added. The solid was filtered off with suction, washed with water and diethyl ether and dried. This gave 92 mg of the exemplary compound.<br>$^1$H-NMR (300 MHz, DMSO-d6): δ = 0.92-1.25 (11H, contains singlet at 1.01 ppm), 1.73-1.91 (m, 4H), 3.36-3.60 (m), 4.02 (s, 1H), 5.08 (s, 2H), 7.91 (s, 1H), 8.23 (d, 2H), 8.37-8.50 (m, 3H), 8.63 (s, 1H), 10.52 (s, 1H). | 1.16 |

TABLE 18

Examples 248-260
The exemplary compounds were prepared by the general experimental procedures 2a-2g from the appropriate intermediates and amines.

| Ex. No. | Structure/Name | Prepared from | $^1$H-NMR/LC-MS |
|---|---|---|---|
| 248 | 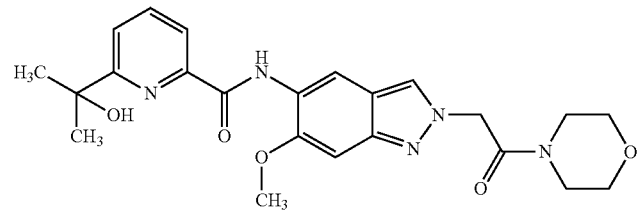<br>6-(2-hydroxypropan-2-yl)-N-{6-methoxy-2-[2-(morpholin-4-yl)-2-oxoethyl]-2H-indazol-5-yl}pyridine-2-carboxamide | Intermediate 9-23 and morpholine | (400 MHz, DMSO-d6): δ = 1.57 (s, 6 H), 3.42-3.52 (m, 2 H), 3.52-3.62 (m, 4 H), 3.62-3.68 (m, 2 H), 3.99 (s, 3 H), 5.39 (s, 2 H), 5.47 (s, 1 H), 7.10 (s, 1 H), 7.93 (dd, 1 H), 7.99-8.10 (m, 2 H), 8.19-8.23 (m, 1 H), 8.68 (s, 1 H), 10.93 (s, 1 H).<br>UPLC-MS (Method A1): Rt = 0.88 min<br>MS (ESIpos): m/z = 454 (M + H)+ |

TABLE 18-continued

Examples 248-260
The exemplary compounds were prepared by the general experimental procedures 2a-2g from the appropriate intermediates and amines.

| Ex. No. | Structure/Name | Prepared from | ¹H-NMR/LC-MS |
|---|---|---|---|
| 249 | 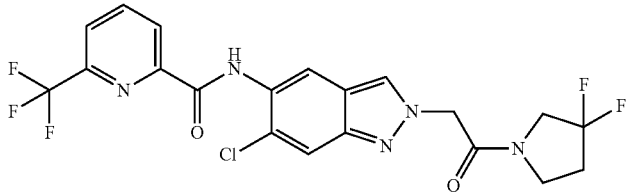<br>N-{6-chloro-2-[2-(3,3-difluoropyrrolidin-1-yl)-2-oxoethyl]-2H-indazol-5-yl}-6-(trifluoromethyl)pyridine-2-carboxamide | Intermediate 9-11 and 3,3-difluoropyrrolidine | (400 MHz, DMSO-d6): δ = 2.38-2.46 (m, 1 H), 2.54-2.61 (m, 1 H), 3.58 (t, 1 H), 3.77 (t, 1 H), 3.87 (t, 1 H), 4.11 (t, 1 H), 5.42 (s, 1 H), 5.48 (s, 1 H), 7.93 (s, 1 H), 8.24 (dd, 1 H), 8.38-8.45 (m, 2 H), 8.45-8.50 (m, 1 H), 8.64-8.67 (m, 1 H), 10.53 (s, 1 H). |
| 250 | 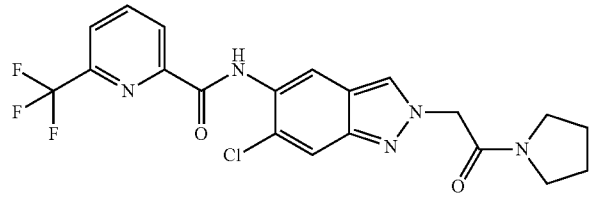<br>N-{6-chloro-2-[2-oxo-2-(pyrrolidin-1-yl)ethyl]-2H-indazol-5-yl}-6-(trifluoromethyl)pyridine-2-carboxamide | Intermediate 9-11 and pyrrolidine | UPLC-MS (Method A2): Rt = 1.21 min MS (ESIpos): m/z = 452 (M + H)⁺ |
| 251 | 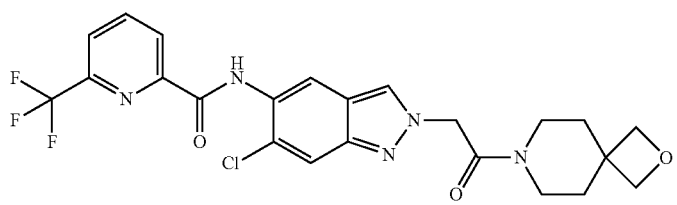<br>N-{6-chloro-2-[2-(2-oxa-7-azaspiro[3.5]non-7-yl)-2-oxoethyl]-2H-indazol-5-yl}-6-(trifluoromethyl)pyridine-2-carboxamide | Intermediate 9-11 and 2-oxa-7-azaspiro[3.5]nonane (CAS241820-91-7) | (300 MHz, DMSO-d6): δ = 1.75 (br. s., 2 H), 1.87 (br. s., 2 H), 3.37-3.51 (m, 4 H), 4.24-4.41 (m, 4 H), 5.50 (s, 2 H), 7.91 (s, 1 H), 8.24 (d, 1 H), 8.36-8.51 (m, 3 H), 8.64 (s, 1 H), 10.53 (s, 1 H). UPLC-MS (Method A1): Rt = 1.22 min MS (ESIpos): m/z = 508 (M + H)⁺ |
| 252 | 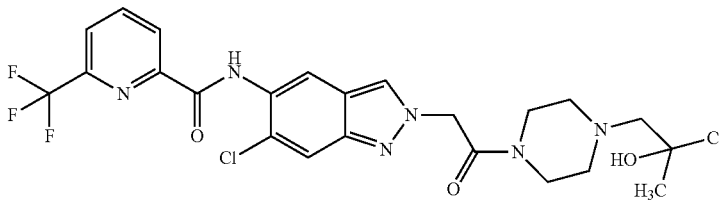<br>N-(6-chloro-2-{2-[4-(2-hydroxy-2-methylpropyl)piperazin-1-yl]-2-oxoethyl}-2H-indazol-5-yl)-6-(trifluoromethyl)pyridine-2-carboxamide | Intermediate 9-11 and 2-methyl-1-(piperazin-1-yl)propan-2-ol | (300 MHz, DMSO-d6, selected signals): δ = 1.11 (s, 6 H), 2.23 (s, 2 H), 2.59 (br. s., 2 H), 3.46 (br. s., 2 H), 3.53 (br. s., 2 H), 4.16 (s, 1 H), 5.49 (s, 2 H), 7.92 (s, 1 H), 8.24 (dd, J = 7.4, 1.2 Hz, 1 H), 8.37-8.51 (m, 3 H), 8.64 (s, 1 H), 10.53 (s, 1 H). |

TABLE 18-continued

Examples 248-260
The exemplary compounds were prepared by the general experimental procedures 2a-2g from the appropriate intermediates and amines.

| Ex. No. | Structure/Name | Prepared from | ¹H-NMR/LC-MS |
|---|---|---|---|
| 253 | 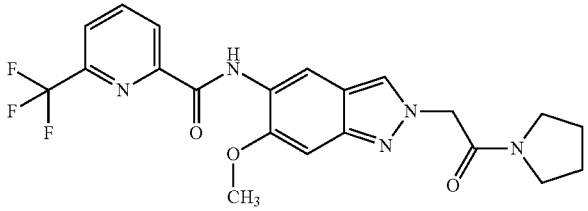<br>N-{6-methoxy-2-[2-oxo-2-(pyrrolidin-1-yl)ethyl]-2H-indazol-5-yl}-6-(trifluoromethyl)pyridine-2-carboxamide | Intermediate 9-12 and pyrrolidine | (400 MHz, DMSO-d6): δ = 1.81 (s, 2 H), 1.91-1.98 (m, 2 H), 3.33-3.37 (m, 2 H), 3.54 (t, 2 H), 3.99 (s, 3 H), 5.27 (s, 2 H), 7.12 (s, 1 H), 8.19-8.25 (m, 2 H), 8.42 (d, 1 H), 8.44-8.49 (m, 1 H), 8.71 (s, 1 H), 10.51 (s, 1 H).<br>UPLC-MS (Method A2): Rt = 1.14 min<br>MS (ESIpos): m/z = 448 (M + H)⁺ |
| 254 | 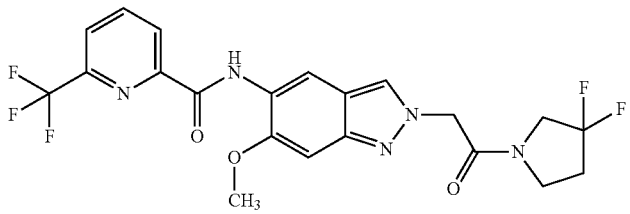<br>N-{2-[2-(3,3-difluoropyrrolidin-1-yl)-2-oxoethyl]-6-methoxy-2H-indazol-5-yl}-6-(trifluoromethyl)pyridine-2-carboxamide | Intermediate 9-12 and 3,3-difluoropyrrolidine | (400 MHz, DMSO-d6): δ = 2.37-2.44 (m, 1 H), 2.54-2.61 (m, 1 H), 3.58 (t, 1 H), 3.76 (t, 1 H), 3.86 (t, 1 H), 3.99 (s, 3 H), 4.10 (t, 1 H), 5.27-5.34 (m, 1 H), 5.37 (s, 1 H), 7.12 (s, 1 H), 8.15-8.30 (m, 2 H), 8.37-8.45 (m, 1 H), 8.45-8.51 (m, 1 H), 8.71 (s, 1 H), 10.51 (s, 1 H).<br>UPLC-MS (Method A2): Rt = 1.17 min<br>MS (ESIpos): m/z = 484 (M + H)⁺ |
| 255 | 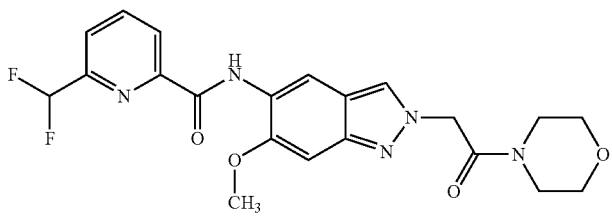<br>6-(difluoromethyl)-N-{6-methoxy-2-[2-(morpholin-4-yl)-2-oxoethyl]-2H-indazol-5-yl}pyridine-2-carboxamide | Intermediate 9-24 and morpholine | (400 MHz, DMSO-d6): δ = 3.40-3.49 (m, 2 H), 3.53-3.62 (m, 4 H), 3.62-3.68 (m, 2 H), 4.00 (s, 3 H), 5.40 (s, 2 H), 7.16 (t, 1 H), 7.11 (s, 1 H), 8.00 (d, 1 H), 8.23 (s, 1 H), 8.27-8.38 (m, 2 H), 8.71 (s, 1 H), 10.56 (s, 1 H).<br>HPLC-MS (Method A1): Rt = 0.99 min<br>MS (ESIpos): m/z = 446 (M + H)⁺ |
| 256 | 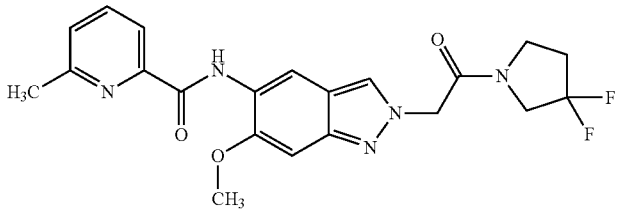<br>N-{2-[2-(3,3-difluoropyrrolidin-1-yl)-2-oxoethyl]-6-methoxy-2H-indazol-5-yl}-6-methylpyridine-2-carboxamide | Intermediate 9-19 and 3,3-difluoropyrrolidine | (400 MHz, DMSO-d6): δ = 2.35-2.48 (m, 1 H), 2.54-2.60 (m, 1 H), 2.63 (s, 3 H), 3.58 (t, 1 H), 3.76 (s, 1 H), 3.86 (t, 1 H), 4.01 (s, 3 H), 4.04-4.16 (m, 1 H), 5.30 (s, 1 H), 5.36 (s, 1 H), 7.10 (s, 1 H), 7.56 (dd, 1 H), 7.94-8.02 (m, 2 H), 8.20-8.24 (m, 1 H), 8.72 (s, 1 H), 10.71 (s, 1 H).<br>HPLC-MS (Method A1): Rt = 1.17 min<br>MS (ESIpos): m/z = 430 (M + H)⁺ |

TABLE 18-continued

Examples 248-260
The exemplary compounds were prepared by the general experimental procedures 2a-2g from the appropriate intermediates and amines.

| Ex. No. | Structure/Name | Prepared from | ¹H-NMR/LC-MS |
|---|---|---|---|
| 257 | 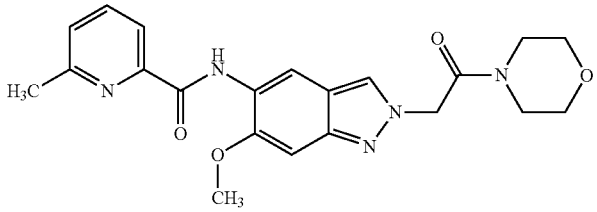<br>N-{6-methoxy-2-[2-(morpholin-4-yl)-2-oxoethyl]-2H-indazol-5-yl}-6-methylpyridine-2-carboxamide | Intermediate 9-19 and morpholine | (400 MHz, DMSO-d6): δ = 2.63 (s, 3 H), 3.47 (s, 2 H), 3.53-3.62 (m, 4 H), 3.64 (s, 2 H), 4.01 (s, 3 H), 5.39 (s, 2 H), 7.09 (s, 1 H), 7.56 (dd, J = 7.1, 1.5 Hz, 1 H), 7.93-8.03 (m, 2 H), 8.21 (s, 1 H), 8.72 (s, 1 H), 10.71 (s, 1 H).<br>UPLC-MS (Method A1):<br>Rt = 1.00 min<br>MS (ESIpos): m/z = 410 (M + H)⁺ |
| 258 | 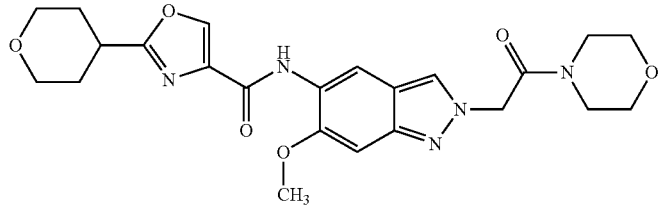<br>N-{6-methoxy-2-[2-(morpholin-4-yl)-2-oxoethyl]-2H-indazol-5-yl}-2-(tetrahydro-2H-pyran-4-yl)-1,3-oxazole-4-carboxamide | Intermediate 9-20 and morpholine | (400 MHz, DMSO-d6): δ = 1.71-1.84 (m, 2 H), 1.92-2.02 (m, 2 H), 3.16-3.28 (m, 1 H), 3.42-3.50 (m, 4 H), 3.53-3.62 (m, 4 H), 3.64 (d, 2 H), 3.88-3.95 (m, 2 H), 3.97 (s, 3 H), 5.38 (s, 2 H), 7.08 (s, 1 H), 8.20 (s, 1 H), 8.56 (s, 1 H), 8.74 (s, 1 H), 9.41 (s, 1 H).<br>UPLC-MS (Method A1):<br>Rt = 0.88 min<br>MS (ESIpos): m/z = 470 (M + H)⁺ |
| 259 | 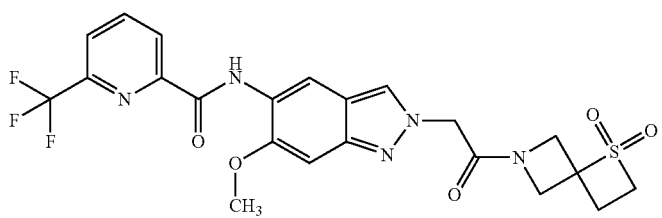<br>N-{2-[2-(1,1-dioxido-1-thia-6-azaspiro[3.3]hept-6-yl)-2-oxoethyl]-6-methoxy-2H-indazol-5-yl}-6-(trifluoromethyl)pyridine-2-carboxamide | Intermediate 9-12 and 1-thia-6-azaspiro[3.3] heptane-1,1-dioxide (CAS1352546-75-8) | UPLC-MS (Method A2):<br>Rt = 1.12 min<br>MS (ESIpos): m/z = 524 (M + H)⁺ |
| 260 | 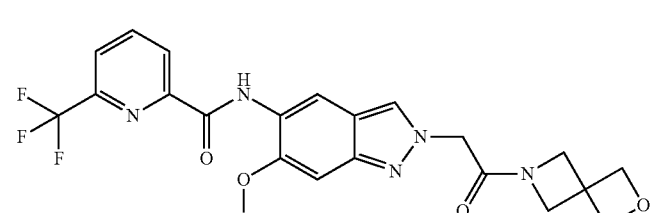<br>N-{6-methoxy-2-[2-(2-oxa-6-azaspiro[3.3]hept-6-yl)-2-oxoethyl]-2H-indazol-5-yl}-6-(trifluoromethyl)pyridine-2-carboxamide | Interermediate 9-12 and 2-oxa-6-azaspiro[3.3] heptane (CAS 174-78-7) | (300 MHz, DMSO-d6): δ = 3.99 (s, 3 H), 4.10 (s, 2 H), 4.32 (s, 2 H), 4.67 (s, 4 H), 5.06 (s, 2 H), 7.12 (s, 1 H), 8.22 (d, J = 7.6 Hz, 1 H), 8.25 (s, 1 H), 8.41 (s, 1 H), 8.46 (s, 1 H), 8.70 (s, 1 H), 10.51 (s, 1 H).<br>UPLC-MS (Method A2):<br>Rt = 1.08 min<br>MS (ESIpos): m/z = 476 (M + H)⁺ |

Example 261

N-{6-(3-Hydroxy-2,2-dimethylpropoxy)-2-[2-(morpholin-4-yl)-2-oxoethyl]-2H-indazol-5-yl}-6-(trifluoromethyl)pyridine-2-carboxamide

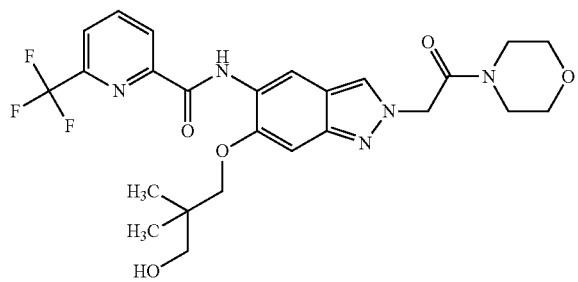 [SMILES: CC(C)(CO)COc1cc2nn(CC(=O)N3CCOCC3)cc2cc1NC(=O)c1cccc(C(F)(F)F)n1]

Step A

N-{6-(3-{[tert-Butyl(dimethyl)silyl]oxy}-2,2-dimethylpropoxy)-2-[2-(morpholin-4-yl)-2-oxoethyl]-2H-indazol-5-yl}-6-(trifluoromethyl)pyridine-2-carboxamide

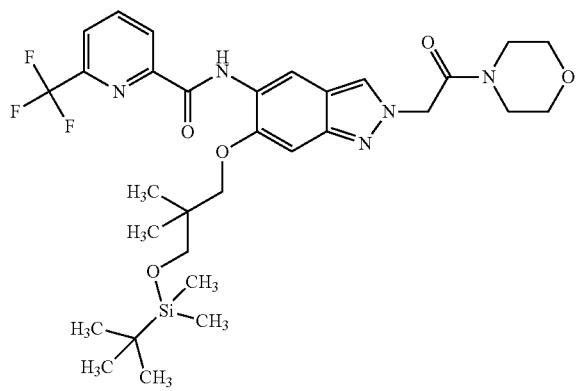 [SMILES: CC(C)(COc1cc2nn(CC(=O)N3CCOCC3)cc2cc1NC(=O)c1cccc(C(F)(F)F)n1)CO[Si](C)(C)C(C)(C)C]

100 mg (0.22 mmol) of N-{6-hydroxy-2-[2-(morpholin-4-yl)-2-oxoethyl]-2H-indazol-5-yl}-6-(trifluoromethyl)pyridine-2-carboxamide (Example 287) were dissolved in 2.0 ml of N,N-dimethylformamide, and 46 mg (0.33 mmol) of potassium carbonate were added with stirring. The suspension was stirred at 25° C. for 10 minutes, and 94 mg (0.33 mmol) (3-bromo-2,2-dimethylpropoxy)(tert-butyl)dimethylsilane were then added. The reaction mixture was stirred in the microwave at 100° C. for 1 h. The reaction mixture was then filtered and by preparative HPLC. This gave 34 mg (24% of theory) of the title compound.

UPLC-MS (Method A1): $R_t$=1.70 min

MS (ESIpos): m/z=650 (M+H)$^+$ $^1$H-NMR (400 MHz, DMSO-d6): δ=−0.17--0.09 (m, 6H), 0.75 (s, 9H), 1.07 (s, 6H), 3.42-3.51 (m, 2H), 3.54-3.64 (m, 2H), 3.54-3.64 (m, 4H), 3.64-3.71 (m, 2H), 3.88 (s, 2H), 5.40 (s, 2H), 7.05 (s, 1H), 8.17-8.27 (m, 2H), 8.42 (t, 1H), 8.49-8.56 (m, 1H), 8.79 (s, 1H), 10.42 (s, 1H).

Step B 40 mg (0.06 mmol) of N-{6-(3-{[tert-butyl(dimethyl)silyl]oxy}-2,2-dimethylpropoxy)-2-[2-(morpholin-4-yl)-2-oxoethyl]-2H-indazol-5-yl}-6-(trifluoromethyl)pyridine-2-carboxamide were dissolved in 2.5 ml of tetrahydrofuran, 185 µl (0.18 mmol) of a 1 M solution of tetrabutylammonium fluorid in tetrahydrofuran were added and the mixture was stirred at 25° C. for 2 h. 5 ml of water were added, and the reaction mixture was concentrated. The resulting precipitate was filtered off with suction, washed with water and diethyl ether and dried under reduced pressure. This gave 26 mg (48% of theory) of N-{6-(3-hydroxy-2,2-dimethylpropoxy)-2-[2-(morpholin-4-yl)-2-oxoethyl]-2H-indazol-5-yl}-6-(trifluoromethyl)pyridine-2-carboxamide.

UPLC-MS (Method A1): $R_t$=1.09 min

MS (ESIpos): m/z=536 (M+H)$^+$ $^1$H NMR (400 MHz, DMSO-d6): δ=1.06 (s, 6H), 3.42 (d, Hz, 2H), 3.45-3.51 (m, 2H), 3.54-3.63 (m, 4H), 3.63-3.68 (m, 2H), 3.90 (s, 2H), 4.63-4.69 (m, 1H), 5.40 (s, 2H), 7.05 (s, 1H), 8.17-8.25 (m, 2H), 8.41 (t, 1H), 8.51 (d, 1H), 8.81 (s, 1H), 10.44 (s, 1H).

Example 262

6-Ethyl-N-{6-methoxy-2-[2-(morpholin-4-yl)-2-oxoethyl]-2H-indazol-5-yl}pyridine-2-carboxamide

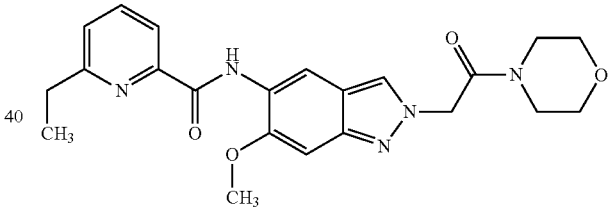

50 mg (0.11 mmol) of 6-bromo-N-{6-methoxy-2-[2-(morpholin-4-yl)-2-oxoethyl]-2H-indazol-5-yl}pyridine-2-carboxamide (Intermediate 15-2) were suspended in 750 µl of dry dioxane, 86 µl (0.09 mmol) of a 1.1 M solution of diethyl zinc in toluene and 4 mg (0.01 mmol) of 1,1'-bis(diphenylphospino)ferrocenepalladium(II) dichloride dichloromethane complex were added and the mixture was stirred at 40° C. for 24 h. Another 86 µl (0.09 mmol) of a 1.1 M solution of diethyl zinc in toluene and 4 mg (0.01 mmol) of 1,1'-bis(diphenylphospino)ferrocenepalladium(II) dichloride dichloromethane complex were added and the mixture was stirred at 60° C. for a further 24 h. A further 86 µl (0.09 mmol) of a 1.1 M solution of diethyl zinc in toluene and 4 mg (0.01 mmol) of 1,1'-bis(diphenylphospino)ferrocenepalladium(II) dichloride dichloromethane complex were added and the mixture was stirred at 60° C. for a further 24 h. The reaction mixture was filtered and the filtrate was concentrated. The crude product was dissolved in 2.5 ml of dimethyl sulphoxide and purified by preparative HPLC according to Method P1. The product fraction was lyophilized. This gave 5.8 mg (11% of theory) of the title compound.

UPLC-MS (Method A1): $R_t$=1.11 min

MS (ESIpos): m/z=424 (M+H)$^+$ $^1$H-NMR (300 MHz, DMSO-d6): δ=1.37 (t, 3H), 2.92 (q, 2H), 3.42-3.50 (m, 2H), 3.58 (br. s., 4H), 3.62-3.69 (m, 2H), 4.00 (s, 3H), 5.39 (s, 2H), 7.10 (s, 1H), 7.57 (dd, 2H), 7.97-8.02 (m, 2H), 8.21 (s, 1H), 8.71 (s, 1H), 10.88 (s, 1H).

Example 263

6-Isobutyl-N-{6-methoxy-2-[2-(morpholin-4-yl)-2-oxoethyl]-2H-indazol-5-yl}pyridine-2-carboxamide

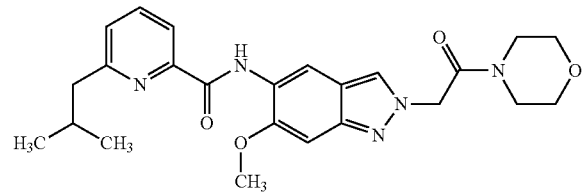 [SMILES: COc1cc2nn(CC(=O)N3CCOCC3)cc2cc1NC(=O)c1cccc(CC(C)C)n1]

50 mg (0.11 mmol) of 6-bromo-N-{6-methoxy-2-[2-(morpholin-4-yl)-2-oxoethyl]-2H-indazol-5-yl}pyridine-2-carboxamide (Intermediate 15-2) were dissolved in 1.5 ml of tetrahydrofuran, 316 μl (0.16 mmol) of a 0.5 M solution of 2-methylpropylzinc bromide in tetrahydrofuran and 3 mg (0.01 mmol) of bis(tri-tert-butylphosphine)palladium(0) were added and the mixture was stirred at 25° C. for 48 h. The reaction mixture was filtered and the filtrate was concentrated. The crude product was dissolved in 2.5 ml of dimethyl sulphoxide and purified by preparative HPLC according to Method P1. The product fraction was lyophilized. This gave 2.8 mg (6% of theory) of the title compound.

UPLC-MS (Method A1): $R_t$=1.27 min

MS (ESIpos): m/z=452 (M+H)$^+$ $^1$H-NMR (300 MHz, DMSO-d6): δ=0.99 (d, 6H) 2.15-2.29 (m, 1H) 2.77 (d, 2H) 3.47 (d, 2H) 3.53-3.69 (m, 6H) 3.99 (s, 3H) 5.39 (s, 2H) 7.09 (s, 1H) 7.53 (dd, 1H) 7.94-8.03 (m, 2H) 8.21 (s, 1H) 8.71 (s, 1H) 10.85 (s, 1H).

Example 264

Methyl 2-[2-(morpholin-4-yl)-2-oxoethyl]-5-({[6-(trifluoromethyl)pyridin-2-yl]carbonyl}amino)-2H-indazole-6-carboxylate

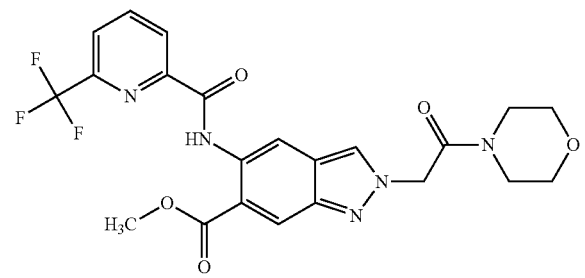 [SMILES: COC(=O)c1cc2nn(CC(=O)N3CCOCC3)cc2cc1NC(=O)c1cccc(C(F)(F)F)n1]

100 mg (0.60 mmol) of methyl 5-({[6-(trifluoromethyl)pyridin-2-yl]carbonyl}amino)-1H-indazole-6-carboxylate (Intermediate 14-9) were dissolved in 1 ml of tetrahydrofuran, 228 mg (1.10 mmol) of 2-bromo-1-(morpholin-4-yl)ethanone and 235 μl (1.10 mmol) of N,N-dicyclohexylmethylamine were added and the mixture was stirred at 75° C. for 24 h. The reaction mixture was filtered using a membrane filter and the filtrate was diluted with 1 ml of dimethyl sulphoxide and purified by preparative HPLC. The product fractions were lyophilized. This gave 15 mg (11% of theory) of the title compound.

UPLC-MS (Method A2): $R_t$=1.10 min

MS (ESIpos): m/z=492 (M+H)$^+$ $^1$H NMR (400 MHz, CHLOROFORM-d): δ=3.45-3.50 (m, 2H), 3.54-3.64 (m, 4H), 3.64-3.70 (m, 2H), 3.97 (s, 3H), 5.59 (s, 2H), 8.21 (dd, 1H), 8.36-8.43 (m, 1H), 8.44-8.49 (m, 3H), 9.08 (s, 1H), 12.52 (s, 1H).

Example 265

Methyl 5-{[(6-methylpyridin-2-yl)carbonyl]amino}-2-[2-(morpholin-4-yl)-2-oxoethyl]-2H-indazole-6-carboxylate

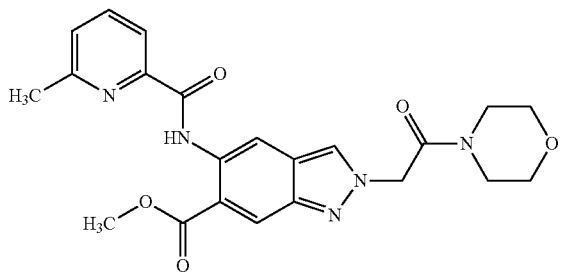 [SMILES: COC(=O)c1cc2nn(CC(=O)N3CCOCC3)cc2cc1NC(=O)c1cccc(C)n1]

50 mg (0.16 mmol) of (Intermediat 14-10) were dissolved in 2.5 ml of tetrahydrofuran, 134 mg (0.64 mmol) of 2-bromo-1-(morpholin-4-yl)ethanone and 138 μl (0.64 mmol) of N,N-dicyclohexylmethylamine were added and the mixture was stirred at 80° C. for 16 h. The reaction mixture was filtered and the filtrate was concentrated. The residue was dissolved in dichloromethane and washed three times with 1 M hydrochloric acid solution and three times with saturated sodium chloride solution, filtered through a hydrophobic filter and, during concentration, adsorbed on Isolute® HM-N (Biotage). The Isolute was applied to a cartridge (40 g; Puriflash) pre-equilibrated with hexane and chromatography was carried out using the Isolera® flash purification system (Biotage) (mobile phase: hexane/ethyl acetate; flow rate: 25 ml/min; gradient: 90:10->25:75). The combined product fractions were concentrated and dried. This gave 20 mg (28% of theory) of the title compound.

UPLC-MS (Method A2): $R_t$=1.05 min

MS (ESIpos): m/z=438 (M+H)$^+$ $^1$H-NMR (400 MHz, CHLOROFORM-d): δ=2.65 (s, 3H), 3.48 (d, 2H), 3.59 (dd, 4H), 3.67 (d, 2H), 3.99 (s, 3H), 5.58 (s, 2H), 7.55 (dd, 1H), 7.81-8.04 (m, 2H), 8.38-8.47 (m, 2H), 9.09 (s, 1H), 12.57 (s, 1H).

TABLE 19

Examples 266-286
The exemplary compounds were prepared by the general experimental procedures 1a-1e from the appropriate intermediates and carboxylic acids.

| Ex. No. | Structure/Name | Prepared from | ¹H-NMR/LC-MS |
|---|---|---|---|
| 266 | 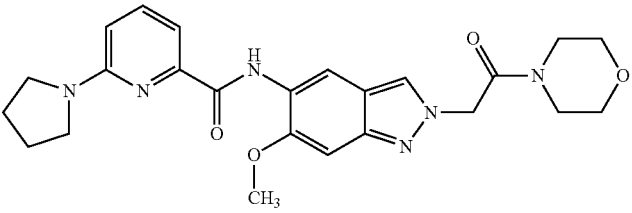<br>N-{6-methoxy-2-[2-(morpholin-4-yl)-2-oxoethyl]-2H-indazol-5-yl}-6-(pyrrolidin-1-yl)pyridine-2-carboxamide | Intermediate 6-16 and 6-(pyrrolidin-1-yl)pyridine-2-carboxylic acid (CAS 450368-20-4) | (400 MHz, DMSO-d6): δ = 1.98-2.06 (m, 4 H), 3.44-3.49 (m, 2 H), 3.51 (br. s., 4 H), 3.54-3.61 (m, 4 H), 3.61-3.68 (m, 2 H), 3.98 (s, 3 H), 5.38 (s, 2 H), 6.73 (d, 1 H), 7.07 (s, 1 H), 7.33 (d, 1 H), 7.72 (dd, 1 H), 8.19 (s, 1 H), 8.67 (s, 1 H), 10.93 (s, 1 H). UPLC-MS (Method A1): Rt = 1.16 min<br>MS (ESIpos): m/z = 465 (M + H)+ |
| 267 | 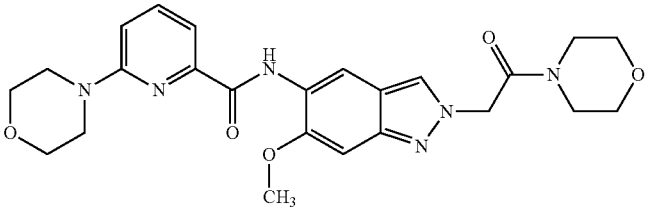<br>N-{6-methoxy-2-[2-(morpholin-4-yl)-2-oxoethyl]-2H-indazol-5-yl}-6-(morpholin-4-yl)pyridine-2-carboxamide | Intermediate 6-16 and 6-(morpholin-4-yl)pyridine-2-carboxylic acid (CAS 554405-17-3) | (400 MHz, DMSO-d6): δ = 3.42-3.50 (m, 2 H), 3.53-3.68 (m, 10 H), 3.75-3.84 (m, 4 H), 3.97 (s, 3 H), 5.38 (s, 2 H), 7.09 (s, 1 H), 7.15 (d, 1 H), 7.46 (d, 1 H), 7.81 (dd, 1 H), 8.17-8.21 (m, 1 H), 8.66 (s, 1 H), 10.79 (s, 1 H). UPLC-MS (Method A1): Rt = 0.96 min<br>MS (ESIpos): m/z = 481 (M + H)+ |
| 268 | 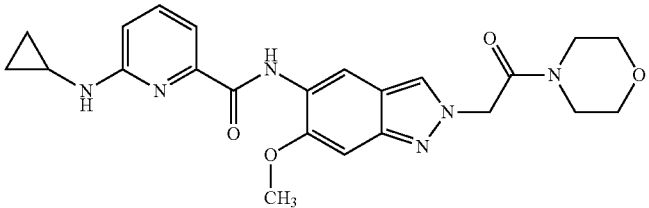<br>6-(cyclopropylamino)-N-{6-methoxy-2-[2-(morpholin-4-yl)-2-oxoethyl]-2H-indazol-5-yl}pyridine-2-carboxamide | Intermediate 6-16 and 6-(cyclopropylamino)pyridine-2-carboxylic acd (prepared according to Synthesis Scheme 8, obtainable from Ukrogsyntez Ltd., Order Number BBV-33897980) | (300 MHz, DMSO-d6): δ = 0.40-0.58 (m, 2 H), 0.74-0.89 (m, 2 H), 2.60-2.79 (m, 1 H), 3.41-3.53 (m, 2 H), 3.53-3.69 (m, 6 H), 3.96 (s, 3 H), 5.38 (s, 2 H), 6.78 (d, 1 H), 7.06 (s, 1 H), 7.26 (s, 1 H), 7.36 (d, 1 H), 7.64 (d, 1 H), 8.19 (s, 1 H), 8.72 (s, 1 H), 10.80 (s, 1 H). LC-MS (Method A3): Rt = 0.95 min<br>MS (ESIpos): m/z = 451 (M + H)+ |
| 269 | 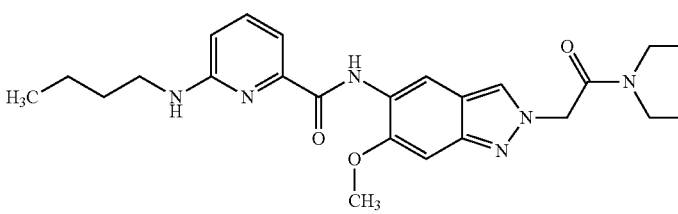<br>6-(butylamino)-N-{6-methoxy-2-[2-(morpholin-4-yl)-2-oxoethyl]-2H-indazol-5-yl}pyridine-2-carboxamide | Intermediate 6-16 and 6-(butylamino)pyridine-2-carboxylic acid (CAS 1250403-97-4) | (300 MHz, DMSO-d6):<br>δ = 0.95 (t, 3 H), 1.44 (dq, 2 H), 1.63 (quin, 2 H), 3.36-3.44 (m, 2 H), 3.44-3.51 (m, 2 H), 3.58 (br. s., 4 H), 3.62-3.70 (m, 2 H), 3.98 (s, 3 H), 5.38 (s, 2 H), 6.72 (d, 1 H), 7.02 (t, 1 H), 7.07 (s, 1 H), 7.26 (d, 1 H), 7.50-7.62 (m, 1 H), 8.19 (s, 1 H), 8.69 (s, 1 H), 10.82 (s, 1 H).<br>LC-MS (Method A3):<br>Rt = 1.07 min<br>MS (ESIpos): m/z = 467 (M + H)+ |

TABLE 19-continued

Examples 266-286
The exemplary compounds were prepared by the general experimental procedures 1a-1e from the appropriate intermediates and carboxylic acids.

| Ex. No. | Structure/Name | Prepared from | $^1$H-NMR/LC-MS |
|---|---|---|---|
| 270 | 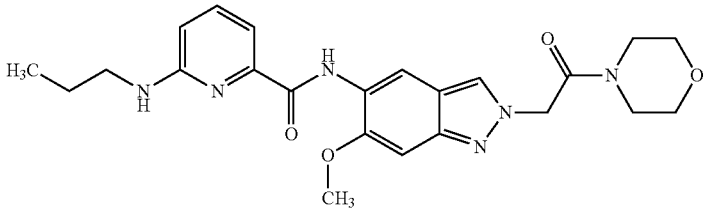<br>N-{6-methoxy-2-[2-(morpholin-4-yl)-2-oxoethyl]-2H-indazol-5-yl}-6-(propylamino)pyridine-2-carboxamide | Intermediate 6-16 and 6-(propyl-amino)pyridine-2-carboxylic acid (prepared according to Synthesis Scheme 8, obtainable from Ukrorgsyntez Ltd., Order Number BBV-33897968) | (300 MHz, DMSO-d6): δ = 1.00 (t, 3 H), 1.59-1.74 (m, 2 H), 3.34-3.42 (m, 2 H), 3.42-3.50 (m, 2 H), 3.58 (br. s., 4 H), 3.62-3.68 (m, 2 H), 3.98 (s, 3 H), 5.38 (s, 2 H), 6.72 (d, 1 H), 7.03-7.12 (m, 2 H), 7.26 (d, 1 H), 7.50-7.66 (m, 1 H), 8.19 (s, 1 H), 8.69 (s, 1 H), 10.83 (s, 1 H). UPLC-MS (Method A1): Rt = 1.05 min MS (ESIpos): m/z = 453 (M + H)$^+$ |
| 271 | 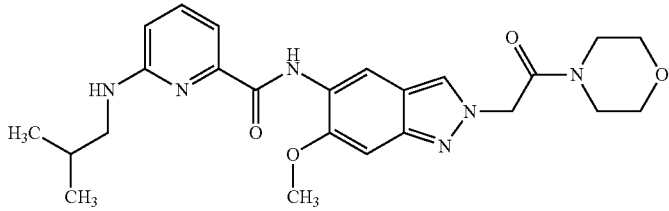<br>6-(isobutylamino)-N-{6-methoxy-2-[2-(morpholin-4-yl)-2-oxoethyl]-2H-indazol-5-yl}pyridine-2-carboxamide | Intermediate 6-16 and potassium 6-(isobutylami-no)pyridine-2-carboxylate (Intermediate 19-15) | (300 MHz, DMSO-d6): δ = 1.00 (d, 6 H) 1.84-2.02 (m, 1 H) 3.25 (t, 2 H) 3.47 (d, 2 H) 3.52-3.72 (m, 6 H) 3.99 (s, 3 H) 5.38 (s, 2 H) 6.75 (d, 1 H) 6.98-7.13 (m, 2 H) 7.26 (d, 1 H) 7.57 (dd, 1 H) 8.19 (s, 1 H) 8.70 (s, 1 H) 10.75 (s, 1 H). UPLC-MS (Method A1): Rt = 1.12 min MS (ESIpos): m/z = 467 (M + H)$^+$ |
| 272 | 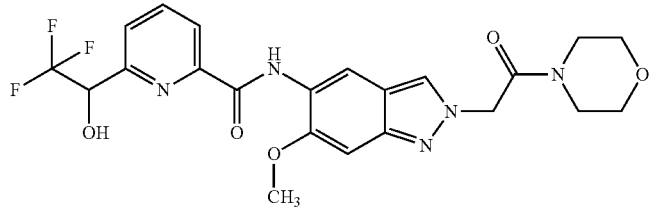<br>N-{6-methoxy-2-[2-(morpholin-4-yl)-2-oxoethyl]-2H-indazol-5-yl}-6-(2,2,2-trifluoro-1-hydroxyethyl)pyridine-2-carboxamide (Enantiomer 1)* | Intermediate 6-16 and potassium 6-(2,2,2-trifluoro-1-hydroxyethyl)pyridine-2-carboxylate (Intermediate 19-10) | (300 MHz, DMSO-d6): δ = 3.42-3.52 (m, 2 H), 3.58 (br. s., 4 H), 3.62-3.67 (m, 2 H), 3.97 (s, 3 H), 5.29-5.39 (m, 1 H), 5.40 (s, 2 H), 7.09 (s, 1 H), 7.31 (d, J = 6.0 Hz, 1 H), 7.91 (t, J = 4.5 Hz, 1 H), 8.16-8.25 (m, 3 H), 8.67 (s, 1 H), 10.70 (s, 1 H). UPLC-MS (Method A2): Rt = 0.95 min MS (ESIpos): 494 (M + H)$^+$ |
| 273 | 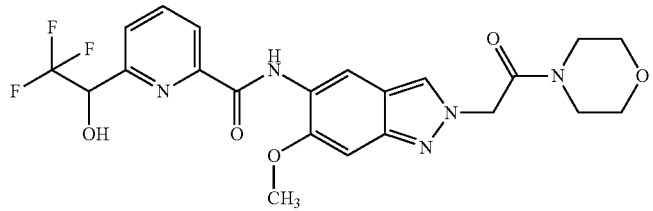<br>N-{6-methoxy-2-[2-(morpholin-4-yl)-2-oxoethyl]-2H-indazol-5-yl}-6-(2,2,2-trifluoro-1-hydroxyethyl)pyridine-2-carboxamide (Enantiomer 2)* | Intermediate 6-16 and potassium 6-(2,2,2-trifluoro-1-hydroxyethyl)pyridine-2-carboxylate (Intermediate 19-10) | (300 MHz, DMSO-d6): δ = 3.42-3.52 (m, 2 H), 3.58 (br. s., 4 H), 3.62-3.67 (m, 2 H), 3.97 (s, 3 H), 5.29-5.39 (m, 1 H), 5.40 (s, 2 H), 7.09 (s, 1 H), 7.31 (d, J = 6.0 Hz, 1 H), 7.91 (t, J = 4.5 Hz, 1 H), 8.16-8.25 (m, 3 H), 8.67 (s, 1 H), 10.70 (s, 1 H). UPLC-MS (Method A2): Rt = 0.95 min MS (ESIpos): m/z = 494 (M + H)$^+$ |

TABLE 19-continued

Examples 266-286
The exemplary compounds were prepared by the general experimental procedures 1a-1e from the appropriate intermediates and carboxylic acids.

| Ex. No. | Structure/Name | Prepared from | ¹H-NMR/LC-MS |
|---|---|---|---|
| 274 | 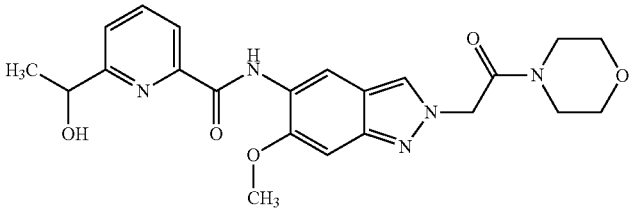<br>6-(1-hydroxyethyl)-N-{6-methoxy-2-[2-(morpholin-4-yl)-2-oxoethyl]-2H-indazol-5-yl}pyridine-2-carboxamide | Intermediate 6-16 and potassium 6-(1-hydroxyethyl)pyridine-2-carboxylate (Intermediate 19-1) | (300 MHz, DMSO-d6): δ = 1.52 (d, 3 H), 3.41-3.51 (m, 2 H), 3.58 (br. s., 4 H), 3.63-3.69 (m, 2 H), 4.00 (s, 2 H), 4.80-4.92 (m, 1 H), 5.39 (s, 2 H), 5.59 (d, 1 H), 7.10 (s, 1 H), 7.80 (dd, 1 H), 8.00-8.13 (m, 2 H), 8.21 (s, 1 H), 8.69 (s, 1 H), 10.79 (s, 1 H). UPLC-MS (Method A1): Rt = 0.85 min MS (ESIpos): m/z = 440 (M + H)⁺ |
| 275 | 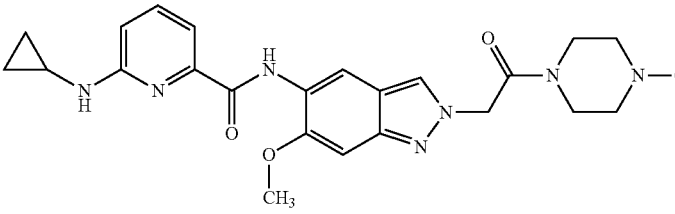<br>6-(cyclopropylamino)-N-{6-methoxy-2-[2-(4-methylpiperazin-1-yl)-2-oxoethyl]-2H-indazol-5-yl}pyridine-2-carboxamide | Intermediate 6-17 and 6-(cyclopropyl amino) pyridine-2-carboxylic acid | (400 MHz, DMSO-d6): δ = 0.44-0.56 (m, 2 H), 0.77-0.87 (m, 3 H), 2.20 (s, 3 H), 2.25-2.31 (m, 2 H), 2.36 (br. s., 2 H), 2.63-2.74 (m, 1 H), 3.46 (br. s., 2 H), 3.54 (br. s., 2 H), 3.96 (s, 3 H), 5.36 (s, 2 H), 6.78 (d, 1 H), 7.06 (s, 1 H), 7.24 (s, 1H), 7.36 (d, 1 H), 7.65 (t, 1 H), 8.18 (s, 1 H), 8.71 (s, 1 H), 10.79 (s, 1 H). UPLC-MS (Method A1): Rt = 0.89 min MS (ESIpos): m/z = 464 (M + H)⁺ |
| 276 | 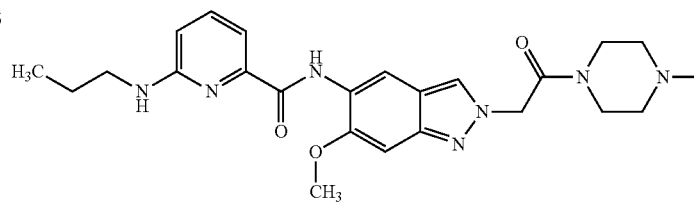<br>N-{6-methoxy-2-[2-(4-methylpiperazin-1-yl)-2-oxoethyl]-2H-indazol-5-yl}-6-(propylamino)pyridine-2-carboxamide | Intermediate 6-17 and 6-(propylamino) pyridine-2-carboxylic acid | (300 MHz, DMSO-d6, selected signals): δ = 1.00 (t, 3 H), 1.59-1.74 (m, 2 H), 2.28 (s, 3 H), 2.41 (br. s., 2 H) 3.21-3.43 (m, 2 H), 3.49 (br. s., 2 H), 3.58 (br. s., 2 H), 3.98 (s, 3 H), 5.38 (s, 2 H), 6.72 (d, 1 H), 7.00-7.09 (m, 2 H), 7.26 (d, 1 H), 7.57 (dd, 1 H), 8.18 (s, 1 H), 8.69 (s, 1 H), 10.82 (s, 1 H). UPLC-MS (Method A1): Rt = 0.86 min MS (ESIpos): m/z = 466 (M + H)⁺ |
| 277 | 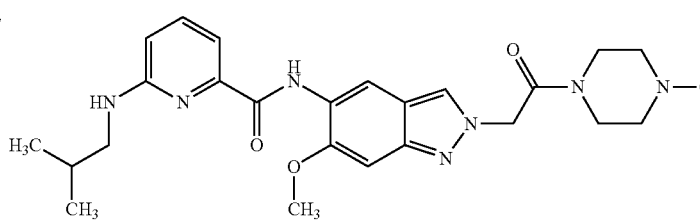<br>6-(isobutylamino)-N-{6-methoxy-2-[2-(4-methylpiperazin-1-yl)-2-oxoethyl]-2H-indaozl-5-yl}pyridine-2-carboxamide | Intermediate 6-17 and potassium 6-(isobutylamino)pyridine-2-carboxylate (Intermediate 19-15) | (400 MHz, DMSO-d6): δ = 1.00 (d, 6 H) 1.94 (dt, 1 H) 2.20 (s, 3 H) 2.25-2.33 (m, 2 H) 2.33-2.41 (m, 2 H) 3.25 (t, 2 H) 3.41-3.50 (m, 2 H) 3.50-3.59 (m, 2 H) 3.99 (s, 3 H) 5.36 (s, 2 H) 6.71-6.80 (m, 1 H) 7.00-7.11 (m, 2 H) 7.22-7.30 (m, 1 H) 7.57 (dd, 1 H) 8.18 (s, 1 H) 8.70 (s, 1 H) 10.75 (s, 1 H). UPLC-MS (Method A1): Rt = 0.90 min MS (ESIpos): m/z = 480 (M + H)⁺ |

TABLE 19-continued

Examples 266-286
The exemplary compounds were prepared by the general experimental procedures 1a-1e from the appropriate intermediates and carboxylic acids.

| Ex. No. | Structure/Name | Prepared from | $^1$H-NMR/LC-MS |
|---|---|---|---|
| 278 | 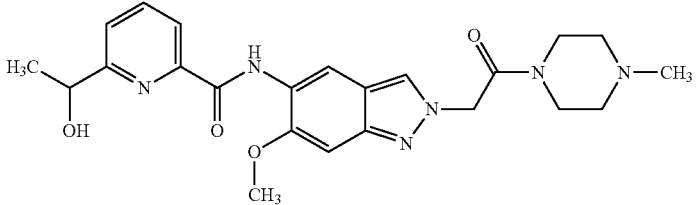<br>6-(1-hydroxyethyl)-N-{6-methoxy-2-[2-(4-methylpiperazin-1-yl)-2-oxoethyl]-2H-indazol-5-yl}pyridine-2-carboxamide | Intermediate 6-17 and potassium 6-(1-hydroxyethyl)pyridine-2-carboxylate (Intermediate 19-1) | (400 MHz, DMSO-d6): δ = 1.52 (d, 3 H), 2.21 (s, 3 H), 2.26-2.32 (m, 2 H), 2.34-2.39 (m, 2H), 3.41-3.50 (m, 2 H), 3.51-3.58 (m, 2 H), 4.00 (s, 3 H), 4.87 (dd, 1 H), 5.37 (s, 2 H), 5.59 (d, 1 H), 7.09 (s, 1 H), 7.80 (dd, 1 H), 7.98-8.12 (m, 2 H), 8.21 (s, 1 H), 8.68 (s, 1 H), 10.79 (s, 1 H). UPLC-MS (Method A1): Rt = 0.69 min<br>MS (ESIpos): m/z = 453 (M + H)$^+$ |
| 279 | 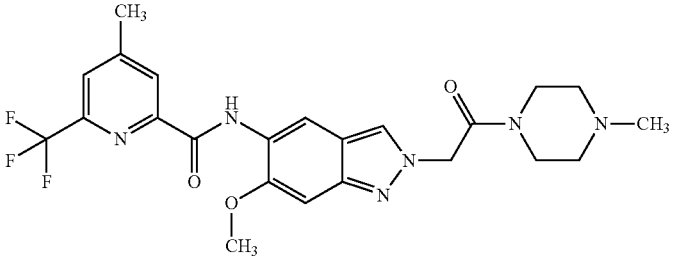<br>N-{6-methoxy-2-[2-(4-methylpiperazin-1-yl)-2-oxoethyl]-2H-indazol-5-yl}-4-methyl-6-(trifluoromethyl)pyridine-2-carboxamide | Intermediate 6-17 and 4-methyl-6-(trifluoromethyl)pyridine-2-carboxylic acid (obtainable from Anichem Inc. USA) | (300 MHz, DMSO-d6): δ = 2.21 (s, 3 H), 2.25-2.33 (m, 2 H), 2.37 (br. s., 2 H), 2.58 (s, 3 H), 3.46 (br. s., 2 H), 3.54 (br. s., 2 H), 3.98 (s, 3 H), 5.38 (s, 2 H), 7.11 (s, 1 H), 8.08 (s, 1 H), 8.23 (s, 1 H), 8.30 (s, 1 H), 8.70 (s, 1 H), 10.52 (s, 1 H). UPLC-MS (Method A1): Rt = 0.99 min<br>MS (ESIpos): m/z = 491 (M + H)$^+$ |
| 280 | 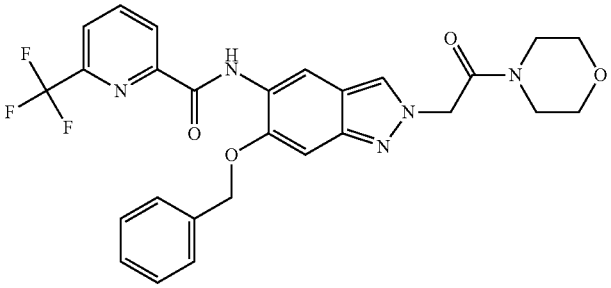<br>N-{6-(benzyloxy)-2-[2-(morpholin-4-yl)-2-oxoethyl]-2H-indazol-5-yl}-6-(trifluoromethyl)pyridine-2-carboxamide | Intermediate 6-21 and 2-[5-amino-6-(benzyloxy)-2H-indazol-2-yl]-1-(morpholin-4-yl)ethanone (Intermediate 6-20) | (300 MHz, DMSO-d6): δ = 3.43-3.53 (m, 2 H), 3.54-3.63 (m, 4 H), 3.63-3.69 (m, 2 H), 5.31 (s, 2 H), 5.41 (s, 2 H), 7.30 (s, 1 H), 7.41 (d, 3 H), 7.58 (d, 2 H), 8.18 (d, 1 H), 8.26 (s, 1 H), 8.35-8.44 (m, 1H), 8.44-8.52 (m, 1 H), 8.81 (s, 1 H), 10.47 (s, 1 H). UPLC-MS (Method A1): Rt = 1.26 min<br>MS (ESIpos): m/z = 540 (M + H)$^+$ |

TABLE 19-continued

Examples 266-286
The exemplary compounds were prepared by the general experimental procedures 1a-1e from the appropriate intermediates and carboxylic acids.

| Ex. No. | Structure/Name | Prepared from | $^1$H-NMR/LC-MS |
|---|---|---|---|
| 281 | 6-(cyclopropylamino)-N-(2-{2-[4-(2-hydroxypropan-2-yl)piperidin-1-yl]-2-oxoethyl}-6-methoxy-2H-indazol-5-yl)pyridine-2-carboxamide | Intermediate 6-5 and 6-(cyclopropylamino)pyridine-2-carboxylic acid | (400 MHz, DMSO-d6): δ = 0.47-0.55 (m, 2 H), 0.76-0.86 (m, 2 H), 1.00-1.11 (m, 7 H), 1.16-1.31 (m, 1 H), 1.37-1.50 (m, 1 H), 1.75 (t, 2H), 2.64-2.77 (m, 1 H), 2.99 (t, 1 H), 3.95 (s, 3 H), 4.03 (d, 1 H), 4.18 (s, 1 H), 4.42 (d, 1 H), 5.32 (d, 1 H), 5.38 (d, 1 H), 6.78 (d, 1 H), 7.06 (s, 1 H), 7.25 (d, 1 H), 7.36 (d, 1 H), 7.65 (dd, 1 H), 8.19 (s, 1 H), 8.71 (s, 1 H), 10.79 (s, 1 H). LC-MS (Method A3): Rt = 1.10 min MS (ESIpos): m/z = 507 (M + H)$^+$ |
| 282 | 6-(butylamino)-N-(2-{2-[4-(2-hydroxypropan-2-yl)piperidin-1-yl]-2-oxoethyl}-6-methoxy-2H-indaozl-5-yl)pyridine-2-carboxamide | Intermediate 6-5 and 6-(butylamino)pyridine-2-carboxylic acid | (300 MHz, DMSO-d6): δ = 0.95 (t, 3 H), 1.04 (s, 7 H), 1.18-1.31 (m, 1 H), 1.37-1.51 (m, 3 H), 1.55-1.68 (m, 2 H), 1.68-1.81 (m, 2 H), 2.87-3.05 (m, 1 H), 3.36-3.47 (m, 2 H), 3.97 (s, 3 H), 4.05 (br. s., 1 H), 4.18 (s, 1 H), 4.41 (d, 1 H), 5.38 (d, 1 H), 5.32 (d, 1 H), 6.72 (d, 1 H), 7.02 (t, 1 H), 7.07 (s, 1 H), 7.26 (d, 1 H), 7.50-7.63 (m, 1 H), 8.19 (s, 1 H), 8.69 (s, 1 H), 10.81 (s, H). LC-MS (Method A3): Rt = 1.12 min MS (ESIpos): m/z = 523 (M + H)$^+$ |
| 283 | N-(2-{2-[4-(2-hydroxypropan-2-yl)piperidin-1-yl]-2-oxoethyl}-6-methoxy-2H-indazol-5-yl)-6-[(2-methoxyethyl)amino]pyridine-2-carboxamide | Intermediate 6-5 and 6-[(2-methoxyethyl)amino]pyridine-2-carboxylic acd (prepared according to Synthesis Scheme 8, obtainable from Ukrorgsyntez Ltd., Order Number BBV-33897975) | (300 MHz, DMSO-d6, selected signals): δ = 1.04 (s, 7 H), 1.17-1.31 (m, 1 H), 1.35-1.51 (m, 1 H), 1.75 (t, 2 H), 2.99 (t, 1 H), 3.60 (s, 4 H), 3.94-4.09 (m, 1 H), 3.99 (s, 3 H), 4.18 (s, 1 H), 4.42 (d, 1 H), 5.38 (d, 1 H), 5.32 (d, 1 H), 6.77 (d, 1 H), 7.07 (s, 1 H), 7.14 (br. s., 1 H), 7.28 (d, 1 H), 7.52-7.64 (m, 1 H), 8.19 (s, 1 H), 8.68 (s, 1 H), 10.82 (s, 1 H). LC-MS (Method A3): Rt = 0.90 min MS (ESIpos): m/z = 525 (M + H)$^+$ |
| 284 | N-(2-{2-[4-(2-hydroxypropan-2-yl)piperidin-1-yl]-2-oxoethyl}-6-methoxy-2H-indazol-5-yl)-6-(propylamino)pyridine-2-carboxamide | Intermediate 6-5 and 6-(propylamino)pyridine-2-carboxylic acid | (300 MHz, DMSO-d6): δ = 1.04 (s, 6 H), 1.00 (t, 3 H), 1.12 (br. s., 1 H), 1.15-1.30 (m, 1 H), 1.34-1.51 (m, 1 H), 1.58-1.83 (m, 2 H), 1.67 (sxt, 2 H), 2.91-3.07 (m, 1 H), 3.35-3.42 (m, 2 H), 3.98 (s, 4 H), 4.05 (br. s., 1 H), 4.18 (s, 1 H), 4.42 (d, 1 H), 5.35 (d, 2 H), 6.72 (d, 1 H), 7.02-7.10 (m, 2 H), 7.26 (d, 1 H), 7.57 (dd, 1 H), 8.19 (s, 1 H), 8.69 (s, 1 H), 10.82 (s, 1 H). UPLC-MS (Method A1): Rt = 1.09 min MS (ESIpos): m/z = 509 (M + H)$^+$ |

TABLE 19-continued

Examples 266-286
The exemplary compounds were prepared by the general experimental procedures 1a-1e from the appropriate intermediates and carboxylic acids.

| Ex. No. | Structure/Name | Prepared from | $^1$H-NMR/LC-MS |
|---|---|---|---|
| 285 | N-(2-{2-[4-(2-hydroxypropan-2-yl)piperidin-1-yl]-2-oxoethyl}-6-methoxy-2H-indazol-5-yl)-6-(isobutylamino)pyridine-2-carboxamide | Intermediate 6-5 and 6-(isobutylamino)pyridine-2-carboxylic acid | (300 MHz, DMSO-d6): δ = 0.99 (s, 3 H), 1.01 (s, 3 H), 1.03-1.08 (m, 7 H), 1.19-1.28 (m, 1 H), 1.38-1.50 (m, 1 H), 1.75 (t, 2 H), 1.94 (dt, 1 H), 2.99 (br. s., 1 H), 3.25 (t, 2 H), 3.99 (s, 3 H), 4.03 (d, 1 H), 4.16 (s, 1 H), 4.42 (d, 1 H), 5.38 (d, 1 H), 5.32 (d, 1H), 6.75 (dd, 1 H), 7.07 (s, 1 H), 7.05 (t, 1 H), 7.23-7.29 (m, 1 H), 7.57 (dd, 1 H), 8.15-8.20 (m, 1 H), 8.70 (s, 1 H), 10.75 (s, 1 H). UPLC-MS (Method A1): Rt = 1.16 min MS (ESIpos): m/z = 523 (M + H)$^+$ |
| 286 | 5-fluoro-N-(2-{2-[4-(2-hydroxypropan-2-yl)piperidin-1-yl]-2-oxoethyl}-6-methoxy-2H-indazol-5-yl)-6-methylpyridine-2-carboxamide | Intermediate 6-5 and 5-fluoro-6-methylpyridine-2-carboxylic acid | (300 MHz, DMSO-d6): δ = 1.04 (s, 6 H), 1.07-1.15 (m, 1 H), 1.17-1.35 (m, 1 H), 1.36-1.52 (m, 1 H), 1.75 (t, 2 H), 2.59 (d, 3 H), 2.99 (t, 1 H), 3.96-4.08 (m, 1 H), 4.00 (s, 3 H), 4.19 (s, 1 H), 4.41 (d, 1 H), 5.33 (d, 1 H), 5.39 (d, 1 H), 7.09 (s, 1 H), 7.90 (t, 1 H), 8.09 (dd, 1 H), 8.21 (s, 1 H), 8.68 (s, 1 H), 10.52 (s, 1 H). |

*The reaction of Intermediate 6-16 and potassium 6-(2,2,2-trifluoro-1-hydroxyethyl)pyridine-2-carboxylate gave N-{6-methoxy-2-[2-(morpholin-4-yl)-2-oxoethyl]-2H-indazol-5-yl}-6-(2,2,2-trifluoro-1-hydroxyethyl)pyridine-2-carboxamide as a racemic mixture. This mixture was separated into the pure enantiomers by preparative chiral HPLC using the following conditions:

System: Agilent: Prep 1200, 2×Prep Pump, DLA, MWD, Gilson: Liquid Handler 215
Column: Chiralpak IC 5 μm 250×30 mm
Solvent: ethanol/methanol 50:50 (v/v)
Flow rate: 35 ml/min
Temperature: room temperature
Solution: 401 mg/8 ml dichloromethane/MeOH
Injection: 10×0.8 ml
Detection: UV 280 nm

| Fraction | Rt in min | Purity in % | Amount in mg | Peak assignment |
|---|---|---|---|---|
| corresponds to Example 273 | 8.0-8.7 | 98.8 | 70 | peak 2 - 2.88 min |
| corresponds to Example 272 | 10.1-11.1 | 99.1 | 59 | peak 4 - 3.81 min |

Workup: The fractions were concentrated by evaporation, admixed with tBuOH, frozen at −65° C. and then freeze-dried.

Example 287

N-{6-Hydroxy-2-[2-(morpholin-4-yl)-2-oxoethyl]-2H-indazol-5-yl}-6-(trifluoromethyl)pyridine-2-carboxamide

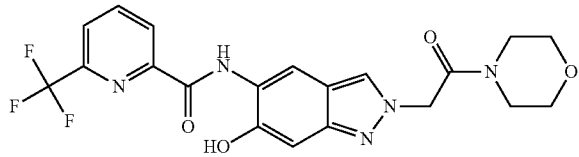 [SMILES: O=C(Nc1cc2cn(CC(=O)N3CCOCC3)nc2cc1O)c1cccc(C(F)(F)F)n1]

2.43 g (4.50 mmol) of N-{6-(benzyloxy)-2-[2-(morpholin-4-yl)-2-oxoethyl]-2H-indazol-5-yl}-6-(trifluoromethyl)pyridine-2-carboxamide (Beispiel 280) were suspended in 470 ml of tetrahydrofuran, and the flask was evacuated and then flushed with nitrogen (this procedure was repeated two more times). 958 mg (0.9 mmol, 10%) of palladium on carbon and 95 ml (370.6 mmol) of a 25% strength ammonium formate solution was added and the mixture was stirred vigorously at 25° C. for 40 minutes. The reaction mixture was filtered through Celite and concentrated. The precipitate formed was filtered off with suction, washed repeatedly with water and dried in a drying cabinet at 50° C. under reduced pressure. This gave 2.01 g (90% of theory) of the title compound.

UPLC-MS (Method A2): Rt=0.64 min
MS (ESIpos): m/z=450 (M+H)$^+$
$^1$H NMR (400 MHz, DMSO-d6): δ=3.40-3.50 (m, 2H), 3.52-3.61 (m, 4H), 3.61-3.67 (m, 2H), 5.36 (s, 2H), 6.91 (s, 1H), 8.16-8.23 (m, 2H), 8.40 (t, 1H), 8.47 (d, 1H), 8.69 (s, 1H), 10.55 (s, 1H), 10.65 (s, 1H).

General Procedure 3a 1.0 equivalent of N-{6-hydroxy-2-[2-(morpholin-4-yl)-2-oxoethyl]-2H-indazol-5-yl}-6-(trifluoromethyl)pyridine-2-carboxamide was stirred with 1.5 equivalents of the appropriate halide and 3.0 equivalents of potassium carbonate in N,N-dimethylformamide at 100° C. in the microwave for 1 h. Water was added to the reaction mixture, and the resulting precipitate was filtered off, washed with water and diethyl ether and dried.

General Procedure 3b 1.0 equivalent of N-{6-hydroxy-2-[2-(morpholin-4-yl)-2-oxoethyl]-2H-indazol-5-yl}-6-(trifluoromethyl)pyridine-2-carboxamide was stirred with 1.5 equivalents of the appropriate halide and 3.0 equivalents of potassium carbonate in N,N-dimethylformamide at 100° C. in the microwave for 1 h. The reaction mixture was filtered, dimethyl sulphoxide was added and the product was purified by preparative HPLC according to Method P1.

General Procedure 3c 1.0 equivalent of N-{6-hydroxy-2-[2-(morpholin-4-yl)-2-oxoethyl]-2H-indazol-5-yl}-6-(trifluoromethyl)pyridine-2-carboxamide was stirred with 3.0 equivalents of the appropriate halide, 5.0 equivalents of potassium carbonate and 0.1 equivalent of potassium iodide in N,N-dimethylformamide at 150° C. in the microwave for 1 h. The reaction mixture was filtered, dimethyl sulphoxide was added and the product was purified by preparative HPLC according to Method P5 (gradient: 0-15 min 10-50% B).

TABLE 20

Examples 304-328
The exemplary compounds were prepared from N-{6-hydroxy-2-[2-(morpholin-4-yl)-2-oxoethyl]-2H-indazol-5-yl}-6-(trifluoromethyl)pyridine-2-carboxamide and the halides listed in the table according to General Procedures 3a, 3b or 3c.

| Ex. No. | Structure/Name | Prepared by reaction with | *see key | $^1$H-NMR/LC-MS |
|---|---|---|---|---|
| 288 | N-{6-(3-cyanopropoxy)-2-[2-(morpholin-4-yl)-2-oxoethyl]-2H-indaozl-5-yl}-6-(trifluoromethyl)pyridine-2-carboxamide | 4-bromobutane nitrile | 3a (87%) | (400 MHz, DMSO-d6): δ = 2.21 (quin, 2 H), 2.77 (t, 2 H), 3.43-3.51 (m, 2 H), 3.53-3.62 (m, 4 H), 3.63-3.69 (m, 2 H), 4.25 (t, 2 H), 5.40 (s, 2 H), 7.13 (s, 1 H), 8.22 (dd, 1 H), 8.24-8.26 (m, 1 H), 8.37-8.45 (m, 1 H), 8.45-8.50 (m, 1 H), 8.74 (s, 1 H), 10.55 (s, 1 H). UPLC-MS (Method A1): Rt = 1.05 min MS (ESIpos): m/z = 517 (M + H)+ |

TABLE 20-continued

Examples 304-328
The exemplary compounds were prepared from N-{6-hydroxy-2-[2-(morpholin-4-yl)-2-oxoethyl]-
2H-indazol-5-yl}-6-(trifluoromethyl)pyridine-2-carboxamide and the halides listed in the table
according to General Procedures 3a, 3b or 3c.

| Ex. No. | Structure/Name | Prepared by reaction with | *see key | $^1$H-NMR/LC-MS |
|---|---|---|---|---|
| 289 | N-{2-[2-(morpholin-4-yl)-2-oxoethyl]-6-(2,2,2-trifluoroethoxy)-2H-indazol-5-yl}-6-(trifluoromethyl)pyridine-2-carboxamide | 1,1,1-trifluoro-2-iodoethane | 3b[b] (21%) | (300 MHz, DMSO-d6): δ = 3.43-3.50 (m, 2 H), 3.53-3.63 (m, 5 H), 3.63-3.69 (m, 2 H), 5.01 (d, 1 H), 4.95 (d, 1 H), 5.43 (s, 2 H), 7.30 (s, 1 H), 8.21 (d, 1 H), 8.30 (s, 1 H), 8.41 (t, 1 H), 8.45-8.51 (m, 1 H), 8.81 (s, 1 H), 10.53 (s, 1 H). UPLC-MS (Method A1): Rt = 1.16 min MS (ESIpos): m/z = 532 (M + H)+ |
| 290 | N-{6-(cyclohexylmethoxy)-2-[2-(morpholin-4-yl)-2-oxoethyl]-2H-indazol-5-yl}-6-(trifluoromethyl)pyridine-2-carboxamide | (bromomethyl)cyclohexane | 3b (70%) | (300 MHz, DMSO-d6): δ = 1.07-1.37 (m, 6 H), 1.64-1.81 (m, 2 H), 1.86-2.02 (m, 3 H), 3.42-3.50 (m, 2 H), 3.53-3.69 (m, 6 H), 3.97 (d, 2 H), 5.39 (s, 2 H), 7.08 (s, 1 H), 8.18-8.25 (m, 2 H), 8.40 (t, 1 H), 8.48 (d, 1 H), 8.79 (s, 1 H), 10.48 (s, 1 H). LC-MS (Method A3): Rt = 1.40 min MS (ESIpos): m/z = 546 (M + H)+ |
| 291 | N-{6-(2,2-dimethylpropoxy)-2-[2-(morpholin-4-yl)-2-oxoethyl]-2H-indazol-5-yl}-6-(trifluoromethyl)pyridine-2-carboxamide | 1-iodi-2,2-dimethylpropane | 3b (22%) | (300 MHz, DMSO-d6): δ = 1.03-1.21 (m, 9 H), 3.39-3.53 (m, 2 H), 3.53-3.73 (m, 6 H), 3.84 (s, 2 H), 5.40 (s, 2 H), 7.07 (s, 1 H), 8.18-8.26 (m, 2 H), 8.41 (t, 1 H), 8.51 (d, 1 H), 8.82 (s, 1 H), 10.47 (s, 1 H). LC-MS (Method A3): Rt = 1.30 min MS (ESIpos): m/z = 520 (M + H)+ |

TABLE 20-continued

Examples 304-328
The exemplary compounds were prepared from N-{6-hydroxy-2-[2-(morpholin-4-yl)-2-oxoethyl]-2H-indazol-5-yl}-6-(trifluoromethyl)pyridine-2-carboxamide and the halides listed in the table according to General Procedures 3a, 3b or 3c.

| Ex. No. | Structure/Name | Prepared by reaction with | *see key | $^1$H-NMR/LC-MS |
|---|---|---|---|---|
| 292 | 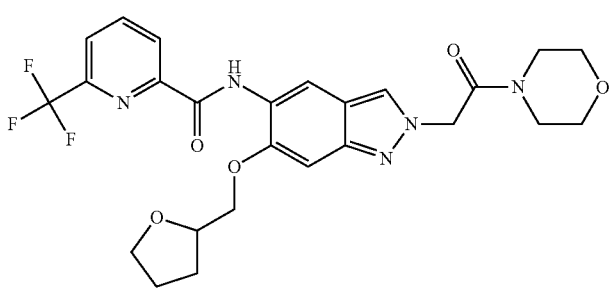<br>N-{2-[2-(morpholin-4-yl)-2-oxoethyl]-6-(tetrahydrofuran-2-ylmethoxy)-2H-indazol-5-yl}-6-(trifluoromethyl)pyridine-2-carboxamide | 2-(bromomethyl)tetrahydrofuran | 3b (41%) | (300 MHz, DMSO-d6): δ = 1.70-2.00 (m, 3 H), 2.05-2.20 (m, 1 H), 3.47 (d, 2 H), 3.53-3.68 (m, 7 H), 3.68-3.77 (m, 1 H), 3.77-3.89 (m, 1 H), 4.07-4.22 (m, 2 H), 4.22-4.34 (m, 1 H), 5.40 (s, 2 H), 7.14 (s, 1 H), 8.17-8.29 (m, 2 H), 8.41 (t, 1 H), 8.48 (d, 1 H), 8.75 (s, 1 H), 10.51 (s, 1 H).<br>LC-MS (Method A3): Rt = 1.07 min<br>MS (ESIpos): m/z = 534 (M + H)+ |
| 293 | 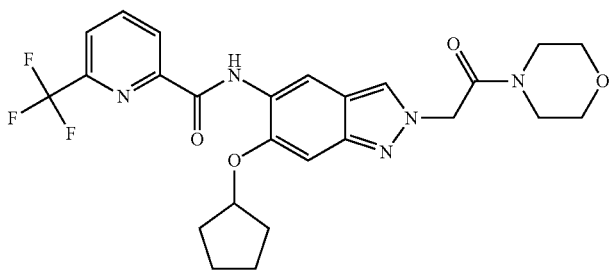<br>N-{6-(cyclopentyloxy)-2-[2-(morpholin-4-yl)-2-oxoethyl]-2H-indazol-5-yl}-6-(trifluoromethyl)pyridine-2-carboxamide | iodocyclopentane | 3b[c] (23%) | (300 MHz, DMSO-d6): δ = 1.67 (dd, 2 H), 1.80 (dd, 2 H), 1.86-1.96 (m, 2 H), 1.97-2.10 (m, 2 H), 3.47 (d, 2 H), 3.54-3.62 (m, 4 H), 3.65 (d, 2 H), 5.07 (t, 1 H), 5.38 (s, 2 H), 7.07 (s, 1 H), 8.18-8.24 (m, 2 H), 8.40 (t, 1 H), 8.47 (d, 1 H), 8.75 (s, 1 H), 10.62 (s, 1 H).<br>UPLC-MS (Method A2): Rt = 1.29 min<br>MS (ESIpos): m/z = 518 (M + H)+ |
| 294 | 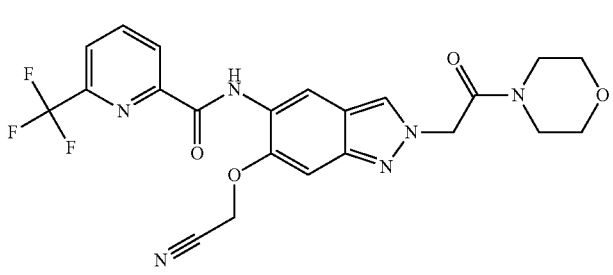<br>N-{6-(cyanomethoxy)-2-[2-(morpholin-4-yl)-2-oxoethyl]-2H-indazol-5-yl}-6-(trifluoromethyl)pyridine-2-carboxamide | bromoacetonitrile | 3b[d] (10%) | (300 MHz, DMSO-d6): δ = 3.47 (d, 2 H), 3.55-3.62 (m, 4 H), 3.65 (d, 2 H), 5.39 (s, 2 H), 5.44 (s, 2 H), 7.31 (s, 1 H), 8.23 (dd, 1 H), 8.30 (s, 1 H), 8.42 (d, 1 H), 8.46 (s, 1 H), 8.73 (s, 1 H), 10.41 (s, 1 H).<br>UPLC-MS (Method A2): Rt = 1.01 min<br>MS (ESIpos): m/z = 489 (M + H)+ |

TABLE 20-continued

Examples 304-328
The exemplary compounds were prepared from N-{6-hydroxy-2-[2-(morpholin-4-yl)-2-oxoethyl]-
2H-indazol-5-yl}-6-(trifluoromethyl)pyridine-2-carboxamide and the halides listed in the table
according to General Procedures 3a, 3b or 3c.

| Ex. No. | Structure/Name | Prepared by reaction with | *see key | ¹H-NMR/LC-MS |
|---|---|---|---|---|
| 295 | 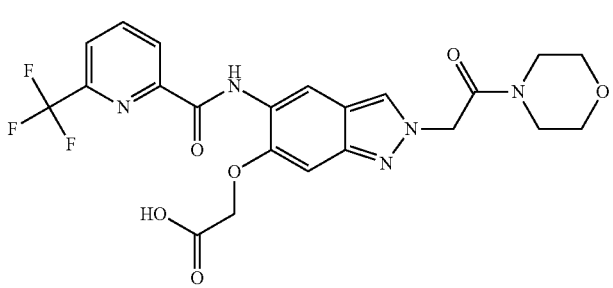<br>({2-[2-(morpholin-4-yl)-2-oxoethyl]-5-({[6-(trifluoromethyl)pyridin-2-yl]carbonyl}amino)-2H-indazol-6-yl}oxy)acetic acid | bromoacetic acid | 3c (9%) | (300 MHz, DMSO-d6): δ = 3.47 (d, 2 H), 3.52-3.71 (m, 6 H), 4.90 (s, 2 H), 5.41 (s, 2 H), 7.12 (s, 1 H), 8.16-8.29 (m, 2 H), 8.40 (t, 1 H), 8.48 (d, 1 H), 8.77 (s, 1 H), 10.58 (s, 1 H), 13.20 (br. s., 1 H).<br>UPLC-MS (Method A2): Rt = 0.61 min<br>MS (ESIpos): m/z = 508 (M + H)+ |
| 296 | 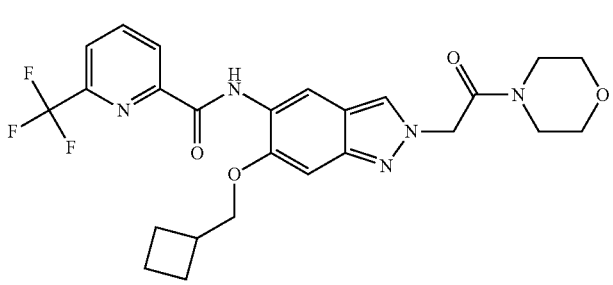<br>N-{6-(cyclobutylmethoxy)-2-[2-(morpholin-4-yl)-2-oxoethyl]-2H-indazol-5-yl}-6-(trifluoromethyl)pyridine-2-carboxamide | (bromomethyl) cyclobutane | 3a (59%) | (300 MHz, DMSO-d6): δ = 1.82-2.04 (m, 4 H), 2.09-2.24 (m, 2 H), 2.78-2.95 (m, 1 H), 3.47 (d, 2 H), 3.52-3.73 (m, 6 H), 4.15 (d, 2 H), 5.40 (s, 2 H), 7.10 (s, 1 H), 8.16-8.28 (m, 2 H), 8.40 (t, 1 H), 8.48 (d, 1 H), 8.76 (s, 1 H), 10.52 (s, 1 H).<br>UPLC-MS (Method A1): Rt = 1.32 min<br>MS (ESIpos): m/z = 518 (M + H)+ |
| 297 | 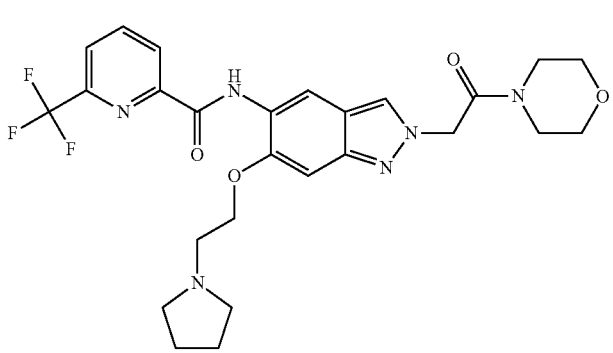<br>N-{2-[2-(morpholin-4-yl)-2-oxoethyl]-6-[2-(pyrrolidin-1-yl)ethoxy]-2H-indazol-5-yl}-6-(trifluoromethyl)pyridine-2-carboxamide | 1-(2-chloroethyl) pyrrolidine hydrochloride | 3a (54%) | (400 MHz, DMSO-d6): δ = 1.65 (dt, 4 H), 2.57 (br. s., 4 H), 2.97 (t, 2 H), 3.42-3.50 (m, 2 H), 3.54-3.61 (m, 4 H), 3.61-3.68 (m, 2 H), 4.28 (t, 2 H), 5.39 (s, 2 H), 7.13 (s, 1 H), 8.19-8.25 (m, 2 H), 8.41 (t, 1 H), 8.48 (d, 1 H), 8.75 (s, 1 H), 10.58 (s, 1 H).<br>UPLC-MS (Method A1): Rt = 0.77 min<br>MS (ESIpos): m/z = 547 (M + H)+ |

TABLE 20-continued

Examples 304-328
The exemplary compounds were prepared from N-{6-hydroxy-2-[2-(morpholin-4-yl)-2-oxoethyl]-
2H-indazol-5-yl}-6-(trifluoromethyl)pyridine-2-carboxamide and the halides listed in the table
according to General Procedures 3a, 3b or 3c.

| Ex. No. | Structure/Name | Prepared by reaction with | *see key | $^1$H-NMR/LC-MS |
|---|---|---|---|---|
| 298 | N-{6-[2-(morpholin-4-yl)ethoxy]-2-[2-(morpholin-4-yl)-2-oxoethyl]-2H-indazol-5-yl}-6-(trifluoromethyl)pyridine-2-carboxamide | 4-(2-chloroethyl)morpholine hydrochloride | 3a (64%) | (400 MHz, DMSO-d6, selected signals): δ = 2.84-2.93 (m, 2 H), 3.43-3.51 (m, 2 H), 3.51-3.62 (m, 8 H), 3.62-3.69 (m, 2 H), 4.31 (t, 2 H), 5.40 (s, 2 H), 7.16 (s, 1 H), 8.18-8.26 (m, 2 H), 8.41 (t, 1 H), 8.48 (d, 1 H), 8.74 (s, 1 H), 10.57 (s, 1 H). UPLC-MS (Method A1): Rt = 0.75 min MS (ESIpos): m/z = 563 (M + H)+ |
| 299 | N-{2-[2-(morpholin-4-yl)-2-oxoethyl]-6-[2-(piperidin-1-yl)ethoxy]-2H-indazol-5-yl}-6-(trifluoromethyl)pyridine-2-carboxamide | 1-(2-chloroethyl)piperidine hydrochloride | 3a (72%) | (300 MHz, DMSO-d6, selected signals): δ = 1.29-1.40 (m, 2 H), 1.40-1.53 (m, 4 H), 2.73 (s, 1 H), 2.84 (t, 2 H), 3.42-3.51 (m, 2 H), 3.58 (br. s., 4 H), 3.62-3.68 (m, 2 H), 4.27 (t, 2 H), 5.40 (s, 2 H), 7.14 (s, 1 H), 8.19-8.25 (m, 2 H), 8.41 (t, 1 H), 8.48 (d, 1 H), 8.74 (s, 1 H), 10.58 (s, 1 H). UPLC-MS (Method A1): Rt = 0.83 min MS (ESIpos): m/z = 561 (M + H)+ |
| 300 | N-{6-(3-hydroxypropoxy)-2-[2-(morpholin-4-yl)-2-oxoethyl]-2H-indazol-5-yl}-6-(trifluoromethyl)pyridine-2-carboxamide | (3-bromopropoxy)(tert-butyl)dimethylsilane | 3a (72%)[/] (49%) | (300 MHz, DMSOd6): δ = 1.93-2.08 (m, 2 H), 3.43-3.52 (m, 2 H), 3.52-3.77 (m, 8 H), 4.24 (t, 2 H), 4.59 (t, 1 H), 5.40 (s, 2 H), 7.10 (s, 1 H), 8.17-8.25 (m, 2 H), 8.36-8.44 (m, 1 H), 8.45-8.50 (m, 1 H), 8.75 (s, 1 H), 10.64 (s, 1 H). UPLC-MS (Method A1): Rt = 0.97 min MS (ESIpos): m/z = 508 (M + H)+ |

TABLE 20-continued

Examples 304-328

The exemplary compounds were prepared from N-{6-hydroxy-2-[2-(morpholin-4-yl)-2-oxoethyl]-2H-indazol-5-yl}-6-(trifluoromethyl)pyridine-2-carboxamide and the halides listed in the table according to General Procedures 3a, 3b or 3c.

| Ex. No. | Structure/Name | Prepared by reaction with | *see key | ¹H-NMR/LC-MS |
|---|---|---|---|---|
| 301 | 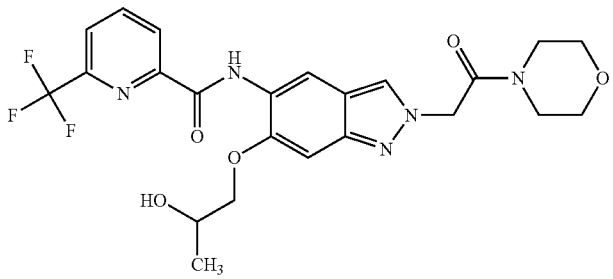<br>N-{6-(2-hydroxypropoxy)-2-[2-(morpholin-4-yl)-2-oxoethyl]-2H-indazol-5-yl}-6-(trifluoromethyl)pyridine-2-carboxamide | [(1-bromopropan-2-yl)oxy](tert-butyl)dimethylsilane | 3a (66%)[*f*] (46%) | (300 MHz, DMSO-d6): δ = 1.32 (d, 3 H), 3.42-3.51 (m, 2 H), 3.51-3.61 (m, 4 H), 3.61-3.69 (m, 2 H), 3.86-3.95 (m, 1 H), 4.05-4.16 (m, 2 H), 4.96 (d, 1 H), 5.40 (s, 2 H), 7.09 (s, 1 H), 8.18-8.25 (m, 2 H), 8.35-8.44 (m, 1 H), 8.44-8.52 (m, 1 H), 8.76 (s, 1 H), 10.54 (s, 1 H). UPLC-MS (Method A2): Rt = 0.98 min MS (ESIpos): m/z = 508 (M + H)+ |
| 302 | 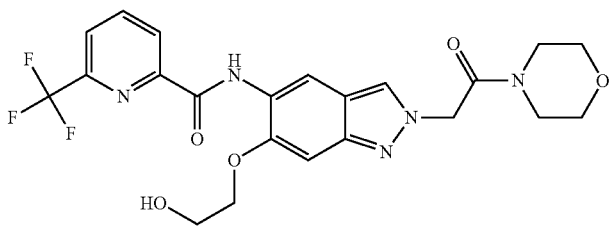<br>N-{6-(2-hydroxyethoxy)-2-[2-(morpholin-4-yl)-2-oxoethyl]-2H-indazol-5-yl}-6-(trifluoromethyl)pyridine-2-carboxamide | tert-Butyl(2-iodoethoxy)dimethylsilane | 3a (52%)[*f*] (77%) | (300 MHz, DMSO-d6): δ = 3.42-3.51 (m, 2 H), 3.58 (br. s., 4 H), 3.62-3.68 (m, 2 H), 3.89 (q, 2 H), 4.20 (t, 2 H), 4.89 (t, 1 H), 5.40 (s, 2 H), 7.12 (s, 1 H), 8.21 (dd, 1 H), 8.24 (s, 1 H), 8.35-8.44 (m, 1 H), 8.44-8.49 (m, 1 H), 8.73 (s, 1 H), 10.66 (s, 1 H). LC-MS (Method A3): Rt = 0.84 min MS (ESIpos): m/z = 494 (M + H)+ |
| 303 | 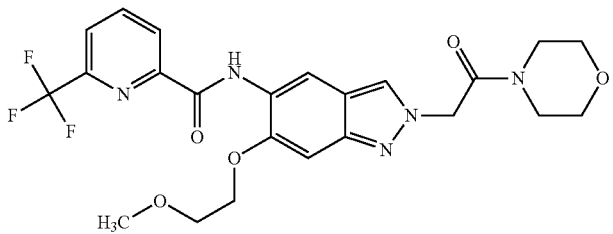<br>N-{6-(2-methoxyethoxy)-2-[2-(morpholin-4-yl)-2-oxoethyl]-2H-indaozl-5-yl}-6-(trifluoromethyl)pyridine-2-carboxamide | 1-bromo-2-methoxyethane | 3b[*h*] (27%) | (300 MHz, DMSO-d6): δ = 3.36 (s, 3 H), 3.42-3.51 (m, 2 H), 3.54-3.62 (m, 4 H), 3.62-3.69 (m, 2 H), 3.82 (dd, 2 H), 4.30 (dd, 2 H), 5.40 (s, 2 H), 7.13 (s, 1 H), 8.20-8.25 (m, 2 H), 8.37-8.44 (m, 1 H), 8.45-8.50 (m, 1 H), 8.77 (s, 1 H), 10.58 (s, 1 H). LC-MS (Method A3): Rt = 1.01 min MS (ESIpos): m/z = 508 (M + H)+ |

TABLE 20-continued

Examples 304-328
The exemplary compounds were prepared from N-{6-hydroxy-2-[2-(morpholin-4-yl)-2-oxoethyl]-
2H-indazol-5-yl}-6-(trifluoromethyl)pyridine-2-carboxamide and the halides listed in the table
according to General Procedures 3a, 3b or 3c.

| Ex. No. | Structure/Name | Prepared by reaction with | *see key | 1H-NMR/LC-MS |
|---|---|---|---|---|
| 304 | 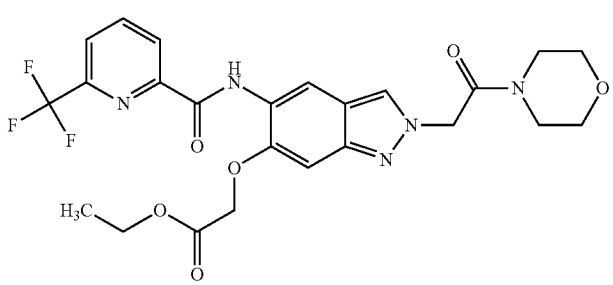 ethyl ({2-[2-(morpholin-4-yl)-2-oxoethyl]-5-({[6-(trifluoromethyl)pyridin-2-yl]carbonyl}amino)-2H-indazol-6-yl}oxy)acetate | ethyl bromoacetate | 3b[h] (59%) | (300 MHz, DMSO-d6): δ = 1.21 (t, 3 H), 3.42-3.50 (m, 2 H), 3.52-3.62 (m, 4 H), 3.63-3.68 (m, 2 H), 4.20 (q, 2 H), 5.02 (s, 2 H), 5.41 (s, 2 H), 8.22 (dd, 1 H), 8.26 (s, 1 H), 8.36-8.45 (m, 1 H), 8.46-8.51 (m, 1 H), 8.76 (s, 1 H), 10.56 (s, 1 H). LC-MS (Method A3): Rt = 1.05 min MS (ESIpos): m/z = 536 (M + H)+ |
| 305 | 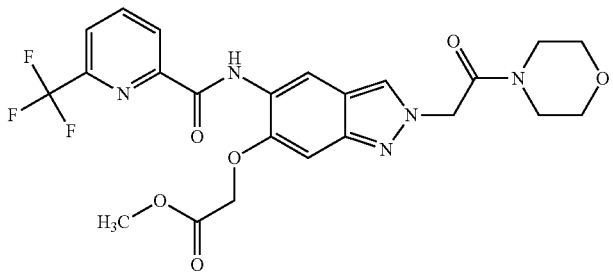 methyl 4-({2-[2-(morpholin-4-yl)-2-oxoethyl]-5-({[6-(trifluoromethyl)pyridin-2-yl]carbonyl}amino)-2H-indazol-6-yl}oxy)butanoate | methyl 4-bromo-butanoate | 3b[h] (46%) | (300 MHz, DMSO-d6): δ = 2.07-2.23 (m, 2 H), 2.62 (t, 2 H), 3.40-3.51 (m, 2 H), 3.59 (s, 3 H), 3.53-3.63 (m, 4 H), 3.65 (br. s., 2 H), 4.19 (t, 2 H), 5.40 (s, 2 H), 7.08 (s, 1 H), 8.21 (dd, 1 H), 8.23 (s, 1 H), 8.34-8.52 (m, 1 H), 8.40 (t, 1 H), 8.74 (s, 1 H), 10.58 (s, 1 H). LC-MS (Method A3: Rt = 1.05 min MS (ESIpos): m/z = 550 (M + H)+ |
| 306 | 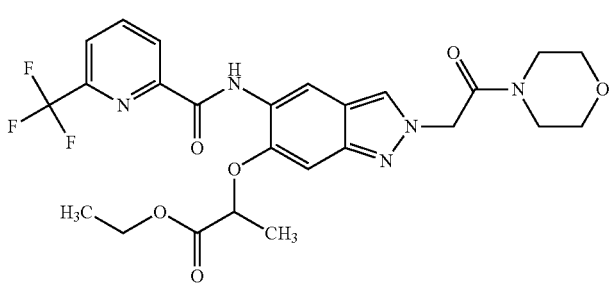 ethyl 2-({2-[2-(morpholin-4-yl)-2-oxoethyl]-5-({[6-(trifluoromethyl)pyridin-2-yl]carbonyl}amino)-2H-indazol-6-yl}oxy)propanoate | ethyl 2-bromo-propanoate | 3b[h] (46%) | (300 MHz, DMSO-d6): δ = 1.13 (t, 3 H), 1.68 (d, 3 H), 3.43-3.52 (m, 2 H), 3.53-3.62 (m, 4 H), 3.62-3.69 (m, 2 H), 4.13 (q, 2 H), 5.28 (q, 1 H), 5.40 (s, 2 H), 7.07 (s, 1 H), 8.22 (dd, 1 H), 8.26 (s, 1 H), 8.38-8.44 (m, 1 H), 8.46-8.51 (m, 1 H), 8.75 (s, 1 H), 10.81 (s, 1 H). LC-MS (Method A3): Rt = 1.12 min MS (ESIpos): m/z = 550 (M + H)+ |

TABLE 20-continued

Examples 304-328
The exemplary compounds were prepared from N-{6-hydroxy-2-[2-(morpholin-4-yl)-2-oxoethyl]-2H-indazol-5-yl}-6-(trifluoromethyl)pyridine-2-carboxamide and the halides listed in the table according to General Procedures 3a, 3b or 3c.

| Ex. No. | Structure/Name | Prepared by reaction with | *see key | ¹H-NMR/LC-MS |
|---|---|---|---|---|
| 307 | 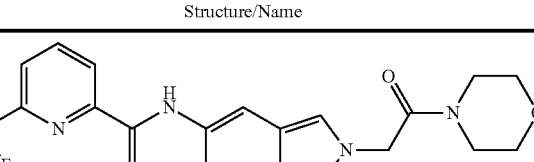  ethyl 3-methyl-2-({2-[2-(morpholin-4-yl)-2-oxoethyl]-5-({[6-(trifluoromethyl)pyridin-2-yl]carbonyl}amino)-2H-indazol-6-yl}oxy)butanoate | ethyl 2-bromopropanoate | 3b[h] (51%) | (300 MHz, DMSO-d6): δ = 1.09-1.18 (m, 9 H), 2.38 (d, 1 H), 3.43-3.49 (m, 2 H), 3.53-3.62 (m, 4 H), 3.62-3.67 (m, 2 H), 4.16 (q, 2 H), 4.99 (d, 1 H), 5.40 (s, 2 H), 6.99 (s, 1 H), 8.22 (dd, 1 H), 8.26 (s, 1 H), 8.42 (t, 1 H), 8.50-8.54 (m, 1 H), 8.82 (s, 1 H), 10.53-10.56 (m, 1 H). LC-MS (Method A3): Rt = 1.24 min MS (ESIpos): m/z = 578 (M + H)+ |

*Prepared according to the stated procedure, the yield in % is indicated in brackets
[a]After 60 minutens, another 1 equivalent of the halide was added and the mixture was stirred in the microwave at 120° C. for a further 60 minutes.
[b]The crude product was purified by preparative HPLC.
[c]The crude product was purified by preparative HPLC according to Method P5 (gradient: 0-15 min 30-70% B).
[d]The reaction mixture was added to water, the precipitate was filtered off with suction and washed with diethyl ether. The crude product was purified by preparative HPLC according to Method P5 (gradient: 0-15 min 15-55% B).
[e]The crude product was purified by preparative HPLC according to Method P5 (gradient: 0-15 min 15-55% B).
[f] The following procedure was used for deprotecting the alkylated intermediate (the 2nd yield in % indicated in the table refers to the deprotection). 1 equivalent of the silyl-protected intermediate was dissolved in tetrahydrofuran, 3 equivalents of a 1 M solution of tetrabutylammonium fluoride in tetrahydrofuran were added and the mixture was stirred at 25° C. for 24 h. Water was added to the reaction mixture and the resulting precipitate was filtered off with suction, washed with water and dried in a drying cabinet at 50° C. under reduced pressure.
[g]Another 0.1 equivalent of potassium iodide was added to the reaction mixture.
[h]The crude product was purified by preparative HPLC (column: XBridge C18 5 μm 100 × 30 mm).

Example 308

2-({2-[2-(Morpholin-4-yl)-2-oxoethyl]-5-({[6-(trifluoromethyl)pyridin-2-yl]carbonyl}amino)-2H-indazol-6-yl}oxy)propanoic acid

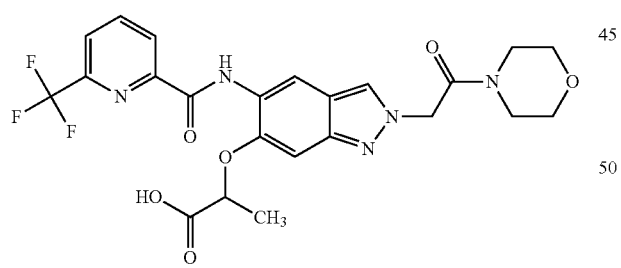

Analogously to Intermediate 4-1, 50 mg (0.09 mmol) of ethyl 2-({2-[2-(morpholin-4-yl)-2-oxoethyl]-5-({[6-(trifluoromethyl)pyridin-2-yl]carbonyl}amino)-2H-indazol-6-yl}oxy)propanoate (Example 306) were dissolved in 0.5 ml of tetrahydrofuran, a solution of 11 mg (0.45 mmol) of lithium hydroxide monohydrate in 164 μl of water was added and the mixture was stirred at 25° C. for 24 h. The reaction mixture was filtered, dimethyl sulphoxide was added and the product was purified by preparative HPLC (column: XBridge C18 5 μm 100×30 mm) This gave 7 mg (15% of theory) of the title compound.
UPLC-MS (Method A2): Rt=0.67 min
MS (ESIpos): m/z=522 (M+H)+
¹H NMR (400 MHz, DMSO-d6): δ=1.64 (d, 3H), 3.46 (br. s., 2H), 3.58 (br. s., 4H), 3.64 (d, 2H), 4.99 (d, 1H), 5.38 (s, 2H), 6.97 (s, 1H), 8.15-8.25 (m, 2H), 8.35-8.45 (m, 1H), 8.45-8.51 (m, 1H), 8.73 (s, 1H), 10.82 (s, 1H).

Example 309

N-{6-(2-Hydroxypropan-2-yl)-2-[2-(morpholin-4-yl)-2-oxoethyl]-2H-indazol-5-yl}-6-(trifluoromethyl)pyridine-2-carboxamide 536 mg (4 equiv.) of 2-bromo-1-(morpholin-4-yl)ethanone were added to a mixture of 250 mg (0.69 mmol) of N-[6-(2-hydroxypropan-2-yl)-1H-indazol-5-yl]-6-(trifluoromethyl)pyridine-2-carboxamide (Intermediate 14-11) and 0.59 ml of N,N-dicyclohexylmethylamine in 1.5 ml of THF, and the mixture was stirred at 70° C. overnight. Water was added, the mixture was extracted with ethyl acetate and the extract was washed with saturated aqueous sodium chloride solution, filtered through a hydrophobic filter and concentrated. The residue was purified by column chromatography on silica gel (dichloromethane/methanol). This gave 46 mg (14% of theory) of the title compound.

$^1$H-NMR (400 MHz, DMSO-$d_6$): δ [ppm]=1.62 (s, 6H), 3.46 (d, 3H), 3.42-3.69 (m), 5.45 (s, 2H), 5.95 (s, 1H), 7.54 (s, 1H), 8.15 (dd, 1H), 8.25 (s, 1H), 8.36 (t, 1H), 8.45 (d, 1H), 8.73 (s, 1H), 12.35 (s, 1H).

UPLC-MS (Method A2): Rt=0.99 min (UV-TIC), mass found 491.00.

Example 310

N-{6-Chloro-2-[2-(4-methylpiperazin-1-yl)-2-oxo-ethyl]-2H-indazol-5-yl}-6-(difluoromethyl)pyridine-2-carboxamide

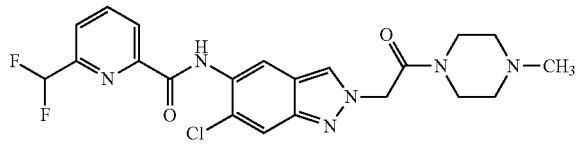 [SMILES: CN1CCN(C(=O)Cn2cc3cc(NC(=O)c4cccc(C(F)F)n4)c(Cl)cc3n2)CC1]

98 mg (0.32 mmol) of 2-(5-amino-6-chloro-2H-indazol-2-yl)-1-(4-methylpiperazin-1-yl)ethanone (Intermediate 6-21) and 82 mg of 6-(difluoromethyl)pyridine-2-carboxylic acid were initially charged in 3.0 ml of THF, 49 mg of 1-hydroxy-1H-benzotriazole hydrate, 121 mg of 1-(3-dimethylaminopropyl)-3-ethylcarbodiimide hydrochloride and 0.13 ml of triethylamine were added and the mixture was stirred at room temperature for 19.5 h. The mixture was diluted with water and the precipitated solid was filtered off, washed twice with water and three times with diethyl ether and dried under reduced pressure. This gave 129 mg of the title compound.

$^1$H-NMR (300 MHz, DMSO-$d_6$): δ [ppm]=2.21 (s, 3H), 2.25-2.42 (m, 4H), 3.42-3.59 (m, 4H), 5.50 (s, 2H), 7.14 (t, 1H), 7.91 (s, 1H), 8.02 (dd, 1H), 8.29-8.44 (m, 3H), 8.64 (s, 1H), 10.60 (s, 1H).

UPLC-MS (Method A2): Rt=1.06 min (UV-TIC), mass found 462.00.

Example 311

N-{6-Chloro-2-[2-(morpholin-4-yl)-2-oxoethyl]-2H-indazol-5-yl}-6-(difluoromethyl)pyridine-2-carboxamide

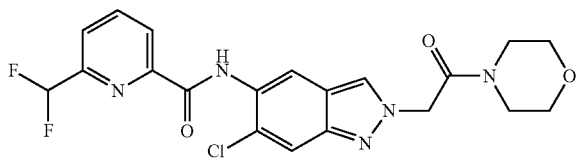 [SMILES: O=C(Nc1cc2cn(CC(=O)N3CCOCC3)nc2cc1Cl)c1cccc(C(F)F)n1]

Analogously to the preparation of Example 310, 137 mg of 2-(5-amino-6-chloro-2H-indazol-2-yl)-1-(morpholin-4-yl)ethanone (Intermediate 6-22) were reacted with 70 mg of 6-(difluoromethyl)pyridine-2-carboxylic acid at room temperature for 68 h. Water was added and the solid was filtered off with suction, washed with acetone, water and diethyl ether and dried under reduced pressure. This gave 91 mg of the title compound.

UPLC-MS (Method A1): Rt=1.06 min (UV-TIC), mass found 449.00.

$^1$H-NMR (400 MHz, DMSO-$d_6$): δ [ppm]=3.42-3.68 (m, 8H), 5.50 (s, 2H), 7.90 (s, 1H), 8.01 (dd, 1H), 8.29-8.36 (m, 2H), 8.41 (d, 1H), 8.64 (s, 1H), 10.59 (s, 1H).

Assessment of Physiological Efficacy

The in-vitro activity of the compounds according to the invention can be shown in the following assays:

Irak4 Kinase Assay

The Irak4-inhibitory activity of the substances according to the invention of the present invention was measured in the Irak4 TR-FRET assay (TR-FRET=Time Resolved Fluorescence Resonance Energy Transfer) described in the paragraphs that follow.

Recombinant fusion protein from N-terminal GST (glutathione S-transferase) and human Irak4, expressed in baculovirus-infected insect cells (Hi5, BTI-TN-5B1-4, cell line purchased from Invitrogen, catalogue No. B855-02) and purified via affinity chromatography, was used as enzyme. The substrate used for the kinase reaction was the biotinylated peptide biotin-Ahx-KKARFSRFAGSSPSQAS-FAEPG (C-terminus in amide form) which can be purchased, for example, from Biosyntan GmbH (Berlin-Buch).

For the assay, 11 different concentrations in the range from 20 μM to 0.073 nM were prepared from a 2 mM solution of the test substance in DMSO. For the assay, 50 nl of the respective solution were pipetted into a black low-volume 384-well microtitre plate (Greiner Bio-One, Frickenhausen, Germany), 2 μl of a solution of Irak4 in assay buffer [50 mM HEPES pH 7.5, 5 mM MgCl2, 1.0 mM dithiothreitol, 30 μM activated sodium orthovanadate, 0.1% (w/v) of bovine gamma-globulin (BGG) 0.04% (v/v) nonidet-P40 (Sigma)] were added and the mixture was incubated for 15 min to allow prebinding of the substances to the enzyme prior to the kinase reaction. The kinase reaction was then started by addition of 3 μl of a solution of adenosine triphosphate (ATP, 1.67 mM=final concentration in 5 μl of assay volume: 1 μM) and peptide substrate (0.83 μM=final concentration in 5 μl assay volume: 0.5 μM) in assay buffer, and the resulting mixture was incubated at 22° C. for the reaction time of 45 min. The concentration of the Irak4 was adjusted to the respective activity of the enzyme and set such that the assay was carried out in the linear range. Typical concentrations were in the order of about 0.2 nM. The reaction was stopped by addition of 5 μl of a solution of TR-FRET detection reagents [0.1 μM streptavidin-XL665 (Cisbio Bioassays; France, catalogue No. 610SAXLG) and 1.5 nM anti-phosphoserin antibody [Merck Millipore, "STK Antibody", catalogue No. 35-002] and 0.6 nM LANCE EU-W1024-labelled anti-mouse-IgG antibody (Perkin-Elmer, product No. AD0077, alternatively it is possible to use a terbium cryptate-labelled anti-mouse-IgG antibody from Cisbio Bioassays) in aqueous EDTA solution (100 mM EDTA, 0.4% [w/v] bovine serum albumin [BSA] in 25 mM HEPES pH 7.5).

The resulting mixture was incubated at 22° C. for 1 h to allow formation of a complex of the biotinylated phosphorylated substrate and the detection reagents. The amount of the phosphorylated substrate was then evaluated by measuring the resonance energy transfer from europium chelate-labelled anti-mouse-IgG antibody to streptavidin-XL665. To this end, the fluorescence emissions at 620 nm and 665 nm were measured after excitation at 350 nm in a TR-FRET measuring instrument, for example a Rubystar (BMG Labtechnologies, Offenburg, Germany) or a Viewlux (Perkin-Elmer). The ratio of the emissions at 665 nm and 622 nm was taken as a measure of the amount of phosphorylated substrate. The data were normalized (enzyme reaction without test substance=0% inhibition; all other assay components but no enzyme=100% inhibition). Typically, the test substances were tested on the same microtitre plate at 11 different concentrations in the range from 20 µM to 0.073 nM (20 µM, 5.7 µM, 1.6 µM, 0.47 µM, 0.13 µM, 38 nM, 11 nM, 3.1 nM, 0.89 nM, 0.25 nM and 0.073 nM). The dilution series were prepared prior to the assay (2 mM to 7.3 nM in 100% DMSO) by serial dilutions. The IC50 values were calculated using a 4-parameter fit.

TABLE 21

IC$_{50}$ values of the exemplary compounds in the IRAK4 kinase assay

| Example | IC$_{50}$ [nM] |
|---|---|
| 1 | 111 |
| 2 | 253 |
| 3 | 4012 |
| 4 | 237 |
| 5 | 662 |
| 6 | 26 |
| 7 | 29 |
| 8 | 32 |
| 9 | 90 |
| 10 | 40 |
| 11 | 7 |
| 12 | 38 |
| 13 | 62 |
| 14 | 1913 |
| 15 | 172 |
| 16 | 134 |
| 17 | 83 |
| 18 | 2611 |
| 19 | 33 |
| 20 | 126 |
| 21 | 536 |
| 22 | 158 |
| 23 | 628 |
| 24 | 521 |
| 25 | 532 |
| 26 | 1615 |
| 27 | 177 |
| 28 | 83 |
| 29 | 273 |
| 30 | 961 |
| 31 | 1271 |
| 32 | 501 |
| 33 | 25 |
| 34 | 11 |
| 35 | 56 |
| 36 | 18 |
| 37 | 88 |
| 38 | 104 |
| 39 | 237 |
| 40 | 827 |
| 41 | 107 |
| 42 | 151 |
| 43 | 67 |
| 44 | 190 |
| 45 | 160 |
| 46 | 3 |
| 47 | 2 |
| 48 | 4 |
| 49 | 10 |
| 50 | 19 |
| 51 | 30 |
| 52 | 17 |
| 53 | 20 |
| 54 | 51 |
| 55 | 72 |
| 56 | 77 |
| 57 | 28 |
| 58 | 63 |
| 59 | 75 |
| 60 | 207 |
| 61 | 649 |
| 62 | 165 |
| 63 | 62 |
| 64 | 33 |
| 65 | 12 |
| 66 | 2 |
| 67 | 4 |
| 68 | 5 |
| 69 | 6 |
| 70 | 21 |
| 71 | 14 |
| 72 | 1043 |
| 73 | 731 |
| 74 | 175 |
| 75 | 56 |
| 76 | 630 |
| 77 | 189 |
| 78 | 6919 |
| 79 | 78 |
| 80 | 206 |
| 81 | 652 |
| 82 | 38 |
| 83 | 929 |
| 84 | 616 |
| 85 | 732 |
| 86 | 95 |
| 87 | 196 |
| 88 | 566 |
| 89 | 274 |
| 90 | 45 |
| 91 | 312 |
| 92 | 667 |
| 93 | 498 |
| 95 | 638 |
| 96 | 425 |
| 97 | 224 |
| 98 | 281 |
| 99 | 170 |
| 100 | 772 |
| 101 | 638 |
| 102 | 242 |
| 103 | 37 |
| 104 | 830 |
| 105 | 475 |
| 106 | 979 |
| 107 | 190 |
| 108 | 101 |
| 109 | 16 |
| 110 | 93 |
| 111 | 27 |
| 112 | 92 |
| 113 | 20 |
| 114 | 537 |
| 115 | 817 |
| 116 | 270 |
| 117 | 47 |
| 118 | 528 |
| 119 | 31 |
| 120 | 814 |
| 121 | 127 |
| 122 | 189 |
| 123 | 850 |
| 124 | 547 |
| 125 | 442 |
| 126 | 821 |
| 127 | 348 |
| 128 | 568 |
| 129 | 434 |
| 130 | 661 |
| 131 | 810 |

TABLE 21-continued

IC$_{50}$ values of the exemplary compounds in the IRAK4 kinase assay

| Example | IC$_{50}$ [nM] |
|---|---|
| 132 | 381 |
| 133 | 224 |
| 134 | 623 |
| 135 | 882 |
| 136 | 344 |
| 137 | 779 |
| 138 | 549 |
| 139 | 540 |
| 140 | 539 |
| 141 | 600 |
| 142 | 695 |
| 143 | 338 |
| 144 | 616 |
| 145 | 891 |
| 146 | 889 |
| 147 | 868 |
| 148 | 930 |
| 149 | 722 |
| 150 | 905 |
| 151 | 736 |
| 152 | 756 |
| 153 | 227 |
| 154 | 321 |
| 155 | 746 |
| 156 | 707 |
| 157 | 690 |
| 158 | 799 |
| 159 | 612 |
| 160 | 463 |
| 161 | 348 |
| 162 | 358 |
| 163 | 388 |
| 164 | 776 |
| 165 | 969 |
| 166 | 507 |
| 167 | 292 |
| 168 | 268 |
| 169 | 511 |
| 170 | 625 |
| 171 | 421 |
| 172 | 455 |
| 173 | 606 |
| 174 | 422 |
| 175 | 578 |
| 176 | 965 |
| 177 | 599 |
| 178 | 245 |
| 179 | 157 |
| 180 | 275 |
| 181 | 662 |
| 182 | 352 |
| 183 | 317 |
| 184 | 313 |
| 185 | 546 |
| 186 | 748 |
| 187 | 383 |
| 188 | 412 |
| 189 | 994 |
| 190 | 652 |
| 191 | 917 |
| 192 | 460 |
| 193 | 463 |
| 194 | 413 |
| 195 | 612 |
| 196 | 434 |
| 197 | 528 |
| 198 | 361 |
| 199 | 284 |
| 200 | 531 |
| 201 | 99 |
| 202 | 142 |
| 203 | 27 |
| 204 | 91 |
| 205 | 53 |
| 206 | 60 |
| 207 | 12 |
| 208 | 37 |
| 209 | 29 |
| 210 | 32 |
| 211 | 53 |
| 212 | 366 |
| 213 | 980 |
| 214 | 787 |
| 215 | 959 |
| 216 | 421 |
| 217 | 5 |
| 218 | 8 |
| 219 | 4 |
| 220 | 13 |
| 221 | 4 |
| 222 | 4 |
| 223 | 471 |
| 224 | 338 |
| 225 | 312 |
| 226 | 603 |
| 227 | 709 |
| 228 | 28 |
| 229 | 60 |
| 230 | 638 |
| 231 | 888 |
| 232 | 49 |
| 233 | 553 |
| 234 | 171 |
| 235 | 45 |
| 236 | 12 |
| 237 | 233 |
| 238 | 7 |
| 239 | 533 |
| 240 | 117 |
| 241 | 33 |
| 242 | 108 |
| 243 | 127 |
| 244 | 49 |
| 245 | 506 |
| 246 | 1672 |
| 247 | 742 |
| 248 | 20 |
| 249 | 135 |
| 250 | 278 |
| 251 | 222 |
| 252 | 285 |
| 253 | 24 |
| 254 | 18 |
| 255 | 8 |
| 256 | 52 |
| 257 | 51 |
| 258 | 195 |
| 259 | 55 |
| 260 | 32 |
| 261 | 16 |
| 262 | 113 |
| 263 | 314 |
| 264 | 10 |
| 265 | 44 |
| 266 | 355 |
| 267 | 29 |
| 268 | 74 |
| 269 | 97 |
| 270 | 49 |
| 271 | 35 |
| 272 | 9 |
| 273 | 158 |
| 274 | 29 |
| 275 | 87 |
| 276 | 29 |
| 277 | 20 |
| 278 | 42 |
| 279 | 7143 |

TABLE 21-continued

IC$_{50}$ values of the exemplary compounds in the IRAK4 kinase assay

| Example | IC$_{50}$ [nM] |
|---|---|
| 280 | 103 |
| 281 | 105 |
| 282 | 120 |
| 283 | 32 |
| 284 | 63 |
| 285 | 28 |
| 286 | 100 |
| 287 | 25 |
| 288 | 15 |
| 289 | 9 |
| 290 | 39 |
| 291 | 18 |
| 292 | 15 |
| 293 | 6 |
| 294 | 20 |
| 295 | 3370 |
| 296 | 8 |
| 297 | 381 |
| 298 | 53 |
| 299 | 722 |
| 300 | 4 |
| 301 | 15 |
| 302 | 16 |
| 303 | 48 |
| 304 | 20 |
| 305 | 41 |
| 306 | 197 |
| 307 | 1384 |
| 308 | 1753 |
| 309 | 25 |
| 310 | 28 |
| 311 | 31 |

TNF-α Secretion in THP-1 Cells

Using this test, it is possible to test substances for their ability to inhibit secretion of TNF-α (tumour necrosis factor alpha) in THP-1 cells (human monocytic acute leukaemia cell line). TNF-α is a cytokine involved in inflammatory processes. In this test, TNF-α secretion is triggered by incubation with bacterial lipopolysaccharide (LPS).

THP-1 cells are kept in continuous suspension cell culture [RPMI 1460 medium with L-Glutamax (Gibco, Cat No. 61870-044) supplemented with foetal calf serum (FCS) 10% (Invitrogen, Cat No. 10082-147), 1% penicillin/streptomycin (Gibco BRL, Cat No. 15140-114)] and should not exceed a cell concentration of 1×10$^6$ cells/ml.

The assay is carried out in cell culture medium (RPMI 1460 medium with L-Glutamax supplemented with FCS 10%).

In each case 2-2.5 µl of the cell suspension (corresponds to 4000 cells) per well were dispensed into a 384-well test plate (Greiner, Cat No. 784076) in which in each case 40-50 nl substance had been dissolved in 100% DMSO. Here, in each case 10 different concentrations in the range from 20 µM to 0.073 nM were used for each substance. The cells were incubated at room temperature for 15 min. 2-2.5 µl of 0.1 µg/ml LPS (Sigma, *Escherichia coli* 055:B5, Cat. No. L5418) dissolved in cell culture medium (final concentration 0.05 µg/ml) were then dispensed into each well. As a neutral control, cells were treated with 0.05 µg/ml LPS and 1% DMSO and, as inhibitor control, only once with 1% DMSO.

The plates are centrifuged at 80 g for 30 s and incubated at 37° C., 5% CO$_2$ and 95% atmospheric humidity for 17 h. The amount of TNF-α was determined using the TNF-alpha HTRF Detection Kit (Cisbio, Cat No. 62TNFPEB/C). To this end, in each case 2 µl of the detection solution consisting of anti-TNF-α-XL665 conjugate and anti-TNF-α-cryptate conjugate, dissolved in accordance with the instructions of the manufacturer in the reconstitution buffer, were added for the HTRF (Homogeneous Time-Resolved Fluorescence) test. After the addition, the mixture was incubated either at room temperature for 3 h or at 4° C. overnight. The signals were then read at 620/665 nm using an HTRF-enabled measuring instrument such as the BMG PheraStar.

The activity of the substances is expressed as the ratio between neutral and inhibitor control in percent. The IC$_{50}$ values were calculated using a 4-parameter fit.

TABLE 22

IC$_{50}$ values of the exemplary compounds with respect to the secretion of TNF-α in THP-1 cells

| Example | IC$_{50}$ [µM] |
|---|---|
| 1 | 0.63 |
| 2 | 1.97 |
| 3 | ≥20.0* |
| 4 | 4.72 |
| 5 | 11.53 |
| 6 | 0.34 |
| 7 | 0.46 |
| 8 | 0.6 |
| 9 | 0.56 |
| 10 | 1.3 |
| 11 | 1.27 |
| 12 | 2.0 |
| 13 | 0.76 |
| 14 | 18.24 |
| 15 | 19.47 |
| 16 | 10.4 |
| 17 | 1.55 |
| 18 | 2.9 |
| 19 | 4.36 |
| 20 | ≥20.0* |
| 21 | 4.71 |
| 22 | 1.12 |
| 23 | 5.56 |
| 24 | 6.53 |
| 25 | 12.14 |
| 26 | 13.9 |
| 27 | 7.31 |
| 28 | 18.43 |
| 29 | 18.56 |
| 30 | 19.19 |
| 31 | ≥20.0* |
| 32 | 13.52 |
| 33 | 1.02 |
| 34 | 0.31 |
| 35 | 0.47 |
| 36 | 0.19 |
| 37 | 0.74 |
| 38 | 1.87 |
| 39 | 8.47 |
| 40 | 6.33 |
| 41 | 1.13 |
| 42 | 2.09 |
| 43 | 0.52 |
| 44 | 1.1 |
| 45 | 0.84 |
| 46 | 0.83 |
| 47 | 0.39 |
| 48 | 0.59 |
| 49 | ≥20.0* |
| 50 | 0.86 |
| 51 | 0.45 |
| 52 | 2.12 |
| 53 | ≥20.0* |
| 54 | 0.48 |
| 55 | 0.49 |
| 56 | 0.82 |
| 57 | 3.53 |
| 58 | 2.72 |

TABLE 22-continued

IC$_{50}$ values of the exemplary compounds with respect to the secretion of TNF-α in THP-1 cells

| Example | IC$_{50}$ [μM] |
|---|---|
| 59 | 1.22 |
| 60 | 19.2 |
| 61 | ≥20.0* |
| 62 | ≥20.0* |
| 63 | 4.98 |
| 64 | 0.63 |
| 65 | 0.7 |
| 66 | 0.41 |
| 67 | 0.56 |
| 68 | 0.42 |
| 69 | 3.16 |
| 70 | 0.4 |
| 71 | 0.46 |
| 72 | ≥20.0* |
| 73 | 15.85 |
| 74 | 2.7 |
| 75 | 0.79 |
| 76 | 10.2 |
| 77 | 18.88 |
| 78 | 2.92 |
| 79 | 2.4 |
| 80 | 17.61 |
| 81 | 4.66 |
| 82 | 0.82 |
| 83 | ≥20.0* |
| 84 | 5.46 |
| 85 | ≥20.0* |
| 86 | 3.7 |
| 87 | 3.37 |
| 88 | 3.88 |
| 89 | 5.18 |
| 90 | 0.42 |
| 91 | 4.76 |
| 92 | 11.76 |
| 93 | 16.02 |
| 95 | 12.89 |
| 96 | 5.49 |
| 97 | 14.03 |
| 98 | ≥20.0* |
| 99 | 1.46 |
| 100 | 5.46 |
| 101 | 8.09 |
| 102 | 0.82 |
| 103 | 0.69 |
| 104 | 10.65 |
| 105 | — |
| 106 | 11.25 |
| 107 | ≥20.0* |
| 108 | 5.69 |
| 109 | 2.17 |
| 110 | 0.52 |
| 111 | 0.42 |
| 112 | 5.35 |
| 113 | 0.66 |
| 114 | ≥20.0* |
| 115 | ≥20.0* |
| 116 | 13.05 |
| 117 | 6.51 |
| 118 | 6.95 |
| 119 | 4.61 |
| 120 | 18.3 |
| 121 | 17.28 |
| 122 | 2.9 |
| 123 | 11.89 |
| 124 | 7.26 |
| 125 | 10.55 |
| 126 | 13.82 |
| 127 | 9.78 |
| 128 | 11.57 |
| 129 | 1.41 |
| 130 | 9.07 |
| 131 | ≥20.0* |
| 132 | 4.38 |
| 133 | 3.7 |
| 134 | 10.87 |
| 135 | 10.86 |
| 136 | 7.3 |
| 137 | ≥20.0* |
| 138 | 12.94 |
| 139 | 10.81 |
| 140 | 6.89 |
| 141 | ≥20.0* |
| 142 | ≥20.0* |
| 143 | 12.51 |
| 144 | ≥20.0* |
| 145 | 18.22 |
| 146 | 17.54 |
| 147 | 19.01 |
| 148 | ≥20.0* |
| 149 | 17.12 |
| 150 | 17.49 |
| 151 | 17.6 |
| 152 | 11.43 |
| 153 | 5.97 |
| 154 | 7.22 |
| 155 | 14.26 |
| 156 | 9.39 |
| 157 | 19.3 |
| 158 | 17.85 |
| 159 | 9.87 |
| 160 | 10.27 |
| 161 | 13.67 |
| 162 | ≥20.0* |
| 163 | 12.61 |
| 164 | 15.1 |
| 165 | 7.75 |
| 166 | 10.0 |
| 167 | 11.25 |
| 168 | >20.0* |
| 169 | 9.23 |
| 170 | 13.7 |
| 171 | 7.55 |
| 172 | 18.92 |
| 173 | 16.12 |
| 174 | 5.2 |
| 175 | 16.36 |
| 176 | 11.34 |
| 177 | 9.03 |
| 178 | 5.31 |
| 179 | 10.28 |
| 180 | 6.95 |
| 181 | 11.8 |
| 182 | 11.59 |
| 183 | 10.79 |
| 184 | 9.67 |
| 185 | ≥20.0* |
| 186 | 11.9 |
| 187 | 8.75 |
| 188 | 7.74 |
| 189 | 19.17 |
| 190 | 18.08 |
| 191 | ≥20.0* |
| 192 | 14.68 |
| 193 | 19.24 |
| 194 | 14.51 |
| 195 | ≥20.0* |
| 196 | 13.1 |
| 197 | ≥20.0* |
| 198 | 15.09 |
| 199 | ≥20.0* |
| 200 | ≥20.0* |
| 201 | 1.68 |
| 202 | 4.59 |
| 203 | 0.63 |
| 204 | 1.25 |
| 205 | 0.94 |

TABLE 22-continued

IC$_{50}$ values of the exemplary compounds with respect to the secretion of TNF-α in THP-1 cells

| Example | IC$_{50}$ [μM] |
|---|---|
| 206 | 0.75 |
| 207 | 4.58 |
| 208 | 0.55 |
| 209 | 1.47 |
| 210 | 3.57 |
| 211 | 12.02 |
| 212 | 15.22 |
| 213 | 18.81 |
| 214 | 17.19 |
| 215 | >20.0* |
| 216 | 8.51 |
| 217 | 0.33 |
| 218 | 0.24 |
| 219 | 0.13 |
| 220 | 0.33 |
| 221 | 0.26 |
| 222 | 0.22 |
| 223 | 15.34 |
| 224 | 12.25 |
| 225 | 2.36 |
| 226 | 4.96 |
| 227 | 19.82 |
| 228 | 2.45 |
| 229 | 1.18 |
| 230 | 13.82 |
| 231 | 16.34 |
| 232 | 1.22 |
| 233 | >20.0* |
| 234 | 14.66 |
| 235 | 3.36 |
| 236 | 0.7 |
| 237 | 19.1 |
| 238 | 1.16 |
| 239 | >20.0* |
| 240 | 2.87 |
| 241 | 0.64 |
| 242 | 0.57 |
| 243 | 6.89 |
| 244 | 0.88 |
| 245 | 14.66 |
| 246 | >20.0* |
| 247 | >20.0* |
| 248 | 1.27 |
| 249 | 1.06 |
| 250 | >20.0* |
| 251 | >20.0* |
| 252 | >20.0* |
| 253 | 0.67 |
| 254 | 0.31 |
| 255 | 0.34 |
| 256 | >20.0* |
| 257 | not determined |
| 258 | >20.0* |
| 259 | 1.58 |
| 260 | 0.89 |
| 261 | >20.0* |
| 262 | 2.18 |
| 263 | >20.0* |
| 264 | 0.27 |
| 265 | 0.74 |
| 266 | not determined |
| 267 | >20.0* |
| 268 | 2.13 |
| 269 | 0.90 |
| 270 | 0.45 |
| 271 | 0.86 |
| 272 | 0.55 |
| 273 | 3.99 |
| 274 | 0.68 |
| 275 | 3.50 |
| 276 | 0.53 |
| 277 | 0.41 |
| 278 | 0.91 |
| 279 | >20.0* |
| 280 | >20.0* |
| 281 | >20.0* |
| 282 | 0.23 |
| 283 | 1.09 |
| 284 | 0.97 |
| 285 | 0.61 |
| 286 | 0.99 |
| 287 | 0.60 |
| 288 | 0.46 |
| 289 | 0.73 |
| 290 | 9.63 |
| 291 | >20.0* |
| 292 | 0.82 |
| 293 | 0.53 |
| 294 | not determined |
| 295 | >20.0* |
| 296 | 0.32 |
| 297 | >20.0* |
| 298 | >20.0* |
| 299 | >20.0* |
| 300 | 0.21 |
| 301 | 0.44 |
| 302 | 0.46 |
| 303 | 0.41 |
| 304 | 5.00 |
| 305 | 7.04 |
| 306 | 2.84 |
| 307 | 19.47 |
| 308 | >20.0* |
| 309 | 0.45 |
| 310 | 0.27 |
| 311 | 0.20 |

*highest IC$_{50}$ value that can be determined owing to assay limitations

In Vitro LPS (Lipopolysaccharide)-Induced Cytokine Production in Human PBMCs (Peripheral Blood Mononuclear Cells)

The effect of the compounds according to the invention on the induced cytokine production in human PBMCs was examined. Here, cytokine production was induced by LPS, a TLR4 ligand, which leads to activation of the IRAK4-mediated signal path.

The human PBMCs were obtained from anti-coagulated human whole blood. To this end, 15 ml of Ficoll-Paque (Biochrom, Cat. No. L6115) were initially charged in Leucosep tubes and 20 ml of human blood were added. After centrifugation of the blood at 800 g for 15 min at room temperature, the plasma including the platelets was removed and discarded. The PBMCs were transferred into centrifugation tubes and made up with PBS (phosphate-buffered saline) (Gibco, Cat. No. 14190). The cell suspension was centrifuged at room temperature at 250 g for 10 min and the supernatant was discarded. The PBMCs were resuspended in complete medium (RPMI 1640, without L-glutamine (PAA, Cat. No. E15-039), 10% FCS; 50 U/ml penicillin, 50 μg/ml streptomycin (PAA, Cat. No. P11-010) and 1% L-glutamine (Sigma, Cat. No. G7513)).

The assay was also carried out in complete medium. The PBMCs were sown in 96-well plates at a cell density of 2.5×10$^5$ cells/well. The compounds according to the invention were subjected to serial dilution in a constant volume of 100% DMSO and employed in the assay at 8 different concentrations in the range from 10 μM to 3 nM such that the final DMSO concentration was 0.4% DMSO. Prior to the actual stimulation, the cells were then pre-incubated therewith for 30 min. To induce cytokine secretion, the cells were stimulated with 0.1 µg/ml LPS (Sigma, Cat. No. L4516) for 24 hours. Cell viability was determined using the CellTiter-Glo luminescent assay (Promega, Cat. No. G7571 (G755/G756A)) in accordance with the instructions of the manufacturer. The amount of secreted TNF-α in the cell culture supernatant was determined using the Human ProInflammatory 9-Plex Tissue Culture Kit (MSD, Cat. No. K15007B) in accordance with the instructions of the manufacturer. By way of example, the Exemplary Compound 1 having an activity between 1 and 10 µM and the Exemplary Compounds 47, 64 and 71 having an activity of 1 µM are mentioned.

In Vitro Tumour-Associated NF-kB Reporter Activity

The effect of the compounds according to the invention on the NF-kB signal pathway was examined in human DLBCL (diffuse large B cell lymphoma) cell lines. TMD-8, HBL-1, U2932, HT and WSU-DLCL2 cells were stably transduced with a lentivirus NF-kB reporter construct (Cignal Lenti NFκB Reporter (luc) kit: CLS-013L, Qiagen), thus generating TMD-8-NF-kB-luc, HBL-1-NF-kB-luc, U2932-NF-kB-luc, HT-NF-kB-luc and WSU-DLCL2-NF-kB-luc reporter cell lines. 10,000 cells were transferred into 30 µl/well in growth medium (RPMI (Biochrom, Cat. No. FG 1215), 20% FCS (Biochrom, Cat. No. S 0615)) or into RPMI 1640 medium supplemented with 10% FCS in a 384-well plate (Perkin Elmer, white) and incubated at 37° C. overnight. After 24 h, the cells were treated with test substances and incubated at 37° C. for 6 h and 24 h. The test substances were added to the cells in 7-fold dilution either alone or as combination of two test substances of different concentrations (ratios substance 1 and substance 2:1:0, 0.85:0.15; 0.7:0.3; 0.5:0.5; 0.3:0.7; 0.15:0.85; 0:1) using an HP D300 digital dispenser. As control, the cells were treated with vehicle (DMSO). After 6 h and 24 h, the cells were treated with 30 µl/well One-Glo solution (Promega, Cat. No. E6110) and incubated at room temperature for 10 min, and the luminescence was measured using a VICTOR V (Perkin Elmer) in order to determine the NF-KB reporter activity at the end of the treatment. The effect on the NF-KB reporter activity in percent and the $IC_{50}$ values derived therefrom were determined for each test substance. The $IC_{50}$ values were calculated using a 4-parameter fit.

By way of example, the Exemplary Compound 289 having an activity between 1 and 10 µM with the cell lines TMD-8-NF-kB-luc, HBL-1-NF-kB-luc, U2932-NF-kB-luc and WSU-DLCL2-NF-kB-luc is mentioned.

In Vitro Tumour-Associated Secretion of Interleukin-6 and Interleukin-10

The effect of the compounds according to the invention on the secretion interleukin-6 and interleukin-10 was examined in human TMD-8 DLBCL cells. 15000 cells/well were sown in 100 µl of fresh growth medium (RPMI (Biochrom, Cat. No. FG 1215), 20% FCS (Biochrom, Cat. No. S 0615)) in a 96-well plate (Perkin Elmer). The test substances were added to the cells in 7-fold dilution using an HP D300 digital dispenser and incubated for 24 h. After the incubation time had ended, the supernatants were collected and the interleukin concentration was determined using the Human IL-6/IL-10 Elisa Kit, (Life Technologies, Cat. No. KHC0062, KHC0101) in accordance with the instructions of the manufacturer. The effect on the interleukin secretion in percent was determined for each test substance.

By way of example, the Exemplary Compound 289 having an activity between 1 and 10 µM on the secretion of interleukin-6 and interleukin-10 is mentioned.

The suitability of the compounds according to the invention for the treatment of inflammatory disorders, tumour disorders and ophthalmological disorders such as wet AMD (age-related macular degeneration) can be shown in the following animal models:

In Vivo Model of TLR-Mediated Inflammation

The compounds according to the invention were examined in a model of in vivo TLR-mediated inflammation for their in vivo efficacy. This mechanistic model shows in particular the potential effect of the compounds according to the invention on TLR4-mediated disorders since an LPS-mediated inflammation model was used. Here, female Balb/c mice (about 8 weeks old; Charles River Laboratories, Germany) were divided into groups of 5 animals each. The control group was treated with the vehicle in which the substance had been dissolved (substance vehicle) and also with the vehicle in which the LPS had been dissolved. 0.2 mg of LPS/kg body weight (Sigma, Cat. No. L4391) (lipopolysaccharides from *E. coli* 0111:B4) was administered intraperitoneally (i.p.) to the groups treated with substance, and also to the positive control group. In addition, the positive control group was treated with the substance vehicle described above. The substance was administered orally 8 hours before induction of inflammation by administration of LPS. To examine the effect of the compounds according to the invention on the inflammation, a final blood sample was taken from the animals after 1.5 hours. The concentration of certain cytokines in the plasma was determined using the Mouse ProInflammatory 7-Plex Tissue Culture Kit (MSD, Cat. No. K15012B) in accordance with the instructions of the manufacturer. FIG. 1 shows the amount of TNF-α in the plasma, which is reduced in a dose-dependent manner by administration of Exemplary Compound 64 in comparison with the LPS-induced concentration.

In Vivo Model of IL-1β-Mediated Inflammation

Figure 2:
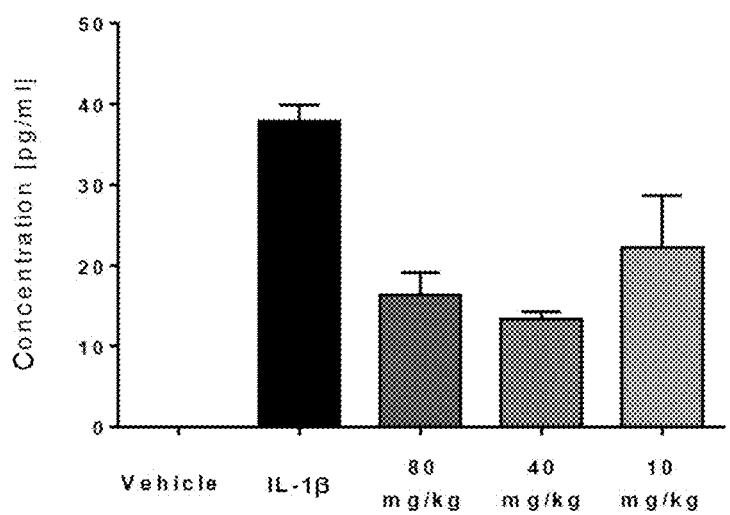
FIG. 2 Treatment of an IL-1β-induced inflammation with Exemplary Compound 64 leads to a reduced amount of secreted TNF-α.

To evaluate the potential efficacy of the compounds according to the invention in IL-1β-mediated disorders, IL-1β was administered i.p. to female Balb/c mice (about 8 weeks old, Charles River Laboratories, Germany) and the effect of the compounds according to the invention on IL-1β-mediated cytokine secretion was examined. In each case, the group size was 5 animals. The control group was treated with the vehicles used for dissolving the substance and the IL-1β. In each case 90 lag of IL-1β/kg body weight (R&D, Cat. No. 401-ML/CF) were administered i.p to the groups treated with substance and the positive control group. The substance or its vehicle in the positive control group were administered 4 hours before the administration of IL-1β. The determination of TNF-α in the plasma after the final removal of blood was carried out 2 hours after administration of the IL-1β using the Mouse ProInflammatory 7-Plex Tissue Culture Kit (MSD, Cat. No. K15012B) in accordance with the instructions of the manufacturer. Administration of IL-1β lead to an elevated TNF-α plasma concentration which was inhibited by treatment with Exemplary Compound 64. This is illustrated by FIG. 2.

Oxygen-Induced In Vivo Retinopathy (OIR) Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia. The ischaemic situation caused in this manner results in an abnormal neovascularization which has some similarities with pathophysiological neovascularization in eye disorders such as wet AMD (age-related macular degeneration). In addition, the neovascularization caused is highly reproducible, quantifiable and an important parameter for examining the disease mechanisms and possible treatments for various forms of retinal disorders. This is why this model is suitable for examining the effect of the compounds according to the invention on this pathological process.

To this end, young murine animals of an age of 7 days, for example young $C_{57}B1/6$ animals, are exposed to a hyperoxic environment (70% oxygen) for 5 days. From day 12 to day 17, the mice are kept under normoxic conditions Normoxic means room air with 21% oxygen. During this period, the animals are then assigned to groups treated with substance and vehicle group and treated according to the group. The animals are sacrificed on day 17, and the eyes are then removed and fixated in 4% formalin. After washing in phosphate-buffered saline, the retina is excised, a flat preparation thereof is produced and this is stained with isolectin B4 antibody (Tual-Chalot, Allinson, et al., J. Vis. Exp., 2013). Quantification of neovascularization is carried out using a Zeiss ApoTome.

In Vivo Model of Laser-Induced Choroidal Neovascularization

This study serves to investigate the efficacy of a test substance on reduction of extravasation/oedema formation and/or choroidal neovascularization in the rat model of laser-induced choroidal neovascularization. In the animal model, laser-mediated photocoagulation leads to destruction of Bruch's membrane with concomitant damage to the vessels and inflammation-associated neovascularization. Both processes correspond to the pathomechanism of macular degeneration (Grossniklaus, Kang, Berglin, Prog Retin Eye Res., 2010).

To determine the effect of the compounds according to the invention, Brown Norway Rats (Charles River Laboratories) are assigned to the appropriate groups (substance and vehicle) and anaesthetized, and 0.5% tropicamide is instilled into the eyes to dilate the pupils. After the animals have been anaesthetized (15 mg/kg xylazine and 80 mg/kg ketamine), choroidal neovascularization is triggered by burning six holes into the retina in each eye of each animal using a 532 nm argon laser (lesion size: 50 μm-75 μm; laser intensity: 150 mW; duration: 100 ms). The treatment of the animals with the substance according to the invention or the corresponding vehicle is carried out either from day 1 or from day 7 up to and including day 23. Angiography is carried out on day 21. To this end, the animals are in each case anaesthetised, the pupils are dilated and 10% sodium fluoroescein solution is injected subcutaneously. The angiogram is recorded at most 10 minutes after the injection and assessed by three blinded observers using a score system (0=no staining=no tissue injury, 1=slight staining=slight tissue injury, 2=moderate staining=moderate tissue injury, 3=maximum staining=maximum tissue injury). The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The volume or the area of choroidal neovascularization is calculated by morphometric analysis using Axiovision 4.6 software.

Working Examples of Pharmaceutical Compositions

The compounds according to the invention can be converted to pharmaceutical formulations as follows:
Tablet:
Composition:
100 mg of the compound of Example 64, 50 mg of lactose (monohydrate), 50 mg of maize starch (native), 10 mg of polyvinylpyrrolidone (PVP 25) (from BASF, Ludwigshafen, Germany) and 2 mg of magnesium stearate.
Tablet weight 212 mg. Diameter 8 mm, radius of curvature 12 mm.
Production:
The mixture of inventive compound, lactose and starch is granulated with a 5% solution (w/w) of the PVP in water. The granules are dried and then mixed with the magnesium stearate for 5 minutes. This mixture is compressed in a conventional tablet press (see above for format of the tablet). The guide value used for the pressing is a pressing force of 15 kN.
Solution for oral administration:
Composition
500 mg of the compound of Example 64, 2.5 g of polysorbate and 97 g of polyethylene glycol 400. 20 g of oral solution correspond to a single dose of 100 mg of the compound according to the invention.
Production
The compound according to the invention is suspended in the mixture of polyethylene glycol and polysorbate with stirring. The stirring operation is continued until dissolution of the compound according to the invention is complete.
Composition:
1 mg of the compound of Example 64, 15 g of polyethylene glycol 400 and 250 g of water for injection purposes.
Production:
The compound according to the invention, together with polyethylene glycol 400, is dissolved in the water by stirring. The solution is sterilized by filtration (pore diameter 0.22 μm) and dispensed under aseptic conditions into heat-sterilized infusion bottles. The latter are closed with infusion stoppers and crimped caps.

The invention claimed is:
1. A compound of the formula (I)

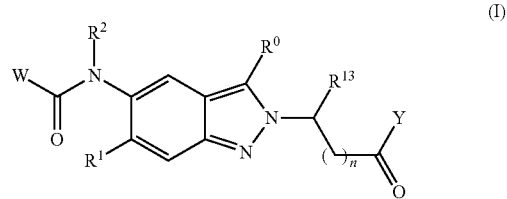

in which:
$R^0$ represents hydrogen or $C_1$-$C_4$-alkyl, where the $C_1$-$C_4$-alkyl radical may optionally be mono- or polysubstituted by identical or different radicals from the group consisting of hydroxy and halogen;
$R^1$ represents hydrogen, halogen, cyano, C(=O)OH, C(=O)OR$^a$, C(=O)NH$_2$, C(=O)N(H)R$^a$, C(=O)N(R$^a$)R$^b$, C(=O)R$^d$, hydroxy or $C_1$-$C_6$-alkyl, where the $C_1$-$C_6$-alkyl radical is optionally mono- or polysubstituted by identical or different radicals from the group consisting of hydroxy, halogen, cyano, C(=O)OH, C(=O)OR$^a$, S(=O)$_2$—C$_1$-C$_6$-alkyl, NH$_2$, NHR$^a$, N(R$^a$)R$^b$, C$_1$-C$_6$-alkoxy which is optionally mono- or polysubstituted by identical or different radicals from the group consisting of halogen, C$_3$-C$_8$-cycloalkoxy which is optionally mono- or polysubstituted by identical or different radicals from the group consisting of halogen, heterocycloalkyl which is optionally mono- or polysubstituted by identical or different radicals from the group consisting of R$^c$, or represents C$_1$-C$_6$-alkoxy, where the C$_1$-C$_6$-alkoxy radical may optionally be mono- or polysubstituted by identical or different radicals from the group consisting of hydroxy, halogen, cyano, C(=O)OH, C(=O)OR$^a$, S(=O)$_2$—C$_1$-C$_6$-alkyl, NH$_2$, NHR$^a$, N(R$^a$)R$^b$, C$_3$-C$_8$-cycloalkyl which is optionally mono- or polysubstituted by identical or different radicals from the group consisting of halogen, C$_1$-C$_6$-alkoxy which is optionally mono- or polysubstituted by identical or different radicals from the group consisting of halogen, C$_3$-C$_8$-cycloalkoxy which is optionally mono- or polysubstituted by identical or different radicals from the group consisting of halogen, heterocycloalkyl which is optionally mono- or polysubstituted by identical or different radicals from the group consisting of R$^c$, aryl which is optionally mono- or polysubstituted by identical or different radicals from the group consisting of R$^c$, or 5- or 6-membered heteroaryl which is optionally mono- or polysubstituted by identical or different radicals from the group consisting of R$^c$, or represents C$_3$-C$_8$-cycloalkoxy or heterocycloalkoxy which may optionally be mono- or polysubstituted by identical or different radicals from the group consisting of hydroxy, halogen, cyano and C$_1$-C$_6$-alkyl, or represents aryloxy or 5- or 6-membered heteroaryloxy in which aryloxy and 5- or 6-membered heteroaryloxy may optionally be mono- or polysubstituted by identical or different radicals from the group consisting of hydroxy, halogen, cyano, C(=O)OH, C(=O)OR$^a$, C$_1$-C$_6$-alkyl and C$_1$-C$_6$-alkoxy, or represents C$_3$-C$_8$-cycloalkyl or heterocycloalkyl which may optionally be mono- or polysubstituted by identical or different radicals from the group consisting of hydroxy, halogen, cyano and C$_1$-C$_6$-alkyl, or represents C$_2$-C$_6$-alkenyl or C$_2$-C$_6$-alkynyl, or represents aryl, 5- to 10-membered heteroaryl, aryl-C$_1$-C$_4$-alkyl or 5- or 6-membered heteroaryl-C$_1$-C$_4$-alkyl, where aryl and heteroaryl may optionally be mono- or polysubstituted by identical or different radicals from the group consisting of halogen, hydroxy, cyano, C(=O)OH, C(=O)OR$^a$, C$_1$-C$_6$-alkyl, C$_3$-C$_8$-cycloalkyl and C$_1$-C$_6$-alkoxy;

R$^a$ represents C$_1$-C$_6$-alkyl, C$_3$-C$_{10}$-cycloalkyl, heterocycloalkyl, aryl or heteroaryl, where alkyl, cycloalkyl, heterocycloalkyl, aryl and heteroaryl may optionally be mono- or polysubstituted by identical or different radicals from the group consisting of halogen, hydroxy, cyano, C$_1$-C$_3$-alkyl, C$_1$-C$_3$-alkoxy, heterocycloalkyl, —C(=O)O—C$_1$-C$_6$-alkyl and S(=O)$_2$—C$_1$-C$_6$-alkyl;

R$^b$ represents C$_1$-C$_6$-alkyl or C$_3$-C$_{10}$-cycloalkyl;

or R$^a$ and R$^b$ together with the nitrogen atom form a 5- or 6-membered heterocycle which may optionally be mono- or polysubstituted by identical or different radicals from the group consisting of hydroxy, halogen, cyano, and C$_1$-C$_6$-alkyl;

R$^c$ represents hydroxy, halogen, cyano, C$_1$-C$_3$-alkyl or C$_1$-C$_3$-alkoxy;

R$^d$ represents hydrogen, C$_1$-C$_6$-alkyl or C$_3$-C$_{10}$-cycloalkyl;

R$^2$ represents hydrogen, C$_1$-C$_6$-alkyl or C$_3$-C$_6$-cycloalkyl;

R$^{13}$ represents hydrogen or C$_1$-C$_6$-alkyl;

W represents 5-membered heteroaryl which contains one to three heteroatoms selected from the group consisting of N, O and S and may optionally be monosubstituted by R$^3$ and optionally be mono- or polysubstituted by identical or different radicals R$^4$ or W represents pyridyl, pyrazinyl, pyridazinyl, 1,2,4-triazinyl or 1,3,5-triazinyl which may optionally be monosubstituted by R$^3$ and optionally be mono- or polysubstituted by identical or different radicals R$^4$;

R$^3$ represents hydrogen, halogen, cyano, C(=O)R$^a$, NH$_2$, NHR$^a$, N(R$^a$)R$^b$, N(H)C(=O)R$^a$ or C$_1$-C$_6$-alkyl, where C$_1$-C$_6$-alkyl may optionally be mono- or polysubstituted by identical or different radicals from the group consisting of hydroxy, halogen, cyano, C(=O)R$^a$, C(=O)OH, C(=O)OR$^a$, S(=O)$_2$—C$_1$-C$_6$-alkyl, NH$_2$, NHR$^a$, N(R$^a$)R$^b$, C$_1$-C$_6$-alkoxy, C$_3$-C$_8$-cycloalkoxy, where C$_1$-C$_6$-alkoxy and C$_3$-C$_8$-cycloalkoxy may optionally be mono- or polysubstituted by identical or different halogen radicals;

or C$_1$-C$_6$-alkyl is optionally mono- or polysubstituted by identical or radicals from the group consisting of C$_3$-C$_6$-cycloalkyl and heterocycloalkyl, where C$_3$-C$_6$-cycloalkyl and heterocycloalkyl may optionally be mono-, di- or trisubstituted by identical or different radicals from the group consisting of halogen, cyano, C$_1$-C$_3$-alkyl and C$_1$-C$_3$-alkoxy, or C$_1$-C$_6$-alkyl is optionally mono- or polysubstituted by identical or different radicals from the group consisting of aryl and 5- or 6-membered heteroaryl, where aryl and 5- or 6-membered heteroaryl may optionally be mono-, di- or trisubstituted by identical or different radicals from the group consisting of halogen, cyano, C$_1$-C$_3$-alkyl and C$_1$-C$_3$-alkoxy, or R$^3$ represents C$_1$-C$_6$-alkoxy, where C$_1$-C$_6$-alkoxy may optionally be mono- or polysubstituted by identical or different radicals from the group consisting of hydroxy, halogen, cyano, C(=O)OR$^a$, S(=O)$_2$—C$_1$-C$_6$-alkyl, N(R$^a$)R$^b$, C$_3$-C$_8$-cycloalkyl, C$_1$-C$_4$-alkoxy, C$_3$-C$_8$-cycloalkoxy, or represents C$_3$-C$_6$-cycloalkyl, heterocycloalkyl or C$_5$-C$_{11}$-spirocycloalkyl, where cycloalkyl, heterocycloalkyl and spirocycloalkyl may optionally be mono- or polysubstituted by identical or different radicals from the group consisting of hydroxy, halogen, cyano, C(=O)R$^a$, C(=O)OH, C(=O)OR$^a$, C$_1$-C$_6$-alkyl and C$_1$-C$_4$-alkoxy;

or represents aryl or 5- to 10-membered heteroaryl, where aryl and heteroaryl may optionally be mono- or polysubstituted by identical or different radicals from the group consisting of halogen, hydroxy, cyano, C(=O)OR$^a$, S(=O)$_2$—C$_1$-C$_6$-alkyl, NO$_2$, NH$_2$, NHR$^a$, N(R$^a$)R$^b$, N(H)C(=O)R$^a$, C$_3$-C$_8$-cycloalkyl, C$_1$-C$_3$-alkoxy and C$_1$-C$_3$-alkyl, where C$_1$-C$_3$-alkyl may optionally be mono- or polysubstituted by identical or different halogen radicals;

R⁴ represents halogen, hydroxy, cyano or $C_1$-$C_6$-alkyl, where $C_1$-$C_6$-alkyl may optionally be mono- or polysubstituted by identical or different radicals from the group consisting of halogen, $C_1$-$C_6$-alkoxy, where $C_1$-$C_6$-alkoxy may optionally be mono- or polysubstituted by identical or different radicals from the group consisting of halogen, $C_2$-$C_6$-alkenyl, $C_2$-$C_6$-alkynyl, $C_3$-$C_{10}$-cycloalkyl, 3- to 10-membered heterocycloalkyl and aryl, where aryl may optionally be mono- or polysubstituted by identical or different radicals R, or R⁴ represents aryl or heteroaryl which may optionally be mono- or polysubstituted by identical or different radicals R, or R⁴ represents C(=O)R$^a$, C(=O)NH$_2$, C(=O)N(H)R$^a$, C(=O)N(R$^a$)R$^b$, C(=O)OR$^a$, NH$_2$, NHR$^a$, N(R$^a$)R$^b$, N(H)C(=O)R$^a$, N(R$^a$)C(=O)R$^a$, N(H)C(=O)NH$_2$, N(H)C(=O)NHR$^a$, N(H)C(=O)N(R$^a$)R$^b$, N(R$^a$)C(=O)NH$_2$, N(R$^a$)C(=O)NHR$^a$, N(R$^a$)C(=O)N(R$^a$)R$^b$, N(H)C(=O)OR$^a$, N(R$^a$)C(=O)OR$^a$, NO$_2$, N(H)S(=O)R$^a$, N(R$^a$)S(=O)R$^a$, N(H)S(=O)$_2$R$^a$, N(R$^a$)S(=O)$_2$R$^a$, N=S(=O)(R$^a$)R$^b$, OC(=O)R$^a$, OC(=O)NH$_2$, OC(=O)NHR$^a$, OC(=O)N(R$^a$)R$^b$, SH, SR$^a$, S(=O)R$^a$, S(=O)$_2$R$^a$, S(=O)$_2$NH$_2$, S(=O)$_2$NHR$^a$, S(=O)$_2$N(R$^a$)R$^b$ or S(=O)(=N—R$^a$)R$^b$;

R represents halogen, cyano, $C_1$-$C_6$-alkyl, $C_2$-$C_6$-alkenyl, $C_2$-$C_6$-alkynyl, $C_3$-$C_{10}$-cycloalkyl, 3- to 10-membered heterocycloalkyl, aryl, heteroaryl, C(=O)R$^a$, C(=O)NH$_2$, C(=O)N(H)R$^a$, C(=O)N(R$^a$)R$^b$, C(=O)OR$^a$, NH$_2$, NHR$^a$, N(R$^a$)R$^b$, N(H)C(=O)R$^a$, N(R$^a$)C(=O)R$^a$, N(H)C(=O)NH$_2$, N(H)C(=O)NHR$^a$, N(H)C(=O)N(R$^a$)R$^b$, N(R$^a$)C(=O)NH$_2$, N(R$^a$)C(=O)NHR$^a$, N(R$^a$)C(=O)N(R$^a$)R$^b$, N(H)C(=O)OR$^a$, N(R$^a$)C(=O)OR$^a$, NO$_2$, N(H)S(=O)R$^a$, N(R$^a$)S(=O)R$^a$, N(H)S(=O)$_2$R$^a$, N(R$^a$)S(=O)$_2$R$^a$, N=S(=O)(R$^a$)R$^b$, OH, $C_1$-$C_6$-alkoxy, OC(=O)R$^a$, OC(=O)NH$_2$, OC(=O)NHR$^a$, OC(=O)N(R$^a$)R$^b$, SH, SR$^a$, S(=O)R$^a$, S(=O)$_2$R$^a$, S(=O)$_2$NH$_2$, S(=O)$_2$NHR$^a$, S(=O)$_2$N(R$^a$)R$^b$ or S(=O)(=NR$^a$)R$^b$;

n represents 0 or 1;

Y represents a group selected from:

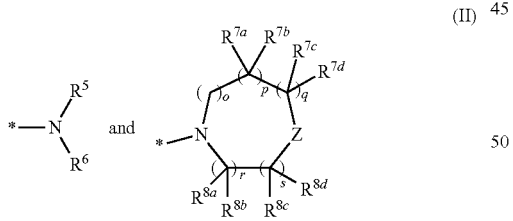

(II)

where * represents the point of attachment of the group to the remainder of the molecule;

R⁵ represents hydrogen, $C_1$-$C_6$-alkyl or $C_3$-$C_{10}$-cycloalkyl, where
  $C_1$-$C_6$-alkyl may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, N(R$^a$)R$^b$, $C_1$-$C_4$-alkoxy and $C_3$-$C_8$-cycloalkyl;

R⁶ represents hydrogen or $C_1$-$C_6$-alkyl, where
  $C_1$-$C_6$-alkyl may optionally be mono- or polysubstituted by identical or different radicals from the group consisting of hydroxy, halogen, cyano, $C_3$-$C_{10}$-cycloalkyl, C(=O)R$^a$, C(=O)OH, C(=O)OR$^a$, S(=O)$_2$—$C_1$-$C_6$-alkyl, N(R$^a$)R$^b$, $C_1$-$C_4$-alkoxy and $C_3$-$C_8$-cycloalkoxy, or represents $C_3$-$C_{10}$-cycloalkyl, where
  $C_3$-$C_{10}$-cycloalkyl may optionally be mono- or polysubstituted by identical or different radicals from the group consisting of hydroxy, halogen, cyano and $C_1$-$C_6$-alkyl, where
  $C_1$-$C_6$-alkyl may optionally be substituted by hydroxy, or represents heterocycloalkyl, where
heterocycloalkyl may optionally be mono- or polysubstituted by identical or different radicals from the group consisting of halogen, cyano, $C_1$-$C_3$-alkyl and $C_1$-$C_3$-alkoxy, or represents aryl or 5- or 6-membered heteroaryl, where
aryl and 5- or 6-membered heteroaryl may optionally be mono- or polysubstituted by identical or different radicals from the group consisting of halogen, cyano, $C_1$-$C_3$-alkyl, $C_1$-$C_3$-alkoxy, S(=O)$_2$NH$_2$, S(=O)$_2$NHR$^a$ and S(=O)$_2$N(R$^a$)R$^b$;

R$^{7a}$ represents hydrogen, halogen, N(R$^a$)R$^b$, $C_1$-$C_6$-alkyl or $C_3$-$C_{10}$-cycloalkyl, where
  $C_1$-$C_6$-alkyl may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, N(R$^a$)R$^b$, $C_1$-$C_4$-alkoxy, $C_3$-$C_8$-cycloalkyl and heterocycloalkyl;

R$^{7b}$ represents hydrogen, halogen or $C_1$-$C_6$-alkyl, where
  $C_1$-$C_6$-alkyl may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, N(R$^a$)R$^b$, $C_1$-$C_4$-alkoxy, $C_3$-$C_8$-cycloalkyl and heterocycloalkyl;

or R$^{7a}$ and R$^{7b}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, or R$^{7a}$ and R$^{7b}$ together represent an oxo group;

R$^{7c}$ represents hydrogen, halogen, N(R$^a$)R$^b$, $C_1$-$C_6$-alkyl or $C_3$-$C_{10}$-cycloalkyl, where
  $C_1$-$C_6$-alkyl may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, N(R$^a$)R$^b$, $C_1$-$C_4$-alkoxy, $C_3$-$C_8$-cycloalkyl and heterocycloalkyl;

R$^{7d}$ represents hydrogen, halogen or $C_1$-$C_6$-alkyl, where
  $C_1$-$C_6$-alkyl may optionally be mono- or polysubstituted by identical or different radicals from the group consisting of hydroxy, halogen, cyano, C(=O)OH, C(=O)OR$^a$, S(=O)$_2$—$C_1$-$C_6$-alkyl, N(R$^a$)R$^b$, $C_1$-$C_4$-alkoxy, $C_3$-$C_8$-cycloalkyl and heterocycloalkyl;

or R$^{7c}$ and R$^{7d}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, or R$^{7c}$ and R$^{7d}$ together represent an oxo group;

R$^{8a}$ represents hydrogen, halogen, N(R$^a$)R$^b$, $C_1$-$C_6$-alkyl or $C_3$-$C_{10}$-cycloalkyl, where $C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

$R^{8b}$ represents hydrogen, halogen or $C_1$-$C_6$-alkyl, where
$C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

or $R^{8a}$ and $R^{8b}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, $R^{8c}$ represents hydrogen, halogen, $N(R^a)R^b$, $C_1$-$C_6$-alkyl or $C_3$-$C_{10}$-cycloalkyl, where
$C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

$R^{8d}$ represents hydrogen, halogen or $C_1$-$C_6$-alkyl, where
$C_1$-$C_6$-alkyl may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_1$-$C_4$-alkoxy, $C_3$-$C_8$-cycloalkyl and heterocycloalkyl;

or $R^{8c}$ and $R^{8d}$ together with the carbon atom form $C_3$-$C_6$-cycloalkyl which may optionally be mono- or polysubstituted by identical or different radicals from the group consisting of hydroxy, halogen, cyano and $C_1$-$C_6$-alkyl, or $R^{8c}$ and $R^{8d}$ together represent an oxo group;
o represents 0, 1 or 2,
p represents 0, 1 or 2,
q represents 0, 1 or 2,
r represents 0, 1 or 2,
s represents 0, 1 or 2,
where o, p, q, r and s do not simultaneously represent 0;
Z represents a group selected from $C(=O)$, $CR^9R^{10}$, $NR^{11}$, $O$, $S$, $S(=O)$ and $S(=O)_2$;
$R^9$ represents hydrogen or $C_1$-$C_6$-alkyl,
$R^{10}$ represents hydrogen, halogen, cyano, $C(=O)R^a$, $C(=O)OH$, $C(=O)OR^a$, $C(=O)NH_2$, $C(=O)N(H)R^a$, $C(=O)N(R^a)R^b$, $N(H)C(=O)R^a$, $N(R^b)C(=O)R^a$, $S(=O)_2R^a$, hydroxy, $N(R^a)R^b$ and $C_1$-$C_6$-alkyl, where
$C_1$-$C_6$-alkyl may optionally be mono- or polysubstituted by identical or different radicals from the group consisting of hydroxy, halogen, cyano, $C(=O)R^a$, $C(=O)OH$, $C(=O)OR^a$, $S(=O)_2$—$C_1$-$C_6$-alkyl, $N(R^a)R^b$, $C_1$-$C_4$-alkoxy and $C_3$-$C_8$-cycloalkoxy,
or represents $C_1$-$C_6$-alkoxy, where
$C_1$-$C_6$-alkoxy may optionally be mono- or polysubstituted by identical or different radicals from the group consisting of hydroxy, halogen, cyano, $C(=O)OH$, $C(=O)OR^a$, $S(=O)_2$—$C_1$-$C_6$-alkyl, $N(R^a)R^b$, $C_3$-$C_8$-cycloalkyl, $C_1$-$C_4$-alkoxy, $C_3$-$C_8$-cycloalkoxy, heterocycloalkyl, aryl and 5- or 6-membered heteroaryl, where
aryl and 5- or 6-membered heteroaryl may optionally be mono- or polysubstituted by identical or different radicals from the group consisting of halogen, cyano, $C_1$-$C_3$-alkyl and $C_1$-$C_3$-alkoxy,
or represents aryloxy or 5- or 6-membered heteroaryloxy in which
aryloxy and 5- or 6-membered heteroaryloxy may optionally be mono- or polysubstituted by identical or different radicals from the group consisting of hydroxy, halogen, cyano, $C(=O)OH$, $C(=O)OR^a$, $C_1$-$C_3$-alkyl and $C_1$-$C_3$-alkoxy,
or represents $C_3$-$C_8$-cycloalkyl, $C_3$-$C_8$-cycloalkyl-$C_1$-$C_4$-alkyl, heterocycloalkyl or heterocycloalkyl-$C_1$-$C_4$-alkyl, which may optionally be mono- or polysubstituted by identical or different radicals from the group consisting of hydroxy, halogen, cyano, $C(=O)R^a$, $C(=O)OH$, $C(=O)OR^a$, $C_1$-$C_6$-alkyl and $C_1$-$C_6$-alkoxy, where
$C_1$-$C_6$-alkoxy may optionally be mono- or polysubstituted by identical or different halogen radicals or an oxo group;
or represents $C_2$-$C_6$-alkenyl or $C_2$-$C_6$-alkynyl,
or represents aryl, 5- to 10-membered heteroaryl, aryl-$C_1$-$C_4$-alkyl or 5- or 6-membered heteroaryl-$C_1$-$C_4$-alkyl, where
aryl and heteroaryl may optionally be mono- or polysubstituted by identical or different radicals from the group consisting of halogen, hydroxy, cyano, $C(=O)OH$, $C(=O)OR^a$, $NHR^a$, $N(R^a)R^b$, $C_1$-$C_3$-alkyl, $C_3$-$C_8$-cycloalkyl and $C_1$-$C_3$-alkoxy;
or $R^9$ and $R^{10}$ together with the carbon atom form $C_3$-$C_8$-cycloalkyl or a 4- to 6-membered heterocycle, where
the $C_3$-$C_8$-cycloalkyl radical or the 4- to 6-membered heterocycle may optionally be mono- or polysubstituted by identical or different radicals from the group consisting of hydroxy, halogen, cyano, $C_1$-$C_6$-alkyl, $C(=O)R^a$ and an oxo group;
$R^{11}$ represents hydrogen, $C(=O)R^a$, $C(=O)OR^a$, $C(=O)NH_2$, $C(=O)N(H)R^a$, $C(=O)N(R^a)R^b$, $S(=O)_2R^a$, $S(=O)_2N(R^a)R^b$ or $C_1$-$C_6$-alkyl, where
$C_1$-$C_6$-alkyl may optionally be mono- or polysubstituted by identical or different radicals from the group consisting of hydroxy, halogen, cyano, $C(=O)R^a$, $C(=O)OR^a$, $C(=O)NH_2$, $C(=O)N(H)R^a$, $C(=O)N(R^a)R^b$, $S(=O)_2$—$C_1$-$C_6$-alkyl, $N(R^a)R^b$, $C_3$-$C_8$-cycloalkyl, $C_1$-$C_4$-alkoxy and $C_3$-$C_8$-cycloalkoxy, where
$C_3$-$C_8$-cycloalkyl, $C_1$-$C_4$-alkoxy and $C_3$-$C_8$-cycloalkoxy may optionally be mono- or polysubstituted by identical or different radicals from the group consisting of hydroxy and halogen;
or represents $C_3$-$C_8$-cycloalkyl, heterocycloalkyl or heterocycloalkyl-$C_1$-$C_4$-alkyl which may optionally be mono- or polysubstituted by identical or different radicals from the group consisting of hydroxy, halogen, cyano, $C_1$-$C_6$-alkyl, $C_1$-$C_6$-alkoxy, where alkyl and alkoxy may optionally be mono- or polysubstituted by identical or different radicals from the group consisting of halogen and an oxo group,
or represents $C_2$-$C_6$-alkenyl or $C_2$-$C_6$-alkynyl,
or represents aryl, 5- to 10-membered heteroaryl, aryl-$C_1$-$C_4$-alkyl or 5- or 6-membered heteroaryl-$C_1$-$C_4$-alkyl, where
aryl and heteroaryl may optionally be mono- or polysubstituted by identical or different radicals from the group consisting of halogen, hydroxy, cyano, $C(=O)OH$, $C(=O)OR^a$, $C_1$-$C_3$-alkyl, $C_3$-$C_8$-cycloalkyl and $C_1$-$C_3$-alkoxy;

and their diastereomers, enantiomers, their metabolites, their salts, their solvates or the solvates of their salts.

2. The compound of claim 1 in which $R^1$ represents hydrogen, halogen, hydroxy, cyano, $C_1$-$C_6$-alkyl, $C_1$-$C_5$-alkyl substituted by hydroxy, $C_1$-$C_6$-alkoxy, $C_1$-$C_6$-alkoxy substituted by $C_3$-$C_8$-cycloalkyl, $C_1$-$C_6$-alkoxy substituted by up to three fluorine atoms, $C_1$-$C_6$-alkoxy substituted by aryl which is optionally mono- or polysubstituted by identical or different radicals from the group consisting of $R^c$ or represents 5- or 6-membered heteroaryl which is optionally mono- or polysubstituted by identical or different radicals from the group consisting of $R^c$.

3. The compound of claim 1 in which W represents a group selected from formulae (III) to (IX):

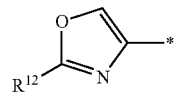

III

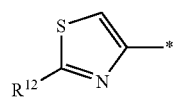

IV

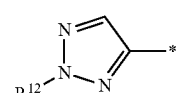

V

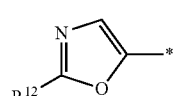

VI

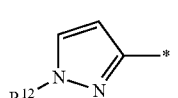

VII

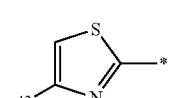

VIII

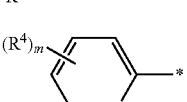

IX in which
$R^{12}$ represents hydrogen, halogen, $C_1$-$C_6$-alkyl which is optionally mono- or polysubstituted by identical or different halogen radicals, $C_3$-$C_6$-cycloalkyl which is optionally mono- or polysubstituted by identical or different halogen radicals, aryl which is optionally mono- or polysubstituted by identical or different radicals from the group consisting of $R^c$ or 5- or 6-membered heteroaryl which is optionally mono- or polysubstituted by identical or different radicals from the group consisting of $R^c$ or represents $NHR^a$;
m represents 0, 1, 2 or 3 and
$R^3$ and $R^4$ have the meanings given above and
* represents the point of attachment of the group to the remainder of the molecule.

4. The compound of claim 1 in which W represents a group of the general formula (X)

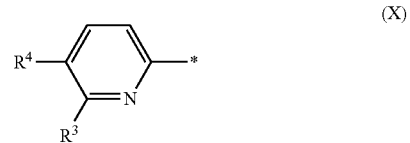

and $R^3$ and $R^4$ have the meaning given in claim 1.

5. The compound of claim 1 in which Y is formula (II) where $R^{7a}$, $R^{7b}$, $R^{7c}$, $R^{7d}$, $R^{8a}$, $R^{8b}$, $R^{8c}$ and $R^{8d}$ are as defined in claim 1:

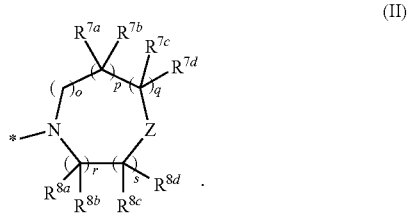

6. The compound of claim 1 in which Y is a radical $NR^5R^6$ where $R^5$ and $R^6$ are as defined in claim 1.

7. The compound of claim 1 in which W represents a group of the general formula (IX)

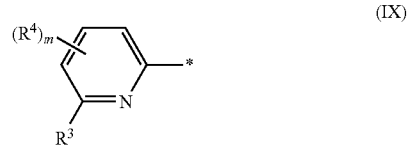

in which
m represents 0 and $R^2$, $R^o$ and $R^{13}$ all represent hydrogen and $R^3$ represents trifluoromethyl, ethyl, methyl, cyclopropyl, 2,2,2-trifluoro-1-hydroxyethyl or 1-hydroxyethyl; Y represents 4-methylpiperazin-1-yl, 4-ethylpiperazin-1-yl or morpholin-4-yl, n represents 0 and $R^1$ represents cyclopropylmethoxy, trifluoromethoxy, 2,2,2-trifluoroethoxy, chlorine, ethoxy, methoxy, 2-hydroxypropan-2-yl or 3-hydroxypentan-3-yl.

8. The compound of claim 7 in which $R^1$ represents cyclopropylmethoxy, methoxy, ethoxy or 2-hydroxypropan-2-yl.

9. The compound of claim 7 in which $R^3$ is a trifluoromethyl or a cyclopropyl radical.

10. The compound of claim 1, wherein the compound is selected from the group consisting of:
N-{2-[2-(4-benzoylpiperazin-1-yl)-2-oxoethyl]-6-methyl-2H-indazol-5-yl}-6-(trifluoromethyl)pyridine-2-carboxamide;
6-ethyl-N-(6-methyl-2-{2-oxo-2-[4-(pyrrolidin-1-yl)piperidin-1-yl]ethyl}-2H-indazol-5-yl)pyridine-2-carboxamide;
5-fluoro-N-(6-methyl-2-{2-oxo-2-[4-(pyrrolidin-1-yl)piperidin-1-yl]ethyl}-2H-indazol-5-yl)pyridine-2-carboxamide;
N-(2-{2-[4-(3-hydroxy-2,2-dimethylpropanoyl)piperazin-1-yl]-2-oxoethyl}-6-methyl-2H-indazol-5-yl)-6-(trifluoromethyl)pyridine-2-carboxamide;
N-(2-{2-[4-(methoxyacetyl)piperazin-1-yl]-2-oxoethyl}-6-methyl-2H-indazol-5-yl)-6-(trifluoromethyl)pyridine-2-carboxamide;

N-(2-{2-[4-(2-hydroxypropan-2-yl)piperidin-1-yl]-2-oxoethyl}-6-methoxy-2H-indazol-5-yl)-6-(trifluoromethyl)pyridine-2-carboxamide;
N-(2-{2-[4-(2-hydroxypropan-2-yl)piperidin-1-yl]-2-oxoethyl}-6-methoxy-2H-indazol-5-yl)-6-methylpyridine-2-carboxamide;
N-(2-{2-[4-(cyclopropylmethyl)piperazin-1-yl]-2-oxoethyl}-6-methoxy-2H-indazol-5-yl)-6-(trifluoromethyl)pyridine-2-carboxamide;
N-(2-{2-[4-(cyclopropylmethyl)piperazin-1-yl]-2-oxoethyl}-6-methoxy-2H-indazol-5-yl)-6-methylpyridine-2-carboxamide;
N-{2-[2-(4-benzoylpiperazin-1-yl)-2-oxoethyl]-6-methoxy-2H-indazol-5-yl}-6-cyclopropylpyridine-2-carboxamide;
N-{2-[2-(4-benzoylpiperazin-1-yl)-2-oxoethyl]-6-methoxy-2H-indazol-5-yl}-6-(1-hydroxyethyl)pyridine-2-carboxamide;
N-{2-[2-(4-methylpiperazin-1-yl)-2-oxoethyl]-6-(trifluoromethoxy)-2H-indazol-5-yl}-6-(trifluoromethyl)pyridine-2-carboxamide;
6-methyl-N-{2-[2-(4-methylpiperazin-1-yl)-2-oxoethyl]-6-(trifluoromethoxy)-2H-indazol-5-yl}pyridine-2-carboxamide;
tert-butyl 3-{[4-({2-[2-(4-methylpiperazin-1-yl)-2-oxoethyl]-6-(trifluoromethoxy)-2H-indazol-5-yl}carbamoyl)-1,3-thiazol-2-yl]amino}azetidine-1-carboxylate;
N-{6-bromo-2-[2-(4-methylpiperazin-1-yl)-2-oxoethyl]-2H-indazol-5-yl}-6-(trifluoromethyl)pyridine-2-carboxamide;
N-{6-bromo-2-[2-(4-methylpiperazin-1-yl)-2-oxoethyl]-2H-indazol-5-yl}-6-methylpyridine-2-carboxamide;
N-{6-bromo-2-[2-(4-methylpiperazin-1-yl)-2-oxoethyl]-2H-indazol-5-yl}-2-cyclopropyl-1,3-oxazole-4-carboxamide;
tert-butyl 3-{[4-({6-bromo-2-[2-(4-methylpiperazin-1-yl)-2-oxoethyl]-2H-indazol-5-yl}carbamoyl)-1,3-thiazol-2-yl]amino}azetidine-1-carboxylate;
2-(azetidin-3-ylamino)-N-{2-[2-(4-methylpiperazin-1-yl)-2-oxoethyl]-6-(trifluoromethoxy)-2H-indazol-5-yl}-1,3-thiazole-4-carboxamide;
N-{6-cyano-2-[2-(4-methylpiperazin-1-yl)-2-oxoethyl]-2H-indazol-5-yl}-6-(trifluoromethyl)pyridine-2-carboxamide;
6'-methyl-N-{2-[2-(4-methylpiperazin-1-yl)-2-oxoethyl]-2H-indazol-5-yl}-2,3'-bipyridine-6-carboxamide;
5'-methyl-N-{2-[2-(4-methylpiperazin-1-yl)-2-oxoethyl]-2H-indazol-5-yl}-2,3'-bipyridine-6-carboxamide;
4'-methyl-N-{2-[2-(4-methylpiperazin-1-yl)-2-oxoethyl]-2H-indazol-5-yl}-2,3'-bipyridine-6-carboxamide;
6'-methoxy-N-{2-[2-(4-methylpiperazin-1-yl)-2-oxoethyl]-2H-indazol-5-yl}-2,3'-bipyridine-6-carboxamide;
6'-acetamido-N-{2-[2-(4-methylpiperazin-1-yl)-2-oxoethyl]-2H-indazol-5-yl}-2,3'-bipyridine-6-carboxamide;
N-{2-[2-(4-methylpiperazin-1-yl)-2-oxoethyl]-2H-indazol-5-yl}-6'-nitro-2,3'-bipyridine-6-carboxamide;
6'-amino-N-{2-[2-(4-methylpiperazin-1-yl)-2-oxoethyl]-2H-indazol-5-yl}-2,3'-bipyridine-6-carboxamide;
N-{2-[2-(4-benzoylpiperazin-1-yl)-2-oxoethyl]-6-fluoro-2H-indazol-5-yl}-6-(trifluoromethyl)pyridine-2-carboxamide;
N-(2-{2-[4-(cyclopropylcarbonyl)piperazin-1-yl]-2-oxoethyl}-6-fluoro-2H-indazol-5-yl)-6-(trifluoromethyl)pyridine-2-carboxamide;
N-{6-fluoro-2-[2-(4-methylpiperazin-1-yl)-2-oxoethyl]-2H-indazol-5-yl}-6-(trifluoromethyl)pyridine-2-carboxamide;
N-(2-{2-[4-(cyclopropylcarbonyl)piperazin-1-yl]-2-oxoethyl}-6-fluoro-2H-indazol-5-yl)-6-methylpyridine-2-carboxamide;
N-{6-fluoro-2-[2-(4-methylpiperazin-1-yl)-2-oxoethyl]-2H-indazol-5-yl}-6-methylpyridine-2-carboxamide;
N-(2-{2-[4-(cyclopropylcarbonyl)piperazin-1-yl]-2-oxoethyl}-6-fluoro-2H-indazol-5-yl)-6-(1-methyl-1H-pyrazol-4-yl)pyridine-2-carboxamide;
N-{2-[2-(4-benzoylpiperazin-1-yl)-2-oxoethyl]-6-fluoro-2H-indazol-5-yl}-6-(1-methyl-1H-pyrazol-4-yl)pyridine-2-carboxamide;
N-{6-fluoro-2-[2-(4-methylpiperazin-1-yl)-2-oxoethyl]-2H-indazol-5-yl}-6-(1-methyl-1H-pyrazol-4-yl)pyridine-2-carboxamide;
N-{2-[2-(4-benzoylpiperazin-1-yl)-2-oxoethyl]-6-fluoro-2H-indazol-5-yl}-5-fluoro-6-(1-methyl-1H-pyrazol-4-yl)pyridine-2-carboxamide;
N-(2-{2-[4-(cyclopropylcarbonyl)piperazin-1-yl]-2-oxoethyl}-6-fluoro-2H-indazol-5-yl)-5-fluoro-6-(1-methyl-1H-pyrazol-4-yl)pyridine-2-carboxamide;
N-{2-[2-(4-benzoylpiperazin-1-yl)-2-oxoethyl]-6-fluoro-2H-indazol-5-yl}-6-(morpholin-4-yl)pyridine-2-carboxamide;
N-(2-{2-[4-(cyclopropylcarbonyl)piperazin-1-yl]-2-oxoethyl}-6-fluoro-2H-indazol-5-yl)-6-(morpholin-4-yl)pyridine-2-carboxamide;
N-{6-fluoro-2-[2-(4-methylpiperazin-1-yl)-2-oxoethyl]-2H-indazol-5-yl}-6-(morpholin-4-yl)pyridine-2-carboxamide;
N-{6-(benzyloxy)-2-[2-(4-methylpiperazin-1-yl)-2-oxoethyl]-2H-indazol-5-yl}-6-(trifluoromethyl)pyridine-2-carboxamide;
N-{6-isobutoxy-2-[2-(4-methylpiperazin-1-yl)-2-oxoethyl]-2H-indazol-5-yl}-6-(trifluoromethyl)pyridine-2-carboxamide;
N-{6-isobutoxy-2-[2-(morpholin-4-yl)-2-oxoethyl]-2H-indazol-5-yl}-6-(trifluoromethyl)pyridine-2-carboxamide;
N-(2-{2-[4-(2-hydroxypropan-2-yl)piperidin-1-yl]-2-oxoethyl}-6-isobutoxy-2H-indazol-5-yl)-6-(trifluoromethyl)pyridine-2-carboxamide;
N-(2-{2-[(cyclopropylmethyl)(methyl)amino]-2-oxoethyl}-6-isobutoxy-2H-indazol-5-yl)-6-(trifluoromethyl)pyridine-2-carboxamide;
N-{6-(cyclopropylmethoxy)-2-[2-(4-methylpiperazin-1-yl)-2-oxoethyl]-2H-indazol-5-yl}-6-(trifluoromethyl)pyridine-2-carboxamide;
N-{6-(cyclopropylmethoxy)-2-[2-(morpholin-4-yl)-2-oxoethyl]-2H-indazol-5-yl}-6-(trifluoromethyl)pyridine-2-carboxamide;
N-[6-(cyclopropylmethoxy)-2-{2-[4-(2-hydroxypropan-2-yl)piperidin-1-yl]-2-oxoethyl}-2H-indazol-5-yl]-6-(trifluoromethyl)pyridine-2-carboxamide;
N-[6-(cyclopropylmethoxy)-2-{2-[(cyclopropylmethyl)(methyl)amino]-2-oxoethyl}-2H-indazol-5-yl]-6-(trifluoromethyl)pyridine-2-carboxamide;
N-{2-[2-(4-methylpiperazin-1-yl)-2-oxoethyl]-6-(pyridin-2-ylmethoxy)-2H-indazol-5-yl}-6-(trifluoromethyl)pyridine-2-carboxamide;
N-{2-[2-(morpholin-4-yl)-2-oxoethyl]-6-(pyridin-2-ylmethoxy)-2H-indazol-5-yl}-6-(trifluoromethyl)pyridine-2-carboxamide;

N-[2-{2-[4-(2-hydroxypropan-2-yl)piperidin-1l-yl]-2-oxoethyl}-6-(pyridin-2-ylmethoxy)-2H-indazol-5-yl]-6-(trifluoromethyl)pyridine-2-carboxamide;

N-[2-{2-[(cyclopropylmethyl)(methyl)amino]-2-oxoethyl}-6-(pyridin-2-ylmethoxy)-2H-indazol-5-yl]-6-(trifluoromethyl)pyridine-2-carboxamide;

N-{2-[2-(4-benzoylpiperazin-1-yl)-2-oxoethyl]-6-chloro-2H-indazol-5-yl}-6-(trifluoromethyl)pyridine-2-carboxamide;

N-{6-chloro-2-[2-(morpholin-4-yl)-2-oxoethyl]-2H-indazol-5-yl}-6-(trifluoromethyl)pyridine-2-carboxamide;

ethyl 4-{[6-chloro-5-({[6-(trifluoromethyl)pyridin-2-yl]carbonyl}amino)-2H-indazol-2-yl]acetyl}piperazine-1-carboxylate;

N-(6-chloro-2-{oxo-2-[4-(pyrrolidin-1-yl)piperidin-1-yl]ethyl}-2H-indazol-5-yl)-6-(trifluoromethyl)pyridine-2-carboxamide;

N-(6-chloro-2-{2-[4-(2-hydroxypropan-2-yl)piperidin-1-yl]-2-oxoethyl}-2H-indazol-5-yl)-6-(trifluoromethyl)pyridine-2-carboxamide;

N-(6-chloro-2-{2-[4-(3-hydroxy-2,2-dimethylpropanoyl)piperazin-1-yl]-2-oxoethyl}-2H-indazol-5-yl)-6-(trifluoromethyl)pyridine-2-carboxamide;

N-(6-chloro-2-{2-[3-(dimethylamino)azetidin-1-yl]-2-oxoethyl}-2H-indazol-5-yl)-6-(trifluoromethyl)pyridine-2-carboxamide;

N-(6-chloro-2-{2-oxo-2-[3-(piperidin-1-yl)azetidin-1-yl]ethyl}-2H-indazol-5-yl)-6-(trifluoromethyl)pyridine-2-carboxamide;

N-(6-chloro-2-{2-[4-(2-hydroxy-2-methylpropyl)piperidin-1-yl]-2-oxoethyl}-2H-indazol-5-yl)-6-(trifluoromethyl)pyridine-2-carboxamide;

N-{6-chloro-2-[2-(4-hydroxy-1,4'-bipiperidin-1'-yl)-2-oxoethyl]-2H-indazol-5-yl}-6-(trifluoromethyl)pyridine-2-carboxamide;

N-{6-methoxy-2-[2-(4-methylpiperazin-1-yl)-2-oxoethyl]-2H-indazol-5-yl}-6-(trifluoromethyl)pyridine-2-carboxamide;

N-{6-methoxy-2-[2-(morpholin-4-yl)-2-oxoethyl]-2H-indazol-5-yl}-6-(trifluoromethyl)pyridine-2-carboxamide;

N-(2-{2-[4-(dimethylamino)piperidin-1-yl]-2-oxoethyl}-6-ethoxy-2H-indazol-5-yl)-6-(trifluoromethyl)pyridine-2-carboxamide;

N-(6-ethoxy-2-{2-oxo-2-[4-(pyrrolidin-1-yl)piperidin-1-yl]ethyl}-2H-indazol-5-yl)-6-(trifluoromethyl)pyridine-2-carboxamide;

N-{6-ethoxy-2-[2-(4-methylpiperazin-1-yl)-2-oxoethyl]-2H-indazol-5-yl}-6-(trifluoromethyl)pyridine-2-carboxamide;

N-{2-[2-(4-benzoylpiperazin-1-yl)-2-oxoethyl]-6-ethoxy-2H-indazol-5-yl}-6-(trifluoromethyl)pyridine-2-carboxamide;

N-(6-ethoxy-2-{2-[4-(2-hydroxypropan-2-yl)piperidin-1-yl]-2-oxoethyl}-2H-indazol-5-yl)-6-(trifluoromethyl)pyridine-2-carboxamide;

N-{6-ethoxy-2-[2-(morpholin-4-yl)-2-oxoethyl]-2H-indazol-5-yl}-6-(trifluoromethyl)pyridine-2-carboxamide;

N-{2-[2-(4-benzoylpiperazin-1-yl)-2-oxoethyl]-3-methyl-2H-indazol-5-yl}-6-(trifluoromethyl)pyridine-2-carboxamide;

N-{2-[3-(4-benzoylpiperazin-1-yl)-3-oxopropyl]-2H-indazol-5-yl}-6-(trifluoromethyl)pyridine-2-carboxamide;

N-(2-{2-[4-(cyclopropylcarbonyl)piperazin-1-yl]-2-oxoethyl}-2H-indazol-5-yl)-2-(pyridin-3-yl)-1,3-thiazole-4-carboxamide;

N-(2-{2-[4-(cyclopropylcarbonyl)piperazin-1-yl]-2-oxoethyl}-2H-indazol-5-yl)-2-(pyridin-4-yl)-1,3-thiazole-4-carboxamide;

N-(2-{2-[4-(cyclopropylcarbonyl)piperazin-1-yl]-2-oxoethyl}-2H-indazol-5-yl)-6-(trifluoromethyl)pyridine-2-carboxamide;

6-(azetidin-3-ylamino)-N-(2-{2-[4-(cyclopropylcarbonyl)piperazin-1-yl]-2-oxoethyl}-2H-indazol-5-yl)pyridine-2-carboxamide;

N-{2-[2-(4-methylpiperazin-1-yl)-2-oxoethyl]-2H-indazol-5-yl}-2-(pyridin-3-yl)-1,3-thiazole-4-carboxamide;

N-{2-[2-(4-methylpiperazin-1-yl)-2-oxoethyl]-2H-indazol-5-yl}-6-(1-methyl-1H-pyrazol-4-yl)pyridine-2-carboxamide;

N-{2-[2-(4-methylpiperazin-1-yl)-2-oxoethyl]-2H-indazol-5-yl}-6-(1H-pyrazol-4-yl)pyridine-2-carboxamide;

6-(1,3-dimethyl-1H-pyrazol-4-yl)-N-{2-[2-(4-methylpiperazin-1-yl)-2-oxoethyl]-2H-indazol-5-yl}pyridine-2-carboxamide;

N-{2-[2-(4-methylpiperazin-1-yl)-2-oxoethyl]-2H-indazol-5-yl}-6-[3-(trifluoromethyl)-1H-pyrazol-4-yl]pyridine-2-carboxamide;

6-ethyl-N-{2-[2-(4-methylpiperazin-1-yl)-2-oxoethyl]-2H-indazol-5-yl}pyridine-2-carboxamide;

6-(1-methyl-1H-pyrazol-4-yl)-N-(2-{2-oxo-2-[4-(2,2,2-trifluoroethyl)piperazin-1-yl]ethyl}-2H-indazol-5-yl)pyridine-2-carboxamide;

N-(2-{2-oxo-2-[4-(2,2,2-trifluoroethyl)piperazin-1-yl]ethyl}-2H-indazol-5-yl)-6-(trifluoromethyl)pyridine-2-carboxamide;

N-{2-[2-(4-ethyl-3-oxopiperazin-1-yl)-2-oxoethyl]-2H-indazol-5-yl}-6-(1-methyl-1H-pyrazol-4-yl)pyridine-2-carboxamide;

N-{2-[2-(4-benzoylpiperazin-1-yl)-2-oxoethyl]-2H-indazol-5-yl}-6-(trifluoromethyl)pyridine-2-carboxamide;

N-{2-[2-(4-benzoylpiperazin-1-yl)-2-oxoethyl]-2H-indazol-5-yl}-6-methylpyridine-2-carboxamide;

N-{2-[2-(4-benzoylpiperazin-1-yl)-2-oxoethyl]-2H-indazol-5-yl}-6-(morpholin-4-yl)pyridine-2-carboxamide;

N-{2-[2-(4-benzoylpiperazin-1-yl)-2-oxoethyl]-2H-indazol-5-yl}-2-(pyridin-4-yl)-1,3-thiazole-4-carboxamide;

N-{2-[2-(4-benzoylpiperazin-1-yl)-2-oxoethyl]-2H-indazol-5-yl}-6-chloropyridine-2-carboxamide;

N-{2-[2-(4-benzoylpiperazin-1-yl)-2-oxoethyl]-2H-indazol-5-yl}-2-methyl-1,3-oxazole-5-carboxamide;

6-amino-N-{2-[2-(4-benzoylpiperazin-1-yl)-2-oxoethyl]-2H-indazol-5-yl}pyridine-2-carboxamide;

N-{2-[2-(4-benzoylpiperazin-1-yl)-2-oxoethyl]-2H-indazol-5-yl}-2-methyl-1,3-oxazole-4-carboxamide;

N-{2-[2-(4-benzoylpiperazin-1-yl)-2-oxoethyl]-2H-indazol-5-yl}-6-methoxypyridine-2-carboxamide;

N-{2-[2-(4-benzoylpiperazin-1-yl)-2-oxoethyl]-2H-indazol-5-yl}-2-cyclopropyl-1,3-oxazole-4-carboxamide;

N-{2-[2-(4-benzoylpiperazin-1-yl)-2-oxoethyl]-2H-indazol-5-yl}-6-(4H-1,2,4-triazol-4-yl)pyridine-2-carboxamide;

N-{2-[2-(4-benzoylpiperazin-1-yl)-2-oxoethyl]-2H-indazol-5-yl}-2-phenyl-2H-1,2,3-triazole-4-carboxamide;

N-{2-[2-(4-benzoylpiperazin-1-yl)-2-oxoethyl]-2H-indazol-5-yl}-6-(1-methyl-1H-pyrazol-5-yl)pyridine-2-carboxamide;

N-{2-[2-(4-benzoylpiperazin-1-yl)-2-oxoethyl]-2H-indazol-5-yl}-2-(trifluoromethyl)-1,3-thiazole-4-carboxamide;

N-{2-[2-(4-benzoylpiperazin-1-yl)-2-oxoethyl]-2H-indazol-5-yl}-6-(1H-pyrazol-1-yl)pyridine-2-carboxamide;
N-{2-[2-(4-benzoylpiperazin-1-yl)-2-oxoethyl]-2H-indazol-5-yl}-6-(1-methyl-1H-pyrazol-4-yl)pyridine-2-carboxamide;
N-{2-[2-(4-benzoylpiperazin-1-yl)-2-oxoethyl]-2H-indazol-5-yl}-1-ethyl-1H-pyrazole-3-carboxamide;
N-{2-[2-(4-benzoylpiperazin-1-yl)-2-oxoethyl]-2H-indazol-5-yl}-6-(4-chloro-1H-pyrazol-1-yl)pyridine-2-carboxamide;
N-{2-[2-(4-benzoylpiperazin-1-yl)-2-oxoethyl]-2H-indazol-5-yl}-4-(trifluoromethyl)-1,3-thiazole-2-carboxamide;
N-{2-[2-(4-benzoylpiperazin-1-yl)-2-oxoethyl]-2H-indazol-5-yl}-6-(1,3-dimethyl-1H-pyrazol-4-yl)pyridine-2-carboxamide;
N-{2-[2-(4-benzoylpiperazin-1-yl)-2-oxoethyl]-2H-indazol-5-yl}-2,4'-bipyridine-6-carboxamide;
N-{2-[2-(4-benzoylpiperazin-1-yl)-2-oxoethyl]-2H-indazol-5-yl}-6-(1H-pyrazol-4-yl)pyridine-2-carboxamide;
N-{2-[2-(4-benzoylpiperazin-1-yl)-2-oxoethyl]-2H-indazol-5-yl}-5-fluoro-6-(1-methyl-1H-pyrazol-4-yl)pyridine-2-carboxamide;
N-{2-[2-(4-benzoylpiperazin-1-yl)-2-oxoethyl]-2H-indazol-5-yl}-6-(3-methyl-1H-pyrazol-4-yl)pyridine-2-carboxamide;
N-{2-[2-(4-benzoylpiperazin-1-yl)-2-oxoethyl]-2H-indazol-5-yl}-6-(1H-1,2,4-triazol-1-yl)pyridine-2-carboxamide;
N-{2-[2-(4-benzoylpiperazin-1-yl)-2-oxoethyl]-2H-indazol-5-yl}-6-[3-(trifluoromethyl)-1H-pyrazol-4-yl]pyridine-2-carboxamide;
N-{2-[2-(4-benzoylpiperazin-1-yl)-2-oxoethyl]-2H-indazol-5-yl}-6-ethoxypyridine-2-carboxamide;
N-{2-[2-(4-benzoylpiperazin-1-yl)-2-oxoethyl]-2H-indazol-5-yl}-6-(cyclopropylmethoxy)pyridine-2-carboxamide;
N-{2-[2-(4-benzoylpiperazin-1-yl)-2-oxoethyl]-2H-indazol-5-yl}-6-ethylpyridine-2-carboxamide;
N-{2-[2-(4-benzoylpiperazin-1-yl)-2-oxoethyl]-2H-indazol-5-yl}-2-(4-methoxyphenyl)-1,3-thiazole-4-carboxamide;
N-{2-[2-(4-benzoylpiperazin-1-yl)-2-oxoethyl]-2H-indazol-5-yl}-2-bromo-1,3-thiazole-4-carboxamide;
N-{2-[2-(4-benzoylpiperazin-1-yl)-2-oxoethyl]-2H-indazol-5-yl}-2-(4-fluorophenyl)-1,3-thiazole-4-carboxamide;
N-{2-[2-(4-benzoylpiperazin-1-yl)-2-oxoethyl]-2H-indazol-5-yl}-6-fluoropyridine-2-carboxamide;
N-{2-[2-(4-benzoylpiperazin-1-yl)-2-oxoethyl]-2H-indazol-5-yl}-6-bromopyridine-2-carboxamide;
N-(2-{2-[4-(4-fluorobenzoyl)piperazin-1-yl]-2-oxoethyl}-2H-indazol-5-yl)-6-(trifluoromethyl)pyridine-2-carboxamide;
N-(2-{2-oxo-2-[4-(pyridin-2-yl)piperazin-1-yl]ethyl}-2H-indazol-5-yl)-6-(trifluoromethyl)pyridine-2-carboxamide;
N-(2-{2-[4-(methoxyacetyl)piperazin-1-yl]-2-oxoethyl}-2H-indazol-5-yl)-6-(trifluoromethyl)pyridine-2-carboxamide;
N-{2-[2-(4-cyclopentyl-3-oxopiperazin-1-yl)-2-oxoethyl]-2H-indazol-5-yl}-6-(trifluoromethyl)pyridine-2-carboxamide;
N-{2-[2-oxo-2-(3-oxo-4-phenylpiperazin-1-yl)ethyl]-2H-indazol-5-yl}-6-(trifluoromethyl)pyridine-2-carboxamide;
N-(2-{2-[4-(2,2-dimethylpropanoyl)piperazin-1-yl]-2-oxoethyl}-2H-indazol-5-yl)-6-(trifluoromethyl)pyridine-2-carboxamide;
N-(2-{2-[4-(cyclopropylmethyl)piperazin-1-yl]-2-oxoethyl}-2H-indazol-5-yl)-6-(trifluoromethyl)pyridine-2-carboxamide;
N-{2-[2-oxo-2-(pyridazin-4-ylamino)ethyl]-2H-indazol-5-yl}-6-(trifluoromethyl)pyridine-2-carboxamide;
N-(2-{2-[4-(2-hydroxy-2-methylpropanoyl)piperazin-1-yl]-2-oxoethyl}-2H-indazol-5-yl)-6-(trifluoromethyl)pyridine-2-carboxamide;
N-(2-{2-oxo-2-[4-(1-phenyl ethyl)piperazin-1-yl]ethyl}-2H-indazol-5-yl)-6-(trifluoromethyl)pyridine-2-carboxamide;
N-(2-{2-oxo-2-[4-(pyridin-3-ylcarbonyl)piperazin-1-yl]ethyl}-2H-indazol-5-yl)-6-(trifluoromethyl)pyridine-2-carboxamide;
N-{2-[2-(4-isonicotinoylpiperazin-1-yl)-2-oxoethyl]-2H-indazol-5-yl}-6-(trifluoromethyl)pyridine-2-carboxamide;
N-(2-{2-[4-(morpholin-4-ylcarbonyl)piperazin-1-yl]-2-oxoethyl}-2H-indazol-5-yl)-6-(trifluoromethyl)pyridine-2-carboxamide;
N-[2-(2-{4-[2-(methylamino)-2-oxoethyl]piperazin-1-yl}-2-oxoethyl)-2H-indazol-5-yl]-6-(trifluoromethyl)pyridine-2-carboxamide;
N-(2-{2-oxo-2-[4-(pyrazin-2-yl)piperazin-1-yl]ethyl}-2H-indazol-5-yl)-6-(trifluoromethyl)pyridine-2-carboxamide;
N-(2-{2-[4-(1-hydroxyethyl)piperidin-1-yl]-2-oxoethyl}-2H-indazol-5-yl)-6-(trifluoromethyl)pyridine-2-carboxamide;
N-{2-[2-(2-methyl-2,8-diazaspiro[4.5]dec-8-yl)-2-oxoethyl]-2H-indazol-5-yl}-6-(trifluoromethyl)pyridine-2-carboxamide;
N-{2-[2-(6-acetyl-2,6-diazaspiro[3.3]hept-2-yl)-2-oxoethyl]-2H-indazol-5-yl}-6-(trifluoromethyl)pyridine-2-carboxamide;
N-{2-[2-oxo-2-(3-oxo-2,8-diazaspiro[4.5]dec-8-yl)ethyl]-2H-indazol-5-yl}-6-(trifluoromethyl)pyridine-2-carboxamide;
N-{2-[2-(6-methyl-2,6-diazaspiro[3.5]non-2-yl)-2-oxoethyl]-2H-indazol-5-yl}-6-(trifluoromethyl)pyridine-2-carboxamide;
N-{2-[2-(7-oxa-2-azaspiro[3.5]non-2-yl)-2-oxoethyl]-2H-indazol-5-yl}-6-(trifluoromethyl)pyridine-2-carboxamide;
N-{2-[2-(1,4'-bipiperidin-1'-yl)-2-oxoethyl]-2H-indazol-5-yl}-6-(trifluoromethyl)pyridine-2-carboxamide;
N-(2-{2-[2-(hydroxymethyl)piperidin-1-yl]-2-oxoethyl}-2H-indazol-5-yl)-6-(trifluoromethyl)pyridine-2-carboxamide;
N-(2-{2-[3-(hydroxymethyl)piperidin-1-yl]-2-oxoethyl}-2H-indazol-5-yl)-6-(trifluoromethyl)pyridine-2-carboxamide;
N-{2-[2-(4-carbamoylpiperidin-1-yl)-2-oxoethyl]-2H-indazol-5-yl}-6-(trifluoromethyl)pyridine-2-carboxamide;
N-(2-{2-[3-(dimethylamino)piperidin-1-yl]-2-oxoethyl}-2H-indazol-5-yl)-6-(trifluoromethyl)pyridine-2-carboxamide;
N-(2-{2-[3-(morpholin-4-ylmethyl)piperidin-1-yl]-2-oxoethyl}-2H-indazol-5-yl)-6-(trifluoromethyl)pyridine-2-carboxamide;
N-[2-(2-{4-[(cyclopropylcarbonyl)amino]piperidin-1-yl}-2-oxoethyl)-2H-indazol-5-yl]-6-(trifluoromethyl)pyridine-2-carboxamide;

N-(2-{2-[4-(3-ethyl-1,2,4-oxadiazol-5-yl)piperidin-1-yl]-2-oxoethyl}-2H-indazol-5-yl)-6-(trifluoromethyl)pyridine-2-carboxamide;

N-[2-(2-{4-[(5-cyclopropyl-1,2,4-oxadiazol-3-yl)methyl]piperidin-1-yl}-2-oxoethyl)-2H-indazol-5-yl]-6-(trifluoromethyl)pyridine-2-carboxamide;

N-(2-{2-oxo-2-[4-(pyrrolidin-1-ylcarbonyl)piperidin-1-yl]ethyl}-2H-indazol-5-yl)-6-(trifluoromethyl)pyridine-2-carboxamide;

N-(2-{2-[4-(4-methylpiperazin-1-yl)piperidin-1-yl]-2-oxoethyl}-2H-indazol-5-yl)-6-(trifluoromethyl)pyridine-2-carboxamide;

N-[2-(2-{4-[2-(morpholin-4-yl)ethyl]piperidin-1-yl}-2-oxoethyl)-2H-indazol-5-yl]-6-(trifluoromethyl)pyridine-2-carboxamide;

N-[2-(2-{4-[(5-methyl-1,2,4-oxadiazol-3-yl)methyl]piperidin-1l-yl}-2-oxoethyl)-2H-indazol-5-yl]-6-(trifluoromethyl)pyridine-2-carboxamide;

N-(2-{2-oxo-2-[3-(pyrrolidin-1-ylmethyl)piperidin-1-yl]ethyl}-2H-indazol-5-yl)-6-(trifluoromethyl)pyridine-2-carboxamide;

N-[2-(2-{[3-(dimethylsulphamoyl)phenyl]amino}-2-oxoethyl)-2H-indazol-5-yl]-6-(trifluoromethyl)pyridine-2-carboxamide;

N-{2-[2-(1,2-oxazol-4-ylamino)-2-oxoethyl]-2H-indazol-5-yl}-6-(trifluoromethyl)pyridine-2-carboxamide;

N-(2-{2-[4-(methylsulphonyl)piperidin-1-yl]-2-oxoethyl}-2H-indazol-5-yl)-6-(trifluoromethyl)pyridine-2-carboxamide;

N-[2-(2-oxo-2-{4-[2-oxo-2-(pyrrolidin-1-yl)ethyl]piperazin-1-yl}ethyl)-2H-indazol-5-yl]-6-(trifluoromethyl)pyridine-2-carboxamide;

N-(2-{2-oxo-2-[4-(phenylsulphonyl)piperidin-1-yl]ethyl}-2H-indazol-5-yl)-6-(trifluoromethyl)pyridine-2-carboxamide;

N-(2-{2-oxo-2-[(3-sulphamoylphenyl)amino]ethyl}-2H-indazol-5-yl)-6-(trifluoromethyl)pyridine-2-carboxamide;

N-[2-(2-{4-[isonicotinoyl(methyl)amino]piperidin-1-yl}-2-oxoethyl)-2H-indazol-5-yl]-6-(trifluoromethyl)pyridine-2-carboxamide;

N-[2-(2-{4-[2-(isopropylamino)-2-oxoethyl]piperazin-1-yl}-2-oxoethyl)-2H-indazol-5-yl]-6-(trifluoromethyl)pyridine-2-carboxamide;

N-(2-{2-[4-(1,1-dioxidotetrahydrothiophen-3-yl)piperazin-1-yl]-2-oxoethyl}-2H-indazol-5-yl)-6-(trifluoromethyl)pyridine-2-carboxamide;

N-[2-(2-{4-[(methoxyacetyl)(methyl)amino]piperidin-1-yl}-2-oxoethyl)-2H-indazol-5-yl]-6-(trifluoromethyl)pyridine-2-carboxamide;

ethyl 4-{[5-({[6-(trifluoromethyl)pyridin-2-yl]carbonyl}amino)-2H-indazol-2-yl]acetyl}piperazine-1-carboxylate;

N-(2-{2-[4-(cyclohexylcarbonyl)piperazin-1-yl]-2-oxoethyl}-2H-indazol-5-yl)-6-(trifluoromethyl)pyridine-2-carboxamide;

N-[2-(2-{4-[2-(cyclopropylamino)-2-oxoethyl]piperazin-1-yl}-2-oxoethyl)-2H-indazol-5-yl]-6-(trifluoromethyl)pyridine-2-carboxamide;

N-(2-{2-[2-(2-hydroxyethyl)piperidin-1-yl]-2-oxoethyl}-2H-indazol-5-yl)-6-(trifluoromethyl)pyridine-2-carboxamide;

N-(2-{2-oxo-2-[4-(pyrrolidin-1-yl)piperidin-1-yl]ethyl}-2H-indazol-5-yl)-6-(trifluoromethyl)pyridine-2-carboxamide;

N-(2-{2-oxo-2-[4-(1H-pyrrol-1-yl)piperidin-1-yl]ethyl}-2H-indazol-5-yl)-6-(trifluoromethyl)pyridine-2-carboxamide;

N-(2-{2-[4-(3-hydroxypropyl)piperazin-1-yl]-2-oxoethyl}-2H-indazol-5-yl)-6-(trifluoromethyl)pyridine-2-carboxamide;

4-{[5-({[6-(trifluoromethyl)pyridin-2-yl]carbonyl}amino)-2H-indazol-2-yl]acetyl}piperazine-1-carboxamide;

N-(2-{2-oxo-2-[4-(2-oxopyrrolidin-1l-yl)piperidin-1-yl]ethyl}-2H-indazol-5-yl)-6-(trifluoromethyl)pyridine-2-carboxamide;

N-{2-[2-(morpholin-4-yl)-2-oxoethyl]-2H-indazol-5-yl}-6-(trifluoromethyl)pyridine-2-carboxamide;

N-(2-{2-[4-(2-amino-2-oxoethyl)piperazin-1-yl]-2-oxoethyl}-2H-indazol-5-yl)-6-(trifluoromethyl)pyridine-2-carboxamide;

N-{2-[2-(1,1-dioxidothiomorpholin-4-yl)-2-oxoethyl]-2H-indazol-5-yl}-6-(trifluoromethyl)pyridine-2-carboxamide;

N-{2-[2-(4-isopropylpiperazin-1-yl)-2-oxoethyl]-2H-indazol-5-yl}-6-(trifluoromethyl)pyridine-2-carboxamide;

N-(2-{2-oxo-2-[4-(2-thienylcarbonyl)piperazin-1-yl]ethyl}-2H-indazol-5-yl)-6-(trifluoromethyl)pyridine-2-carboxamide;

N-(2-{2-[4-(2-cyclopropyl-2-oxoethyl)piperazin-1-yl]-2-oxoethyl}-2H-indazol-5-yl)-6-(trifluoromethyl)pyridine-2-carboxamide;

N-[2-(2-{4-[(1-methyl-1H-pyrazol-4-yl)methyl]piperazin-1-yl}-2-oxoethyl)-2H-indazol-5-yl]-6-(trifluoromethyl)pyridine-2-carboxamide;

N-[2-(2-{4-[(1,5-dimethyl-1H-pyrazol-3-yl)carbonyl]piperazin-1-yl}-2-oxoethyl)-2H-indazol-5-yl]-6-(trifluoromethyl)pyridine-2-carboxamide;

N,N-diethyl-4-{[5-({[6-(trifluoromethyl)pyridin-2-yl]carbonyl}amino)-2H-indazol-2-yl]acetyl}piperazine-1-carboxamide;

N-{2-[2-oxo-2-(thiomorpholin-4-yl)ethyl]-2H-indazol-5-yl}-6-(trifluoromethyl)pyridine-2-carboxamide;

N-(2-{2-[4-(2-furylmethyl)piperazin-1-yl]-2-oxoethyl}-2H-indazol-5-yl)-6-(trifluoromethyl)pyridine-2-carboxamide;

N-(2-{2-oxo-2-[4-(3-thienylmethyl)piperazin-1-yl]ethyl}-2H-indazol-5-yl)-6-(trifluoromethyl)pyridine-2-carboxamide;

N-{2-[2-(4'-methyl-1,4'-bipiperidin-1'-yl)-2-oxoethyl]-2H-indazol-5-yl}-6-(trifluoromethyl)pyridine-2-carboxamide;

N-{2-[2-(6-methyl-2,6-diazaspiro[3.3]hept-2-yl)-2-oxoethyl]-2H-indazol-5-yl}-6-(trifluoromethyl)pyridine-2-carboxamide;

N-{2-[2-(4-cyclopentylpiperazin-1-yl)-2-oxoethyl]-2H-indazol-5-yl}-6-(trifluoromethyl)pyridine-2-carboxamide;

N-[2-(2-{4-[2-(2-hydroxyethoxy)ethyl]piperazin-1-yl}-2-oxoethyl)-2H-indazol-5-yl]-6-(trifluoromethyl)pyridine-2-carboxamide;

N-(2-{2-oxo-2-[4-(pyridin-4-ylmethyl)piperazin-1-yl]ethyl}-2H-indazol-5-yl)-6-(trifluoromethyl)pyridine-2-carboxamide;

N-(2-{2-[4-(dimethylsulphamoyl)piperazin-1-yl]-2-oxoethyl}-2H-indazol-5-yl)-6-(trifluoromethyl)pyridine-2-carboxamide;

N-(2-{2-oxo-2-[4-(pyridin-4-yl)piperazin-1-yl]ethyl}-2H-indazol-5-yl)-6-(trifluoromethyl)pyridine-2-carboxamide;

N-(2-{2-[4-(methylsulphonyl)piperazin-1-yl]-2-oxo-ethyl}-2H-indazol-5-yl)-6-(trifluoromethyl)pyridine-2-carboxamide;
formic acid N-[2-(2-{4-[2-(1H-imidazol-1-yl)ethyl]piperazin-1-yl}-2-oxoethyl)-2H-indazol-5-yl]-6-(trifluoromethyl)pyridine-2-carboxamide (1:1);
N-(2-{2-[4-(diethylsulphamoyl)piperazin-1-yl]-2-oxoethyl}-2H-indazol-5-yl)-6-(trifluoromethyl)pyridine-2-carboxamide;
N-(2-{2-oxo-2-[4-(pyridin-3-yl)piperazin-1-yl]ethyl}-2H-indazol-5-yl)-6-(trifluoromethyl)pyridine-2-carboxamide;
N-(2-{2-oxo-2-[4-(piperidin-1-ylsulphonyl)piperazin-1-yl]ethyl}-2H-indazol-5-yl)-6-(trifluoromethyl)pyridine-2-carboxamide;
N-[2-(2-{4-[(1,5-dimethyl-1H-pyrazol-4-yl)sulphonyl]piperazin-1-yl}-2-oxoethyl)-2H-indazol-5-yl]-6-(trifluoromethyl)pyridine-2-carboxamide;
N-(2-{2-[4-(cyclopropylmethyl)piperazin-1-yl]-2-oxoethyl}-2H-indazol-5-yl)-6-(1-methyl-1H-pyrazol-4-yl)pyridine-2-carboxamide;
N-(2-{2-[4-(2-hydroxypropan-2-yl)piperidin-1-yl]-2-oxoethyl}-2H-indazol-5-yl)-6-(1-methyl-1H-pyrazol-4-yl)pyridine-2-carboxamide;
6-(1-methyl-1H-pyrazol-4-yl)-N-(2-{2-oxo-2-[4-(pyrrolidin-1-yl)piperidin-1-yl]ethyl}-2H-indazol-5-yl)pyridine-2-carboxamide;
N-{2-[2-(4-ethylpiperazin-1-yl)-2-oxoethyl]-2H-indazol-5-yl}-6-(1-methyl-1H-pyrazol-4-yl)pyridine-2-carboxamide;
N-(2-{2-[4-(dimethylamino)piperidin-1-yl]-2-oxoethyl}-2H-indazol-5-yl)-6-(1-methyl-1H-pyrazol-4-yl)pyridine-2-carboxamide;
N-(2-{2-[(cyclopropylmethyl)(methyl)amino]-2-oxoethyl}-6-methoxy-2H-indazol-5-yl)-6-methylpyridine-2-carboxamide;
N-(2-{2-[(cyclopropylmethyl)(methyl)amino]-2-oxoethyl}-6-ethoxy-2H-indazol-5-yl)-6-(trifluoromethyl)pyridine-2-carboxamide;
N-(2-{2-[(cyclopropylmethyl)(methyl)amino]-2-oxoethyl}-6-methoxy-2H-indazol-5-yl)-6-(trifluoromethyl)pyridine-2-carboxamide;
6-cyclopropyl-N-(2-{2-[4-(2-hydroxypropan-2-yl)piperidin-1-yl]-2-oxoethyl}-6-methoxy-2H-indazol-5-yl)pyridine-2-carboxamide;
6-(1-hydroxyethyl)-N-(2-{2-[4-(2-hydroxypropan-2-yl)piperidin-1-yl]-2-oxoethyl}-6-methoxy-2H-indazol-5-yl)pyridine-2-carboxamide;
6-(azetidin-3-ylamino)-N-{2-[2-(4-benzoylpiperazin-1-yl)-2-oxoethyl]-2H-indazol-5-yl}pyridine-2-carboxamide;
6-[(azetidin-2-ylmethyl)amino]-N-{2-[2-(4-benzoylpiperazin-1-yl)-2-oxoethyl]-2H-indazol-5-yl}pyridine-2-carboxamide;
N-{2-[2-(4-benzoylpiperazin-1-yl)-2-oxoethyl]-2H-indazol-5-yl}-6-(3-hydroxyazetidin-1-yl)pyridine-2-carboxamide;
6-[(2R,6S)-2,6-dimethylmorpholin-4-yl]-N-(6-methyl-2-{2-oxo-2-[4-(pyrrolidin-1-yl)piperidin-1-yl]ethyl}-2H-indazol-5-yl)pyridine-2-carboxamide;
N-[2-(2-{4-methyl-4-[(4-methylpiperazin-1-yl)carbonyl]piperidin-1-yl}-2-oxoethyl)-2H-indazol-5-yl]-6-(trifluoromethyl)pyridine-2-carboxamide;
N-(6-chloro-2-{2-oxo-2-[(3R)-piperidin-3-ylamino]ethyl}-2H-indazol-5-yl)-6-(trifluoromethyl)pyridine-2-carboxamide;
N-(2-{2-[4-(cyclopropylcarbonyl)piperazin-1-yl]-2-oxoethyl}-6-isopropoxy-2H-indazol-5-yl)-6-methylpyridine-2-carboxamide;
N-(2-{2-[4-(cyclopropylcarbonyl)piperazin-1-yl]-2-oxoethyl}-6-isopropoxy-2H-indazol-5-yl)-6-(trifluoromethyl)pyridine-2-carboxamide;
N-{2-[2-(4-benzoylpiperazin-1-yl)-2-oxoethyl]-6-isopropoxy-2H-indazol-5-yl}-6-methylpyridine-2-carboxamide;
N-{2-[2-(4-benzoylpiperazin-1-yl)-2-oxoethyl]-6-isopropoxy-2H-indazol-5-yl}-6-(trifluoromethyl)pyridine-2-carboxamide;
N-{6-isopropoxy-2-[2-(4-methylpiperazin-1-yl)-2-oxoethyl]-2H-indazol-5-yl}-6-(trifluoromethyl)pyridine-2-carboxamide;
N-{6-isopropoxy-2-[2-(4-methylpiperazin-1-yl)-2-oxoethyl]-2H-indazol-5-yl}-6-methylpyridine-2-carboxamide;
N-(2-{2-[4-(cyclobutylcarbonyl)piperazin-1-yl]-2-oxoethyl}-2H-indazol-5-yl)-6-(trifluoromethyl)pyridine-2-carboxamide;
N-(2-{2-[4-(cyclopentylcarbonyl)piperazin-1-yl]-2-oxoethyl}-2H-indazol-5-yl)-6-(trifluoromethyl)pyridine-2-carboxamide;
N-[2-(2-{4-[3-(methylsulphonyl)benzoyl]piperazin-1-yl}-2-oxoethyl)-2H-indazol-5-yl]-6-(trifluoromethyl)pyridine-2-carboxamide;
N-[2-(2-{4-[2-methoxy-5-(methylsulphonyl)benzoyl]piperazin-1-yl}-2-oxoethyl)-2H-indazol-5-yl]-6-(trifluoromethyl)pyridine-2-carboxamide;
6-bromo-N-(6-methyl-2-{2-oxo-2-[4-(pyrrolidin-1-yl)piperidin-1-yl]ethyl}-2H-indazol-5-yl)pyridine-2-carboxamide;
2-(4-methoxyphenyl)-N-(6-methyl-2-{2-oxo-2-[4-(pyrrolidin-1-yl)piperidin-1-yl]ethyl}-2H-indazol-5-yl)-1,3-thiazole-4-carboxamide;
2-(4-fluorophenyl)-N-(6-methyl-2-{2-oxo-2-[4-(pyrrolidin-1-yl)piperidin-1-yl]ethyl}-2H-indazol-5-yl)-1,3-thiazole-4-carboxamide;
N-(6-methyl-2-{2-oxo-2-[4-(pyrrolidin-1-yl)piperidin-1-yl]ethyl}-2H-indazol-5-yl)-6-(trifluoromethyl)pyridine-2-carboxamide;
6-bromo-N-{2-[2-(4-methylpiperazin-1-yl)-2-oxoethyl]-2H-indazol-5-yl}pyridine-2-carboxamide;
6-bromo-N-{2-[2-(4-methylpiperazin-1-yl)-2-oxoethyl]-6-(trifluoromethoxy)-2H-indazol-5-yl}pyridine-2-carboxamide;
N-{2-[2-(4-methylpiperazin-1-yl)-2-oxoethyl]-6-(trifluoromethoxy)-2H-indazol-5-yl}-6-(4H-1,2,4-triazol-4-yl)pyridine-2-carboxamide;
2-bromo-N-{6-bromo-2-[2-(4-methylpiperazin-1-yl)-2-oxoethyl]-2H-indazol-5-yl}-1,3-thiazole-4-carboxamide;
N-{6-hydroxy-2-[2-(4-methylpiperazin-1-yl)-2-oxoethyl]-2H-indazol-5-yl}-6-(trifluoromethyl)pyridine-2-carboxamide;
N-[6-(benzyloxy)-2-{2-[4-(2-hydroxypropan-2-yl)piperidin-1-yl]-2-oxoethyl}-2H-indazol-5-yl]-6-methylpyridine-2-carboxamide;
6-bromo-N-{6-bromo-2-[2-(4-methylpiperazin-1-yl)-2-oxoethyl]-2H-indazol-5-yl}pyridine-2-carboxamide;
N-{6-(benzyloxy)-2-[2-(4-methylpiperazin-1-yl)-2-oxoethyl]-2H-indazol-5-yl}-6-methylpyridine-2-carboxamide;
2-(azetidin-3-ylamino)-N-{2-[2-(4-benzoylpiperazin-1-yl)-2-oxoethyl]-2H-indazol-5-yl}-1,3-thiazole-4-carboxamide;

6-acetamido-N-{6-methoxy-2-[2-(morpholin-4-yl)-2-oxoethyl]-2H-indazol-5-yl}pyridine-2-carboxamide;

6-(dimethylamino)-N-(2-{2-[4-(2-hydroxypropan-2-yl)piperidin-1-yl]-2-oxoethyl}-6-methoxy-2H-indazol-5-yl)pyridine-2-carboxamide;

6-(dimethylamino)-N-{6-methoxy-2-[2-(morpholin-4-yl)-2-oxoethyl]-2H-indazol-5-yl}pyridine-2-carboxamide;

6-acetamido-N-(2-{2-[4-(2-hydroxypropan-2-yl)piperidin-1-yl]-2-oxoethyl}-6-methoxy-2H-indazol-5-yl)pyridine-2-carboxamide;

6-(dimethylamino)-N-{6-methoxy-2-[2-(4-methylpiperazin-1-yl)-2-oxoethyl]-2H-indazol-5-yl}pyridine-2-carboxamide;

N-{2-[2-(4-methylpiperazin-1-yl)-2-oxoethyl]-2H-indazol-5-yl}-6-[3-(methylsulphonyl)phenyl]pyridine-2-carboxamide;

N-{2-[1-(4-benzoylpiperazin-1-yl)-1-oxopropan-2-yl]-2H-indazol-5-yl}-6-(trifluoromethyl)pyridine-2-carboxamide;

N-[6-chloro-2-(2-{[trans-4-(2-hydroxypropan-2-yl)cyclohexyl]amino}-2-oxoethyl)-2H-indazol-5-yl]-6-(trifluoromethyl)pyridine-2-carboxamide;

6-(2-hydroxypropan-2-yl)-N-{6-methoxy-2-[2-(morpholin-4-yl)-2-oxoethyl]-2H-indazol-5-yl}pyridine-2-carboxamide;

N-{6-chloro-2-[2-(3,3-difluoropyrrolidin-1-yl)-2-oxoethyl]-2H-indazol-5-yl}-6-(trifluoromethyl)pyridine-2-carboxamide;

N-{6-chloro-2-[2-oxo-2-(pyrrolidin-1-yl)ethyl]-2H-indazol-5-yl}-6-(trifluoromethyl)pyridine-2-carboxamide;

N-{6-chloro-2-[2-(2-oxa-7-azaspiro[3.5]non-7-yl)-2-oxoethyl]-2H-indazol-5-yl}-6-(trifluoromethyl)pyridine-2-carboxamide;

N-(6-chloro-2-{2-[4-(2-hydroxy-2-methylpropyl)piperazin-1-yl]-2-oxoethyl}-2H-indazol-5-yl)-6-(trifluoromethyl)pyridine-2-carboxamide;

N-{6-methoxy-2-[2-oxo-2-(pyrrolidin-1-yl)ethyl]-2H-indazol-5-yl}-6-(trifluoromethyl)pyridine-2-carboxamide;

N-{2-[2-(3,3-difluoropyrrolidin-1-yl)-2-oxoethyl]-6-methoxy-2H-indazol-5-yl}-6-(trifluoromethyl)pyridine-2-carboxamide;

6-(difluoromethyl)-N-{6-methoxy-2-[2-(morpholin-4-yl)-2-oxoethyl]-2H-indazol-5-yl}pyridine-2-carboxamide;

N-{2-[2-(3,3-difluoropyrrolidin-1-yl)-2-oxoethyl]-6-methoxy-2H-indazol-5-yl}-6-methylpyridine-2-carboxamide;

N-{6-methoxy-2-[2-(morpholin-4-yl)-2-oxoethyl]-2H-indazol-5-yl}-6-methylpyridine-2-carboxamide;

N-{6-methoxy-2-[2-(morpholin-4-yl)-2-oxoethyl]-2H-indazol-5-yl}-2-(tetrahydro-2H-pyran-4-yl)-1,3-oxazole-4-carboxamide;

N-{2-[2-(1,1-dioxido-1-thia-6-azaspiro[3.3]hept-6-yl)-2-oxoethyl]-6-methoxy-2H-indazol-5-yl}-6-(trifluoromethyl)pyridine-2-carboxamide;

N-{6-methoxy-2-[2-(2-oxa-6-azaspiro[3.3]hept-6-yl)-2-oxoethyl]-2H-indazol-5-yl}-6-(trifluoromethyl)pyridine-2-carboxamide;

N-{6-(3-hydroxy-2,2-dimethylpropoxy)-2-[2-(morpholin-4-yl)-2-oxoethyl]-2H-indazol-5-yl}-6-(trifluoromethyl)pyridine-2-carboxamide;

6-ethyl-N-{6-methoxy-2-[2-(morpholin-4-yl)-2-oxoethyl]-2H-indazol-5-yl}pyridine-2-carboxamide;

6-isobutyl-N-{6-methoxy-2-[2-(morpholin-4-yl)-2-oxoethyl]-2H-indazol-5-yl}pyridine-2-carboxamide;

methyl 2-[2-(morpholin-4-yl)-2-oxoethyl]-5-({[6-(trifluoromethyl)pyridin-2-yl]carbonyl}amino)-2H-indazole-6-carboxylate;

methyl 5-{[(6-methylpyridin-2-yl)carbonyl]amino}-2-[2-(morpholin-4-yl)-2-oxoethyl]-2H-indazole-6-carboxylate;

N-{6-methoxy-2-[2-(morpholin-4-yl)-2-oxoethyl]-2H-indazol-5-yl}-6-(pyrrolidin-1-yl)pyridine-2-carboxamide;

N-{6-methoxy-2-[2-(morpholin-4-yl)-2-oxoethyl]-2H-indazol-5-yl}-6-(morpholin-4-yl)pyridine-2-carboxamide;

6-(cyclopropylamino)-N-{6-methoxy-2-[2-(morpholin-4-yl)-2-oxoethyl]-2H-indazol-5-yl}pyridine-2-carboxamide;

6-(butylamino)-N-{6-methoxy-2-[2-(morpholin-4-yl)-2-oxoethyl]-2H-indazol-5-yl}pyridine-2-carboxamide;

N-{6-methoxy-2-[2-(morpholin-4-yl)-2-oxoethyl]-2H-indazol-5-yl}-6-(propylamino)pyridine-2-carboxamide;

6-(isobutylamino)-N-{6-methoxy-2-[2-(morpholin-4-yl)-2-oxoethyl]-2H-indazol-5-yl}pyridine-2-carboxamide;

R—N-{6-methoxy-2-[2-(morpholin-4-yl)-2-oxoethyl]-2H-indazol-5-yl}-6-(2,2,2-trifluoro-1-hydroxyethyl)pyridine-2-carboxamide;

S—N-{6-methoxy-2-[2-(morpholin-4-yl)-2-oxoethyl]-2H-indazol-5-yl}-6-(2,2,2-trifluoro-1-hydroxyethyl)pyridine-2-carboxamide;

6-(1-hydroxyethyl)-N-{6-methoxy-2-[2-(morpholin-4-yl)-2-oxoethyl]-2H-indazol-5-yl}pyridine-2-carboxamide;

6-(cyclopropylamino)-N-{6-methoxy-2-[2-(4-methylpiperazin-1-yl)-2-oxoethyl]-2H-indazol-5-yl}pyridine-2-carboxamide;

N-{6-methoxy-2-[2-(4-methylpiperazin-1-yl)-2-oxoethyl]-2H-indazol-5-yl}-6-(propylamino)pyridine-2-carboxamide;

6-(isobutylamino)-N-{6-methoxy-2-[2-(4-methylpiperazin-1-yl)-2-oxoethyl]-2H-indazol-5-yl}pyridine-2-carboxamide;

6-(1-hydroxyethyl)-N-{6-methoxy-2-[2-(4-methylpiperazin-1-yl)-2-oxoethyl]-2H-indazol-5-yl}pyridine-2-carboxamide;

N-{6-methoxy-2-[2-(4-methylpiperazin-1-yl)-2-oxoethyl]-2H-indazol-5-yl}-4-methyl-6-(trifluoromethyl)pyridine-2-carboxamide;

N-{6-(benzyloxy)-2-[2-(morpholin-4-yl)-2-oxoethyl]-2H-indazol-5-yl}-6-(trifluoromethyl)pyridine-2-carboxamide;

6-(cyclopropylamino)-N-(2-{2-[4-(2-hydroxypropan-2-yl)piperidin-1-yl]-2-oxoethyl}-6-methoxy-2H-indazol-5-yl)pyridine-2-carboxamide;

6-(butylamino)-N-(2-{2-[4-(2-hydroxypropan-2-yl)piperidin-1-yl]-2-oxoethyl}-6-methoxy-2H-indazol-5-yl)pyridine-2-carboxamide;

N-(2-{2-[4-(2-hydroxypropan-2-yl)piperidin-1-yl]-2-oxoethyl}-6-methoxy-2H-indazol-5-yl)-6-[(2-methoxyethyl)amino]pyridine-2-carboxamide;

N-(2-{2-[4-(2-hydroxypropan-2-yl)piperidin-1l-yl]-2-oxoethyl}-6-methoxy-2H-indazol-5-yl)-6-(propylamino)pyridine-2-carboxamide;

N-(2-{2-[4-(2-hydroxypropan-2-yl)piperidin-1-yl]-2-oxoethyl}-6-methoxy-2H-indazol-5-yl)-6-(isobutylamino)pyridine-2-carboxamide;

5-fluoro-N-(2-{2-[4-(2-hydroxypropan-2-yl)piperidin-1-yl]-2-oxoethyl}-6-methoxy-2H-indazol-5-yl)-6-methylpyridine-2-carboxamide;

N-{6-hydroxy-2-[2-(morpholin-4-yl)-2-oxoethyl]-2H-indazol-5-yl}-6-(trifluoromethyl)pyridine-2-carboxamide;
N-{6-(3-cyanopropoxy)-2-[2-(morpholin-4-yl)-2-oxoethyl]-2H-indazol-5-yl}-6-(trifluoromethyl)pyridine-2-carboxamide;
N-{2-[2-(morpholin-4-yl)-2-oxoethyl]-6-(2,2,2-trifluoroethoxy)-2H-indazol-5-yl}-6-(trifluoromethyl)pyridine-2-carboxamide;
N-{6-(cyclohexylmethoxy)-2-[2-(morpholin-4-yl)-2-oxoethyl]-2H-indazol-5-yl}-6-(trifluoromethyl)pyridine-2-carboxamide;
N-{6-(2,2-dimethylpropoxy)-2-[2-(morpholin-4-yl)-2-oxoethyl]-2H-indazol-5-yl}-6-(trifluoromethyl)pyridine-2-carboxamide;
N-{2-[2-(morpholin-4-yl)-2-oxoethyl]-6-(tetrahydrofuran-2-ylmethoxy)-2H-indazol-5-yl}-6-(trifluoromethyl)pyridine-2-carboxamide;
N-{6-(cyclopentyloxy)-2-[2-(morpholin-4-yl)-2-oxoethyl]-2H-indazol-5-yl}-6-(trifluoromethyl)pyridine-2-carboxamide;
N-{6-(cyanomethoxy)-2-[2-(morpholin-4-yl)-2-oxoethyl]-2H-indazol-5-yl}-6-(trifluoromethyl)pyridine-2-carboxamide;
({2-[2-(morpholin-4-yl)-2-oxoethyl]-5-({[6-(trifluoromethyl)pyridin-2-yl]carbonyl}amino)-2H-indazol-6-yl}oxy)acetic acid;
N-{6-(cyclobutylmethoxy)-2-[2-(morpholin-4-yl)-2-oxoethyl]-2H-indazol-5-yl}-6-(trifluoromethyl)pyridine-2-carboxamide;
N-{2-[2-(morpholin-4-yl)-2-oxoethyl]-6-[2-(pyrrolidin-1-yl)ethoxy]-2H-indazol-5-yl}-6-(trifluoromethyl)pyridine-2-carboxamide;
N-{6-[2-(morpholin-4-yl)ethoxy]-2-[2-(morpholin-4-yl)-2-oxoethyl]-2H-indazol-5-yl}-6-(trifluoromethyl)pyridine-2-carboxamide;
N-{2-[2-(morpholin-4-yl)-2-oxoethyl]-6-[2-(piperidin-1-yl)ethoxy]-2H-indazol-5-yl}-6-(trifluoromethyl)pyridine-2-carboxamide;
N-{6-(3-hydroxypropoxy)-2-[2-(morpholin-4-yl)-2-oxoethyl]-2H-indazol-5-yl}-6-(trifluoromethyl)pyridine-2-carboxamide;
N-{6-(2-hydroxypropoxy)-2-[2-(morpholin-4-yl)-2-oxoethyl]-2H-indazol-5-yl}-6-(trifluoromethyl)pyridine-2-carboxamide;
N-{6-(2-hydroxyethoxy)-2-[2-(morpholin-4-yl)-2-oxoethyl]-2H-indazol-5-yl}-6-(trifluoromethyl)pyridine-2-carboxamide;
N-{6-(2-methoxyethoxy)-2-[2-(morpholin-4-yl)-2-oxoethyl]-2H-indazol-5-yl}-6-(trifluoromethyl)pyridine-2-carboxamide;
ethyl ({2-[2-(morpholin-4-yl)-2-oxoethyl]-5-({[6-(trifluoromethyl)pyridin-2-yl]carbonyl}amino)-2H-indazol-6-yl}oxy)acetate;
methyl 4-({2-[2-(morpholin-4-yl)-2-oxoethyl]-5-({[6-(trifluoromethyl)pyridin-2-yl]carbonyl}amino)-2H-indazol-6-yl}oxy)butanoate;
ethyl 2-({2-[2-(morpholin-4-yl)-2-oxoethyl]-5-({[6-(trifluoromethyl)pyridin-2-yl]carbonyl}amino)-2H-indazol-6-yl})oxy)propanoate;
ethyl 3-methyl-2-({2-[2-(morpholin-4-yl)-2-oxoethyl]-5-({[6-(trifluoromethyl)pyridin-2-yl]carbonyl}amino)-2H-indazol-6-yl)}oxy)butanoate 2-({2-[2-(morpholin-4-yl)-2-oxoethyl]-5-({[6-(trifluoromethyl)pyridin-2-yl]carbonyl}amino)-2H-indazol-6-yl}oxy)propanoic acid;
N-{6-(2-hydroxypropan-2-yl)-2-[2-(morpholin-4-yl)-2-oxoethyl]-2H-indazol-5-yl}-6-(trifluoromethyl)pyridine-2-carboxamide;
N-{6-chloro-2-[2-(4-methylpiperazin-1-yl)-2-oxoethyl]-2H-indazol-5-yl}-6-(difluoromethyl)pyridine-2-carboxamide; and
N-{6-chloro-2-[2-(morpholin-4-yl)-2-oxoethyl]-2H-indazol-5-yl}-6-(difluoromethyl)pyridine-2-carboxamide.

11. A method of treating a disease that is mediated by IRAK4 selected from the group consisting of lymphomas, macular degeneration, endometriosis, psoriasis, lupus erythematosus, multiple sclerosis, COPD, and rheumatoid arthritis comprising administering an effective amount of the compound of claim 1.

12. A method of inhibiting IRAK4 in a patient in need thereof comprising administering an effective amount of the compound of claim 1 to said patient.

13. A method of treating lymphomas, macular degeneration, endometriosis, psoriasis, lupus erythematosus, multiple sclerosis, COPD, or rheumatoid arthritis comprising administering an effective amount of the compound of claim 1.

14. A method of making a medicament for the treatment of tumor disorders, dermatological disorders, gynaecological disorders, cardiovascular disorders, pulmonary disorders, ophthalmological disorders, neurological disorders, metabolic disorders, inflammatory disorders, autoimmune disorders, or pain comprising combining the compound of claim 1 with an inert, non-toxic, pharmaceutically suitable excipient.

15. A method of making a medicament for the treatment of lymphomas, macular degeneration, endometriosis, psoriasis, lupus erythematosus, multiple sclerosis, chronic obstructive pulmonary disease (COPD), or rheumatoid arthritis comprising combining the compound of claim 1 with an inert, non-toxic, pharmaceutically suitable excipient.

16. A medicament comprising the compound of claim 1 in combination with an inert, non-toxic, pharmaceutically suitable excipient.

17. A method of making a compound of formula (III) from a compound of formula (II)

in which $R^{14}$ is either a methyl or an ethyl radical by Grignard reaction with methyl- or ethylmagnesium bromide.

18. A compound of the formula (III)

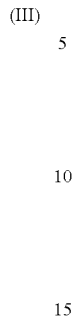

(III)

in which $R^{14}$ is either a methyl or an ethyl radical.

19. A method of treating IL-1 receptor mediated diseases, MyD88 associated diseases, and TLR-associated diseases with the exception of TLR3 comprising administering an effective amount of the compound of claim 1, wherein the disease is selected from the group consisting of lymphomas, macular degeneration, endometriosis, psoriasis, lupus erythematosus, multiple sclerosis, COPD, and rheumatoid arthritis.

* * * * *